(12) United States Patent
Cotesta et al.

(10) Patent No.: US 9,365,576 B2
(45) Date of Patent: Jun. 14, 2016

(54) PYRROLOPYRROLIDINONE COMPOUNDS

(71) Applicants: Simona Cotesta, Basel (CH); Pascal Furet, Thann (FR); Vito Guagnano, Basel (CH); Philipp Holzer, Sissach (CH); Joerg Kallen, Basel (CH); Robert Mah, Muttenz (CH); Keiichi Masuya, Basel (CH); Achim Schlapbach, Lorrach (DE); Stefan Stutz, Basel (CH); Andrea Vaupel, Riehen (CH)

(72) Inventors: Simona Cotesta, Basel (CH); Pascal Furet, Thann (FR); Vito Guagnano, Basel (CH); Philipp Holzer, Sissach (CH); Joerg Kallen, Basel (CH); Robert Mah, Muttenz (CH); Keiichi Masuya, Basel (CH); Achim Schlapbach, Lorrach (DE); Stefan Stutz, Basel (CH); Andrea Vaupel, Riehen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/900,061

(22) Filed: May 22, 2013

(65) Prior Publication Data
US 2013/0317024 A1 Nov. 28, 2013

Related U.S. Application Data

(60) Provisional application No. 61/776,052, filed on Mar. 11, 2013, provisional application No. 61/651,354, filed on May 24, 2012.

(51) Int. Cl.
| | |
|---|---|
| C07D 487/04 | (2006.01) |
| A61K 31/407 | (2006.01) |
| A61K 31/44 | (2006.01) |
| A61K 31/5377 | (2006.01) |
| A61K 31/506 | (2006.01) |
| A61K 31/41 | (2006.01) |
| A61K 31/4439 | (2006.01) |
| A61K 45/06 | (2006.01) |

(52) U.S. Cl.
CPC ............ *C07D 487/04* (2013.01); *A61K 31/407* (2013.01); *A61K 31/41* (2013.01); *A61K 31/4439* (2013.01); *A61K 31/506* (2013.01); *A61K 31/5377* (2013.01); *A61K 45/06* (2013.01)

(58) Field of Classification Search
None
See application file for complete search history.

(56) References Cited

U.S. PATENT DOCUMENTS

| | | |
|---|---|---|
| 3,829,420 A | 8/1974 | Inaba et al. |
| 3,865,827 A | 2/1975 | Yamamoto et al. |
| 3,923,710 A | 12/1975 | Ishizumi et al. |
| 4,099,002 A | 7/1978 | Inaba et al. |
| 4,258,187 A | 3/1981 | Middleton |
| 4,335,127 A | 6/1982 | Vandenberk et al. |
| 4,695,633 A | 9/1987 | Berneth et al. |
| 6,479,499 B1 | 11/2002 | Kuo et al. |
| 6,734,302 B2 | 5/2004 | Kong et al. |
| 7,541,354 B2 | 6/2009 | Fancelli et al. |
| 8,101,644 B2 | 1/2012 | Kai et al. |
| 8,222,288 B2 | 7/2012 | Wang et al. |
| 8,440,693 B2 | 5/2013 | Berghausen et al. |
| 2003/0153580 A1 | 8/2003 | Kong et al. |
| 2006/0069085 A1 | 3/2006 | Zhao et al. |
| 2008/0153791 A1 | 6/2008 | Wilckens |
| 2009/0163545 A1 | 6/2009 | Goldfarb |
| 2010/0160356 A1 | 6/2010 | Heinrich et al. |
| 2010/0210632 A1 | 8/2010 | Hiroyuki et al. |
| 2011/0183939 A1 | 7/2011 | Kai et al. |
| 2011/0230457 A1 | 9/2011 | Berghausen et al. |
| 2011/0301133 A1 | 12/2011 | Wu et al. |
| 2012/0065210 A1 | 3/2012 | Chu et al. |
| 2012/0129871 A1 | 5/2012 | Berghausen et al. |
| 2013/0245036 A1 | 9/2013 | Berghausen et al. |
| 2013/0281396 A1 | 10/2013 | McLure et al. |
| 2013/0281473 A1 | 10/2013 | Berghausen et al. |
| 2013/0317024 A1 | 11/2013 | Cotesta et al. |

(Continued)

FOREIGN PATENT DOCUMENTS

| | | |
|---|---|---|
| EP | 1657238 A1 | 5/2006 |
| EP | 2 143 713 A1 | 1/2010 |
| JP | 57021388 | 2/1982 |
| JP | 2001302515 A | 10/2001 |

(Continued)

OTHER PUBLICATIONS

Andreichikov, Yu.S. et al., "Chemistry of Oxalyl Derivatives of Methyl Ketones XLIV. Synthesis of 4-Aroyl-1,5-Diphenyltetrahydropyrrole-2,3-Diones and their Reaction with Amines and Hydrazine", Journal of Organic Chemistry vol. XXII, Issue 8, 1986.

(Continued)

*Primary Examiner* — Nyeemah A Grazier
(74) *Attorney, Agent, or Firm* — Qian Zhang

(57) ABSTRACT

The invention relates to compounds of formula (I):

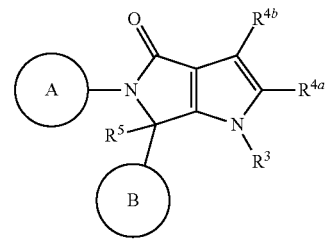

as described herein, pharmaceutical preparations comprising such compounds, uses and methods of use for such compounds in the treatment of a disorder or a disease mediated by the activity of MDM2 and/or MDM4, and combinations comprising such compounds.

12 Claims, No Drawings

(56) References Cited

U.S. PATENT DOCUMENTS

| | | |
|---|---|---|
| 2014/0011798 A1 | 1/2014 | Furet et al. |
| 2014/0135306 A1 | 5/2014 | Buschmann et al. |
| 2014/0275158 A1 | 9/2014 | Furet et al. |
| 2014/0343084 A1 | 11/2014 | Furet et al. |
| 2014/0349990 A1 | 11/2014 | Blank et al. |
| 2014/0350010 A1 | 11/2014 | Furet et al. |
| 2015/0353551 A1 | 12/2015 | Furet et al. |
| 2015/0353563 A1 | 12/2015 | Furet et al. |

FOREIGN PATENT DOCUMENTS

| | | |
|---|---|---|
| JP | 2006-524228 | 10/2006 |
| JP | 2014-533745 | 12/2014 |
| WO | 93/04047 A1 | 3/1993 |
| WO | 95/19362 A1 | 7/1995 |
| WO | 98/19362 A1 | 7/1995 |
| WO | 98/01467 A2 | 1/1998 |
| WO | 98/45276 A2 | 10/1998 |
| WO | 00/66560 A1 | 11/2000 |
| WO | 02/12242 A2 | 2/2002 |
| WO | 03/051359 | 6/2003 |
| WO | 03051359 | 6/2003 |
| WO | 03/062392 A2 | 7/2003 |
| WO | 03/095625 A2 | 11/2003 |
| WO | 03/101985 A1 | 12/2003 |
| WO | 2004/014916 | 2/2004 |
| WO | 2004/094421 A1 | 11/2004 |
| WO | 2004/094429 A1 | 11/2004 |
| WO | 2004/096134 A2 | 11/2004 |
| WO | 2005/027882 A1 | 3/2005 |
| WO | 2005/051922 A1 | 6/2005 |
| WO | 2005110996 | 11/2005 |
| WO | 2005/117876 A1 | 12/2005 |
| WO | 2006/024837 A1 | 3/2006 |
| WO | 2006074262 | 7/2006 |
| WO | 2006/097337 A1 | 9/2006 |
| WO | 2006/100038 A1 | 9/2006 |
| WO | 2006/136606 A2 | 12/2006 |
| WO | 2007068637 | 6/2007 |
| WO | 2007096334 | 8/2007 |
| WO | 2007/144384 A1 | 12/2007 |
| WO | 2008034039 | 3/2008 |
| WO | 2008/045529 A1 | 4/2008 |
| WO | 2008/120725 A1 | 10/2008 |
| WO | 2008/130614 A2 | 10/2008 |
| WO | 2010/007116 A2 | 1/2010 |
| WO | 2010/035727 A1 | 4/2010 |
| WO | 2010/047956 A1 | 4/2010 |
| WO | 2010/141738 A2 | 12/2010 |
| WO | 2010141738 | 12/2010 |
| WO | 2011/076786 A1 | 6/2011 |
| WO | 2011/161031 A1 | 12/2011 |
| WO | 2012/034954 A1 | 3/2012 |
| WO | 2012046030 | 4/2012 |
| WO | 2012/065022 A2 | 5/2012 |
| WO | 2012/151512 A2 | 11/2012 |
| WO | 2012/174487 A2 | 12/2012 |
| WO | 2012/175487 A1 | 12/2012 |
| WO | 2012/175520 A1 | 12/2012 |
| WO | 2013/027168 A2 | 2/2013 |
| WO | 2013/033268 A2 | 3/2013 |
| WO | 2013/033270 A2 | 3/2013 |
| WO | 2013/080141 A1 | 6/2013 |
| WO | 2013/097052 A1 | 7/2013 |
| WO | 2013/111105 A1 | 8/2013 |
| WO | 2013/156869 A1 | 10/2013 |
| WO | 2013/158952 A1 | 10/2013 |
| WO | 2013/175281 A1 | 11/2013 |
| WO | 2013/175417 A1 | 11/2013 |

OTHER PUBLICATIONS

Dohrn, M. et al., Berichte der Deutschen Chemischen Gesellschaft [Abteilung] B: Abhandlungen (1931), 64B.

Gein, V. L. et al., "5-Membered 2,3-Dioxoheterocyclic Compounds", Journal of General Chemistry, vol. 63, Issue 10, pp. 2324-2328, 1993.

Gein, V. L. et al., "Reactions of 4-Acyl-1-alkoxyaryl-5-aryl-3-hydroxy-2,5-dihydro-1H-pyrrol-2-ones with Nucleophilic Reagents", Russian Journal of Organic Chemistry, 2011, vol. 47, No. 1, pp. 95-99, Pleiades Publishing, Ltd., 2011.

Westphal, Gunter, "The formation of pyrrolo[3,4-c]pyrazoles", Journal for Practical Chemistry, vol. 311, pp. 379-384, 1969.

Richter, et al., "An Optimised Small-Molecule Stabiliser of the 14-3-3-PMA2 Protein-Protein Interaction", Chem. Eur. J., 2012, pp. 6520-6527, vol. 18, No. 21, Wiley-VCH Verlag GmbH & Co.

Miyazaki, et al., "Lead optimization of novel p53-MDM2 interaction inhibitors possessing dihydroimidazothiazole scaffold", Bioorganic and Medicinal Chemistry Letters, 2013, pp. 728-732, vol. 23, Elsevier Ltd.

Wang, et al., "Benzimidazole-2-one: A novel anchoring principle for antagonizing p53-Mdm2", Bioorganic & Medicinal Chemistry, 2013, pp. 3982-3995, vol. 21, Elsevier Ltd.

Lee, et al., "Novel Pyrrolopyrimidine-Based alpha-Helix Mimetics: Cell Permeable Inhibitors of Protein-Protein Interactions", Journal of the American Chemical Society, 2010, pp. 676-679, vol. 133, American Chemical Society.

Vanotti, et al., "Cdc7 Kinase Inhibitors: Pyrrolopyrimidinones as Potential Antitumor Agents. 1. Synthesis and Structure-Activity Relationships", Journal of Medicinal Chemistry, 2008, pp. 487-501, vol. 51, American Chemical Society.

No Auhtor Listed, WedMD "Leukemia." Available from: <http://www.webmd.com/cancer/tc/leukemia-prevention?print=true#> @2010.

No Author Listed, American Cancer Society. "Leukemia—Acute Myeloid (Myelogenous)." © 2013. Available from: <http://www.cancer.org/cancer/leukemia-acutemyeloidaml/detailedguide/leukemia-acute-myeloid-myelogenous-what-is-aml>.

No Author Listed, Mayo Clinic "Leukemia Medications." Available from: <http://www.drugs.com/condition/leukemia.html> @2013.

No Author Listed, National Cancer Institute. "Drugs Approved for Leukemia." © 2013. Available from: http://www.cancer.gov/cancertopics/druginfo/leukemia/print>.

Sun et al., Single-Nucleotide Polymorphisms in p53 Pathway and Aggressiveness of Prostate Cancer in a Caucasian Population. Clin. Cancer Res. 2010;16:5244-51.

Wade et al., Targeting Mdm2 and Mdmx in Cancer Therapy: Better Living through Medicinal Chemistry? Mol. Cancer Res. 2009;7:1-11.

Chung et al., Fragment-based discovery of bromodomain inhibitors part 1: inhibitor binding modes and implications for lead discovery. J Med Chem. Jan. 26, 2012; 55(2):576-86.

Filippakopoulos et al., Benzodiazepines and benzotriazepines as protein interaction inhibitors targeting bromodomains of the BET family. Bioorg Med Chem. Mar. 15, 2012; 20(6):1878-86.

Filippakopoulos et al., Selective inhibition of BET bromodomains. Nature. Dec. 23, 2010; 468(7327):1067-73.

Hackam et al., Translation of research evidence from animals to humans. JAMA. Oct. 11, 2006; 296(14):1731-2.

Jordan, Tamoxifen: a most unlikely pioneering medicine. Nat Rev Drug Discov. Mar. 2003; 2(3):205-13.

Wu et al., The double bromodomain-containing chromatin adaptor Brd4 and transcriptional regulation. J Biol Chem. May 4, 2007; 282(18):13141-5.

Acharya, B.P. et al., "Friedel-Crafts Acylation with 2-Isocyanatobenzoyl Chlorides: The Structure of the Intermediate Complex," Journal of Chemical Research, Synopses, (4):96-7 (1987)[Abstract only].

Bahloul, A. et al., "1,3-Dipolar Cycloaddition of Diarylnitrilimines with 4-Arylidene-1,2-Diphenyl-1,4-Dihydro-3(2H)soquinolin-3-Ones," Journal de la Societe Marocaine de Chimie, 2(1):12-17 (French)(1993)[Abstract only].

Chen, R. et al., "Ytterbium(III) Triflate-Catalyzed Stereoselective Synthesis of Beta-lactams via [2+2] Cyclocondensation in Ionic Liquid," Synthetic Communications, 36(21):3167-3174, Taylor & Francis Group, LLC (English)(2006).

(56) References Cited

OTHER PUBLICATIONS

De Luca et al., "3D Pharmacophore Models for 1,2,3,4-Tetrahydroisoquinoline Derivatives Acting as Anticonvulsant Agents" Arch. Pharm. Chem. Life Sci., 2006, 339, 388-400.

Dietz, G. et al.; "Synthesis and Conversion of 3,4-Dihydroquinazolin-4-ols. Part 2: Conversion of 3,4-Dihydroquinazolin-4-ols;" Direktionsber. Forsch. Entwickl., VEB Pharm. Komb. Germed Dresden, Dresden, Ger. Dem. Rep.; Pharmazie; 35(12):751-5 (German)(1980)[Abstract only].

Dudkina, Anna S. et al. "Small Molecule Protein—Protein Inhibitors for the p53-MDM2 Interaction", Current Topics in Medicinal Chemistry, 2007, 7, pp. 952-960.

Ishiwaka, N. et al., "o-Aminobenzophenone Derivatives. V. Reactions of 2-Amino-5-Chloro-Benzophenone with Isocyanates and Isothiocyanates," Kagaku Zasshi, 90(9):917-20 (Japanese)(1969)[Abstract only].

Ishiwaka, N. et al., "Reaction of 2-Amino-5-Chlorobenzophenone with P-Substituted Phenyl Isocyanates," Kagaku Zasshi, 91(10):994-7 (Japanese)(1970)[Abstract only].

Ivanov et al., Polyphosphoric acid-induced construction of quinazolinone skeleton from 1-(3,4-dimethoxyphenyl)-3-phenylurea and carboxylic acids. Heterocycles. May 12, 2006; 68(7):1443-9.

Ivanov, I., "Synthesis of 6,7-Dimethoxy-3,4-Diphenyl-2(1H)-Quinazolinone from 1-(3,4-Dimethoxyphenyl)Urea and Benzoic Acid in Polyphosphoric Acid," Molbank M492/1-M492/2 (English)(2006)[Abstract only].

Mollov, N.M. et al., "Internal Alpha-Amidoalkylation Leading to 1,4-Dihydro-3(2H)-Isoquinolinones," Acta Chimica Academiae Scientiarum Hungaricae, 98(3):315-19 (English)(1978).

Mollov, N.M. et al., "Reactivity of Adducts Obtained from Arylacetyl Chloride and Aromatic Schiff Bases," Izvestiya po Khimiya, 10(4):616-20 (English)(1977).

Mollov, N.M. et al., "Synthesis of 3(2H)-isoquinolinones by Means of Inner Alpha-Amidoalkylation," Doklady Bolgarskoi Akademii Nauk, 28(8):1055-7 (English)(1975)[Abstract only].

Mumm, O. et al., "Diacylamides," Berichte der Deutschen Chemischen Gesellschaft, 48:379-91 (1915)[Abstract only].

Pfeiffer, P. et al., "Autoxidation Phenomena in the Anils of the Indandione Series. II," Journal fuer Praktische Chemie (Leipzig), 159:13-35 (1941)[Abstract and Article].

Pfeiffer, P. et al., "Autoxidation Phenomena. VI," Justus Liebigs Annalen der Chemie, 563:73-85 (1949)[Abstract and Article].

Pfeiffer, P. et al., "Autoxidation Reaction. VII," Justus Liebigs Annalen der Chemie, 581:149-59 (1953)[Abstract and Article].

Richter, D., "Anthraquinone Coloring Matters: Ruberythric Acid," Journal of the Chemical Society, 1701-3 (1936).

Richter, P. et al., "Synthesis of Derivatives of 2-Hydrazino-1,4- or 3,4-Dihydroquinazolines," Pharmazie, 45 (10):721-4 (German)(1990)[Abstract only].

Schonberg, A. et al., "Autoxidation Effects in the Indone Series," Naturwissenschaften, 24:620 (1936)[Abstract only].

Schonberg, A. et al., "Autoxidation Phenomena and Valency Tautomerism in the Indone Series," Journal of the Chemical Society, 109-12 (1937).

Shangary, Sanjeev et al., "Targeting the MDM2-p53 Interaction for Cancer Therapy", Clin. Cancer Res., 2008, 14, 5318-5324.

Venkov, A. et al., "An Improved Synthesis of N-Substituted 1-Aryl-3-Oxo-1,2,3,4-Tetrahydroisoquinolines," Synthesis, 216-17, Stuttgart, New York (English)(1982).

Ventsov, A. et al., "Synthesis of N-Substituted 1,4-Dihydro-3(2H)-Isoquinolinones from 3,4,5-Trimethoxyphenylacety chloride and Schiff Bases," Bolgarskoi Akademii Nauk, 34(10):1405-7 (English)(1981)[Abstract only].

Yamamoto, M. et al., "Synthetic Studies on Quinazoline Derivatives. II. The Reactions of 2-Trichloro- and 2-Trifluoroacetamidobenzophenones with Primary Amines," Chemical & Pharmaceutical Bulletin, 29(8):2135-56 (English)(1981).

Zhang, Y. et al., "Superacid-Promoted Reactions of N-Acyliminium Ions: An Effective Route to Substituted 3-Oxo-1,2,3,4-Tetrahydroisoquinolines and Related Products," Synthesis (11):1775-1780 (English)(2006).

Zin'Kovskaya, V.R. et al., "Ring-chain transformations involving the carbonyl group. XVI. Amides of 2-benzoylphenyl-α,α-dimethylacetic acid," Latvijas PSR Zinatnu, Akademijas Vestis, Kimijas Serija, (1)65-8 (Russian)(1976)[Abstract only].

Sheng, R. et al, Pharmacophore model construction of p53-MDM2 binding inhibitors, ACTA Physico-Chimica Sinica, Aug. 6, 2007, vol. 23, No. 11, p. 1815-1820.

Aebi, A. et al, Pharmaceutica Acta Helvetiae, vol. 38, Issue: 7-8, pp. 616-622, Journal, 1963.

Shams El-Dine, S. A et al Pharmazie, vol. 56, Issue: 12, pp. 933-937, Journal, 2001.

Chaudhari, P.V., Oriental Journal of Chemistry (2012), 28(1), 507-512.

Journal of Enzyme Inhibition and Medicinal Chemistry (2011), 26(4), 472-479.

J. D. Akbari et al.: Indian Journal of Chemistry, Section B: Organic Chemistry Including Medicinal Chemistry (2008), 47B(3), 477-480.

Raj et al.: Organic Chemistry: An Indian Journal (2007), 3(4), 176-179.

Ahmed Kamal et al.: Expert opinion on therapeutic patents 2012, vol. 22, No. 2, pp. 95-105, XP055107028.

PYRROLOPYRROLIDINONE COMPOUNDS

BACKGROUND

1. Field of the Invention

The present invention relates to novel pyrrolopyrrolidinone compounds, capable of inhibiting the interaction between p53, or variants thereof, and MDM2 and/or MDM4, or variants thereof, respectively, especially binding to MDM2 and/or MDM4, or variants thereof, a process for the preparation of such compounds, pharmaceutical preparations comprising such compounds, uses and methods of use for such compounds in the treatment (including therapy and/or prophylaxis), and/or related subject matter as specified below. p53 refers to all genes and/or proteins encoded thereof with the names TP53, p53, TP73, p73, TP63, TP73L, p63. MDM2 refers to all genes and/or proteins encoded thereof with the names MDM2, Mdm2, HDM2, Hdm2. MDM4 refers to all genes and/or proteins encoded thereof with the names MDM4, Mdm4, HDM4, Hdm4, MDMX, MdmX, HDMX, HdmX.

2. Background of the Invention

Protein p53 is known as a tumor suppressor protein which helps to control cellular integrity and prevents the proliferation of permanently damaged cells by initiating, among other responses, growth arrest or apoptosis (controlled cell death). p53 mediates its effects in that it is a transcription factor capable of regulating a number of genes that regulate e.g. cell cycle and apoptosis. Thus, p53 is an important cell cycle inhibitor. These activities are tightly controlled by MDM2, an important negative regulator of the p53 tumor supressor. "MDM2" (originally from the oncogene "murine double minute 2") refers both to the name of the gene as well as the protein encoded by that gene. MDM2 protein functions both as an E3 ubiquitin ligase that recognizes the N-terminal transactivation domain (TAD) of the p53 tumor suppressor and thus mediates the ubiquitin-dependent degradation of p53, and as an inhibitor of p53 transcriptional activation.

The original mouse oncogene, which codes for the MDM2 protein, was originally cloned from a transformed mouse cell line. The human homologue of this protein was later identified and is sometimes also called HDM2 (for "human double minute 2"). Further supporting the role of MDM2 as an oncogene, several human tumor and proliferative disease types have been shown to have increased levels of MDM2, including inter alia soft tissue sarcomas, bone cancer, e.g. osteosarcomas, breast tumors, bladder cancer, Li-Fraumeni syndrome, brain tumor, rhabdomyosarcoma and adrenocortical carcinoma and the like. Another protein belonging to the MDM2 family is MDM4, also known as MDMX.

Dysregulation of the MDM2/p53 ratio, e.g. due to mutations, polymorphisms or molecular defects in the affected cells, can thus be found in many proliferative diseases. MDM2, in view of its mentioned effects, is capable to inhibit the activity of the tumor suppressor protein p53, thus leading to loss of p53's tumor suppressor activity and inhibiting regulatory mechanisms that impede cells from uncontrolled proliferation. As a consequence, uncontrolled proliferation can take place, leading to cancers such as tumors, leukemias or other proliferative diseases.

There is a need for new drugs that are capable of interfering with the interaction between p53 and MDM2 or especially oncogenic variants thereof and that thus allow p53 to exert its beneficial effect against uncontrolled tumor growth, allowing it e.g. to accumulate, to arrest the cell cycle and/or to cause apoptosis of affected cells.

It has now been found that a novel class of pyrrolopyrrolidinone compounds shows inhibition of the MDM2/p53 and/or MDM4/p53 interaction (this term including in particular Hdm2/p53 and Hdm4/p53 interaction), and in particular potent inhibition of the MDM2/p53 interaction. The corresponding compounds thus represent a novel type of compound that are useful in the treatment of a number of disorders, such as proliferative diseases, especially cancer. The invention relates therefore to these compounds as drugs as well as to the other inventive embodiments indicated herein.

Particularly interesting compounds of the invention herein are highly potent in the p53-Hdm2 inhibition (TR-FRET) Assay described herein. Compounds of particular interest possess favourable pharmacokinetic properties. They should be non-toxic and demonstrate few side-effects. Furthermore, the ideal drug candidate will exist in a physical form that is stable, non-hygroscopic and easily formulated.

SUMMARY OF THE INVENTION

According to a first aspect of the invention, there is provided a compound of formula (I) or a salt thereof,

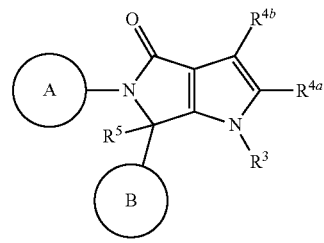

wherein:
A is selected from:

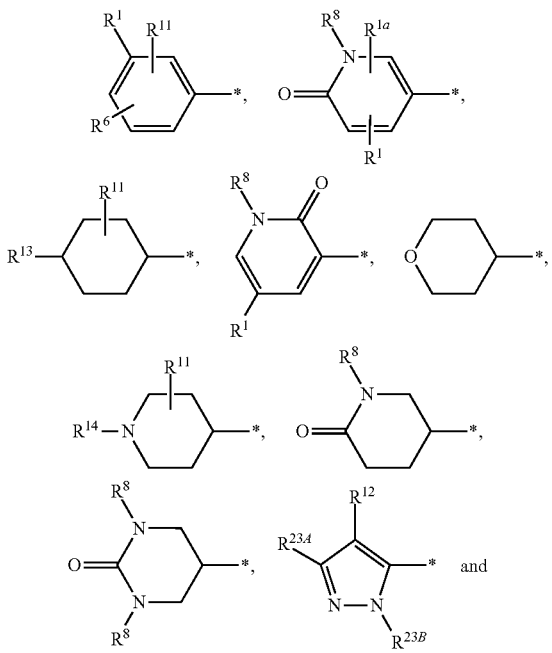

-continued

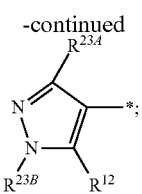

B is selected from:

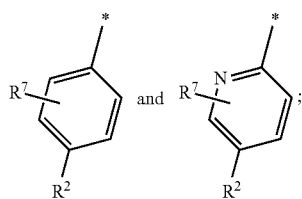

each $R^1$ is independently selected from halo and methyl;
$R^{1a}$ is selected from H, halo and $(C_1-C_4)$alkyl;
$R^2$ is selected from chloro, fluoro, trifluoromethyl, methyl and cyano;
$R^3$ is selected from ethyl, isopropyl, cyclopropyl, isobutyl, cyclobutyl and cyclopentyl, or $R^3$ is:

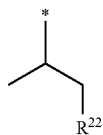

wherein $R^{22}$ is selected from OH, $OCH_3$, $NH_2$, NHMe, $NMe_2$, NHCOMe and NHCOH;
$R^5$ is selected from:
H,
$(C_1-C_4)$alkyl-, said $(C_1-C_4)$alkyl- being optionally substituted with 1 or 2 substituents independently selected from OH and =O,
$(C_1-C_4)$alkyl-O—C(O)—$(CH_2)_m$—, and cyano;
$R^6$ is selected from:
H,
$(C_1-C_4)$alkyl,
$(C_1-C_4)$alkoxy,
halo,
cyano, and
$R^9(R^{19})N$—$(CH_2)_m$—;
$R^7$ is selected from H, halo and $(C_1-C_4)$alkyl;
each $R^8$ is independently selected from H, $(C_1-C_4)$alkyl, —$CHF_2$, hydroxyethyl and methoxyethyl-;
each $R^9$ is independently selected from H, methyl or ethyl;
each $R^{10}$ is independently selected from H, $(C_1-C_4)$alkoxy and $(C_1-C_4)$alkyl wherein said $(C_1-C_4)$alkoxy and $(C_1-C_4)$alkyl are each independently optionally substituted by 1 or 2 substituents independently selected from methoxy, ethoxy, hydroxy, halo and $S(O)_vR^y$;
$R^{11}$ is H, $(C_1-C_4)$alkyl, $(C_1-C_4)$alkoxy or halo;
$R^{12}$ is H or halo;
$R^{13}$ is selected from hydroxy, $(C_1-C_2)$alkoxy, $NH_2$, —C(O)OH, —NH(C(O)—$CH_3$) and —C(O)—NH($CH_3$);
$R^{14}$ is selected from H, —C(O)—$NR^9(R^{10})$, $(C_1-C_4)$alkyl, —C(O)$(C_1-C_4)$alkyl, —C(O)O$(C_1-C_4)$alkyl;
$R^{23A}$ is selected from H, halo and $(C_1-C_4)$alkyl;
$R^{23B}$ is selected from H and $(C_1-C_4)$alkyl;

$R^{4a}$ is selected from:

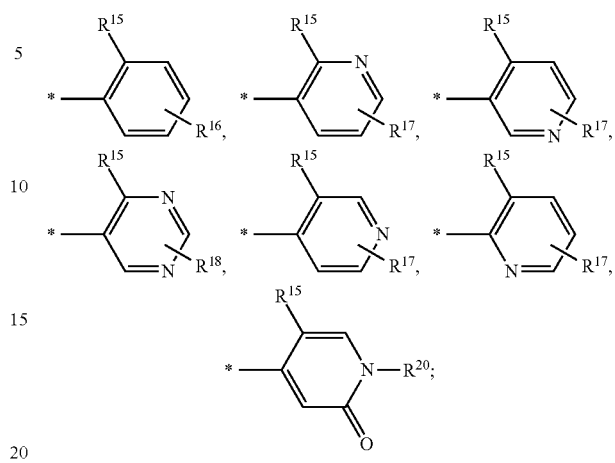

$R^{15}$ is independently selected from $OCH_3$, $OCD_3$, OH, $CH_2CH_3$, $OCF_3$ and H;
$R^{16}$ is selected from H, —$C(O)NR^9R^{10}$, halo, CN, —O—$(C_1-C_4)$alkyl, —C(O)-morpholinyl-4-yl, tetrazolyl, —C(O)OH, —$CH_2C(O)OH$, —$S(O)_vNR^9R^{10}$, —$CH_2C(O)NR^9R^{10}$, $S(O)_vR^y$, $OCF_3$, hydroxy-azetidin-1-yl-carbonyl, —$CH_2NR^9R^{10}$, —$CH_2NR^9$—$C(O)R^{10}$, $CH_2CN$, methyl-imidazolyl-, —$CH_2C(O)O$—$(C_1-C_4)$alkyl, —$N(R^9)$—$C(O)$—$(C_1-C_4)$alkyl, —$NR^9R^{10}$ and $(C_1-C_4)$alkyl, wherein said $(C_1-C_4)$alkyl is optionally substituted by 1 or 2 OH;
$R^{17}$ is selected from H, $O(C_1-C_4)$alkyl, —$CH_2C(O)O$—$(C_1-C_4)$alkyl, —$CH_2C(O)OH$, —$CH_2C(O)NR^9R^{10}$, —$CH_2CN$, —$NR^9R^{10}$, —$C(O)NR^9R^{10}$, —$CH_2NR^9R^{10}$ and —$C(O)O$—$(C_1-C_4)$alkyl;
$R^{18}$ is selected from $O(C_1-C_4)$alkyl, $OCD_3$, H, —$NR^9R^{10}$, $CH_2NR^9R^{10}$ and azetidin-1-yl, said azetidin-1-yl being optionally substituted with OH or both $CH_3$ and OH;
$R^{20}$ is selected from $CH_3$, H and —$CH_2CH_3$;
$R^{4b}$ is selected from H, CN, halo, $(C_1-C_4)$alkyl, —C(O)OH, $CH_2C(O)OH$ and —$C(O)O$—$(C_1-C_4)$alkyl;
$R^y$ is selected from H, $(C_1-C_4)$alkyl and $NR^9R^{10}$;
m is 0, 1 or 2; and
v is 0, 1 or 2.
* indicates the point of attachment to the remainder of the molecule.

Unless specified otherwise, the term "compounds of the present invention" refers to compounds of formula (I) and subformulae thereof (add other additional genus structures as necessary), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

DESCRIPTION OF PREFERRED EMBODIMENTS

Various embodiments of the invention are described herein. It will be recognized that features specified in each embodiment may be combined with other specified features to provide further embodiments. For purposes of interpreting this specification, terms used in the singular will also include the plural and vice versa.

In another embodiment, A is selected from:
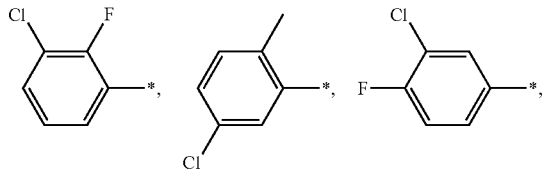
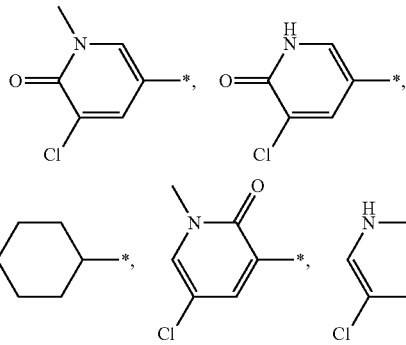
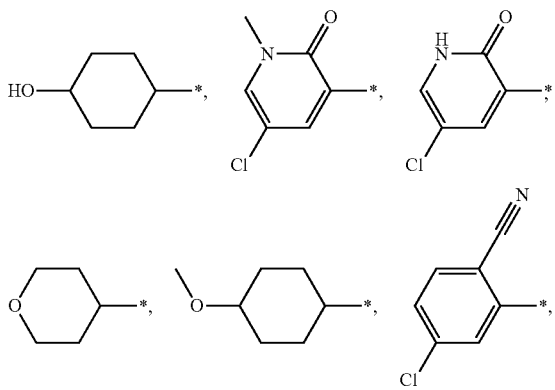
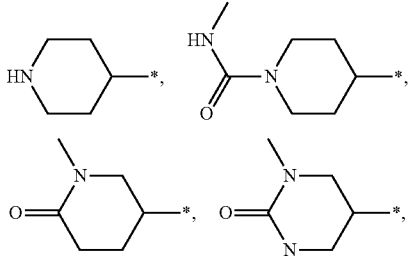
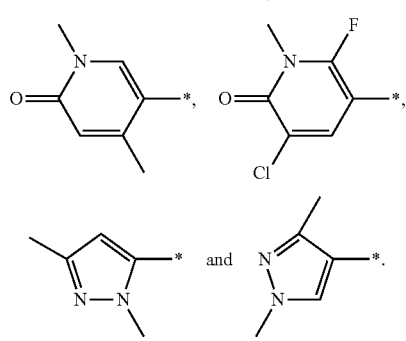
In another embodiment, A is selected from:
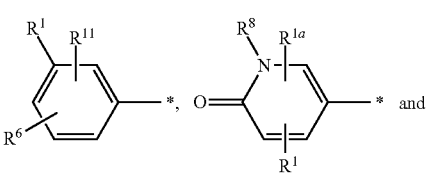
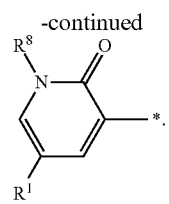
In another embodiment, when A is selected from a group which is or includes
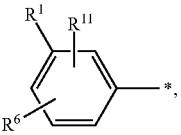
$R^6$ is substituted at the following positions and $R^{11}$ is H
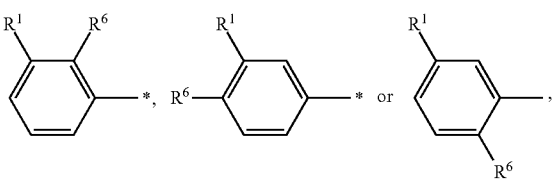
in particular
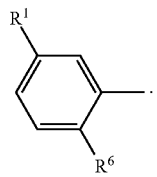
In another embodiment, B is:
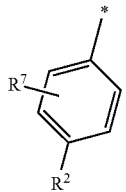
In another embodiment, B is:
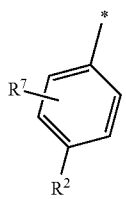
wherein $R^2$ is chloro or cyano.

In a further embodiment, B is selected from:

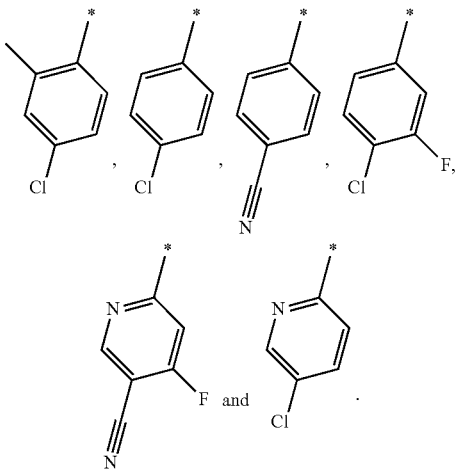

In a still further embodiment, B is selected from:

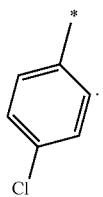

In another embodiment, each $R^1$ is independently selected from chloro and methyl. In a further embodiment, $R^1$ is chloro.

In another embodiment, $R^{1a}$ is selected from H, halo and methyl, in particular H, fluoro and methyl.

In another embodiment, $R^2$ is selected from chloro and cyano.

In another embodiment, $R^3$ is selected from ethyl and isopropyl.

In further embodiment, $R^3$ is isopropyl.

In another embodiment, $R^5$ is selected from:
H, and
$(C_1-C_4)$alkyl-, said $(C_1-C_4)$alkyl- being optionally substituted with 1 or 2 substituents independently selected from OH and $=$O.

In further embodiment, $R^5$ is selected from H and $(C_1-C_2)$ alkyl.

In a still further embodiment, $R^5$ is selected from H and methyl, preferably H.

In another embodiment, $R^6$ is selected from H, halo, $(C_1-C_4)$alkyl and cyano.

In further embodiment, $R^6$ is selected from H, fluoro, methyl and cyano, in particular fluoro and methyl.

In another embodiment, $R^7$ is selected from methyl, H and fluoro.

In another embodiment, each $R^8$ is independently selected from H, methyl, ethyl, hydroxyethyl and methoxyethyl-, in particular H, methyl and ethyl.

In further embodiment, each $R^8$ is independently selected from methyl and H.

In another embodiment, each $R^{10}$ is independently selected from H and $(C_1-C_4)$alkyl, in particular H and methyl.

In another embodiment, $R^{11}$ is H.

In another embodiment, $R^{12}$ is H.

In another embodiment, $R^{13}$ is selected from hydroxy and methoxy.

In another embodiment, $R^{14}$ is selected from H and —C(O)—$NR^9(R^{10})$.

In a further embodiment, $R^{14}$ is selected from H and —C(O)—N(CH_3)H.

In another embodiment, $R^{23A}$ is selected from H, halo and methyl, in particular methyl.

In another embodiment, $R^{23B}$ is selected from H and methyl, in particular methyl.

In a further embodiment, $R^{15}$ is independently selected from $OCH_3$ and OH.

In a further embodiment, $R^{16}$ is selected from H, —C(O)$NR^9R^{10}$, halo, CN, —O—$(C_1-C_4)$alkyl, —C(O)-morpholinyl-4-yl, tetrazolyl, —C(O)OH, —CH_2C(O)OH, —S(O)_v$NR^9R^{10}$, —CH_2C(O)NR^9R^{10}$, S(O)_vR^y$ and $(C_1-C_4)$alkyl, wherein said $(C_1-C_4)$alkyl is optionally substituted by 1 or 2 OH.

In another embodiment, when $R^{4a}$ is selected from a group which is or includes:

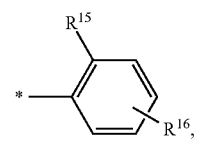

$R^{16}$ is substituted at the following positions:

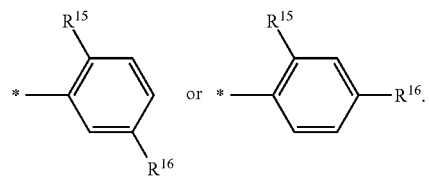

in particular

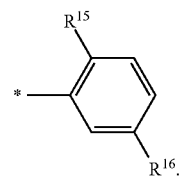

In another embodiment, $R^{17}$ is selected from H, $O(C_1-C_4)$ alkyl, —CH_2C(O)O—$(C_1-C_4)$alkyl, —CH_2C(O)OH, —CH_2C(O)NR^9R^{10}$, —CH_2CN, —NR^9R^{10}$, —C(O)$NR^9R^{10}$, —CH_2NR^9R^{10}$ and —C(O)OCH_3. In a further embodiment, $R^{17}$ is selected from H, $O(C_1-C_4)$alkyl, —CH_2C(O)O—$(C_1-C_4)$alkyl, —CH_2C(O)OH, —CH_2C(O)NR^9R^{10}$ and —CH_2CN.

In another embodiment, when $R^{4a}$ is selected from a group which is or includes:

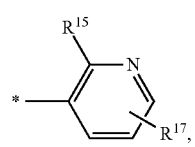

$R^{17}$ is substituted at the following positions:

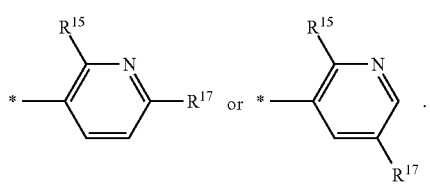

In another embodiment, when $R^{4a}$ is selected from a group which is or includes:

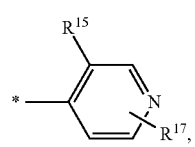

$R^{17}$ is substituted at the following position:

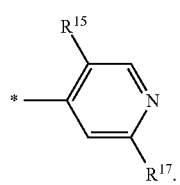

In a further embodiment, $R^{18}$ is selected from $O(C_1-C_4)$ alkyl, H and $-NR^9R^{10}$.

In another embodiment, when $R^{4a}$ is selected from a group which is or includes:

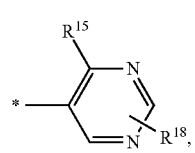

$R^{18}$ is substituted at the following position:

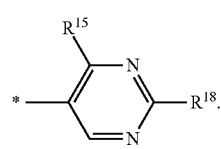

In a further embodiment, $R^{20}$ is $CH_3$.

In another embodiment, $R^{4a}$ is selected from:

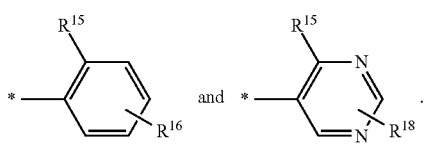

In a further embodiment, $R^{4a}$ is selected from:

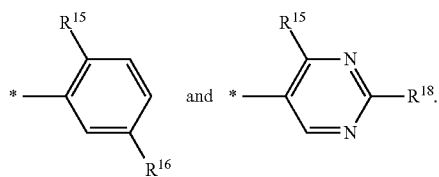

In a still further embodiment, $R^{4a}$ is selected from:

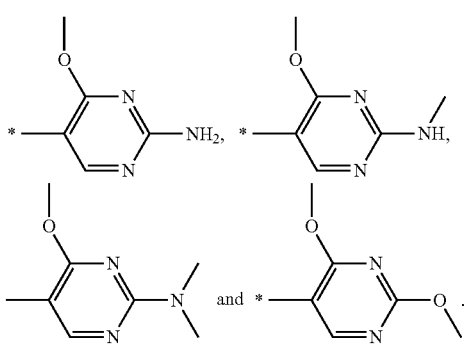

In another embodiment, $R^{4b}$ is selected from H, CN, halo, $(C_1-C_4)$alkyl and $-C(O)OH$.

In a further embodiment, $R^{4b}$ is selected from H, CN, fluoro, methyl and $-C(O)OH$.

In a still further embodiment, $R^{4b}$ is H.

In another embodiment, $R^y$ is selected from methyl, $NH_2$ and $-NH(CH_3)$.

In another embodiment, v is 2.

In another embodiment, m is 0 or 1.

In another embodiment, the compound of formula (I) has the stereochemistry shown in formula (IA):

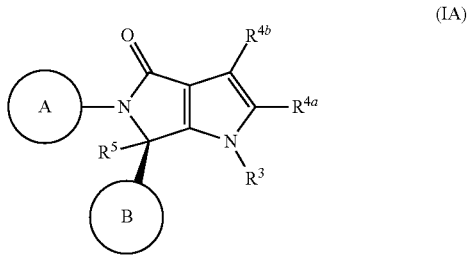

In a preferred embodiment, the compound of formula (I) has the stereochemistry shown in formula (IB):

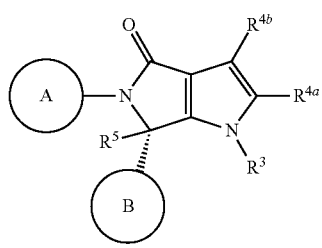

(IB)

In another embodiment there is provided a compound of formula (I), (IA) or (IB) wherein:

A is selected from:

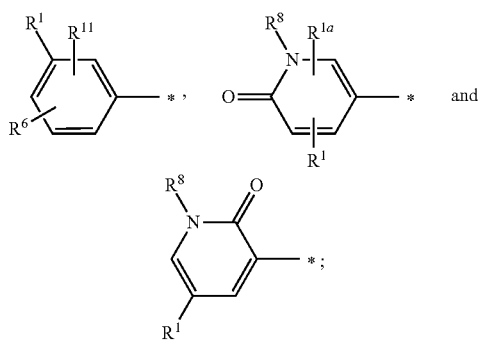

B is:

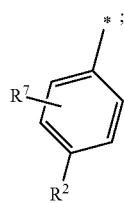

$R^5$ is H;
$R^3$ is isopropyl;
$R^{4a}$ is selected from:

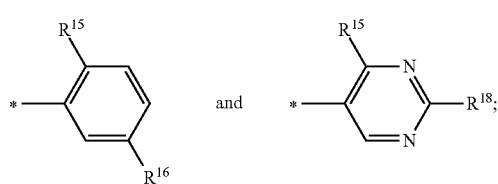

$R^{4b}$ is H;
$R^1$ is chloro or methyl;
$R^6$ is selected from H, fluoro, methyl and cyano;
$R^{11}$ is H;
$R^8$ is selected from H, methyl and ethyl;
$R^{1a}$ is selected from H, fluoro and methyl;
$R^7$ is selected from methyl, H and fluoro;
$R^2$ is selected from chloro and cyano;
$R^{15}$ is selected from $OCH_3$ and OH;
$R^{16}$ is selected from H, —C(O)$NR^9R^{10}$, halo, CN, —O—($C_1$-$C_4$)alkyl, —C(O)-morpholinyl-4-yl, tetrazolyl, —C(O)OH, —$CH_2$C(O)OH, —S(O)$_v NR^9R^{10}$, —$CH_2$C(O)$NR^9R^{10}$, S(O)$_v R^y$ and ($C_1$-$C_4$)alkyl, wherein said ($C_1$-$C_4$) alkyl is optionally substituted by 1 or 2 OH;

$R^{18}$ is selected from O($C_1$-$C_4$)alkyl, H and —$NR^9R^{10}$;

$R^9$ is independently selected from H, methyl or ethyl;

$R^{10}$ is independently selected from H and ($C_1$-$C_4$)alkyl, in particular H and methyl;

$R^y$ is selected from methyl, $NH_2$ and —NH($CH_3$); and v is 2.

Described below are a number of embodiments (E) of the first aspect of the invention, where for convenience E1 is identical thereto.

E1 A compound of formula (I) as defined above, or a salt thereof.

E2 A compound of formula (I) or a salt thereof, according to E1, wherein A is selected from:

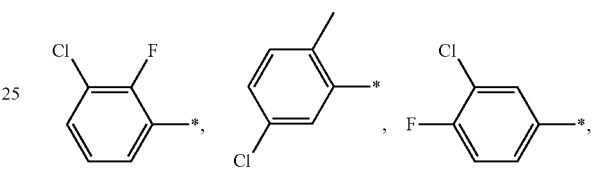

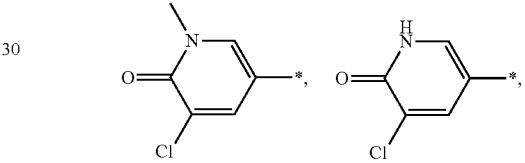

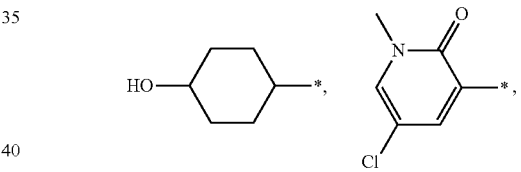

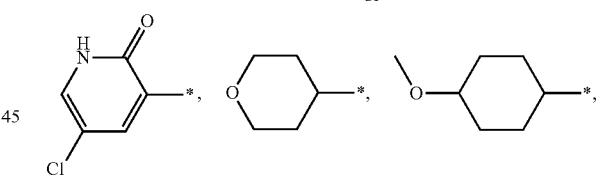

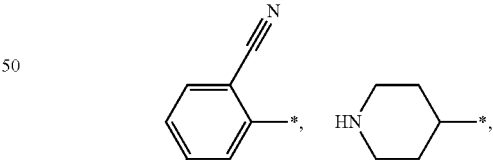

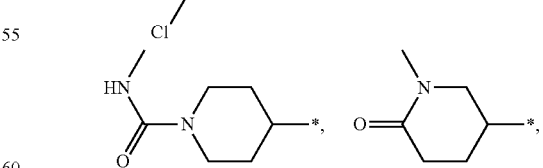

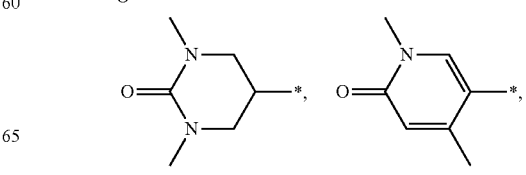

-continued

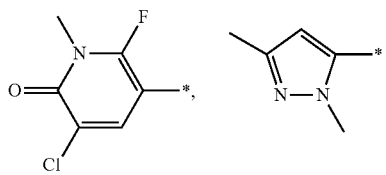 and

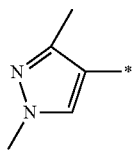

E3 A compound of formula (I) or a salt thereof, according to E1, wherein A is selected from:

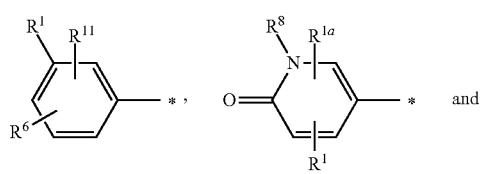 and

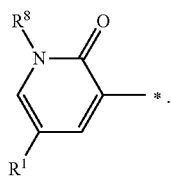

E4 A compound of formula (I) or a salt thereof according to E1 or E3, wherein when A is selected from a group which is or includes

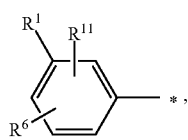

$R^6$ is substituted at the following positions and $R^{11}$ is H

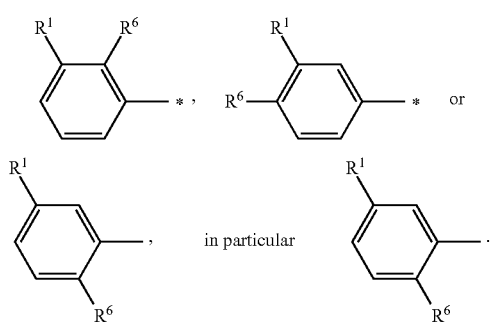 in particular

E5 A compound of formula (I) or a salt thereof, according to any of E1 to E4, wherein B is:

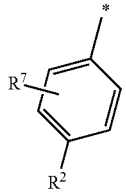

E6 A compound of formula (I) or a salt thereof, according to any of E1 to E5, wherein B is:

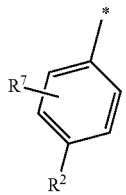

wherein $R^2$ is chloro or cyano.

E7 A compound of formula (I) or a salt thereof, according to any of E1 to E4, wherein B is selected from:

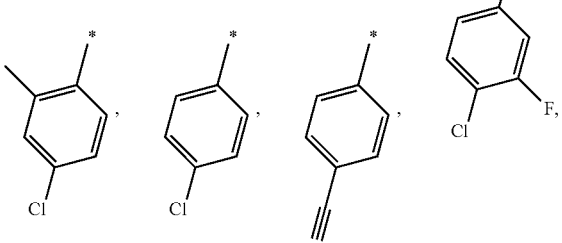

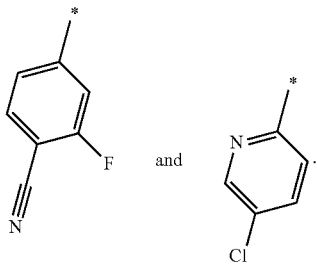 and

E8 A compound of formula (I) or a salt thereof, according to any of E1 to E7, wherein B is selected from:

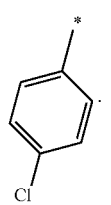

E9 A compound of formula (I) or a salt thereof, according to any of E1 or E3 to E8, wherein each $R^1$ is independently selected from chloro and methyl.

E10 A compound of formula (I) or a salt thereof, according to any of E1 or E3 to E9, wherein $R^1$ is chloro.

E11 A compound of formula (I) or a salt thereof, according to any of E1, E3 or E5 to E10, wherein $R^{1a}$ is selected from H, halo and methyl, in particular H, fluoro and methyl.

E12 A compound of formula (I) or a salt thereof, according to any of E1 to E6 or E9 to E11, wherein $R^2$ is selected from chloro and cyano.

E13 A compound of formula (I) or a salt thereof, according to any of E1 to E12, wherein $R^3$ is selected from ethyl and isopropyl.

E14 A compound of formula (I) or a salt thereof, according to any of E1 to E13, wherein $R^3$ is isopropyl.

E15 A compound of formula (I) or a salt thereof, according to any of E1 to E14, wherein $R^5$ is selected from:

H, and $(C_1$-$C_4)$alkyl-, said $(C_1$-$C_4)$alkyl- being optionally substituted with 1 or 2 substituents independently selected from OH and =O.

E16 A compound of formula (I) or a salt thereof, according to any of E1 to E15, wherein $R^5$ is selected from H and $(C_1$-$C_2)$alkyl.

E17 A compound of formula (I) or a salt thereof, according to any of E1 to E16, wherein $R^5$ is selected from H and methyl, preferably H.

E18 A compound of formula (I) or a salt thereof, according to any of E1, E3 to E10 or E12 to E17, wherein $R^6$ is selected from H, halo, $(C_1$-$C_4)$alkyl and cyano.

E19 A compound of formula (I) or a salt thereof, according to any of E1, E3 to E10 or E12 to E18, wherein $R^6$ is selected from H, fluoro, methyl and cyano, in particular fluoro and methyl.

E20 A compound of formula (I) or a salt thereof, according to any of E1 to E6 or E9 to E19, wherein $R^7$ is selected from methyl, H and fluoro.

E21 A compound of formula (I) or a salt thereof, according to any of E1, E3, E5 to E17 or E20, wherein each $R^8$ is independently selected from H, methyl, ethyl, hydroxyethyl and methoxyethyl-, in particular H, methyl and ethyl.

E22 A compound of formula (I) or a salt thereof, according to any of E1, E3, E5 to E17, E20 or E21, wherein each $R^8$ is independently selected from methyl and H.

E23 A compound of formula (I) or a salt thereof, according to any of E1 to E22, wherein each $R^{10}$ is independently selected from H and $(C_1$-$C_4)$alkyl, in particular H and methyl.

E24 A compound of formula (I) or a salt thereof, according to any of E1, E3 to E10, E12 to E20, or E23, $R^{11}$ is H.

E25 A compound of formula (I) or a salt thereof, according to any of E1, E5 to E8, E12 to E17, E20 or E23, wherein $R^{12}$ is H.

E26 A compound of formula (I) or a salt thereof, according to any of E1, E5 to E8, E12 to E17, E20, E23 or E24, wherein $R^{13}$ is selected from hydroxy and methoxy.

E27 A compound of formula (I) or a salt thereof, according to any of E1, E5 to E8, E12 to E17, E20, E23 or E24, wherein $R^{14}$ is selected from H and —C(O)—NR$^9$(R$^{10}$).

E28 A compound of formula (I) or a salt thereof, according to any of E1, E5 to E8, E12 to E17, E20, E23, E24 or E27 wherein $R^{14}$ is selected from H and —C(O)—N(CH$_3$)H.

E29 A compound of formula (I) or a salt thereof, according to any of E1, E5 to E8, E12 to E17, E20 or E23, wherein $R^{23A}$ is selected from H, halo and methyl, in particular methyl.

E30 A compound of formula (I) or a salt thereof, according to any of E1, E5 to E8, E12 to E17, E20 or E23, wherein $R^{23B}$ is selected from H and methyl, in particular methyl.

E31 A compound of formula (I) or a salt thereof, according to any of E1 to E30, wherein $R^{15}$ is independently selected from OCH$_3$ and OH.

E32 A compound of formula (I) or a salt thereof, according to any of E1 to E31, wherein $R^{16}$ is selected from H, —C(O)NR$^9$R$^{10}$, halo, CN, —O—(C$_1$-C$_4$)alkyl, —C(O)-morpholinyl-4-yl, tetrazolyl, —C(O)OH, —CH$_2$C(O)OH, —S(O)$_x$NR$^9$R$^{10}$, —CH$_2$C(O)NR$^9$R$^{10}$, S(O)$_x$R$^y$ and (C$_1$-C$_4$)alkyl, wherein said (C$_1$-C$_4$)alkyl is optionally substituted by 1 or 2 OH.

E33 A compound of formula (I) or a salt thereof, according to any of E1 to E32, wherein when $R^{4a}$ is selected from a group which is or includes:

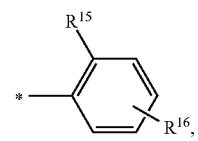

$R^{16}$ is substituted at the following positions:

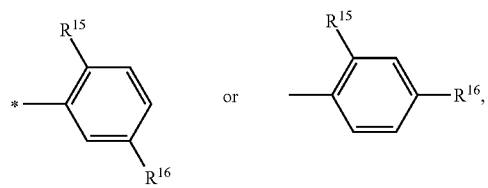

in particular

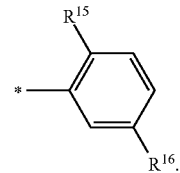

E34 A compound of formula (I) or a salt thereof, according to any of E1 to E31, wherein $R^{17}$ is selected from H, O(C$_1$-C$_4$)alkyl, —CH$_2$C(O)O—(C$_1$-C$_4$)alkyl, —CH$_2$C(O)OH, —CH$_2$C(O)NR$^9$R$^{10}$, —CH$_2$CN, —NR$^9$R$^{10}$, —C(O)NR$^9$R$^{10}$, —CH$_2$NR$^9$R$^{10}$ and —C(O)OCH$_3$, in particular, H, O(C$_1$-C$_4$)alkyl, —CH$_2$C(O)O—(C$_1$-C$_4$)alkyl, —CH$_2$C(O)OH, —CH$_2$C(O)NR$^9$R$^{10}$ and —CH$_2$CN.

E35 A compound of formula (I) or a salt thereof, according to any of E1 to E31 or E34, wherein when $R^{4a}$ is selected from a group which is or includes:

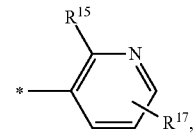

$R^{17}$ is substituted at the following positions:

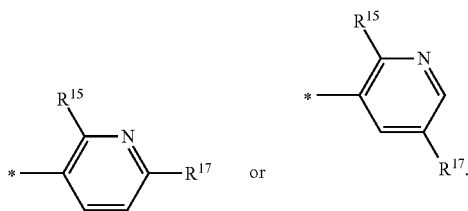

E36 A compound of formula (I) or a salt thereof, according to any of E1 to E31 or E34, wherein when $R^{4a}$ is selected from a group which is or includes:

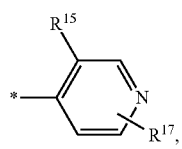

$R^{17}$ is substituted at the following position:

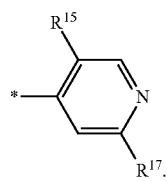

E37 A compound of formula (I) or a salt thereof, according to any of E1 to E31, wherein $R^{18}$ is selected from $O(C_1\text{-}C_4)$ alkyl, H and $-NR^9R^{10}$.

E38 A compound of formula (I) or a salt thereof, according to any of E1 to E31 or E37, wherein when $R^{4a}$ is selected from a group which is or includes:

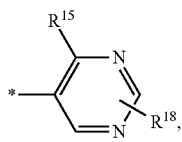

$R^{18}$ is substituted at the following position:

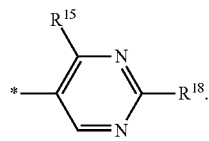

E39 A compound of formula (I) or a salt thereof, according to any of E1 to E31, wherein $R^{20}$ is $CH_3$.

E40 A compound of formula (I) or a salt thereof, according to any of E1 to E31, wherein $R^{4a}$ is selected from:

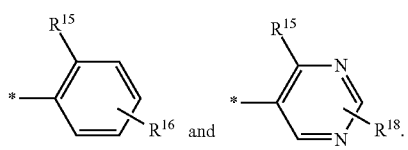

E41 A compound of formula (I) or a salt thereof, according to any of E1 to E31, wherein $R^{4a}$ is selected from:

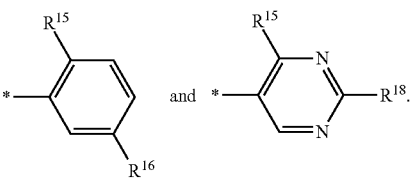

E42 A compound of formula (I) or a salt thereof, according to any of E1 to E31, E37, E38, E40 or E41, wherein $R^{4a}$ is selected from

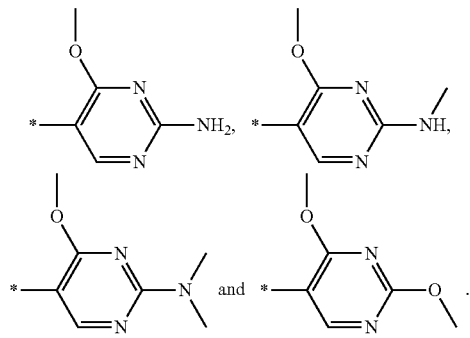

E43 A compound of formula (I) or a salt thereof, according to any of E1 to E42, wherein $R^{ob}$ is selected from H, CN, halo, $(C_1\text{-}C_4)$alkyl and $-C(O)OH$, preferably H, CN, fluoro, methyl and $-C(O)OH$, in particular H.

E44 A compound of formula (I) or a salt thereof, according to any of E1 to E43, wherein the compound of formula (I) has the stereochemistry shown in formula (IA):

(IA)

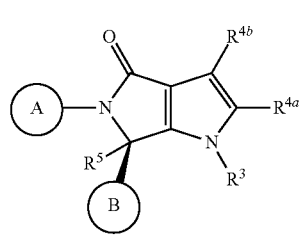

E45 A compound of formula (I) or a salt thereof, according to any of E1 to E43, wherein the compound of formula (I) has the stereochemistry shown in formula (IB):

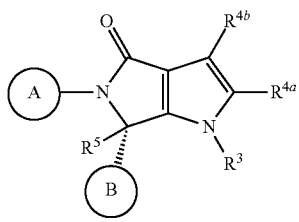
(IB)

In another embodiment, the invention provides a compound or a salt thereof, selected from:

1: 5-(3-Chloro-2-fluoro-phenyl)-6-(4-chloro-2-methyl-phenyl)-1-isopropyl-2-(2-methoxy-phenyl)-5,6-dihydro-1H-pyrrolo[3,4-b]pyrrol-4-one
2: 3-[5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide
3: 5-(3-Chloro-2-fluoro-phenyl)-6-(4-chloro-2-methyl-phenyl)-2-(5-fluoro-2-methoxy-phenyl)-1-isopropyl-5,6-dihydro-1H-pyrrolo[3,4-b]pyrrol-4-one
4: 5-(3-Chloro-2-fluoro-phenyl)-6-(4-chloro-2-methyl-phenyl)-2-(5-hydroxymethyl-2-methoxy-phenyl)-1-isopropyl-5,6-dihydro-1H-pyrrolo[3,4-b]pyrrol-4-one
5: 5-(3-Chloro-2-fluoro-phenyl)-6-(4-chloro-2-methyl-phenyl)-1-isopropyl-2-(2-methoxy-pyridin-3-yl)-5,6-dihydro-1H-pyrrolo[3,4-b]pyrrol-4-one
6: 5-(3-Chloro-2-fluoro-phenyl)-6-(4-chloro-2-methyl-phenyl)-1-isopropyl-2-(4-methoxy-pyridin-3-yl)-5,6-dihydro-1H-pyrrolo[3,4-b]pyrrol-4-one
7: 3-[(S)-5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide
8: 3-[(R)-5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide
9: 5-(5-Chloro-2-methyl-phenyl)-6-(4-chloro-phenyl)-1-isopropyl-2-(2-methoxy-phenyl)-5,6-dihydro-1H-pyrrolo[3,4-b]pyrrol-4-one
10: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide
11: 5-(5-Chloro-2-methyl-phenyl)-6-(4-chloro-phenyl)-2-(5-hydroxymethyl-2-methoxy-phenyl)-1-isopropyl-5,6-dihydro-1H-pyrrolo[3,4-b]pyrrol-4-one
12: 5-(5-Chloro-2-methyl-phenyl)-6-(4-chloro-phenyl)-1-isopropyl-2-(2-methoxy-pyridin-3-yl)-5,6-dihydro-1H-pyrrolo[3,4-b]pyrrol-4-one
13: 5-(5-Chloro-2-methyl-phenyl)-6-(4-chloro-phenyl)-1-isopropyl-2-(4-methoxy-pyridin-3-yl)-5,6-dihydro-1H-pyrrolo[3,4-b]pyrrol-4-one
14: 5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one
15: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide
16: 5-(5-Chloro-2-methyl-phenyl)-6-(4-chloro-phenyl)-1-isopropyl-2-(4-methoxy-pyrimidin-5-yl)-5,6-dihydro-1H-pyrrolo[3,4-b]pyrrol-4-one
17: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzonitrile
18: 3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide
19: 3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide
20: 3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide
21: 3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide
22: 5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-b]pyrrol-4-one
23: (S)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one
24: (R)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one
25: 2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-b]pyrrol-4-one
26: 5-(5-Chloro-2-methyl-phenyl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one
27: 5-(5-Chloro-2-methyl-phenyl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one
28: 5-(5-Chloro-2-methyl-phenyl)-6-(4-chloro-phenyl)-1-isopropyl-2-[2-methoxy-5-(morpholine-4-carbonyl)-phenyl]-5,6-dihydro-1H-pyrrolo[3,4-b]pyrrol-4-one
29: 5-(5-Chloro-2-methyl-phenyl)-6-(4-chloro-phenyl)-2-(2-hydroxy-phenyl)-1-isopropyl-5,6-dihydro-1H-pyrrolo[3,4-b]pyrrol-4-one
30: 5-(5-Chloro-2-methyl-phenyl)-6-(4-chloro-2-methyl-phenyl)-1-isopropyl-2-(2-methoxy-phenyl)-5,6-dihydro-1H-pyrrolo[3,4-b]pyrrol-4-one
31: 3-[5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide
32: 3-[(S)-5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide
33: 3-[(R)-5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide
34: 5-(5-Chloro-2-methyl-phenyl)-6-(4-chloro-phenyl)-1-isopropyl-2-[2-methoxy-5-(1H-tetrazol-5-yl)-phenyl]-5,6-dihydro-1H-pyrrolo[3,4-b]pyrrol-4-one
35: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid
36: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-N-(2-methanesulfonyl-ethyl)-4-methoxy-benzamide
37: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-N-(2-hydroxy-ethoxy)-4-methoxy-benzamide
38: 5-(5-Chloro-2-methyl-phenyl)-6-(4-chloro-phenyl)-2-(2,4-dimethoxy-phenyl)-1-isopropyl-5,6-dihydro-1H-pyrrolo[3,4-b]pyrrol-4-one
39: 4-[2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile 40: 4-[5-(3-Chloro-4-fluoro-phenyl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 41: 4-[2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile 42: 4-[5-(3-Chloro-2-fluoro-phenyl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 43: 4-[2-(2-Amino-4-methoxy-pyrimidin-5-yl)-5-(5-chloro-2-methyl-phenyl)-1-isopropyl-4-oxo-1,4,5,6-tetrahydro-pyrrolo[3,4-b]pyrrol-6-yl]-benzonitrile 44: 4-[5-(5-Chloro-2-methyl-phenyl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 45: 5-(5-Chloro-2-methyl-phenyl)-6-(4-chloro-phenyl)-2-(2,4-dimethoxy-pyrimidin-5-yl)-1-ethyl-5,6-dihydro-1H-pyrrolo[3,4-b]pyrrol-4-one 46: 5-(5-Chloro-1-methyl-6-oxo-1,6-dihydro-pyridin-3-yl)-6-(4-chloro-phenyl)-1-isopropyl-2-(2-methoxy-phenyl)-5,6-dihydro-1H-pyrrolo[3,4-b]pyrrol-4-one 47: 5-(5-Chloro-1-methyl-6-oxo-1,6-dihydro-pyridin-3-yl)-6-(4-chloro-phenyl)-1-isopropyl-2-[2-methoxy-5-(morpholine-4-carbonyl)-phenyl]-5,6-dihydro-1H-pyrrolo[3,4-B]pyrrol-4-one 48: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 49: 3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrol-2-yl]-4-methoxy-N-methyl-benzamide 50: 3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4S-b]pyrrol-2-yl]-4-methoxy-benzoic acid 51: 2-(2-Amino-4-methoxy-pyrimidin-5-yl)-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one 52: 5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 53: 3-[5-(3-Chloro-4-fluoro-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide 54: 5-(3-Chloro-4-fluoro-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one 55: 5-(3-Chloro-4-fluoro-phenyl)-6-(4-chloro-phenyl)-1-isopropyl-2-[2-methoxy-5-(morpholine-4-carbonyl)-phenyl]-5,6-dihydro-1H-pyrrolo[3,4-b]pyrrol-4-one 56: 3-[5-(3-Chloro-4-fluoro-phenyl)-6-(4-chloro-phenyl)-1-isopropyl-4-oxo-1,4,5,6-tetrahydro-pyrrolo[3,4-b]pyrrol-2-yl]-4-methoxy-benzoic acid 57: 2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-b]pyrrol-4-one 58: 5-(3-Chloro-4-fluoro-phenyl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 59: 5-(5-Chloro-2-methyl-phenyl)-6-(4-chloro-phenyl)-1-isopropyl-2-(2-methoxy-phenyl)-4-oxo-1,4,5,6-tetrahydro-pyrrolo[3,4-b]pyrrole-3-carbonitrile 60: {3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid 61: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzamide 62: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzenesulfonamide 63: 6-(4-Chloro-phenyl)-5-(trans-4-hydroxy-cyclohexyl)-1-isopropyl-2-(2-methoxy-phenyl)-5,6-dihydro-1H-pyrrolo[3,4-b]pyrrol-4-one 64: 3-[6-(4-Chloro-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-N-methyl-benzamide 65: 3-[6-(4-Chloro-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-benzoic acid 66: 6-(4-Chloro-phenyl)-2-(2,4-dimethoxy-pyrimidin-5-yl)-5-(trans-4-hydroxy-cyclohexyl)-1-isopropyl-5,6-dihydro-1H-pyrrolo[3,4-b]pyrrol-4-one 67: 3-[6-(4-Chloro-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-benzonitrile 68: 2-(2-Amino-4-methoxy-pyrimidin-5-yl)-6-(4-chloro-phenyl)-5-(trans-4-hydroxy-cyclohexyl)-1-isopropyl-5,6-dihydro-1H-pyrrolo[3,4-b]pyrrol-4-one 69: 6-(4-Chloro-phenyl)-2-(2-dimethylamino-4-methoxy-pyrimidin-5-yl)-5-(trans-4-hydroxy-cyclohexyl)-1-isopropyl-5,6-dihydro-1H-pyrrolo[3,4-b]pyrrol-4-one 70: 5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 71: 2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-b]pyrrol-4-one 72: 5-(5-Chloro-1-methyl-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one 73: 5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 74: 6-(4-Chloro-phenyl)-1-isopropyl-2-(2-methoxy-phenyl)-5-(tetrahydro-pyran-4-yl)-5,6-dihydro-1H-pyrrolo[3,4-b]pyrrol-4-one 75: 3-[6-(4-Chloro-phenyl)-1-isopropyl-4-oxo-5-(tetrahydro-pyran-4-yl)-1,4,5,6-tetrahydro-pyrrolo[3,4-b]pyrrol-2-yl]-4-methoxy-N-methyl-benzamide 76: 6-(4-Chloro-phenyl)-2-(2,4-dimethoxy-pyrimidin-5-yl)-1-isopropyl-5-(tetrahydro-pyran-4-yl)-5,6-dihydro-1H-pyrrolo[3,4-b]pyrrol-4-one 77: 3-[6-(4-Chloro-phenyl)-1-isopropyl-4-oxo-5-(tetrahydro-pyran-4-yl)-1,4,5,6-tetrahydro-pyrrolo[3,4-b]pyrrol-2-yl]-4-methoxy-benzonitrile 78: 2-(2-Amino-4-methoxy-pyrimidin-5-yl)-6-(4-chloro-phenyl)-1-isopropyl-5-(tetrahydro-pyran-4-yl)-5,6-dihydro-1H-pyrrolo[3,4-b]pyrrol-4-one 79: 6-(4-Chloro-phenyl)-2-(2-dimethylamino-4-methoxy-pyrimidin-5-yl)-1-isopropyl-5-(tetrahydro-pyran-4-yl)-5,6-dihydro-1H-pyrrolo[3,4-b]pyrrol-4-one 80: 2-{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetamide 81: 2-{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-N-methyl-acetamide
82: 2-{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-N,N-dimethyl-acetamide
83: {5-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-acetic acid ethyl ester
84: {4-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-acetic acid
85: 2-{5-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-N-methyl-acetamide
86: 2-{4-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-N-methyl-acetamide
87: 4-[5-(3-Chloro-2-fluoro-phenyl)-2-(2-cyanomethyl-5-methoxy-pyridin-4-yl)-1-isopropyl-4-oxo-1,4,5,6-tetrahydro-pyrrolo[3,4-b]pyrrol-6-yl]benzonitrile
88: 4-[5-(3-Chloro-2-fluoro-phenyl)-2-(5-cyanomethyl-2-methoxy-pyridin-3-yl)-1-isopropyl-4-oxo-1,4,5,6-tetrahydro-pyrrolo[3,4-b]pyrrol-6-yl]-benzonitrile
89: 3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid
90: 3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid
91: {3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid
92: {3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid
93: 4-[5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile
94: 4-[5-(3-Chloro-2-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile
95: 4-[5-(5-Chloro-2-methyl-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile
96: 4-Chloro-2-[6-(4-chloro-phenyl)-1-isopropyl-2-(2-methoxy-phenyl)-4-oxo-4,6-dihydro-1H-pyrrolo[3,4-b]pyrrol-5-yl]-benzonitrile
97: 3-[5-(5-Chloro-2-cyano-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide
98: 4-Chloro-2-[6-(4-chloro-phenyl)-2-(2,4-dimethoxy-pyrimidin-5-yl)-1-isopropyl-4-oxo-4,6-dihydro-1H-pyrrolo[3,4-b]pyrrol-5-yl]-benzonitrile
99: 2-[2-(2-Amino-4-methoxy-pyrimidin-5-yl)-6-(4-chloro-phenyl)-1-isopropyl-4-oxo-4,6-dihydro-1H-pyrrolo[3,4-b]pyrrol-5-yl]-4-chloro-benzonitrile
100: 4-Chloro-2-[6-(4-chloro-phenyl)-2-(2-dimethylamino-4-methoxy-pyrimidin-5-yl)-1-isopropyl-4-oxo-4,6-dihydro-1H-pyrrolo[3,4-b]pyrrol-5-yl]-benzonitrile
101: 6-(4-Chloro-2-methyl-phenyl)-5-(trans-4-hydroxy-cyclohexyl)-1-isopropyl-2-(2-methoxy-phenyl)-5,6-dihydro-1H-pyrrolo[3,4-b]pyrrol-4-one
102: 3-[6-(4-Chloro-2-methyl-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-N-methyl-benzamide
103: 6-(4-Chloro-2-methyl-phenyl)-2-(2,4-dimethoxy-pyrimidin-5-yl)-5-(trans-4-hydroxy-cyclohexyl)-1-isopropyl-5,6-dihydro-1H-pyrrolo[3,4-b]pyrrol-4-one
104: 6-(4-Chloro-2-methyl-phenyl)-1-isopropyl-2-(2-methoxy-phenyl)-5-(tetrahydro-pyran-4-yl)-5,6-dihydro-1H-pyrrolo[3,4-b]pyrrol-4-one
105: 6-(4-Chloro-2-methyl-phenyl)-2-(2,4-dimethoxy-pyrimidin-5-yl)-1-isopropyl-5-(tetrahydro-pyran-4-yl)-5,6-dihydro-1H-pyrrolo[3,4-b]pyrrol-4-one
106: 6-(4-Chloro-phenyl)-2-(2,4-dimethoxy-pyrimidin-5-yl)-1-isopropyl-5-piperidin-4-yl-5,6-dihydro-1H-pyrrolo[3,4-b]pyrrol-4-one
107: 4-[6-(4-Chloro-phenyl)-2-(2,4-dimethoxy-pyrimidin-5-yl)-1-isopropyl-4-oxo-4,6-dihydro-1H-pyrrolo[3,4-b]pyrrol-5-yl]-piperidine-1-carboxylic acid methylamide
108: 2-(2-Amino-4-methoxy-pyrimidin-5-yl)-6-(4-chloro-phenyl)-1-isopropyl-5-(1-methyl-6-oxo-piperidin-3-yl)-5,6-dihydro-1H-pyrrolo[3,4-b]pyrrol-4-one
109: 6-(4-Chloro-phenyl)-2-(2,4-dimethoxy-pyrimidin-5-yl)-1-isopropyl-5-(1-methyl-6-oxo-piperidin-3-yl)-5,6-dihydro-1H-pyrrolo[3,4-b]pyrrol-4-one
110: 6-(4-Chloro-phenyl)-2-(2,4-dimethoxy-pyrimidin-5-yl)-5-(1,3-dimethyl-2-oxo-hexahydro-pyrimidin-5-yl)-1-isopropyl-5,6-dihydro-1H-pyrrolo[3,4-b]pyrrol-4-one
111: 6-(4-Chloro-phenyl)-2-(2,4-dimethoxy-pyrimidin-5-yl)-5-(1,4-dimethyl-6-oxo-1,6-dihydro-pyridin-3-yl)-1-isopropyl-5,6-dihydro-1H-pyrrolo[3,4-b]pyrrol-4-one
112: 6-(4-Chloro-phenyl)-2-(2-dimethylamino-4-methoxy-pyrimidin-5-yl)-5-(1,4-dimethyl-6-oxo-1,6-dihydro-pyridin-3-yl)-1-isopropyl-5,6-dihydro-1H-pyrrolo[3,4-b]pyrrol-4-one
113: 5-(5-Chloro-2-methyl-phenyl)-6-(4-chloro-phenyl)-1-isopropyl-2-(3-methoxy-pyridin-2-yl)-5,6-dihydro-1H-pyrrolo[3,4-b]pyrrol-4-one
114: 5-(5-Chloro-2-methyl-phenyl)-6-(4-chloro-phenyl)-1-isopropyl-2-(5-methanesulfonyl-2-methoxy-phenyl)-5,6-dihydro-1H-pyrrolo[3,4-b]pyrrol-4-one
115: 5-(5-Chloro-2-methyl-phenyl)-6-(4-chloro-phenyl)-3-fluoro-1-isopropyl-2-(2-methoxy-phenyl)-5,6-dihydro-1H-pyrrolo[3,4-b]pyrrol-4-one
116: 5-(5-Chloro-2-methyl-phenyl)-6-(4-chloro-phenyl)-1-isopropyl-2-(2-methoxy-phenyl)-6-methyl-5,6-dihydro-1H-pyrrolo[3,4-b]pyrrol-4-one
117: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one
118: {3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid
119: 5-(5-Chloro-1-methyl-6-oxo-1,6-dihydro-pyridin-3-yl)-6-(4-chloro-phenyl)-1-isopropyl-2-(5-methanesulfonyl-2-methoxy-phenyl)-5,6-dihydro-1H-pyrrolo[3,4-b]pyrrol-4-one
120: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carbonitrile
121: (S)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 122: (R)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 123: 5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 124: 5-(5-Chloro-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one 125: 4-[2-(2-Amino-4-methoxy-pyrimidin-5-yl)-5-(5-chloro-2-oxo-1,2-dihydro-pyridin-3-yl)-1-isopropyl-4-oxo-1,4,5,6-tetrahydro-pyrrolo[3,4-b]pyrrol-6-yl]-benzonitrile 126: 4-[5-(5-Chloro-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 127: 4-[5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 128: 4-[5-(5-Chloro-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 129: 4-[2-(2-Amino-4-methoxy-pyrimidin-5-yl)-5-(5-chloro-1-methyl-2-oxo-1,2-dihydro-pyridin-3-yl)-1-isopropyl-4-oxo-1,4,5,6-tetrahydro-pyrrolo[3,4-b]pyrrol-6-yl]-benzonitrile 130: 4-[5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 131: 4-[5-(5-Chloro-1-methyl-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 132: 4-[5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 133: 4-[5-(5-Chloro-1-methyl-6-oxo-1,6-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 134: 4-[2-(2-Amino-4-methoxy-pyrimidin-5-yl)-5-(5-chloro-6-oxo-1,6-dihydro-pyridin-3-yl)-1-isopropyl-4-oxo-1,4,5,6-tetrahydro-pyrrolo[3,4-b]pyrrol-6-yl]-benzonitrile 135: 4-[5-(5-Chloro-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 136: 4-[5-(5-Chloro-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 137: 4-[5-(5-Chloro-6-oxo-1,6-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 138: 2-(2-Amino-4-methoxy-pyrimidin-5-yl)-5-(5-chloro-6-oxo-1,6-dihydro-pyridin-3-yl)-6-(4-chloro-phenyl)-1-isopropyl-5,6-dihydro-1H-pyrrolo[3,4-b]pyrrol-4-one 139: 5-(5-Chloro-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 140: 5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 141: 2-(2-Amino-4-methoxy-pyrimidin-5-yl)-6-(4-chloro-phenyl)-1-isopropyl-5-(trans-4-methoxy-cyclohexyl)-5,6-dihydro-1H-pyrrolo[3,4-b]pyrrol-4-one 142: 6-(4-Chloro-phenyl)-2-(2-dimethylamino-4-methoxy-pyrimidin-5-yl)-1-isopropyl-5-(trans-4-methoxy-cyclohexyl)-5,6-dihydro-1H-pyrrolo[3,4-b]pyrrol-4-one 143: 6-(4-Chloro-phenyl)-2-(2,4-dimethoxy-pyrimidin-5-yl)-1-isopropyl-5-(trans-4-methoxy-cyclohexyl)-5,6-dihydro-1H-pyrrolo[3,4-b]pyrrol-4-one 144: 5-(5-Chloro-1-methyl-6-oxo-1,6-dihydro-pyridin-3-yl)-6-(4-chloro-2-methyl-phenyl)-1-isopropyl-2-(2-methoxy-phenyl)-5,6-dihydro-1H-pyrrolo[3,4-b]pyrrol-4-one 145: 3-[5-(5-Chloro-1-methyl-6-oxo-1,6-dihydro-pyridin-3-yl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide 146: 5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one 147: 5-(5-Chloro-1-methyl-6-oxo-1,6-dihydro-pyridin-3-yl)-6-(4-chloro-2-methyl-phenyl)-2-(2-dimethylamino-4-methoxy-pyrimidin-5-yl)-1-isopropyl-5,6-dihydro-1H-pyrrolo[3,4-b]pyrrol-4-one 148: 2-(2-Amino-4-methoxy-pyrimidin-5-yl)-5-(5-chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one 149: 5-(5-Chloro-2-methyl-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-b]pyrrol-4-one 150: 5-(5-Chloro-1-methyl-6-oxo-1,6-dihydro-pyridin-3-yl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-b]pyrrol-4-one 151: 5-(5-Chloro-1-methyl-6-oxo-1,6-dihydro-pyridin-3-yl)-6-(4-chloro-2-methyl-phenyl)-1-isopropyl-2-(4-methoxy-2-methylamino-pyrimidin-5-yl)-5,6-dihydro-1H-pyrrolo[3,4-b]pyrrol-4-one 152: 5-(5-Chloro-6-oxo-1,6-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one 153: 4-[5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 154: 4-[(S)-2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile 155: 4-[(R)-2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile 156: 5-(5-Chloro-2-fluoro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 157: 4-[2-(2,4-Dimethoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile 158: 4-[2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile 159: 6-(4-Chloro-phenyl)-2-(2-dimethylamino-4-methoxy-pyrimidin-5-yl)-5-(1,3-dimethyl-2-oxo-hexahydro-pyrimidin-5-yl)-1-isopropyl-5,6-dihydro-1H-pyrrolo[3,4-b]pyrrol-4-one 160: (S)-5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one 161: (R)-5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one 162: (S)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one 163: (R)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one 164: 5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-4-oxo-1,4,5,6-tetrahydro-pyrrolo[3,4-b]pyrrole-3-carbonitrile 165: 4-[(S)-5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 166: 4-[(R)-5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 167: 4-[(S)-5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 168: 4-[(R)-5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 169: 4-[(S)-5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 170: 4-[(R)-5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 171: 4-[(S)-2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile 172: 4-[(R)-2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile 173: 4-[2-(2,4-Dimethoxy-pyrimidin-5-yl)-5-(trans-4-hydroxy-cyclohexyl)-1-isopropyl-4-oxo-1,4,5,6-tetrahydro-pyrrolo[3,4-b]pyrrol-6-yl]-benzonitrile 174: 4-[2-(2-Dimethylamino-4-methoxy-pyrimidin-5-yl)-5-(trans-4-hydroxy-cyclohexyl)-1-isopropyl-4-oxo-1,4,5,6-tetrahydro-pyrrolo[3,4-b]pyrrol-6-yl]-benzonitrile 175: 2-(2-Amino-4-methoxy-pyrimidin-5-yl)-6-(4-chloro-phenyl)-5-(2,5-dimethyl-2H-pyrazol-3-yl)-1-isopropyl-5,6-dihydro-1H-pyrrolo[3,4-b]pyrrol-4-one 176: 6-(4-Chloro-phenyl)-2-(2,4-dimethoxy-pyrimidin-5-yl)-5-(2,5-dimethyl-2H-pyrazol-3-yl)-1-isopropyl-5,6-dihydro-1H-pyrrolo[3,4-b]pyrrol-4-one 177: 6-(4-Chloro-phenyl)-2-(2-dimethylamino-4-methoxy-pyrimidin-5-yl)-5-(2,5-dimethyl-2H-pyrazol-3-yl)-1-isopropyl-5,6-dihydro-1H-pyrrolo[3,4-b]pyrrol-4-one 178: 6-(4-Chloro-phenyl)-5-(2,5-dimethyl-2H-pyrazol-3-yl)-1-isopropyl-2-(5-methoxy-1-methyl-2-oxo-1,2-dihydro-pyridin-4-yl)-5,6-dihydro-1H-pyrrolo[3,4-b]pyrrol-4-one 179: 4-[2-(2,4-Dimethoxy-pyrimidin-5-yl)-5-(2,5-dimethyl-2H-pyrazol-3-yl)-1-isopropyl-4-oxo-1,4,5,6-tetrahydro-pyrrolo[3,4-b]pyrrol-6-yl]-benzonitrile 180: 4-[2-(2-Dimethylamino-4-methoxy-pyrimidin-5-yl)-5-(2,5-dimethyl-2H-pyrazol-3-yl)-1-isopropyl-4-oxo-1,4,5,6-tetrahydro-pyrrolo[3,4-b]pyrrol-6-yl]-benzonitrile 181: 6-(4-Chloro-phenyl)-2-(2,4-dimethoxy-pyrimidin-5-yl)-5-(1,3-dimethyl-1H-pyrazol-4-yl)-1-isopropyl-5,6-dihydro-1H-pyrrolo[3,4-b]pyrrol-4-one 182: 6-(4-Chloro-phenyl)-2-(2-dimethylamino-4-methoxy-pyrimidin-5-yl)-5-(1,3-dimethyl-1H-pyrazol-4-yl)-1-isopropyl-5,6-dihydro-1H-pyrrolo[3,4-b]pyrrol-4-one 183: 6-(4-Chloro-phenyl)-5-(1,3-dimethyl-1H-pyrazol-4-yl)-1-isopropyl-2-(5-methanesulfonyl-2-methoxy-phenyl)-5,6-dihydro-1H-pyrrolo[3,4-b]pyrrol-4-one 184: 6-(4-Chloro-phenyl)-5-(1,3-dimethyl-1H-pyrazol-4-yl)-1-isopropyl-2-(5-methoxy-1-methyl-2-oxo-1,2-dihydro-pyridin-4-yl)-5,6-dihydro-1H-pyrrolo[3,4-b]pyrrol-4-one 185: 4-[5-(5-Chloro-1-methyl-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 186: 4-[(S)-5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 187: 4-[(R)-5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 188: (S)-5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 189: (R)-5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 190: 4-[(S)-2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile 191: 4-[(R)-2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile 192: 6-(4-Chloro-3-fluoro-phenyl)-5-(5-chloro-1-methyl-6-oxo-1,6-dihydro-pyridin-3-yl)-2-(2,4-dimethoxy-pyrimidin-5-yl)-1-isopropyl-5,6-dihydro-1H-pyrrolo[3,4-b]pyrrol-4-one 193: 6-(4-Chloro-3-fluoro-phenyl)-5-(5-chloro-1-methyl-6-oxo-1,6-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 194: 4-[5-(5-Chloro-1-methyl-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-2-fluoro-benzonitrile 195: 4-[5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile 196: 6-(4-Chloro-3-fluoro-phenyl)-5-(5-chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-b]pyrrol-4-one 197: 6-(4-Chloro-3-fluoro-phenyl)-5-(5-chloro-1-methyl-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 198: 4-[5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile 199: 4-[5-(5-Chloro-1-methyl-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-2-fluoro-benzonitrile 200: 4-[5-(5-Chloro-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile 201: 4-[5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-2-fluoro-benzonitrile 202: 6-(4-Chloro-3-fluoro-phenyl)-5-(5-chloro-2-oxo-1,2-dihydro-pyridin-3-yl)-2-(2,4-dimethoxy-pyrimidin-5-yl)-1-isopropyl-5,6-dihydro-1H-pyrrolo[3,4-b]pyrrol-4-one 203: 6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 204: 5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 205: 5-(5-Chloro-2-methoxy-pyridin-3-yl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-b]pyrrol-4-one 206: 2-(2-Amino-4-methoxy-pyrimidin-5-yl)-5-(5-chloro-2-methoxy-pyridin-3-yl)-6-(4-chloro-phenyl)-1-isopropyl-5,6-dihydro-1H-pyrrolo[3,4-b]pyrrol-4-one 207: 4-[5-(5-Chloro-2-methoxy-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 208: 6-(4-Chloro-phenyl)-5-(4-fluoro-2,5-dimethyl-2H-pyrazol-3-yl)-1-isopropyl-2-(5-methoxy-1-methyl-2-oxo-1,2-dihydro-pyridin-4-yl)-5,6-dihydro-1H-pyrrolo[3,4-b]pyrrol-4-one 209: 6-(4-Chloro-phenyl)-2-(2-dimethylamino-4-methoxy-pyrimidin-5-yl)-5-(4-fluoro-2,5-dimethyl-2H-pyrazol-3-yl)-1-isopropyl-5,6-dihydro-1H-pyrrolo[3,4-b]pyrrol-4-one 210: 2-(2-Amino-4-methoxy-pyrimidin-5-yl)-6-(4-chloro-phenyl)-5-(4-fluoro-2,5-dimethyl-2H-pyrazol-3-yl)-1-isopropyl-5,6-dihydro-1H-pyrrolo[3,4-b]pyrrol-4-one 211: 4-[2-(2,4-Dimethoxy-pyrimidin-5-yl)-5-(4-fluoro-2,5-dimethyl-2H-pyrazol-3-yl)-1-isopropyl-4-oxo-1,4,5,6-tetrahydro-pyrrolo[3,4-b]pyrrol-6-yl]-benzonitrile 212: 6-(4-Chloro-2-fluoro-phenyl)-2-(2-dimethylamino-4-methoxy-pyrimidin-5-yl)-5-(2,5-dimethyl-2H-pyrazol-3-yl)-1-isopropyl-5,6-dihydro-1H-pyrrolo[3,4-b]pyrrol-4-one 213: 5-(5-Chloro-1-methyl-2-oxo-1,2-dihydro-pyridin-3-yl)-6-(5-chloro-pyridin-2-yl)-2-(2,4-dimethoxy-pyrimidin-5-yl)-1-isopropyl-5,6-dihydro-1H-pyrrolo[3,4-b]pyrrol-4-one 214: 5-(3-Chloro-4-fluoro-phenyl)-6-(5-chloro-pyridin-2-yl)-2-(2,4-dimethoxy-pyrimidin-5-yl)-1-isopropyl-5,6-dihydro-1H-pyrrolo[3,4-b]pyrrol-4-one 215: 4-[(S)-5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 216: 4-[(R)-5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 217: 5-(5-Chloro-1-methyl-6-oxo-1,6-dihydro-pyridin-3-yl)-6-(4-chloro-phenyl)-2-(2,4-$d_6$-dimethoxy-pyrimidin-5-yl)-1-isopropyl-5,6-dihydro-1H-pyrrolo[3,4-b]pyrrol-4-one 218: (S)-5-(5-Chloro-1-methyl-6-oxo-1,6-dihydro-pyridin-3-yl)-6-(4-chloro-phenyl)-2-(2,4-$d_6$-dimethoxy-pyrimidin-5-yl)-1-isopropyl-5,6-dihydro-1H-pyrrolo[3,4-b]pyrrol-4-one 219: (R)-5-(5-Chloro-1-methyl-6-oxo-1,6-dihydro-pyridin-3-yl)-6-(4-chloro-phenyl)-2-(2,4-$d_6$-dimethoxy-pyrimidin-5-yl)-1-isopropyl-5,6-dihydro-1H-pyrrolo[3,4-b]pyrrol-4-one 220: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carboxylic acid ethyl ester 221: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carboxylic acid 222: 4-[(R,S)-5-(3-Chloro-4-fluoro-phenyl)-2-(2,4-dimethoxy-pyrimidin-5-yl)-1-((R)-2-methoxy-1-methyl-ethyl)-4-oxo-1,4,5,6-tetrahydro-pyrrolo[3,4-b]pyrrol-6-yl]-benzonitrile 223: 4-[(R,S)-2-(2-Amino-4-methoxy-pyrimidin-5-yl)-5-(3-chloro-4-fluoro-phenyl)-1-((R)-2-methoxy-1-methyl-ethyl)-4-oxo-1,4,5,6-tetrahydro-pyrrolo[3,4-b]pyrrol-6-yl]-benzonitrile 224: (R,S)-2-(2-Amino-4-methoxy-pyrimidin-5-yl)-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one 225: (R,S)-5-(5-Chloro-1-methyl-6-oxo-1,6-dihydro-pyridin-3-yl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-b]pyrrol-4-one 226: 5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-4-oxo-1,4,5,6-tetrahydro-pyrrolo[3,4-b]pyrrole-3-carboxylic acid 227: (S)-6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 228: (R)-6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 229: (S)-2-(2-Amino-4-methoxy-pyrimidin-5-yl)-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one 230: (R)-2-(2-Amino-4-methoxy-pyrimidin-5-yl)-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one 231: 4-(2-(2-(Dimethylamino)-4-methoxypyrimidin-5-yl)-5-(4-fluoro-1,3-dimethyl-1H-pyrazol-5-yl)-1-isopropyl-4-oxo-1,4,5,6-tetrahydropyrrolo[3,4-b]pyrrol-6-yl)benzonitrile 232: (S)-4-(5-(5-Chloro-1-methyl-6-oxo-1,6-dihydropyridin-3-yl)-2-(2-(dimethylamino)-4-methoxypyrimidin-5-yl)-1-isopropyl-4-oxo-1,4,5,6-tetrahydropyrrolo[3,4-b]pyrrol-6-yl)benzonitrile 233: (R)-4-(5-(5-Chloro-1-methyl-6-oxo-1,6-dihydropyridin-3-yl)-2-(2-(dimethylamino)-4-methoxypyrimidin-5-yl)-1-isopropyl-4-oxo-1,4,5,6-tetrahydropyrrolo[3,4-b]pyrrol-6-yl)benzonitrile 234: 5-(3-Chloro-2-fluorophenyl)-6-(5-chloropyridin-2-yl)-2-(2-(dimethylamino)-4-methoxypyrimidin-5-yl)-1-isopropyl-5,6-dihydropyrrolo[3,4-b]pyrrol-4(1H)-one 235: 5-(5-Chloro-2-methylphenyl)-6-(5-chloropyridin-2-yl)-2-(2,4-dimethoxypyrimidin-5-yl)-1-isopropyl-5,6-dihydropyrrolo[3,4-b]pyrrol-4(1H)-one 236: 4-(5-(5-Chloro-1-methyl-6-oxo-1,6-dihydropyridin-3-yl)-1-isopropyl-2-(4-methoxypyrimidin-5-yl)-4-oxo-1,4,5,6-tetrahydropyrrolo[3,4-b]pyrrol-6-yl)benzonitrile 237: (S)-4-(5-(5-Chloro-1-methyl-6-oxo-1,6-dihydropyridin-3-yl)-2-(2,4-dimethoxypyrimidin-5-yl)-1-isopropyl-4-oxo-1,4,5,6-tetrahydropyrrolo[3,4-b]pyrrol-6-yl)-2-fluorobenzonitrile 238: (R)-4-(5-(5-Chloro-1-methyl-6-oxo-1,6-dihydropyridin-3-yl)-2-(2,4-dimethoxypyrimidin-5-yl)-1-isopropyl-4-oxo-1,4,5,6-tetrahydropyrrolo[3,4-b]pyrrol-6-yl)-2-fluorobenzonitrile 239: 6-(4-Chlorophenyl)-2-(2,4-dimethoxypyrimidin-5-yl)-5-(1,5-dimethyl-2-oxo-1,2-dihydropyridin-3-yl)-1-isopropyl-5,6-dihydropyrrolo[3,4-b]pyrrol-4(1H)-one 240: 6-(4-Chlorophenyl)-1-cyclopropyl-2-(2,4-dimethoxypyrimidin-5-yl)-5-(1,5-dimethyl-6-oxo-1,6-dihydropyridin-3-yl)-5,6-dihydropyrrolo[3,4-b]pyrrol-4(1H)-one 241: 6-(4-Chlorophenyl)-1-cyclopropyl-5-(1,5-dimethyl-6-oxo-1,6-dihydropyridin-3-yl)-2-(2-methoxypyrimidin-5-yl)-5,6-dihydropyrrolo[3,4-b]pyrrol-4(1H)-one 242: 6-(4-Chlorophenyl)-1-cyclopropyl-5-(1,5-dimethyl-6-oxo-1,6-dihydropyridin-3-yl)-2-(1-methyl-2-oxo-1,2-dihydropyridin-4-yl)-5,6-dihydropyrrolo[3,4-b]pyrrol-4(1H)-one 243: 5-(5-Chloro-1-methyl-6-oxo-1,6-dihydropyridin-3-yl)-6-(4-chlorophenyl)-1-cyclopropyl-2-(1-methyl-2-oxo-1,2-dihydropyridin-4-yl)-5,6-dihydropyrrolo[3,4-b]pyrrol-4(1H)-one 244: 5-(5-Chloro-1-methyl-6-oxo-1,6-dihydropyridin-3-yl)-6-(4-chlorophenyl)-1-cyclopropyl-2-(2,4-dimethoxypyrimidin-5-yl)-5,6-dihydropyrrolo[3,4-b]pyrrol-4(1H)-one 245: 5-(5-Chloro-1-methyl-6-oxo-1,6-dihydropyridin-3-yl)-6-(4-chlorophenyl)-1-cyclopropyl-2-(2-methoxypyrimidin-5-yl)-5,6-dihydropyrrolo[3,4-b]pyrrol-4(1H)-one In the above definitions, halo means fluoro, chloro or bromo, particularly fluoro or chloro.

Alkyl, and alkoxy groups, containing the requisite number of carbon atoms, can be unbranched or branched. Examples of alkyl include, but are not limited to, methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

'=O' means an oxo substituent.

Specific preferred compounds according to the invention are those listed in the Examples section below.

Where there is more than one R group of the same type in the compound of formula (I), each may be selected independently of the other; they need not be the same group or atom.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn- Ingold- Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

p53 refers to the human protein itself as described by Matlashewski et al. in EMBO J. 3, 3257-62 (1984) or related family members (e.g. p73 as described in Kaghad et al. in Cell 90, 809-19 (1997) and p63 as described in Yang et al in Mol Cell 2, 305-16 (1998)) (named also p53 wild type herein) or to any variant thereof (e.g. a splice variant, mutant, fragment or isoform due to deletion, insertion and/or exchange of one or more, e.g. one to 200, of the amino acids) that is still capable to retain preferably at least 1%, more preferably at least 5%, yet more preferably at least 10%, 20%, 30%, 40%, 50% or more than 50% of the p53 activity in growth suppression, e.g. in the growth suppression assay described in Pietenpol et al., Proc. Nat. Acad. Sci. USA 91, 1998-2002 (1994) and, if compared with the corresponding sequence of p53 wild type, shows at least 20%, more preferably at least 25% identity with the full sequence, e.g. at least 90% identity with a partial sequence thereof. Where not mentioned otherwise, p53 generally relates to TP53, p53, TP73, p73, TP63, TP73L, p63, or variants thereof, respectively, as just defined.

As already indicated above, MDM2 (especially when mentioned as MDM2 or variants thereof) generally refers to all genes and/or proteins encoded thereof with the names MDM2, Mdm2, HDM2, Hdm2, or a variant thereof. MDM4 (especially when mentioned as MDM4 or variants thereof) refers to all genes and/or proteins encoded thereof with the names MDM4, Mdm4, HDM4, Hdm4, MDMX, MdmX, HDMX, HdmX, or a variant thereof.

MDM2 specifically relates to MDM2 as described in EMBO J. 10, 1565-9, Fakharzadeh et al., 1991, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

MDM4 specifically relates to MDM4 as described in Genomics 43, 34-42, Shvarts et al., 1997, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM4 to p53, and have at least 20%, more preferably at least 25%, sequence identity to MDM4, to MDMX, to HDM4 or to HDM2 as originally described or as mentioned below specifically. Where not mentioned otherwise, MDM4 generally relates to MDM4, Mdm4, HDM4, Hdm4, MDMX, MdmX, HDMX or HdmX, or variants thereof, respectively, as just defined.

The percentage of sequence identity, often also termed homology, between a protein and a variant thereof is preferably determined by a computer program commonly employed for this purpose, such as the Gap program (Wisconsin Sequence Analysis Package, Version 8 for Unix, Genetics Computer Group, University Reseach Park, Madison Wis., USA, which uses the algorithm of Smith and Waterman (Adv. Appl. Math. 2: 482-489 (1981)., especially using an affine gap search with a gap open penalty of 12 and a gap extension penalty of 1.

"Variants thereof" where mentioned means one or more variant(s).

A proto-oncogene is a normal gene that can become an oncogene, either after mutation or increased expression. Proto-oncogenes code for proteins that help to regulate cell growth and differentiation. Proto-oncogenes are often involved in signal transduction and execution of mitogenic signals, usually through their protein products. Upon activation, a proto-oncogene (or its product) becomes a tumor inducing agent, an oncogene.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by MDM2 and/or MDM4, or (ii) associated with MDM2 and/or MDM4 activity, or (iii) characterized by activity (normal or abnormal) of MDM2 and/or MDM4, or (2) reducing or inhibiting the activity of MDM2 and/or MDM4, or (3) reducing or inhibiting the expression of MDM2 and/or MDM4. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of MDM2 and/or MDM4; or at least partially reducing or inhibiting the expression of MDM2 and/or MDM4.

In a further embodiment, the compounds of formula (I) are particularly useful for the treatment of disorders of diseases associated with the activity of MDM2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the present invention, including salts, hydrates and solvates thereof, may inherently or by design form polymorphs.

In another aspect, the present invention provides a pharmaceutical composition comprising compound of formula (I) or salt thereof as defined herein, and one or more pharmaceutically acceptable carriers. In another aspect, the present invention provides a pharmaceutical composition comprising a therapeutically effective amount of a compound of formula (I) or salt thereof as defined herein, and one or more pharmaceutically acceptable carriers.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc. Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compounds of formula I in free form or in salt form exhibit valuable pharmacological properties, e.g. MDM2 and/or MDM4 modulating properties, e.g. as indicated in tests as provided in the next sections, and are therefore indicated for therapy.

Having regard to their inhibitory effect on p53/MDM2 and/or p53/MDM4 interaction, compounds of the formula (I) in free or pharmaceutically acceptable salt form, are useful in the treatment of conditions which are mediated by the activity (including normal activity or especially overactivity) of MDM2 and/or MDM4, or variants thereof, respectively, as described, such as proliferative and/or inflammatory conditions, e.g. by activation of the P53/MDM2 interaction, and/or that are responsive (meaning especially in a therapeutically beneficial way) to inhibition of the p53/MDM2 interaction, most especially a disease or disorder as mentioned herein below.

Compounds of the invention are believed to be useful in the treatment of a disease based on dysregulation of cell cycle, such as a proliferative disorder or disease, for example cancer or tumour diseases. In particular, such diseases or disorders include benign or malignant tumors, a soft tissue sarcoma or a sarcoma such as liposarcoma, rhabdomyosarcoma or bone cancer, e.g. osteosarcomas, a carcinoma, such as of the brain, kidney, liver, adrenal gland, bladder, breast, gastric, ovary, colon, rectum, prostate, pancreas, lung, vagina or thyroid, a glioblastoma, meningioma, glioma, mesothelioma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia such as acute myeloid leukemia or B-cell chronic lymphocytic leukemia, a lymphoma, such as of B- or T-cell origin, and metastases in other organs), viral infections (e.g. herpes, papilloma, HIV, Kaposi's, viral hepatitis).

Compounds of the invention are also believed to be useful in the treatment of or a disorder or disease involving the immune system, in particular autoimmune diseases or immune diseases resulting due to transplantation (such as rheumatoid arthritis, graft-versus-host disease, systemic lupus erythematosus, Sjögren's syndrome, multiple sclerosis, Hashimoto's thyreoiditis, polymyositis), chronic inflammatory conditions, such as asthma, osteoarthritis, atherosclerosis, Morbus Crohn or inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, pemphigus, epidermolysis bullosa acquisita, or other inflammatory or allergic conditions of the skin or hyperproliferative disorders, (e.g. Li-Fraumeni syndrome).

In another embodiment there is provided a compound of the formula (I) or salt thereof as defined herein, for use as a pharmaceutical.

A further embodiment provides a compound of the formula (I) or salt thereof as defined herein, for use in the treatment of a disorder or a disease mediated by the activity of MDM2 and/or MDM4.

A still further embodiment provides the use of a compound of formula (I) or salt thereof as defined herein, for the manufacture of a medicament for the treatment of a disorder or a disease in a subject mediated by the activity of MDM2 and/or MDM4.

As a further embodiment, the present invention provides the use of a compound of formula (I) in therapy. In a further embodiment, the therapy is selected from a disease which may be treated by inhibition of the MDM2/p53 and/or MDM4/p53 interaction, in particular the diseases or disorders listed herein.

In another embodiment, the invention provides a method of treating a disease or disorder which is treated by inhibition of the MDM2/p53 and/or MDM4/p53 interaction, comprising administration of a therapeutically acceptable amount of a compound of formula (I) or salt thereof, in particular a method of treating the diseases or disorders listed herein.

In another embodiment, the invention provides a method for the treatment of a disorder or a disease mediated by the activity of MDM2 and/or MDM4, comprising the step of administering to a subject a therapeutically acceptable amount of a compound of formula (I) or salt thereof as defined herein, in particular a method of treating the diseases or disorders listed herein.

A further embodiment provides a method of modulating MDM2 and/or MDM4 activity in a subject, comprising the step of administering to a subject a therapeutically effective amount of a compound of formula (I) or salt thereof as defined herein.

The compounds of the formula (I) have advantageous pharmacological properties and disturb the binding interaction (also referred to herein as p53/MDM2 and p53/MDM4 interaction or as p53/MDM2 interaction solely) between p53 on the one side and MDM2 and/or MDM4 or (especially oncogenic) variants thereof which still are capable of binding to p53, on the other side.

The invention also relates to the use of a compound of the formula (I) (or a pharmaceutical formulation comprising a compound of the formula (I)) in the treatment of one or more of the diseases mentioned above and below where the disease(s) respond or responds (in a beneficial way, e.g. by partial or complete removal of one or more of its symptoms up to complete cure or remission) to an inhibition of the MDM2/p53 and/or MDM4/p53 interaction, especially where the involved MDM2 or MDM4 and/or variant shows (e.g. in the context of other regulatory mechanisms, due to overexpression, to mutation or the like) inadequately high or more higher than normal activity.

The invention can also relate to the use of a compound of the formula (I) to induce cell cycle deceleration or preferably arrest and/or apoptosis in cells containing p53 or variants thereof that are still functional, for sensitizing cells to one or more additional pharmaceutically active agents, such as inducers of apoptosis and/or of cell cycle deceleration or arrest, and to chemoprotection of normal cells through the induction of cell cycle deceleration or arrest prior to treatment with one or more other chemotherapeutic agents, to the use in rendering normal cells resistant to chemotherapeutic agents and/or treatments, and/or the use in protecting cells from toxic side effects of chemotherapeutic agents or treatments, such as side effects resulting in mucositis, stomatitis, xerostomia, gastrointestinal disorders and/or alopecia.

A compound of the formula (I) may also be used to advantage in combination with other anti-proliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as fludarabine; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODAL™); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; MEK inhibitors such as ARRY142886 from Array PioPharma, AZD6244 from AstraZeneca, PD181461 from Pfizer, leucovorin, EDG binders, antileukemia compounds, ribonucleotide reductase inhibitors, S-adenosylmethionine decarboxylase inhibitors, regulators of apoptosis, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, ful-vestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX™), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the an thracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL™. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R. P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;
b) compounds targeting, decreasing or inhibiting the activity of the fibroblast growth factor-receptors (FGFR);
c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;
d) compounds targeting, decreasing or inhibiting the activity of the Trk receptor tyrosine kinase family, or ephrin B4 inhibitors;
e) compounds targeting, decreasing or inhibiting the activity of the Axl receptor tyrosine kinase family;
f) compounds targeting, decreasing or inhibiting the activity of the Ret receptor tyrosine kinase;
g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;
h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825);
i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor);
j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);
k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™) Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d] pyrimidine derivatives which are disclosed in WO 03/013541; and
l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;
m) compounds targeting, decreasing or inhibiting the activity of PI3K, such as BEZ235 or BKM120;
n) compounds targeting, decreasing or inhibiting the activity of the cyclin dependent kinase family, such as PD 0332991.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune™), everolimus (Certican™ or Afinitor™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetrazolyle derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors. An example HSP90 inhibitor is AUY922.

The term "regulators of apoptosis" as used herein includes, but is not limited to, compounds targeting, decreasing or inhibiting the activity of Bcl2 family members (such as ABT-263) and IAP family members (such as AEG40826); or inducing apoptosis by known or unknown mechanism(s) of action (e.g. TRAIL antibody, DR5 antibody).

The term "antiproliferative antibodies" as used herein includes, but is not limited to, trastuzumab (Herceptin™), Trastuzumab-DM1, erbitux, bevacizumab (Avastin™), rituximab (Rituxan™) PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the formula (I) can be used in combination with standard leukemia therapies, especially in combination with therapies used for the treatment of AML. In particular, compounds of the formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A, LDH589 disclosed in WO 02/22577 and compounds disclosed in U.S. Pat. No. 6,552,065, in particular, N-hydroxy-3-[4-[[[2-(2-methyl-1H-indol-3-yl)-ethyl]-amino]-methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

Somatostatin receptor antagonists as used herein refer to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4th Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy include treatment with compounds, such as e.g. VISUDYNE™ and porfimer sodium.

Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The above-mentioned compounds, which can be used in combination with a compound of the formula (I), can be prepared and administered as described in the art, such as in the documents cited above.

A compound of the formula (I) can be administered alone or in combination with one or more other therapeutic compounds, possible combination therapy taking the form of fixed combinations or the administration of a compound of the invention and one or more other therapeutic (including prophylactic) compounds being staggered or given independently of one another, or the combined administration of fixed combinations and one or more other therapeutic compounds. A compound of the formula (I) can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

In another embodiment, the invention provides a compound of the formula (I) or salt thereof as defined herein, in combination with one or more therapeutically active agents.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by inhibition of the MDM2/p53 and/or MDM4/p53 interaction. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by inhibition of the MDM2/p53 and/or MDM4/p53 interaction, wherein the medicament is prepared for administration with another therapeutic agent. The invention also provides the use of another therapeutic agent for treating a disease or condition mediated by inhibition of the MDM2/p53 and/or MDM4/p53 interaction, wherein the medicament is administered with a compound of formula (I).

The invention also provides a compound of formula (I) for use in a method of treating a disease or condition mediated by inhibition of the MDM2/p53 and/or MDM4/p53 interaction, wherein the compound of formula (I) is prepared for administration with another therapeutic agent. The invention also provides another therapeutic agent for use in a method of treating a disease or condition mediated by inhibition of the MDM2/p53 and/or MDM4/p53 interaction, wherein the other therapeutic agent is prepared for administration with a compound of formula (I). The invention also provides a compound of formula (I) for use in a method of treating a disease or condition mediated by inhibition of the MDM2/p53 and/or MDM4/p53 interaction, wherein the compound of formula (I) is administered with another therapeutic agent. The invention also provides another therapeutic agent for use in a method of treating a disease or condition mediated by inhibition of the MDM2/p53 and/or MDM4/p53 interaction, wherein the other therapeutic agent is administered with a compound of formula (I).

The invention also provides the use of a compound of formula (I) for treating a disease or condition mediated by inhibition of the MDM2/p53 and/or MDM4/p53 interaction, wherein the patient has previously (e.g. within 24 hours) been treated with another therapeutic agent. The invention also provides the use of another therapeutic agent for treating a disease or condition mediated by inhibition of the MDM2/p53 and/or MDM4/p53 interaction, wherein the patient has previously (e.g. within 24 hours) been treated with a compound of formula (I).

In another aspect of the invention, there is provided a compound or salt thereof, as named herein, or as defined by structure herein.

Processes for Making Compounds of the Invention

The R groups of the generic schemes below are illustrative only, and may or may not be the same as R groups defined in embodiments of the invention herein.

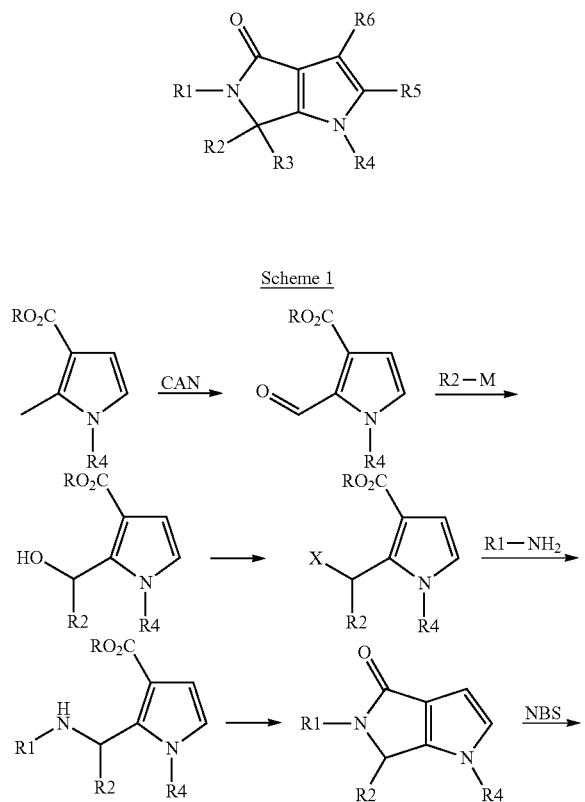

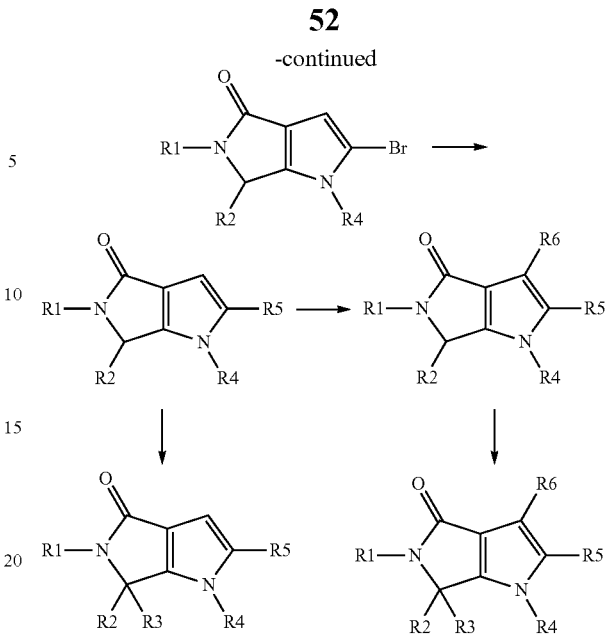

Scheme 1 illustrates one method for preparing compounds of the invention (e.g. Example 1). A 2-methyl-pyrrole-3-ester derivative is oxidized with ceric ammonium nitrate (CAN) to provide an aldehyde derivative which can be reacted with an organometallic reagent (M=Mg or Li) to generate the corresponding secondary alcohol adduct. Conversion of the alcohol into a leaving group, for example with (a) methanesulfonyl chloride or methanesulfonic anhydride in the presence of an organic base such as pyridine (together with a catalytic amount of 4-dimethylaminopyridine) or triethylamine or (b) 1-chloro-N,N,2-trimethylpropenylamine, followed by reaction with an amine at temperatures between −30° C. and 50° C. results in the introduction of the R1-containing amine. Cyclization to the lactam can be effected either (a) directly from the amino-ester using either trimethylaluminium, dimethylaluminium chloride or diethylaluminium chloride or (b) in two steps by initial saponification of the ester group on treatment with a base such as an alkali metal hydroxide (e.g. lithium hydroxide or sodium hydroxide) in a solvent such as wet cycloalkylether or alcohol (e.g. dioxane/water or methanol/water), at a temperature between 20° C. and 100° C., preferably between 30° C. and 80° C. The freed amino-acid intermediate obtained after neutralization of the reaction mixture with an acid (such as a mineral acid, e.g. hydrochloric acid or a weak organic acid, e.g. citric acid), extraction and evaporation to dryness is then cyclized intramolecularly using peptide coupling reagents such as O-(7-azabenzotriazol-1-yl)-N,N,N',N'-tetramethyluronium-hexafluorophosphate (HATU), O-benzotriazolyl tetramethylisouronium tetrafluoroborate (TBTU) or 1-chloro-N,N,2-trimethylpropenylamine. The resulting pyrrolo-pyrrolidinone is treated with N-bromosuccinimide in a solvent such as carbon tetrachloride, dichloromethane or tetrahydrofuran at a temperature between 0° C. and 40° C., preferably between 0° C. and room temperature. Cross coupling reactions of the resulting 2-bromo-pyrrolo-pyrrolidinone intermediates with aryl- or heteroarylboronic esters or -acids are conducted under Suzuki-type conditions, i.e. utilizing catalysts such as Pd(PPh$_3$)$_4$, (Ph$_3$P)$_2$PdCl$_2$ or Pd(dppf)Cl$_2$.CH$_2$Cl$_2$ complex in the presence of excess of an inorganic base (e.g. K$_3$PO$_4$) in solvent systems such as dioxane/water in a temperature range from 80° C. to 100° C. Alternatively, the 2-bromo-pyrrolo-pyrrolidinone intermediates can be converted to the corresponding boronic esters on treatment with bis(pinacolato)-diborane using a catalyst such as PdCl$_2$(dppf)-CH$_2$Cl$_2$ complex in the presence of potassium acetate in a solvent such as dioxane in a temperature range from 80° C. to 100° C. and then coupled under the aforementioned Suzuki-type conditions with the matching aryl- or heteroaryl-bromides. Introduction of R3 can be accomplished for example by alkylation of the sp3 C(4) of the pyrrolidinone ring using a base such as lithium-, sodium- or potassium hexamethyldisilazide at low temperature (−78° C.) in tetrahydrofuran. Introduction of R6 can be affected either (a) directly using for example either (i) chlorosulfonylisocyanate (R6=CN), or (ii) 1-fluoro-2,4,6-trimethyl-pyridinium (R6=F) or (b) in several steps for example either (i) bromination (with either N-bromosuccinimide or bromine/acetic acid) followed by metallation and carboxylation or (ii) cyanation followed by hydrolysis/saponification (R6=CO$_2$H).

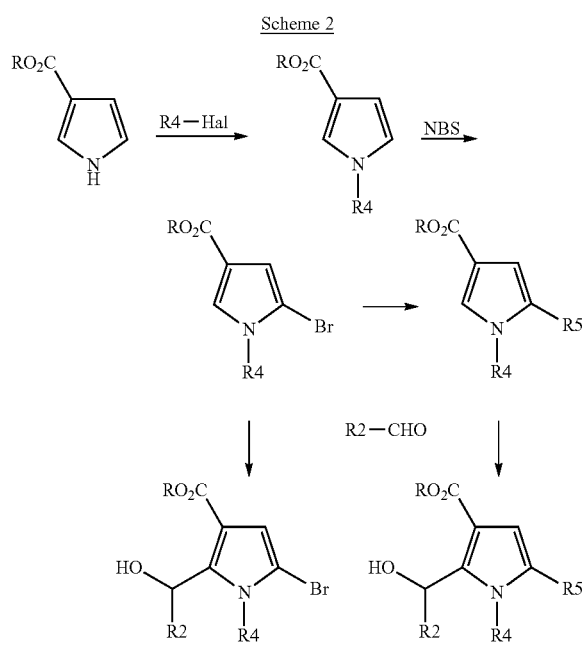

Scheme 2 illustrates a modification of the method shown in Scheme 1 for preparing compounds of the invention (e.g. Examples 53-58). This method is similar to the one described in Scheme 1 except that the order and/or manner of introducing the various substituents is slighty modified. A pyrrole-3-ester derivative is treated with a base such as either (a) sodium hydride in N,N-dimethylformamide at a temperature between 0° C. and room temperature or (b) potassium hydroxide in an ionic liquid such as 1-butyl-3-methylimidazolium hexafluorophosphate at a temperature between 50° C. and 80° C., and subsequently reacted with a halogenated reagent R4-Hal wherein Hal refers to halogen preferably iodine or bromine, e.g. isopropyl iodide. Following bromination with N-bromosuccinimide, the 5-bromo-pyrrole-3-ester derivative can be metallated with a base such as lithium diisopropylamide in tetrahydrofuran at −78° C. and quenched by addition of an aldehyde (R2-CHO). Alternatively, the 5-bromo-pyrrole-3-ester derivative can first be coupled with aryl- or heteroarylboronic esters or -acids under Suzuki-type conditions and then metallated and reacted with the R2-CHO aldehyde. In both instances, the resulting secondary alcohol products can be further processed as described in Scheme 1.

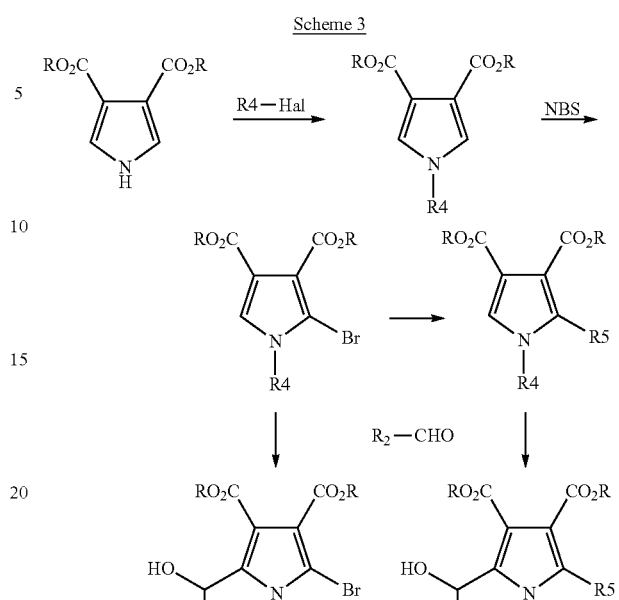

Scheme 3 illustrates a modification of the method shown in Scheme 2 for an alternative way of preparing compounds of the invention with R6=CO$_2$R or CO$_2$H (e.g. Examples 220-221). This method is similar to the one described in Scheme 2 except that a pyrrole-3,4-diester derivative is used as a starting material. In the course of the synthesis, subsequent cyclization from the amino-diester intermediate to the lactam is preferably effected directly using either trimethylaluminium, dimethylaluminium chloride or diethylaluminium chloride in order to prevent (premature) concomitant hydrolysis of the 3-ester group (i.e. ease of handling in subsequent steps). In a final step (for R6=CO$_2$H), saponification of the 3-ester group is effected by treatment with a base such as an alkali metal hydroxide (e.g. lithium hydroxide or sodium hydroxide) in a solvent such as wet cycloalkylether or alcohol (e.g. dioxane/water or methanol/water), at a temperature between 20° C. and 100° C., preferably between 30° C. and 80° C.

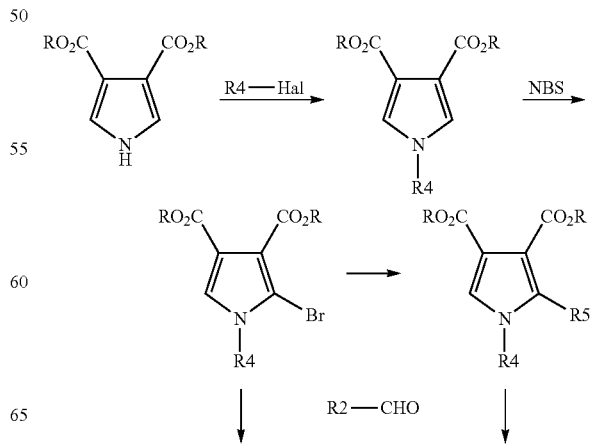

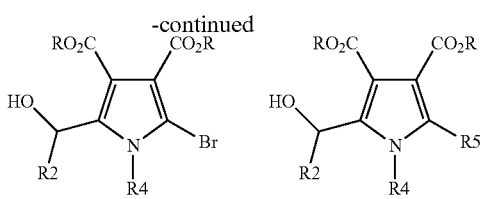

Scheme 4 illustrates a modification of the method shown in Scheme 1 for preparing compounds of the invention (e.g. Examples 222-225). This method is similar to the one described in Scheme 1 except that the R4-group can be varied to encompass groups that are either not available or else not easily accessible from commercially available 2-methyl-pyrrole-3-ester derivatives. The R4-group can either be introduced either directly at the time of generating the pyrrole or else after the pyrrole system has been formed (e.g. alkylation of a pendant alcohol with a base such as sodium hydride in N,N-dimethylformamide).

Temperatures are measured in degrees Celsius. Unless otherwise indicated, the reactions take place under an argon atmosphere at rt and the MS are obtained with ESI. $^1$H-NMR measurements were performed on a Bruker Ultrashield™ 400 (400 MHz), Bruker Ultrashield™ 600 (600 MHz) or a 500 MHz DRX Bruker CryoProbe (500 MHz) spectrometer with or without tetramethylsilane as an internal standard. Chemical shifts (δ-values) are reported in ppm downfield from tetramethylsilane, coupling constants (J) are given in Hz, spectra splitting pattern are designated as singlet (s), doublet (d), doublet doublet (dd), triplet (t), quadruplet (q), multiplet or more overlapping signals (m) and broad signal (br). Solvents are given in parentheses. The following HPLC and LC-MS methods are used in the preparation and analysis of the intermediates and examples:

HPLC Methods:
HPLC 1:
Column: HP Hypersil BDS C18, 4×125 mm, 5 micron. Flow: 1.5 mL/min. Column temperature: 25° C. Gradient: 10% to 100% B in 5 min, 100% B for 2.5 min, 100% to 10% B in 1 min; A=0.1% v/v TFA in water, B=0.1% v/v TFA in $CH_3CN$
HPLC 2:
Column: Nucleosil 100-3 C18HD, 4×125 mm, 3 micron. Flow: 1.0 mL/min. Column temperature: 30° C. Gradient: 2% to 100% B in 7 min, 100% B for 2 min, 100% to 2% B in 1 min; A=0.1% v/v TFA in water, B=0.1% v/v TFA in $CH_3CN$
HPLC 3:
Column: Acquity UPLC, BEH, C18, 2.1×50 mm, 1.7 micron. Flow: 1.0 mL/min. Column temperature: 40° C. Gradient: 0.1 min 2% B, 2% to 100% B in 1.5 min, 0.4 min 100% B, 100% to 2% B in 0.2 min and 0.3 min 2% B; A=0.1% v/v TFA in water, B=0.1% v/v TFA in $CH_3CN$
HPLC 4:
Column: Nucleosil 100-3 C18 HD, 4.0×70 mm. Flow: 1.0 mL/min. Column temperature: 30° C. Gradient: 2% to 100% B in 5 min, 100% B for 1.5 min, 100% to 2% B in 0.5 min; A=0.1% v/v TFA in water, B=0.1% v/v TFA in $CH_3CN$
HPLC 5:
Column: Acquity UPLC, BEH, C18, 2.1×50 mm, 1.7 micron. Flow: 0.6 mL/min. Column temperature: 35° C. Gradient: 0.5 min 5% B, 5% to 100% B in 3.5 min, 1.5 min 100% B, 100% to 5% B in 1 min; A=0.1% v/v TFA in water, B=0.1% v/v TFA in $CH_3CN$
HPLC 6:
Column: Zorbax Eclipse XDB-C18, 4.6×50 mm, 1.8 micron. Flow: 1.0 mL/min. Column temperature: 35° C. Gradient: 5% to 100% B in 6 min, 100% B for 1.5 min, 100% to 5% B in 0.5 min; A=0.05% v/v TFA in water, B=0.05% v/v TFA in $CH_3CN$
HPLC 7:
Column: Waters Chromolith Performance RP-18e 100-4,6. Flow: 2 mL/min. Column temperature: rt. Gradient: 2% B for 1 min, 2% to 100% B in 8 min, 100% B for 2 min, A=0.1% HCOOH in water, B=0.1% HCOOH in $CH_3CN$ LC-MS Methods:
LC-MS 1:
Column: Acquity HSS T3, 2.1×50 mm, 1.8 micron. Flow: 1.2 mL/min. Column temperature: 50° C. Gradient: 2% to 98% B in 1.4 min, 98% B for 0.75 min, 98% to 2% B in 0.04 min, 2% B for 0.01 min; A=water+0.05% formic acid+3.75 mM ammonium acetate, B=$CH_3CN$+0.04% formic acid
LC-MS 2:
Column: Acquity HSS T3, 2.1×50 mm, 1.8 micron. Flow: 1.2 mL/min. Column temperature: 50° C. Gradient: 2% to 98% B in 1.4 min, 98% B for 0.75 min, 98% to 2% B in 0.04 min, 2% B for 0.01 min; A=water+0.05% formic acid+0.05% ammonium acetate, B=$CH_3CN$+0.04% formic acid
LC-MS 3:
Column: Ascentis Express C18, 2.1×30 mm, 2.7 micron. Flow: 1.2 mL/min. Column temperature: 50° C. Gradient: 2% to 98% B in 1.4 min, 98% B for 0.75 min, 98% to 2% B in 0.04 min, 98% B for 0.01 min; A=water+0.05% formic acid+0.05% ammonium acetate, B=$CH_3CN$+0.04% formic acid
LC-MS 4:
Column: Acquity HSS T3 2.1×50 mm, 1.8 μm. Flow: 1.2 mL/min. Column temperature: 50° C. Gradient: 2% to 98% B in 1.7 min, 98% B for 0.45 min, 98% to 2% B in 0.05 min; A=water+0.05% formic acid+3.75 mM ammonium acetate, B=$CH_3CN$+0.04% formic acid
LC-MS 5:
Column: Waters Acquity HSS T3, 1.8 μm, 2.1×50 mm, oven at 50° C. Flow: 1.2 mL/min. Gradient: 2% to 98% B in 1.40 min, then 98% B for 0.40 min, 98% to 2% B in 0.10 min, 2% B for 0.10 min; A=water+0.05% formic acid+3.75 mM ammonium acetate, B=$CH_3CN$+0.04% formic acid. Detection UV/VIS (DAD), ESI (+/−). Mass spectrometer range: 100-1600 Da.
LC-MS 6:
Column: Waters Acquity HSS T3, 1.8 μm, 2.1×50 mm, oven at 60° C. Flow: 1.0 mL/min. Gradient: 5% to 98% B in 1.40 min, then 98% B for 0.40 min, 98% to 5% B in 0.10 min, 5% B for 0.10 min; A=water+0.05% formic acid+3.75 mM ammonium acetate, B=$CH_3CN$+0.04% formic acid. Detection UV/VIS (DAD), ESI (+/−). Mass spectrometer range: 100-1200 Da.

MS Method:
MS 1:
ESI+/−: 120-750 m/z. Flow: 0.050 mL/min isocratic. Eluent: water:methanol 3:7+2% ammonia hydroxide solution 25%.

Preparative Chiral-HPLC Method:
Chiral-HPLC 1: Column: Chiralpak IC 5 μm, 250×20 mm. Flow 15 mL/min. Heptane/EtOH/$CH_3OH$ 50:25:25. Detection: UV 210 nm
Chiral-HPLC 2: Column: Chiralcel OD-H 5 μm, 250×20 mm. Flow 15 mL/min. Heptane/EtOH/MeOH 90:5:5. Detection: UV 210 nm Chiral-HPLC 3: Column: Chiralpak AS-H 5 μm, 250×30 mm. Flow 80 mL/min. scCO$_2$/EtOH 60:40. Detection: UV 220 nm Chiral-HPLC 4: Column: Lux Cel2 5 μm, 250×21.2 mm. Flow 80 mL/min. scCO$_2$/MeOH 50:50. Detection: UV 215 nm Chiral-HPLC 5: Column: Chiralcel Oz i 20 μm, 420×50 mm. Flow 60 mL/min. Heptane/EtOH 50:50. Detection: UV 235 nm Chiral-HPLC 6: Column: Chiralpak AD-H 5 μm, 250×20 mm. Flow 6 mL/min. EtOH. Detection: UV 220 nm Chiral-HPLC 7: Column: Chiralcel IC, 250×30 mm. Flow 80 mL/min. scCO$_2$/EtOH 60:40. Detection: UV 215 nm Chiral-HPLC 8: Column: Chiralpak IA, 250×20 mm. Flow 10 mL/min. EtOH. Detection: UV 240 nm Chiral-HPLC 9: Column: Chiralpak AY, 237×50 mm. Flow 45 mL/min. 1:1 EtOH/MeOH. Detection: UV 220 nm Chiral-HPLC 10: Column: Chiralpak IC 20 μm, 375×76.5 mm. Flow 90-200 mL/min. EtOH. Detection: UV 255 nm Preparative HPLC Method:

Gilson gx-281. Column: sunfire C18, 30×100 mm, Flow: 30 mL/min. Solvents: A=0.1% TFA in H$_2$O, B=CH$_3$CN. Detection UV.

ABBREVIATIONS

API atmospheric pressure ionization
aq. Aqueous
Ar Argon
Boc tert-butoxycarbonyl
brine saturated (at rt) sodium chloride solution
CAN ceric ammonium nitrate
CH$_2$Cl$_2$ dichloromethane
CH$_3$CN acetonitrile
CCl$_4$ carbon tetrachloride
CPS In 1 L of water: 10 g of Ce(SO$_4$)$_2$*4H$_2$O, 25 g of phosphomolybdic acid and 60 ml of sulfuric acid 100%
DIEA diisopropyl ethyl amine
DMAP 4-dimethylaminopyridine
DME dimethoxyethane
DMF N,N-dimethylformamide
DMSO dimethylsulfoxide
EDC.HCl 1-ethyl-3-(3-dimethylaminopropyl)carbodiimide hydrochloride
EDCI 1-[3-(dimethylamino)propyl]-3-ethyl carbodiimide
ES-MS electrospray mass spectrometry
Et ethyl
Et$_3$N triethylamine
EtOAc ethyl acetate
EtOH ethanol
h hour(s)
HATU O-(7-azabenzotriazol-1-yl)-N,N,N',N'-tetramethyluronium-hexafluorophosphate HCl hydrogen chloride
HOBt 1-hydroxybenzotriazole
HPLC high-performance liquid chromatography
KHMDS potassium hexamethyldisilazide
K$_2$CO$_3$ potassium carbonate
K$_3$PO$_4$ potassium phosphate
LDA lithium diisopropylamide
LiOH lithium hydroxide
Me methyl
MeOH methanol
MgSO$_4$ magnesium sulfate
min minute(s)
mL milliliter(s)
MS mass spectrometry
Ms$_2$O methanesulfonic anhydride
MTBE methyl tert-butyl ether
MW microwave
NaH sodium hydride
NaHCO$_3$ sodium bicarbonate
NaOH sodium hydroxide
Na$_2$SO$_4$ sodium sulfate
Na$_2$S$_2$O$_3$ sodium thiosulfate
NBS N-bromosuccinimide
NH$_4$Cl ammonium chloride
NMM N-methylmorpholine
NMR nuclear magnetic resonance
Pd(PPh$_3$)$_4$ tetrakis(triphenylphosphine)palladium(0)
PdCl2(dppf).CH2Cl2 adduct 1,1'-bis(diphenylphosphino)ferrocene-palladium(II)dichloride dichloromethane complex
Ph phenyl
R$_f$ ratio of fronts
rt (or RT) room temperature
Rochelle's salt potassium sodium tartrate in solution in water
SFC supercritical fluid chromatography
t$_R$ retention time
TBAF tetrabutylammonium fluoride
TBME tert-butylmethylether
TBTU O-benzotriazolyltetramethylisouronium tetrafluoroborate
TFA trifluoroacetic acid
THF tetrahydrofuran
TLC thin layer chromatography
TurboGrignard Isopropylmagnesium chloride lithium chloride complex solution 1.3 M in THF Intermediate A: 2-Bromo-5-(3-chloro-2-fluoro-phenyl)-6-(4-chloro-2-methyl-phenyl)-1-isopropyl-5,6-dihydro-1H-pyrrolo[3,4-b]pyrrol-4-one NBS (1.926 mmol) was added to a mixture of 5-(3-chloro-2-fluoro-phenyl)-6-(4-chloro-2-methyl-phenyl)-1-isopropyl-5,6-dihydro-1H-pyrrolo[3,4-b]pyrrol-4-one (Step A1) (1.965 mmol) in CCl$_4$ (65 mL). After 1.5 h, the reaction mixture was diluted with EtOAc and successively washed with a saturated aqueous solution of NaHCO$_3$, water and brine, dried (Na$_2$SO$_4$), filtered and concentrated. The residue was purified using a RediSep® silica gel column to afford the title compound as a white solid. $t_R$: 5.69 min (HPLC 1); ESI-MS: $t_R$=1.39 min, [M+H]$^+$ 495/497/499 (LC-MS 1); TLC: $R_f$=0.12 (CH$_2$Cl$_2$).

Step A1: 5-(3-Chloro-2-fluoro-phenyl)-6-(4-chloro-2-methyl-phenyl)-1-isopropyl-5,6-dihydro-1H-pyrrolo[3,4-b]pyrrol-4-one

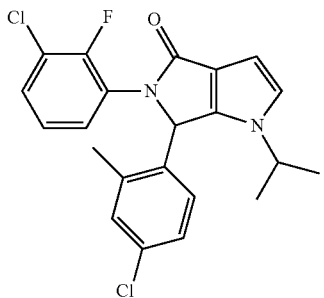 [SMILES: Cc1cc(Cl)ccc1C1c2c(ccn2C(C)C)C(=O)N1c1cccc(Cl)c1F]

A mixture of 2-[(3-chloro-2-fluoro-phenylamino)-(4-chloro-2-methyl-phenyl)-methyl]-1-isopropyl-1H-pyrrole-3-carboxylic acid (Step A2) (2.257 mmol), HATU (2.482 mmol) and NMM (6.77 mmol) in DMF (30 mL) was heated at 80° C. for 18 h. After cooling to rt, the reaction mixture was diluted with EtOAc and washed with a saturated aqueous solution of NaHCO$_3$. The aqueous phase was extracted with EtOAc (2×). The combined organic phases were washed with brine, dried (Na$_2$SO$_4$), filtered and concentrated. The residue was purified using a RediSep® silica gel column to afford the title compound as a white solid. $t_R$: 5.31 min (HPLC 1); ESI-MS: $t_R$=1.29 min, [M+H]$^+$ 417/419 (LC-MS 1); TLC: $R_f$=0.13 (1:3 EtOAc/heptanes).

Step A2: 2-[(3-Chloro-2-fluoro-phenylamino)-(4-chloro-2-methyl-phenyl)-methyl]-1-isopropyl-1H-pyrrole-3-carboxylic acid

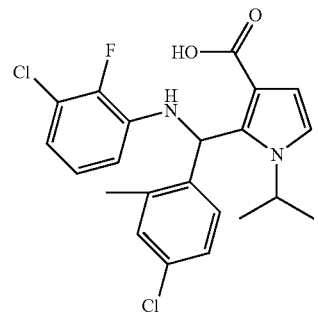 [SMILES: Cc1cc(Cl)ccc1C(Nc1cccc(Cl)c1F)c1c(C(=O)O)ccn1C(C)C]

A mixture of 2-[(3-chloro-2-fluoro-phenylamino)-(4-chloro-2-methyl-phenyl)-methyl]-1-isopropyl-1H-pyrrole-3-carboxylic acid ethyl ester (Step A3) (2.154 mmol) and 1N aqueous LiOH (8.62 mmol) in dioxane (25 mL) was heated at 100° C. for 26 h. After cooling to rt, the reaction mixture was partitioned between EtOAc and 10% w/w aqueous citric acid. The aqueous phase was extracted with EtOAc (2×). The combined organic phases were dried (Na$_2$SO$_4$), filtered and concentrated to afford the title compound as a pale yellow solid which was used in the next step without further purification. $t_R$: 5.48 min (HPLC 1); ESI-MS: $t_R$=1.33 min, [M−H] 433/435 (LC-MS 1).

Step A3: 2-[(3-Chloro-2-fluoro-phenylamino)-(4-chloro-2-methyl-phenyl)-methyl]-1-isopropyl-1H-pyrrole-3-carboxylic acid ethyl ester

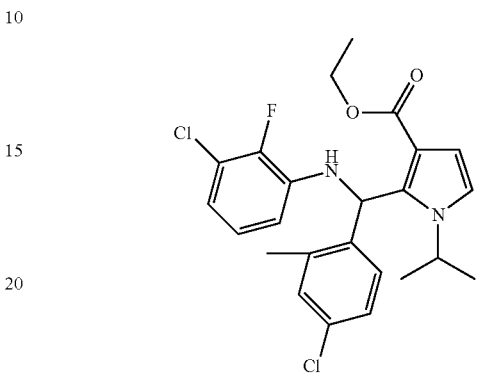

Methanesulfonyl chloride (10.62 mmol) was added to a mixture of 2-[(4-chloro-2-methyl-phenyl)-hydroxy-methyl]-1-isopropyl-1H-pyrrole-3-carboxylic acid ethyl ester (Step A4) (4.09 mmol), pyridine (14.01 mmol) and DMAP (1.226 mmol) in CH$_2$Cl$_2$ (70 mL). After stirring for 20 h, the reaction mixture was diluted with CH$_2$Cl$_2$ and washed with a saturated aqueous solution of NH$_4$Cl (2×). The combined aqueous phases were back-extracted with CH$_2$Cl$_2$. The combined organic phases were dried (Na$_2$SO$_4$), filtered and concentrated. A mixture of the crude intermediate and 3-chloro-2-fluoro-phenylamine [2106-04-9] (11.64 mmol) in dioxane (90 mL) was stirred at 90° C. for 11 h. After cooling to rt, the reaction mixture was diluted with EtOAc and successively washed with 10% w/w aqueous citric acid and brine. The combined aqueous phases were back-extracted with EtOAc. The combined organic phases were dried (Na$_2$SO$_4$), filtered and concentrated. The residue was purified using a RediSep® silica gel column to afford the title compound as a yellow solid. $t_R$: 9.08 min (HPLC 2); ESI-MS: $t_R$=1.54 min, [M]$^+$ 318/320 (i.e. fragmented pyrrolium ion) (LC-MS 1); TLC: $R_f$=0.45 (1:4 EtOAc/hexanes).

Step A4: 2-[(4-Chloro-2-methyl-phenyl)-hydroxy-methyl]-1-isopropyl-1H-pyrrole-3-carboxylic acid ethyl ester

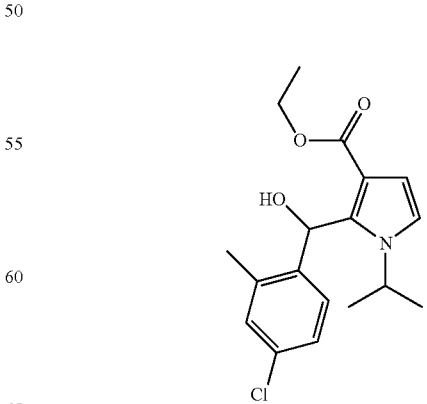

A solution (0.5 M in THF) of 4-chloro-2-methylphenyl-magnesium bromide [480438-47-9] (68.8 mmol) was added to a mixture of 2-formyl-1-isopropyl-1H-pyrrole-3-carboxylic acid ethyl ester (Step A5) (68.8 mmol) in THF (160 mL) at 0° C. After stirring for 2 h, the reaction mixture was quenched with a saturated aqueous solution of NH₄Cl and extracted with MTBE (2×). The combined organic phases were successively washed with water and brine, dried (Na₂SO₄), filtered and concentrated. The residue was suspended in hexanes, stirred for 30 min and then filtered to afford the title compound as a white solid. $t_R$: 7.74 min (HPLC 2); ESI-MS: $t_R$=1.26 min, [M]⁺318/320 (i.e. fragmented pyrrolium ion) (LC-MS 1); TLC: $R_f$=0.20 (1:6 EtOAc/hexanes).

Step A5:
2-Formyl-1-isopropyl-1H-pyrrole-3-carboxylic acid ethyl ester

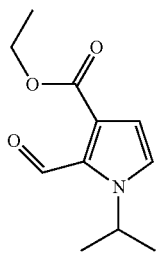

CAN (979 mmol) was added to a mixture of 1-isopropyl-2-methyl-1H-pyrrole-3-carboxylic acid ethyl ester [224180-70-5] (218 mmol) in CH₃CN (1800 mL) and water (360 mL) at 15° C. After 10 min, the reaction mixture was quenched with ice and extracted with MTBE. The organic phase was successively washed with a saturated aqueous solution of NaHCO₃ (2×) and brine, dried (Na₂SO₄), filtered and concentrated. The residue was purified by silica gel column chromatography to afford the title compound as a yellow oil. $t_R$: 4.43 min (HPLC 1); ESI-MS: $t_R$=1.06 min, [M+H]⁺ 210 (LC-MS 1); TLC: $R_f$=0.21 (1:9 EtOAc/heptanes).

Intermediate B: 2-Bromo-5-(5-chloro-2-methyl-phenyl)-6-(4-chloro-phenyl)-1-isopropyl-5,6-dihydro-1H-pyrrolo[3,4-b]pyrrol-4-one

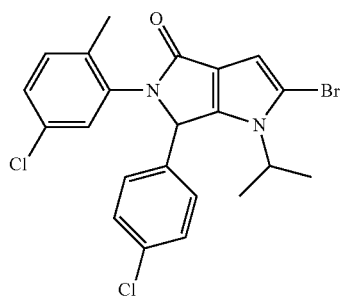 [SMILES: Cc1ccc(Cl)cc1N1C(=O)c2cc(Br)n(C(C)C)c2C1c1ccc(Cl)cc1]

The title compound was prepared in analogy to the procedures described for Intermediate A but in the steps corresponding to Step A3 and Step A4,5-chloro-2-methyl-phenylamine [95-79-4] was used instead of 3-chloro-2-fluoro-phenylamine and 4-chloro-phenylmagnesium bromide [873-77-8] was used instead of 4-chloro-2-methylphenylmagnesium bromide respectively. The title compound was obtained as a light pink solid. $t_R$: 5.60 min (HPLC 1); ESI-MS: $t_R$=1.42 min, [M+H]⁺477/479/481/483 (LC-MS 1); TLC: $R_f$=0.33 (1:2 EtOAc/hexanes).

Intermediate C: 2-Bromo-5-(5-chloro-2-methyl-phenyl)-6-(4-chloro-2-methyl-phenyl)-1-isopropyl-5,6-dihydro-1H-pyrrolo[3,4-b]pyrrol-4-one

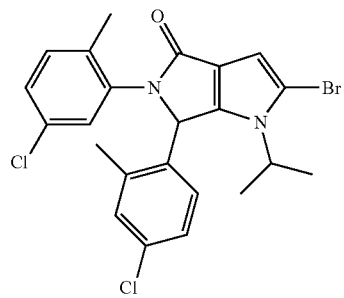 [SMILES: Cc1cc(Cl)ccc1C1c2c(cc(Br)n2C(C)C)C(=O)N1c1cc(Cl)ccc1C]

The title compound was prepared in analogy to the procedures described for Intermediate A but in the step corresponding to Step A3,5-chloro-2-methyl-phenylamine [95-79-4] was used instead of 3-chloro-2-fluoro-phenylamine. The title compound was obtained as a beige solid. $t_R$: 5.72/5.81 min (rotamers) (HPLC 2); ESI-MS: $t_R$=1.43 min, [M+H]⁺ 491/493/495 (LC-MS 1); TLC: $R_f$=0.47 (99:1 CH₂Cl₂/MeOH).

Intermediate D: 2-Bromo-5-(3-chloro-4-fluoro-phenyl)-6-(4-chloro-phenyl)-1-isopropyl-5,6-dihydro-1H-pyrrolo[3,4-b]pyrrol-4-one

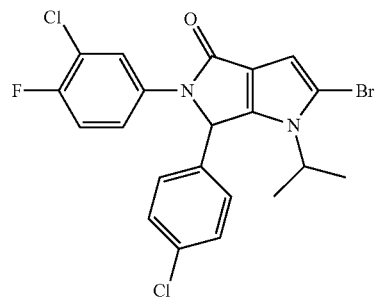 [SMILES: CC(C)n1c(Br)cc2c1C(c1ccc(Cl)cc1)N(c1ccc(F)c(Cl)c1)C2=O]

A mixture of 5-bromo-2-[(3-chloro-4-fluoro-phenylamino)-(4-chloro-phenyl)-methyl]-1-isopropyl-1H-pyrrole-3-carboxylic acid (Step D1) (1.483 mmol), HATU (1.632 mmol) and NMM (4.45 mmol) in dioxane (75 mL) was heated at 80° C. for 17 h. After cooling to rt, the reaction mixture was diluted with EtOAc and washed with a saturated aqueous solution of NaHCO₃. The aqueous phase was extracted with EtOAc (2×). The combined organic phases were washed with brine, dried (Na₂SO₄), filtered and concentrated. The residue was purified using a RediSep® silica gel column to afford the title compound as a light-yellow solid. $t_R$: 5.31 min (HPLC 2); ESI-MS: $t_R$=1.40 min, [M+H]⁺481/483/485 (LC-MS 1); TLC: $R_f$=0.27 (1:3 EtOAc/hexanes).

Step D1: 5-Bromo-2-[(3-chloro-4-fluoro-phenylamino)-(4-chloro-phenyl)-methyl]-1-isopropyl-1H-pyrrole-3-carboxylic acid

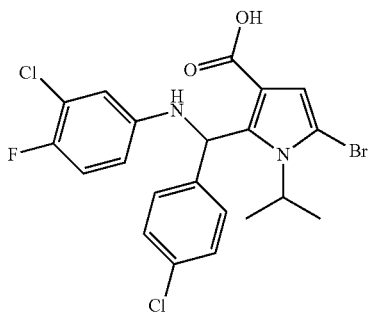 [SMILES: CC(C)n1c(Br)cc(C(=O)O)c1C(Nc1ccc(F)c(Cl)c1)c1ccc(Cl)cc1]

2N aqueous NaOH (32 mmol) was added to a solution of 5-bromo-2-[(3-chloro-4-fluoro-phenylamino)-(4-chloro-phenyl)-methyl]-1-isopropyl-1H-pyrrole-3-carboxylic acid methyl ester (Step D2) (1.517 mmol) in 1:1 THF/MeOH (32 mL) and the mixture was stirred at 80° C. for 10 h. After evaporation of MeOH, the pH was adjusted to 5 with addition of 10% w/w aqueous citric acid (35 mL) and extracted with EtOAc. The organic phase was dried (Na$_2$SO$_4$), filtered and concentrated to afford a light brown solid. t$_R$: 8.05 min (HPLC 2); ESI-MS: t$_R$=1.38 min, [M−H] 497/499/501 (LC-MS 2).

Step D2: 5-Bromo-2-[(3-chloro-4-fluoro-phenylamino)-(4-chloro-phenyl)-methyl]-1-isopropyl-1H-pyrrole-3-carboxylic acid methyl ester

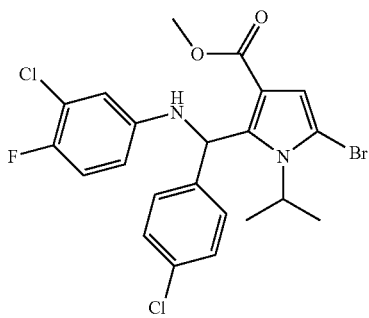 [SMILES: COC(=O)c1cc(Br)n(C(C)C)c1C(Nc1ccc(F)c(Cl)c1)c1ccc(Cl)cc1]

Pyridine (5.59 mmol), DMAP (0.486 mmol) and then Ms$_2$O (4.22 mmol) were added to a solution of 5-bromo-2-[(4-chloro-phenyl)-hydroxy-methyl]-1-isopropyl-1H-pyrrole-3-carboxylic acid methyl ester (step D3) (1.622 mmol) in CH$_2$Cl$_2$ (20 mL) and the reaction mixture was stirred at rt 17.5 h. The reaction mixture was diluted with H$_2$O/brine and extracted with CH$_2$Cl$_2$ (3×). The combined organic layers were dried (Na$_2$SO$_4$), filtered and concentrated. The residue was diluted with CH$_2$Cl$_2$ (20 mL) and 3-chloro-4-fluoroaniline [367-21-5] (1.865 mmol) was added and the mixture was stirred at rt for 20.5 h. The reaction mixture was diluted with H$_2$O/brine and extracted with CH$_2$Cl$_2$ (3×). The combined organic layers were washed with brine, dried (Na$_2$SO$_4$), filtered and concentrated. The residue was purified using a RediSep® silica gel column to afford the title compound as a yellow foam. t$_R$: 6.29 min (HPLC 1); ESI-MS: t$_R$=1.57 min, [M+H]$^+$ 513/515/517 (LC-MS 1); TLC: R$_f$=0.45 (1:6 EtOAc/heptanes).

Step D3: 5-Bromo-2-[(4-chloro-phenyl)-hydroxy-methyl]-1-isopropyl-1H-pyrrole-3-carboxylic acid methyl ester

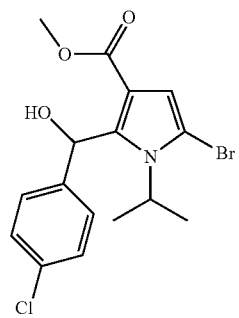 [SMILES: COC(=O)c1cc(Br)n(C(C)C)c1C(O)c1ccc(Cl)cc1]

LDA (6.20 mmol) was added dropwise to a solution of 5-bromo-1-isopropyl-1H-pyrrole-3-carboxylic acid methyl ester (Step D4) (2.066 mmol) in THF (15 mL) at −78° C. and the mixture was stirred for 2 h. A solution of 4-chlorobenzaldehyde [104-88-1] (6.20 mmol) in THF (5 mL) was added and the mixture was stirred for 1 h. The mixture was warmed to −20° C., quenched with HOAc and stirred at rt overnight. The reaction mixture was diluted with H$_2$O and extracted with EtOAc (3×). The combined organic layers were washed with brine, dried (Na$_2$SO$_4$), filtered and concentrated. The residue was purified using a RediSep® silica gel column to afford the title compound as an off-white solid. t$_R$: 5.57 min (HPLC 1); ESI-MS: t$_R$=1.36 min, [M+H]$^+$ 368/370/372 (LC-MS 1); TLC: R$_f$=0.23 (1:6 EtOAc/heptanes).

Step D4: 5-Bromo-1-isopropyl-1H-pyrrole-3-carboxylic acid methyl ester

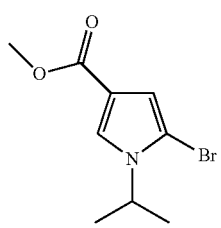

NBS (36.6 mmol) was added to a mixture of 1-isopropyl-1H-pyrrole-3-carboxylic acid methyl ester (Step D5) (37.4 mmol) in CCl$_4$ (250 mL). After 4 h, the reaction mixture was successively washed with a saturated aqueous solution of NaHCO$_3$, water and brine, dried (Na$_2$SO$_4$), filtered and concentrated. The residue was purified using a RediSep® silica gel column to afford the title compound as a pale yellow-pink oil. t$_R$: 4.56 min (HPLC 1); ESI-MS: t$_R$=1.13 min, [M+H]$^+$ 246/248 (LC-MS 1); TLC: R$_f$=0.35 (1:6 EtOAc/heptanes).

Step D5: 1-Isopropyl-1H-pyrrole-3-carboxylic acid methyl ester

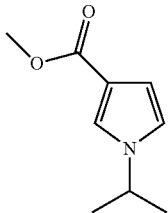

NaH (58.1 mmol) was added to a solution of 1H-pyrrole-3-carboxylic acid methyl ester [2703-17-5] (38.8 mmol) in DMF (80 mL) at 0° C. and the mixture was stirred for 1.5 h. 2-Iodo-propane (78 mmol) was added and the mixture was stirred at rt for 4 h. The reaction mixture was quenched with 1N aqueous KHSO$_4$ and extracted with EtOAc (3×). The combined organic layers were washed with brine, dried (Na$_2$SO$_4$) and concentrated. The residue was purified using a RediSep® silica gel column to afford the title compound as an orange-brown oil. t$_R$: 3.80 min (HPLC 1); ESI-MS: t$_R$=0.92 min, [M+H]$^+$ 168 (LC-MS 1); TLC: R$_f$=0.22 (1:6 EtOAc/heptanes).

Intermediate E: 2-Bromo-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one

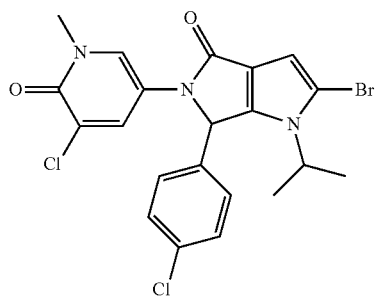 [SMILES: CC(C)n1c(Br)cc2c1C(c1ccc(Cl)cc1)N(c1cc(Cl)c(=O)n(C)c1)C2=O]

The title compound was prepared in analogy to the procedure described for Intermediate A but 5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one (Step E1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one and THF was used instead of CCl$_4$. The title compound was obtained as a beige solid. t$_R$: 4.62 min (HPLC 1); ESI-MS: t$_R$=1.10 min, [M+H]$^+$ 494/496/498 (LC-MS 1); TLC: R$_f$=0.24 (EtOAc).

Step E1: 5-(5-Chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one

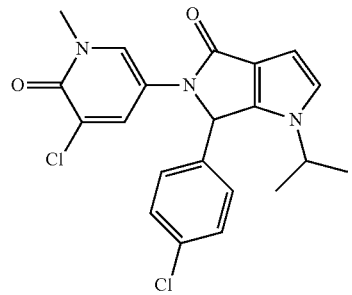 [SMILES: CC(C)n1ccc2c1C(c1ccc(Cl)cc1)N(c1cc(Cl)c(=O)n(C)c1)C2=O]

The title compound was prepared in analogy to the procedure for Step A1 but 2-[(5-chloro-1-methyl-6-oxo-1,6-dihydro-pyridin-3-ylamino)-(4-chloro-phenyl)-ethyl]-1-isopropyl-1H-pyrrole-3-carboxylic acid (Step E2) (2.59 mmol) was used instead of 2-[(3-chloro-2-fluoro-phenylamino)-(4-chloro-2-methyl-phenyl)-methyl]-1-isopropyl-1H-pyrrole-3-carboxylic acid. The title compound was obtained as a brown foam. t$_R$: 6.25 min (HPLC 2); ESI-MS: t$_R$=1.00 min, [M+H]$^+$ 416/418 (LC-MS 1); TLC: R$_f$=0.16 (EOAc).

Step E2: 2-[(5-Chloro-1-methyl-6-oxo-1,6-dihydro-pyridin-3-ylamino)-(4-chloro-phenyl)-ethyl]-1-isopropyl-1H-pyrrole-3-carboxylic acid

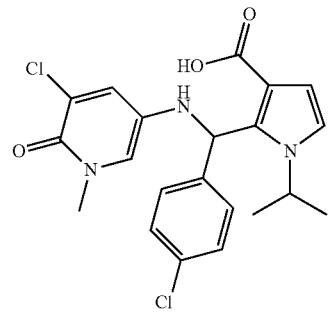 [SMILES: CC(C)n1ccc(C(=O)O)c1C(Nc1cc(Cl)c(=O)n(C)c1)c1ccc(Cl)cc1]

The title compound was prepared in analogy to the procedure described for Step D1 but 2-[(5-chloro-1-methyl-6-oxo-1,6-dihydro-pyridin-3-ylamino)-(4-chloro-phenyl)-methyl]-1-isopropyl-1H-pyrrole-3-carboxylic acid ethyl ester (Step E3) was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound as a brown foam. t$_R$: 6.26 min (HPLC 2); ESI-MS: t$_R$=1.00 min, [M+H]$^+$434/436 (LC-MS 1).

Step E3: 2-[(5-Chloro-1-methyl-6-oxo-1,6-dihydro-pyridin-3-ylamino)-(4-chloro-phenyl)-methyl]-1-isopropyl-1H-pyrrole-3-carboxylic acid ethyl ester

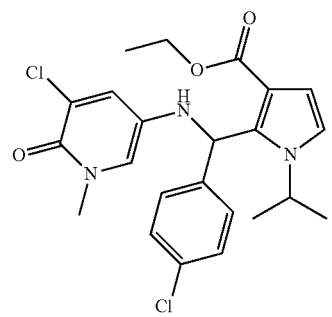 [SMILES: CCOC(=O)c1ccn(C(C)C)c1C(Nc1cc(Cl)c(=O)n(C)c1)c1ccc(Cl)cc1]

The title compound was prepared in analogy to the procedure described for Step D2, but 2-[(4-chloro-phenyl)-hydroxy-methyl]-1-isopropyl-1H-pyrrole-3-carboxylic acid ethyl ester (Step E4) and 5-amino-3-chloro-1-methyl-1H-pyridin-2-one (Step E5) were used instead of 5-bromo-2-[(4-chloro-phenyl)-hydroxy-methyl]-1-isopropyl-1H-pyrrole-3-carboxylic acid methyl ester and 3-chloro-4-fluoroaniline respectively to afford the title compound as a white solid. t$_R$: 7.36 min (HPLC 2); ESI-MS: t$_R$=1.25 min, [M+H]$^+$ 462/464 (LC-MS 1); TLC: R$_f$=0.31 (EtOAc).

Step E4: 2-[(4-Chloro-phenyl)-hydroxy-methyl]-1-isopropyl-1H-pyrrole-3-carboxylic acid ethyl ester

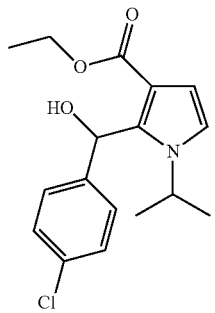 [SMILES: CCOC(=O)c1ccn(C(C)C)c1C(O)c1ccc(Cl)cc1]

The title compound was prepared in analogy to the procedure described for Step A4, but a solution (1 M in ether) of 4-chloro-2-phenylmagnesium bromide [873-77-8] was used instead of 4-chloro-2-methylphenylmagnesium bromide. The title compound was obtained as a light-brown solid. $t_R$: 7.58 min (HPLC 2); ESI-MS: $t_R$=1.29 min, [M+H]$^+$ 304/306 (LC-MS 1); TLC: $R_f$=0.30 (1:4 EtOAc/hexanes).

Step E5: 5-Amino-3-chloro-1-methyl-1H-pyridin-2-one

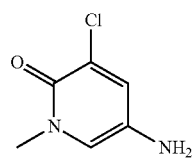

Ra—Ni (EtOH) (230 mmol) was added to a solution of 3-chloro-1-methyl-5-nitro-1H-pyridin-2-one (Step E6) (136 mmol) in MeOH (400 mL) and the mixture was stirred at rt under a hydrogen atmosphere for 97 h. The reaction mixture was filtered over celite and concentrated. The product was purified by flash chromatography to afford the title compound as a black solid. ESI-MS: $t_R$=0.33 min, [M+H]$^+$ 159/161 (LC-MS 1); TLC: $R_f$=0.28 (9:1 CH$_2$Cl$_2$/MeOH).

Step E6: 3-Chloro-1-methyl-5-nitro-1H-pyridin-2-one

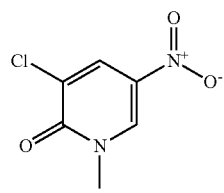

To a solution of 3-chloro-2-hydroxy-5-nitropyridine [22353-38-4] (143 mmol) and K$_2$CO$_3$ (286 mmol) in DMF (250 mL) was added methyl iodide (215 mmol) at 0° C. and the reaction mixture was stirred at rt for 3 h. The reaction mixture was concentrated, diluted with H$_2$O and extracted with EtOAc (2×). The combined organic layers were washed with H$_2$O, dried (Na$_2$SO$_4$) and concentrated to afford the title compound as a yellow solid. $t_R$: 2.90 min (HPLC 3); ESI-MS: $t_R$=0.63 min, [M+H]$^+$189/191 (LC-MS 1).

Intermediate F: 2-Bromo-6-(4-chloro-phenyl)-5-(trans-4-hydroxy-cyclohexyl)-1-isopropyl-5,6-dihydro-1H-pyrrolo[3,4-b]pyrrol-4-one

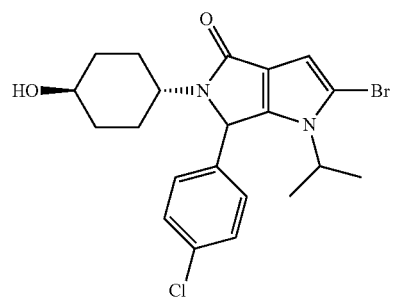 [SMILES: CC(C)n1c(Br)cc2c1C(c1ccc(Cl)cc1)N([C@H]1CC[C@H](O)CC1)C2=O]

The title compound was prepared in analogy to the procedure described for Intermediate A but 6-(4-chloro-phenyl)-5-(trans-4-hydroxy-cyclohexyl)-1-isopropyl-5,6-dihydro-1H-pyrrolo[3,4-b]pyrrol-4-one (Step F1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one and THF was used instead of CCl$_4$. The title compound was obtained as an off-white solid. $t_R$: 4.48 min (HPLC 1); ESI-MS: $t_R$=1.10 min, [M+H]$^+$451/453/455 (LC-MS 1); TLC: $R_f$=0.28 (EtOAc).

Step F1: 6-(4-Chloro-phenyl)-5-(trans-4-hydroxy-cyclohexyl)-1-isopropyl-5,6-dihydro-1H-pyrrolo[3,4-b]pyrrol-4-one

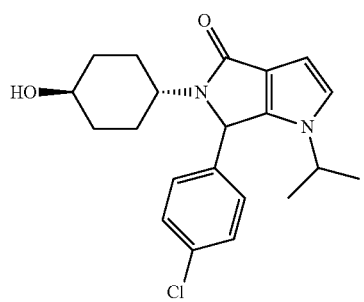 [SMILES: CC(C)n1ccc2c1C(c1ccc(Cl)cc1)N([C@H]1CC[C@H](O)CC1)C2=O]

A solution of trimethylaluminium (2M in toluene) [75-24-1] (16.75 mmol) was added to a solution of 2-[(4-chloro-phenyl)-(trans-4-hydroxy-cyclohexylamino)-methyl]-1-isopropyl-1H-pyrrole-3-carboxylic acid ethyl ester (Step F2) (5.58 mmol) in toluene (25 mL) and the mixture was stirred at 75° C. for 25 h. The mixture was cooled to rt, poured onto a stirring ice-cold solution of saturated Rochelle's salt and then diluted with EtOAc. The phases were separated. The aqueous layer was extracted with EtOAc (2×). The combined organic layers were washed with brine, dried (Na$_2$SO$_4$) and concentrated. The residue was purified using a RediSep® silica gel column to afford the title compound as a beige solid. $t_R$: 3.99 min (HPLC 1); ESI-MS: $t_R$=0.97 min, [M+H]$^+$ 373/375 (LC-MS 1); TLC: $R_f$=0.27 (EtOAc).

Step F2: 2-[(4-Chloro-phenyl)-(trans-4-hydroxy-cyclohexylamino)-methyl]-1-isopropyl-1H-pyrrole-3-carboxylic acid ethyl ester

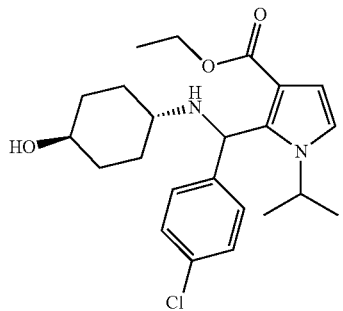 [SMILES: CCOC(=O)c1ccn(C(C)C)c1C(N[C@H]1CC[C@H](O)CC1)c1ccc(Cl)cc1]

The title compound was prepared in analogy to the procedure described for Step E3, but trans-4-aminocyclohexanol [27489-62-9] (4 equivalents) was used instead of 5-amino-3-chloro-1-methyl-1H-pyridin-2-one and the substitution was done at 50° C. The title compound was obtained as a pale yellow solid. $t_R$: 4.40 min (HPLC 1); ESI-MS: $t_R$=0.92 min, [M+H]$^+$ 419/421 (LC-MS 1); TLC: $R_f$=0.22 (1:1 EtOAc/heptanes).

Intermediate G: 2-Bromo-6-(4-chloro-phenyl)-1-isopropyl-5-(tetrahydro-pyran-4-yl)-5,6-dihydro-1H-pyrrolo[3,4-b]pyrrol-4-one

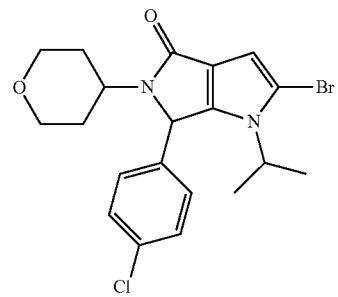 [SMILES: CC(C)n1c(Br)cc2c1C(c1ccc(Cl)cc1)N(C1CCOCC1)C2=O]

The title compound was prepared in analogy to the procedure described for Intermediate A, but 6-(4-chloro-phenyl)-1-isopropyl-5-(tetrahydro-pyran-4-yl)-5,6-dihydro-1H-pyrrolo[3,4-b]pyrrol-4-one (Step G1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one and THF was used instead of CCl$_4$. The title compound was obtained as a white solid. $t_R$: 7.07 min (HPLC 2); ESI-MS: $t_R$=1.15 min, [M+H]$^+$437/439/441 (LC-MS 1); TLC: $R_f$=0.38 (EtOAc).

Step G1: 6-(4-Chloro-phenyl)-1-isopropyl-5-(tetrahydro-pyran-4-yl)-5,6-dihydro-1H-pyrrolo[3,4-b]pyrrol-4-one

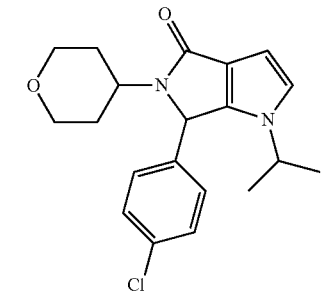 [SMILES: CC(C)n1ccc2c1C(c1ccc(Cl)cc1)N(C1CCOCC1)C2=O]

The title compound was prepared in analogy to the procedure described for Step A1, but 2-[(4-chloro-phenyl)-(tetrahydro-pyran-4-ylamino)-methyl]-1-isopropyl-1H-pyrrole-3-carboxylic acid (Step G2) was used instead of 2-[(3-chloro-2-fluoro-phenylamino)-(4-chloro-2-methyl-phenyl)-methyl]-1-isopropyl-1H-pyrrole-3-carboxylic acid. The title compound was obtained as a white solid. $t_R$: 4.31 min (HPLC 1); ESI-MS: $t_R$=1.02 min, [M+H]$^+$ 359/361 (LC-MS 1); TLC: $R_f$=0.26 (EOAc).

Step G2: 2-[(4-Chloro-phenyl)-(tetrahydro-pyran-4-ylamino)-methyl]-1-isopropyl-1H-pyrrole-3-carboxylic acid The title compound was prepared in analogy to the procedure described for Step A1, but 2-[(4-chloro-phenyl)-(tetrahydro-pyran-4-ylamino)-methyl]-1-isopropyl-1H-pyrrole-3-carboxylic acid methyl ester (Step G3) was used instead of 2-[(3-chloro-2-fluoro-phenylamino)-(4-chloro-2-methyl-phenyl)-methyl]-1-isopropyl-1H-pyrrole-3-carboxylic acid ethyl ester. The title compound was obtained as a white solid (Li-carboxylate salt). $t_R$: 3.82 min (HPLC 1); ESI-MS: $t_R$=0.73 min, [M+H]$^+$377/379 (LC-MS 1).

Step G3: 2-[(4-Chloro-phenyl)-(tetrahydro-pyran-4-ylamino)-methyl]-1-isopropyl-1H-pyrrole-3-carboxylic acid methyl ester

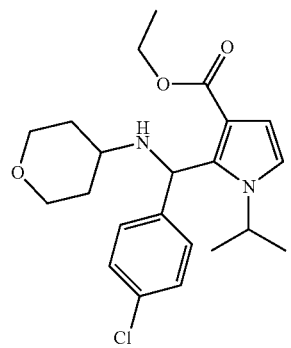 [SMILES: CCOC(=O)c1ccn(C(C)C)c1C(NC1CCOCC1)c1ccc(Cl)cc1]

The title compound was prepared in analogy to the procedure described for Step F2, but tetrahydro-pyran-4-ylamine [38041-19-9] was used instead of trans-4-aminocyclohexanol. The title compound was obtained as a yellow oil. $t_R$: 4.58 min (HPLC 1); ESI-MS: $t_R$=1.01 min, [M+H]$^+$405/407 (LC-MS 1); TLC: $R_f$=0.28 (1:3 EtOAc/heptanes).

Intermediate H: 4-[2-Bromo-5-(3-chloro-4-fluoro-phenyl)-1-isopropyl-4-oxo-1,4,5,6-tetrahydro-pyrrolo[3,4-b]pyrrol-6-yl]-benzonitrile

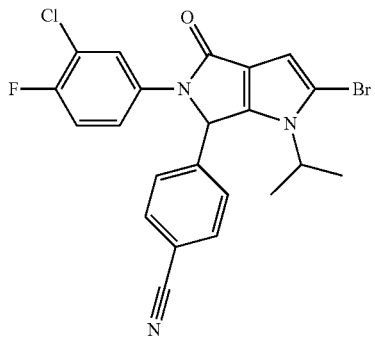 [SMILES: CC(C)n1c(Br)cc2c1C(c1ccc(C#N)cc1)N(c1ccc(F)c(Cl)c1)C2=O]

The title compound was prepared in analogy to the procedure described for Intermediate A, but 4-[5-(3-chloro-4-fluoro-phenyl)-1-isopropyl-4-oxo-1,4,5,6-tetrahydro-pyrrolo[3,4-b]pyrrol-6-yl]-benzonitrile (Step H1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one to afford the title compound as a white-purple foam. $t_R$: 5.57 min (HPLC 4); ESI-MS: $t_R$=1.21 min, [M+H]$^+$ 472/474 (LC-MS 1).

Step H1: 4-[5-(3-Chloro-4-fluoro-phenyl)-1-isopropyl-4-oxo-1,4,5,6-tetrahydro-pyrrolo[3,4-b]pyrrol-6-yl]-benzonitrile

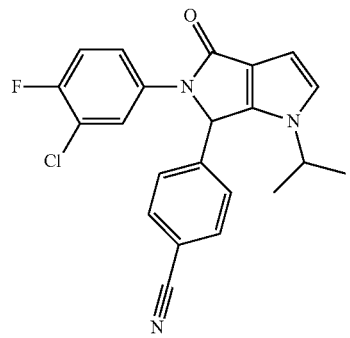 [SMILES: CC(C)n1ccc2c1C(c1ccc(C#N)cc1)N(c1ccc(F)c(Cl)c1)C2=O]

The title compound was prepared in analogy to the procedure described for Step F1, but 2-[(3-chloro-4-fluoro-phenylamino)-(4-cyano-phenyl)-methyl]-1-isopropyl-1H-pyrrole-3-carboxylic acid ethyl ester (Step H2) was used instead of 2-[(4-chloro-phenyl)-(4-hydroxy-cyclohexylamino)-methyl]-1-isopropyl-1H-pyrrole-3-carboxylic acid ethyl ester to afford the title compound as a white foam. $t_R$: 5.29 min (HPLC 4); ESI-MS: [M+H]$^+$ 394/396 (MS 1).

Step H2: 2-[(3-Chloro-4-fluoro-phenylamino)-(4-cyano-phenyl)-methyl]-1-isopropyl-1H-pyrrole-3-carboxylic acid ethyl ester

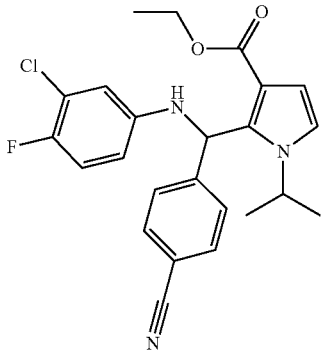 [SMILES: CCOC(=O)c1ccn(C(C)C)c1C(Nc1ccc(F)c(Cl)c1)c1ccc(C#N)cc1]

3-Chloro-4-fluoroaniline (6.40 mmol) was added at 0° C. to a solution of 2-[chloro-(4-cyano-phenyl)-methyl]-1-isopropyl-1H-pyrrole-3-carboxylic acid ethyl ester (Step H3) (3.20 mmol). Then Et$_3$N (9.60 mmol) was added and the mixture was stirred at rt for 1 h. The mixture was diluted with EtOAc. The organic layer was washed successively with H$_2$O (2×), brine, dried (Na$_2$SO$_4$), filtered and concentrated. The product was purified by flash chromatography to afford the title compound. $t_R$: 5.96 min (HPLC 4); ESI-MS: $t_R$=1.35 min, [M+H]$^+$ 440/442 (LC-MS 1).

Step H3: 2-[Chloro-(4-cyano-phenyl)-methyl]-1-isopropyl-1H-pyrrole-3-carboxylic acid ethyl ester

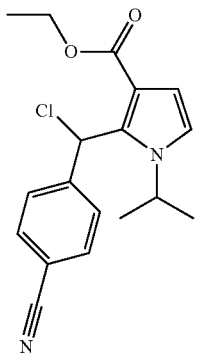 [SMILES: CCOC(=O)c1ccn(C(C)C)c1C(Cl)c1ccc(C#N)cc1]

1-Chloro-N,N,2-trimethylpropenylamine [26189-59-3] (4.80 mmol) was added to a solution of 2-[(4-cyano-phenyl)-hydroxy-methyl]-1-isopropyl-1H-pyrrole-3-carboxylic acid ethyl ester (Step H4) (3.20 mmol) in CH$_2$Cl$_2$ (15 mL) and the mixture was stirred at rt for 2.5 h. CH$_2$Cl$_2$ was added and the reaction mixture was concentrated to dryness (2×) to afford the title compound as a yellow-orange oil. $t_R$: 5.71 min (sample in MeOH) (HPLC 4); ESI-MS: $t_R$=1.26 min (LC-MS 1).

Step H4: 2-[(4-Cyano-phenyl)-hydroxy-methyl]-1-isopropyl-1H-pyrrole-3-carboxylic acid ethyl ester

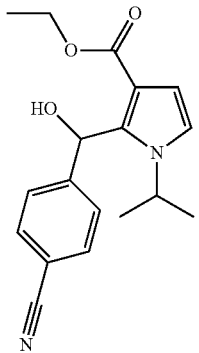 [SMILES: CCOC(=O)c1ccn(C(C)C)c1C(O)c1ccc(C#N)cc1]

The title compound was prepared in analogy to the procedure described for Step A4, but the reaction was performed at −60° C. and 4-cyanophenylmagnesium chloride (Step H5) was used instead of 4-chloro-2-methylphenylmagnesium bromide to afford the title compound as a white solid. $t_R$: 5.17 min (HPLC 4); ESI-MS: $t_R$=1.09 min, [M+H]$^+$ 313 (LC-MS 1).

Step H5: 4-Cyanophenylmagnesium chloride

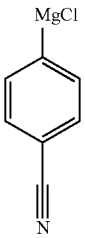

A 1.3 M solution of isopropylmagnesium chloride.LiCl in THF [807329-97-1] (19.78 mmol) was added dropwise at 0° C. to a solution of 4-bromobenzonitrile [623-00-7] (16.48 mmol) in THF (8.5 mL) and the mixture was stirred between 0° C. and 5° C. for 2 h. The product was used without further purification. $t_R$: 4.25 min (sample in MeOH) (HPLC 4).

Intermediate I: 4-[2-Bromo-5-(3-chloro-2-fluoro-phenyl)-1-isopropyl-4-oxo-1,4,5,6-tetrahydro-pyrrolo[3,4-b]pyrrol-6-yl]-benzonitrile

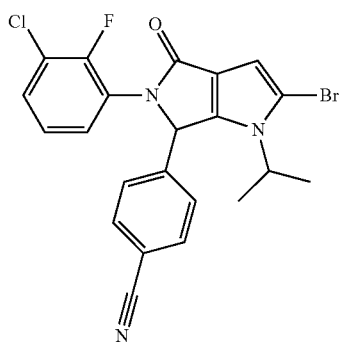 [SMILES: CC(C)n1c(Br)cc2c1C(c1ccc(C#N)cc1)N(c1cccc(Cl)c1F)C2=O]

The title compound was prepared in analogy to the procedure described for Intermediate A, but 4-[5-(3-chloro-2-fluoro-phenyl)-1-isopropyl-4-oxo-1,4,5,6-tetrahydro-pyrrolo[3,4-b]pyrrol-6-yl]-benzonitrile (Step I1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one to afford the title compound as a white-purple foam. $t_R$: 5.57 min (HPLC 4); ESI-MS: [M+H]⁺ 472/474 (MS 1).

Step I1: 4-[5-(3-Chloro-2-fluoro-phenyl)-1-isopropyl-4-oxo-1,4,5,6-tetrahydro-pyrrolo[3,4-b]pyrrol-6-yl]-benzonitrile

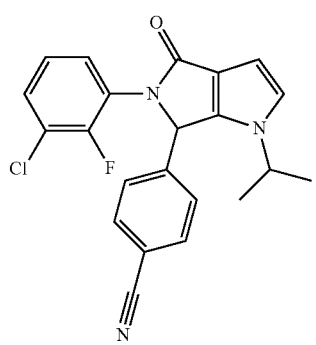 [SMILES: CC(C)n1ccc2c1C(c1ccc(C#N)cc1)N(c1cccc(Cl)c1F)C2=O]

The title compound was prepared in analogy to the procedure described for Step H1, but dimethylaluminium chloride (1M in hexanes) [1184-58-3] was used instead of trimethylaluminium chloride, and 2-[(3-chloro-2-fluoro-phenylamino)-(4-cyano-phenyl)-methyl]-1-isopropyl-1H-pyrrole-3-carboxylic acid ethyl ester (Step I2) was used instead of 2-[(4-chloro-phenyl)-(4-hydroxy-cyclohexylamino)-methyl]-1-isopropyl-1H-pyrrole-3-carboxylic acid ethyl ester to afford the title compound as a yellow foam. $t_R$: 5.18 min (HPLC 4); ESI-MS: $t_R$=1.11 min, [M+H]⁺ 394/396 (LC-MS 1).

Step I2: 2-[(3-Chloro-2-fluoro-phenylamino)-(4-cyano-phenyl)-methyl]-1-isopropyl-1H-pyrrole-3-carboxylic acid ethyl ester

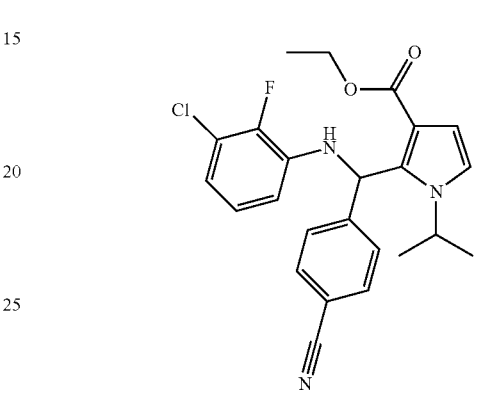

The title compound was prepared in analogy to the procedure described for Step H2, but 3-chloro-2-fluoroaniline was used instead of 3-chloro-4-fluoroaniline to afford the title compound as a white foam. $t_R$: 6.06 min (HPLC 4); ESI-MS: [M−H] 438/440 (MS 1).

Intermediate J: 4-[2-Bromo-5-(5-chloro-2-methyl-phenyl)-1-isopropyl-4-oxo-1,4,5,6-tetrahydro-pyrrolo[3,4-b]pyrrol-6-yl]-benzonitrile

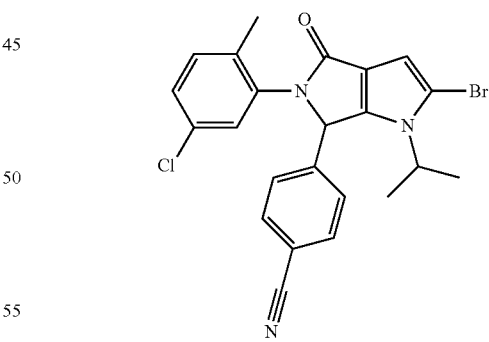

The title compound was prepared in analogy to the procedure described for Intermediate A, but 4-[5-(5-chloro-2-methyl-phenyl)-1-isopropyl-4-oxo-1,4,5,6-tetrahydro-pyrrolo[3,4-b]pyrrol-6-yl]-benzonitrile (Step J1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one to afford the title compound as a white-purple solid. $t_R$: 5.50 min (HPLC 4); ESI-MS: $t_R$=1.20 min, [M+H]⁺ 468/470 (LC-MS 1).

Step J1: 4-[5-(5-Chloro-2-methyl-phenyl)-1-isopropyl-4-oxo-1,4,5,6-tetrahydro-pyrrolo[3,4-b]pyrrol-6-yl]-benzonitrile

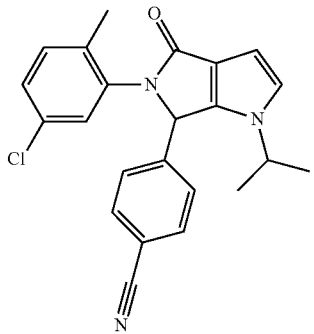 [SMILES: Cc1ccc(Cl)cc1N1C(=O)c2ccn(C(C)C)c2C1c1ccc(C#N)cc1]

The title compound was prepared in analogy to the procedure described for Step I1, but 2-[(5-chloro-2-methyl-phenylamino)-(4-cyano-phenyl)-methyl]-1-isopropyl-1H-pyrrole-3-carboxylic acid ethyl ester (Step J2) was used instead of 2-[(3-chloro-2-fluoro-phenylamino)-(4-cyano-phenyl)-methyl]-1-isopropyl-1H-pyrrole-3-carboxylic acid ethyl ester to afford the title compound as a yellow solid. $t_R$: 5.22 min (HPLC 4); ESI-MS: $t_R$=1.09 min, [M+H]$^+$390/392 (LC-MS 1).

Step J2: 2-[(5-Chloro-2-methyl-phenylamino)-(4-cyano-phenyl)-methyl]-1-isopropyl-1H-pyrrole-3-carboxylic acid ethyl ester

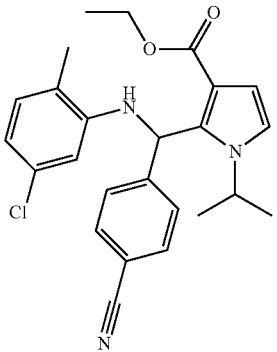 [SMILES: CCOC(=O)c1ccn(C(C)C)c1C(Nc1cc(Cl)ccc1C)c1ccc(C#N)cc1]

The title compound was prepared in analogy to the procedure described for Step H2, but 5-chloro-2-methylaniline was used instead of 3-chloro-4-fluoroaniline to afford the title compound as a white-yellow foam. $t_R$: 6.12 min (HPLC 4); ESI-MS: [M−H] 434/436 (MS 1).

Intermediate K: 2-Bromo-5-(5-chloro-2-methyl-phenyl)-6-(4-chloro-phenyl)-1-ethyl-5,6-dihydro-1H-pyrrolo[3,4-b]pyrrol-4-one

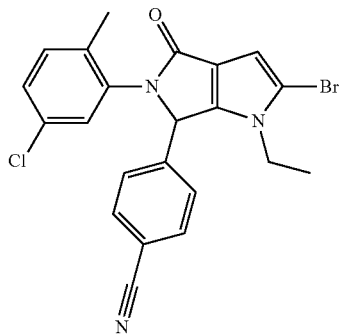 [SMILES: CCn1c(Br)cc2c1C(c1ccc(C#N)cc1)N(c1cc(Cl)ccc1C)C2=O]

A solution of 5-bromo-2-[(5-chloro-2-methyl-phenylamino)-(4-chloro-phenyl)-methyl]-1-ethyl-1H-pyrrole-3-carboxylic acid (Step K1) (3.11 mmol), TBTU (4.36 mmol) and DIEA (9.33 mmol) was stirred at 80° C. for 1 h. The reaction mixture was diluted with H$_2$O and extracted with EtOAc (2×). The combined organic layers were washed successively with H$_2$O and brine, dried (MgSO$_4$), filtered and concentrated. The product was purified by chromatography column to afford the title compound as a colorless oil. $t_R$: 5.90 min (HPLC 4); ESI-MS: $t_R$=1.35 min, [M+H]$^+$ not ionized (LC-MS 1).

Step K1: 5-Bromo-2-[(5-chloro-2-methyl-phenylamino)-(4-chloro-phenyl)-methyl]-1-ethyl-1H-pyrrole-3-carboxylic acid

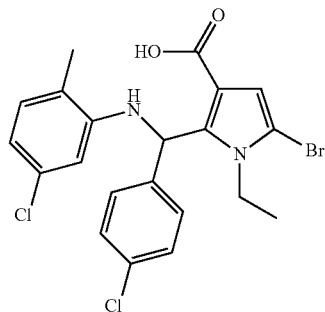 [SMILES: CCn1c(Br)cc(C(=O)O)c1C(Nc1cc(Cl)ccc1C)c1ccc(Cl)cc1]

The title compound was prepared in analogy to the procedure described for Step D1 but 5-bromo-2-[(5-chloro-2-methyl-phenylamino)-(4-chloro-phenyl)-methyl]-1-ethyl-1H-pyrrole-3-carboxylic acid ethyl ester (Step K2) was used instead of was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound as a colorless oil. $t_R$: 5.97 min (HPLC 4); ESI-MS: $t_R$=1.41 min, [M−H] 479/481/483 (LC-MS 1).

Step K2: 5-Bromo-2-[(5-chloro-2-methyl-phenylamino)-(4-chloro-phenyl)-methyl]-1-ethyl-1H-pyrrole-3-carboxylic acid ethyl ester

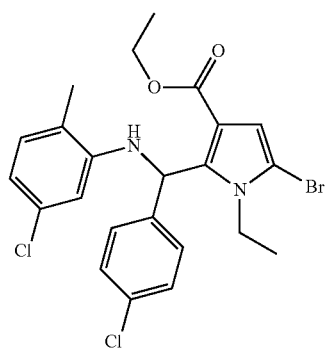 [SMILES: CCOC(=O)c1cc(Br)n(CC)c1C(Nc1cc(Cl)ccc1C)c1ccc(Cl)cc1]

The title compound was prepared in analogy to the procedure described for Step H2, but 5-bromo-2-[chloro-(4-chloro-phenyl)-methyl]-1-ethyl-1H-pyrrole-3-carboxylic acid ethyl ester (Step K3) was used instead of 2-[chloro-(4-cyano-phenyl)-methyl]-1-isopropyl-1H-pyrrole-3-carboxylic acid ethyl ester to afford the title compound as a colorless oil. $t_R$: 6.69 min (HPLC 4); ESI-MS: $t_R$=1.57 min, [M+H]$^+$ 511 (LC-MS 1).

Step K3: 5-Bromo-2-[chloro-(4-chloro-phenyl)-methyl]-1-ethyl-1H-pyrrole-3-carboxylic acid ethyl ester

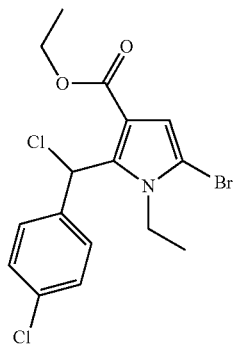 [SMILES: CCOC(=O)c1cc(Br)n(CC)c1C(Cl)c1ccc(Cl)cc1]

The title compound was prepared in analogy to the procedure described for Step H3, but 5-bromo-2-[(4-chloro-phenyl)-hydroxy-methyl]-1-ethyl-1H-pyrrole-3-carboxylic acid ethyl ester (Step K4) was used instead of 2-[(4-cyano-phenyl)hydroxy-methyl]-1-isopropyl-1H-pyrrole-3-carboxylic acid ethyl ester to afford the title compound. $t_R$: 6.52 min (HPLC 4).

Step K4: 5-Bromo-2-[(4-chloro-phenyl)-hydroxy-methyl]-1-ethyl-1H-pyrrole-3-carboxylic acid ethyl ester

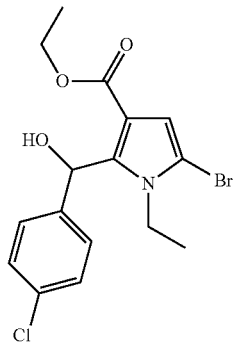 [SMILES: CCOC(=O)c1cc(Br)n(CC)c1C(O)c1ccc(Cl)cc1]

The title compound was prepared in analogy to the procedure described for Step D3, but 5-bromo-1-ethyl-1H-pyrrole-3-carboxylic acid ethyl ester (Step K5) was used instead of 5-bromo-1-isopropyl-1H-pyrrole-3-carboxylic acid methyl ester to afford the title compound as a beige solid. ESI-MS: $t_R$=1.34 min, [M]$^+$368/370/372 ("pyrrolium" ion) (LC-MS 1).

Step K5: 5-Bromo-1-ethyl-1H-pyrrole-3-carboxylic acid ethyl ester

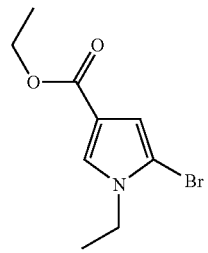

The title compound was prepared in analogy to the procedure described for Step D4, but 1-ethyl-1H-pyrrole-3-carboxylic acid ethyl ester (Step K6) was used instead of 1-isopropyl-1H-pyrrole-3-carboxylic acid methyl ester to afford the title compound as a colorless oil. $t_R$: 5.24 min (HPLC 4); ESI-MS: $t_R$=1.08 min, [M+H]$^+$ not ionized (LC-MS 1).

Step K6: 1-Ethyl-1H-pyrrole-3-carboxylic acid ethyl ester

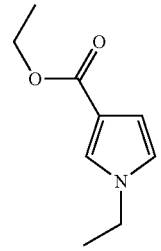

1H-Pyrrole-3-carboxylic acid [931-03-3] (22.50 mmol) was added to a solution of KOH (67.5 mmol) in DMSO (45 mL) and stirred at rt for 30 min. Then iodoethane [74-88-4] was added dropwise and the solution was stirred at 60° C. for 1.5 h. The mixture was cooled to rt, quenched with a 1N solution of KHSO4 and then extracted with EtOAc (4×). The combined organic layers were washed with brine, dried (MgSO$_4$), filtered and concentrated. The product was purified by chromatography column to afford the title compound. $t_R$: 4.57 min (HPLC 4); ESI-MS: $t_R$=0.89 min, [M+H]$^+$ 168 (LC-MS 1).

Intermediate L: 2-Bromo-5-(5-chloro-1-methyl-2-oxo-1,2-dihydro-pyridin-3-yl)-6-(4-chloro-phenyl)-1-isopropyl-5,6-dihydro-1H-pyrrolo[3,4-b]pyrrol-4-one

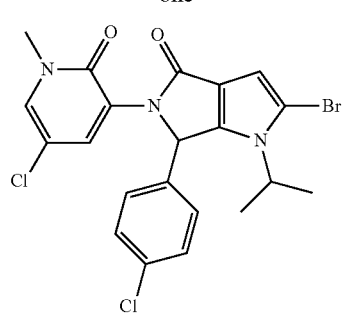

The title compound was prepared in analogy to the procedure described for Intermediate A, but 5-(5-chloro-1-methyl-2-oxo-1,2-dihydro-pyridin-3-yl)-6-(4-chloro-phenyl)-1-isopropyl-5,6-dihydro-1H-pyrrolo[3,4-b]pyrrol-4-one (Step L1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one to afford the title compound as a white solid. ESI-MS: $t_R$=1.19 min, [M+H]$^+$ 494/496/498 (LC-MS 1).

Step L1: 5-(5-Chloro-1-methyl-2-oxo-1,2-dihydro-pyridin-3-yl)-6-(4-chloro-phenyl)-1-isopropyl-5,6-dihydro-1H-pyrrolo[3,4-b]pyrol-4-one

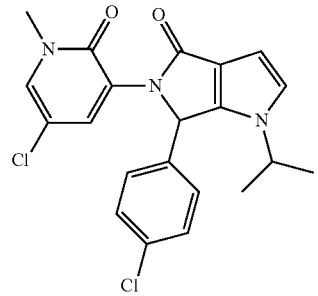 [SMILES: CC(C)n1ccc2c1C(c1ccc(Cl)cc1)N(c1cc(Cl)cn(C)c1=O)C2=O]

The title compound was prepared in analogy to the procedure described for Intermediate K, but 2-[(5-chloro-1-methyl-2-oxo-1,2-dihydro-pyridin-3-ylamino)-(4-chloro-phenyl)-methyl]-1-isopropyl-1H-pyrrole-3-carboxylic acid (Step L2) was used instead of 5-bromo-2-[(5-chloro-2-methyl-phenylamino)-(4-chloro-phenyl)-methyl]-1-ethyl-1H-pyrrole-3-carboxylic acid to afford the title compound as an off-white solid. ESI-MS: $t_R$=1.08 min, [M+H]$^+$ 416/418 (LC-MS 1).

Step L2: 2-[(5-Chloro-1-methyl-2-oxo-1,2-dihydro-pyridin-3-ylamino)-(4-chloro-phenyl)-methyl]-1-isopropyl-1H-pyrrole-3-carboxylic acid

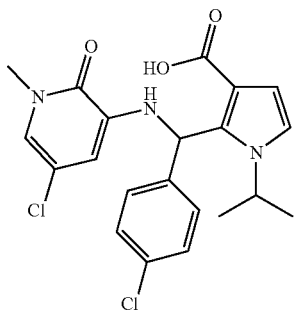 [SMILES: CC(C)n1ccc(C(=O)O)c1C(Nc1cc(Cl)cn(C)c1=O)c1ccc(Cl)cc1]

The title compound was prepared in analogy to the procedure described for Step D1 but 2-[(5-chloro-1-methyl-2-oxo-1,2-dihydro-pyridin-3-ylamino)-(4-chloro-phenyl)-methyl]-1-isopropyl-1H-pyrrole-3-carboxylic acid ethyl ester (Step L3) was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound as a white solid. ESI-MS: $t_R$=1.11 min, [M+H]$^+$ 434/436 (LC-MS 1).

Step L3: 2-[(5-Chloro-1-methyl-2-oxo-1,2-dihydro-pyridin-3-ylamino)-(4-chloro-phenyl)-methyl]-1-isopropyl-1H-pyrrole-3-carboxylic acid ethyl ester

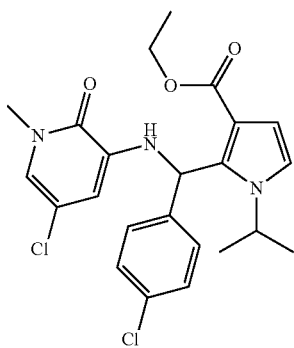 [SMILES: CCOC(=O)c1ccn(C(C)C)c1C(Nc1cc(Cl)cn(C)c1=O)c1ccc(Cl)cc1]

Ms$_2$O (18.65 mmol) was added at −30° C. to a solution of 2-[(4-chloro-phenyl)-hydroxy-methyl]-1-isopropyl-1H-pyrrole-3-carboxylic acid ethyl ester (Step E4) (9.32 mmol) and Et$_3$N (46.6 mmol) in CH$_2$Cl$_2$ (60 mL) and stirred at −30° C. for 15 min. 3-Amino-5-chloro-1-methyl-1H-pyridin-2-one (Step L4) (11.19 mmol) was added and the mixture was stirred at −10° C. for 30 min. The mixture was diluted with H$_2$O and extracted with CH$_2$Cl$_2$ (3×). The combined organic phases were washed successively with H$_2$O and brine, dried (Na$_2$SO$_4$), filtered and concentrated. The residue was purified by flash chromatography to afford the title compound as a white solid. ESI-MS: $t_R$=1.37 min, [M+]$^+$462/464 (LC-MS 1).

Step L4: 3-Amino-5-chloro-1-methyl-1H-pyridin-2-one

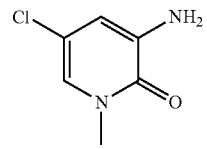

The title compound was prepared in analogy to the procedure for Step E5, but 5-chloro-1-methyl-3-nitro-1H-pyridin-2-one (Step L5) was used instead of 3-chloro-1-methyl-5-nitro-1H-pyridin-2-one to afford the title compound as a gray solid. ESI-MS: $t_R$=0.54 min, [M+H]$^+$ 159/161 (LC-MS 1).

Step L5: 5-Chloro-1-methyl-3-nitro-1H-pyridin-2-one

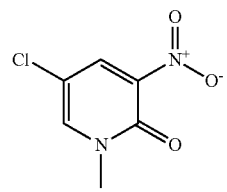

NaH (52.6 mmol) was slowly added at 5° C. to a solution of 5-chloro-2-hydroxy-3-nitropyridine [21427-61-2] (43.8 mmol) and the mixture was stirred at 5° C. for 30 min. Methyl iodide (65.7 mmol) was added and the mixture was stirred at rt for 20 h. The mixture was diluted with H$_2$O and extracted with EtOAc (3×). The combined organic phases were washed successively with H$_2$O and brine, dried (Na$_2$SO$_4$), filtered and concentrated to afford the title compound. ESI-MS: $t_R$=0.55 min, [M+H]$^+$ 189/191 (LC-MS 1).

Intermediate M: 2-Bromo-5-(5-chloro-2-oxo-1,2-dihydro-pyridin-3-yl)-6-(4-chloro-phenyl)-1-isopropyl-5,6-dihydro-1H-pyrrolo[3,4-b]pyrrol-4-one

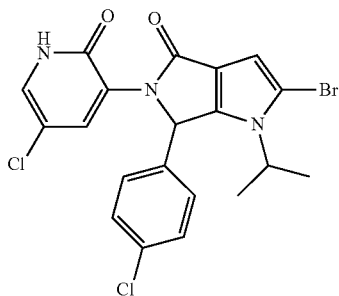 [SMILES: CC(C)n1c(Br)cc2c1C(c1ccc(Cl)cc1)N(c1cc(Cl)c[nH]c1=O)C2=O]

The title compound was prepared in analogy to the procedure described for Intermediate A, but 5-(5-chloro-2-oxo-1,2-dihydro-pyridin-3-yl)-6-(4-chloro-phenyl)-1-isopropyl-5,6-dihydro-1H-pyrrolo[3,4-b]pyrrol-4-one (Step M1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one to afford the title compound as a white solid. ESI-MS: $t_R$=1.12 min, [M+H]$^+$ 480/482/484 (LC-MS 1).

Step M1: 5-(5-Chloro-2-oxo-1,2-dihydro-pyridin-3-yl)-6-(4-chloro-phenyl)-1-isopropyl-5,6-dihydro-1H-pyrrolo[3,4-b]pyrrol-4-one

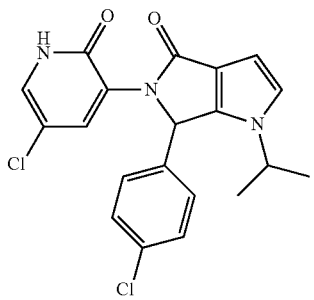 [SMILES: CC(C)n1ccc2c1C(c1ccc(Cl)cc1)N(c1cc(Cl)c[nH]c1=O)C2=O]

The title compound was prepared in analogy to the procedure described for Intermediate K, but 2-[(5-chloro-2-oxo-1,2-dihydro-pyridin-3-ylamino)-(4-chloro-phenyl)-methyl]-1-isopropyl-1H-pyrrole-3-carboxylic acid (Step M2) was used instead of 5-bromo-2-[(5-chloro-2-methyl-phenylamino)-(4-chloro-phenyl)-methyl]-1-ethyl-1H-pyrrole-3-carboxylic acid to afford the title compound as an off-white solid. ESI-MS: $t_R$=0.99 min, [M+H]$^+$ 402/404 (LC-MS 1).

Step M2: 2-[(5-Chloro-2-oxo-1,2-dihydro-pyridin-3-ylamino)-(4-chloro-phenyl)-methyl]-1-isopropyl-1H-pyrrole-3-carboxylic acid

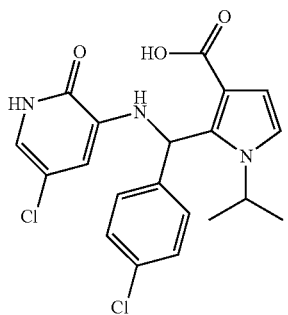 [SMILES: CC(C)n1ccc(C(=O)O)c1C(Nc1cc(Cl)c[nH]c1=O)c1ccc(Cl)cc1]

The title compound was prepared in analogy to the procedure described for Step D1 but 2-[(5-chloro-2-oxo-1,2-dihydro-pyridin-3-ylamino)-(4-chloro-phenyl)-methyl]-1-isopropyl-1H-pyrrole-3-carboxylic acid ethyl ester (Step M3) was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound as a white solid. ESI-MS: $t_R$=1.02 min, [M+H]$^+$ 420/422 (LC-MS 1).

Step M3: 2-[(5-Chloro-2-oxo-1,2-dihydro-pyridin-3-ylamino)-(4-chloro-phenyl)-methyl]-1-isopropyl-1H-pyrrole-3-carboxylic acid ethyl ester

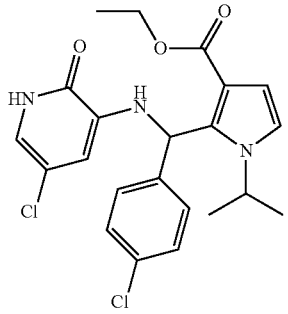 [SMILES: CCOC(=O)c1ccn(C(C)C)c1C(Nc1cc(Cl)c[nH]c1=O)c1ccc(Cl)cc1]

The title compound was prepared in analogy to the procedure described for Step L3 but 3-amino-5-chloro-1H-pyridin-2-one [98027-36-2] was used instead of 3-amino-5-chloro-1-methyl-1H-pyridin-2-one and the reaction was done at −78° C. to afford the title compound as a white solid. ESI-MS: $t_R$=1.02 min, [M+H]$^+$ 420/422 (LC-MS 1).

Intermediate N: 2-Bromo-5-(5-chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one

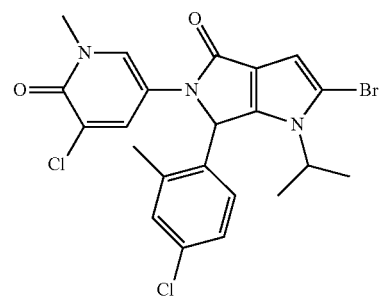 [SMILES: Cc1cc(Cl)ccc1C1c2c(cc(Br)n2C(C)C)C(=O)N1c1cc(Cl)c(=O)n(C)c1]

The title compound was prepared in analogy to the procedure described for Intermediate A, but 5-(5-chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one (Step N1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one and THF was used instead of CCl$_4$ to afford the title compound as a brown solid. $t_R$: 6.96 min (HPLC 2); ESI-MS: $t_R$=1.14 min, [M+H]$^+$ 508/510/512 (LC-MS 1); TLC: R$_f$=0.24 (EtOAc).

Step N1: 5-(5-Chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one

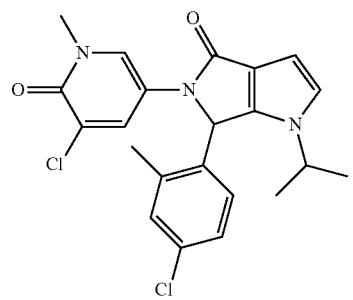 [SMILES: Cc1cc(Cl)ccc1C1c2c(ccn2C(C)C)C(=O)N1c1cc(Cl)c(=O)n(C)c1]

The title compound was prepared in analogy to the procedure described for Step A1, but 2-[(5-chloro-1-methyl-6-oxo-1,6-dihydro-pyridin-3-ylamino)-(4-chloro-2-methyl-phenyl)-methyl]-1-isopropyl-1H-pyrrole-3-carboxylic acid (Step N2) was used instead of 2-[(3-chloro-2-fluoro-phenylamino)-(4-chloro-2-methyl-phenyl)-methyl]-1-isopropyl-1H-pyrrole-3-carboxylic acid to afford the title compound as a brown solid. $t_R$: 6.41 min (HPLC 2); ESI-MS: $t_R$=1.02 min, [M+H]$^+$ 430/432 (LC-MS 1); TLC: R$_f$=0.20 (EtOAc).

Step N2: 2-[(5-Chloro-1-methyl-6-oxo-1,6-dihydro-pyridin-3-ylamino)-(4-chloro-2-methyl-phenyl)-methyl]-1-isopropyl-1H-pyrrole-3-carboxylic acid

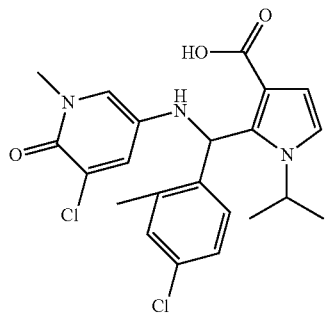 [SMILES: Cc1cc(Cl)ccc1C(Nc1cc(Cl)c(=O)n(C)c1)c1c(C(=O)O)ccn1C(C)C]

The title compound was prepared in analogy to the procedure described for Step D1 but 2-[(5-chloro-1-methyl-6-oxo-1,6-dihydro-pyridin-3-ylamino)-(4-chloro-2-methyl-phenyl)-methyl]-1-isopropyl-1H-pyrrole-3-carboxylic acid ethyl ester (Step N3) was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound (partially cyclized) as a dark purple foam. $t_R$: 4.36 min (HPLC 1); ESI-MS: $t_R$=1.04 min, [M+H]$^+$ 448/450/452 (LC-MS 1).

Step N3: 2-[(5-Chloro-1-methyl-6-oxo-1,6-dihydro-pyridin-3-ylamino)-(4-chloro-2-methyl-phenyl)-methyl]-1-isopropyl-1H-pyrrole-3-carboxylic acid ethyl ester

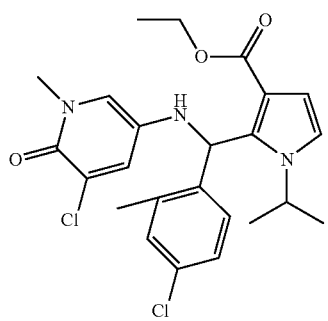 [SMILES: CCOC(=O)c1ccn(C(C)C)c1C(Nc1cc(Cl)c(=O)n(C)c1)c1ccc(Cl)cc1C]

The title compound was prepared in analogy to the procedure described for Step D2, but 2-[(4-chloro-2-methyl-phenyl)-hydroxy-methyl]-1-isopropyl-1H-pyrrole-3-carboxylic acid ethyl ester (Step A4) and 5-amino-3-chloro-1-methyl-1H-pyridin-2-one (Step E5) were used instead of 5-bromo-2-[(4-chloro-phenyl)-hydroxy-methyl]-1-isopropyl-1H-pyrrole-3-carboxylic acid methyl ester and 3-chloro-4-fluoroaniline respectively to afford the title compound as a dark blue-green foam. $t_R$: 5.19 min (HPLC 1); ESI-MS: $t_R$=1.27 min, [M+H]$^+$ 476/478/480 (LC-MS 1); TLC: $R_f$=0.53 (EtOAc).

Intermediate O: 2-Bromo-5-[5-chloro-1-(4-methoxy-benzyl)-6-oxo-1,6-dihydro-pyridin-3-yl]-6-(4-chloro-phenyl)-1-isopropyl-5,6-dihydro-1H-pyrrolo[3,4-b]pyrrol-4-one

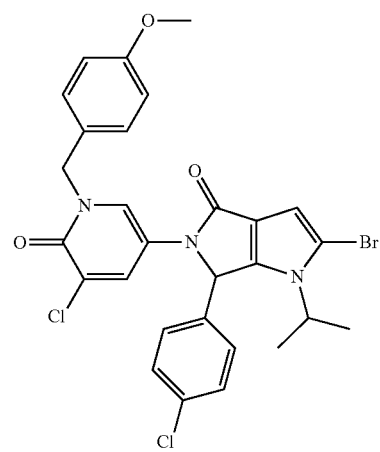 [SMILES: COc1ccc(Cn2cc(N3C(=O)c4cc(Br)n(C(C)C)c4C3c3ccc(Cl)cc3)cc(Cl)c2=O)cc1]

The title compound was prepared in analogy to the procedure described for Intermediate N, but 5-[5-chloro-1-(4-methoxy-benzyl)-6-oxo-1,6-dihydro-pyridin-3-yl]-6-(4-chloro-phenyl)-1-isopropyl-5,6-dihydro-1H-pyrrolo[3,4-b]pyrrol-4-one (Step O1) was used instead of 5-(5-chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one to afford the title compound as a pink solid. $t_R$: 7.33 min (HPLC 2); ESI-MS: $t_R$=1.25 min, [M+H]$^+$ 600/602/604 (LC-MS 1); TLC: $R_f$=0.31 (1:2 EtOAc/hexanes).

Step O1: 5-[5-Chloro-1-(4-methoxy-benzyl)-6-oxo-1,6-dihydro-pyridin-3-yl]-6-(4-chloro-phenyl)-1-isopropyl-5,6-dihydro-1H-pyrrolo[3,4-b]pyrrol-4-one

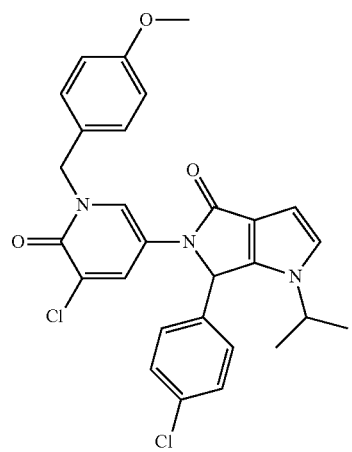 [SMILES: COc1ccc(Cn2cc(N3C(=O)c4ccn(C(C)C)c4C3c3ccc(Cl)cc3)cc(Cl)c2=O)cc1]

1-Chloro-N,N,2-trimethylpropenylamine [26189-59-3] (2.90 mmol) was added to a solution of 2-[[5-chloro-1-(4- methoxy-benzyl)-6-oxo-1,6-dihydro-pyridin-3-ylamino]-(4-chloro-phenyl)-methyl]-1-isopropyl-1H-pyrrole-3-carboxylic acid (Step O2) (1.943 mmol) in CH$_2$Cl$_2$ (20 mL) at 0° C. After stirring for 2 h, the reaction mixture was diluted with CH$_2$Cl$_2$ and successively washed with a saturated aqueous solution of NaHCO$_3$ and brine, dried (Na$_2$SO$_4$), filtered and concentrated. The residue was purified using a RediSep® silica gel column to afford the title compound as a light brown solid. $t_R$: 6.81 min (HPLC 2); ESI-MS: $t_R$=1.13 min, [M+H]$^+$ 522/524/526 (LC-MS 1); TLC: R$_f$=0.48 (EtOAc).

Step O2: 2-[[5-Chloro-1-(4-methoxy-benzyl)-6-oxo-1,6-dihydro-pyridin-3-ylamino]-(4-chloro-phenyl)-methyl]-1-isopropyl-1H-pyrrole-3-carboxylic acid

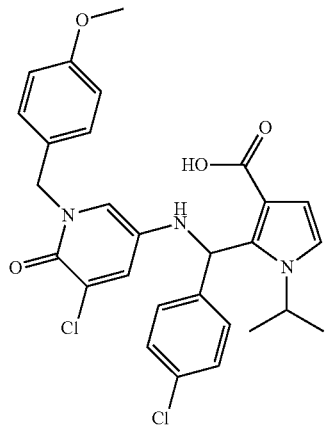 [SMILES: COc1ccc(Cn2cc(NC(c3ccc(Cl)cc3)c3c(C(=O)O)ccn3C(C)C)cc(Cl)c2=O)cc1]

The title compound was prepared in analogy to the procedure described for Step D1 but 2-[[5-chloro-1-(4-methoxy-benzyl)-6-oxo-1,6-dihydro-pyridin-3-ylamino]-(4-chloro-phenyl)-methyl]-1-isopropyl-1H-pyrrole-3-carboxylic acid ethyl ester (Step O3) was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound (partially cyclized) as a brown foam. $t_R$: 6.75 min (HPLC 2); ESI-MS: $t_R$=1.11 min, [M+H]$^+$ 540/542/544 (LC-MS 1).

Step O3: 2-[[5-Chloro-1-(4-methoxy-benzyl)-6-oxo-1,6-dihydro-pyridin-3-ylamino]-(4-chloro-phenyl)-methyl]-1-isopropyl-1H-pyrrole-3-carboxylic acid ethyl ester

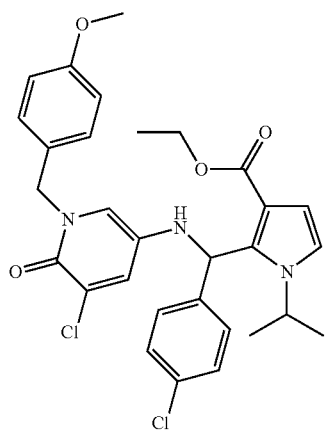 [SMILES: CCOC(=O)c1ccn(C(C)C)c1C(Nc1cc(Cl)c(=O)n(Cc2ccc(OC)cc2)c1)c1ccc(Cl)cc1]

The title compound was prepared in analogy to the procedure described for Step D2, but 2-[(4-chloro-phenyl)-hydroxy-methyl]-1-isopropyl-1H-pyrrole-3-carboxylic acid ethyl ester (Step E4) and 5-amino-3-chloro-1-(4-methoxy-benzyl)-1H-pyridin-2-one (Step O4) were used instead of 5-bromo-2-[(4-chloro-phenyl)-hydroxy-methyl]-1-isopropyl-1H-pyrrole-3-carboxylic acid methyl ester and 3-chloro-4-fluoroaniline respectively to afford the title compound as a green-blue foam. $t_R$: 5.47 min (HPLC 1); ESI-MS: $t_R$=1.33 min, [M+H]$^+$ 568/570/572 (LC-MS 1); TLC: R$_f$=0.30 (1:1 EtOAc/heptanes).

Step O4: 5-Amino-3-chloro-1-(4-methoxy-benzyl)-1H-pyridin-2-one

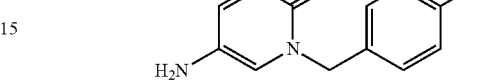

A saturated aqueous solution of NH$_4$Cl (99 mL) was added to a solution of 3-chloro-1-(4-methoxy-benzyl)-5-nitro-1H-pyridin-2-one (Step O5) (6.8 g, 23.0 mmol) in EtOH (300 mL). After stirring for 15 min, iron powder (6.4 g, 115 mmol) was added and the resulting mixture was heated to reflux, stirred for 1 h, cooled to rt and concentrated. The residue was diluted with EtOH and the mixture was filtered through a pad of celite. The filtrate was concentrated. The residue was purified by silica gel column chromatography (CH$_2$Cl$_2$/MeOH, 100:0→96.5:3.5). ESI-MS: $t_R$=0.61 min, [M+H]$^+$ 265/267 (LC-MS 1); R$_f$=0.53 (9:1 CH$_2$Cl$_2$/MeOH).

Step O5: 3-Chloro-1-(4-methoxy-benzyl)-5-nitro-1H-pyridin-2-one

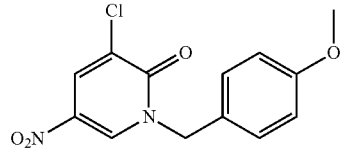 [SMILES: COc1ccc(Cn2cc([N+](=O)[O-])cc(Cl)c2=O)cc1]

4-Methoxybenzyl bromide (5.0 mL, 34.4 mmol) was added to a cold (0° C.) mixture 3-chloro-2-hydroxy-5-nitro-pyridine (5 g, 28.6 mmol) and K$_2$CO$_3$ (7.9 g, 57.3 mmol) in DMF (25 mL). The reaction mixture was allowed to warm to rt, stirred for 2 h, quenched by addition of a saturated aqueous NaHCO$_3$ solution, and extracted with EtOAc. The organic layer was washed with brine, dried (Na$_2$SO$_4$), filtered, and concentrated. The residue was purified by trituration in EtOAc. ESI-MS: $t_R$=0.98 min (LC-MS 1).

Intermediate P: 2-Bromo-6-(4-chloro-phenyl)-5-(1,3-dimethyl-2-oxo-hexahydro-pyrimidin-5-yl)-1-isopropyl-5,6-dihydro-1H-pyrrolo[3,4-b]pyrrol-4-one

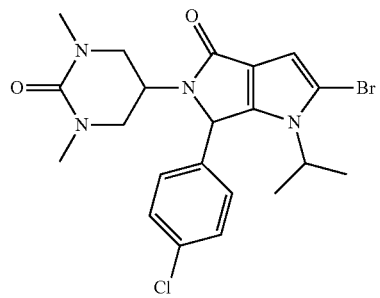 [SMILES: CC(C)n1c(Br)cc2c1C(c1ccc(Cl)cc1)N(C1CN(C)C(=O)N(C)C1)C2=O]

The title compound was prepared in analogy to the procedure described for Intermediate N, but 6-(4-chloro-phenyl)-5-(1,3-dimethyl-2-oxo-hexahydro-pyrimidin-5-yl)-1-isopropyl-5,6-dihydro-1H-pyrrolo[3,4-b]pyrrol-4-one (Step P1) was used instead of 5-(5-chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one to afford the title compound as a solid. $t_R$: 3.19 min (HPLC 5); ESI-MS: $t_R$=1.07 min, [M+H]$^+$ 479/481/483 (LC-MS 1).

Step P1: 6-(4-Chloro-phenyl)-5-(1,3-dimethyl-2-oxo-hexahydro-pyrimidin-5-yl)-1-isopropyl-5,6-dihydro-1H-pyrrolo[3,4-b]pyrrol-4-one

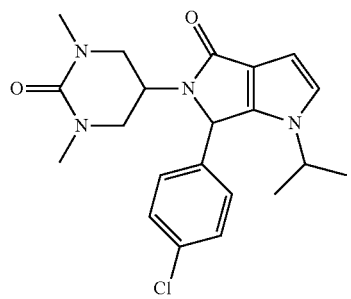 [SMILES: CC(C)n1ccc2c1C(c1ccc(Cl)cc1)N(C1CN(C)C(=O)N(C)C1)C2=O]

The title compound was prepared in analogy to the procedure described for Step A1, but 2-[(4-chloro-phenyl)-(1,3-dimethyl-2-oxo-hexahydro-pyrimidin-5-ylamino)-methyl]-1-isopropyl-1H-pyrrole-3-carboxylic acid (Step P2) was used instead of 2-[(3-chloro-2-fluoro-phenylamino)-(4-chloro-2-methyl-phenyl)-methyl]-1-isopropyl-1H-pyrrole-3-carboxylic acid to afford the title compound as a yellow oil. $t_R$: 2.88 min (HPLC 5); ESI-MS: $t_R$=0.94 min, [M+H]$^+$ 401/403 (LC-MS 1).

Step P2: 2-[(4-Chloro-phenyl)-(1,3-dimethyl-2-oxo-hexahydro-pyrimidin-5-ylamino)-methyl]-1-isopropyl-1H-pyrrole-3-carboxylic acid

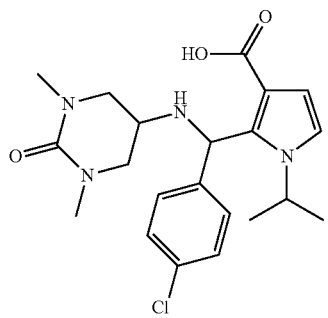 [SMILES: CC(C)n1ccc(C(=O)O)c1C(NC1CN(C)C(=O)N(C)C1)c1ccc(Cl)cc1]

The title compound was prepared in analogy to the procedure described for Step D1 but 2-[(4-chloro-phenyl)-(1,3-dimethyl-2-oxo-hexahydro-pyrimidin-5-ylamino)-methyl]-1-isopropyl-1H-pyrrole-3-carboxylic acid ethyl ester (Step P3) was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound as a beige solid. $t_R$: 2.54 min (HPLC 5); ESI-MS: $t_R$=0.81 min, [M+H]$^+$ 419/421 (LC-MS 1).

Step P3: 2-[(4-Chloro-phenyl)-(1,3-dimethyl-2-oxo-hexahydro-pyrimidin-5-ylamino)-methyl]-1-isopropyl-1H-pyrrole-3-carboxylic acid ethyl ester

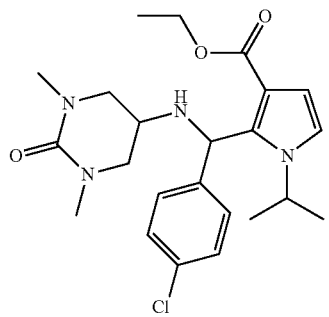 [SMILES: CCOC(=O)c1ccn(C(C)C)c1C(NC1CN(C)C(=O)N(C)C1)c1ccc(Cl)cc1]

The title compound was prepared in analogy to the procedure described for Step M3 but 5-amino-1,3-dimethyl-tetrahydro-pyrimidin-2-one (Step P4) was used instead of 3-amino-5-chloro-1H-pyridin-2-one to afford the title compound. $t_R$: 2.85 min (HPLC 5); ESI-MS: $t_R$=1.19 min, [M+H]$^+$ 447/449 (LC-MS 1).

Step P4: 5-Amino-1,3-dimethyl-tetrahydro-pyrimidin-2-one

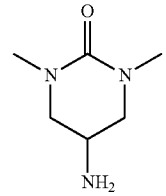

A mixture of 5-azido-1,3-dimethyl-tetrahydro-pyrimidin-2-one (Step P5) (2.5 g, 11.1 mmol) and Pd/C 10% (500 mg) in EtOH (70 mL) was stirred at rt under a hydrogen atmosphere for 13.5 h. The reaction mixture was filtered through a pad of celite, washed with THF and MeOH and concentrated. The residue was dissolved in EtOAc and extracted with cold 1N HCl. The aqueous phase was basified with a saturated aqueous NaHCO$_3$ solution. The resulting aqueous phase was extracted with CH$_2$Cl$_2$/isopropanol 3:1 (3×). The combined organic layers were dried (Na$_2$SO$_4$), filtered and concentrated to afford the title compound. ESI-MS: [M+H]$^+$ 144.1 (MS 1).

Step P5: 5-Azido-1,3-dimethyl-tetrahydro-pyrimidin-2-one

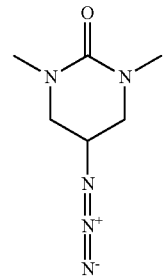

To a solution of methanesulfonic acid 1,3-dimethyl-2-oxo-hexahydro-pyrimidin-5-yl ester (Step P6) (3.2 g, 14.3 mmol) in DMF (75 mL) at rt was added sodium azide (1.9 g, 28.7 mmol) and the mixture was stirred at 70° C. for 13 h. The mixture was diluted with CH$_2$Cl$_2$/isopropanol 3:1 and extracted with a saturated aqueous NaHCO$_3$ solution. The organic phase was dried (Na$_2$SO$_4$), filtered and concentrated to afford the title compound. ESI-MS: [M+H]$^+$ 170.1 (MS 1).

Step P6: Methanesulfonic acid 1,3-dimethyl-2-oxo-hexahydro-pyrimidin-5-yl ester

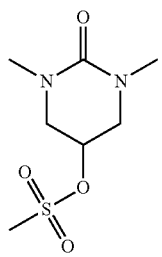

The title compound was prepared in analogy to the mesylation procedure described for Step L3 but using 5-hydroxy-1,3-dimethyl-tetrahydro-pyrimidin-2-one (Step P7) instead of 2-[(4-chloro-phenyl)-hydroxy-methyl]-1-isopropyl-1H-pyrrole-3-carboxylic acid ethyl ester. The reaction mixture was diluted with H$_2$O and a saturated aqueous NaHCO$_3$ solution and extracted with CH$_2$Cl$_2$/isopropanol 3:1 (3×). The combined organic layers were dried (Na$_2$SO$_4$), filtered and concentrated to afford the title compound. ESI-MS: 223.1 [M+H]$^+$ (MS 1).

Step P7: 5-Hydroxy-1,3-dimethyl-tetrahydro-pyrimidin-2-one

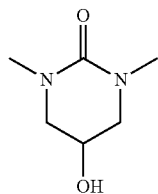

To a solution of 1,3-dimethyl-5-triisopropylsilanyloxy-tetrahydro-pyrimidin-2-one (Step P8) (9.1 g, 28 mmol) in EtOH (70 mL) was added a 1M HCl (140 mL, 140 mmol) and the mixture was stirred for 3 h at 70° C. The mixture was concentrated, and the pH of the resulting aqueous phase was adjusted to 5 with a saturated aqueous NaHCO$_3$ solution. The aqueous layer was saturated with NaCl and was extracted with CH$_2$Cl$_2$/isopropanol 3:1. The organic layer was dried (Na$_2$SO$_4$), filtered and concentrated to afford the title compound. ESI-MS: t$_R$=0.33 min, [M+H]$^+$ 145.1 (LC-MS 1).

Step P8: 1,3-Dimethyl-5-triisopropylsilanyloxy-tetrahydro-pyrimidin-2-one

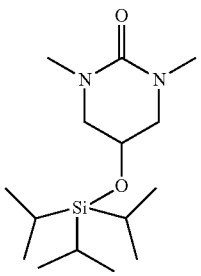 [SMILES: CC(C)[Si](OC1CN(C)C(=O)N(C)C1)(C(C)C)C(C)C]

NaH (141 mmol) was added portionwise to a solution of 5-triisopropylsilanyloxy-tetrahydro-pyrimidin-2-one (Step P9) (28.2 mmol) in DMF (200 mL) at 0° C. After 15 min, the reaction was warmed to rt. After 2 h, the mixture was cooled to 0° C., treated with methyl iodide (197 mmol) and then allowed to warm to rt overnight. The reaction mixture was quenched by addition of water and extracted with toluene. The aqueous layer was washed with EtOAc. The combined organic layers were washed with a saturated aqueous NaHCO$_3$ solution, dried (Na$_2$SO$_4$), filtered, and concentrated. The residue was used without further purification. ESI-MS: t$_R$=1.33 min, [M+H]$^+$ 301.3 (LC-MS 1).

Step P9: 5-Triisopropylsilanyloxy-tetrahydro-pyrimidin-2-one

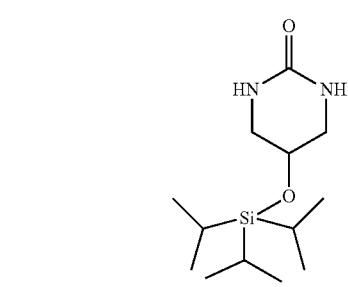 [SMILES: CC(C)[Si](OC1CNC(=O)NC1)(C(C)C)C(C)C]

To a solution of 2-triisopropylsilanyloxy-propane-1,3-diamine (Step P10) (27.8 g, 113 mmol) in MeOH (450 mL) was added S,S-dimethyl carbonodithioate (17.7 mL, 169 mmol) and the mixture was stirred at 60° C. for 20 h. The reaction mixture was concentrated. The residue was purified by flash chromatography(CH$_2$Cl$_2$/MeOH, 100:0→5:1) to afford the title compound. ESI-MS: [M+H]$^+$273.3 (LC-MS 1-flow injection).

Step P10: 2-Triisopropylsilanyloxy-propane-1,3-diamine

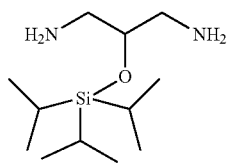 [SMILES: CC(C)[Si](OC(CN)CN)(C(C)C)C(C)C]

To a solution of 1,3-diaminopropan-2-ol (19.4 g, 215 mmol) in CH$_2$Cl$_2$ (250 mL) at 0° C. was added TIPS-Cl (50.2 mL, 237 mmol) and Et$_3$N (90 mL, 646 mmol) and the reaction mixture was stirred at rt for 20 h. The mixture was diluted with CH$_2$Cl$_2$. The organic layer was washed with a saturated aqueous NaHCO$_3$ solution, dried (Na$_2$SO$_4$), filtered and concentrated. The product was used without further purification. ESI-MS: [M+H]$^+$ 247.3 (LC-MS 1-flow injection).

Intermediate Q: 2-Bromo-6-(4-chloro-phenyl)-1-isopropyl-5-(1-methyl-6-oxo-piperidin-3-yl)-5,6-dihydro-1H-pyrrolo[3,4-b]pyrrol-4-one

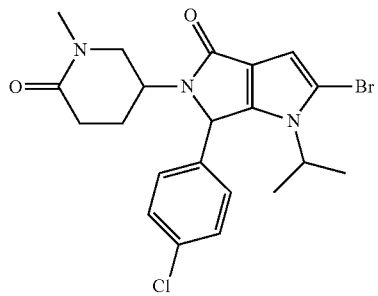 [SMILES: CC(C)n1c(Br)cc2c1C(c1ccc(Cl)cc1)N(C1CCC(=O)N(C)C1)C2=O]

The title compound was prepared in analogy to the procedure described for Intermediate A but 6-(4-chloro-phenyl)-1-isopropyl-5-(1-methyl-6-oxo-piperidin-3-yl)-5,6-dihydro-1H-pyrrolo[3,4-b]pyrrol-4-one (Step Q1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one. The title compound was obtained as a beige solid. t$_R$: 3.20 min (HPLC 5); ESI-MS: t$_R$=1.06 min, [M+H]$^+$ 464/466/468 (LC-MS 1).

Step Q1: 6-(4-Chloro-phenyl)-1-isopropyl-5-(1-methyl-6-oxo-piperidin-3-yl)-5,6-dihydro-1H-pyrrolo[3,4-b]pyrrol-4-one

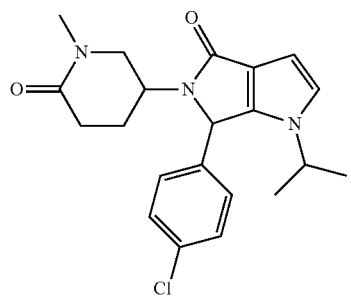 [SMILES: CC(C)n1ccc2c1C(c1ccc(Cl)cc1)N(C1CCC(=O)N(C)C1)C2=O]

The title compound was prepared in analogy to the procedure described for Step A1, but 2-[(4-chloro-phenyl)-(1-methyl-6-oxo-piperidin-3-ylamino)-methyl]-1-isopropyl-1H-pyrrole-3-carboxylic acid (Step Q2) was used instead of 2-[(3-chloro-2-fluoro-phenylamino)-(4-chloro-2-methyl-phenyl)-methyl]-1-isopropyl-1H-pyrrole-3-carboxylic acid to afford the title compound. t$_R$: 2.88 min (HPLC 5); ESI-MS: t$_R$=0.94 min, [M+H]$^+$ 386/388 (LC-MS 1).

Step Q2: 2-[(4-Chloro-phenyl)-(1-methyl-6-oxo-piperidin-3-ylamino)-methyl]-1-isopropyl-1H-pyrrole-3-carboxylic acid

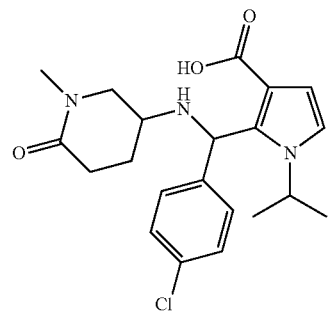 [SMILES: CC(C)n1ccc(C(=O)O)c1C(NC1CCC(=O)N(C)C1)c1ccc(Cl)cc1]

The title compound was prepared in analogy to the procedure described for Step D1 but 2-[(4-chloro-phenyl)-(1-methyl-6-oxo-piperidin-3-ylamino)-methyl]-1-isopropyl-1H-pyrrole-3-carboxylic acid ethyl ester (Step Q3) was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound as a solid. t$_R$: 2.50 min (HPLC 5); ESI-MS: t$_R$=0.77 min, [M+H]$^+$ 404/406 (LC-MS 1).

Step Q3: 2-[(4-Chloro-phenyl)-(1-methyl-6-oxo-piperidin-3-ylamino)-methyl]-1-isopropyl-1H-pyrrole-3-carboxylic acid ethyl ester

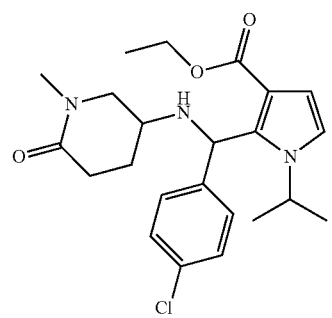 [SMILES: CCOC(=O)c1ccn(C(C)C)c1C(NC1CCC(=O)N(C)C1)c1ccc(Cl)cc1]

The title compound was prepared in analogy to the procedure described for Step D2, but 2-[(4-chloro-phenyl)-hydroxy-methyl]-1-isopropyl-1H-pyrrole-3-carboxylic acid ethyl ester (Step E4) and 5-amino-1-methylpiperidin-2-one [1228838-10-5] (free base was made from the purchased HCl salt) were used instead of 5-bromo-2-[(4-chloro-phenyl)hydroxy-methyl]-1-isopropyl-1H-pyrrole-3-carboxylic acid methyl ester and 3-chloro-4-fluoroaniline respectively to afford the title compound (diastereomeric mixture) as an off-white solid. t$_R$: 4.31 min (HPLC 1); ESI-MS: t$_R$=1.13/1.15 min, [M+H]$^+$ 432/434 (LC-MS 1); TLC: R$_f$=0.25 (EtOAc).

Intermediate R:
5-N-Methyl-carboxamido-2-methoxy-phenylboronic acid

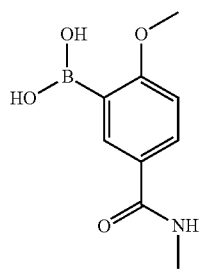

5-Carboxy-2-methoxyphenylboronic acid [730971-32-1] (1 mmol) was dissolved in DMF (6 mL) and methylamine (2 M solution in THF, 2 mmol) was added followed by HATU (1.1 mmol) and NMM (4 mmol). The reaction mixture was stirred at rt for 2 days and concentrated. The residue was dissolved with EtOAc and the organic solution washed with brine, dried ($Na_2SO_4$) and concentrated to give the crude product which was recrystallized from $CH_2Cl_2$ to give the title compound as a white solid. ESI-MS: $t_R$=0.47 min, [M+H]$^+$ 210 (LC-MS 1). $^1$H-NMR ($d_6$-DMSO, 400 MHz) 8.23 (b s, 1H), 8.00 (s, 1H), 7.83-7.85 (d, 1H), 6.98-7.00 (d, 1H), 3.81 (s, 3H), 2.72-2.73 (s, 3H).

Intermediate S:
5-Dimethylcarbamoyl-2-methoxyphenylboronic acid

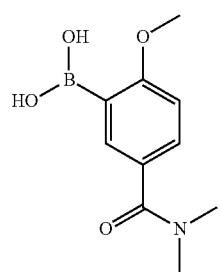 [SMILES: COc1ccc(C(=O)N(C)C)cc1B(O)O]

The title compound was prepared in analogy to the procedure described for Intermediate R, but dimethylamine (2M solution in THF) was used instead of methylamine. ESI-MS: $t_R$=0.56 min, [M+H]$^+$ 224 (LC-MS 1). $^1$H-NMR ($d_6$-DMSO, 400 MHz) 7.77 (s, 2H), 7.55 (d, 1H), 7.43 (dd, 1H), 6.97 (d, 1H), 3.81 (s, 3H), 2.93 (s, 6H).

Intermediate T: 4-Methoxy-5-(4,4,5,5-tetramethyl-[1,3,2]dioxaborolan-2-yl)-pyrimidine

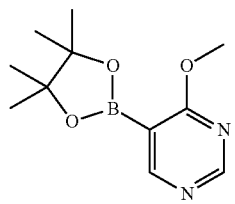

A mixture of 5-bromo-4-methoxy-pyrimidine (step T1) (15.9 mmol), bis(pinacolato)diboron (17.5 mmol), PdCl$_2$(dppf).CH$_2$Cl$_2$ adduct (0.794 mmol) and potassium acetate (47.6 mmol) in DMSO (2 mL) was stirred at 100° C. for 2 h, allowed to cool to rt, diluted with EtOAc/water, and extracted with EtOAc. The organic layer was washed successively with water and brine, dried (Na$_2$SO$_4$), filtered, and concentrated. The residue was boiled in diethyl ether and filtered. The filtrate was concentrated, triturated in hexanes, and filtered to afford the title compound as a yellow solid. ESI-MS: $t_R$=0.36 min, [M+H]$^+$ 155 (boronic acid) (LC-MS 2).

Step T1: 5-Bromo-4-methoxy-pyrimidine

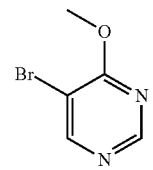

A mixture of 5-bromo-3H-pyrimidin-4-one (Step T2) (17.9 mmol) and POCl$_3$ (179 mmol) was stirred at 80° C. for 1 h and concentrated. The residue was dissolved in CH$_2$Cl$_2$ (30 mL) and cooled to 5° C. MeOH (20 mL) was added and the mixture was stirred for at rt 1 h and concentrated. The residue was triturated in CH$_2$Cl$_2$ to afford the title compound as a white solid. ESI-MS: [M+H]$^+$ 189/191 (MS 1).

Step T2: 5-Bromo-3H-pyrimidin-4-one

A mixture of 5-bromo-4-hydroxypymidine [19808-30-1] (114 mmol), bromine (126 mmol), and potassium acetate (343 mmol) in acetic acid (100 mL) was stirred at rt for 30 min. The resulting precipitate was filtered. The solid was dissolved in CH$_2$Cl$_2$/water and extracted with 9:1 CH$_2$Cl$_2$/MeOH (5×). The combined organic layer were dried (Na$_2$SO$_4$), filtered, and concentrated to afford the title compound as a white solid. ESI-MS: $t_R$=0.35 min, [M+H]$^+$ 175/177 (LC-MS 2).

Intermediate U: 4-Methoxy-5-(4,4,5,5-tetramethyl-[1,3,2]dioxaborolan-2-yl)-pyrimidin-2-ylamine

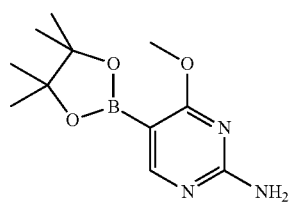 [SMILES: COc1nc(N)ncc1B1OC(C)(C)C(C)(C)O1]

A mixture of 2-amino-5-bromo-4-methoxypyrimidine [36082-45-8] (11.1 mmol), bis(pinacolato)diboron (12.2 mmol), PdCl$_2$(dppf).CH$_2$Cl$_2$ adduct (0.555 mmol) and potassium acetate (33.3 mmol) in dioxane (60 mL) was stirred at 115° C. under argon for 20 h, allowed to cool to rt, diluted with toluene (60 mL), sonicated, and filtered through celite. The celite cake was rinsed with hot toluene (2×). The filtrate was concentrated to afford the title compound (30% purity) which was used without purification. ESI-MS: $t_R$=0.22 min; [M+H]$^+$ 170 (boronic acid) (LC-MS 1).

Intermediate V: [4-Methoxy-5-(4,4,5,5-tetramethyl-[1,3,2]dioxaborolan-2-yl)-pyrimidin-2-yl]-methyl-amine

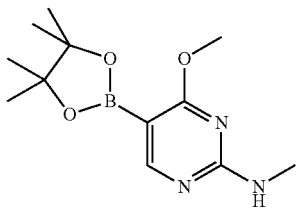

The title compound was prepared in analogy to the procedure described for Intermediate U, but 5-bromo-4-methoxy-pyrimidin-2-yl-methyl-amine (Step V1) was used instead of 2-amino-5-bromo-4-methoxypyrimidine. The reaction was performed at 105° C. for 16 h to afford the title compound (50% purity) as a brown oil. ESI-MS: $t_R$=0.35 min; [M+H]$^+$ 184 (boronic acid) (LC-MS 1).

Step V1:
5-Bromo-4-methoxy-pyrimidin-2-yl-methyl-amine

5-Bromo-2-chloro-4-methoxypyrimidine [57054-92-9] (8.68 mmol) and methylamine (2M in THF) (19.54 mmol) in THF (15 mL) were stirred at rt for 32 h and the reaction mixture was concentrated. The residue was purified by flash chromatography to afford the title compound as a white solid. ESI-MS: $t_R$=0.81 min, [M+H]$^+$ 218/220 (LC-MS 2).

Intermediate W: 4-Methoxy-N,N-dimethyl-5-(4,4,5,5-tetramethyl-1,3,2-dioxaborolan-2-yl)pyrimidin-2-amine

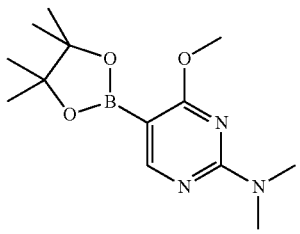

The title compound was prepared in analogy to the procedure described for intermediate V but (5-bromo-4-methoxy-pyrimidin-2-yl)-dimethyl-amine (Step W1) was used instead of 5-bromo-4-methoxy-pyrimidin-2-yl-methyl-amine to afford the title compound (50% purity) as a brown solid. ESI-MS: $t_R$=0.40 min, [M+H]$^+$ 198 (boronic acid) (LC-MS 1).

Step W1:
(5-Bromo-4-methoxy-pyrimidin-2-yl)-dimethyl-amine

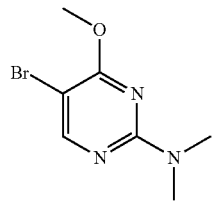

The title compound was prepared in analogy to the procedure described for Step V1, but dimethylamine (2M in THF) was used instead of methylamine to afford the title compound as a white solid. ESI-MS: $t_R$=1.04 min, [M+H]$^+$ 232/234 (LC-MS 1).

Intermediate X:
5-(Morpholine-4-carbonyl)-2-methoxyphenylboronic acid

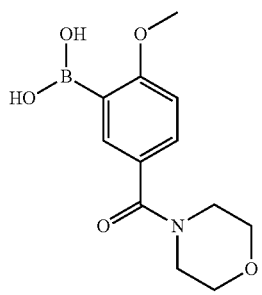 [SMILES: COc1ccc(C(=O)N2CCOCC2)cc1B(O)O]

The title compound was prepared in analogy to the procedure described for intermediate R but morpholine was used instead of methylamine to afford the title compound as a white solid. ESI-MS: $t_R$=0.53 min, [M+H]$^+$ 266 (LC-MS 1).

Intermediate Y: 2-(4-Methoxy-3-(4,4,5,5-tetramethyl-1,3,2-dioxaborolan-2-yl)phenyl)acetic acid

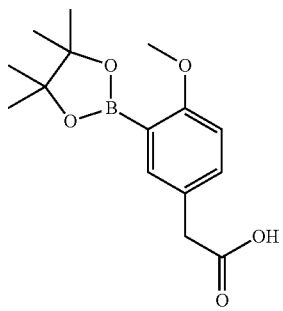 [SMILES: COc1ccc(CC(=O)O)cc1B1OC(C)(C)C(C)(C)O1]

The title compound was prepared in analogy to the procedure described for Intermediate U, but (3-bromo-4-methoxy-phenyl)-acetic acid [774-81-2] was used instead of 2-amino- 5-bromo-4-methoxypyrimidine. The reaction was performed at 100° C. for 17 h. The title compound (50% purity) was obtained as a brown oil. $t_R$: 4.18 min (HPLC 2); ESI-MS: [M−H]⁻ 291 (MS 1).

Intermediate Z: 4-Methoxy-3-(4,4,5,5-tetramethyl-[1,3,2]dioxaborolan-2-yl)-benzamide

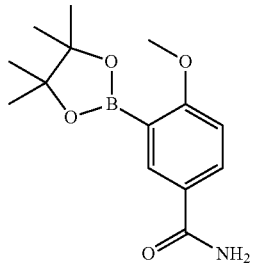 [SMILES: COc1ccc(C(N)=O)cc1B1OC(C)(C)C(C)(C)O1]

The title compound was prepared in analogy to the procedure described for Intermediate U, but 3-bromo-4-methoxy-benzamide [200956-55-4] was used instead of 2-amino-5-bromo-4-methoxypyrimidine to afford the title compound (77% purity) as a brown solid. $t_R$: 3.50 min (HPLC 2); ESI-MS: [M+H]⁺ 278 (MS 1).

Intermediate AA: 4-Methoxy-N-methyl-3-(4,4,5,5-tetramethyl-[1,3,2]dioxaborolan-2-yl)-benzenesulfonamide

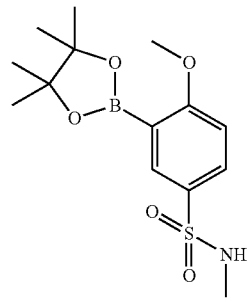

The title compound was prepared in analogy to the procedure described for Intermediate U, but 3-bromo-4-methoxy-N-methyl-benzenesulfonamide [358665-54-0] was used instead of 2-amino-5-bromo-4-methoxypyrimidine to afford the title compound (61% purity) as a brown solid. $t_R$: 4.10 min (HPLC 2); ESI-MS: [M+H]⁺ 328 (MS 1).

Intermediate AB: 2-[2-Bromo-6-(4-chloro-phenyl)-1-isopropyl-4-oxo-4,6-dihydro-1H-pyrrolo[3,4-b]pyrrol-5-yl]-4-chloro-benzonitrile

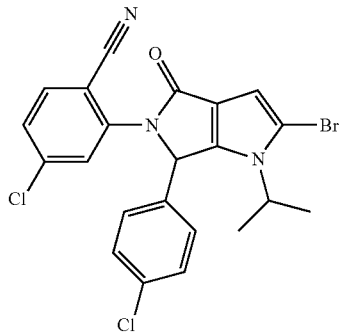 [SMILES: CC(C)n1c(Br)cc2c1C(c1ccc(Cl)cc1)N(c1cc(Cl)ccc1C#N)C2=O]

The title compound was prepared in analogy to the procedure described for Intermediate N, but 4-chloro-2-[6-(4-chloro-phenyl)-1-isopropyl-4-oxo-4,6-dihydro-1H-pyrrolo[3,4-b]pyrrol-5-yl]-benzonitrile (Step AB1) was used instead of 5-(5-chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one to afford the title compound as an off-white solid. $t_R$: 5.32 min (HPLC 1); ESI-MS: $t_R$=1.28 min, [M+H]⁺ 488/490/492 (LC-MS 1); TLC: $R_f$=0.15 (CH₂Cl₂).

Step AB1: 4-Chloro-2-[6-(4-chloro-phenyl)-1-isopropyl-4-oxo-4,6-dihydro-1H-pyrrolo[3,4-b]pyrrol-5-yl]-benzonitrile

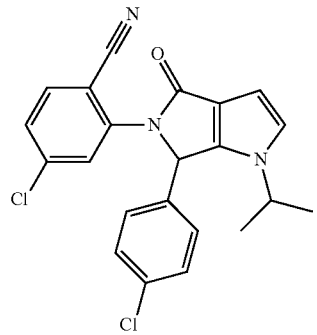 [SMILES: CC(C)n1ccc2c1C(c1ccc(Cl)cc1)N(c1cc(Cl)ccc1C#N)C2=O]

A solution of propylphosphonic anhydride (T3P/PPA) (50% in EtOAc) (7.13 mmol) was added dropwise to a solution of 4-chloro-2-[6-(4-chloro-phenyl)-1-isopropyl-4-oxo-4,6-dihydro-1H-pyrrolo[3,4-b]pyrrol-5-yl]benzamide (Step AB2) (3.10 mmol) and Et₃N (3.41 mmol) in EtOAc (25 mL) at 45° C. After 23 h, the reaction mixture was cooled to rt and partitioned between EtOAc and H₂O. The organice phase was successively washed with a saturated aqueous solution of NaHCO₃, water and brine, dried (Na₂SO₄), filtered and concentrated. The residue was purified using a RediSep® silica gel column to afford the title compound as a white solid. $t_R$: 4.97 min (HPLC 1); ESI-MS: $t_R$=1.19 min, [M+H]⁺ 410/412/414 (LC-MS 1); TLC: $R_f$=0.16 (1:3 EtOAc/heptanes).

Step AB2: 4-Chloro-2-[6-(4-chloro-phenyl)-1-isopropyl-4-oxo-4,6-dihydro-1H-pyrrolo[3,4-b]pyrrol-5-yl]-benzamide

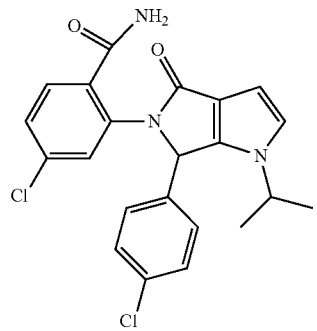 [SMILES: CC(C)n1ccc2c1C(c1ccc(Cl)cc1)N(c1cc(Cl)ccc1C(N)=O)C2=O]

The title compound was prepared in analogy to the procedure described for Step A1, but 2-[(2-carbamoyl-5-chloro-phenylamino)-(4-chloro-phenyl)-methyl]-1-isopropyl-1H-pyrrole-3-carboxylic acid (Step AB3) was used instead of 2-[(3-chloro-2-fluoro-phenylamino)-(4-chloro-2-methyl-phenyl)-methyl]-1-isopropyl-1H-pyrrole-3-carboxylic acid to afford the title compound as a pale yellow foam. $t_R$: 4.36 min (HPLC 1); ESI-MS: $t_R$=1.04 min, [M+H]⁺ 428/430/432 (LC-MS 1); TLC: $R_f$=0.46 (EtOAc).

Step AB3: 2-[(2-Carbamoyl-5-chloro-phenylamino)-(4-chloro-phenyl)-methyl]-1-isopropyl-1H-pyrrole-3-carboxylic acid

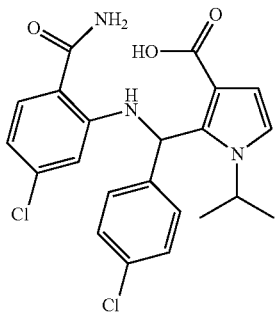 [SMILES: CC(C)n1ccc(C(=O)O)c1C(Nc1cc(Cl)ccc1C(N)=O)c1ccc(Cl)cc1]

The title compound was prepared in analogy to the procedure described for Step D1 but 2-[(5-chloro-2-cyano-phenylamino)-(4-chloro-phenyl)-methyl]-1-isopropyl-1H-pyrrole-3-carboxylic acid ethyl ester (Step AB4) was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound as a pale yellow solid. $t_R$: 4.57 min (HPLC 1); ESI-MS: $t_R$=1.09 min, [M+H]$^+$ 446/448/450 (LC-MS 1).

Step AB4: 2-[(5-Chloro-2-cyano-phenylamino)-(4-chloro-phenyl)-methyl]-1-isopropyl-1H-pyrrole-3-carboxylic acid ethyl ester

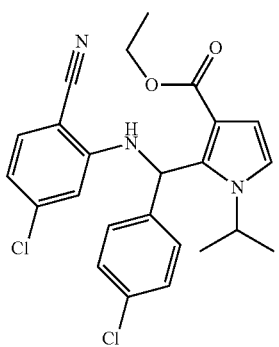 [SMILES: CCOC(=O)c1ccn(C(C)C)c1C(Nc1cc(Cl)ccc1C#N)c1ccc(Cl)cc1]

The title compound was prepared in analogy to the procedure described for Step D2, but 2-amino-4-chloro-benzonitrile [38487-86-4] was used instead of 3-chloro-4-fluoroaniline respectively to afford the title compound as a light yellow solid. $t_R$: 5.98 min (HPLC 1); ESI-MS: $t_R$=1.50 min, [M–H] 454/456 (LC-MS 1); TLC: R$_f$=0.43 (1:6 EtOAc/heptanes).

Intermediate AC: 2-Bromo-6-(4-chloro-phenyl)-5-(1,4-dimethyl-6-oxo-1,6-dihydro-pyridin-3-yl)-1-isopropyl-5,6-dihydro-1H-pyrrolo[3,4-b]pyrrol-4-one

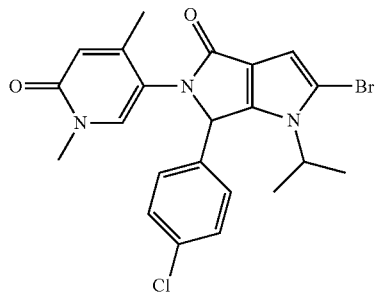 [SMILES: Cc1cc(=O)n(C)cc1N1C(=O)c2cc(Br)n(C(C)C)c2C1c1ccc(Cl)cc1]

The title compound was prepared in analogy to the procedure described for Intermediate N, but 6-(4-chloro-phenyl)-5-(1,4-dimethyl-6-oxo-1,6-dihydro-pyridin-3-yl)-1-isopropyl-5,6-dihydro-1H-pyrrolo[3,4-b]pyrrol-4-one (Step AC1) was used instead of 5-(5-chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one to afford the title compound as a light yellow oil. $t_R$: 3.16 min (HPLC 5); ESI-MS: $t_R$=1.04 min, [M+H]$^+$ 474/476/478 (LC-MS 1).

Step AC1: 6-(4-Chloro-phenyl)-5-(1,4-dimethyl-6-oxo-1,6-dihydro-pyridin-3-yl)-1-isopropyl-5,6-dihydro-1H-pyrrolo[3,4-b]pyrrol-4-one

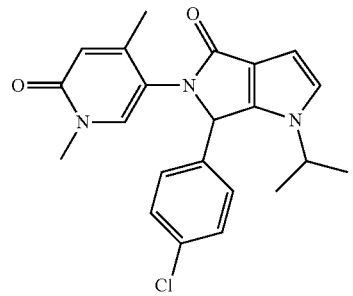 [SMILES: Cc1cc(=O)n(C)cc1N1C(=O)c2ccn(C(C)C)c2C1c1ccc(Cl)cc1]

The title compound was prepared in analogy to the procedure described for Step O1, but 2-[(4-chloro-phenyl)-(1,4-dimethyl-6-oxo-1,6-dihydro-pyridin-3-ylamino)-methyl]-1-isopropyl-1H-pyrrole-3-carboxylic acid (Step AC2) was used instead of 2-[[5-chloro-1-(4-methoxy-benzyl)-6-oxo-1,6-dihydro-pyridin-3-ylamino]-(4-chloro-phenyl)-methyl]-1-isopropyl-1H-pyrrole-3-carboxylic acid to afford the title compound as a beige solid. $t_R$: 2.86 min (HPLC 5); ESI-MS: $t_R$=0.93 min, [M+H]$^+$ 396/398 (LC-MS 1).

Step AC2: 2-[(4-Chloro-phenyl)-(1,4-dimethyl-6-oxo-1,6-dihydro-pyridin-3-ylamino)-methyl]-1-isopropyl-1H-pyrrole-3-carboxylic acid

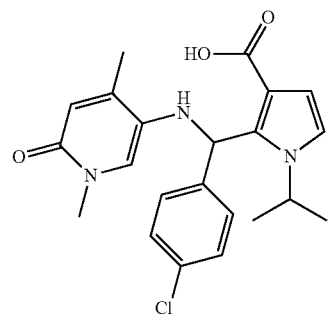 [SMILES: Cc1cc(=O)n(C)cc1NC(c1ccc(Cl)cc1)c1c(C(=O)O)ccn1C(C)C]

The title compound was prepared in analogy to the procedure described for Step D1 but 2-[(4-chloro-phenyl)-(1,4-dimethyl-6-oxo-1,6-dihydro-pyridin-3-ylamino)-methyl]-1-isopropyl-1H-pyrrole-3-carboxylic acid ethyl ester (Step AC3) was used instead of 5-bromo-2-[(3-chloro-4-fluoro-phenylamino)-(4-chloro-phenyl)-methyl]-1-isopropyl-1H-pyrrole-3-carboxylic acid methyl ester to afford the title compound as a beige solid. $t_R$: 2.92 min (HPLC 5); ESI-MS: $t_R$=0.97 min, [M+H]$^+$ 414/416 (LC-MS 1).

Step AC3: 2-[(4-Chloro-phenyl)-(1,4-dimethyl-6-oxo-1,6-dihydro-pyridin-3-ylamino)-methyl]-1-isopropyl-1H-pyrrole-3-carboxylic acid ethyl ester

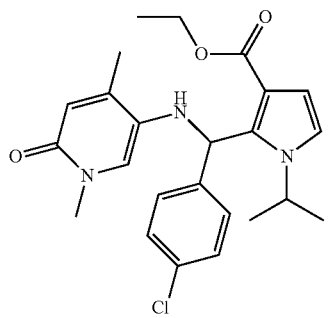 [SMILES: CCOC(=O)c1ccn(C(C)C)c1C(Nc1cn(C)c(=O)cc1C)c1ccc(Cl)cc1]

The title compound was prepared in analogy to the procedure described for Step D2, but 5-amino-1,4-dimethyl-1H-pyridin-2-one (Step AC4) was used instead of 3-chloro-4-fluoroaniline respectively to afford the title compound as a brown foam. $t_R$: 5.03 min (HPLC 1); ESI-MS: $t_R$=1.20 min, [M−H] 442/444 (LC-MS 1).

Step AC4: 5-Amino-1,4-dimethyl-1H-pyridin-2-one

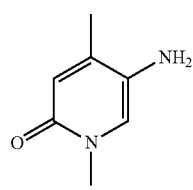

The title compound was prepared in analogy to the procedure described for Step E5 but 1,4-dimethyl-5-nitro-1H-pyridin-2-one (Step AC5) was used instead of 3-chloro-1-methyl-5-nitro-1H-pyridin-2-one to afford the title compound as a dark green solid. $t_R$: 1.56 min (HPLC 2); ESI-MS: $t_R$=0.26 min, [M+H]$^+$ 139 (LC-MS 1).

Step AC5: 1,4-Dimethyl-5-nitro-1H-pyridin-2-one

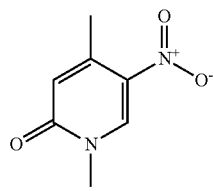

The title compound was prepared in analogy to the procedure described for Step E6 but 4-methyl-5-nitro-pyridin-2-ol [21901-41-7] was used instead of 3-chloro-2-hydroxy-5-nitropyridine to afford the title compound as a light brown solid. $t_R$: 4.18 min (HPLC 2); ESI-MS: $t_R$=0.55 min, [M+H]$^+$ 169 (LC-MS 1).

Intermediate AD: (S)-2-Bromo-6-(4-chloro-phenyl)-1-isopropyl-5-(trans-4-methoxy-cyclohexyl)-5,6-dihydro-1H-pyrrolo[3,4-b]pyrrol-4-one

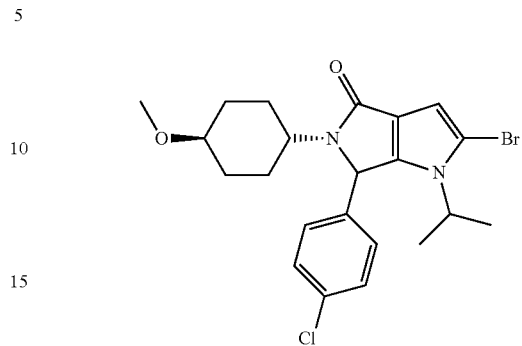

The title compound was prepared in analogy to the procedures described for Intermediate G but in the step corresponding to Step G3, trans-4-methoxy-cyclohexylamine [121588-79-2] was used instead of tetrahydro-pyran-4-ylamine. Moreover, in the step corresponding to Step G1, 1-chloro-N,N,2-trimethylpropenylamine was used for the cyclization as described in Step O1. The title compound was obtained as a white solid. $t_R$: 5.10 min (HPLC 1); ESI-MS: $t_R$=1.23 min, [M+H]$^+$465/467/469 (LC-MS 1); TLC: $R_f$=0.20 (1:1 EtOAc/hexanes).

Intermediate AE: 4-[2-Bromo-5-(5-chloro-1-methyl-6-oxo-1,6-dihydro-pyridin-3-yl)-1-isopropyl-4-oxo-1,4,5,6-tetrahydro-pyrrolo[3,4-b]pyrrol-6-yl]-benzonitrile

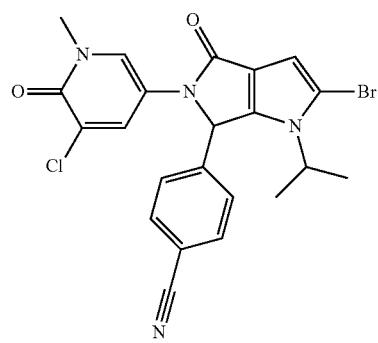 [SMILES: CC(C)n1c(Br)cc2c1C(c1ccc(C#N)cc1)N(c1cc(Cl)c(=O)n(C)c1)C2=O]

The title compound was prepared in analogy to the procedures described for Intermediate G but in the step corresponding to Step G3, 5-amino-3-chloro-1-methyl-1H-pyridin-2-one (Step E5) and 2-[(4-cyano-phenyl)-hydroxy-methyl]-1-isopropyl-1H-pyrrole-3-carboxylic acid ethyl ester (Step H4) were used instead of tetrahydro-pyran-4-ylamine and 2-[(4-chloro-phenyl)-hydroxy-methyl]-1-isopropyl-1H-pyrrole-3-carboxylic acid ethyl ester respectively. Moreover, the lactam cyclization was performed as described in Step F1 but dimethylaluminium chloride [1184-58-3] (1M/hexanes) was used instead of trimethylaluminium. The title compound was obtained as a brown solid. $t_R$: 3.16 min (HPLC 5); ESI-MS: $t_R$=0.98 min, [M+H]$^+$ 485/487/489 (LC-MS 1).

Intermediate AF: 4-{2-Bromo-5-[5-chloro-1-(4-methoxy-benzyl)-6-oxo-1,6-dihydro-pyridin-3-yl]-1-isopropyl-4-oxo-1,4,5,6-tetrahydro-pyrrolo[3,4-b]pyrrol-6-yl}-benzonitrile

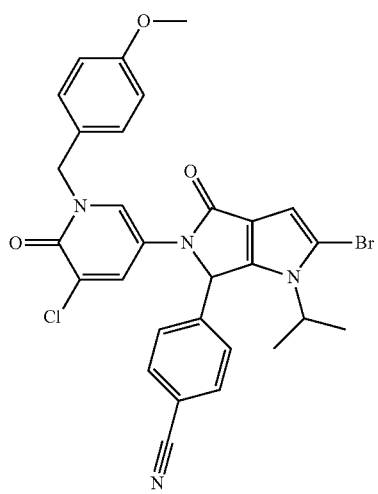 [SMILES: COc1ccc(Cn2cc(N3C(=O)c4cc(Br)n(C(C)C)c4C3c3ccc(C#N)cc3)cc(Cl)c2=O)cc1]

The title compound was prepared in analogy to the procedure described for Intermediate A but 4-{5-[5-chloro-1-(4-methoxy-benzyl)-6-oxo-1,6-dihydro-pyridin-3-yl]-1-isopropyl-4-oxo-1,4,5,6-tetrahydro-pyrrolo[3,4-b]pyrrol-6-yl}-benzonitrile (Step AF1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one. The title compound was obtained as a red solid. ESI-MS: $t_R$=1.11 min, [M+H]$^+$ 591/593 (LC-MS 1).

Step AF1: 4-{5-[5-Chloro-1-(4-methoxy-benzyl)-6-oxo-1,6-dihydro-pyridin-3-yl]-1-isopropyl-4-oxo-1,4,5,6-tetrahydro-pyrrolo[3,4-b]pyrrol-6-yl}-benzonitrile

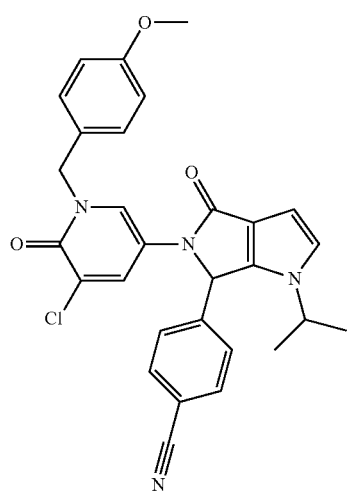 [SMILES: COc1ccc(Cn2cc(N3C(=O)c4ccn(C(C)C)c4C3c3ccc(C#N)cc3)cc(Cl)c2=O)cc1]

The title compound was prepared in analogy to the procedure described for Step F1, but 2-[[5-chloro-1-(4-methoxy-benzyl)-6-oxo-1,6-dihydro-pyridin-3-ylamino]-(4-cyano-phenyl)-methyl]-1-isopropyl-1H-pyrrole-3-carboxylic acid ethyl ester (Step AF2) was used instead of 2-[(4-chloro-phenyl)-(4-hydroxy-cyclohexylamino)-methyl]-1-isopropyl-1H-pyrrole-3-carboxylic acid ethyl ester, and dimethylaluminium chloride [1184-58-3] (1M/hexanes) was used instead of trimethylaluminium. The title compound was obtained as a white solid. ESI-MS: $t_R$=1.00 min, [M+H]$^+$ 513/515 (LC-MS 1).

Step AF2: 2-[[5-Chloro-1-(4-methoxy-benzyl)-6-oxo-1,6-dihydro-pyridin-3-ylamino]-(4-cyano-phenyl)-methyl]-1-isopropyl-1H-pyrrole-3-carboxylic acid ethyl ester

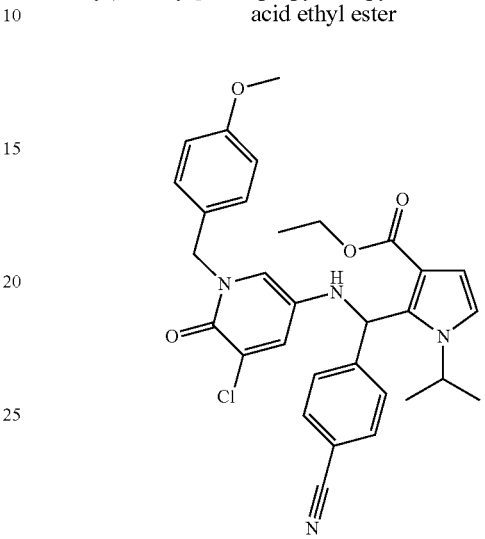

The title compound was prepared in analogy to the procedure described for Step L3, but 2-[(4-cyano-phenyl)-hydroxy-methyl]-1-isopropyl-1H-pyrrole-3-carboxylic acid ethyl ester (Step H4) and 5-amino-3-chloro-1-(4-methoxy-benzyl)-1H-pyridin-2-one (Step O4) were used instead of 2-[(4-chloro-phenyl)-hydroxy-methyl]-1-isopropyl-1H-pyrrole-3-carboxylic acid ethyl ester and 3-amino-5-chloro-1-methyl-1H-pyridin-2-one respectively. The title compound was obtained as a white solid. ESI-MS: $t_R$=1.20 min, [M+H]$^+$ 559/561 (LC-MS 1).

Intermediate AG: 4-[2-Bromo-5-(5-chloro-1-methyl-2-oxo-1,2-dihydro-pyridin-3-yl)-1-isopropyl-4-oxo-1,4,5,6-tetrahydro-pyrrolo[3,4-b]pyrrol-6-yl]-benzonitrile

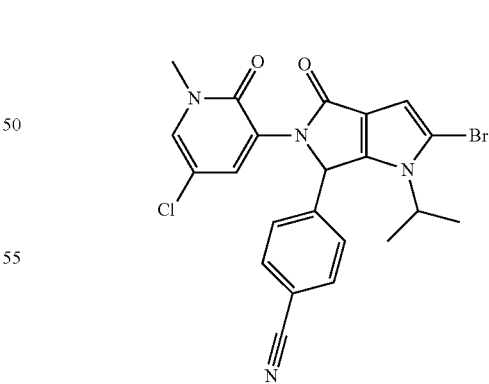

The title compound was prepared in analogy to the procedures described for Intermediate AF but in the step corresponding to Step AF2, 3-amino-5-chloro-1-methyl-1H-pyridin-2-one (Step L4) was used instead of 5-amino-3-chloro-1-(4-methoxy-benzyl)-1H-pyridin-2-one. The title compound was obtained as a white solid. ESI-MS: $t_R$=1.03 min, [M+H]$^+$ 485/487 (LC-MS 1).

Intermediate AH: 4-{2-Bromo-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-benzonitrile

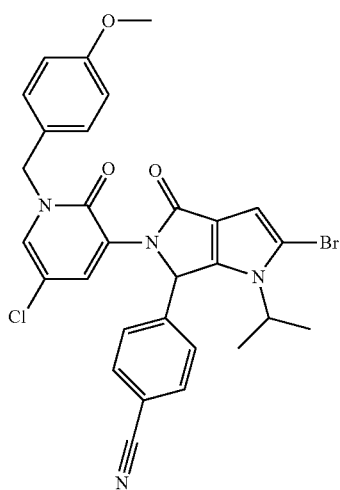 [SMILES: COc1ccc(Cn2cc(Cl)cc(N3C(=O)c4cc(Br)n(C(C)C)c4C3c3ccc(C#N)cc3)c2=O)cc1]

The title compound was prepared in analogy to the procedures described for Intermediate AF but in the step corresponding to Step AF2, 3-amino-5-chloro-1-(4-methoxy-benzyl)-1H-pyridin-2-one (Step AH1) was used instead of 5-amino-3-chloro-1-(4-methoxy-benzyl)-1H-pyridin-2-one. The title compound was obtained as a red solid. ESI-MS: $t_R$=1.19 min, [M+H]$^+$ 591/593/595 (LC-MS 1).

Step AH1: 3-Amino-5-chloro-1-(4-methoxy-benzyl)-1H-pyridin-2-one

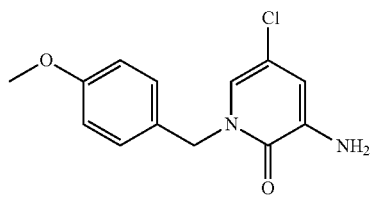 [SMILES: COc1ccc(Cn2cc(Cl)cc(N)c2=O)cc1]

The title compound was prepared in analogy to the procedure described for Step L4 but using 5-chloro-1-(4-methoxy-benzyl)-3-nitro-1H-pyridin-2-one (Step AH2) instead of 5-chloro-1-methyl-3-nitro-1H-pyridin-2-one to afford the title compound as a beige solid. ESI-MS: $t_R$=0.86 min, [M+H]$^+$ 265/267 (LC-MS 1).

Step AH2: 5-Chloro-1-(4-methoxy-benzyl)-3-nitro-1H-pyridin-2-one

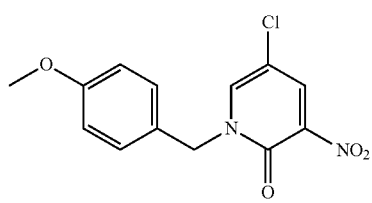 [SMILES: COc1ccc(Cn2cc(Cl)cc([N+](=O)[O-])c2=O)cc1]

The title compound was prepared in analogy to the procedure described for Step L5 but using 4-methoxybenzyl chloride instead of methyl iodide to afford the title compound as a dark yellow solid. ESI-MS: $t_R$=0.92 min, [M+H]$^+$ 295/297 (LC-MS 1).

Intermediate AI: 4-[2-Bromo-6-(4-chloro-phenyl)-1-isopropyl-4-oxo-4,6-dihydro-1H-pyrrolo[3,4-b]pyrrol-5-yl]-piperidine-1-carboxylic acid tert-butyl ester

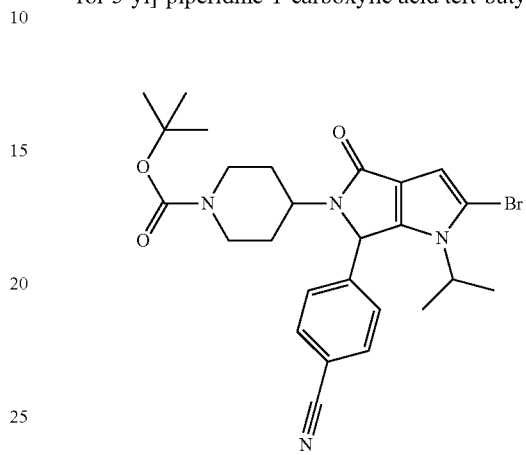

The title compound was prepared in analogy to the procedures described for Intermediate L, but in the step corresponding to Step L3, 4-amino-piperidine-1-carboxylic acid tert-butyl ester was used instead of 3-amino-5-chloro-1-methyl-1H-pyridin-2-one. Moreover, in the step corresponding to Step L1, 1-chloro-N,N,2-trimethylpropenylamine was used for the cyclization as described in Step O1. The title compound was obtained as a white foam. $t_R$: 6.01 min (HPLC 4); ESI-MS: $t_R$=1.34 min, [M+H]$^+$ 536/538/540 (LC-MS 1).

Intermediate AJ: 2-Bromo-6-(4-chloro-2-methyl-phenyl)-5-(trans-4-hydroxy-cyclohexyl)-1-isopropyl-5,6-dihydro-1H-pyrrolo[3,4-b]pyrrol-4-one

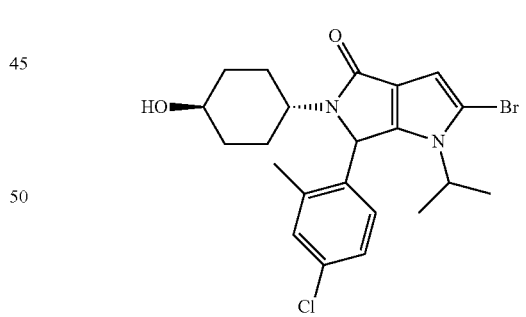

The title compound was prepared in analogy to the procedures described for Intermediate G but in the step corresponding to Step G3, trans-4-aminocyclohexanol and 2-[(4-chloro-2-methyl-phenyl)-hydroxy-methyl]-1-isopropyl-1H-pyrrole-3-carboxylic acid ethyl ester (Step A4) were used instead of tetrahydro-pyran-4-ylamine and 2-[(4-chloro-phenyl)hydroxy-methyl]-1-isopropyl-1H-pyrrole-3-carboxylic acid ethyl ester respectively. The title compound was obtained as a white solid. $t_R$: 6.90 min (HPLC 2); ESI-MS: $t_R$=1.11 min, [M+H]$^+$ 465/467/469 (LC-MS 1); TLC: $R_f$=0.24 (EtOAc).

Intermediate AK: 2-Bromo-6-(4-chloro-2-methyl-phenyl)-1-isopropyl-5-(tetrahydro-pyran-4-yl)-5,6-dihydro-1H-pyrrolo[3,4-b]pyrrol-4-one

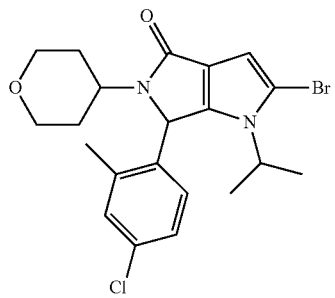 [SMILES: Cc1cc(Cl)ccc1C1c2c(cc(Br)n2C(C)C)C(=O)N1C1CCOCC1]

The title compound was prepared in analogy to the procedures described for Intermediate G but in the step corresponding to Step G3, 2-[(4-chloro-2-methyl-phenyl)-hydroxy-methyl]-1-isopropyl-1H-pyrrole-3-carboxylic acid ethyl ester (Step A4) was used instead of 2-[(4-chloro-phenyl)-hydroxy-methyl]-1-isopropyl-1H-pyrrole-3-carboxylic acid ethyl ester. The title compound was obtained as a white solid. $t_R$: 4.97 min (HPLC 1); ESI-MS: $t_R$=1.19 min, [M+H]⁺ 451/453/455 (LC-MS 1); TLC: $R_f$=0.33 (1:1 EtOAc/hexanes).

Intermediate AL: [5-Methoxy-4-(4,4,5,5-tetramethyl-[1,3,2]dioxaborolan-2-yl)-pyridin-2-yl]-acetonitrile

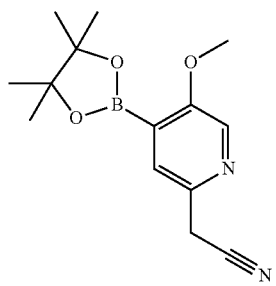 [SMILES: COc1cnc(CC#N)cc1B1OC(C)(C)C(C)(C)O1]

The title compound was prepared in analogy to the procedure described for Intermediate U but using (4-bromo-5-methoxy-pyridin-2-yl)-acetonitrile (Step AL1) to afford the title compound (60% purity). ¹H-NMR (DMSO, 400 MHz) δ ppm: 8.33 (s, 1H), 7.92 (s, 1H), 4.10 (s, 2H), 3.84 (s, 3H), 1.27 (s, 6H), 1.14 (s, 6H).

Step AL1:
(4-Bromo-5-methoxy-pyridin-2-yl)-acetonitrile

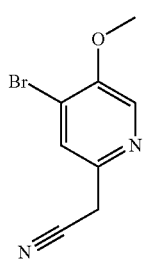

A suspension of 4-bromo-2-bromomethyl-5-methoxy-pyridine (Step AL2) (1.2 g, 4.3 mmol), KCN (417 mg, 6.4 mmol) and aliquat 336 (35 mg, 0.085 mmol) in H₂O was stirred at 50° C. for 2 h. The reaction mixture was dissolved in CH₂Cl₂, extracted with a saturated aqueous solution of NaHCO₃, washed with brine, dried (Na₂SO₄), filtered and concentrated. The crude product was purified by silica gel column chromatography (hexane/EtOAc, 100:0→1:1). $t_R$: 3.83 min (HPLC 7).

Step AL2:
4-Bromo-2-bromomethyl-5-methoxy-pyridine

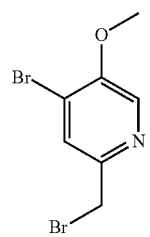

A solution of 4-bromo-5-methoxy-2-methyl-pyridine (Step AL3) (1.9 g, 9.4 mmol), NBS (1.8 g, 9.9 mmol), AIBN (15 mg, 0.094 mmol) and benzoyl peroxide (23 mg, 0.094 mmol) in CCl₄ (2 mL) was stirred at rt for 18 h. The reaction mixture was dissolved in EtOAc and extracted with a saturated aqueous solution of NaHCO₃, washed with brine, dried (Na₂SO₄), filtered and concentrated. The crude product was purified by silica gel column chromatography (hexane/EtOAc, 100:0→70:30). ESI-MS: $t_R$=0.90 min, [M+H]⁺ 281.9 (LC-MS 1).

Step AL3: 4-Bromo-5-methoxy-2-methyl-pyridine

To a solution of 4-bromo-5-methoxy-2-methyl-pyridine 1-oxide (Step AL4) (150 mg, 0.7 mmol) in CHCl₃ (2 mL) at 10° C. was added dropwise PBr₃ (78 μL, 0.826 mmol). The mixture was stirred at rt for 4 h, then at 50° C. for 1 h. The reaction mixture was dissolved in CH₂Cl₂ and extracted with a saturated aqueous solution of NaHCO₃, washed with brine, dried (Na₂SO₄), filtered and concentrated. The product was crystallised (CH₂Cl₂/TBME). ESI-MS: $t_R$=0.69 min, [M+H]⁺ 202.0/204.0 (LC-MS 1).

Step AL4: 4-Bromo-5-methoxy-2-methyl-pyridine 1-oxide

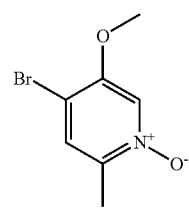

5-Methoxy-2-methyl-4-nitro-pyridine-1-oxide (Step AL5) (1.9 g, 10.3 mmol) and acetyl bromide (22.9 mL, 310 mmol) was added to acetic acid (40 mL) and the reaction was stirred at 80° C. for 1 h. The mixture was concentrated (1/3) and a solution of NaOH was added. The resulting mixture was extracted with EtOAc, washed with brine, dried ($Na_2SO_4$), filtered and concentrated. The product was crystallised (EtOAc/TBME). ESI-MS: $t_R$=0.54 min, [M+H]$^+$ 218.1/220.1 (LC-MS 1).

Step AL5:
5-Methoxy-2-methyl-4-nitro-pyridine-1-oxide

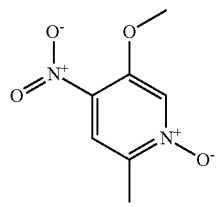

5-Methoxy-2-methylpyridine-1-oxide [35392-66-6] (6 g, 43.1 mmol) and nitric acid (18.4 mL, 431 mmol, 1.48 g/mL) was added to acetic acid (50 mL) and the reaction was stirred at 90° C. for 6 h. The mixture was concentrated (1/4) and neutralized at 0° C. was addition of ammonium hydroxide. The mixture was extracted with EtOAc, washed with brine and water, dried ($Na_2SO_4$), filtered and concentrated. The product crystallised during concentration. ESI-MS: $t_R$=0.50 min, [M+H]$^+$ 185.1 (LC-MS 1).

Intermediate AM: [6-Methoxy-5-(4,4,5,5-tetramethyl-[1,3,2]dioxaborolan-2-yl)-pyridin-3-yl]-acetonitrile

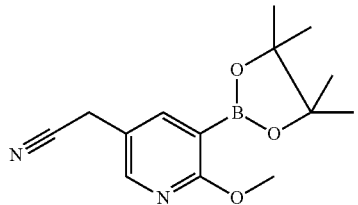 [SMILES: COc1ncc(CC#N)cc1B1OC(C)(C)C(C)(C)O1]

The title compound was prepared in analogy to the procedure described for Intermediate U but using (5-bromo-6-methoxy-pyridin-3-yl)-acetonitrile (Step AM1) to afford the title compound. ESI-MS: $t_R$=0.98 min, [M+H]$^+$ 275.1 (LC-MS 1).

Step AM1:
(5-Bromo-6-methoxy-pyridin-3-yl)-acetonitrile

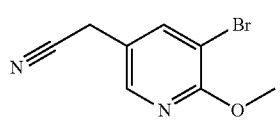

To a suspension of 3-bromo-5-bromomethyl-2-methoxy-pyridine (Step AM2) (3.9 g, 14.0 mmol) in $H_2O$ was added NaCN (750 mg, 15.3 mmol) and the mixture was stirred at 50° C. for 1.5 h. $CH_2Cl_2$ and a saturated aqueous solution of $NaHCO_3$ were added and the phases were separated. The organic layer was washed with $H_2O$ and brine, dried ($MgSO_4$), filtered and concentrated. The crude product was purified by silica gel column chromatography (heptane/EtOAc, 80:20→0:100). $t_R$: 0.88 min (LC-MS 1).

Step AM2:
3-Bromo-5-bromomethyl-2-methoxy-pyridine

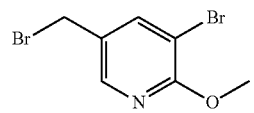

To a solution of 3-bromo-2-methoxy-5-methyl-pyridine (Step AM3) (3.0 g, 14.7 mmol), was added NBS (3.1 g, 17.6 mmol) and AIBN (121 mg, 0.7 mmol) and the mixture was stirred at 80° C. for 1 h. $H_2O$ and $CH_2Cl_2$ were added and the phases were separated. The organic layer was dried ($MgSO_4$), filtered and concentrated. The crude product was purified by silica gel column chromatography (heptane/EtOAc, 95:5→0:100). $t_R$: 1.10 min (LC-MS 1).

Step AM3: 3-Bromo-2-methoxy-5-methyl-pyridine

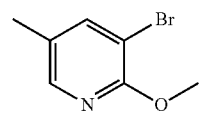

To a solution of 3-bromo-2-chloro-5-methylpyridine [17282-03-0] (5 g, 24.2 mmol) in MeOH (80 mL) was added a solution of sodium methoxide (5.4M in MeOH) (25 mL, 135 mmol) and the mixture was stirred at 65° C. for 32 h. The resulting suspension was filtered and the mother liquor was concentrated. $Et_2O$ and $H_2O$ were added and the phases were separated. The organic layer was washed with $H_2O$ and brine, dried ($MgSO_4$), filtered and concentrated. The residue was purified by flash chromatography (heptane/EtOAc: 90:10→0:100) to afford the title compound. $t_R$: 1.03 min (LC-MS 1).

Intermediate AN: [6-Methoxy-5-(4,4,5,5-tetramethyl-[1,3,2]dioxaborolan-2-yl)-pyridin-3-yl]-acetic acid ethyl ester

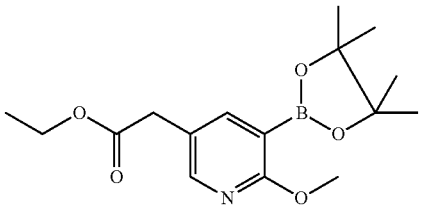 [SMILES: CCOC(=O)Cc1cnc(OC)c(B2OC(C)(C)C(C)(C)O2)c1]

The title compound was prepared in analogy to the procedure described for Intermediate U but using (5-bromo-6-methoxy-pyridin-3-yl)-acetic acid ethyl ester (Step AN1) to afford the title compound. ESI-MS: $t_R$=1.11 min, [M+H]$^+$ 322.3 (LC-MS 1).

Step AN1: (5-Bromo-6-methoxy-pyridin-3-yl)-acetic acid ethyl ester

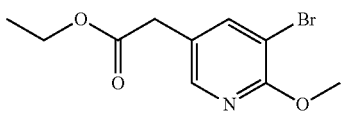

To a solution of (5-bromo-6-methoxy-pyridin-3-yl)-acetic acid (Step AN2) (400 mg, 1.6 mmol) in CH$_2$Cl$_2$ (0.8 mL) was added DCC (18 mg, 0.09 mmol), DMAP (one spatula) and EtOH (4.88 mmol) and the mixture was stirred at rt for 15 h. H$_2$O and EtOAc were added and the phases were separated. The organic layer was washed with brine, dried (MgSO$_4$), filtered and concentrated. The residue was purified by flash chromatography (heptane/EtOAc, 85:15→0:100). ESI-MS: $t_R$=1.05 min, [M+H]$^+$ 274.1/276.1 (LC-MS 1).

Step AN2: (5-Bromo-6-methoxy-pyridin-3-yl)-acetic acid

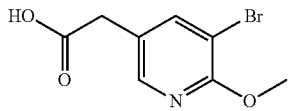

To a suspension of (5-bromo-6-methoxy-pyridin-3-yl)-acetonitrile (Step AM1) (6.61 mmol) in EtOH (19 mL) was added a solution of KOH (26.7 mmol) in H$_2$O (19 mL) and the mixture was stirred at 80° C. for 45 min. After cooling to rt, the pH was adjusted to 3-4 with 1M aqueous HCl and the mixture was extracted with CH$_2$Cl$_2$ (2×). The combined organic layers were dried (MgSO$_4$), filtered and concentrated to afford the title compound. ESI-MS: $t_R$=0.75 min, [M+H]$^+$ 246/248 (LC-MS 1).

Intermediate AO: [5-Methoxy-4-(4,4,5,5-tetramethyl-[1,3,2]dioxaborolan-2-yl)-pyridin-2-yl]-acetic acid ethyl ester

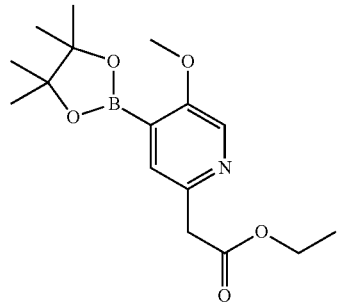 [SMILES: CCOC(=O)Cc1cc(B2OC(C)(C)C(C)(C)O2)c(OC)cn1]

The title compound was prepared in analogy to the Intermediate U, but (4-chloro-5-methoxy-pyridin-2-yl)-acetic acid ethyl ester (Step AO1) was used instead of 2-amino-5-bromo-4-methoxypyrimidine to afford the title compound as a brown oil. ESI-MS: $t_R$=0.53 min, [M+H]$^+$ 240 (boronic acid) (LC-MS 1).

Step AO1: (4-Chloro-5-methoxy-pyridin-2-yl)-acetic acid ethyl ester

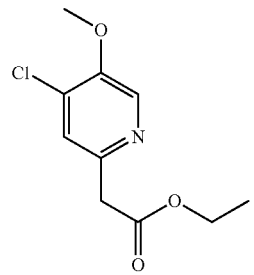

The title compound was prepared in analogy to the procedure described for Step AN1, but (4-chloro-5-methoxy-pyridin-2-yl)-acetic acid (Step AO2) was used instead of (5-bromo-6-methoxy-pyridin-3-yl)-acetic acid to afford the title compound as a yellow gum. ESI-MS: $t_R$=0.89 min, [M+H]$^+$230/232 (LC-MS 1).

Step AO2: (4-Chloro-5-methoxy-pyridin-2-yl)-acetic acid

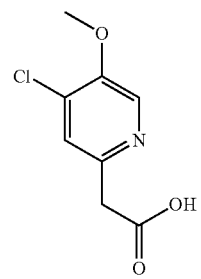

The title compound was prepared in analogy to the procedure described for Step AN2, but (4-chloro-5-methoxy-pyridin-2-yl)-acetonitrile [204862-71-5] was used instead of (5-bromo-6-methoxy-pyridin-3-yl)-acetonitrile to afford the title compound as a light brown solid. ESI-MS: $t_R$=0.60 min, [M+H]$^+$ 202/204 (LC-MS 1).

Intermediate AP: 2-(5-Methanesulfonyl-2-methoxyphenyl)-4,4,5,5-tetramethyl-[1,3,2]dioxaborolane

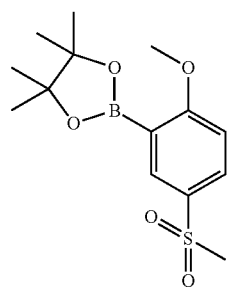

The title compound was prepared in analogy to the procedure described for Intermediate T, but 2-bromo-4-methanesulfonyl-1-methoxy-benzene [20951-42-2] and DME were used instead of 5-bromo-4-methoxy-pyrimidine and DMSO respectively to afford the title compound (85% purity) as a brown solid. $t_R$: 3.92 min (HPLC 2).

Intermediate AQ: [4-Methoxy-3-(4,4,5,5-tetramethyl-[1,3,2]dioxaborolan-2-yl)-phenyl]-acetic acid ethyl ester

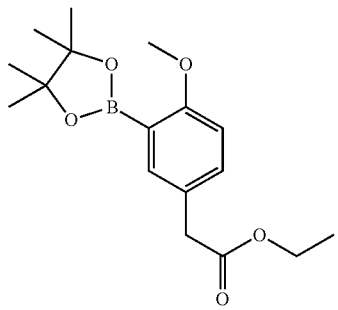 [SMILES: CCOC(=O)Cc1ccc(OC)c(B2OC(C)(C)C(C)(C)O2)c1]

The title compound was prepared in analogy to the procedure described for Intermediate T, but (3-bromo-4-methoxyphenyl)-acetic acid ethyl ester [100125-96-0] and DME were used instead of 5-bromo-4-methoxy-pyrimidine and DMSO respectively to afford the title compound (82% purity) as a yellow oil. $t_R$: 4.89 min (HPLC 2); TLC: $R_f$=0.47 (1:2 EtOAc/hexanes).

Intermediate AR: 5-Methoxy-1-methyl-4-(4,4,5,5-tetramethyl-[1,3,2]dioxaborolan-2-yl)-1H-pyridin-2-one

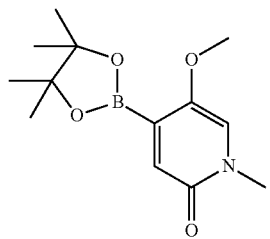

The title compound was prepared in analogy to the procedure described for Intermediate U but using 4-bromo-5-methoxy-1-methyl-1H-pyridin-2-one (Step AR1) instead of 2-amino-5-bromo-4-methoxypyrimidine to afford the title compound (28% purity) as a brown solid. ESI-MS: $t_R$=0.33 min, [M+H]$^+$ 184 (boronic acid) (LC-MS 1).

Step AR1: 4-Bromo-5-methoxy-1-methyl-1H-pyridin-2-one

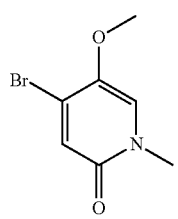

A solution of 4-bromo-2-chloro-5-methoxypyridine [1020253-15-9] (1 g, 4.5 mmol) in dimethyl sulfate (1.9 mL, 19.5 mmol) was stirred at 120° C. for 16 h in a sealed tube. After cooling to rt, CH$_3$CN and a saturated aqueous NaHCO$_3$ solution were added and the mixture was stirred at rt over the weekend. CH$_2$Cl$_2$ was added and the phases were separated. The organic layer was dried (Na$_2$SO$_4$), filtered and concentrated to give the title compound as a white powder. ESI-MS: $t_R$=0.57 min; [M+H]$^+$ 218/220 (LC-MS 1).

Intermediate AS: 4-[2-Bromo-5-(5-chloro-1-methyl-6-oxo-1,6-dihydro-pyridin-3-yl)-1-isopropyl-4-oxo-1,4,5,6-tetrahydro-pyrrolo[3,4-b]pyrrol-6-yl]-benzonitrile

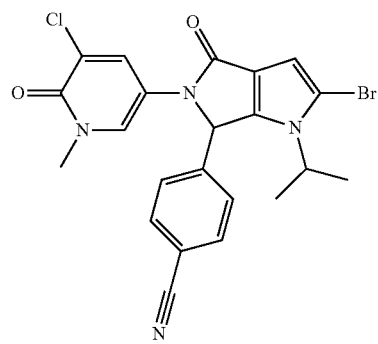 [SMILES: CC(C)n1c(Br)cc2c1C(c1ccc(C#N)cc1)N(c1cc(Cl)c(=O)n(C)c1)C2=O]

The title compound was prepared in analogy to the procedure described for Intermediate A but 4-[5-(5-chloro-1-methyl-6-oxo-1,6-dihydro-pyridin-3-yl)-1-isopropyl-4-oxo-1,4,5,6-tetrahydro-pyrrolo[3,4-b]pyrrol-6-yl]benzonitrile (Step AS1) was used instead of 5-(3-chloro-2-fluoro-phenyl)-6-(4-chloro-2-methyl-phenyl)-1-isopropyl-5,6-dihydro-1H-pyrrolo[3,4-b]pyrrol-4-one and THF was used instead of CCl$_4$. The title compound was obtained as a brown solid. $t_R$: 2.89 min (HPLC 5); ESI-MS: $t_R$=0.98 min, [M+H]$^+$ 485/487/489 (LC-MS 1).

Step AS1: 4-[5-(5-Chloro-1-methyl-6-oxo-1,6-dihydro-pyridin-3-yl)-1-isopropyl-4-oxo-1,4,5,6-tetrahydro-pyrrolo[3,4-b]pyrrol-6-yl]-benzonitrile

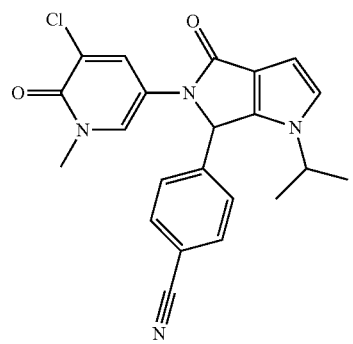 [SMILES: CC(C)n1ccc2c1C(c1ccc(C#N)cc1)N(c1cc(Cl)c(=O)n(C)c1)C2=O]

The title compound was prepared in analogy to the procedure described for Step H1, but dimethylaluminium chloride (1M in hexanes) was used instead of trimethylaluminium chloride, and 2-[(5-chloro-1-methyl-6-oxo-1,6-dihydro-pyridin-3-ylamino)-(4-cyano-phenyl)-methyl]-1-isopropyl-1H-pyrrole-3-carboxylic acid ethyl ester (Step AS2) was used instead of 2-[(3-chloro-4-fluoro-phenylamino)-(4-cyano-phenyl)-methyl]-1-isopropyl-1H-pyrrole-3-carboxylic acid ethyl ester to afford the title compound as a brown oil. $t_R$: 2.57 min (HPLC 5); ESI-MS: $t_R$=0.86 min, [M+H]⁺ 407/409 (LC-MS 1).

Step AS2: 2-[(5-Chloro-1-methyl-6-oxo-1,6-dihydro-pyridin-3-ylamino)-(4-cyano-phenyl)-methyl]-1-isopropyl-1H-pyrrole-3-carboxylic acid ethyl ester

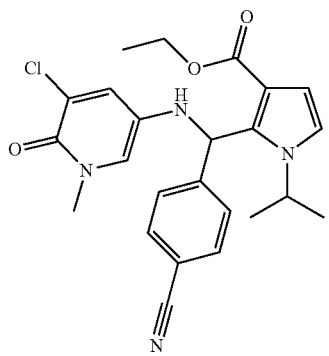 [SMILES: CCOC(=O)c1ccn(C(C)C)c1C(Nc1cc(Cl)c(=O)n(C)c1)c1ccc(C#N)cc1]

The title compound was prepared in analogy to the procedure described for Step E3, but 2-[(4-cyano-phenyl)-hydroxy-methyl]-1-isopropyl-1H-pyrrole-3-carboxylic acid ethyl ester (Step H4) was used instead of 2-[(4-chloro-phenyl)hydroxy-methyl]-1-isopropyl-1H-pyrrole-3-carboxylic acid ethyl ester to afford the title compound as a purple solid. $t_R$: 3.23 min (HPLC 5); ESI-MS: $t_R$=1.08 min, [M+H]⁺ 453/455 (LC-MS 1).

Intermediate AT: 2-Bromo-5-(5-chloro-2-fluoro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one

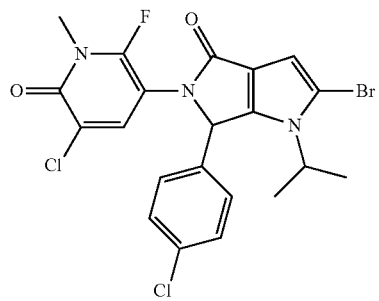 [SMILES: CC(C)n1c(Br)cc2c1C(c1ccc(Cl)cc1)N(c1cc(Cl)c(=O)n(C)c1F)C2=O]

1-Fluoro-2,4,6-trimethyl-pyridinium triflate [107264-00-6] (1.476 mmol) was added to a solution of 2-bromo-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one (Intermediate E) (0.738 mmol) in 1,2-dichloroethane (12 mL) and then the mixture was heated to 80° C. in the dark. After 12 h, the reaction mixture was cooled to rt, poured into a 2% aqueous solution of sodium sulfite and extracted with EtOAc (2×). The combined organic layers were successively washed with 1M aqueous citric acid, 1M aqueous NaHCO₃ and brine, dried (Na₂SO₄), filtered and concentrated. The residue was purified using a RediSep® silica gel column to afford the title compound as a pink foam. ESI-MS: $t_R$=1.16 min, [M]⁺ 512/514/516 (LC-MS 1); TLC: $R_f$=0.10 (1.1 EtOAc/heptanes).

Intermediate AU: 4-[2-Bromo-1-isopropyl-4-oxo-5-(tetrahydro-pyran-4-yl)-1,4,5,6-tetrahydro-pyrrolo[3,4-b]pyrrol-6-yl]-benzonitrile

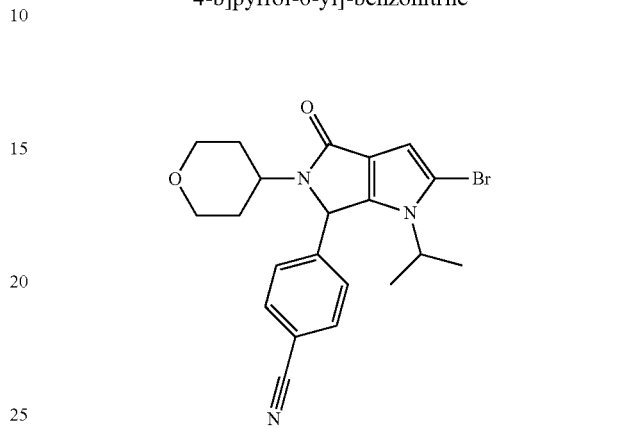

The title compound was prepared in analogy to the procedure described for Intermediate AS but in the step corresponding to Step AS2, tetrahydro-pyran-4-ylamine (4 equivalents) was used instead of 5-amino-3-chloro-1-methyl-1H-pyridin-2-one and the substitution was done at 50° C. The title compound was obtained as a yellow solid. $t_R$: 1.07 min (HPLC 3); ESI-MS: $t_R$=0.98 min, [M+H]⁺ 428/430 (LC-MS 1); TLC: $R_f$=0.08 (1:1 EtOAc/heptanes).

Intermediate AV: 4-[2-Bromo-5-(trans-4-hydroxy-cyclohexyl)-1-isopropyl-4-oxo-1,4,5,6-tetrahydro-pyrrolo[3,4-b]pyrrol-6-yl]-benzonitrile

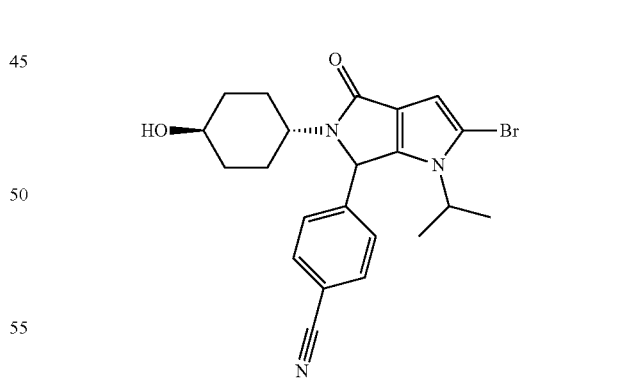

The title compound was prepared in analogy to the procedure described for Intermediate AS but in the step corresponding to Step AS2, trans-4-aminocyclohexanol (4 equivalents) was used instead of 5-amino-3-chloro-1-methyl-1H-pyridin-2-one and the substitution was done at 50° C. The title compound was obtained as a yellow solid. $t_R$: 5.98 min (HPLC 2); ESI-MS: $t_R$=0.93 min, [M+H]⁺ 442/444 (LC-MS 1); TLC: $R_f$=0.32 (EtOAc).

Intermediate AW: 2-Bromo-6-(4-chloro-phenyl)-5-(2,5-dimethyl-2H-pyrazol-3-yl)-1-isopropyl-5,6-dihydro-1H-pyrrolo[3,4-b]pyrrol-4-one

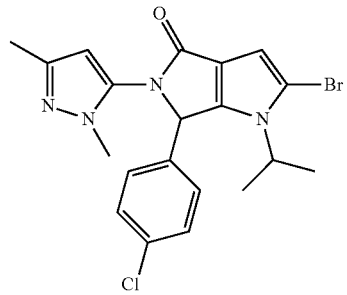 [SMILES: Cc1cc(N2C(=O)c3cc(Br)n(C(C)C)c3C2c2ccc(Cl)cc2)n(C)n1]

The title compound was prepared in analogy to the procedure described for Step O1 but 5-bromo-2-[(4-chloro-phenyl)-(2,5-dimethyl-2H-pyrazol-3-ylamino)-methyl]-1-isopropyl-1H-pyrrole-3-carboxylic acid (Step AW1) was used instead of 2-[[5-chloro-1-(4-methoxy-benzyl)-6-oxo-1,6-dihydro-pyridin-3-ylamino]-(4-chloro-phenyl)-methyl]-1-isopropyl-1H-pyrrole-3-carboxylic acid. The title compound was obtained as a solid. ESI-MS: $t_R$=1.13 min, [M+H]$^+$ 447/449/451 (LC-MS 1); TLC: $R_f$=0.28 (1:1 CH$_2$Cl$_2$/EtOAc).

Step AW1: 5-Bromo-2-[(4-chloro-phenyl)-(2,5-dimethyl-2H-pyrazol-3-ylamino)-methyl]-1-isopropyl-1H-pyrrole-3-carboxylic acid The title compound was prepared in analogy to the procedure described for Step D1 but 5-bromo-2-[(4-chloro-phenyl)-(2,5-dimethyl-2H-pyrazol-3-ylamino)-methyl]-1-isopropyl-1H-pyrrole-3-carboxylic acid methyl ester (Step AW2) was used instead of 5-bromo-2-[(3-chloro-4-fluoro-phenylamino)-(4-chloro-phenyl)-methyl]-1-isopropyl-1H-pyrrole-3-carboxylic acid methyl ester. The title compound was obtained as a solid. ESI-MS: $t_R$=1.09 min, [M+H]$^+$ 465/467/469 (LC-MS 1); TLC: $R_f$=0.16 (4:1 CH$_2$Cl$_2$/THF).

Step AW2: 5-bromo-2-[(4-chloro-phenyl)-(2,5-dimethyl-2H-pyrazol-3-ylamino)-methyl]-1-isopropyl-1H-pyrrole-3-carboxylic acid methyl ester

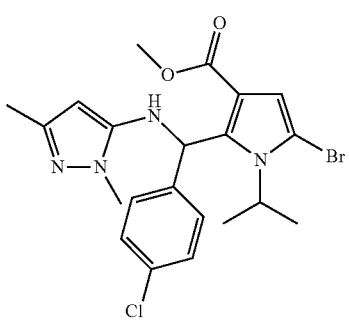 [SMILES: COC(=O)c1cc(Br)n(C(C)C)c1C(Nc1cc(C)nn1C)c1ccc(Cl)cc1]

The title compound was prepared in analogy to the procedure described for Step L3 but 5-bromo-2-[(4-chloro-phenyl)-hydroxy-methyl]-1-isopropyl-1H-pyrrole-3-carboxylic acid methyl ester (step D3) and 2,5-dimethyl-2H-pyrazol-3-ylamine [3524-32-1] were used instead of 2-[(4-chloro-phenyl)-hydroxy-methyl]-1-isopropyl-1H-pyrrole-3-carboxylic acid ethyl ester and 3-amino-5-chloro-1-methyl-1H-pyridin-2-one respectively. The title compound was obtained as a foam. ESI-MS: $t_R$=1.29 min, [M+H]$^+$ 479/481/483 (LC-MS 1); TLC: $R_f$=0.31 (1:1 CH$_2$Cl$_2$/EtOAc).

Intermediate AX: 4-[2-Bromo-5-(2,5-dimethyl-2H-pyrazol-3-yl)-1-isopropyl-4-oxo-1,4,5,6-tetrahydro-pyrrolo[3,4-b]pyrrol-6-yl]-benzonitrile The title compound was prepared in analogy to the procedure described for Step H1, but diethylaluminium chloride (1.8M in toluene) [96-10-6] was used instead of trimethylaluminium chloride, and 5-bromo-2-[(4-cyano-phenyl)-(2,5-dimethyl-2H-pyrazol-3-ylamino)-methyl]-1-isopropyl-1H-pyrrole-3-carboxylic acid methyl ester (Step AX1) was used instead of 2-[(3-chloro-4-fluoro-phenylamino)-(4-cyano-phenyl)-methyl]-1-isopropyl-1H-pyrrole-3-carboxylic acid ethyl ester to afford the title compound as a solid. ESI-MS: $t_R$=0.99 min, [M+H]$^+$ 438/440 (LC-MS 1).

Step AX1: 5-Bromo-2-[(4-cyano-phenyl)-(2,5-dimethyl-2H-pyrazol-3-ylamino)-methyl]-1-isopropyl-1H-pyrrole-3-carboxylic acid methyl ester

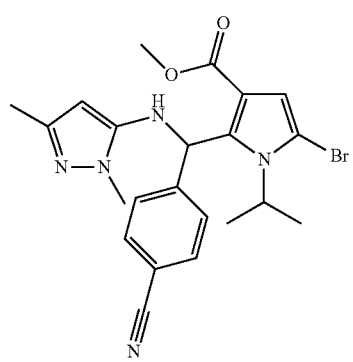 [SMILES: COC(=O)c1cc(Br)n(C(C)C)c1C(Nc1cc(C)nn1C)c1ccc(C#N)cc1]

The title compound was prepared in analogy to the procedure described for Step AW2 but 5-bromo-2-[(4-cyano-phenyl)-hydroxy-methyl]-1-isopropyl-1H-pyrrole-3-carboxylic acid methyl ester (step AX2) was used instead of 5-bromo-2-[(4-chloro-phenyl)-hydroxy-methyl]-1-isopropyl-1H-pyrrole-3-carboxylic acid methyl ester. The title compound was obtained as a light yellow solid. ESI-MS: $t_R$=1.14 min, [M+H]$^+$ 470/472 (LC-MS 1); TLC: $R_f$=0.27 (1:1 CH$_2$Cl$_2$/EtOAc).

Step AX2: 5-Bromo-2-[(4-cyano-phenyl)-hydroxy-methyl]-1-isopropyl-1H-pyrrole-3-carboxylic acid methyl ester

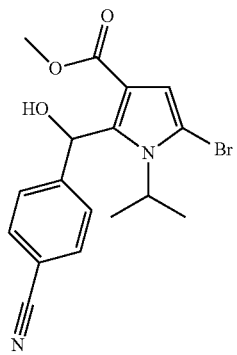 [SMILES: COC(=O)c1cc(Br)n(C(C)C)c1C(O)c1ccc(C#N)cc1]

The title compound was prepared in analogy to the procedure described for Step D3 but 4-formyl-benzonitrile [105-07-7] was used instead of 4-chlorobenzaldehyde. The title compound was obtained as a solid. ESI-MS: $t_R$=1.15 min, [M]$^+$359/361 (i.e. fragmented pyrrolium ion) (LC-MS 1); TLC: $R_f$=0.08 (9:1 heptanes/THF).

Intermediate AY: 2-Bromo-6-(4-chloro-phenyl)-5-(1,3-dimethyl-1H-pyrazol-4-yl)-1-isopropyl-5,6-dihydro-1H-pyrrolo[3,4-b]pyrrol-4-one

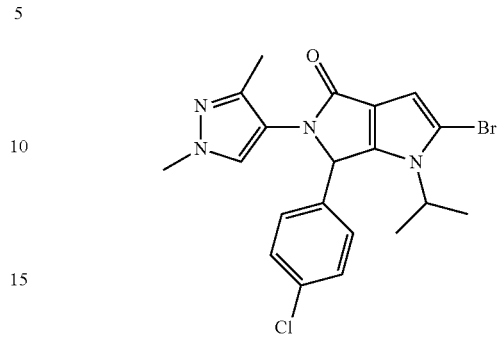

The title compound was prepared in analogy to the procedure described for Intermediate O1 but in the step corresponding to Step O3, 5-bromo-2-[(4-chloro-phenyl)-hydroxy-methyl]-1-isopropyl-1H-pyrrole-3-carboxylic acid methyl ester (Step D3) and 1,3-dimethyl-1H-pyrazol-4-ylamine (free base generated from the hydrochloride salt [1147222-02-3]) were used instead of 2-[(4-chloro-phenyl)-hydroxy-methyl]-1-isopropyl-1H-pyrrole-3-carboxylic acid ethyl ester and 5-amino-3-chloro-1-(4-methoxy-benzyl)-1H-pyridin-2-one respectively. Moreover, in this step, the procedure described for Step L3 using Ms$_2$O and Et$_3$N was used. The title compound was obtained as a beige solid. $t_R$: 1.18 min (HPLC 3); ESI-MS: $t_R$=1.22 min, [M+H]$^+$ 415/417 (LC-MS 1); TLC: $R_f$=0.24 (2:1 EtOAc/hexanes).

Intermediate AZ: 2-Bromo-6-(4-chloro-3-fluorophenyl)-5-(5-chloro-1-methyl-6-oxo-1,6-dihydro-pyridin-3-yl)-1-isopropyl-5,6-dihydro-1H-pyrrolo[3,4-b]pyrrol-4-one

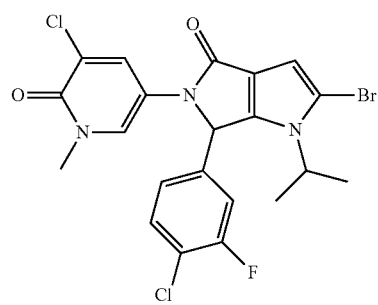 [SMILES: CC(C)n1c(Br)cc2c1C(c1ccc(Cl)c(F)c1)N(c1cc(Cl)c(=O)n(C)c1)C2=O]

The title compound was prepared in analogy to the procedure described for Intermediate AW but in the step corresponding to Step AW2, 5-bromo-2-[(4-chloro-3-fluoro-phenyl)-hydroxy-methyl]-1-isopropyl-1H-pyrrole-3-carboxylic acid methyl ester (Step AZ1) and 5-amino-3-chloro-1-methyl-1H-pyridin-2-one (Step E5) were used instead of 5-bromo-2-[(4-chloro-phenyl)-hydroxy-methyl]-1-isopropyl-1H-pyrrole-3-carboxylic acid methyl ester and 2,5-dimethyl-2H-pyrazol-3-ylamine respectively. Moreover, in this step, the procedures described for Steps H3 and H2 using 1-chloro-N,N,2-trimethylpropenylamine and Et$_3$N were used. The title compound (containing some of the corresponding 2-chloro analog) was obtained as a white foam. $t_R$: 1.18 min (HPLC 3); ESI-MS: $t_R$=1.10 min, [M+H]$^+$ 512/514/516 (LC-MS 1); TLC: $R_f$=0.19 (EtOAc).

Step AZ1: 5-Bromo-2-[(4-chloro-3-fluoro-phenyl)-hydroxy-methyl]-1-isopropyl-1H-pyrrole-3-carboxylic acid methyl ester

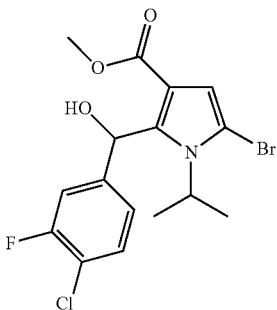 [SMILES: COC(=O)c1cc(Br)n(C(C)C)c1C(O)c1ccc(Cl)c(F)c1]

The title compound was prepared in analogy to the procedure described for Step D3 but 4-chloro-3-fluoro-benzaldehyde [5527-95-7] was used instead of 4-chlorobenzaldehyde. The title compound was obtained as a yellow solid. $t_R$: 1.41 min (HPLC 3); ESI-MS: $t_R$=1.33 min, [M]$^+$386/388/390 (i.e. fragmented pyrrolium ion) (LC-MS 1); TLC: $R_f$=0.35 (CH$_2$Cl$_2$).

Intermediate BA: 2-Bromo-6-(4-chloro-3-fluoro-phenyl)-5-(5-chloro-1-methyl-2-oxo-1,2-dihydro-mridin-3-yl)-1-isopropyl-5,6-dihydro-1H-pyrrolo[3,4-b]pyrrol-4-one

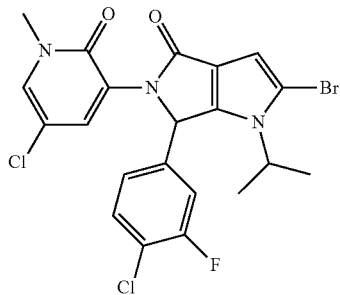 [SMILES: CC(C)n1c(Br)cc2c1C(c1ccc(Cl)c(F)c1)N(c1cc(Cl)cn(C)c1=O)C2=O]

The title compound was prepared in analogy to the procedure described for Intermediate AZ but 3-amino-5-chloro-1-methyl-1H-pyridin-2-one (Step L4) was used instead of 5-amino-3-chloro-1-methyl-1H-pyridin-2-one. The title compound (containing some of the corresponding 2-chloro analog) was obtained as a white foam. $t_R$: 1.24 min (HPLC 3); TLC: $R_f$=0.50 (EtOAc).

Intermediate BB: 2-Bromo-6-(4-chloro-3-fluoro-phenyl)-5-[5-chloro-1-(4-methoxy-benzyl)-2-oxo-1,2-dihydro-pyridin-3-yl]-1-isopropyl-5,6-dihydro-1H-pyrrolo[3,4-b]pyrrol-4-one

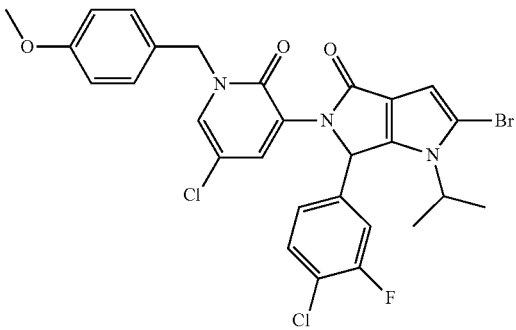 [SMILES: COc1ccc(Cn2cc(Cl)cc(N3C(=O)c4cc(Br)n(C(C)C)c4C3c3ccc(Cl)c(F)c3)c2=O)cc1]

The title compound was prepared in analogy to the procedure described for Intermediate D but in the step corresponding to Step D2,5-bromo-2-[(4-chloro-3-fluoro-phenyl)-hydroxy-methyl]-1-isopropyl-1H-pyrrole-3-carboxylic acid methyl ester (Step AZ1) and 3-amino-5-chloro-1-(4-methoxy-benzyl)-1H-pyridin-2-one (Step AH1) were used instead of 5-bromo-2-[(4-chloro-phenyl)-hydroxy-methyl]-1-isopropyl-1H-pyrrole-3-carboxylic acid methyl ester and 3-chloro-4-fluoroaniline respectively. Moreover, in this step, the procedures described for Steps H3 and H2 using 1-chloro-N,N,2-trimethylpropenylamine and Et$_3$N were used. The title compound (containing some of the corresponding 2-chloro analog) was obtained as a yellow-brown solid. $t_R$: 7.83 min (HPLC 2); ESI-MS: $t_R$=1.36 min, [M+H]$^+$ 618/620/622 (LC-MS 1); TLC: $R_f$=0.50 (98:2 CH$_2$Cl$_2$/MeOH).

Intermediate BC: 4-[2-Bromo-5-(5-chloro-1-methyl-6-oxo-1,6-dihydro-pyridin-3-yl)-1-isopropyl-4-oxo-1,4,5,6-tetrahydro-pyrrolo[3,4-b]pyrrol-6-yl]-2-fluoro-benzonitrile

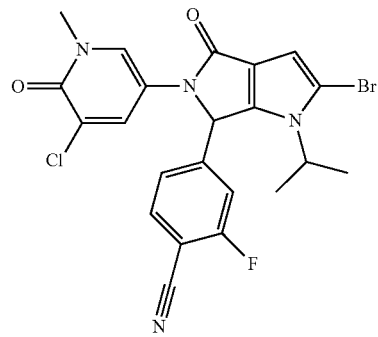 [SMILES: CC(C)n1c(Br)cc2c1C(c1ccc(C#N)c(F)c1)N(c1cc(Cl)c(=O)n(C)c1)C2=O]

The title compound was prepared in analogy to the procedure described for Intermediate AX but in the step corresponding to Step AX1, 5-bromo-2-[(4-cyano-3-fluoro-phenyl)-hydroxy-methyl]-1-isopropyl-1H-pyrrole-3-carboxylic acid methyl ester (Step BC1) and 5-amino-3-chloro-1-methyl-1H-pyridin-2-one (Step E5) were used instead of 5-bromo-2-[(4-cyano-phenyl)-hydroxy-methyl]-1-isopropyl-1H-pyrrole-3-carboxylic acid methyl ester and 2,5-dimethyl-2H-pyrazol-3-ylamine respectively. Moreover, in this step, the procedures described for Steps H3 and H2 using 1-chloro-N,N,2-trimethylpropenylamine and Et$_3$N were used. The title compound (containing some of the corresponding 2-chloro analog) was obtained as a yellow solid. $t_R$: 1.08 min (HPLC 3); ESI-MS: $t_R$=0.99 min, [M+H]$^+$ 503/505/507 (LC-MS 1); TLC: $R_f$=0.18 (EtOAc).

Step BC1: 5-Bromo-2-[(4-cyano-3-fluoro-phenyl)-hydroxy-methyl]-1-isopropyl-1H-pyrrole-3-carboxylic acid methyl ester

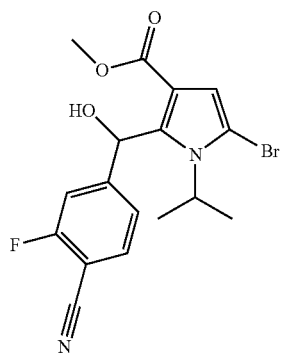 [SMILES: COC(=O)c1cc(Br)n(C(C)C)c1C(O)c1ccc(C#N)c(F)c1]

The title compound was prepared in analogy to the procedure described for Step D3 but 2-fluoro-4-formyl-benzonitrile [101048-76-4] was used instead of 4-chlorobenzaldehyde. The title compound was obtained as a yellow solid. $t_R$: 1.27 min (HPLC 3); ESI-MS: $t_R$=1.20 min, [M]⁺377/379 (i.e. fragmented pyrrolium ion) (LC-MS 1); TLC: $R_f$=0.21 (CH$_2$Cl$_2$).

Intermediate BD: 4-[2-Bromo-5-(5-chloro-1-methyl-2-oxo-1,2-dihydro-pyridin-3-yl)-1-isopropyl-4-oxo-1,4,5,6-tetrahydro-pyrrolo[3,4-b]pyrrol-6-yl]-2-fluoro-benzonitrile

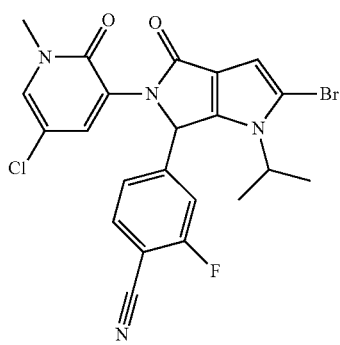 [SMILES: CC(C)n1c(Br)cc2c1C(c1ccc(C#N)c(F)c1)N(c1cc(Cl)cn(C)c1=O)C2=O]

The title compound was prepared in analogy to the procedure described for Intermediate BC but 3-amino-5-chloro-1-methyl-1H-pyridin-2-one (Step L4) was used instead of 5-amino-3-chloro-1-methyl-1H-pyridin-2-one. The title compound (containing some of the corresponding 2-chloro analog) was obtained as a yellow solid. $t_R$: 1.11 min (HPLC 3); ESI-MS: $t_R$=1.06 min, [M+H]⁺ 503/505/507 (LC-MS 1); TLC: $R_f$=0.18 (2:1 EtOAc/heptanes).

Intermediate BE: 4-{2-Bromo-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-2-fluoro-benzonitrile

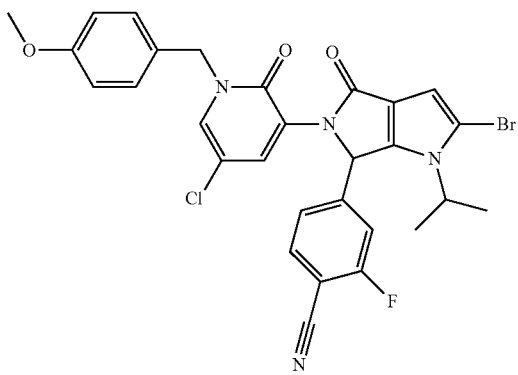 [SMILES: COc1ccc(Cn2cc(Cl)cc(N3C(=O)c4cc(Br)n(C(C)C)c4C3c3ccc(C#N)c(F)c3)c2=O)cc1]

The title compound was prepared in analogy to the procedure described for Intermediate BC but 3-amino-5-chloro-1-(4-methoxy-benzyl)-1H-pyridin-2-one (Step AH1) was used instead of 5-amino-3-chloro-1-methyl-1H-pyridin-2-one. The title compound (containing some of the corresponding 2-chloro analog) was obtained as a light yellow solid. $t_R$: 7.22 min (HPLC 2); ESI-MS: $t_R$=1.23 min, [M−H]⁺ 607/609/611 (LC-MS 1).

Intermediate BF: 2-Bromo-5-(5-chloro-2-methoxy-pyridin-3-yl)-6-(4-chloro-phenyl)-1-isopropyl-5,6-dihydro-1H-pyrrolo[3,4-b]pyrrol-4-one

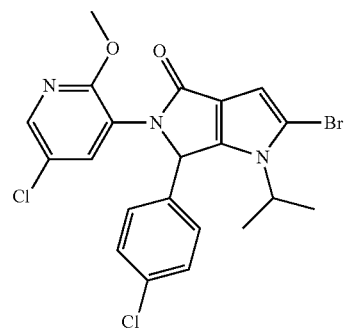 [SMILES: COc1ncc(Cl)cc1N1C(=O)c2cc(Br)n(C(C)C)c2C1c1ccc(Cl)cc1]

The title compound was prepared in analogy to the procedures described for Intermediate D but in the step corresponding to Step D2,5-chloro-2-methoxy-pyridin-3-ylamine [886373-70-2] was used instead of 3-chloro-4-fluoroaniline. Moreover, in this step, the procedures described for Steps H3 and H2 using 1-chloro-N,N,2-trimethylpropenylamine and Et$_3$N were used. In addition, in the step corresponding to Step D1, the procedure described for Step A2 using LiOH was used. The title compound (containing some of the corresponding 2-chloro analog) was obtained as a solid. ESI-MS: $t_R$=1.33 min, [M+H]⁺ 494/496/498 (LC-MS 1).

Intermediate BG: 4-[2-Bromo-5-(5-chloro-2-methoxy-pyridin-3-yl)-1-isopropyl-4-oxo-1,4,5,6-tetrahydro-pyrrolo[3,4-b]pyrrol-6-yl]-benzonitrile

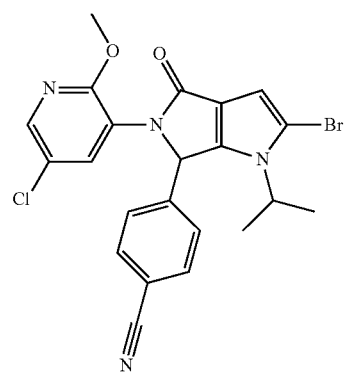 [SMILES: COc1ncc(Cl)cc1N1C(=O)c2cc(Br)n(C(C)C)c2C1c1ccc(C#N)cc1]

The title compound was prepared in analogy to the procedure described for Intermediate AX but in the step corresponding to Step AX1, 5-chloro-2-methoxy-pyridin-3-ylamine [886373-70-2] was used instead of 2,5-dimethyl-2H-pyrazol-3-ylamine. Moreover, in this step, the procedures described for Steps H3 and H2 using 1-chloro-N,N,2-trimethylpropenylamine and Et$_3$N were used. The title compound (containing some of the corresponding 2-chloro analog) was obtained as a solid. ESI-MS: $t_R$=1.17 min, [M+H]⁺ 485/487/489 (LC-MS 1).

Intermediate BH: 2-Bromo-6-(4-chloro-phenyl)-5-(4-fluoro-2,5-dimethyl-2H-pyrazol-3-yl)-1-isopropyl-5,6-dihydro-1H-pyrrolo[3,4-b]pyrrol-4-one

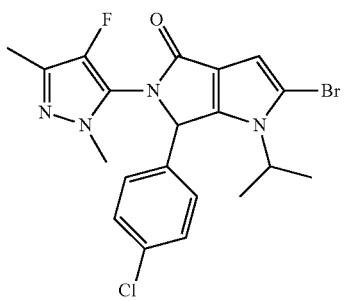 [SMILES: Cc1nn(C)c(N2C(=O)c3cc(Br)n(C(C)C)c3C2c2ccc(Cl)cc2)c1F]

The title compound was prepared in analogy to the procedure described for Intermediate D but in the step corresponding to Step D2,4-fluoro-2,5-dimethyl-2H-pyrazol-3-ylamine (Step BH1) was used instead of 3-chloro-4-fluoroaniline. Moreover, in this step, the procedures described for Steps H3 and H2 using 1-chloro-N,N,2-trimethylpropenylamine and Et$_3$N were used. The title compound (containing some of the corresponding 2-chloro analog) was obtained as a solid. ESI-MS: t$_R$=1.20/1.21 min, [M+H]$^+$ 465/467/469 (LC-MS 1).

Step BH1: 4-Fluoro-2,5-dimethyl-2H-pyrazol-3-ylamine

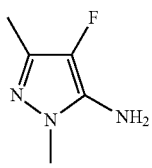

TFA (170 mmol) was added to a solution of (4-fluoro-2,5-dimethyl-2H-pyrazol-3-yl)-carbamic acid tert-butyl ester (Step BH2) (22.68 mmol) in CH$_2$Cl$_2$ (50 mL) at rt. After stirring for 24 h, the reaction mixture was quenched with 2N aqueous NaOH and extracted with CH$_2$Cl$_2$ (3×). The combined organic phases were dried (Na$_2$SO$_4$), filtered and concentrated to afford the title compound as a bright yellow solid which was used in the next step without further purification. ESI-MS: t$_R$=0.38 min, [M+H]$^+$ 130 (LC-MS 1).

Step BH2: (4-Fluoro-2,5-dimethyl-2H-pyrazol-3-yl)-carbamic acid tert-butyl ester

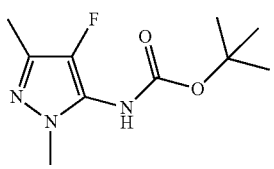 [SMILES: Cc1nn(C)c(NC(=O)OC(C)(C)C)c1F]

Selectfluor® [140681-55-6] (66 mmol) was added portionwise to a solution of (2,5-dimethyl-2H-pyrazol-3-yl)-carbamic acid tert-butyl ester [1246552-45-3] (32.7 mmol) in CH$_2$Cl$_2$ (800 mL) and DMF (800 mL) at 0° C. and then the reaction was warmed to rt. After 1 h, the mixture was quenched with H$_2$O and extracted with CH$_2$Cl$_2$. The organic phase was dried (Na$_2$SO$_4$), filtered and concentrated. The residue was purified using a RediSep® silica gel column to afford the title compound. ESI-MS: t$_R$=0.83 min, [M+H]$^+$ 230 (LC-MS 1).

Intermediate BI: 2-Bromo-6-(4-chloro-2-fluoro-phenyl)-5-(2,5-dimethyl-2H-pyrazol-3-yl)-1-isopropyl-5,6-dihydro-1H-pyrrolo[3,4-b]pyrrol-4-one

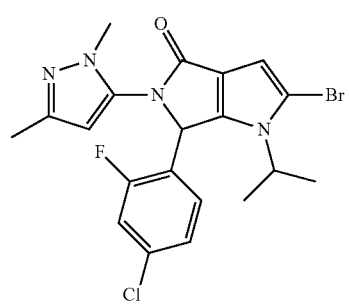 [SMILES: Cc1cc(N2C(=O)c3cc(Br)n(C(C)C)c3C2c2ccc(Cl)cc2F)n(C)n1]

The title compound was prepared in analogy to the procedure described for Intermediate D but in the step corresponding to Step D2, 2,5-dimethyl-2H-pyrazol-3-ylamine [3524-32-1] and 5-bromo-2-[(4-chloro-2-fluoro-phenyl)-hydroxy-methyl]-1-isopropyl-1H-pyrrole-3-carboxylic acid methyl ester (Step BI1) were used instead of 3-chloro-4-fluoroaniline and 5-bromo-2-[(4-chloro-phenyl)-hydroxy-methyl]-1-isopropyl-1H-pyrrole-3-carboxylic acid methyl ester respectively. Moreover, in this step, the procedure described for Step L3 using Ms$_2$O and Et$_3$N was used. The title compound (containing some of the corresponding 2-chloro analog) was obtained as a solid. ESI-MS: t$_R$=1.14 min, [M+H]$^+$ 465/467/469 (LC-MS 1).

Step BI1: 5-Bromo-2-[(4-chloro-2-fluoro-phenyl)-hydroxy-methyl]-1-isopropyl-1H-pyrrole-3-carboxylic acid methyl ester

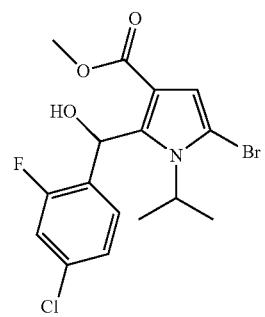 [SMILES: COC(=O)c1cc(Br)n(C(C)C)c1C(O)c1ccc(Cl)cc1F]

The title compound was prepared in analogy to the procedure described for Step D3 but 4-chloro-2-fluoro-benzaldehyde [61072-56-8] was used instead of 4-chlorobenzaldehyde. ESI-MS: t$_R$=1.30 min, [M]$^+$386/388/390 (i.e. fragmented pyrrolium ion) (LC-MS 1).

Intermediate BJ: 4-[2-Bromo-5-(4-fluoro-2,5-dimethyl-2H-pyrazol-3-yl)-1-isopropyl-4-oxo-1,4,5,6-tetrahydro-pyrrolo[3,4-b]pyrrol-6-yl]-benzonitrile

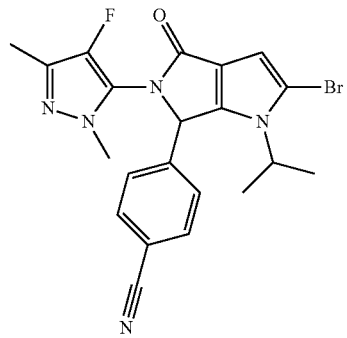 [SMILES: Cc1nn(C)c(N2C(=O)c3cc(Br)n(C(C)C)c3C2c2ccc(C#N)cc2)c1F]

The title compound was prepared in analogy to the procedure described for Intermediate AX but in the step corresponding to Step AX1, 4-fluoro-2,5-dimethyl-2H-pyrazol-3-ylamine (Step BH1) was used instead of 2,5-dimethyl-2H-pyrazol-3-ylamine. Moreover, in this step, the procedures described for Steps H3 and H2 using 1-chloro-N,N,2-trimethylpropenylamine and Et$_3$N were used. The title compound (containing some of the corresponding 2-chloro analog) was obtained as a solid. ESI-MS: t$_R$=1.06 min, [M+H]$^+$ 456/458 (LC-MS 1).

Intermediate BK: 2-Bromo-5-(5-chloro-1-methyl-2-oxo-1,2-dihydro-pyridin-3-yl)-6-(5-chloro-pyridin-2-yl)-1-isopropyl-5,6-dihydro-1H-pyrrolo[3,4-b]pyrrol-4-one

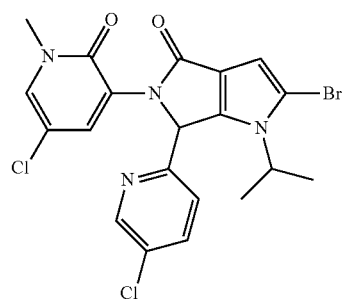 [SMILES: CC(C)n1c(Br)cc2c1C(c1ccc(Cl)cn1)N(c1cc(Cl)cn(C)c1=O)C2=O]

The title compound was prepared in analogy to the procedure described for Step O1 but 5-bromo-2-[(5-chloro-1-methyl-2-oxo-1,2-dihydro-pyridin-3-ylamino)-(5-chloro-pyridin-2-yl)-methyl]-1-isopropyl-1H-pyrrole-3-carboxylic acid (Step BK1) was used instead of 2-[[5-chloro-1-(4-methoxybenzyl)-6-oxo-1,6-dihydro-pyridin-3-ylamino]-(4-chlorophenyl)-methyl]-1-isopropyl-1H-pyrrole-3-carboxylic acid. The title compound was obtained as a yellow solid. ESI-MS: t$_R$=1.05 min, [M+H]$^+$ 495/497/499 (LC-MS 1).

Step BK1: 5-Bromo-2-[(5-chloro-1-methyl-2-oxo-1,2-dihydro-pyridin-3-ylamino)-(5-chloro-pyridin-2-yl)-methyl]-1-isopropyl-1H-pyrrole-3-carboxylic acid

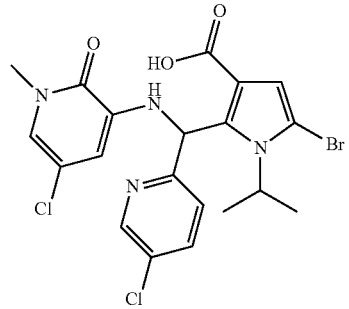 [SMILES: CC(C)n1c(Br)cc(C(=O)O)c1C(Nc1cc(Cl)cn(C)c1=O)c1ccc(Cl)cn1]

The title compound was prepared in analogy to the procedure described for Step L2 but in the step corresponding to Step L3,5-bromo-2-[(5-chloro-pyridin-2-yl)-hydroxy-methyl]-1-isopropyl-1H-pyrrole-3-carboxylic acid methyl ester (Step BK2) was used instead of 2-[(4-chloro-phenyl)-hydroxy-methyl]-1-isopropyl-1H-pyrrole-3-carboxylic acid ethyl ester. The title compound was obtained as an orange-beige solid. ESI-MS: t$_R$=1.15 min, [M+H]$^+$ 513/515/517 (LC-MS 1).

Step BK2: 5-Bromo-2-[(5-chloro-pyridin-2-yl)-hydroxy-methyl]-1-isopropyl-1H-pyrrole-3-carboxylic acid methyl ester

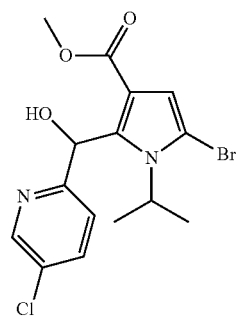 [SMILES: COC(=O)c1cc(Br)n(C(C)C)c1C(O)c1ccc(Cl)cn1]

The title compound was prepared in analogy to the procedure described for Step D3 but 5-chloro-pyridine-2-carbaldehyde [31181-89-2] was used instead of 4-chlorobenzaldehyde. The title compound was obtained as a yellow solid. ESI-MS: t$_R$=1.19 min, [M+H]$^+$ 387/389/391 (LC-MS 1).

Intermediate BL: 2-Bromo-5-(3-chloro-4-fluoro-phenyl)-6-(5-chloro-pyridin-2-yl)-1-isopropyl-5,6-dihydro-1H-pyrrolo[3,4-b]pyrrol-4-one

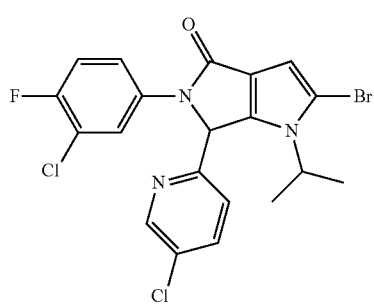 [SMILES: CC(C)n1c(Br)cc2c1C(c1ccc(Cl)cn1)N(c1ccc(F)c(Cl)c1)C2=O]

The title compound was prepared in analogy to the procedure described for Step H1, but diethylaluminium chloride (1.8M in toluene) was used instead of trimethylaluminium chloride, and 5-bromo-2-[(3-chloro-4-fluoro-phenylamino)-(5-chloro-pyridin-2-yl)-methyl]-1-isopropyl-1H-pyrrole-3-carboxylic acid methyl ester (Step BL1) was used instead of 2-[(3-chloro-4-fluoro-phenylamino)-(4-cyano-phenyl)-methyl]-1-isopropyl-1H-pyrrole-3-carboxylic acid ethyl ester to afford the title compound as a yellow solid. ESI-MS: $t_R$=1.30 min, [M+H]$^+$ 482/484/486 (LC-MS 1).

Step BL1: 5-Bromo-2-[(3-chloro-4-fluoro-phenylamino)-(5-chloro-pyridin-2-yl)-methyl]-1-isopropyl-1H-pyrrole-3-carboxylic acid methyl ester

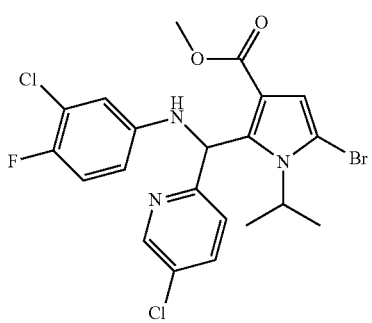 [SMILES: COC(=O)c1cc(Br)n(C(C)C)c1C(Nc1ccc(F)c(Cl)c1)c1ccc(Cl)cn1]

The title compound was prepared in analogy to the procedure described for Step L3 but 5-bromo-2-[(5-chloro-pyridin-2-yl)-hydroxy-methyl]-1-isopropyl-1H-pyrrole-3-carboxylic acid methyl ester (Step BK2) and 3-chloro-4-fluoroaniline [367-21-5] were used instead of 2-[(4-chloro-phenyl)-hydroxy-methyl]-1-isopropyl-1H-pyrrole-3-carboxylic acid ethyl ester and 3-amino-5-chloro-1-methyl-1H-pyridin-2-one respectively. The title compound was obtained as a beige foam. ESI-MS: $t_R$=1.51 min, [M+H]$^+$ 514/516/518 (LC-MS 1).

Intermediate BM: 2-Bromo-5-(5-chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrole-3-carboxylic acid ethyl ester

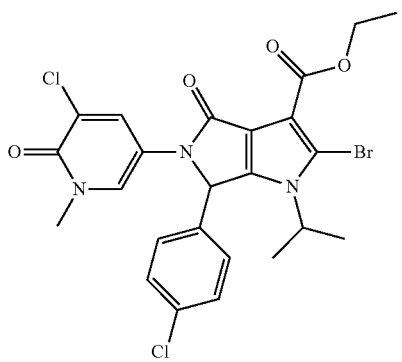 [SMILES: CCOC(=O)c1c2c(n(C(C)C)c1Br)C(c1ccc(Cl)cc1)N(c1cc(Cl)c(=O)n(C)c1)C2=O]

The title compound was prepared in analogy to the procedure described for Step H1, but diethylaluminium chloride (1.8M in toluene) was used instead of trimethylaluminium chloride, and 2-bromo-5-[(5-chloro-1-methyl-6-oxo-1,6-dihydro-pyridin-3-ylamino)-(4-chloro-phenyl)-methyl]-1-isopropyl-1H-pyrrole-3,4-dicarboxylic acid diethyl ester (Step BM1) was used instead of 2-[(3-chloro-4-fluoro-phenylamino)-(4-cyano-phenyl)-methyl]-1-isopropyl-1H-pyrrole-3-carboxylic acid ethyl ester to afford the title compound as a beige solid. $t_R$: 1.16 min (HPLC 3); ESI-MS: $t_R$=1.11 min, [M+H]$^+$ 566/568/570 (LC-MS 1); TLC: $R_f$=0.14 (EtOAc).

Step BM1: 2-Bromo-5-[(5-chloro-1-methyl-6-oxo-1,6-dihydro-pyridin-3-ylamino)-(4-chloro-phenyl)-methyl]-1-isopropyl-1H-pyrrole-3,4-dicarboxylic acid diethyl ester

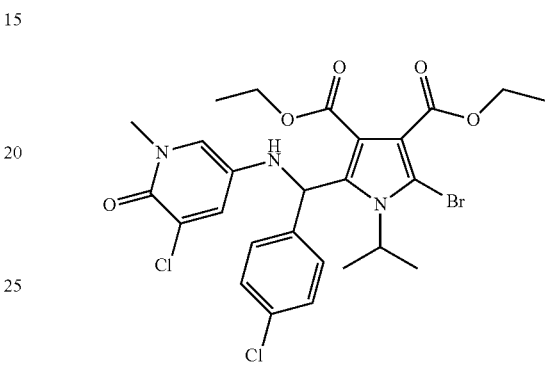

The title compound was prepared in analogy to the procedure described for Step L3 but 2-bromo-5-[(4-chloro-phenyl)-hydroxy-methyl]-1-isopropyl-1H-pyrrole-3,4-dicarboxylic acid diethyl ester (Step BM2) and 5-amino-3-chloro-1-methyl-1H-pyridin-2-one (Step E5) were used instead of 2-[(4-chloro-phenyl)-hydroxy-methyl]-1-isopropyl-1H-pyrrole-3-carboxylic acid ethyl ester and 3-amino-5-chloro-1-methyl-1H-pyridin-2-one respectively. The title compound was obtained as a blue foam. $t_R$: 1.28 min (HPLC 3); ESI-MS: $t_R$=1.25 min, [M+H]$^+$ 612/614/616 (LC-MS 1); TLC: $R_f$=0.17 (2:1 EtOAc/heptanes).

Step BM2: 2-Bromo-5-[(4-chloro-phenyl)-hydroxy-methyl]-1-isopropyl-1H-pyrrole-3,4-dicarboxylic acid diethyl ester

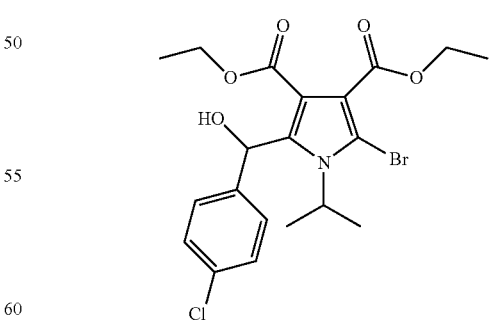

The title compound was prepared in analogy to the procedures described for Step D3 but in the step corresponding to Step D5,1H-pyrrole-3,4-dicarboxylic acid diethyl ester [41969-71-5] was used instead of 1H-pyrrole-3-carboxylic acid methyl ester. The title compound was obtained as a yellow oil. $t_R$: 1.35 min (HPLC 3); ESI-MS: $t_R$=1.37 min, [M+H]⁺ 472/474/476 (LC-MS 1); TLC: $R_f$=0.06 (CH₂Cl₂).

Intermediate BN: 2-Bromo-5-[5-chloro-1-(4-methoxy-benzyl)-2-oxo-1,2-dihydro-pyridin-3-yl]-6-(4-chloro-phenyl)-1-isopropyl-5,6-dihydro-1H-pyrrolo[3,4-b]pyrrol-4-one

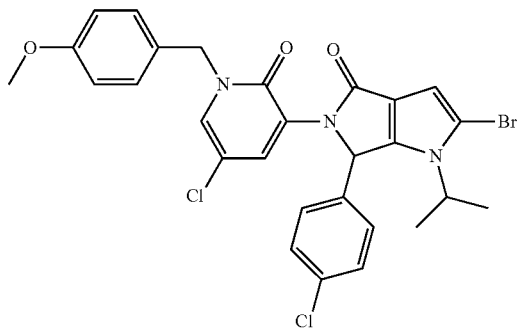 [SMILES: COc1ccc(Cn2cc(Cl)cc(N3C(=O)c4cc(Br)n(C(C)C)c4C3c3ccc(Cl)cc3)c2=O)cc1]

The title compound was prepared in analogy to the procedure described for Intermediate AX but in the step corresponding to Step AX1, 5-bromo-2-[(4-chloro-phenyl)-hydroxy-methyl]-1-isopropyl-1H-pyrrole-3-carboxylic acid methyl ester (step D3) and 3-amino-5-chloro-1-(4-methoxybenzyl)-1H-pyridin-2-one (Step AH1) were used instead of 5-bromo-2-[(4-cyano-phenyl)-hydroxy-methyl]-1-isopropyl-1H-pyrrole-3-carboxylic acid methyl ester and 2,5-dimethyl-2H-pyrazol-3-ylamine respectively. The title compound was obtained as a white solid. $t_R$: 1.38 min (HPLC 3); ESI-MS: $t_R$=1.35 min, [M+H]⁺ 600/602/604 (LC-MS 1); TLC: $R_f$=0.46 (1:1 EtOAc/heptanes).

Intermediate BO: (R,S)-2-Bromo-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one

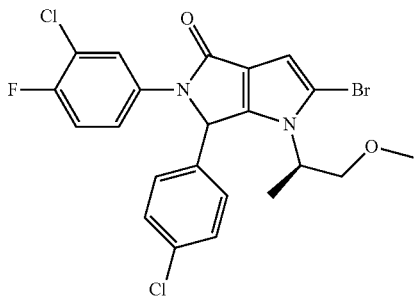 [SMILES: COC[C@@H](C)n1c(Br)cc2c1C(c1ccc(Cl)cc1)N(c1ccc(F)c(Cl)c1)C2=O]

The title compound was prepared in analogy to the procedures described for Intermediate H, but in the step corresponding to Step H1, diethylaluminium chloride (1.8M in toluene) was used instead of trimethylaluminium chloride, and 2-[(R,S)-(3-chloro-4-fluoro-phenylamino)-(4-chloro-phenyl)-methyl]-1-((R)-2-methoxy-1-methyl-ethyl)-1H-pyrrole-3-carboxylic acid ethyl ester (Step BO1) was used instead of 2-[(3-chloro-4-fluoro-phenylamino)-(4-cyano-phenyl)-methyl]-1-isopropyl-1H-pyrrole-3-carboxylic acid ethyl ester. The title compound (mixture of diastereomers) was obtained as a white solid. $t_R$: 7.61/7.75 min (HPLC 2); ESI-MS: $t_R$=1.29/1.32 min, [M+H]⁺ 511/513/515 (LC-MS 1).

Step BO1: 2-[(R,S)-(3-Chloro-4-fluoro-phenylamino)-(4-chloro-phenyl)-methyl]-14(R)-2-methoxy-1-methyl-ethyl)-1H-pyrrole-3-carboxylic acid ethyl ester

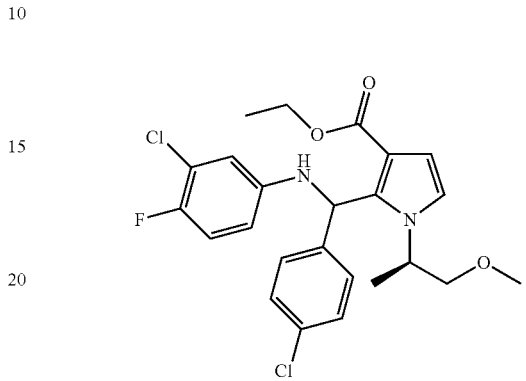

The title compound was prepared in analogy to the procedures described for Step H2 and Step H3 but 2-[(R,S)-(4-chloro-phenyl)-hydroxy-methyl]-1-((R)-2-methoxy-1-methyl-ethyl)-1H-pyrrole-3-carboxylic acid ethyl ester (Step BO2) was used instead of 2-[(4-cyano-phenyl)-hydroxy-methyl]-1-isopropyl-1H-pyrrole-3-carboxylic acid ethyl ester. The title compound (mixture of diastereomers) was obtained as a red-brown solid. $t_R$: 8.30/8.47 min (HPLC 2); ESI-MS: $t_R$=1.44/1.47 min, [M+H]⁺479/481 (LC-MS 1).

Step BO2: 2-[(R,S)-(4-chloro-phenyl)-hydroxy-methyl]-1-((R)-2-methoxy-1-methyl-ethyl)-1H-pyrrole-3-carboxylic acid ethyl ester

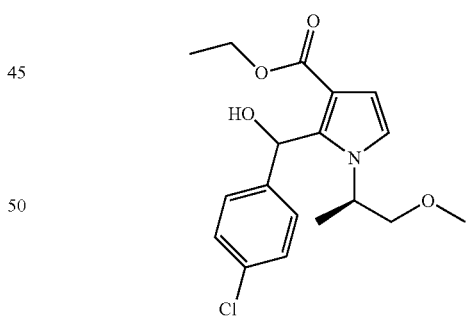

The title compound was prepared in analogy to the procedure described for Step A4 but 4-chloro-phenylmagnesium bromide [873-77-8] and 2-formyl-1-((R)-2-methoxy-1-methyl-ethyl)-1H-pyrrole-3-carboxylic acid ethyl ester (Step BO3) were used instead of 4-chloro-2-methylphenylmagnesium bromide and 2-formyl-1-isopropyl-1H-pyrrole-3-carboxylic acid ethyl ester respectively. The title compound (mixture of diastereomers) was obtained as a light yellow solid. $t_R$: 7.09/7.20 min (HPLC 2); ESI-MS: $t_R$=1.19/1.21 min, [M]⁺334/336 (i.e. fragmented pyrrolium ion) (LC-MS 1); TLC: $R_f$=0.19/0.22 (1:4 EtOAc/hexanes).

Step BO3: 2-Formyl-1-((R)-2-methoxy-1-methyl-ethyl)-1H-pyrrole-3-carboxylic acid ethyl ester

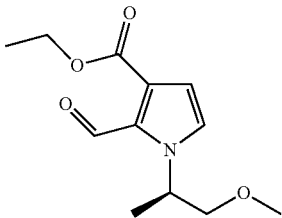 [SMILES: CCOC(=O)c1ccn([C@H](C)COC)c1C=O]

The title compound was prepared in analogy to the procedure described for Step A5 but 1-((R)-2-methoxy-1-methyl-ethyl)-2-methyl-1H-pyrrole-3-carboxylic acid ethyl ester was used instead of 2-formyl-1-isopropyl-1H-pyrrole-3-carboxylic acid ethyl ester. The title compound was obtained as a yellow oil. $t_R$: 6.08 min (HPLC 2); ESI-MS: $t_R$=0.96 min, [M+H]$^+$ 240 (LC-MS 1); TLC: $R_f$=0.24 (1:4 EtOAc/hexanes).

Step BO4: 1-((R)-2-Methoxy-1-methyl-ethyl)-2-methyl-1H-pyrrole-3-carboxylic acid ethyl ester

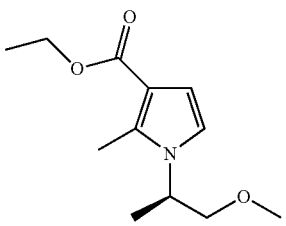 [SMILES: CCOC(=O)c1ccn([C@H](C)COC)c1C]

NaH (49 mmol) was added to a solution of 1-((R)-2-hydroxy-1-methyl-ethyl)-2-methyl-1H-pyrrole-3-carboxylic acid ethyl ester (Step BO5) (40.9 mmol) in DMF (150 mL) at 0° C. After stirring for 1 h, a solution of methyl iodide (53.1 mmol) in DMF (10 mL) was added dropwise via cannula. After stirring for 1 h, the reaction mixture was warmed to rt. After 18 h, the mixture was cooled to 0° C., quenched with 1N aqueous KHSO$_4$ and extracted with EtOAc (5×). The combined organic layers were successively washed with a saturated aqueous solution of NaHCO$_3$ and brine, dried (Na$_2$SO$_4$) and concentrated. The residue was purified using a RediSep® silica gel column to afford the title compound as a yellow oil. $t_R$: 4.16 min (HPLC 1); ESI-MS: $t_R$=0.97 min, [M+H]$^+$ 226 (LC-MS 1); TLC: $R_f$=0.37 (1:3 EtOAc/heptanes).

Step BO5: 1-((R)-2-Hydroxy-1-methyl-ethyl)-2-methyl-1H-pyrrole-3-carboxylic acid ethyl ester

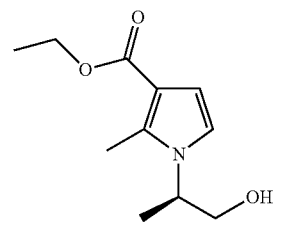

A solution of bromine (126 mmol) in CH$_2$Cl$_2$ (10 mL) was added dropwise to a solution of vinyl acetate (126 mmol) in CH$_2$Cl$_2$ (25 mL) at 0° C. After stirring for 15 min, the mixture was warmed to rt, stirred for 45 min, treated with ethyl acetoacetate (126 mmol) and then re-cooled to 0° C. D-Alaninol [35320-23-1] (253 mmol) was added dropwise over 1 h. After stirring for 30 min, the mixture was warmed to rt. After 2.5 h, the reaction mixture was poured onto ice/H2O/brine and the phases separated. The aqueous phase was extracted with CH$_2$Cl$_2$ (2×). The combined organic phases were washed with brine, dried (Na$_2$SO$_4$), filtered and concentrated. The residue was purified using a RediSep® silica gel column to afford the title compound as an orange-brown solid. $t_R$: 3.32 min (HPLC 1); ESI-MS: $t_R$=0.76 min, [M+H]$^+$ 212 (LC-MS 1); TLC: $R_f$=0.32 (1:1 EtOAc/heptanes).

Intermediate BP: (R,S)-2-Bromo-5-(5-chloro-1-methyl-6-oxo-1,6-dihydro-pyridin-3-yl)-6-(4-chloro-phenyl)-1-((R)-2-methoxy-1-methyl-ethyl)-5,6-dihydro-1H-pyrrolo[3,4-b]pyrrol-4-one

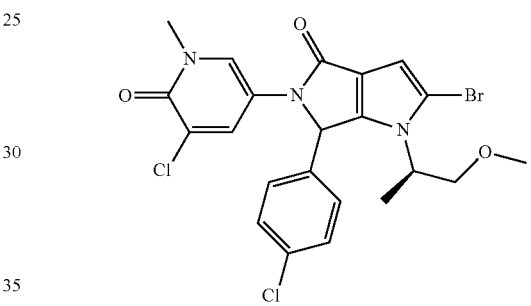

The title compound was prepared in analogy to the procedures described for Intermediate BO but in the step corresponding to Step BO1, 5-amino-3-chloro-1-methyl-1H-pyridin-2-one (Step E5) was used instead of 3-chloro-4-fluoroaniline. The title compound (mixture of diastereomers) was obtained as a green foam. $t_R$: 6.34/6.52 min (HPLC 2); ESI-MS: $t_R$=1.02/1.06 min, [M+H]$^+$ 524/526/528 (LC-MS 1).

Intermediate BQ: (R,S)-4-[2-Bromo-5-(3-chloro-4-fluoro-phenyl)-1-((R)-2-methoxy-1-methyl-ethyl)-4-oxo-1,4,5,6-tetrahydro-pyrrolo[3,4-b]pyrrol-6-yl]-benzonitrile

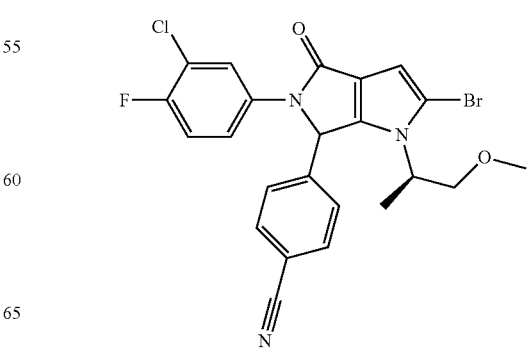

The title compound was prepared in analogy to the procedures described for Intermediate BO but in the step corresponding to Step BO2, 4-cyanophenylmagnesium chloride (Step H5) was used instead of 4-chloro-phenylmagnesium bromide. The title compound (mixture of diastereomers) was obtained as a white solid. $t_R$: 6.88/6.99 min (HPLC 2); ESI-MS: $t_R$=1.15/1.17 min, [M+H]$^+$ 502/504/506 (LC-MS 1).

Intermediate BR: (R,S)-4-[2-Bromo-5-(5-chloro-1-methyl-6-oxo-1,6-dihydro-pyridin-3-yl)-1-((R)-2-methoxy-1-methyl-ethyl)-4-oxo-1,4,5,6-tetrahydro-pyrrolo[3,4-b]pyrrol-6-yl]-benzonitrile

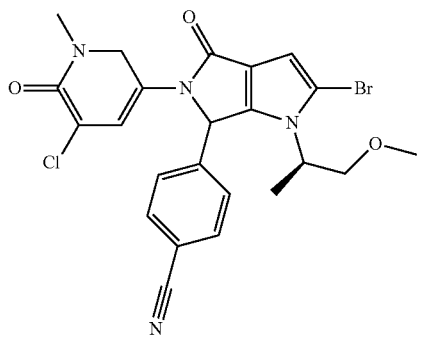

The title compound was prepared in analogy to the procedures described for Intermediate BP but in the step corresponding to Step BO2, 4-cyanophenylmagnesium chloride (Step H5) was used instead of 4-chloro-phenylmagnesium bromide. The title compound (mixture of diastereomers) was obtained as a green foam. $t_R$: 5.79/5.90 min (HPLC 2); ESI-MS: $t_R$=0.90/0.93 min, [M+H]$^+$515/517/519 (LC-MS 1).

Intermediate BS:
2,4-d$_6$-Dimethoxypyrimidineboronic acid

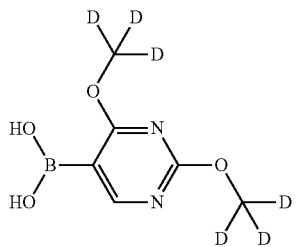 [SMILES: [2H]C([2H])([2H])Oc1ncc(B(O)O)c(OC([2H])([2H])[2H])n1]

n-BuLi (1.6M) (4.6 mmol) was added to a solution of 5-bromo-2,4-d$_6$-dimethoxy-pyrimidine (Step BS1) (4 mmol) in THF (30 mL) at −78° C., stirred for 5 min, cooled to −100° C. and then treated dropwise with triethylborate (5 mmol). The reaction mixture was slowly (over 2 h) warmed to rt and then concentrated. The residue was diluted with H$_2$O (10 mL) and filtered. The filtrate was acidified (pH 3) with 0.2N aqueous HCl and extracted with CH$_2$Cl$_2$. The organic phase was dried (Na$_2$SO$_4$), filtered and concentrated. The residue was recrystallized from CH$_2$Cl$_2$/hexanes to afford the title compound as a white solid. $t_R$: 2.38 min (HPLC 7); ESI-MS: $t_R$=0.48 min, [M+H]$^+$ 191 (LC-MS 1).

Step BS1: 5-Bromo-2,4-d$_6$-dimethoxy-pyrimidine

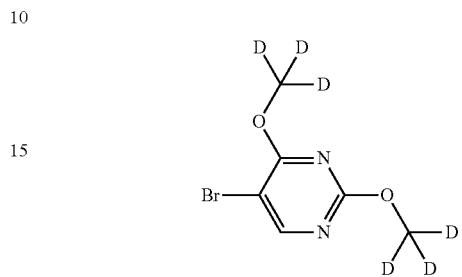

Sodium (54.9 mmol) was added to d3-MeOH (11.63 mL), stirred until all of the metal had dissolved, added to a solution of 5-bromo-2,4-dichloro-pyrimidine [36082-50-5] (21.94 mmol) in THF (100 mL) at 0° C. and then the mixture was warmed to rt. After 18 h, the reaction mixture was quenched with a saturated aqueous solution of NaHCO$_3$ and extracted with EtOAc. The organic phase was dried (Na$_2$SO$_4$) and concentrated. The residue was recrystallized from MTBE/hexanes to afford the title compound as a white solid. $t_R$: 4.79 min (HPLC 7); ESI-MS: $t_R$=0.84 min, [M+H]$^+$ 225/227 (LC-MS 1).

Intermediate BT: 2-Bromo-5-(3-chloro-2-fluorophenyl)-6-(5-chloropyridin-2-yl)-1-isopropyl-5,6-dihydropyrrolo[3,4-b]pyrrol-4(1H)-one

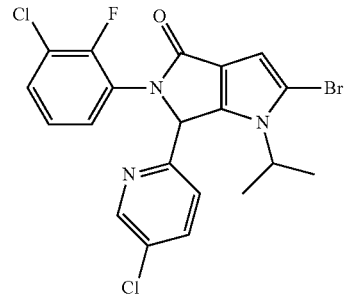 [SMILES: CC(C)n1c(Br)cc2c1C(c1ccc(Cl)cn1)N(c1cccc(Cl)c1F)C2=O]

The title compound was prepared in analogy to the procedure described for Step H1, but diethylaluminium chloride (1.8M in toluene) was used instead of trimethylaluminium chloride, and methyl 5-bromo-2-(((3-chloro-2-fluorophenyl)amino)(5-chloropyridin-2-yl)methyl)-1-isopropyl-1H-pyrrole-3-carboxylate (Step BT1) was used instead of 2-[(3-chloro-4-fluoro-phenylamino)-(4-cyano-phenyl)-methyl]-1-isopropyl-1H-pyrrole-3-carboxylic acid ethyl ester to afford the title compound as a green solid. ESI-MS: $t_R$=1.27 min, [M+H]$^+$ 482/484/486 (LC-MS 1).

Step BT1: Methyl 5-bromo-2-(((3-chloro-2-fluorophenyl)amino)(5-chloropyridin-2-yl)methyl)-1-isopropyl-1H-pyrrole-3-carboxylate

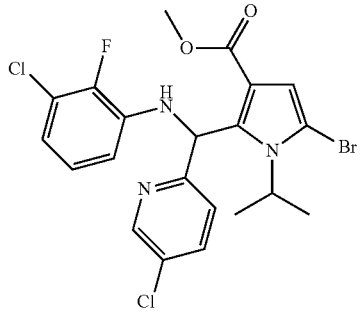 [SMILES: COC(=O)c1cc(Br)n(C(C)C)c1C(Nc1cccc(Cl)c1F)c1ccc(Cl)cn1]

The title compound was prepared in analogy to the procedure described for Step L3 but 5-bromo-2-[(5-chloro-pyridin-2-yl)-hydroxy-methyl]-1-isopropyl-1H-pyrrole-3-carboxylic acid methyl ester (Step BK2) and 3-chloro-2-fluoroaniline [367-21-5] were used instead of 2-[(4-chlorophenyl)-hydroxy-methyl]-1-isopropyl-1H-pyrrole-3-carboxylic acid ethyl ester and 3-amino-5-chloro-1-methyl-1H-pyridin-2-one respectively. The title compound was obtained as a white foam. ESI-MS: $t_R$=1.59 min, [M+H]$^+$ 514/516/518 (LC-MS 1).

Intermediate BU: 2-Bromo-5-(5-chloro-2-methylohenyl)-6-(5-chloropyridin-2-yl)-1-isopropyl-5,6-dihydropyrrolo[3,4-b]pyrrol-4(1H)-one

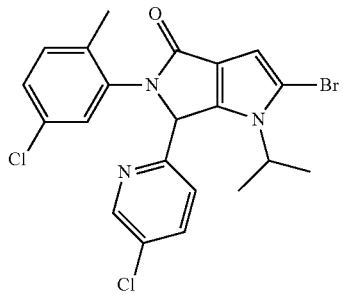 [SMILES: Cc1ccc(Cl)cc1N1C(=O)c2cc(Br)n(C(C)C)c2C1c1ccc(Cl)cn1]

The title compound was prepared in analogy to the procedure described for Step H1, but diethylaluminium chloride (1.8M in toluene) was used instead of trimethylaluminium chloride, and methyl 5-bromo-2-(((5-chloro-2-methyl phenyl)amino)(5-chloropyridin-2-yl)methyl)-1-isopropyl-1H-pyrrole-3-carboxylate (Step BT1) was used instead of 2-[(3-chloro-4-fluoro-phenylamino)-(4-cyano-phenyl)-methyl]-1-isopropyl-1H-pyrrole-3-carboxylic acid ethyl ester to afford the title compound as a yellow solid. ESI-MS: $t_R$=1.28 min, [M+H]$^+$ 478/480/482 (LC-MS 1).

Step BU 1: Methyl 5-bromo-2-(((5-chloro-2-methylphenyl)amino)(5-chloropyridin-2-yl)methyl)-1-isopropyl-1H-pyrrole-3-carboxylate

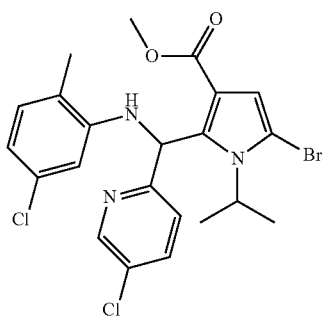 [SMILES: COC(=O)c1cc(Br)n(C(C)C)c1C(Nc1cc(Cl)ccc1C)c1ccc(Cl)cn1]

The title compound was prepared in analogy to the procedure described for Step L3 but 5-bromo-2-[(5-chloro-pyridin-2-yl)-hydroxy-methyl]-1-isopropyl-1H-pyrrole-3-carboxylic acid methyl ester (Step BK2) and 5-chloro-2-methyl-phenylamine were used instead of 2-[(4-chloro-phenyl)-hydroxy-methyl]-1-isopropyl-1H-pyrrole-3-carboxylic acid ethyl ester and 3-amino-5-chloro-1-methyl-1H-pyridin-2-one respectively. The title compound was obtained as a yellow-brown solid. ESI-MS: $t_R$=1.59 min, [M+H]$^+$ 510/512/514 (LC-MS 1).

Intermediate BV: 2-Bromo-6-(4-chlorophenyl)-5-(1,5-dimethyl-2-oxo-1,2-dihydropyridin-3-yl)-1-isopropyl-5,6-dihydropyrrolo[3,4-b]pyrrol-4(1H)-one

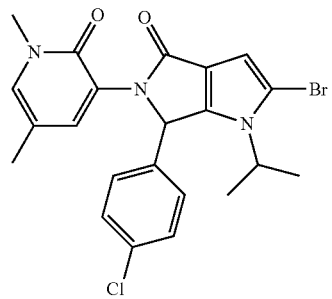 [SMILES: Cc1cc(N2C(=O)c3cc(Br)n(C(C)C)c3C2c2ccc(Cl)cc2)c(=O)n(C)c1]

The title compound was prepared in analogy to the procedure described for Intermediate O but in the step corresponding to Step O3, 3-amino-1,5-dimethylpyridin-2(1H)-one (Step BV1) was used instead of 5-amino-3-chloro-1-(4-methoxy-benzyl)-1H-pyridin-2-one to afford the title compound as a beige solid. ESI-MS: $t_R$=1.12 min, [M+H]$^+$ 474/476/478 (LC-MS 1).

Step BV1: 3-Amino-1,5-dimethylpyridin-2(1H)-one

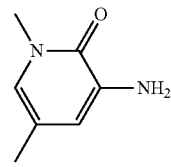

The title compound was prepared in analogy to the procedure for Step E5, but 1,5-dimethyl-3-nitropyridin-2(1H)-one [507473-21-4] was used instead of 3-chloro-1-methyl-5-nitro-1H-pyridin-2-one to afford the title compound as a brown solid. ESI-MS: $t_R$=0.43 min, [M+H]$^+$ 139 (LC-MS 1).

EXAMPLE 1

5-(3-Chloro-2-fluoro-phenyl)-6-(4-chloro-2-methyl-phenyl)-1-isopropyl-2-(2-methoxy-phenyl)-5,6-dihydro-1H-pyrrolo[3,4-b]pyrrol-4-one

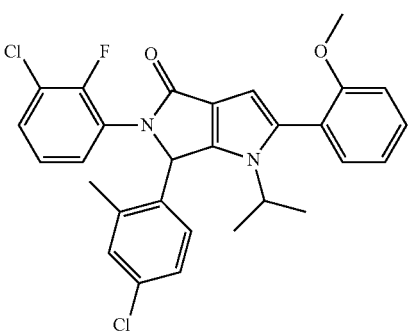

A degassed mixture of 2-bromo-5-(3-chloro-2-fluoro-phenyl)-6-(4-chloro-2-methyl-phenyl)-1-isopropyl-5,6-dihydro-1H-pyrrolo[3,4-b]pyrrol-4-one (Intermediate A) (0.392 mmol), 2-methoxyphenylboronic acid [5720-06-9] (0.549 mmol), (Ph$_3$P)$_2$PdCl$_2$ (0.039 mmol) and K$_3$PO$_4$ (1.569 mmol) in DMF (4 mL) was heated at 100° C. for 8 h. After cooling to rt, the reaction mixture was concentrated. The residue was diluted with a saturated aqueous solution of NaHCO$_3$ and extracted with EtOAc (3×). The combined organic phases were successively washed with water and brine, dried (Na$_2$SO$_4$) and concentrated. The residue was dissolved in MeOH and filtered through a PL-thiol MP SPE cartridge (StratoSpheres), washing through with additional MeOH. The filtrate was re-concentrated and the residue purified using a RediSep® silica gel column to afford the title compound as a light yellow solid. $t_R$: 8.55 min (HPLC 2); ESI-MS: $t_R$=1.43 min, [M+H]$^+$ 523/525 (LC-MS 1); TLC: R$_f$=0.41 (98:2 CH$_2$Cl$_2$/MeOH); $^1$H-NMR (d$_6$-DMSO, 600 MHz): (rotamers) 7.56 (d, 0.5H), 7.50-7.56 (m, 1.5H), 7.45-7.49 (m, 1.5H), 7.30 (d, 1H), 7.27 (m, 1H), 7.19-7.25 (m, 2H), 7.14 (d, 1H), 7.05 (m, 1H), 6.92 (d, 0.5H), 6.51/6.67 (s, 1H), 6.25/6.27 (s, 1H), 3.93/3.97 (m, 1H), 3.77 (s, 3H), 1.87/2.36 (s, 3H), 1.27 (m, 3H), 0.48 (m, 3H).

EXAMPLE 2

3-[5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide

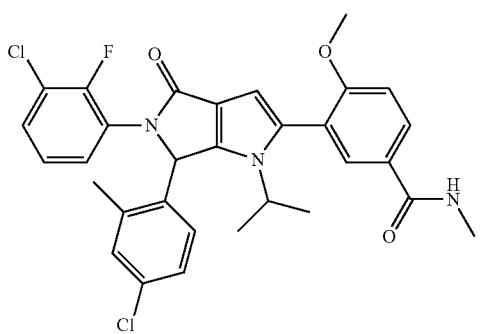

The title compound was prepared in analogy to the procedure described for Example 1 but 2-methoxy-5-[(methylamino)carbonyl]phenylboronic acid (Intermediate R) was used instead of 2-methoxyphenylboronic acid. The title compound was obtained as a white solid. $t_R$: 7.53 min (HPLC 2); ESI-MS: $t_R$=1.24 min, [M+H]$^+$ 580/582 (LC-MS 1); TLC: R$_f$=0.28 (95:5 CH$_2$Cl$_2$/MeOH); $^1$H-NMR (d$_6$-DMSO, 600 MHz): (rotamers) 8.42 (m, 1H), 7.98 (dd, 1H), 7.82 (dd, 1H), 7.57 (d, 0.5H), 7.53 (m, 1H), 7.43/7.47 (m, 1H), 7.27 (m, 1H), 7.23-7.26 (m, 1.5H), 7.19-7.23 (m, 1.5H), 6.90 (d, 0.5H), 6.53/6.58 (s, 1H), 6.31/6.33 (s, 1H), 3.91/3.94 (m, 1H), 3.83 (s, 3H), 2.78 (m, 3H), 1.89/2.36 (s, 3H), 1.28 (m, 3H), 0.48 (m, 3H).

EXAMPLE 3

5-(3-Chloro-2-fluoro-phenyl)-6-(4-chloro-2-methyl-phenyl)-2-(5-fluoro-2-methoxy-phenyl)-1-isopropyl-5,6-dihydro-1H-pyrrolo[3,4-b]pyrrol-4-one

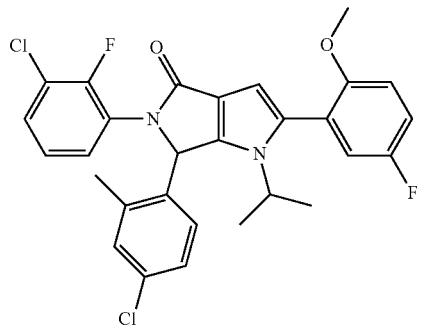 [SMILES: COc1ccc(F)cc1-c1cc2c(n1C(C)C)C(c1ccc(Cl)cc1C)N(c1cccc(Cl)c1F)C2=O]

The title compound was prepared in analogy to the procedure described for Example 1 but 5-fluoro-2-methoxyphenylboronic acid [179897-94-0] was used instead of 2-methoxyphenylboronic acid. The title compound was obtained as an off-white solid. $t_R$: 5.81 min (HPLC 1); ESI-MS: $t_R$=1.44 min, [M+H]$^+$ 541/543 (LC-MS 1); TLC: R$_f$=0.20 (1:2 EtOAc/heptanes); $^1$H-NMR (d$_6$-DMSO, 600 MHz): (rotamers) 7.56 (d, 0.5H), 7.53 (m, 1H), 7.43/7.47 (m, 1H), 7.32 (m, 1H), 7.27 (m, 1H), 7.22-7.25 (m, 1.5H), 7.18-7.22 (m, 1.5H), 7.14/7.15 (d, 1H), 6.91 (d, 0.5H), 6.67 (s, 0.5H), 6.51 (s, 0.5H), 6.32/6.33 (s, 1H), 3.93/3.98 (m, 1H), 3.76/3.76 (s, 3H), 1.88/2.35 (s, 3H), 1.28 (m, 3H), 0.49 (m, 3H).

EXAMPLE 4

5-(3-Chloro-2-fluoro-phenyl)-6-(4-chloro-2-methyl-phenyl)-2-(5-hydroxymethyl-2-methoxy-phenyl)-1-isopropyl-5,6-dihydro-1H-pyrrolo[3,4-b]pyrrol-4-one

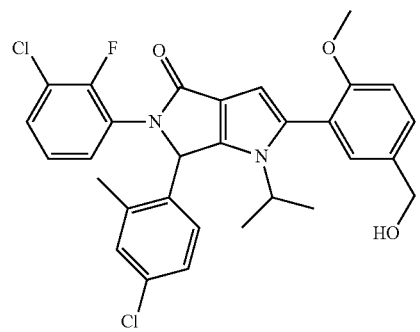 [SMILES: COc1ccc(CO)cc1-c1cc2c(n1C(C)C)C(c1ccc(Cl)cc1C)N(c1cccc(Cl)c1F)C2=O]

The title compound was prepared in analogy to the procedure described for Example 1 but 5-(hydroxymethyl)-2-methoxyphenylboronic acid [1137339-94-6] was used instead of 2-methoxyphenylboronic acid. The title compound was obtained as a brown solid. $t_R$: 7.57 min (H PLC 2); ESI-MS: $t_R$=1.26 min, [M+H]$^+$ 553/555 (LC-MS 1); $^1$H-NMR (d$_6$-DMSO, 600 MHz): (rotamers) 7.54 (d, 0.5H), 7.51 (m, 1H), 7.35-7.47 (m, 2H), 7.18-7.27 (m, 4H), 7.07 (m, 1H), 6.88 (d, 0.5H), 6.49/6.64 (s, 1H), 6.21/6.23 (s, 1H), 4.46 (s, 2H), 3.91/3.95 (m, 1H), 3.73/3.74 (s, 3H), 1.85/2.33 (s, 3H), 1.25 (m, 3H), 0.45 (m, 3H).

EXAMPLE 5

5-(3-Chloro-2-fluoro-phenyl)-6-(4-chloro-2-methyl-phenyl)-1-isopropyl-2-(2-methoxy-pyridin-3-yl)-5,6-dihydro-1H-pyrrolo[3,4-b]pyrrol-4-one

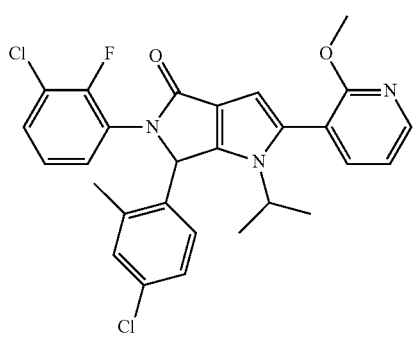

The title compound was prepared in analogy to the procedure described for Example 1 but 2-methoxypyridine-3-boronic acid [163105-90-6] was used instead of 2-methoxyphenylboronic acid. The title compound was obtained as a white solid. $t_R$: 8.12 min (HPLC 2); ESI-MS: $t_R$=1.39 min, [M+H]$^+$ 524/526 (LC-MS 1); TLC: $R_f$=0.30 (1:1 EtOAc/hexanes); $^1$H-NMR (d$_6$-DMSO, 600 MHz): (rotamers) 8.29 (m, 1H), 7.76 (m, 1H), 7.57 (d, 0.5H), 7.53 (m, 1H), 7.43/7.47 (m, 1H), 7.18-7.30 (m, 3H), 7.13 (m, 1H), 6.91 (d, 0.5H), 6.52/6.68 (s, 1H), 6.35/6.37 (s, 1H), 3.92/3.96 (m, 1H), 3.87 (s, 3H), 1.88/2.36 (s, 3H), 1.28 (m, 3H), 0.51 (m, 3H).

EXAMPLE 6

5-(3-Chloro-2-fluoro-phenyl)-6-(4-chloro-2-methyl-phenyl)-1-isopropyl-2-(4-methoxy-Pyridin-3-yl)-5,6-dihydro-1H-pyrrolo[3,4-b]pyrrol-4-one

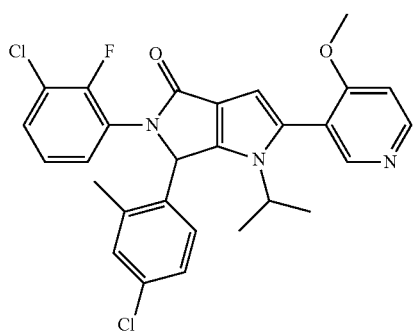 [SMILES: COc1ccncc1-c1cc2c(n1C(C)C)C(c1ccc(Cl)cc1C)N(c1cccc(Cl)c1F)C2=O]

The title compound was prepared in analogy to the procedure described for Example 1 but 4-methoxypyridine-3-boronic acid [163105-89-3] was used instead of 2-methoxyphenylboronic acid. The title compound was obtained as a white solid. $t_R$: 6.29 min (HPLC 2); ESI-MS: $t_R$=1.17 min, [M+H]$^+$ 524/526 (LC-MS 1); TLC: $R_f$=0.18 (EtOAc); $^1$H-NMR (d$_6$-DMSO, 600 MHz, 100° C.): (rotamers) 8.65 (m, 1H), 8.48 (s, 1H), 7.51 (d, 0.5H), 7.30-7.47 (m, 3H), 7.13-7.29 (m, 3H), 6.93 (d, 0.5H), 6.40 (m, 1H), 6.38/6.54 (s, 1H), 3.96 (m, 1H), 3.96 (s, 3H), 1.92/2.34 (s, 3H), 1.27 (m, 3H), 0.62 (m, 3H).

EXAMPLE 7

3-[(S)-5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide

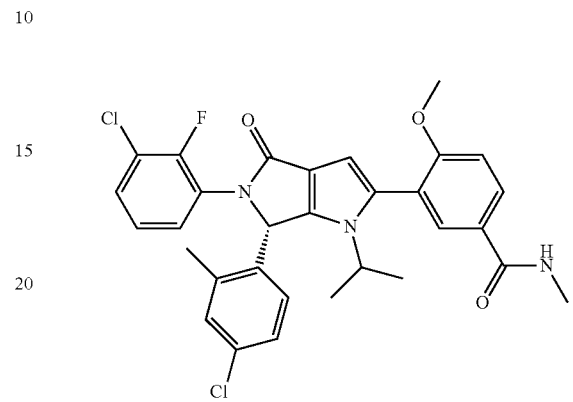

3-[5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide (Example 2) was purified by chiral chromatography (Chiral-HPLC 1) to afford the title compound as a white solid. $t_R$: 7.17 min (Column: Chiralpak IC, 4.6×250 mm. Flow 1 mL/min. heptane/EtOH/MeOH 50:25:25); $t_R$: 7.38 min (HPLC 2); ESI-MS: $t_R$=1.26 min, [M+H]$^+$ 580/582 (LC-MS 1); $^1$H-NMR (d$_6$-DMSO, 600 MHz): (rotamers) 8.40 (m, 1H), 7.96 (m, 1H), 7.80 (s, 1H), 7.55 (d, 0.5H), 7.51 (m, 1H), 7.41/7.45 (m, 1H), 7.25 (m, 1H), 7.16-7.24 (m, 3H), 6.89 (d, 0.5H), 6.51/6.66 (s, 1H), 6.29/6.31 (s, 1H), 3.89/3.93 (m, 1H), 3.81 (s, 3H), 2.76 (s, 3H), 1.87/2.33 (s, 3H), 1.26 (m, 3H), 0.46 (m, 3H).

EXAMPLE 8

3-[(R)-5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide

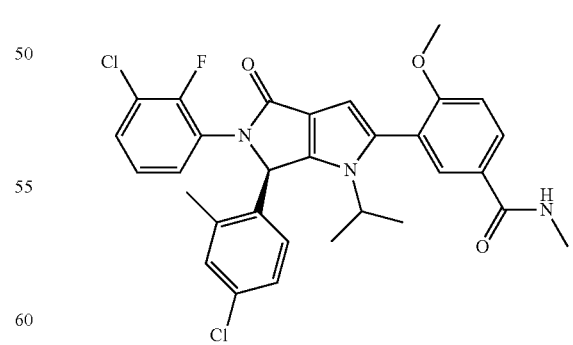

3-[5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide (Example 2) was purified by chiral chromatography (Chiral-HPLC 1) to afford the title compound as a white solid. $t_R$: 11.70 min (Column: Chiralpak IC, 4.6×250 mm. Flow 1 mL/min. heptane/EtOH/MeOH 50:25:25); $t_R$: 7.38 min (HPLC 2); ESI-MS: $t_R$=1.26 min, [M+H]$^+$ 580/582 (LC-MS 1); $^1$H-NMR (d$_6$-DMSO, 600 MHz): (rotamers) 8.40 (m, 1H), 7.96 (m, 1H), 7.80 (s, 1H), 7.55 (d, 0.5H), 7.51 (m, 1H), 7.41/7.45 (m, 1H), 7.25 (m, 1H), 7.17-7.24 (m, 3H), 6.89 (d, 0.5H), 6.51/6.66 (s, 1H), 6.29/6.31 (s, 1H), 3.89/3.93 (m, 1H), 3.81 (s, 3H), 2.76 (s, 3H), 1.87/2.34 (s, 3H), 1.26 (m, 3H), 0.46 (m, 3H).

EXAMPLE 9

5-(5-Chloro-2-methyl-phenyl)-6-(4-chloro-phenyl)-1-isopropyl-2-(2-methoxy-phenyl)-5,6-dihydro-1H-pyrrolo[3,4-b]pyrrol-4-one

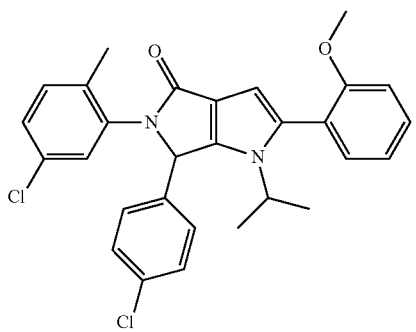 [SMILES: COc1ccccc1-c1cc2c(n1C(C)C)C(c1ccc(Cl)cc1)N(c1cc(Cl)ccc1C)C2=O]

The title compound was prepared in analogy to the procedure described for Example 1 but 2-bromo-5-(5-chloro-2-methyl-phenyl)-6-(4-chloro-phenyl)-1-isopropyl-5,6-dihydro-1H-pyrrolo[3,4-b]pyrrol-4-one (Intermediate B) was used instead of 2-bromo-5-(3-chloro-2-fluoro-phenyl)-6-(4-chloro-2-methyl-phenyl)-1-isopropyl-5,6-dihydro-1H-pyrrolo[3,4-b]pyrrol-4-one. The title compound was obtained as a white solid. $t_R$: 8.32 min (HPLC 2); ESI-MS: $t_R$=1.46 min, [M+H]$^+$ 505/507 (LC-MS 1); TLC: R$_f$=0.19 (1:2 EtOAc/hexanes); $^1$H-NMR (d$_6$-DMSO, 600 MHz): 7.80 (bs, 1H), 7.46 (m, 1H), 7.39 (m, 2H), 7.30 (m, 1H), 7.28 (m, 2H), 7.17 (m, 1H), 7.14 (d, 1H), 7.13 (m, 1H), 7.05 (m, 1H), 6.51 (s, 1H), 6.22 (s, 1H), 3.95 (m, 1H), 3.77 (s, 3H), 1.95 (s, 3H), 1.32 (d, 3H), 0.47 (m, 3H).

EXAMPLE 10

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide

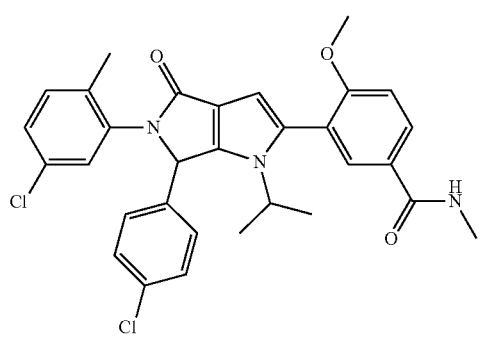 [SMILES: CNC(=O)c1ccc(OC)c(-c2cc3c(n2C(C)C)C(c2ccc(Cl)cc2)N(c2cc(Cl)ccc2C)C3=O)c1]

The title compound was prepared in analogy to the procedure described for Example 9 but 5-N-methyl-carboxamido-2-methoxyphenylboronic acid (Intermediate R) was used instead of 2-methoxyphenylboronic acid. The title compound was obtained as a white solid. $t_R$: 7.36 min (HPLC 2); ESI-MS: $t_R$=1.21 min, [M+H]$^+$ 562/564 (LC-MS 1); TLC: R$_f$=0.17 (EtOAc); $^1$H-NMR (d$_6$-DMSO, 600 MHz): 8.41 (m, 1H), 7.98 (m, 1H), 7.82 (m, 2H), 7.40 (m, 2H), 7.27 (m, 2H), 7.21 (d, 1H), 7.10-7.20 (m, 2H), 6.53 (s, 1H), 6.28 (s, 1H), 3.93 (m, 1H), 3.84 (s, 3H), 2.77 (d, 3H), 1.95 (s, 3H), 1.32 (d, 3H), 0.47 (m, 3H).

EXAMPLE 11

5-(5-Chloro-2-methyl-phenyl)-6-(4-chloro-phenyl)-2-(5-hydroxymethyl-2-methoxy-phenyl)-1-isopropyl-5,6-dihydro-1H-pyrrolo[3,4-b]pyrrol-4-one

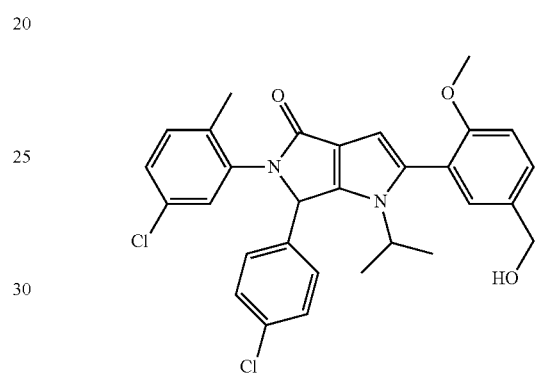

The title compound was prepared in analogy to the procedure described for Example 9 but 5-hydroxymethyl-2-methoxyphenylboronic acid was used instead of 2-methoxyphenylboronic acid. The title compound was obtained as a beige solid. $t_R$: 7.49 min (HPLC 2); ESI-MS: $t_R$=1.24 min, [M+H]$^+$ 535/537 (LC-MS 1).

EXAMPLE 12

5-(5-Chloro-2-methyl-phenyl)-6-(4-chloro-phenyl)-1-isopropyl-2-(2-methoxy-pyridin-3-yl)-5,6-dihydro-1H-pyrrolo[3,4-b]pyrrol-4-one

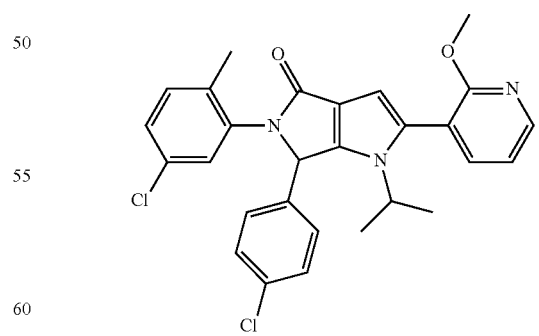

The title compound was prepared in analogy to the procedure described for Example 9 but 2-methoxypyridine-3-boronic acid was used instead of 2-methoxyphenylboronic acid. The title compound was obtained as a white solid. $t_R$: 8.02 min (HPLC 2); ESI-MS: $t_R$=1.38 min, [M+H]$^+$ 506/508 (LC-MS 1); TLC: R$_f$=0.32 (1:1 EtOAc/hexanes); $^1$H-NMR (d$_6$-DMSO, 600 MHz): 8.27 (m, 1H), 7.78 (s, 1H), 7.73 (m, 1H), 7.38 (m, 2H), 7.26 (m, 2H), 7.15 (m, 1H), 7.08-7.13 (m, 2H), 6.51 (s, 1H), 6.30 (s, 1H), 3.92 (m, 1H), 3.85 (s, 3H), 1.92 (s, 3H), 1.31 (m, 3H), 0.47 (m, 3H).

EXAMPLE 13

5-(5-Chloro-2-methyl-phenyl)-6-(4-chloro-phenyl)-1-isopropyl-2-(4-methoxy-pyridin-3-yl)-5,6-dihydro-1H-pyrrolo[3,4-b]pyrrol-4-one

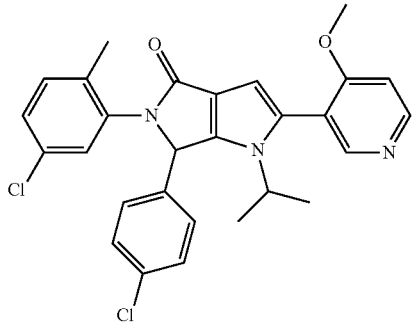

The title compound was prepared in analogy to the procedure described for Example 9 but 4-methoxypyridine-3-boronic acid was used instead of 2-methoxyphenylboronic acid. The title compound was obtained as a white solid. t$_R$: 6.26 min (HPLC 2); ESI-MS: t$_R$=1.15 min, [M+H]$^+$506/508 (LC-MS 1); TLC: R$_f$=0.21 (EtOAc); $^1$H-NMR (d$_6$-DMSO, 600 MHz, 100° C.): 8.68 (m, 1H), 8.51 (s, 1H), 7.33-7.44 (m, 4H), 7.25 (m, 2H), 7.18 (s, 2H), 6.39 (s, 1H), 6.29 (br s, 1H), 3.98 (s, 3H), 3.98 (m, 1H), 2.03 (s, 3H), 1.32 (m, 3H), 0.62 (m, 3H).

EXAMPLE 14

5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one

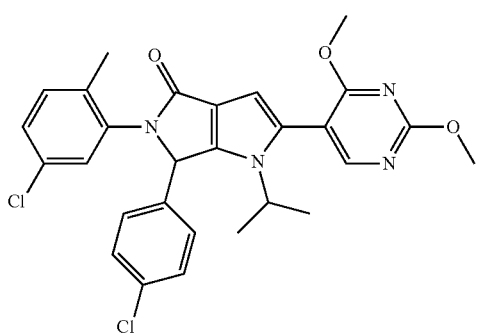 [SMILES: COc1ncc(-c2cc3c(n2C(C)C)C(c2ccc(Cl)cc2)N(c2cc(Cl)ccc2C)C3=O)c(OC)n1]

The title compound was prepared in analogy to the procedure described for Example 9 but 2,4-dimethoxypyridine-5-boronic acid [89641-18-9] was used instead of 2-methoxyphenylboronic acid. The title compound was obtained as a white solid. t$_R$:5.31 min (HPLC 1); ESI-MS: t$_R$=1.33 min, [M+H]$^+$ 537/539 (LC-MS 1); TLC: R$_f$=0.19 (1:1 EtOAc/heptanes); $^1$H-NMR (d$_6$-DMSO, 600 MHz): 8.31 (s, 1H), 7.77 (s, 1H), 7.38 (m, 2H), 7.25 (m, 2H), 7.11 (m, 1H), 7.16 (m, 1H), 6.50 (s, 1H), 6.33 (s, 1H), 3.94 (m, 1H), 3.94 (s, 3H), 3.91 (s, 3H), 1.92 (s, 3H), 1.30 (m, 3H), 0.49 (m, 3H).

EXAMPLE 15

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide

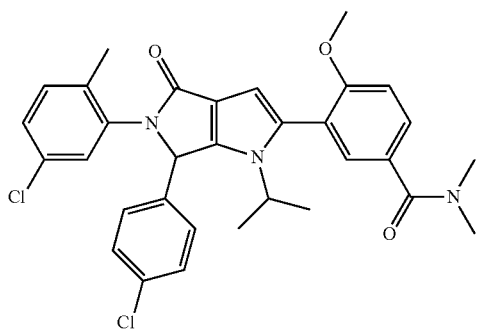

The title compound was prepared in analogy to the procedure described for Example 9 but 5-dimethylcarbamoyl-2-methoxyphenylboronic acid (Intermediate S) was used instead of 2-methoxyphenylboronic acid. The title compound was obtained as a white solid. t$_R$: 7.32 min (H PLC 2); ESI-MS: t$_R$=1.27 min, [M+H]$^+$ 576/578 (LC-MS 1); TLC: R$_f$=0.17 (EtOAc); $^1$H-NMR (d$_6$-DMSO, 600 MHz): 7.78 (s, 1H), 7.54 (m, 1H), 7.37 (m, 2H), 7.33 (m, 1H), 7.25 (m, 2H), 7.17 (d, 1H), 7.15 (m, 1H), 7.10 (m, 1H), 6.50 (s, 1H), 6.25 (s, 1H), 3.93 (m, 1H), 3.80 (s, 3H), 2.96 (m, 6H), 1.92 (s, 3H), 1.30 (m, 3H), 0.46 (m, 3H).

EXAMPLE 16

5-(5-Chloro-2-methyl-phenyl)-6-(4-chloro-phenyl)-1-isopropyl-2-(4-methoxy-pyrimidin-5-yl)-5,6-dihydro-1H-pyrrolo[3,4-b]pyrrol-4-one

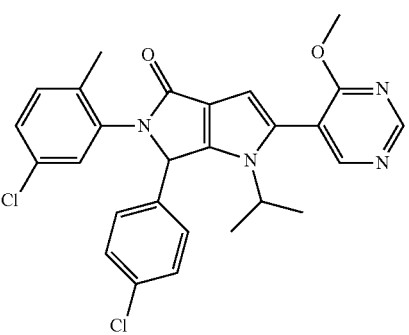 [SMILES: COc1ncncc1-c1cc2c(n1C(C)C)C(c1ccc(Cl)cc1)N(c1cc(Cl)ccc1C)C2=O]

The title compound was prepared in analogy to the procedure described for Example 9 but 4-methoxy-5-(4,4,5,5-tetramethyl-1,3,2-dioxaborolan-2-yl)pyrimidine (Intermediate T) was used instead of 2-methoxyphenylboronic acid. The title compound was obtained as an off-white solid. t$_R$: 5.08 min (HPLC 1); ESI-MS: t$_R$=1.28 min, [M+H]$^+$ 507/509/511 (LC-MS 1); TLC: R$_f$=0.12 (1:1 EtOAc/heptanes); $^1$H-NMR (d$_6$-DMSO, 600 MHz): 8.88 (s, 1H), 8.54 (s, 1H), 7.78 (s, 1H), 7.39 (m, 2H), 7.26 (m, 2H), 7.16 (m, 1H), 7.10 (m, 1H), 6.53 (s, 1H), 6.42 (s, 1H), 3.95 (s, 3H), 3.93 (m, 1H), 1.92 (s, 3H), 1.31 (m, 3H), 0.50 (m, 3H).

EXAMPLE 17

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzonitrile

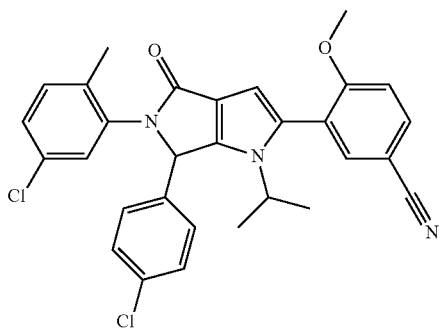 [SMILES: COc1ccc(C#N)cc1-c1cc2c(n1C(C)C)C(c1ccc(Cl)cc1)N(c1cc(Cl)ccc1C)C2=O]

A degassed mixture of 2-bromo-5-(5-chloro-2-methyl-phenyl)-6-(4-chloro-phenyl)-1-isopropyl-5,6-dihydro-1H-pyrrolo[3,4-b]pyrrol-4-one (Intermediate B) (0.337 mmol), 5-cyano-2-methoxyphenylboronic acid [612833-37-1] (0.675 mmol), Pd(PPh$_3$)$_4$ (0.067 mmol) and K$_3$PO$_4$ (1.350 mmol) in 2:1 dioxane/H$_2$O (4.5 mL) was heated at 100° C. for 4 h. After cooling to rt, the reaction mixture was diluted with H$_2$O and extracted with EtOAc (3×). The combined organic phases were dried (Na$_2$SO$_4$) and concentrated. The residue was dissolved in CH$_2$Cl$_2$ and filtered through a PL-thiol MP SPE cartridge (StratoSpheres), washing through with additional CH$_2$Cl$_2$. The filtrate was re-concentrated and the residue purified using a RediSep® silica gel column to afford the title compound as a yellow solid. t$_R$: 5.43 min (HPLC 1); ESI-MS: t$_R$=1.37 min, [M+H]$^+$ 530/532/534 (LC-MS 1); TLC: R$_f$=0.29 (1:1 EtOAc/heptanes); $^1$H-NMR (d$_6$-DMSO, 600 MHz): 8.15 (br s, 1H), 7.95 (m, 1H), 7.77 (m, 2H), 7.37 (m, 2H), 7.31 (d, 1H), 7.24 (m, 1H), 7.15 (m, 1H), 7.10 (m, 1H), 6.51 (s, 1H), 6.31 (s, 1H), 3.85 (m, 1H), 3.85 (s, 3H), 1.91 (s, 3H), 1.29 (m, 3H), 0.46 (m, 3H).

EXAMPLE 18

3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide

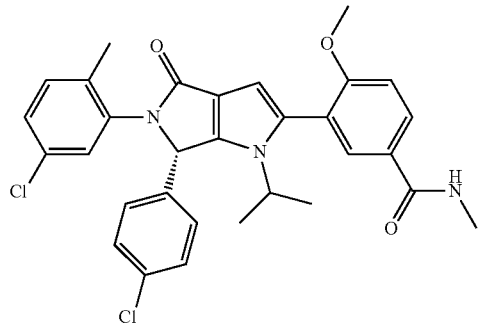 [SMILES: CNC(=O)c1ccc(OC)c(-c2cc3c(n2C(C)C)[C@H](c2ccc(Cl)cc2)N(c2cc(Cl)ccc2C)C3=O)c1]

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide (Example 10) was purified by chiral chromatography (Chiral-HPLC 1) to afford the title compound as a white solid. t$_R$: 6.14 min (Column: Chiralpak IA, 4.6×250 mm. Flow 1.4 mL/min. heptane/EtOH/MeOH 50:25:25); t$_R$: 7.32 min (HPLC 2); ESI-MS: t$_R$=1.24 min, [M+H]$^+$ 562/564 (LC-MS 1); $^1$H-NMR (d$_6$-DMSO, 600 MHz): 8.39 (m, 1H), 7.95 (dd, 1H), 7.76-7.84 (m, 2H), 7.39 (m, 2H), 7.25 (m, 2H), 7.19 (d, 1H), 7.15 (m, 1H), 7.11 (m, 1H), 6.51 (s, 1H), 6.26 (s, 1H), 3.91 (m, 1H), 3.81 (s, 3H), 2.76 (m, 3H), 1.93 (s, 3H), 1.31 (m, 3H), 0.45 (m, 3H).

EXAMPLE 19

3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide

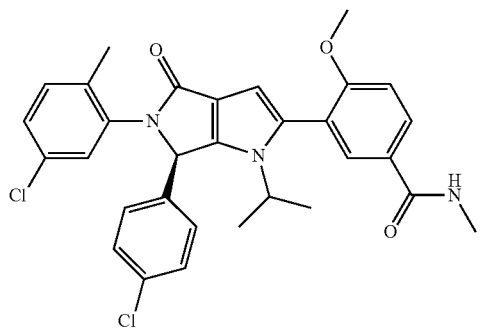 [SMILES: CNC(=O)c1ccc(OC)c(-c2cc3c(n2C(C)C)[C@@H](c2ccc(Cl)cc2)N(c2cc(Cl)ccc2C)C3=O)c1]

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide (Example 10) was purified by chiral chromatography (Chiral-HPLC 1) to afford the title compound as a white solid. t$_R$: 8.53 min (Column: Chiralpak IA, 4.6×250 mm. Flow 1.4 mL/min. heptane/EtOH/MeOH 50:25:25); t$_R$: 7.32 min (HPLC 2); ESI-MS: t$_R$=1.24 min, [M+H]$^+$ 562/564 (LC-MS 1); $^1$H-NMR (d$_6$-DMSO, 600 MHz): 8.39 (m, 1H), 7.95 (dd, 1H), 7.76-7.83 (m, 2H), 7.39 (m, 2H), 7.25 (m, 2H), 7.19 (d, 1H), 7.15 (m, 1H), 7.11 (m, 1H), 6.51 (s, 1H), 6.26 (s, 1H), 3.92 (m, 1H), 3.81 (s, 3H), 2.76 (m, 3H), 1.93 (s, 3H), 1.30 (m, 3H), 0.45 (m, 3H).

EXAMPLE 20

3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide

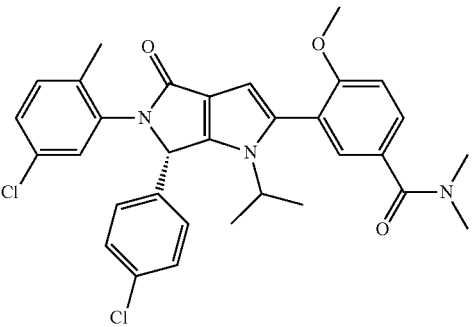 [SMILES: COc1ccc(C(=O)N(C)C)cc1-c1cc2c(n1C(C)C)[C@H](c1ccc(Cl)cc1)N(c1cc(Cl)ccc1C)C2=O]

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide (Example 15) was purified by chiral chromatography (Chiral-HPLC 1) to afford the title compound as a white solid. $t_R$: 11.77 min (Column: Chiralpak IA, 4.6×250 mm. Flow 1.4 mL/min. heptane/EtOH/MeOH 50:25:25); $t_R$: 7.49 min (HPLC 2); ESI-MS: $t_R$=1.27 min, [M+H]$^+$ 576/578 (LC-MS 1); $^1$H-NMR (d$_6$-DMSO, 600 MHz): 7.78 (s, 1H), 7.54 (dd, 1H), 7.37 (m, 2H), 7.33 (d, 1H), 7.25 (m, 2H), 7.17 (d, 1H), 7.16 (m, 1H), 7.11 (m, 1H), 6.50 (s, 1H), 6.25 (s, 1H), 3.93 (m, 1H), 3.80 (m, 3H), 2.96 (s, 6H), 1.92 (s, 3H), 1.30 (m, 3H), 0.46 (m, 3H).

EXAMPLE 21

3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide

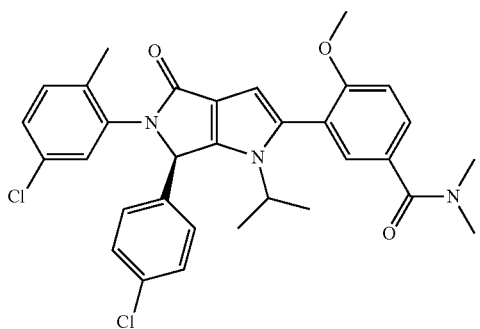 [SMILES: COc1ccc(C(=O)N(C)C)cc1-c1cc2c(n1C(C)C)[C@@H](c1ccc(Cl)cc1)N(c1cc(Cl)ccc1C)C2=O]

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide (Example 15) was purified by chiral chromatography (Chiral-HPLC 1) to afford the title compound as a white solid. $t_R$: 17.88 min (Column: Chiralpak IA, 4.6×250 mm. Flow 1.4 mL/min. heptane/EtOH/MeOH 50:25:25); $t_R$: 7.49 min (HPLC 2); ESI-MS: $t_R$=1.27 min, [M+H]$^+$ 576/578 (LC-MS 1); $^1$H-NMR (d$_6$-DMSO, 600 MHz): 7.78 (s, 1H), 7.53 (dd, 1H), 7.37 (m, 2H), 7.33 (d, 1H), 7.25 (m, 2H), 7.17 (d, 1H), 7.15 (m, 1H), 7.11 (m, 1H), 6.50 (s, 1H), 6.25 (s, 1H), 3.93 (m, 1H), 3.80 (s, 3H), 2.96 (s, 6H), 1.92 (s, 3H), 1.30 (m, 3H), 0.46 (m, 3H).

EXAMPLE 22

5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-b]pyrrol-4-one

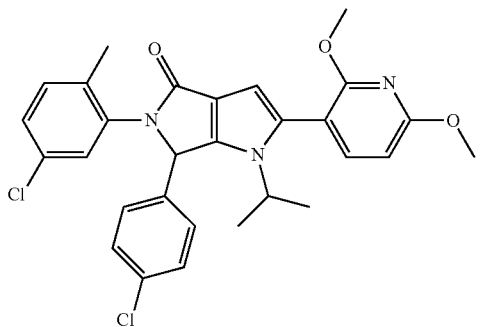 [SMILES: COc1ccc(-c2cc3c(n2C(C)C)C(c2ccc(Cl)cc2)N(c2cc(Cl)ccc2C)C3=O)c(OC)n1]

The title compound was prepared in analogy to the procedure described for Example 17 but 2,6-dimethoxy-3-pyridineboronic acid [221006-70-8] was used instead of 5-cyano-2-methoxyphenylboronic acid. The title compound was obtained as an off-white solid. $t_R$: 5.88 min (HPLC 1); ESI-MS: $t_R$=1.46 min, [M+H]$^+$ 536/538/540 (LC-MS 1); TLC: $R_f$=0.21 (1:3 EtOAc/heptanes); $^1$H-NMR (d$_6$-DMSO, 600 MHz): 7.77 (s, 1H), 7.61 (d, 1H), 7.37 (m, 2H), 7.25 (m, 2H), 7.15 (m, 1H), 7.10 (m, 1H), 6.48 (s, 1H), 6.47 (d, 1H), 6.21 (s, 1H), 3.93 (m, 1H), 3.90 (s, 3H), 3.86 (s, 3H), 1.92 (s, 3H), 1.29 (m, 3H), 0.47 (m, 3H).

EXAMPLE 23

(S)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one

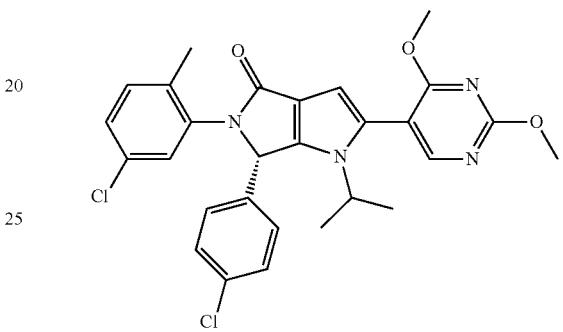

5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one (Example 14) was purified by chiral chromatography (Chiral-HPLC 1) to afford the title compound as a light-yellow solid. $t_R$: 7.98 min (Column: Chiralpak IC, 4.6×250 mm. Flow 1 mL/min. heptane/EtOH/MeOH 50:25:25); $t_R$: 7.64 min (HPLC 2); ESI-MS: $t_R$=1.35 min, [M+H]$^+$ 537/539 (LC-MS 1); $^1$H-NMR (d$_6$-DMSO, 600 MHz): 8.31 (s, 1H), 7.77 (s, 1H), 7.38 (m, 2H), 7.26 (m, 2H), 7.15 (m, 1H), 7.11 (m, 1H), 6.51 (s, 1H), 6.33 (s, 1H), 3.95 (s, 3H), 3.93 (m, 1H), 3.91 (s, 3H), 1.92 (s, 3H), 1.30 (m, 3H), 0.49 (m, 3H).

EXAMPLE 24

(R)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one

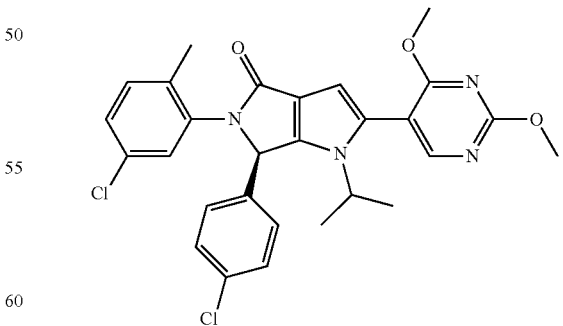

5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one (Example 14) was purified by chiral chromatography (Chiral-HPLC 1) to afford the title compound as a white solid. $t_R$: 13.36 min (Column: Chiralpak IC, 4.6×250 mm. Flow 1 mL/min. heptane/EtOH/MeOH 50:25:25); $t_R$: 7.64 min (HPLC 2); ESI-MS: $t_R$=1.35 min, [M+H]$^+$ 537/539 (LC-MS 1); $^1$H-NMR (d$_6$-DMSO, 600 MHz): 8.31 (s, 1H), 7.77 (s, 1H), 7.38 (m, 2H), 7.26 (m, 2H), 7.15 (m, 1H), 7.11 (m, 1H), 6.51 (s, 1H), 6.33 (s, 1H), 3.95 (s, 3H), 3.93 (m, 1H), 3.91 (s, 3H), 1.92 (s, 3H), 1.30 (m, 3H), 0.49 (m, 3H).

EXAMPLE 25

2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-b]pyrrol-4-one

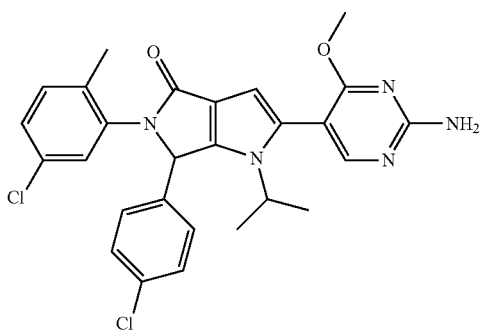 [SMILES: COc1nc(N)ncc1-c1cc2c(n1C(C)C)C(c1ccc(Cl)cc1)N(c1cc(Cl)ccc1C)C2=O]

A degassed mixture of 2-bromo-5-(5-chloro-2-methyl-phenyl)-6-(4-chloro-phenyl)-1-isopropyl-5,6-dihydro-1H-pyrrolo[3,4-b]pyrrol-4-one (Intermediate B) (0.314 mmol), 4-methoxy-5-(4,4,5,5-tetramethyl-[1,3,2]dioxaborolan-2-yl)-pyrimidin-2-ylamine (Intermediate U) (0.627 mmol), PdCl$_2$(dppf).CH$_2$Cl$_2$ adduct (0.047 mmol) and K$_3$PO$_4$ (1.255 mmol) in 3:1 dioxane/H$_2$O (4 mL) was heated at 100° C. for 30 min. After cooling to rt, the reaction mixture was diluted with H$_2$O and extracted with EtOAc (2×). The combined organic phases were washed successively with H$_2$O and brine, dried (Na$_2$SO$_4$) and concentrated. The residue was purified by preparative HPLC (prep-HPLC 1) and then triturated in Et$_2$O to afford the title compound as a white solid. ESI-MS: $t_R$=1.21 min, [M+H]$^+$ 522/524/526 (LC-MS 1); $^1$H-NMR (d$_6$-DMSO, 600 MHz): 7.93 (s, 1H), 7.76 (s, 1H), 7.37 (m, 2H), 7.24 (m, 2H), 7.14 (m, 1H), 7.10 (m, 1H), 6.89 (s, 2H), 6.47 (s, 1H), 6.22 (s, 1H), 3.94 (m, 1H), 3.80 (s, 3H), 1.92 (s, 3H), 1.29 (m, 3H), 0.49 (m, 3H).

EXAMPLE 26

5-(5-Chloro-2-methyl-phenyl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one

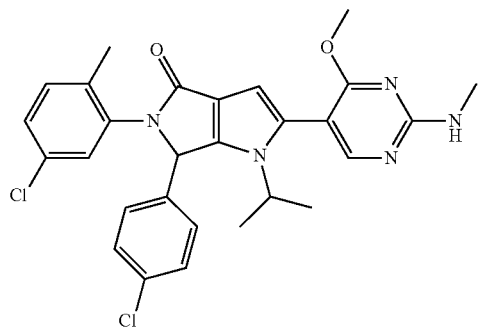 [SMILES: CNc1ncc(-c2cc3c(n2C(C)C)C(c2ccc(Cl)cc2)N(c2cc(Cl)ccc2C)C3=O)c(OC)n1]

The title compound was prepared in analogy to the procedure described for Example 25 but [4-methoxy-5-(4,4,5,5-tetramethyl-[1,3,2]dioxaborolan-2-yl)-pyrimidin-2-yl]-methyl-amine (Intermediate V) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=1.30 min, [M+H]$^+$ 536/538/540 (LC-MS 1); $^1$H-NMR (d$_6$-DMSO, 600 MHz): (rotamers) 7.95/8.02 (s, 1H), 7.76 (s, 1H), 7.37 (m, 2H), 7.32 (m, 1H), 7.24 (m, 2H), 7.15 (m, 1H), 7.10 (m, 1H), 6.47 (s, 1H), 6.22 (s, 1H), 3.94 (m, 1H), 3.80/3.86 (s, 3H), 2.82 (br s, 3H), 1.91 (s, 3H), 1.29 (m, 3H), 0.49 (m, 3H).

EXAMPLE 27

5-(5-Chloro-2-methyl-phenyl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one

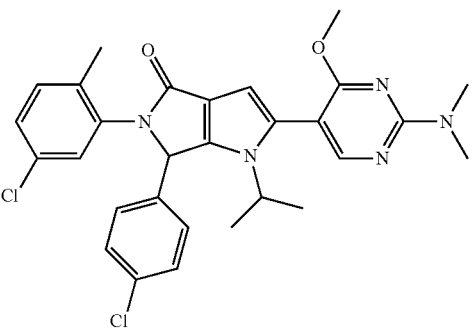 [SMILES: COc1nc(N(C)C)ncc1-c1cc2c(n1C(C)C)C(c1ccc(Cl)cc1)N(c1cc(Cl)ccc1C)C2=O]

The title compound was prepared in analogy to the procedure described for Example 25 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=1.45 min, [M+H]$^+$550/552 (LC-MS 1); $^1$H-NMR (d$_6$-DMSO, 600 MHz): 8.05 (s, 1H), 7.76 (s, 1H), 7.37 (m, 2H), 7.25 (m, 2H), 7.15 (m, 1H), 7.10 (m, 1H), 6.48 (s, 1H), 6.22 (s, 1H), 3.94 (m, 1H), 3.86 (s, 3H), 3.15 (s, 6H), 1.92 (s, 3H), 1.29 (m, 3H), 0.48 (m, 3H).

EXAMPLE 28

5-(5-Chloro-2-methyl-phenyl)-6-(4-chloro-phenyl)-1-isopropyl-2-[2-methoxy-5-(morpholine-4-carbonyl)-phenyl]-5,6-dihydro-1H-pyrrolo[3,4-b]pyrrol-4-one

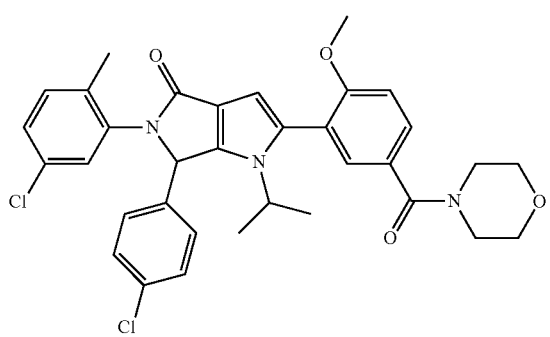 [SMILES: COc1ccc(C(=O)N2CCOCC2)cc1-c1cc2c(n1C(C)C)C(c1ccc(Cl)cc1)N(c1cc(Cl)ccc1C)C2=O]

The title compound was prepared in analogy to the procedure described for Example 17 but 5-morpholine-carbonyl-2-methoxyphenylboronic acid (Intermediate X) was used instead of 5-cyano-2-methoxyphenylboronic acid to afford the title compound as a white solid. $t_R$: 7.38 min (HPLC 2); ESI-MS: $t_R$=1.28 min, [M+H]$^+$ 618/620/622 (LC-MS 1); TLC: $R_f$=0.19 (EtOAc); $^1$H-NMR (d$_6$-DMSO, 600 MHz): 7.79 (s, 1H), 7.54 (m, 1H), 7.37 (m, 2H), 7.33 (s, 1H), 7.25 (m, 2H), 7.19 (d, 1H), 7.15 (m, 1H), 7.11 (m, 1H), 6.50 (s, 1H), 6.28 (s, 1H), 3.93 (m, 1H), 3.80 (s, 3H), 3.41-3.68 (m, 8H), 1.92 (s, 3H), 1.30 (m, 3H), 0.46 (m, 3H).

EXAMPLE 29

5-(5-Chloro-2-methyl-phenyl)-6-(4-chloro-phenyl)-2-(2-hydroxy-phenyl)-1-isopropyl-5,6-dihydro-1H-pyrrolo[3,4-b]pyrrol-4-one

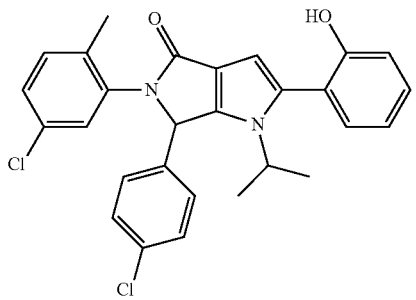 [SMILES: Cc1ccc(Cl)cc1N1C(=O)c2cc(-c3ccccc3O)n(C(C)C)c2C1c1ccc(Cl)cc1]

The title compound was prepared in analogy to the procedure described for Example 17 but 2-(4,4,5,5-tetramethyl-[1,3,2]dioxaborolan-2-yl)-phenol [269409-97-4] was used instead of 5-cyano-2-methoxyphenylboronic acid. After workup, the product was purified by preparative HPLC (prep HPLC 1) to afford the title compound as a white solid. ESI-MS: $t_R$=1.28 min, [M+H]$^+$ 491/493 (LC-MS 1); $^1$H-NMR (d$_6$-DMSO, 400 MHz): 9.69 (s, 1H), 7.75 (br s, 1H), 7.36 (m, 2H), 7.20-7.29 (m, 3H), 7.18 (m, 1H), 7.14 (m, 1H), 7.10 (m, 1H), 6.91 (d, 1H), 6.86 (t, 1H), 6.46 (br s, 1H), 6.17 (s, 1H), 4.05 (m, 1H), 1.91 (s, 3H), 1.29 (m, 3H), 0.49 (m, 3H).

EXAMPLE 30

5-(5-Chloro-2-methyl-phenyl)-6-(4-chloro-2-methyl-phenyl)-1-isopropyl-2-(2-methoxy-phenyl)-5,6-dihydro-1H-pyrrolo[3,4-b]pyrrol-4-one

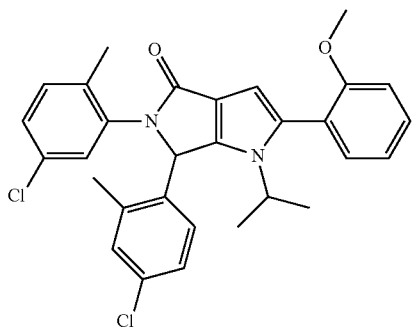 [SMILES: COc1ccccc1-c1cc2c(n1C(C)C)C(c1ccc(Cl)cc1C)N(c1cc(Cl)ccc1C)C2=O]

The title compound was prepared in analogy to the procedure described for Example 1 but 2-bromo-5-(5-chloro-2-methyl-phenyl)-6-(4-chloro-2-methyl-phenyl)-1-isopropyl-5,6-dihydro-1H-pyrrolo[3,4-b]pyrrol-4-one (Intermediate C) was used instead of 2-bromo-5-(3-chloro-2-fluoro-phenyl)-6-(4-chloro-2-methyl-phenyl)-1-isopropyl-5,6-dihydro-1H-pyrrolo[3,4-b]pyrrol-4-one. The title compound was obtained as a white solid. $t_R$: 8.44/8.57 min (HPLC 2); ESI-MS: $t_R$=1.49/1.50 min, [M+H]$^+$ 519/521 (LC-MS 1); TLC: $R_f$=0.22 (EtOAc); $^1$H-NMR (d$_6$-DMSO, 600 MHz): (rotamers) 7.86/7.94 (s, 1H), 7.44 (m, 1H), 7.28 (m, 1H), 7.22 (m, 1H), 7.16-7.20 (m, 2H), 7.12 (m, 1H), 7.10 (m, 1H), 7.03 (m, 1H), 6.96 (m, 1H), 6.51/6.73 (s, 1H), 6.20/6.23 (s, 1H), 3.94 (m, 1H), 3.75 (s, 3H), 1.99/2.29 (s, 3H), 1.86 (s, 3H), 1.22/1.24 (m, 3H), 0.46/0.54 (m, 3H).

EXAMPLE 31

3-[5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide

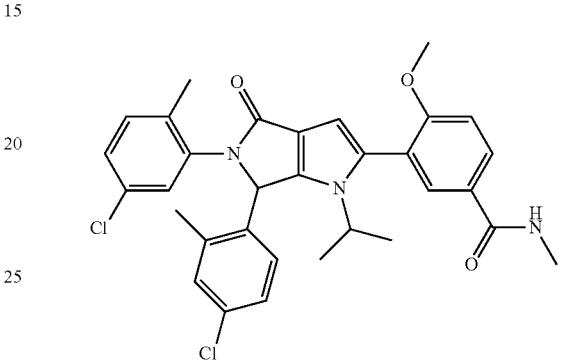

The title compound was prepared in analogy to the procedure described for Example 30 but 5-N-methyl-carboxamido-2-methoxy-phenylboronic acid (Intermediate R) was used instead of 4-methoxyphenylboronic acid to afford the title compound as a white solid. $t_R$: 7.45/7.60 min (HPLC 2); ESI-MS: $t_R$=1.27/1.29 min, [M+H]$^+$ 576/578 (LC-MS 1); TLC: $R_f$=0.21 (EtOAc); $^1$H-NMR (d$_6$-DMSO, 600 MHz): (rotamers) 8.40 (m, 1H), 7.95 (m, 1.5H), 7.80 (m, 1H), 7.23 (m, 1H), 7.17-7.21 (m, 3.5H), 7.10 (m, 1H), 6.93 (m, 1H), 6.54/6.75 (s, 1H), 6.24/6.26 (s, 1H), 3.92 (m, 1H), 3.81 (s, 3H), 2.75 (m, 3H), 2.30 (s, 3H), 1.87 (m, 3H), 1.22/1.25 (m, 3H), 0.47/0.54 (m, 3H).

EXAMPLE 32

3-[(S)-5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide

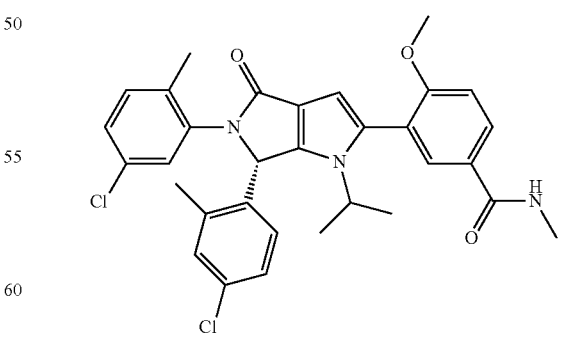

3-[5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide (Example 31) was purified by chiral chromatography (Chiral-HPLC 2) to afford the title compound as a white solid. $t_R$: 11.05 min (Column: Chiralcel OD-H, 4.6×250 mm. Flow 1 mL/min. heptane/EtOH/MeOH 90:5:5); $t_R$: 7.43/7.57 min (HPLC 2); ESI-MS: $t_R$=1.28/1.30 min, [M+H]+ 576/578 (LC-MS 1); $^1$H-NMR (d$_6$-DMSO, 600 MHz): (rotamers) 8.40 (m, 1H), 7.95/7.96 (m, 1.5H), 7.81/7.83 (m, 1H), 7.08-7.41 (m, 5.5H), 6.94 (m, 1H), 6.54/6.75 (s, 1H), 6.24/6.26 (m, 1H), 3.92 (m, 1H), 3.82 (s, 3H), 2.76 (m, 3H), 2.00/2.30 (s, 3H), 1.87/1.88 (s, 3H), 1.23/1.26 (m, 3H), 0.47/0.55 (m, 3H).

EXAMPLE 33

3-[(R)-5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide

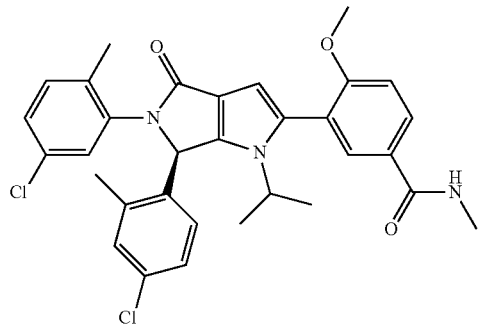 [SMILES: CNC(=O)c1ccc(OC)c(-c2cc3c(n2C(C)C)[C@@H](c2ccc(Cl)cc2C)N(c2cc(Cl)ccc2C)C3=O)c1]

3-[5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide (Example 31) was purified by chiral chromatography (Chiral-HPLC 2) to afford the title compound as a white solid. $t_R$: 16.83 min (Column: Chiralcel OD-H, 4.6×250 mm. Flow 1 mL/min. heptane/EtOH/MeOH 90:5:5); $t_R$: 7.42/7.56 min (HPLC 2); ESI-MS: $t_R$=1.28/1.30 min, [M+H]+ 576/578 (LC-MS 1); $^1$H-NMR (d$_6$-DMSO, 600 MHz): (rotamers) 8.40 (m, 1H), 7.95/7.96 (m, 1.5H), 7.80/7.83 (m, 1H), 7.08-7.41 (m, 5.5H), 6.94 (m, 1H), 6.54/6.75 (s, 1H), 6.24/6.26 (m, 1H), 3.92 (m, 1H), 3.81 (s, 3H), 2.76 (m, 3H), 2.00/2.30 (s, 3H), 1.87/1.88 (s, 3H), 1.23/1.26 (m, 3H), 0.47/0.55 (m, 3H).

EXAMPLE 34

5-(5-Chloro-2-methyl-phenyl)-6-(4-chloro-phenyl)-1-isopropyl-2-[2-methoxy-5-(1H-tetrazol-5-yl)-phenyl]-5,6-dihydro-1H-pyrrolo[3,4-b]pyrrol-4-one

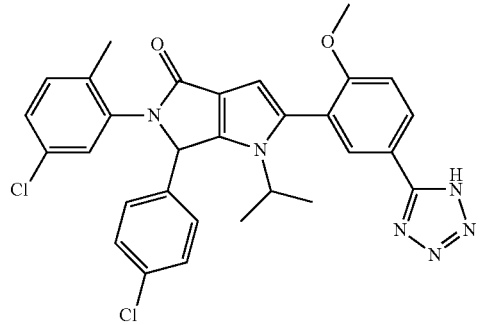 [SMILES: COc1ccc(-c2nnn[nH]2)cc1-c1cc2c(n1C(C)C)C(c1ccc(Cl)cc1)N(c1cc(Cl)ccc1C)C2=O]

A solution of 3-[5-(5-chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzonitrile (Example 17) (0.126 mmol), sodium azide (0.534 mmol) and ammonium chloride (0.534 mmol) in DMF (2 mL) was stirred at 120° C. for 36 h. The mixture was cooled to rt and poured onto ice-H$_2$O and acidified with 1N aqueous HCl. The resulting suspension was filtered. The solid was washed with H$_2$O and dried. The residue was purified by SFC to afford the title compound as a white solid. $t_R$: 4.98 min (HPLC 1); ESI-MS: $t_R$=1.25 min, [M+H]+ 573/575 (LC-MS 1); TLC: R$_f$=0.21 (9:1 CH$_2$Cl$_2$/MeOH); $^1$H-NMR (d$_6$-DMSO, 600 MHz): (rotamers) 8.14 (d, 1H), 7.96 (s, 1H), 7.80 (s, 1H), 7.35-7.47 (m, 3H), 7.26 (m, 2H), 7.16 (m, 1H), 7.11 (m, 1H), 6.53 (s, 1H), 6.33 (s, 1H), 3.97 (m, 1H), 3.86 (s, 3H), 1.94 (s, 3H), 1.33 (m, 3H), 0.48 (s, 3H).

EXAMPLE 35

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid

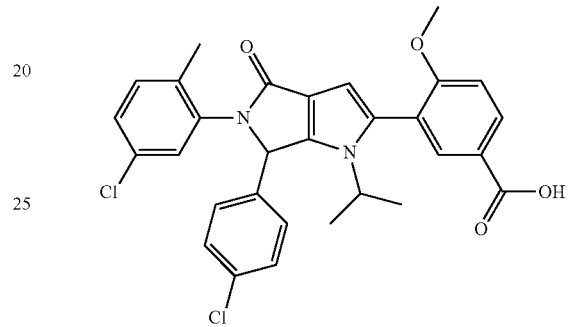

The title compound was prepared in analogy to the procedure described for Example 17 but 5-carboxy-2-methoxyphenylboronic acid was used instead of 5-cyano-2-methoxyphenylboronic acid to afford the title compound as a white solid. $t_R$: 5.05 min (HPLC 1); ESI-MS: $t_R$=1.25 min, [M+H]+ 549/551/553 (LC-MS 1); TLC: R$_f$=0.50 (9:1 CH$_2$Cl$_2$/MeOH); $^1$H-NMR (d$_6$-DMSO, 600 MHz): 12.80 (br s, 1H), 8.03 (dd, 1H), 7.80 (d, 1H), 7.79 (m, 1H), 7.37 (m, 2H), 7.26 (m, 2H), 7.23 (d, 1H), 7.16 (m, 1H), 7.10 (m, 1H), 6.50 (s, 1H), 6.28 (s, 1H), 3.90 (m, 1H), 3.84 (s, 3H), 1.92 (s, 3H), 1.29 (m, 3H), 0.45 (m, 3H).

EXAMPLE 36

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-N-(2-methanesulfonyl-ethyl)-4-methoxy-benzamide

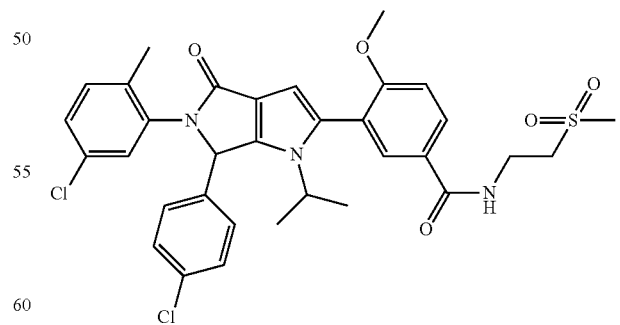

To a solution of 3-[5-(5-chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid (Example 35) (0.147 mmol) in DMF (1 mL), were added 2-methanesulfonyl-ethylamine [49773-20-8] (0.183 mmol), EDC.HCl (0.183 mmol), HOBT.H$_2$O (0.109 mmol) and Et$_3$N (0.513 mmol) and the mixture was stirred at rt for 30 h. The mixture was diluted with H$_2$O and extracted with CH$_2$Cl$_2$ (3×). The combined organic layers were washed with brine, dried (Na$_2$SO$_4$), filtered and concentrated. The residue was purified using a RediSep® silica gel column to afford the title compound as a white solid. t$_R$: 4.84 min (HPLC 1); ESI-MS: t$_R$=1.19 min, [M+H]$^+$ 654/656/658 (LC-MS 1); TLC: R$_f$=0.22 (95:5 CH$_2$Cl$_2$/MeOH); $^1$H-NMR (d$_6$-DMSO, 600 MHz): 8.69 (m, 1H), 7.96 (m, 1H), 7.82 (s, 1H), 7.79 (s, 1H), 7.38 (m, 2H), 7.25 (m, 2H), 7.22 (d, 1H), 7.15 (m, 1H), 7.10 (m, 1H), 6.52 (s, 1H), 6.26 (s, 1H), 3.92 (m, 1H), 3.82 (s, 3H), 3.64 (m, 2H), 3.36 (m, 2H), 3.02 (s, 1H), 1.93 (s, 3H), 1.31 (m, 3H), 0.45 (m, 3H).

EXAMPLE 37

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-N-(2-hydroxy-ethoxy)-4-methoxy-benzamide

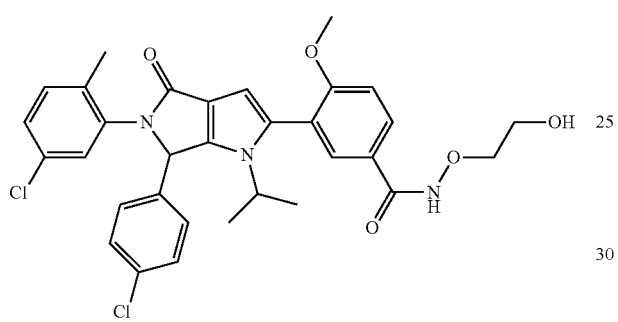

The title compound was prepared in analogy to the procedure described for Example 36 but 2-(aminooxy)ethanol [3279-95-6] was used instead of 2-methanesulfonyl-ethylamine. The title compound was obtained as a white solid. t$_R$: 4.71 min (HPLC 1); ESI-MS: t$_R$=1.13 min, [M+H]$^+$608/610/612 (LC-MS 1); TLC: R$_f$=0.20 (95:5 CH$_2$Cl$_2$/MeOH); $^1$H-NMR (d$_6$-DMSO, 600 MHz): 11.73 (br s, 1H), 7.90 (dd, 1H), 7.81 (s, 1H), 7.73 (d, 1H), 7.40 (m, 2H), 7.27 (m, 2H), 7.22 (d, 1H), 7.17 (m, 1H), 7.13 (m, 1H), 6.52 (s, 1H), 6.28 (s, 1H), 3.94 (m, 1H), 3.91 (t, 2H), 3.84 (s, 3H), 3.61 (t, 2H), 1.95 (s, 3H), 1.32 (m, 3H), 0.48 (m, 3H).

EXAMPLE 38

5-(5-Chloro-2-methyl-phenyl)-6-(4-chloro-phenyl)-2-(2,4-dimethoxy-phenyl)-1-isopropyl-5,6-dihydro-1H-pyrrolo[3,4-b]pyrrol-4-one

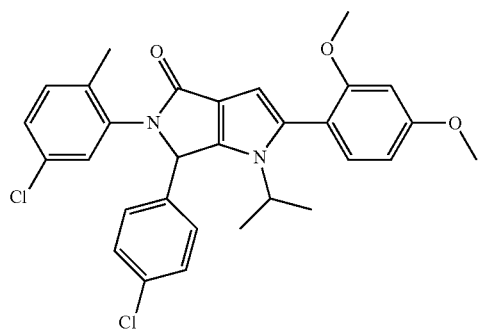 [SMILES: COc1ccc(-c2cc3c(n2C(C)C)C(c2ccc(Cl)cc2)N(c2cc(Cl)ccc2C)C3=O)c(OC)c1]

The title compound was prepared in analogy to the procedure described for Example 17 but 2,4-dimethoxyphenylboronic acid [133730-34-4] was used instead of 5-cyano-2-methoxyphenylboronic acid. The title compound was obtained as a white solid. t$_R$: 8.18 min (HPLC 2); ESI-MS: t$_R$=1.42 min, [M+H]$^+$ 535/537/539 (LC-MS 1); TLC: R$_f$=0.18 (1:2 EtOAc/hexanes); $^1$H-NMR (d$_6$-DMSO, 600 MHz): 7.77 (s, 1H), 7.36 (m, 2H), 7.25 (m, 2H), 7.17 (d, 1H), 7.15 (m, 1H), 7.10 (m, 1H), 6.65 (s, 1H), 6.60 (m, 1H), 6.47 (s, 1H), 6.14 (s, 1H), 3.92 (m, 1H), 3.80 (s, 3H), 3.74 (s, 3H), 1.92 (s, 3H), 1.28 (m, 3H), 0.44 (m, 3H).

EXAMPLE 39

4-[2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile

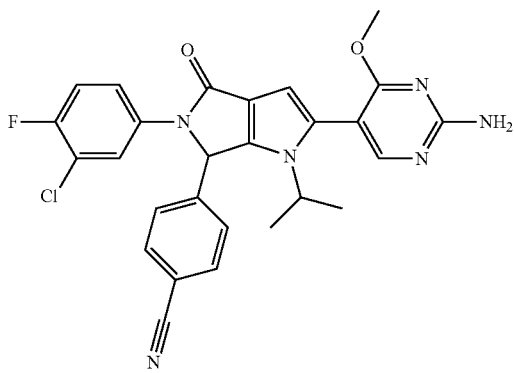

The title compound was prepared in analogy to the procedure described for Example 25 but 4-[2-bromo-5-(3-chloro-4-fluoro-phenyl)-1-isopropyl-4-oxo-1,4,5,6-tetrahydro-pyrrolo[3,4-b]pyrrol-6-yl]-benzonitrile (Intermediate H) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a white foam. t$_R$=4.58 min (HPLC 4); ESI-MS: t$_R$=1.01 min, [M+H]$^+$ 517/519 (LC-MS 1); $^1$H-NMR (d$_6$-DMSO, 600 MHz): 7.91 (s, 1H), 7.86 (m, 1H), 7.81 (m, 2H), 7.52-7.62 (m, 3H), 7.32 (m, 1H), 6.91 (br s, 2H), 6.72 (s, 1H), 6.27 (s, 1H), 3.94 (m, 1H), 3.78 (s, 3H), 1.35 (m, 3H), 0.39 (m, 3H).

EXAMPLE 40

4-[5-(3-Chloro-4-fluoro-phenyl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

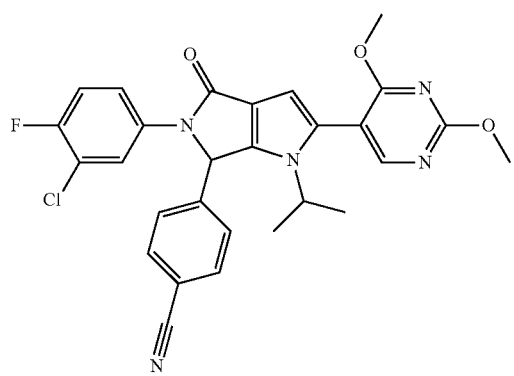 [SMILES: COc1ncc(-c2cc3c(n2C(C)C)C(c2ccc(C#N)cc2)N(c2ccc(F)c(Cl)c2)C3=O)c(OC)n1]

The title compound was prepared in analogy to the procedure described for Example 39 but 2,4-dimethoxypyrimidine-5-boronic acid was used instead of 4-methoxy-5-(4,4,5,5-tetramethyl-[1,3,2]dioxaborolan-2-yl)-pyrimidin-2-ylamine. The title compound was obtained as a white solid. t$_R$=5.41 min (HPLC 4); ESI-MS: t$_R$=1.15 min, [M+H]$^+$ 532/

534 (LC-MS 1); $^1$H-NMR (d$_6$-DMSO, 600 MHz): 8.30 (s, 1H), 7.86 (m, 1H), 7.82 (m, 2H), 7.53-7.63 (m, 3H), 7.33 (m, 1H), 6.76 (s, 1H), 6.39 (s, 1H), 3.94 (m, 1H), 3.94 (s, 3H), 3.89 (s, 3H), 1.36 (m, 3H), 0.39 (m, 3H).

EXAMPLE 41

4-[2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile

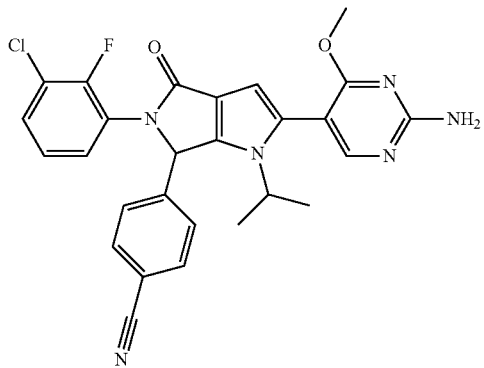 [SMILES: COc1nc(N)ncc1-c1cc2c(n1C(C)C)C(c1ccc(C#N)cc1)N(c1cccc(Cl)c1F)C2=O]

The title compound was prepared in analogy to the procedure described for Example 25, but 4-[2-bromo-5-(3-chloro-2-fluoro-phenyl)-1-isopropyl-4-oxo-1,4,5,6-tetrahydro-pyrrolo[3,4-b]pyrrol-6-yl]-benzonitrile (Intermediate I) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a white foam. $t_R$=4.50 min (HPLC 4); ESI-MS: $t_R$=0.99 min, [M+H]$^+$ 517/519 (LC-MS 1); $^1$H-NMR (d$_6$-DMSO, 600 MHz): 7.93 (s, 1H), 7.81 (m, 2H), 7.46 (m, 2H), 7.38-7.45 (m, 2H), 7.17 (m, 1H), 6.90 (br s, 2H), 6.47 (s, 1H), 6.28 (s, 1H), 3.96 (m, 1H), 3.79 (s, 3H), 1.30 (m, 3H), 0.44 (m, 3H).

EXAMPLE 42

4-[5-(3-Chloro-2-fluoro-phenyl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

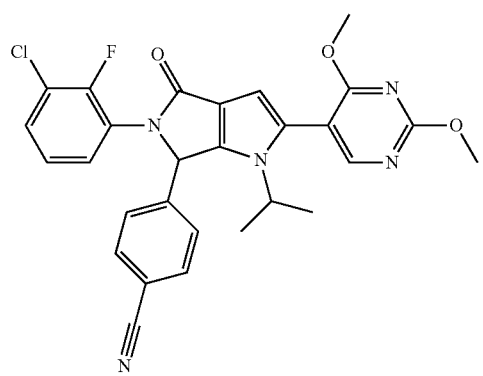 [SMILES: COc1ncc(-c2cc3c(n2C(C)C)C(c2ccc(C#N)cc2)N(c2cccc(Cl)c2F)C3=O)c(OC)n1]

The title compound was prepared in analogy to the procedure described for Example 17 but 4-[2-bromo-5-(3-chloro-2-fluoro-phenyl)-1-isopropyl-4-oxo-1,4,5,6-tetrahydro-pyrrolo[3,4-b]pyrrol-6-yl]-benzonitrile (Intermediate I) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The reaction was performed at 75° C. for 2 h and the product was purified by flash chromatography. The title compound was obtained as a white solid. $t_R$=5.27 min (HPLC 4); ESI-MS: $t_R$=1.13 min, [M+H]$^+$ 532/534 (LC-MS 1); $^1$H-NMR (d$_6$-DMSO, 600 MHz): 8.31 (s, 1H), 7.82 (m, 2H), 7.47 (m, 2H), 7.39-7.46 (m, 2H), 7.18 (m, 1H), 6.51 (s, 1H), 6.40 (s, 1H), 3.95 (m, 1H), 3.94 (s, 3H), 3.90 (s, 3H), 1.31 (m, 3H), 0.43 (m, 3H).

EXAMPLE 43

4-[2-(2-Amino-4-methoxy-pyrimidin-5-yl)-5-(5-chloro-2-methyl-phenyl)-1-isopropyl-4-oxo-1,4,5,6-tetrahydro-pyrrolo[[3,4-b]pyrrol-6-yl]-benzonitrile

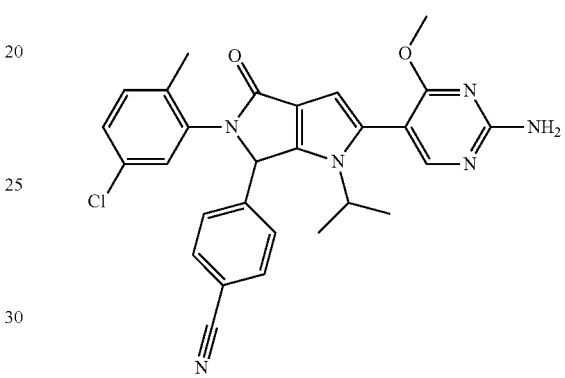

The title compound was prepared in analogy to the procedure described for Example 25 but 4-[2-bromo-5-(5-chloro-2-methyl-phenyl)-1-isopropyl-4-oxo-1,4,5,6-tetrahydro-pyrrolo[3,4-b]pyrrol-6-yl]-benzonitrile (Intermediate J) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a white foam. $t_R$=4.57 min (HPLC 4); ESI-MS: $t_R$=1.01 min, [M+H]$^+$ 513/515 (LC-MS 1); $^1$H-NMR (d$_6$-DMSO, 600 MHz): 7.94 (s, 1H), 7.73-7.86 (m, 3H), 7.44 (m, 2H), 7.16 (m, 1H), 7.10 (m, 1H), 6.89 (br s, 2H), 6.56 (s, 1H), 6.25 (s, 1H), 3.95 (m, 1H), 3.80 (s, 3H), 1.90 (s, 3H), 1.29 (m, 3H), 0.46 (m, 3H).

EXAMPLE 44

4-[5-(5-Chloro-2-methyl-phenyl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

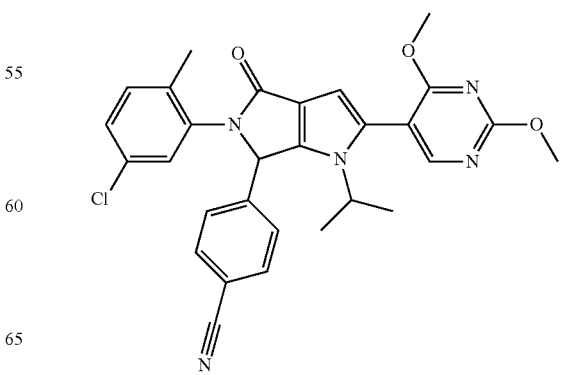

The title compound was prepared in analogy to the procedure described for Example 43 but 2,4-dimethoxypyrimidine-5-boronic acid was used instead of 4-methoxy-5-(4,4,5,5-tetramethyl-[1,3,2]dioxaborolan-2-yl)-pyrimidin-2-ylamine. The reaction was performed at 110° C. for 1 h and the product was purified by preparative HPLC (prep HPLC 1). The title compound was obtained as a white solid. $t_R$=5.33 min (HPLC 4); ESI-MS: $t_R$=1.14 min, [M+H]$^+$ 528/530 (LC-MS 1); $^1$H-NMR (d$_6$-DMSO, 600 MHz): 8.31 (s, 1H), 7.73-7.88 (m, 3H), 7.45 (m, 2H), 7.16 (m, 1H), 7.10 (m, 1H), 6.60 (s, 1H), 6.36 (s, 1H), 3.95 (s, 3H), 3.94 (m, 1H), 3.91 (s, 3H), 1.90 (s, 3H), 1.29 (m, 3H), 0.46 (m, 3H).

EXAMPLE 45

5-(5-Chloro-2-methyl-phenyl)-6-(4-chloro-phenyl)-2-(2,4-dimethoxy-pyrimidin-5-yl)-1-ethyl-5,6-dihydro-1H-pyrrolo[3,4-b]pyrrol-4-one

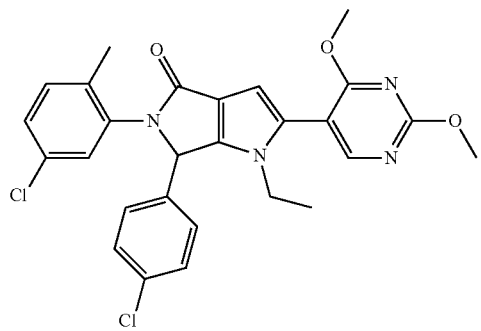 [SMILES: CCn1c(-c2cnc(OC)nc2OC)cc2c1C(c1ccc(Cl)cc1)N(c1cc(Cl)ccc1C)C2=O]

The title compound was prepared in analogy to the procedure described for Example 25 but 2-bromo-5-(5-chloro-2-methyl-phenyl)-6-(4-chloro-phenyl)-1-ethyl-5,6-dihydro-1H-pyrrolo[3,4-b]pyrrol-4-one (Intermediate K) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The product was purified by flash chromatography to afford the title compound as a white solid. $t_R$: 5.69 min (HPLC 4); ESI-MS: $t_R$=1.30 min, [M+H]$^+$ 523/525 (LC-MS 1); $^1$H-NMR (d$_6$-DMSO, 600 MHz, 100° C.): (rotamers) 8.31 (s, 1H), 7.40 (m, 2H), 7.30 (m, 1H), 7.26 (m, 2H), 7.15-7.23 (m, 2H), 6.37 (s, 1H), 6.29 (s, 1H), 4.00 (s, 3H), 3.97 (s, 3H), 3.38/3.59 (m, 2H), 2.07 (s, 3H), 0.86 (m, 3H).

EXAMPLE 46

5-(5-Chloro-1-methyl-6-oxo-1,6-dihydro-pyridin-3-yl)-6-(4-chloro-phenyl)-1-isopropyl-2-(2-methoxy-phenyl)-5,6-dihydro-1H-pyrrolo[3,4-b]pyrrol-4-one

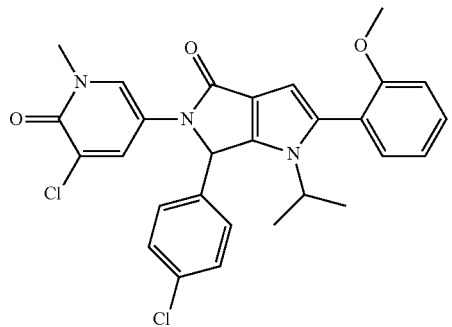 [SMILES: COc1ccccc1-c1cc2c(n1C(C)C)C(c1ccc(Cl)cc1)N(c1cc(Cl)c(=O)n(C)c1)C2=O]

The title compound was prepared in analogy to the procedure described for Example 17 but 2-bromo-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one (Intermediate E) and 2-methoxyphenylboronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$: 7.13 min (HPLC 2); ESI-MS: $t_R$=1.20 min, [M+H]$^+$ 522/524/526 (LC-MS 1); TLC: $R_f$=0.35 (95:5 CH$_2$Cl$_2$/MeOH); $^1$H-NMR (d$_6$-DMSO, 600 MHz): 7.91 (m, 1H), 7.88 (m, 1H), 7.44 (m, 1H), 7.43 (m, 2H), 7.33 (m, 2H), 7.25 (m, 1H), 7.11 (m, 1H), 7.02 (m, 1H), 6.34 (s, 1H), 6.21 (s, 1H), 3.92 (m, 1H), 3.74 (s, 3H), 3.44 (s, 3H), 1.33 (m, 3H), 0.39 (m, 3H).

EXAMPLE 47

5-(5-Chloro-1-methyl-6-oxo-1,6-dihydro-pyridin-3-yl)-6-(4-chloro-phenyl)-1-isopropyl-2-[2-methoxy-5-(morpholine-4-carbonyl)-phenyl]-5,6-dihydro-1H-pyrrolo[3,4-B]pyrrol-4-one

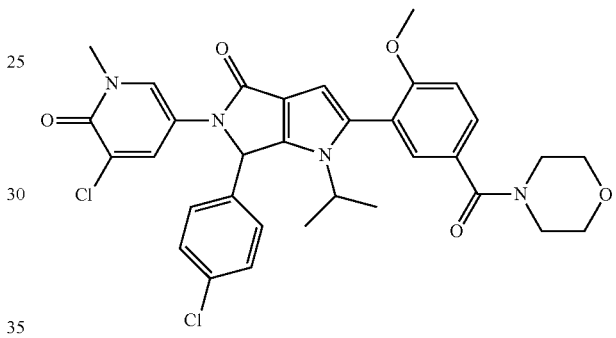

The title compound was prepared in analogy to the procedure described for Example 46 but 5-(morpholine-4-carbonyl)-2-methoxyphenylboronic acid (Intermediate X) was used instead of 2-methoxyphenylboronic acid. The title compound was obtained as a white solid. $t_R$: 6.13 min (HPLC 2); ESI-MS: $t_R$=0.98 min, [M+H]$^+$ 635/637 (LC-MS 1); TLC: $R_f$=0.25 (95:5 CH$_2$Cl$_2$/MeOH); $^1$H-NMR (d$_6$-DMSO, 600 MHz): 7.91 (m, 1H), 7.89 (m, 1H), 7.53 (m, 1H), 7.44 (m, 2H), 7.26-7.36 (m, 3H), 7.18 (m, 1H), 6.35 (s, 1H), 6.29 (s, 1H), 3.92 (m, 1H), 3.79 (s, 3H), 3.44 (s, 3H), 3.42-3.65 (m, 8H), 1.33 (m, 3H), 0.41 (m, 3H).

EXAMPLE 48

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one

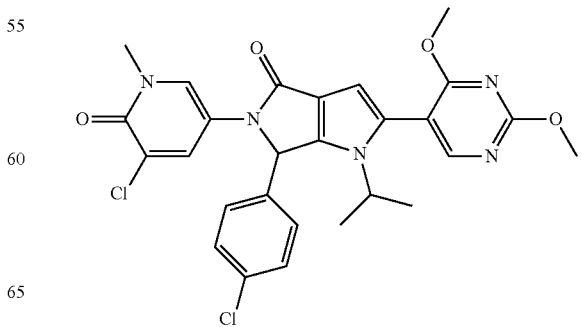

The title compound was prepared in analogy to the procedure described for Example 46 but 2,4-dimethoxypyrimidine-5-boronic acid was used instead of 2-methoxyphenylboronic acid. The title compound was obtained as a white solid. $t_R$: 6.38 min (HPLC 2); ESI-MS: $t_R$=1.06 min, [M+H]$^+$ 554/556 (LC-MS 1); TLC: $R_f$=0.07 (EtOAc); $^1$H-NMR (d$_6$-DMSO, 600 MHz): 8.29 (s, 1H), 7.91 (m, 1H), 7.88 (m, 1H), 7.44 (m, 2H), 7.32 (m, 2H), 6.35 (s, 1H), 6.34 (s, 1H), 3.94 (s, 3H), 3.93 (m, 1H), 3.90 (s, 3H), 3.44 (s, 3H), 1.33 (m, 3H), 0.45 (m, 3H).

EXAMPLE 49

3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrol-2-yl]-4-methoxy-N-methyl-benzamide

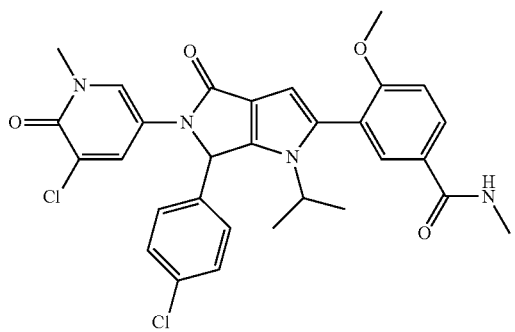 [SMILES: CNC(=O)c1ccc(OC)c(-c2cc3c(n2C(C)C)C(c2ccc(Cl)cc2)N(c2cc(Cl)c(=O)n(C)c2)C3=O)c1]

The title compound was prepared in analogy to the procedure described for Example 46 but 2-methoxy-5-[(methylamino)carbonyl]phenylboronic acid (Intermediate R) was used instead of 2-methoxyphenylboronic acid. The title compound was obtained as a white solid. $t_R$: 6.07 min (HPLC 2); ESI-MS: $t_R$=0.96 min, [M+H]$^+$ 579/581 (LC-MS 1); TLC: $R_f$=0.22 (95:5 CH$_2$Cl$_2$/MeOH); $^1$H-NMR (d$_6$-DMSO, 600 MHz): 8.38 (m, 1H), 7.95 (m, 1H), 7.93 (m, 1H), 7.90 (m, 1H), 7.78 (m, 1H), 7.44 (m, 2H), 7.32 (m, 2H), 7.18 (m, 1H), 6.36 (s, 1H), 6.26 (s, 1H), 3.90 (m, 1H), 3.80 (s, 3H), 3.44 (s, 3H), 2.75 (m, 3H), 1.35 (m, 3H), 0.40 (m, 3H).

EXAMPLE 50

3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4S-b]pyrrol-2-yl]-4-methoxy-benzoic acid

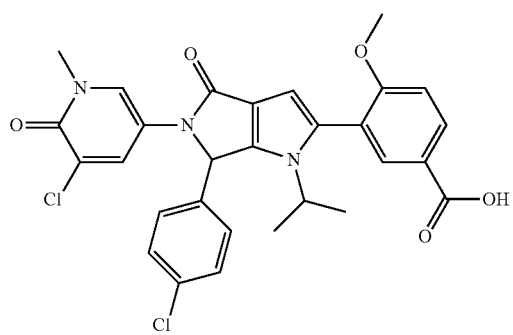 [SMILES: COc1ccc(C(=O)O)cc1-c1cc2c(n1C(C)C)C(c1ccc(Cl)cc1)N(c1cc(Cl)c(=O)n(C)c1)C2=O]

The title compound was prepared in analogy to the procedure described for Example 46 but 5-carboxy-2-methoxyphenylboronic acid was used instead of 2-methoxyphenylboronic acid. The title compound was obtained as a light yellow solid. $t_R$: 6.15 min (HPLC 2); ESI-MS: $t_R$=0.99 min, [M+H]$^+$ 566/568/570 (LC-MS 1); TLC: $R_f$=0.07 (95:5 CH$_2$Cl$_2$/MeOH).

EXAMPLE 51

2-(2-Amino-4-methoxy-pyrimidin-5-yl)-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one

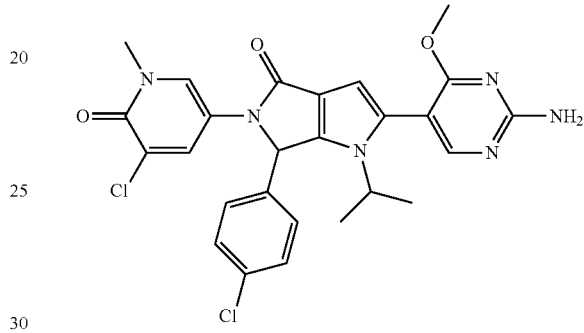

The title compound was prepared in analogy to the procedure described for Example 25 but 2-bromo-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one (Intermediate E) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a white solid. ESI-MS: $t_R$=0.87 min, [M+H]$^+$ 539/541 (LC-MS 1); $^1$H-NMR (d$_6$-DMSO, 600 MHz): 7.89-7.93 (m, 2H), 7.87 (m, 1H), 7.43 (m, 2H), 7.31 (m, 2H), 6.89 (br s, 2H), 6.32 (s, 1H), 6.23 (s, 1H), 3.93 (m, 1H), 3.79 (s, 3H), 3.43 (s, 3H), 1.33 (m, 3H), 0.45 (m, 3H).

EXAMPLE 52

5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one

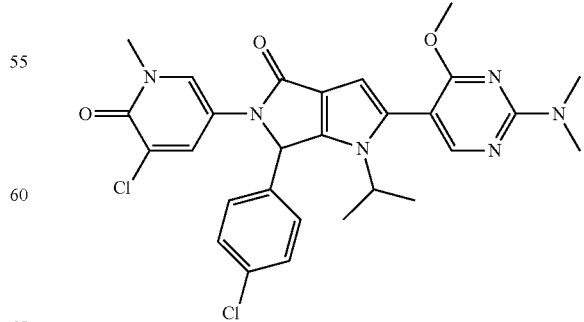

The title compound was prepared in analogy to the procedure described for Example 51 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as an off-white solid. ESI-MS: $t_R$=1.13 min, [M+H]$^+$ 567/569/571 (LC-MS 1); $^1$H-NMR (d$_6$-DMSO, 600 MHz): 8.03 (s, 1H), 7.91 (m, 1H), 7.87 (m, 1H), 7.43 (m, 2H), 7.32 (m, 2H), 6.32 (s, 1H), 6.23 (s, 1H), 3.93 (m, 1H), 3.84 (s, 3H), 3.44 (s, 3H), 3.15 (s, 6H), 1.33 (m, 3H), 0.45 (m, 3H).

EXAMPLE 53

3-[5-(3-Chloro-4-fluoro-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide

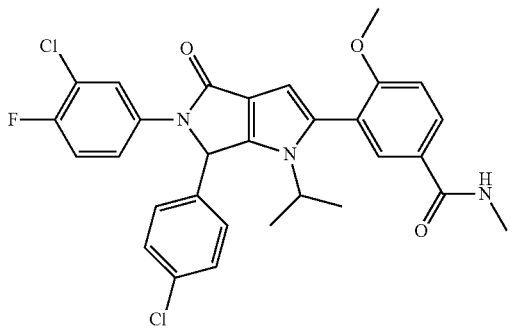 [SMILES: CNC(=O)c1ccc(OC)c(-c2cc3c(n2C(C)C)C(c2ccc(Cl)cc2)N(c2ccc(F)c(Cl)c2)C3=O)c1]

The title compound was prepared in analogy to the procedure described for Example 17 but 2-bromo-5-(3-chloro-4-fluoro-phenyl)-6-(4-chloro-phenyl)-1-isopropyl-5,6-dihydro-1H-pyrrolo[3,4-b]pyrrol-4-one (Intermediate D) and 2-methoxy-5-[(methylamino)carbonyl]phenylboronic acid (Intermediate R) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$: 7.27 min (HPLC 2); ESI-MS: $t_R$=1.24 min, [M+H]$^+$ 566/568/570 (LC-MS 1); TLC: $R_f$=0.07 (98:2 CH$_2$Cl$_2$/MeOH).

EXAMPLE 54

5-(3-Chloro-4-fluoro-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one

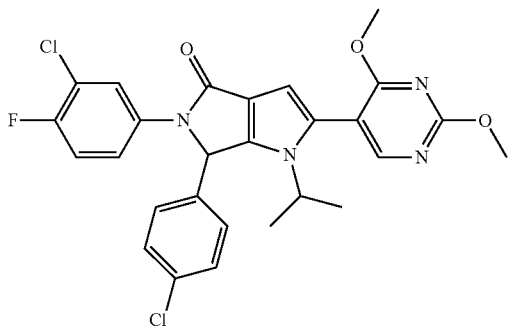 [SMILES: COc1ncc(-c2cc3c(n2C(C)C)C(c2ccc(Cl)cc2)N(c2ccc(F)c(Cl)c2)C3=O)c(OC)n1]

The title compound was prepared in analogy to the procedure described for Example 53 but 2,4-dimethoxypyrimidine-5-boronic acid was used instead of 2-methoxy-5-[(methylamino)carbonyl]phenylboronic acid. The title compound was obtained as a white solid. $t_R$: 7.63 min (HPLC 2); ESI-MS: $t_R$=1.34 min, [M+H]$^+$ 541/543/545 (LC-MS 1); TLC: $R_f$=0.21 (98:2 CH$_2$Cl$_2$/MeOH).

EXAMPLE 55

5-(3-Chloro-4-fluoro-phenyl)-6-(4-chloro-phenyl)-1-isopropyl-2-[2-methoxy-5-(morpholine-4-carbonyl)-phenyl]-5,6-dihydro-1H-pyrrolo[3,4-b]pyrrol-4-one

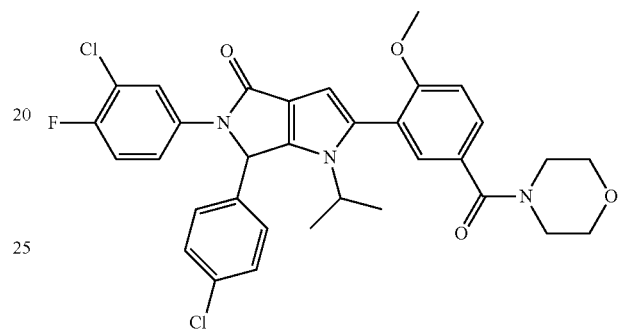

The title compound was prepared in analogy to the procedure described for Example 53 but 5-(morpholine-4-carbonyl)-2-methoxyphenylboronic acid (Intermediate X) was used instead of 2-methoxy-5-[(methylamino)carbonyl]phenylboronic acid. The title compound was obtained as a white solid. $t_R$: 7.36 min (HPLC 2); ESI-MS: $t_R$=1.26 min, [M+H]$^+$ 622/624 (LC-MS 1); TLC: $R_f$=0.12 (98:2 CH$_2$Cl$_2$/MeOH).

EXAMPLE 56

3-[5-(3-Chloro-4-fluoro-phenyl)-6-(4-chloro-phenyl)-1-isopropyl-4-oxo-1,4,5,6-tetrahydro-pyrrolo[3,4-b]pyrrol-2-yl]-4-methoxy-benzoic acid

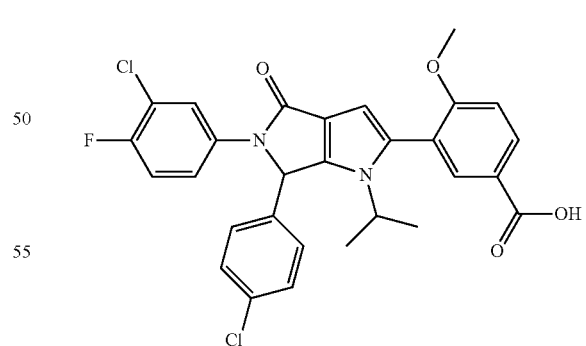

The title compound was prepared in analogy to the procedure described for Example 53 but 5-carboxy-2-methoxyphenylboronic acid was used instead of 2-methoxy-5-[(methylamino)carbonyl]phenylboronic acid. The title compound was obtained as a white solid. $t_R$: 7.31 min (HPLC 2); ESI-MS: $t_R$=1.25 min, [M+H]$^+$ 553/555 (LC-MS 1); TLC: $R_f$=0.02 (98:2 CH$_2$Cl$_2$/MeOH).

EXAMPLE 57

2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-b]pyrrol-4-one

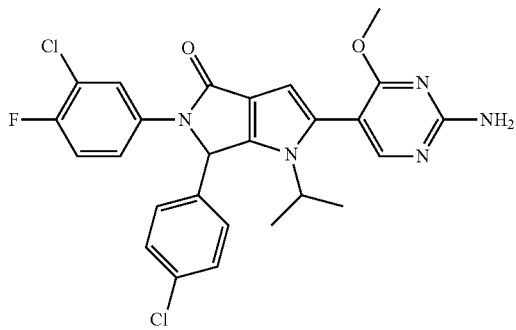 [SMILES: COc1nc(N)ncc1-c1cc2c(n1C(C)C)C(c1ccc(Cl)cc1)N(c1ccc(F)c(Cl)c1)C2=O]

The title compound was prepared in analogy to the procedure described for Example 25 but 2-bromo-5-(3-chloro-4-fluoro-phenyl)-6-(4-chloro-phenyl)-1-isopropyl-5,6-dihydro-1H-pyrrolo[3,4-b]pyrrol-4-one (Intermediate D) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a white solid. ESI-MS: $t_R$=1.20 min, [M+H]$^+$ 526/528/530 (LC-MS 1).

EXAMPLE 58

5-(3-Chloro-4-fluoro-phenyl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one

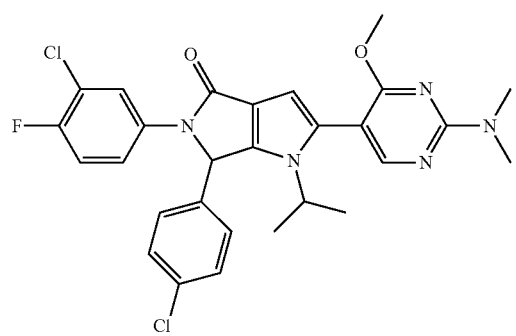 [SMILES: COc1nc(N(C)C)ncc1-c1cc2c(n1C(C)C)C(c1ccc(Cl)cc1)N(c1ccc(F)c(Cl)c1)C2=O]

The title compound was prepared in analogy to the procedure described for Example 57 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=1.44 min, [M+H]$^+$ 554/556 (LC-MS 1).

EXAMPLE 59

5-(5-Chloro-2-methyl-phenyl)-6-(4-chloro-phenyl)-1-isopropyl-2-(2-methoxy-phenyl)-4-oxo-1,4,5,6-tetrahydro-pyrrolo[3,4-b]pyrrole-3-carbonitrile

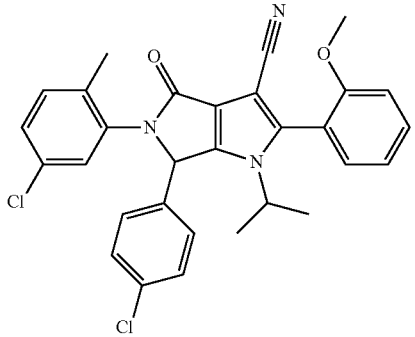 [SMILES: COc1ccccc1-c1c(C#N)c2c(n1C(C)C)C(c1ccc(Cl)cc1)N(c1cc(Cl)ccc1C)C2=O]

Chlorosulfonyl isocyanate [1189-71-5] (0.453 mmol) was added to a mixture of 5-(5-chloro-2-methyl-phenyl)-6-(4-chloro-phenyl)-1-isopropyl-2-(2-methoxy-phenyl)-5,6-dihydro-1H-pyrrolo[3,4-b]pyrrol-4-one (Example 9) (0.302 mmol) in CH$_3$CN (2 mL) at 0° C. After stirring at rt for 2.5 h, additional chlorosulfonyl isocyanate (0.226 mmol) was added. After another 4 h, the reaction mixture was cooled to 0° C., treated with DMF (0.4 mL), stirred for 15 min and then warmed to 50° C. After 30 min, the reaction mixture was cooled to rt, poured onto ice-H$_2$O and extracted with EtOAc. The organic layer was successively washed with a 1N aqueous solution of NaHCO$_3$ and brine, dried (Na$_2$SO$_4$), filtered and concentrated. The residue was purified by silica gel column chromatography to afford the title compound as an off-white solid. $t_R$: 5.59 min (HPLC 1); ESI-MS: $t_R$=1.39 min, [M+H]$^+$ 530/532/534 (LC-MS 1); TLC: R$_f$=0.12 (1:3 EtOAc/heptanes); $^1$H-NMR (d$_6$-DMSO, 600 MHz): (rotamers) 7.79/7.83 (s, 1H), 7.58 (m, 1H), 7.35-7.46 (m, 3H), 7.31 (m, 2H), 7.25 (m, 1H), 7.21 (m, 1H), 7.09-7.17 (m, 2H), 6.61 (s, 1H), 3.97/4.01 (m, 1H), 3.77/3.83 (s, 3H), 1.93 (s, 3H), 1.26/1.35 (m, 3H), 0.42/0.58 (m, 3H).

EXAMPLE 60

{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid

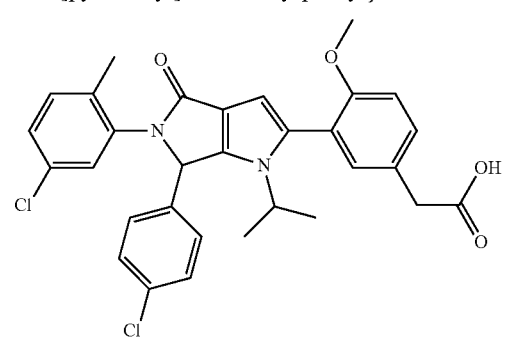

The title compound was prepared in analogy to the procedure described for Example 17 but 2-(4-methoxy-3-(4,4,5,5-tetramethyl-1,3,2-dioxaborolan-2-yl)phenyl)acetic acid (Intermediate Y) was used instead of 5-cyano-2- methoxyphenylboronic acid. The title compound was obtained as a white solid. $t_R$: 7.35 min (HPLC 2); ESI-MS: $t_R$=1.24 min, [M+H]⁺ 563/565/567 (LC-MS 1); TLC: $R_f$=0.20 (EtOAc); ¹H-NMR (d₆-DMSO, 600 MHz): 12.29 (br s, 1H), 7.78 (s, 1H), 7.37 (m, 2H), 7.32 (m, 1H), 7.25 (m, 2H), 7.16 (m, 1H), 7.15 (m, 1H), 7.10 (m, 1H), 7.06 (m, 1H), 6.48 (s, 1H), 6.18 (s, 1H), 3.94 (m, 1H), 3.74 (s, 3H), 3.55 (s, 2H), 1.92 (s, 3H), 1.29 (m, 3H), 0.45 (m, 3H).

EXAMPLE 61

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzamide

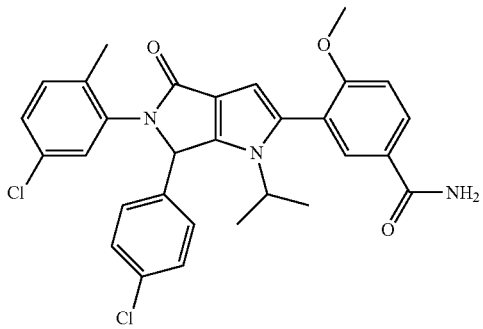 [SMILES: COc1ccc(C(N)=O)cc1-c1cc2c(n1C(C)C)C(c1ccc(Cl)cc1)N(c1cc(Cl)ccc1C)C2=O]

The title compound was prepared in analogy to the procedure described for Example 17 but 4-methoxy-3-(4,4,5,5-tetramethyl-[1,3,2]dioxaborolan-2-yl)-benzamide (Intermediate Z) was used instead of 5-cyano-2-methoxyphenylboronic acid. The title compound was obtained as a white solid. $t_R$: 7.11 min (HPLC 2); ESI-MS: $t_R$=1.17 min, [M+H]⁺ 548/550 (LC-MS 1); TLC: $R_f$=0.25 (EtOAc).

EXAMPLE 62

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzenesulfonamide

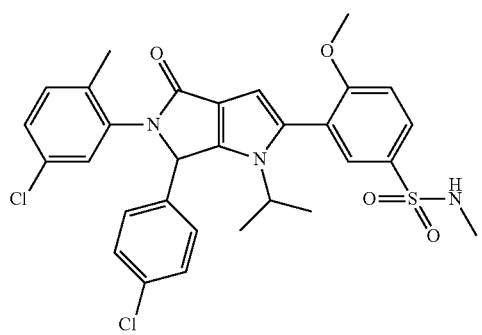 [SMILES: CNS(=O)(=O)c1ccc(OC)c(-c2cc3c(n2C(C)C)C(c2ccc(Cl)cc2)N(c2cc(Cl)ccc2C)C3=O)c1]

The title compound was prepared in analogy to the procedure described for Example 17 but 4-methoxy-N-methyl-3-(4,4,5,5-tetramethyl-[1,3,2]dioxaborolan-2-yl)-benzenesulfonamide (Intermediate AA) was used instead of 5-cyano-2-methoxyphenylboronic acid. The title compound was obtained as a white solid. $t_R$: 7.41 min (HPLC 2); ESI-MS: $t_R$=1.25 min, [M+H]⁺ 598/600 (LC-MS 1); TLC: $R_f$=0.48 (EtOAc).

EXAMPLE 63

6-(4-Chloro-phenyl)-5-(trans-4-hydroxy-cyclohexyl)-1-isopropyl-2-(2-methoxy-phenyl)-5,6-dihydro-1H-pyrrolo[3,4-b]pyrrol-4-one

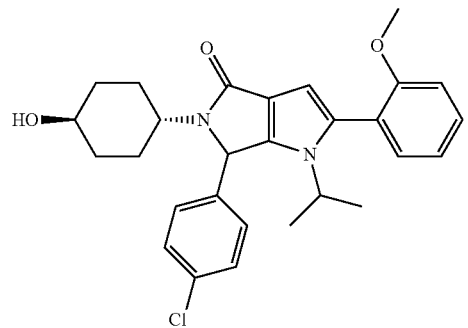 [SMILES: COc1ccccc1-c1cc2c(n1C(C)C)C(c1ccc(Cl)cc1)N([C@H]1CC[C@H](O)CC1)C2=O]

The title compound was prepared in analogy to the procedure described for Example 17 but 2-bromo-6-(4-chloro-phenyl)-5-(trans-4-hydroxy-cyclohexyl)-1-isopropyl-5,6-dihydro-1H-pyrrolo[3,4-b]pyrrol-4-one (Intermediate F) and 2-methoxyphenylboronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$: 6.99 min (HPLC 2); ESI-MS: $t_R$=1.18 min, [M+H]⁺ 479/481 (LC-MS 1); TLC: $R_f$=0.10 (EtOAc).

EXAMPLE 64

3-[6-(4-Chloro-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-N-methyl-benzamide

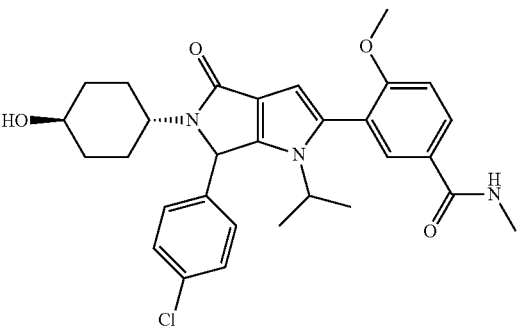 [SMILES: CNC(=O)c1ccc(OC)c(-c2cc3c(n2C(C)C)C(c2ccc(Cl)cc2)N([C@H]2CC[C@H](O)CC2)C3=O)c1]

The title compound was prepared in analogy to the procedure described for Example 63 but 2-methoxy-5-[(methylamino)carbonyl]phenylboronic acid (Intermediate R) was used instead of 2-methoxyphenylboronic acid. The title compound was obtained as a white solid. $t_R$: 5.89 min (HPLC 2); ESI-MS: $t_R$=0.94 min, [M+H]⁺ 536/538 (LC-MS 1); TLC: $R_f$=0.31 (9:1 CH₂Cl₂/MeOH).

EXAMPLE 65

3-[6-(4-Chloro-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-benzoic acid

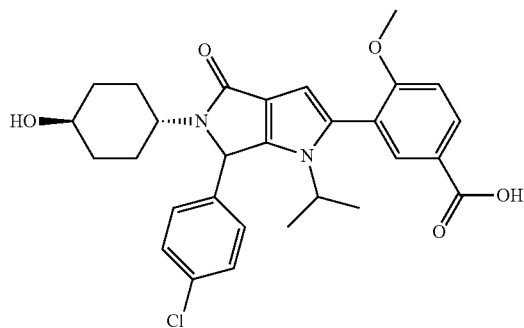 [SMILES: COc1ccc(C(=O)O)cc1-c1cc2c(n1C(C)C)C(c1ccc(Cl)cc1)N([C@H]1CC[C@H](O)CC1)C2=O]

The title compound was prepared in analogy to the procedure described for Example 63 but 5-carboxy-2-methoxyphenylboronic acid was used instead of 2-methoxyphenylboronic acid. The title compound was obtained as a white solid. $t_R$: 5.97 min (HPLC 2); ESI-MS: $t_R$=0.96 min, [M+H]$^+$ 523/525 (LC-MS 1); TLC: $R_f$=0.19 (9:1 CH$_2$Cl$_2$/MeOH).

EXAMPLE 66

6-(4-Chloro-phenyl)-2-(2,4-dimethoxy-pyrimidin-5-yl)-5-(trans-4-hydroxy-cyclohexyl)-1-isopropyl-5,6-dihydro-1H-pyrrolo[3,4-b]pyrrol-4-one

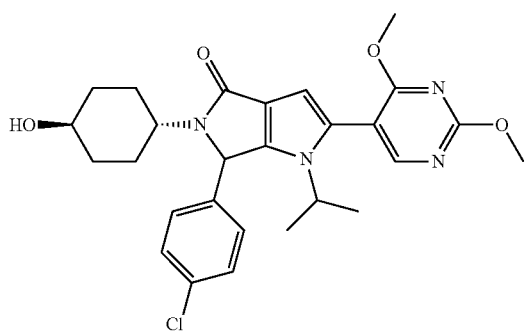 [SMILES: COc1ncc(-c2cc3c(n2C(C)C)C(c2ccc(Cl)cc2)N([C@H]2CC[C@H](O)CC2)C3=O)c(OC)n1]

The title compound was prepared in analogy to the procedure described for Example 63 but 2,4-dimethoxypyrimidine-5-boronic acid was used instead of 2-methoxyphenylboronic acid. The title compound was obtained as a white solid. $t_R$: 6.16 min (HPLC 2); ESI-MS: $t_R$=1.03 min, [M+H]$^+$ 511/513 (LC-MS 1); TLC: $R_f$=0.15 (EtOAc); $^1$H-NMR (d$_6$-DMSO, 600 MHz): 8.23 (s, 1H), 7.46 (m, 2H), 7.15-7.57 (m, 2H), 6.17 (s, 1H), 5.72 (s, 1H), 4.49 (m, 1H), 3.92 (s, 3H), 3.86 (s, 3H), 3.84 (m, 1H), 3.52 (m, 1H), 3.17 (m, 1H), 1.88 (m, 1H), 1.78 (m, 1H), 1.67 (m, 1H), 1.48 (m, 1H), 1.33 (m, 1H), 1.26 (m, 3H), 1.16 (m, 1H), 1.01-1.11 (m, 2H), 0.35 (m, 3H).

EXAMPLE 67

3-[6-(4-Chloro-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-benzonitrile

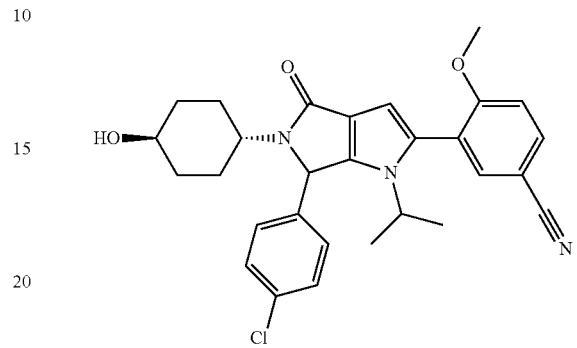

The title compound was prepared in analogy to the procedure described for Example 63 but 5-cyano-2-methoxyphenylboronic acid was used instead of 2-methoxyphenylboronic acid. The title compound was obtained as a white solid. $t_R$: 6.52 min (HPLC 2); ESI-MS: $t_R$=1.08 min, [M+H]$^+$ 504/506 (LC-MS 1); TLC: $R_f$=0.16 (EtOAc).

EXAMPLE 68

2-(2-Amino-4-methoxy-pyrimidin-5-yl)-6-(4-chloro-phenyl)-5-(trans-4-hydroxy-cyclohexyl)-1-isopropyl-5,6-dihydro-1H-pyrrolo[3,4-b]pyrrol-4-one

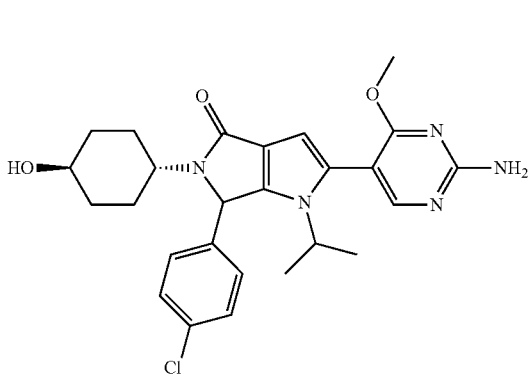 [SMILES: COc1nc(N)ncc1-c1cc2c(n1C(C)C)C(c1ccc(Cl)cc1)N([C@H]1CC[C@H](O)CC1)C2=O]

The title compound was prepared in analogy to the procedure described for Example 25 but 2-bromo-6-(4-chloro-phenyl)-5-(trans-4-hydroxy-cyclohexyl)-1-isopropyl-5,6-dihydro-1H-pyrrolo[3,4-b]pyrrol-4-one (Intermediate F) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a white solid. ESI-MS: $t_R$=0.85 min, [M+H]$^+$ 496/498 (LC-MS 1).

EXAMPLE 69

6-(4-Chloro-phenyl)-2-(2-dimethylamino-4-methoxy-pyrimidin-5-yl)-5-(trans-4-hydroxy-cyclohexyl)-1-isopropyl-5,6-dihydro-1H-pyrrolo[3,4-b]pyrrol-4-one

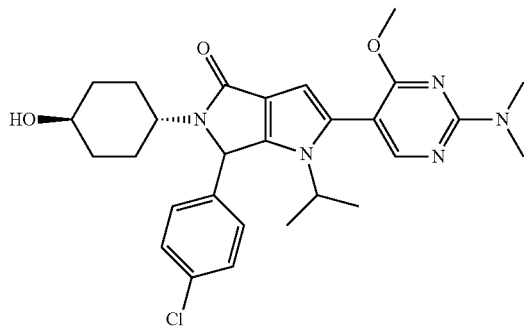 [SMILES: COc1nc(N(C)C)ncc1-c1cc2c(n1C(C)C)C(c1ccc(Cl)cc1)N([C@H]1CC[C@H](O)CC1)C2=O]

The title compound was prepared in analogy to the procedure described for Example 68 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=1.13 min, [M+H]$^+$ 524/526 (LC-MS 1); $^1$H-NMR (d$_6$-DMSO, 600 MHz): 7.97 (s, 1H), 7.45 (m, 2H), 7.12-7.55 (m, 2H), 6.06 (s, 1H), 5.69 (s, 1H), 4.49 (m, 1H), 3.84 (m, 1H), 3.81 (s, 3H), 3.52 (m, 1H), 3.17 (m, 1H), 3.13 (s, 6H), 1.88 (m, 1H), 1.78 (m, 1H), 1.66 (m, 1H), 1.48 (m, 1H), 1.32 (m, 1H), 1.26 (m, 3H), 1.15 (m, 1H), 1.01-1.10 (m, 2H), 0.34 (m, 3H).

EXAMPLE 70

5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one

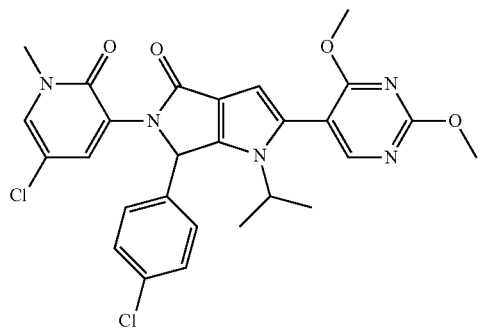 [SMILES: COc1ncc(-c2cc3c(n2C(C)C)C(c2ccc(Cl)cc2)N(c2cc(Cl)cn(C)c2=O)C3=O)c(OC)n1]

The title compound was prepared in analogy to the procedure described for Example 25 but 2-bromo-5-(5-chloro-1-methyl-2-oxo-1,2-dihydro-pyridin-3-yl)-6-(4-chloro-phenyl)-1-isopropyl-5,6-dihydro-1H-pyrrolo[3,4-b]pyrrol-4-one (Intermediate L) and 2,4-dimethoxypyridine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a white solid. ESI-MS: $t_R$=1.12 min, [M+H]$^+$ 554/556/558 (LC-MS 1); $^1$H-NMR (d$_6$-DMSO, 400 MHz): 8.29 (s, 1H), 7.87 (m, 1H), 7.36-7.43 (m, 3H), 7.22 (m, 2H), 6.65 (s, 1H), 6.34 (s, 1H), 3.94 (m, 1H), 3.93 (s, 3H), 3.89 (s, 3H), 3.42 (s, 3H), 1.29 (m, 3H), 0.46 (m, 3H).

EXAMPLE 71

2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-b]pyrrol-4-one

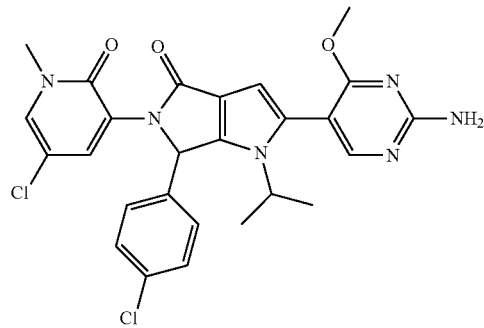 [SMILES: COc1nc(N)ncc1-c1cc2c(n1C(C)C)C(c1ccc(Cl)cc1)N(c1cc(Cl)cn(C)c1=O)C2=O]

The title compound was prepared in analogy to the procedure described for Example 70 but 4-methoxy-5-(4,4,5,5-tetramethyl-[1,3,2]dioxaborolan-2-yl)-pyrimidin-2-ylamine was used instead of 2,4-dimethoxypyridine-5-boronic acid. The title compound was obtained as a white solid. ESI-MS: $t_R$=0.96 min, [M+H]$^+$ 539/541 (LC-MS 1); $^1$H-NMR (d$_6$-DMSO, 400 MHz): 7.91 (s, 1H), 7.86 (m, 1H), 7.35-7.42 (m, 3H), 7.21 (m, 2H), 6.85 (br s, 2H), 6.63 (s, 1H), 6.22 (s, 1H), 3.94 (m, 1H), 3.78 (s, 3H), 3.42 (s, 3H), 1.28 (m, 3H), 0.46 (m, 3H).

EXAMPLE 72

5-(5-Chloro-1-methyl-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one

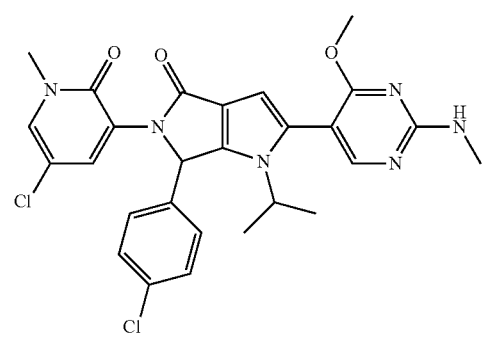 [SMILES: CNc1ncc(-c2cc3c(n2C(C)C)C(c2ccc(Cl)cc2)N(c2cc(Cl)cn(C)c2=O)C3=O)c(OC)n1]

The title compound was prepared in analogy to the procedure described for Example 70 but [4-methoxy-5-(4,4,5,5- tetramethyl-[1,3,2]dioxaborolan-2-yl)-pyrimidin-2-yl]-methyl-amine (Intermediate V) was used instead of 2,4-dimethoxypyridine-5-boronic acid. The title compound was obtained as a white solid. ESI-MS: $t_R$=1.06 min, [M+H]$^+$ 553/555(LC-MS 1).

EXAMPLE 73

5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one

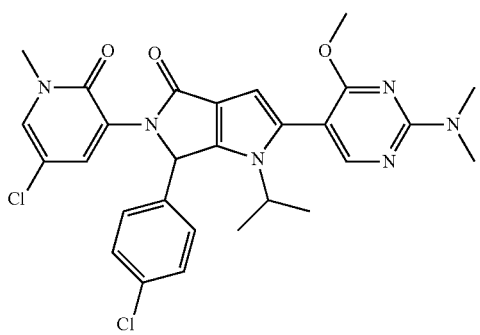 [SMILES: COc1nc(N(C)C)ncc1-c1cc2c(n1C(C)C)C(c1ccc(Cl)cc1)N(c1cc(Cl)cn(C)c1=O)C2=O]

The title compound was prepared in analogy to the procedure described for Example 70 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyridine-5-boronic acid. The title compound was obtained as a white solid. ESI-MS: $t_R$=1.22 min, [M+H]$^+$ 567/569 (LC-MS 1); $^1$H-NMR (d$_6$-DMSO, 400 MHz): 8.03 (s, 1H), 7.86 (m, 1H), 7.36-7.42 (m, 3H), 7.21 (m, 2H), 6.64 (s, 1H), 6.23 (s, 1H), 3.93 (m, 1H), 3.84 (s, 3H), 3.42 (s, 3H), 3.14 (s, 6H), 1.29 (m, 3H), 0.45 (m, 3H).

EXAMPLE 74

6-(4-Chloro-phenyl)-1-isopropyl-2-(2-methoxy-phenyl)-5-(tetrahydro-pyran-4-yl)-5,6-dihydro-1H-pyrrolo[3,4-b]pyrrol-4-one

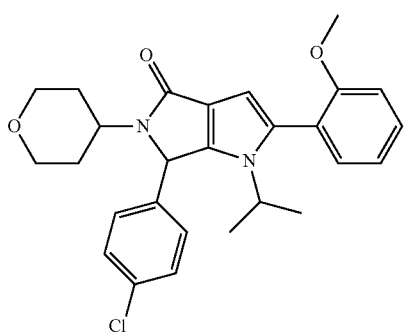 [SMILES: COc1ccccc1-c1cc2c(n1C(C)C)C(c1ccc(Cl)cc1)N(C1CCOCC1)C2=O]

The title compound was prepared in analogy to the procedure described for Example 17 but 2-bromo-6-(4-chloro-phenyl)-1-isopropyl-5-(tetrahydro-pyran-4-yl)-5,6-dihydro-1H-pyrrolo[3,4-b]pyrrol-4-one (Intermediate G) and 2-methoxyphenylboronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$=7.34 min (HPLC 2); ESI-MS: $t_R$=1.21 min, [M+H]$^+$ 465/467 (LC-MS 1); TLC: $R_f$=0.40 (EtOAc).

EXAMPLE 75

3-[6-(4-Chloro-phenyl)-1-isopropyl-4-oxo-5-(tetrahydro-pyran-4-yl)-1,4,5,6-tetrahydro-pyrrolo[3,4-b]pyrrol-2-yl]-4-methoxy-N-methyl-benzamide

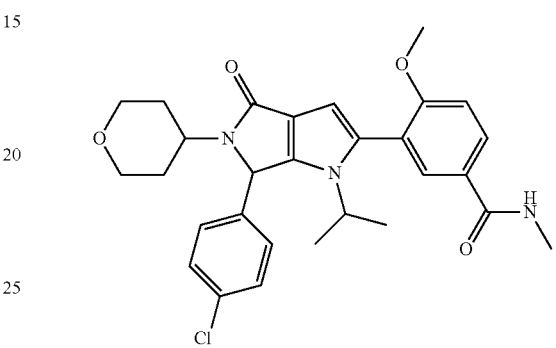

The title compound was prepared in analogy to the procedure described for Example 74 but 2-methoxy-5-[(methylamino)carbonyl]phenylboronic acid (Intermediate R) was used instead of 2-methoxyphenylboronic acid. The title compound was obtained as a white solid. $t_R$=6.25 min (HPLC 2); ESI-MS: $t_R$=0.98 min, [M+H]$^+$ 522/524 (LC-MS 1); TLC: $R_f$=0.11 (EtOAc).

EXAMPLE 76

6-(4-Chloro-phenyl)-2-(2,4-dimethoxy-pyrimidin-5-yl)-1-isopropyl-5-(tetrahydro-pyran-4-yl)-5,6-dihydro-1H-pyrrolo[3,4-b]pyrrol-4-one

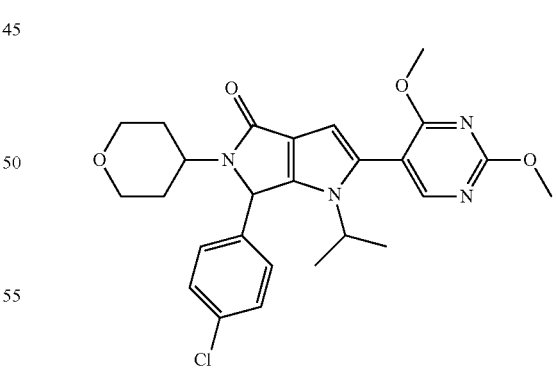

The title compound was prepared in analogy to the procedure described for Example 74 but 2,4-dimethoxypyridine-5-boronic acid was used instead of 2-methoxyphenylboronic acid. The title compound was obtained as a white solid. $t_R$=6.56 min (HPLC 2); ESI-MS: $t_R$=1.08 min, [M+H]$^+$ 497/499 (LC-MS 1); TLC: $R_f$=0.19 (EtOAc); $^1$H-NMR (d$_6$-DMSO, 600 MHz): 8.24 (s, 1H), 7.48 (m, 2H), 7.18-7.59 (m, 2H), 6.19 (s, 1H), 5.80 (s, 1H), 3.92 (s, 3H), 3.87 (s, 3H), 3.79-3.87 (m, 3H), 3.71 (m, 1H), 3.14-3.25 (m, 2H), 2.08 (m, 1H), 1.45 (m, 1H), 1.28-1.37 (m, 2H), 1.28 (m, 3H), 0.36 (m, 3H).

EXAMPLE 77

3-[6-(4-Chloro-phenyl)-1-isopropyl-4-oxo-5-(tetrahydro-pyran-4-yl)-1,4,5,6-tetrahydro-pyrrolo[3,4-b]pyrrol-2-yl]-4-methoxy-benzonitrile

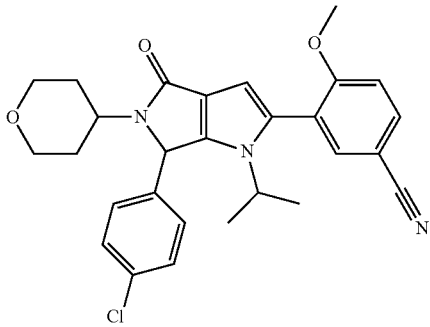 [SMILES: COc1ccc(C#N)cc1-c1cc2c(n1C(C)C)C(c1ccc(Cl)cc1)N(C1CCOCC1)C2=O]

The title compound was prepared in analogy to the procedure described for Example 74 but 5-cyano-2-methoxyphenylboronic acid was used instead of 2-methoxyphenylboronic acid. The title compound was obtained as a white solid. $t_R$=6.88 min (HPLC 2); ESI-MS: $t_R$=1.12 min, [M+H]$^+$490/492 (LC-MS 1); TLC: $R_f$=0.31 (EtOAc).

EXAMPLE 78

2-(2-Amino-4-methoxy-pyrimidin-5-yl)-6-(4-chloro-phenyl)-1-isopropyl-5-(tetrahydro-pyran-4-yl)-5,6-dihydro-1H-pyrrolo[3,4-b]pyrrol-4-one

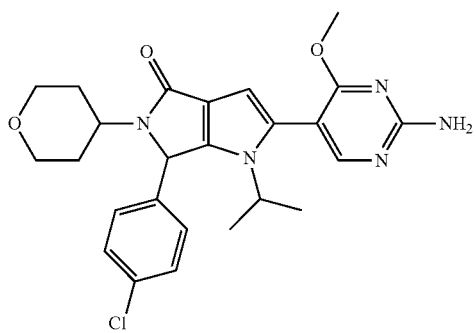 [SMILES: COc1nc(N)ncc1-c1cc2c(n1C(C)C)C(c1ccc(Cl)cc1)N(C1CCOCC1)C2=O]

The title compound was prepared in analogy to the procedure described for Example 25 but 2-bromo-6-(4-chloro-phenyl)-1-isopropyl-5-(tetrahydro-pyran-4-yl)-5,6-dihydro-1H-pyrrolo[3,4-b]pyrrol-4-one (Intermediate G) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a white solid. ESI-MS: $t_R$=0.89 min, [M+H]$^+$ 482/484 (LC-MS 1).

EXAMPLE 79

6-(4-Chloro-phenyl)-2-(2-dimethylamino-4-methoxy-pyrimidin-5-yl)-1-isopropyl-5-(tetrahydro-pyran-4-yl)-5,6-dihydro-1H-pyrrolo[3,4-b]pyrrol-4-one

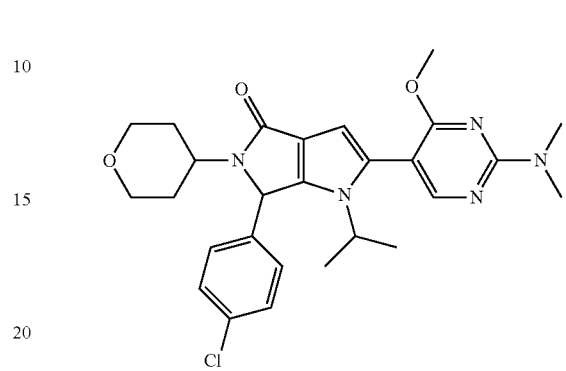

The title compound was prepared in analogy to the procedure described for Example 78 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=1.17 min, [M+H]$^+$ 510/512 (LC-MS 1); $^1$H-NMR (d$_6$-DMSO, 400 MHz): 7.96 (s, 1H), 7.46 (m, 2H), 7.24-7.46 (m, 2H), 6.07 (s, 1H), 5.75 (s, 1H), 3.81 (s, 3H), 3.77-3.89 (m, 3H), 3.70 (m, 1H), 3.13-3.25 (m, 2H), 3.12 (s, 6H), 2.07 (m, 1H), 1.43 (m, 1H), 1.27-1.39 (m, 2H), 1.26 (m, 3H), 0.35 (m, 3H).

EXAMPLE 80

2-{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetamide

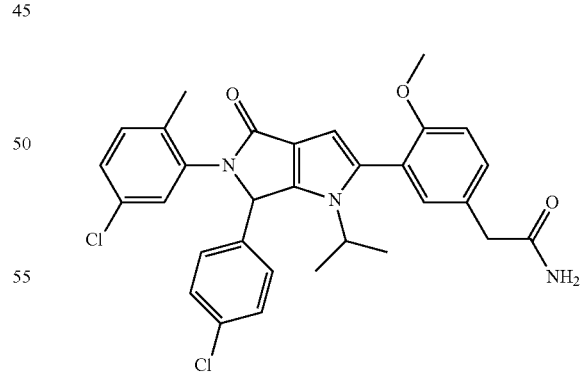

A mixture of {3-[5-(5-chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid (Example 60) (0.177 mmol), EDC.HCl (0.222 mmol), HOBt (0.131 mmol) and Et$_3$N (0.621 mmol) in CH$_2$Cl$_2$ (1.3 mL) at rt was treated with an ammonia solution (0.4N/THF) (0.52 mmol). After stirring for 16 h, the reaction mixture was diluted with H₂O and extracted with CH₂Cl₂ (2×). The combined organic layers were successively washed with H₂O and brine, dried (Na₂SO₄), filtered and concentrated. The residue was purified using a RediSep® silica gel column to afford the title compound as a white solid. t$_R$: 7.08 min (HPLC 2); ESI-MS: t$_R$=1.16 min, [M+H]⁺ 562/564 (LC-MS 1); TLC: R$_f$=0.14 (EtOAc).

EXAMPLE 81

2-{3-[5-(5-Chloro-2-methyl-phenyl)-6-(4-chlorophenyl)-1-isopropyl-4-oxo-1,4,5,6-tetrahydro-pyrrolo[3,4-b]pyrrol-2-yl]-4-methoxy-phenyl}-N-methyl-acetamide

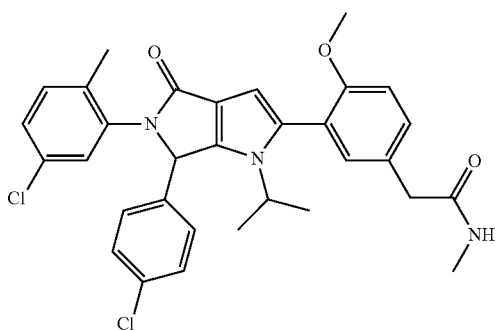 [SMILES: CNC(=O)Cc1ccc(OC)c(-c2cc3c(n2C(C)C)C(c2ccc(Cl)cc2)N(c2cc(Cl)ccc2C)C3=O)c1]

The title compound was prepared in analogy to the procedure described for Example 80 but methylamine.HCl was used instead of the ammonia solution to afford the title compound as a white solid. t$_R$: 7.22 min (HPLC 2); ESI-MS: t$_R$=1.20 min, [M+H]⁺ 576/578/580 (LC-MS 1); TLC: R$_f$=0.15 (EtOAc).

EXAMPLE 82

2-{3-[5-(5-Chloro-2-methyl-phenyl)-6-(4-chlorophenyl)-1-isopropyl-4-oxo-1,4,5,6-tetrahydro-pyrrolo[3,4-b]pyrrol-2-yl]-4-methoxy-phenyl}-N,N-dimethyl-acetamide

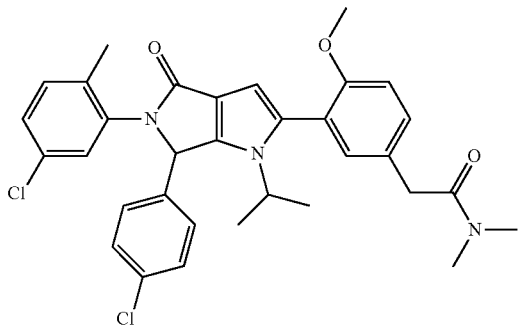 [SMILES: COc1ccc(CC(=O)N(C)C)cc1-c1cc2c(n1C(C)C)C(c1ccc(Cl)cc1)N(c1cc(Cl)ccc1C)C2=O]

The title compound was prepared in analogy to the procedure described for Example 80 but dimethylamine.HCl was used instead of the ammonia solution to afford the title compound as a white solid. t$_R$: 7.47 min (HPLC 2); ESI-MS: t$_R$=1.25 min, [M+H]⁺ 590/592 (LC-MS 1); TLC: R$_f$=0.25 (EtOAc).

EXAMPLE 83

{5-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-acetic acid ethyl ester

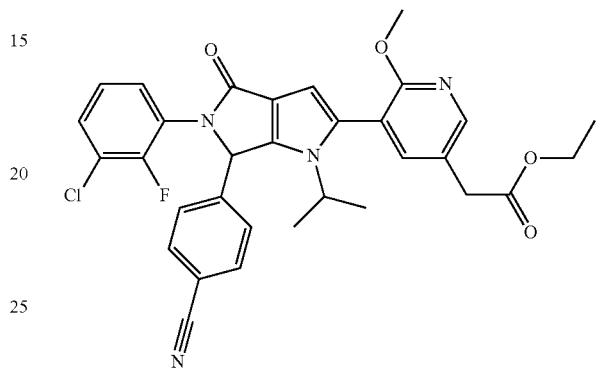

The title compound was prepared in analogy to the procedure described for Example 41, but [6-methoxy-5-(4,4,5,5-tetramethyl-[1,3,2]dioxaborolan-2-yl)-pyridin-3-yl]-acetic acid ethyl ester (Intermediate AN) was used instead of 4-methoxy-5-(4,4,5,5-tetramethyl-[1,3,2]dioxaborolan-2-yl)-pyrimidin-2-ylamine. The title compound was obtained as a white solid. t$_R$=5.47 min (HPLC 4); ESI-MS: t$_R$=1.21 min, [M+H]⁺ 587/589 (LC-MS 1).

EXAMPLE 84

{4-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-acetic acid

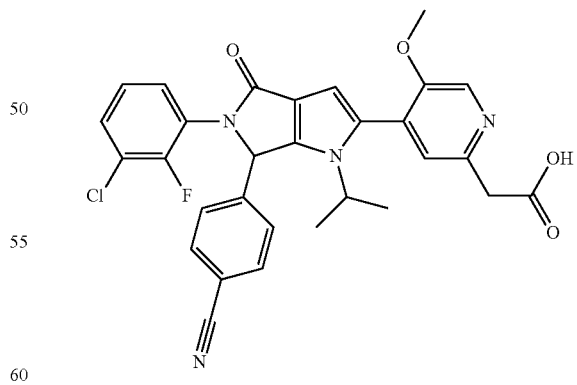

2N Aqueous NaOH (0.906 mmol) was added to a solution of {4-[5-(3-chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-acetic acid ethyl ester (Step 84.1) (0.227 mmol) in MeOH (0.4 mL) and THF (0.4 mL) at 0° C. After stirring for 30 min, the reaction mixture was diluted with H₂O, acidified to pH 3-4 with 1N aqueous HCl and then extracted with EtOAc (2×). The combined organic layers were dried (MgSO₄), filtered and concentrated. The title compound was obtained as a white solid. $t_R$: 4.51 min (HPLC 4); ESI-MS: $t_R$=0.99 min, [M+H]⁺ 559/561 (LC-MS 1).

Step 84.1: {4-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-acetic acid ethyl ester

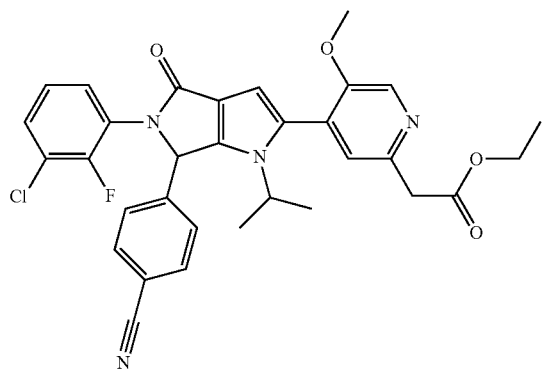 [SMILES: CCOC(=O)Cc1cc(-c2cc3c(n2C(C)C)C(c2ccc(C#N)cc2)N(c2cccc(Cl)c2F)C3=O)c(OC)cn1]

The title compound was prepared in analogy to the procedure described for Example 41, but [5-methoxy-4-(4,4,5,5-tetramethyl-[1,3,2]dioxaborolan-2-yl)-pyridin-2-yl]-acetic acid ethyl ester (Intermediate AO) was used instead of 4-methoxy-5-(4,4,5,5-tetramethyl-[1,3,2]dioxaborolan-2-yl)-pyrimidin-2-ylamine. The title compound was obtained as a white solid. $t_R$=4.88 min (HPLC 4); ESI-MS: $t_R$=1.14 min, [M+H]⁺ 587/589 (LC-MS 1).

EXAMPLE 85

2-{5-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-N-methyl-acetamide

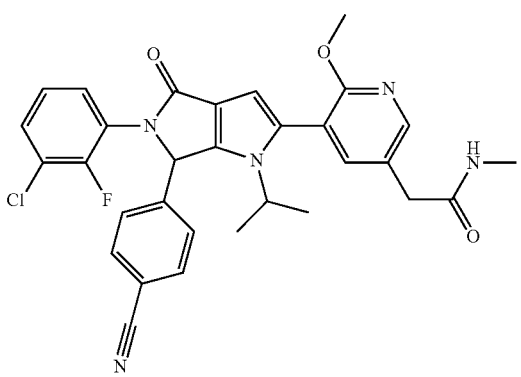 [SMILES: CNC(=O)Cc1cnc(OC)c(-c2cc3c(n2C(C)C)C(c2ccc(C#N)cc2)N(c2cccc(Cl)c2F)C3=O)c1]

A mixture of {5-[5-(3-chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-acetic acid (Step 85.1) (0.054 mmol), HATU (0.161 mmol), NMM (0.215 mmol) and methylamine.HCl (0.081 mmol) in DMF (0.5 mL) at rt was stirred for 2 h. The reaction mixture was diluted with EtOAc and successively washed with a saturated aqueous solution of NaHCO₃ (2×) and brine, dried (MgSO₄), filtered and concentrated. The residue was purified using a silica gel column to afford the title compound as a white solid. $t_R$: 4.96 min (HPLC 4); ESI-MS: $t_R$=1.02 min, [M+H]⁺ 572/574 (LC-MS 1).

Step 85.1: {5-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-acetic acid

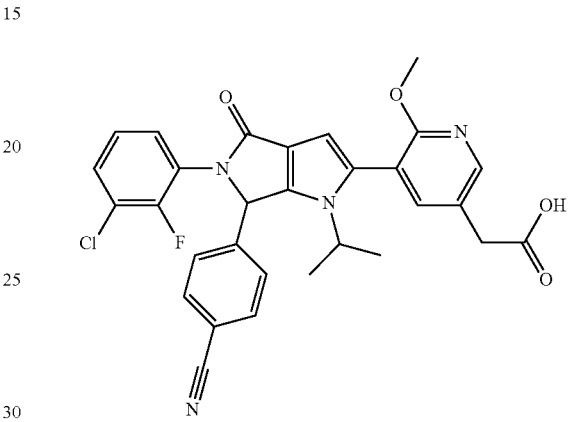

The title compound was prepared in analogy to the procedure described for Example 85, but {5-[5-(3-chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-acetic acid ethyl ester (Example 83) was used instead of {4-[5-(3-chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-acetic acid ethyl ester to afford the title compound. $t_R$=4.95 min (HPLC 4); ESI-MS: $t_R$=1.05 min, [M+H]⁺ 559/561 (LC-MS 1).

EXAMPLE 86

2-{4-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-N-methyl-acetamide

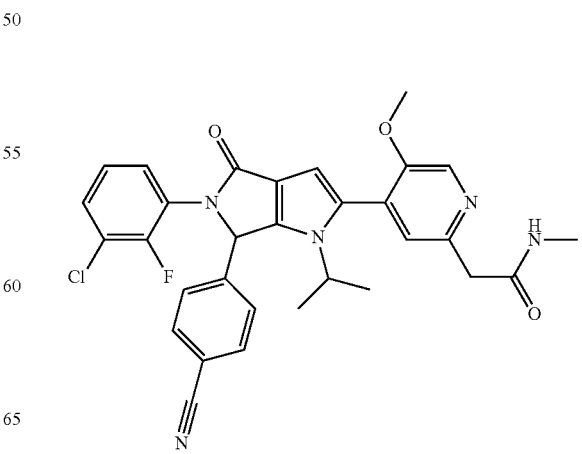

The title compound was prepared in analogy to the procedure described for Example 85, but {4-[5-(3-chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-acetic acid (Example 84) was used instead of {5-[5-(3-chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-acetic acid to afford the title compound as a white solid. $t_R$=4.51 min (HPLC 4); ESI-MS: $t_R$=0.98 min, [M+H]$^+$ 572/574 (LC-MS 1).

EXAMPLE 87

4-[5-(3-Chloro-2-fluoro-phenyl)-2-(2-cyanomethyl-5-methoxy-pyridin-4-yl)-1-isopropyl-4-oxo-1,4,5,6-tetrahydro-pyrrolo[3,4-b]pyrrol-6-yl]-benzonitrile

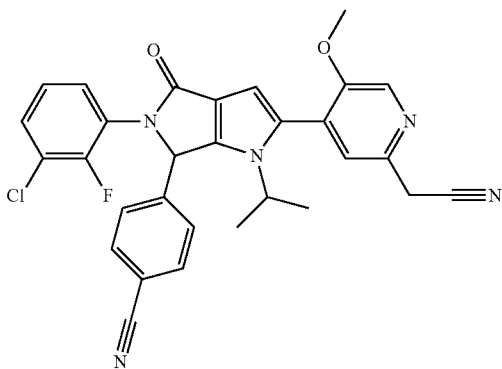 [SMILES: COc1cnc(CC#N)cc1-c1cc2c(n1C(C)C)C(c1ccc(C#N)cc1)N(c1cccc(Cl)c1F)C2=O]

The title compound was prepared in analogy to the procedure described for Example 41, but [5-methoxy-4-(4,4,5,5-tetramethyl-[1,3,2]dioxaborolan-2-yl)-pyridin-2-yl]-acetonitrile (Intermediate AL) was used instead of 4-methoxy-5-(4,4,5,5-tetramethyl-[1,3,2]dioxaborolan-2-yl)-pyrimidin-2-ylamine. The title compound was obtained as a white solid. $t_R$=5.09 min (HPLC 4).

EXAMPLE 88

4-[5-(3-Chloro-2-fluoro-phenyl)-2-(5-cyanomethyl-2-methoxy-pyridin-3-yl)-1-isopropyl-4-oxo-1,4,5,6-tetrahydro-pyrrolo[3,4-b]pyrrol-6-yl]-benzonitrile

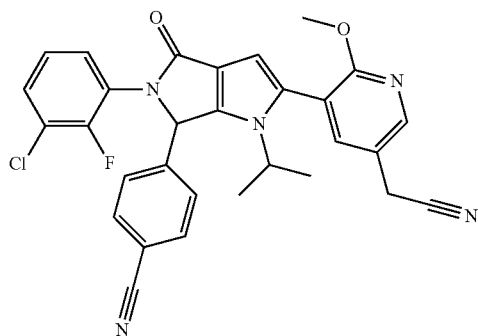 [SMILES: COc1ncc(CC#N)cc1-c1cc2c(n1C(C)C)C(c1ccc(C#N)cc1)N(c1cccc(Cl)c1F)C2=O]

The title compound was prepared in analogy to the procedure described for Example 41, but [6-methoxy-5-(4,4,5,5-tetramethyl-[1,3,2]dioxaborolan-2-yl)-pyridin-3-yl]-aceto-nitrile (Intermediate AM) was used instead of 4-methoxy-5-(4,4,5,5-tetramethyl-[1,3,2]dioxaborolan-2-yl)-pyrimidin-2-ylamine. The title compound was obtained as a white solid. $t_R$=5.24 min (HPLC 4); ESI-MS: $t_R$=1.13 min, [M+H]$^+$ 540/542 (LC-MS 1).

EXAMPLE 89

3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid

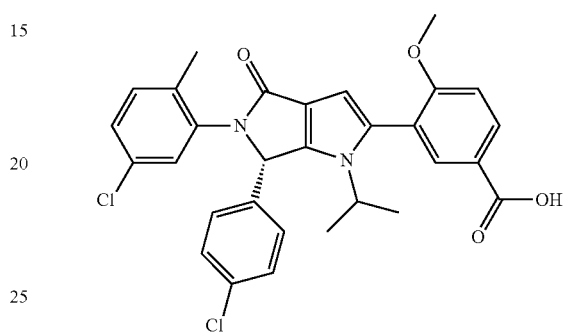

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid (Example 35) was purified by chiral chromatography (Chiral-HPLC 1) to afford the title compound as a white solid. $t_R$: 2.44 min (Column: Chiralpak IC, 4.6×250 mm. Flow 3 mL/min. scCO$_2$/MeOH/IPAm 50:50:0.5); $t_R$: 7.29 min (HPLC 2); ESI-MS: $t_R$=1.23 min, [M+H]$^+$ 549/551/553 (LC-MS 1); $^1$H-NMR (d$_6$-DMSO, 600 MHz): 8.02 (m, 1H), 7.72-7.86 (m, 2H), 7.37 (m, 2H), 7.25 (m, 2H), 7.20 (m, 1H), 7.16 (m, 1H), 7.10 (m, 1H), 6.49 (s, 1H), 6.27 (s, 1H), 3.91 (m, 1H), 3.83 (s, 3H), 1.92 (s, 3H), 1.30 (m, 3H), 0.46 (m, 3H).

EXAMPLE 90

3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid

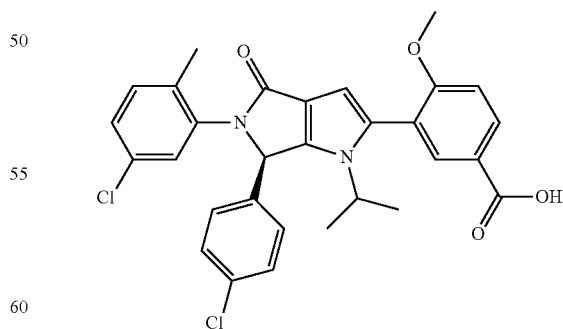

3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid (Example 35) was purified by chiral chromatography (Chiral-HPLC 1) to afford the compound as a light brown solid. $t_R$: 2.95 min (Column:

Chiralpak IC, 4.6×250 mm. Flow 3 mL/min. scCO$_2$/MeOH/IPAm 50:50:0.5); t$_R$: 7.27 min (HPLC 2); ESI-MS: t$_R$=1.23 min, [M+H]$^+$ 549/551/553 (LC-MS 1).

EXAMPLE 91

{3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid

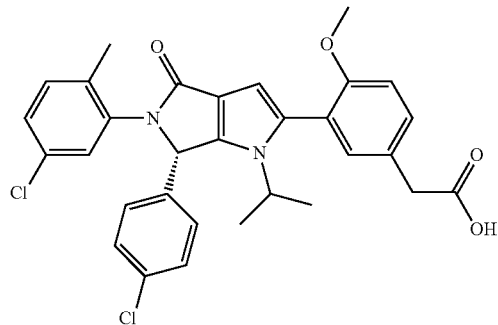

{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid (Example 60) was purified by chiral chromatography (Chiral-HPLC 1) to afford the title compound as a white solid. t$_R$: 3.00 min (Column: Chiralpak IC, 4.6×250 mm. Flow 3 mL/min. scCO$_2$/MeOH/IPAm 50:50:0.5); t$_R$: 7.28 min (HPLC 2); ESI-MS: t$_R$=1.22 min, [M+H]$^+$ 563/565/567 (LC-MS 1); $^1$H-NMR (d$_6$-DMSO, 600 MHz): 12.35 (br s, 1H), 7.78 (m, 1H), 7.37 (m, 2H), 7.31 (m, 1H), 7.25 (m, 2H), 7.16 (m, 1H), 7.15 (m, 1H), 7.10 (m, 1H), 7.06 (m, 1H), 6.48 (s, 1H), 6.18 (s, 1H), 3.94 (m, 1H), 3.74 (s, 3H), 3.54 (s, 2H), 1.92 (s, 3H), 1.28 (m, 3H), 0.45 (m, 3H).

EXAMPLE 92

{3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid

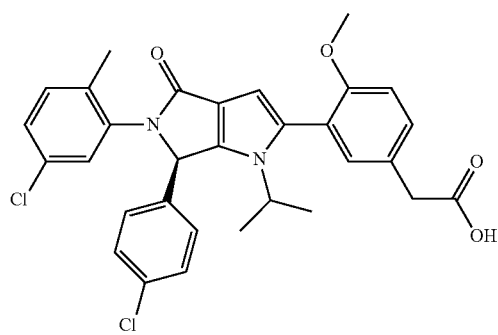 [SMILES: COc1ccc(CC(=O)O)cc1-c1cc2c(n1C(C)C)[C@@H](c1ccc(Cl)cc1)N(c1cc(Cl)ccc1C)C2=O]

{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid (Example 60) was purified by chiral chromatography (Chiral-HPLC 1) to afford the title compound as a white solid. t$_R$: 4.65 min (Column: Chiralpak IC, 4.6×250 mm. Flow 3 mL/min. scCO$_2$/MeOH/IPAm 50:50:0.5); t$_R$: 7.28 min (HPLC 2); ESI-MS: t$_R$=1.22 min, [M+H]$^+$ 563/565 (LC-MS 1).

EXAMPLE 93

4-[5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

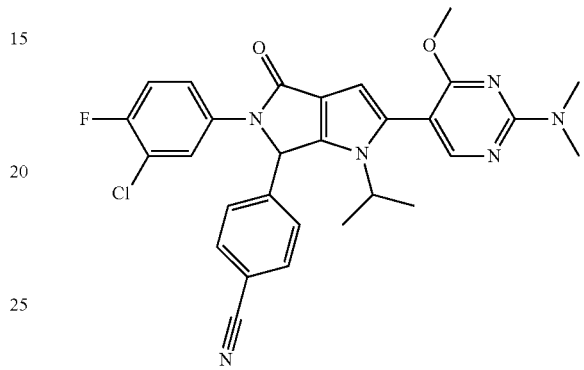

The title compound was prepared in analogy to the procedure described for Example 39 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine. The title compound was obtained as a white solid. t$_R$=4.82 min (HPLC 4); ESI-MS: t$_R$=1.24 min, [M+H]$^+$ 545/547 (LC-MS 1); $^1$H-NMR (d$_6$-DMSO, 600 MHz): 8.03 (s, 1H), 7.85 (m, 1H), 7.81 (m, 2H), 7.51-7.65 (m, 3H), 7.32 (m, 1H), 6.73 (s, 1H), 6.28 (s, 1H), 3.94 (m, 1H), 3.84 (s, 3H), 3.14 (s, 6H), 1.36 (m, 3H), 0.39 (m, 3H).

EXAMPLE 94

4-[5-(3-Chloro-2-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

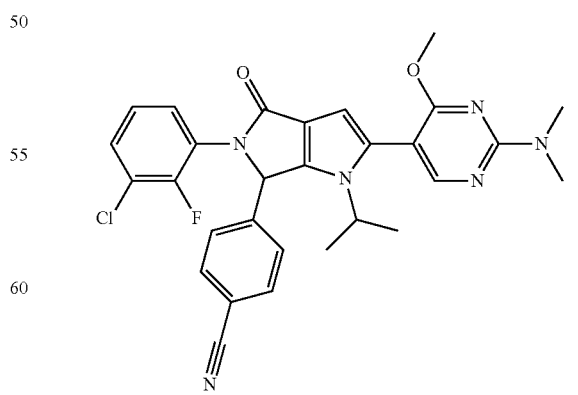

The title compound was prepared in analogy to the procedure described for Example 41 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine. The title compound was obtained as a white solid. $t_R$=4.73 min (HPLC 4); ESI-MS: $t_R$=1.21 min, [M+H]$^+$ 545/547 (LC-MS 1); $^1$H-NMR (d$_6$-DMSO, 600 MHz): 8.05 (s, 1H), 7.82 (m, 2H), 7.47 (m, 2H), 7.37-7.45 (m, 2H), 7.17 (m, 1H), 6.48 (s, 1H), 6.29 (s, 1H), 3.95 (m, 1H), 3.85 (s, 3H), 3.15 (s, 6H), 1.30 (m, 3H), 0.43 (m, 3H).

EXAMPLE 95

4-[5-(5-Chloro-2-methyl-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

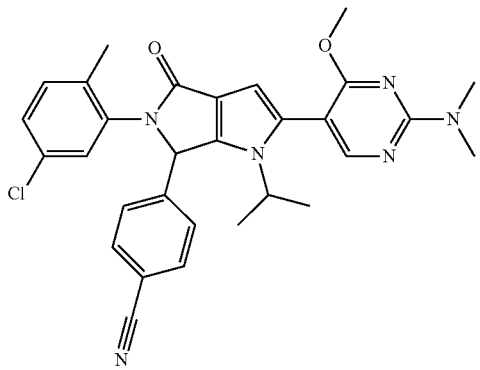 [SMILES: COc1nc(N(C)C)ncc1-c1cc2c(n1C(C)C)C(c1ccc(C#N)cc1)N(c1cc(Cl)ccc1C)C2=O]

The title compound was prepared in analogy to the procedure described for Example 43 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine. The title compound was obtained as a beige solid. $t_R$=4.79 min (HPLC 4); ESI-MS: $t_R$=1.23 min, [M+H]$^+$ 541/543 (LC-MS 1); $^1$H-NMR (d$_6$-DMSO, 600 MHz): 8.05 (s, 1H), 7.73-7.86 (m, 3H), 7.44 (m, 2H), 7.16 (m, 1H), 7.09 (m, 1H), 6.57 (s, 1H), 6.25 (s, 1H), 3.95 (m, 1H), 3.86 (s, 3H), 3.15 (s, 6H), 1.90 (s, 3H), 1.29 (m, 3H), 0.46 (m, 3H).

EXAMPLE 96

4-Chloro-2-[6-(4-chloro-phenyl)-1-isopropyl-2-(2-methoxy-phenyl)-4-oxo-4,6-dihydro-1H-pyrrolo[3,4-b]pyrrol-5-yl]-benzonitrile

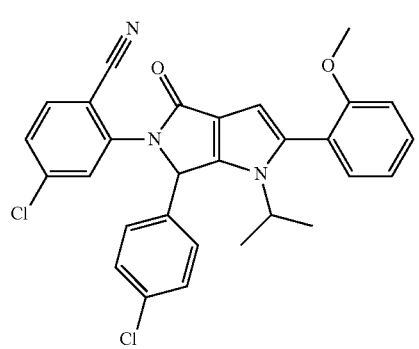 [SMILES: COc1ccccc1-c1cc2c(n1C(C)C)C(c1ccc(Cl)cc1)N(c1cc(Cl)ccc1C#N)C2=O]

The title compound was prepared in analogy to the procedure described for Example 17 but 2-[2-bromo-6-(4-chlorophenyl)-1-isopropyl-4-oxo-4,6-dihydro-1H-pyrrolo[3,4-b]pyrrol-5-yl]-4-chloro-benzonitrile (Intermediate AB) and 2-methoxyphenylboronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a light brown solid. $t_R$: 7.83 min (HPLC 2); ESI-MS: $t_R$=1.32 min, [M+H]$^+$ 516/518 (LC-MS 1); TLC: R$_f$=0.26 (1:4 EtOAc/hexanes).

EXAMPLE 97

3-[5-(5-Chloro-2-cyano-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide

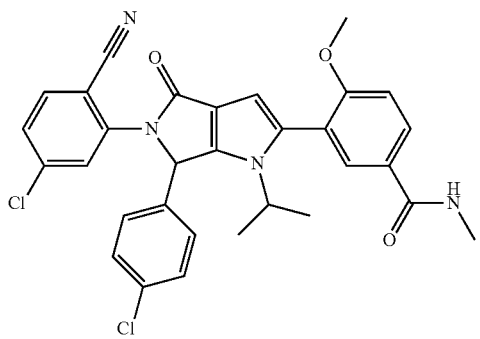 [SMILES: CNC(=O)c1ccc(OC)c(-c2cc3c(n2C(C)C)C(c2ccc(Cl)cc2)N(c2cc(Cl)ccc2C#N)C3=O)c1]

The title compound was prepared in analogy to the procedure described for Example 96 but 2-methoxy-5-[(methylamino)carbonyl]phenylboronic acid (Intermediate R) was used instead of 2-methoxyphenylboronic acid. The title compound was obtained as a white solid. $t_R$: 6.97 min (HPLC 2); ESI-MS: $t_R$=1.14 min, [M+H]$^+$ 573/575 (LC-MS 1); TLC: R$_f$=0.27 (EtOAc).

EXAMPLE 98

4-Chloro-2-[6-(4-chloro-phenyl)-2-(2,4-dimethoxy-pyrimidin-5-yl)-1-isopropyl-4-oxo-4,6-dihydro-1H-pyrrolo[3,4-b]pyrrol-5-yl]-benzonitrile

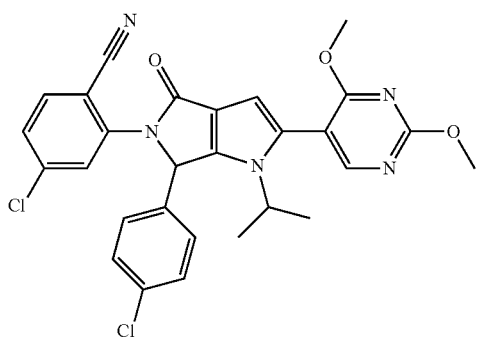 [SMILES: COc1ncc(-c2cc3c(n2C(C)C)C(c2ccc(Cl)cc2)N(c2cc(Cl)ccc2C#N)C3=O)c(OC)n1]

The title compound was prepared in analogy to the procedure described for Example 96 but 2,4-dimethoxypyridine-5-boronic acid was used instead of 2-methoxyphenylboronic acid. The title compound was obtained as a white solid. $t_R$:

7.25 min (HPLC 2); ESI-MS: $t_R$=1.23 min, [M+H]$^+$548/550/552 (LC-MS 1); TLC: $R_f$=0.26 (1:1 EtOAc/hexanes).

EXAMPLE 99

2-[2-(2-Amino-4-methoxy-pyrimidin-5-yl)-6-(4-chloro-phenyl)-1-isopropyl-4-oxo-4,6-dihydro-1H-pyrrolo[3,4-b]pyrrol-5-yl]-4-chloro-benzonitrile

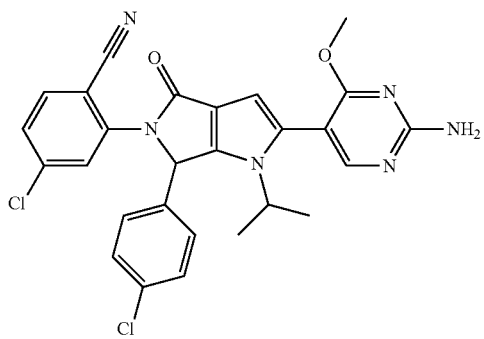 [SMILES: COc1nc(N)ncc1-c1cc2c(n1C(C)C)C(c1ccc(Cl)cc1)N(c1cc(Cl)ccc1C#N)C2=O]

The title compound was prepared in analogy to the procedure described for Example 25 but 2-[2-bromo-6-(4-chloro-phenyl)-1-isopropyl-4-oxo-4,6-dihydro-1H-pyrrolo[3,4-b]pyrrol-5-yl]-4-chloro-benzonitrile (Intermediate AB) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a light brown solid. $t_R$: 6.09 min (HPLC 2); ESI-MS: $t_R$=1.08 min, [M+H]$^+$ 533/535 (LC-MS 1); TLC: $R_f$=0.41 (EtOAc).

EXAMPLE 100

4-Chloro-2-[6-(4-chloro-phenyl)-2-(2-dimethylamino-4-methoxy-pyrimidin-5-yl)-1-isopropyl-4-oxo-4,6-dihydro-1H-pyrrolo[3,4-b]pyrrol-5-yl]-benzonitrile

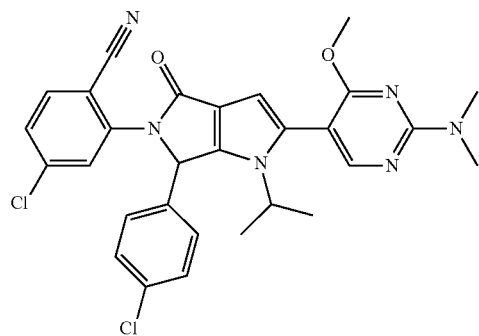 [SMILES: COc1nc(N(C)C)ncc1-c1cc2c(n1C(C)C)C(c1ccc(Cl)cc1)N(c1cc(Cl)ccc1C#N)C2=O]

The title compound was prepared in analogy to the procedure described for Example 99 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a gray-brown solid. $t_R$: 6.33 min (HPLC 2); ESI-MS: $t_R$=1.33 min, [M+H]$^+$ 561/563/565 (LC-MS 1); TLC: $R_f$=0.59 (EtOAc).

EXAMPLE 101

6-(4-Chloro-2-methyl-phenyl)-5-(trans-4-hydroxy-cyclohexyl)-1-isopropyl-2-(2-methoxy-phenyl)-5,6-dihydro-1H-pyrrolo[3,4-b]pyrrol-4-one

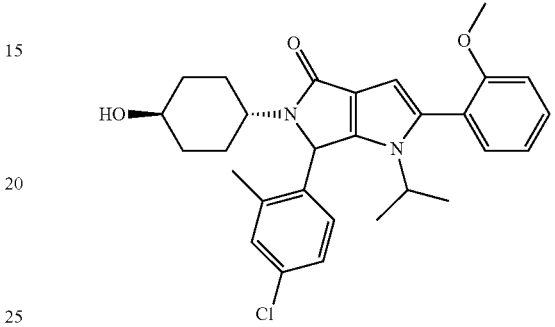

The title compound was prepared in analogy to the procedure described for Example 17 but 2-bromo-6-(4-chloro-2-methyl-phenyl)-5-(trans-4-hydroxy-cyclohexyl)-1-isopropyl-5,6-dihydro-1H-pyrrolo[3,4-b]pyrrol-4-one (Intermediate AJ) and 2-methoxyphenylboronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$: 7.15 min (HPLC 2); ESI-MS: $t_R$=1.18 min, [M+H]$^+$ 494/495 (LC-MS 1); TLC: $R_f$=0.18 (EtOAc).

EXAMPLE 102

3-[6-(4-Chloro-2-methyl-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-N-methyl-benzamide

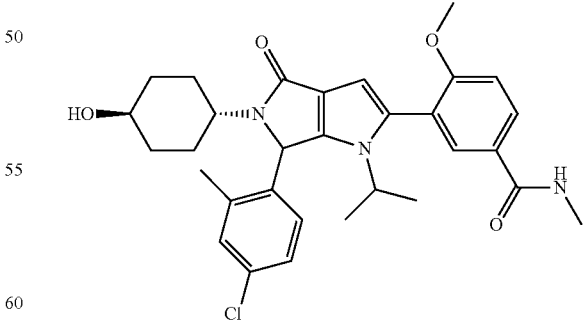

The title compound was prepared in analogy to the procedure described for Example 101 but 2-methoxy-5-[(methylamino)carbonyl]phenylboronic acid (Intermediate R) was used instead of 2-methoxyphenylboronic acid. The title compound was obtained as a white solid. $t_R$: 6.06 min (HPLC 2);

ESI-MS: $t_R$=0.95 min, [M+H]$^+$ 550/552 (LC-MS 1); TLC: $R_f$=0.06 (95:5 CH$_2$Cl$_2$/MeOH).

EXAMPLE 103

6-(4-Chloro-2-methyl-phenyl)-2-(2,4-dimethoxy-pyrimidin-5-yl)-5-(trans-4-hydroxy-cyclohexyl)-1-isopropyl-5,6-dihydro-1H-pyrrolo[3,4-b]pyrrol-4-one

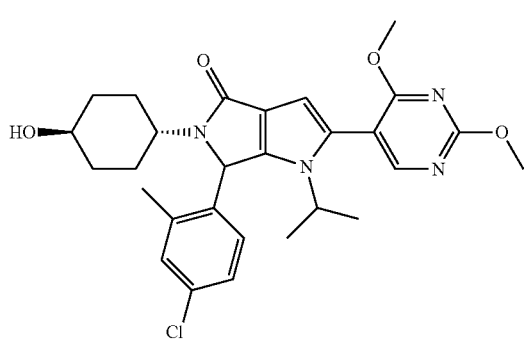 [SMILES: COc1ncc(-c2cc3c(n2C(C)C)C(c2ccc(Cl)cc2C)N([C@H]2CC[C@H](O)CC2)C3=O)c(OC)n1]

The title compound was prepared in analogy to the procedure described for Example 101 but 2,4-dimethoxypyridine-5-boronic acid was used instead of 2-methoxyphenylboronic acid. The title compound was obtained as a white solid. $t_R$: 6.34 min (HPLC 2); ESI-MS: $t_R$=1.05 min, [M+H]$^+$525/527 (LC-MS 1); TLC: $R_f$=0.10 (EtOAc).

EXAMPLE 104

6-(4-Chloro-2-methyl-phenyl)-1-isopropyl-2-(2-methoxy-phenyl)-5-(tetrahydro-pyran-4-yl)-5,6-dihydro-1H-pyrrolo[3,4-b]pyrrol-4-one

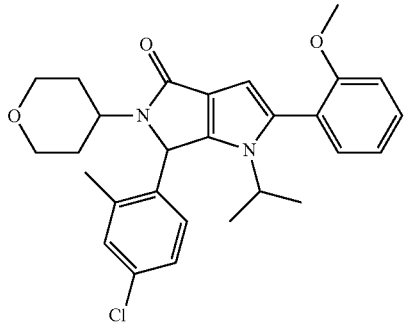 [SMILES: COc1ccccc1-c1cc2c(n1C(C)C)C(c1ccc(Cl)cc1C)N(C1CCOCC1)C2=O]

The title compound was prepared in analogy to the procedure described for Example 17 but 2-bromo-6-(4-chloro-2-methyl-phenyl)-1-isopropyl-5-(tetrahydro-pyran-4-yl)-5,6-dihydro-1H-pyrrolo[3,4-b]pyrrol-4-one (Intermediate AK) and 2-methoxyphenylboronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively.

The title compound was obtained as a white solid. $t_R$: 7.52 min (HPLC 2); ESI-MS: $t_R$=1.25 min, [M+H]$^+$479/481 (LC-MS 1); TLC: $R_f$=0.36 (EtOAc).

EXAMPLE 105

6-(4-Chloro-2-methyl-phenyl)-2-(2,4-dimethoxy-pyrimidin-5-yl)-1-isopropyl-5-(tetrahydro-pyran-4-yl)-5,6-dihydro-1H-pyrrolo[3,4-b]pyrrol-4-one

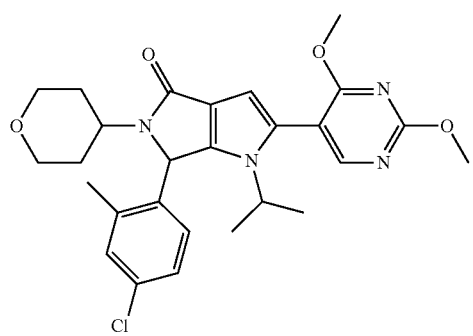 [SMILES: COc1ncc(-c2cc3c(n2C(C)C)C(c2ccc(Cl)cc2C)N(C2CCOCC2)C3=O)c(OC)n1]

The title compound was prepared in analogy to the procedure described for Example 104 but 2,4-dimethoxypyridine-5-boronic acid was used instead of 2-methoxyphenylboronic acid. The title compound was obtained as a white solid. $t_R$: 6.75 min (HPLC 2); ESI-MS: $t_R$=1.12 min, [M+H]$^+$ 511/513 (LC-MS 1); TLC: $R_f$=0.27 (EtOAc).

EXAMPLE 106

6-(4-Chloro-phenyl)-2-(2,4-dimethoxy-pyrimidin-5-yl)-1-isopropyl-5-piperidin-4-yl-5,6-dihydro-1H-pyrrolo[3,4-b]pyrrol-4-one

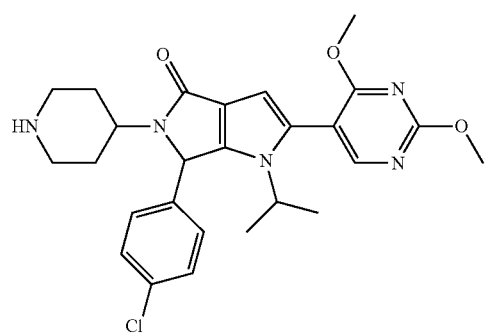 [SMILES: COc1ncc(-c2cc3c(n2C(C)C)C(c2ccc(Cl)cc2)N(C2CCNCC2)C3=O)c(OC)n1]

TFA (32.4 mmol) was added to a solution of 4-[6-(4-chloro-phenyl)-2-(2,4-dimethoxy-pyrimidin-5-yl)-1-isopropyl-4-oxo-4,6-dihydro-1H-pyrrolo[3,4-b]pyrrol-5-yl]-piperidine-1-carboxylic acid tert-butyl ester (Step I06.1) (0.755 mmol) in CH$_2$Cl$_2$ (4 mL) at 0° C. After 1 h, the reaction mixture was quenched with a saturated aqueous solution of NaHCO$_3$ and diluted with EtOAc, THF and NaCl. The separated aqueous phase was extracted with EtOAc/THF (2×). The combined organic phases were dried (MgSO$_4$), filtered and concentrated. The residue was purified using a RediSep® silica gel column to afford the title compound as a white solid (TFA-salt). $t_R$: 4.34 min (HPLC 4); ESI-MS: $t_R$=0.82 min, [M+H]+ 496/498(LC-MS 1).

Step 106.1: 4-[6-(4-Chloro-phenyl)-2-(2,4-dimethoxy-pyrimidin-5-yl)-1-isopropyl-4-oxo-4,6-dihydro-1H-pyrrolo[3,4-b]pyrrol-5-yl]-piperidine-1-carboxylic acid tert-butyl ester

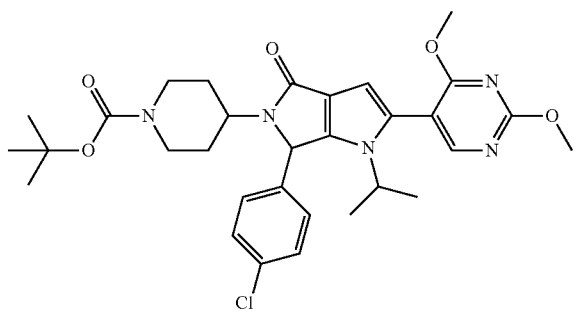 [SMILES: COc1ncc(-c2cc3c(n2C(C)C)C(c2ccc(Cl)cc2)N(C2CCN(C(=O)OC(C)(C)C)CC2)C3=O)c(OC)n1]

The title compound was prepared in analogy to the procedure described for Example 25 but 4-[2-bromo-6-(4-chlorophenyl)-1-isopropyl-4-oxo-4,6-dihydro-1H-pyrrolo[3,4-b]pyrrol-5-yl]-piperidine-1-carboxylic acid tert-butyl ester (Intermediate AI) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a white foam. $t_R$=5.79 min (HPLC 4); ESI-MS: $t_R$=1.26 min, [M+H]+ 596/598 (LC-MS 1).

EXAMPLE 107

4-[6-(4-Chloro-phenyl)-2-(2,4-dimethoxy-pyrimidin-5-yl)-1-isopropyl-4-oxo-4,6-dihydro-1H-pyrrolo[3,4-b]pyrrol-5-yl]-piperidine-1-carboxylic acid methylamide

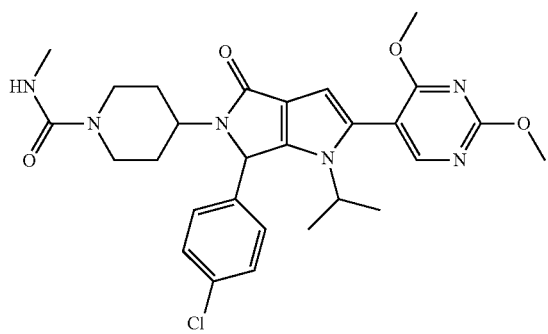 [SMILES: CNC(=O)N1CCC(N2C(=O)c3cc(-c4cnc(OC)nc4OC)n(C(C)C)c3C2c2ccc(Cl)cc2)CC1]

p-Nitrophenyl chloroformate [7693-46-1] (0.339 mmol) was added to a solution of 6-(4-chloro-phenyl)-2-(2,4-dimethoxy-pyrimidin-5-yl)-1-isopropyl-5-piperidin-4-yl-5,6-dihydro-1H-pyrrolo[3,4-b]pyrrol-4-one (Example 106) (0.242 mmol) and Et$_3$N (0.726 mmol) in CH$_2$Cl$_2$ (2 mL). After stirring at rt for 30 min, the reaction mixture was treated with methylamine (2M/THF) (3.63 mmol) and warmed to 35° C. After 20 h, the reaction mixture was diluted with EtOAc and washed with a saturated aqueous solution of NaHCO$_3$ (3×). The organic phase was dried (MgSO$_4$), filtered and concentrated. The residue was purified using a RediSep® silica gel column to afford the title compound as a white solid. $t_R$: 4.93 min (HPLC 4); ESI-MS: $t_R$=0.98 min, [M+H]+ 553/555 (LC-MS 1).

EXAMPLE 108

2-(2-Amino-4-methoxy-pyrimidin-5-yl)-6-(4-chlorophenyl)-1-isopropyl-5-(1-methyl-6-oxo-piperidin-3-yl)-5,6-dihydro-1H-pyrrolo[3,4-b]pyrrol-4-one

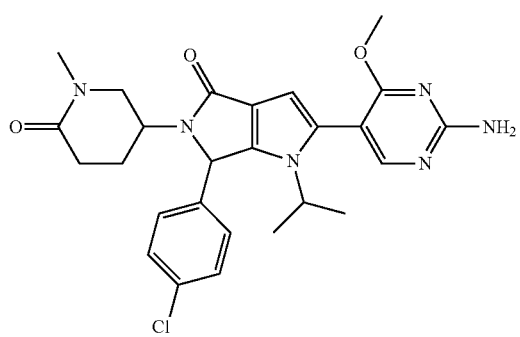 [SMILES: COc1nc(N)ncc1-c1cc2c(n1C(C)C)C(c1ccc(Cl)cc1)N(C1CCC(=O)N(C)C1)C2=O]

The title compound was prepared in analogy to the procedure described for Example 17 but 2-bromo-6-(4-chloro-phenyl)-1-isopropyl-5-(1-methyl-6-oxo-piperidin-3-yl)-5,6-dihydro-1H-pyrrolo[3,4-b]pyrrol-4-one (Intermediate Q) and 4-methoxy-5-(4,4,5,5-tetramethyl-[1,3,2]dioxaborolan-2-yl)-pyrimidin-2-ylamine (Intermediate U) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a beige solid. $t_R$: 2.35 min (HPLC 5); ESI-MS: $t_R$=0.81 min, [M+H]+ 509/511 (LC-MS 1).

EXAMPLE 109

6-(4-Chloro-phenyl)-2-(2,4-dimethoxy-pyrimidin-5-yl)-1-isopropyl-5-(1-methyl-6-oxo-piperidin-3-yl)-5,6-dihydro-1H-pyrrolo[3,4-b]pyrrol-4-one

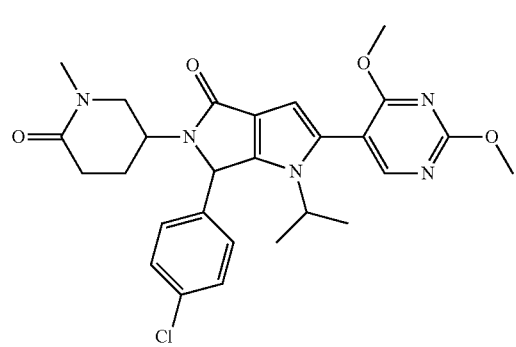 [SMILES: COc1ncc(-c2cc3c(n2C(C)C)C(c2ccc(Cl)cc2)N(C2CCC(=O)N(C)C2)C3=O)c(OC)n1]

The title compound was prepared in analogy to the procedure described for Example 108 but 2,4-dimethoxypyridine-5-boronic acid was used instead of 4-methoxy-5-(4,4,5,5- tetramethyl-[1,3,2]dioxaborolan-2-yl)-pyrimidin-2-ylamine. The title compound was obtained as a white solid. $t_R$: 2.92/2.94 min (HPLC 5); ESI-MS: $t_R$=0.99 min, [M+H]$^+$ 524/526 (LC-MS 1).

EXAMPLE 110

6-(4-Chloro-phenyl)-2-(2,4-dimethoxy-pyrimidin-5-yl)-5-(1,3-dimethyl-2-oxo-hexahydro-pyrimidin-5-yl)-1-isopropyl-5,6-dihydro-1H-pyrrolo[3,4-b]pyrrol-4-one

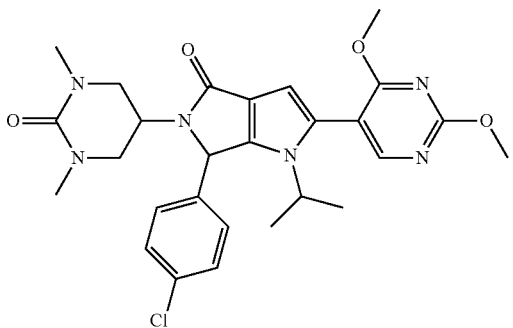

The title compound was prepared in analogy to the procedure described for Example 17 but 2-bromo-6-(4-chloro-phenyl)-5-(1,3-dimethyl-2-oxo-hexahydro-pyrimidin-5-yl)-1-isopropyl-5,6-dihydro-1H-pyrrolo[3,4-b]pyrrol-4-one (Intermediate P) and 2,4-dimethoxypyridine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$: 2.95 min (HPLC 5); ESI-MS: $t_R$=0.99 min, [M+H]$^+$539/541 (LC-MS 1); $^1$H-NMR (d$_6$-DMSO, 400 MHz): 8.26 (s, 1H), 7.51 (m, 2H), 7.24-7.48 (m, 2H), 6.25 (s, 1H), 5.85 (s, 1H), 4.08 (m, 1H), 3.95 (s, 3H), 3.90 (m, 1H), 3.89 (s, 3H), 3.81 (m, 1H), 3.23 (m, 1H), 3.11 (m, 1H), 2.93 (m, 1H), 2.70 (s, 3H), 2.61 (s, 3H), 1.28 (m, 3H), 0.40 (m, 3H).

EXAMPLE 111

6-(4-Chloro-phenyl)-2-(2,4-dimethoxy-pyrimidin-5-yl)-5-(1,4-dimethyl-6-oxo-1,6-dihydro-pyridin-3-yl)-1-isopropyl-5,6-dihydro-1H-pyrrolo[3,4-b]pyrrol-4-one

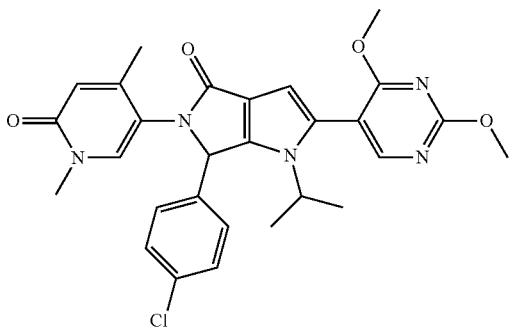 [SMILES: COc1ncc(-c2cc3c(n2C(C)C)C(c2ccc(Cl)cc2)N(c2cn(C)c(=O)cc2C)C3=O)c(OC)n1]

The title compound was prepared in analogy to the procedure described for Example 25 but 2-bromo-6-(4-chloro-phenyl)-5-(1,4-dimethyl-6-oxo-1,6-dihydro-pyridin-3-yl)-1-isopropyl-5,6-dihydro-1H-pyrrolo[3,4-b]pyrrol-4-one (Intermediate AC) and 2,4-dimethoxypyridine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a white solid. $t_R$=2.94 min (HPLC 5); ESI-MS: $t_R$=0.98 min, [M+H]$^+$ 534/536 (LC-MS 1)

EXAMPLE 112

6-(4-Chloro-phenyl)-2-(2-dimethylamino-4-methoxy-pyrimidin-5-yl)-5-(1,4-dimethyl-6-oxo-1,6-dihydro-pyridin-3-yl)-1-isopropyl-5,6-dihydro-1H-pyrrolo[3,4-b]pyrrol-4-one

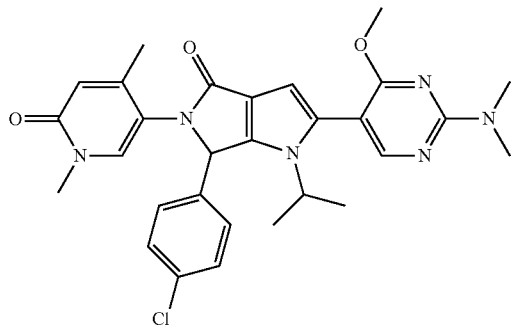 [SMILES: COc1nc(N(C)C)ncc1-c1cc2c(n1C(C)C)C(c1ccc(Cl)cc1)N(c1cn(C)c(=O)cc1C)C2=O]

The title compound was prepared in analogy to the procedure described for Example 111 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. $t_R$=2.52 min (HPLC 5); ESI-MS: $t_R$=1.06 min, [M+H]$^+$ 547/549 (LC-MS 1); $^1$H-NMR (d$_6$-DMSO, 600 MHz): (rotamers) 8.05 (s, 1H), 7.42/7.45 (m, 2H), 7.24 (m, 2H), 6.77/8.01 (s, 1H), 6.22 (s, 1H), 6.04/6.28 (s, 1H), 5.86/6.08 (s, 1H), 3.94 (m, 1H), 3.86 (s, 3H), 3.15 (s, 6H), 3.12/3.38 (s, 3H), 1.63/2.06 (s, 3H), 1.26 (m, 3H), 0.49/0.54 (m, 3H).

EXAMPLE 113

5-(5-Chloro-2-methyl-phenyl)-6-(4-chloro-phenyl)-1-isopropyl-2-(3-methoxy-pyridin-2-yl)-5,6-dihydro-1H-pyrrolo[3,4-b]pyrrol-4-one

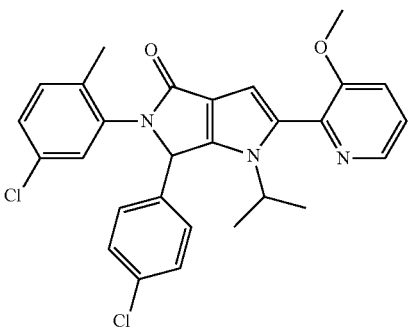

The title compound was prepared in analogy to the procedure described for Example 17 but 2-bromo-3-methoxy-pyridine [24100-18-3] and 5-(5-chloro-2-methyl-phenyl)-6-(4-chloro-phenyl)-1-isopropyl-2-(4,4,5,5-tetramethyl-[1,3,2]dioxaborolan-2-yl)-5,6-dihydro-1H-pyrrolo[3,4-b]pyrrol-4-one (Step 113.1) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a light brown solid. $t_R$: 6.54 min (HPLC 2); ESI-MS: $t_R$=1.27 min, [M+H]$^+$ 506/508/510 (LC-MS 1); TLC: $R_f$=0.21 (98:2 CH$_2$Cl$_2$/MeOH).

Step 113.1: 5-(5-Chloro-2-methyl-phenyl)-6-(4-chloro-phenyl)-1-isopropyl-2-(4,4,5,5-tetramethyl-[1,3,2]dioxaborolan-2-yl)-5,6-dihydro-1H-pyrrolo[3,4-b]pyrrol-4-one

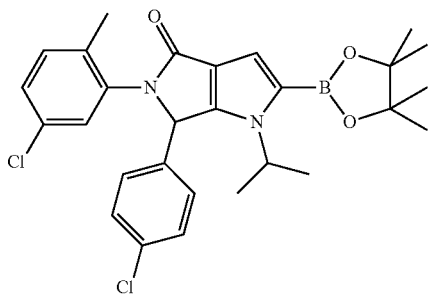 [SMILES: Cc1ccc(Cl)cc1N1C(=O)c2cc(B3OC(C)(C)C(C)(C)O3)n(C(C)C)c2C1c1ccc(Cl)cc1]

The title compound was prepared in analogy to the procedure described for Intermediate T, but 2-bromo-5-(5-chloro-2-methyl-phenyl)-6-(4-chloro-phenyl)-1-isopropyl-5,6-dihydro-1H-pyrrolo[3,4-b]pyrrol-4-one (Intermediate B) and DME were used instead of 5-bromo-4-methoxy-pyrimidine and DMSO respectively. The reaction was performed at 100° C. for 16 h to afford the title compound (20% purity) as a dark brown solid. $t_R$: 8.52 min (HPLC 2); ESI-MS: $t_R$=1.46 min; [M+H]$^+$ 525/527 (LC-MS 1).

EXAMPLE 114

5-(5-Chloro-2-methyl-phenyl)-6-(4-chloro-phenyl)-1-isopropyl-2-(5-methanesulfonyl-2-methoxy-phenyl)-5,6-dihydro-1H-pyrrolo[3,4-b]pyrrol-4-one

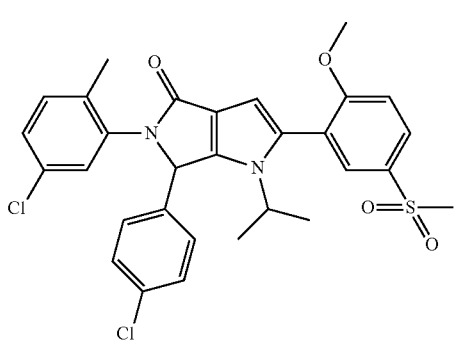 [SMILES: COc1ccc(S(C)(=O)=O)cc1-c1cc2c(n1C(C)C)C(c1ccc(Cl)cc1)N(c1cc(Cl)ccc1C)C2=O]

The title compound was prepared in analogy to the procedure described for Example 17 but 2-(5-methanesulfonyl-2-methoxy-phenyl)-4,4,5,5-tetramethyl-[1,3,2]dioxaborolane (Intermediate AP) was used instead of 5-cyano-2-methoxyphenylboronic acid. The title compound was obtained as a white solid. $t_R$: 7.34 min (HPLC 2); ESI-MS: $t_R$=1.21 min, [M+H]$^+$ 583/585/587 (LC-MS 1); TLC: $R_f$=0.25 (98:2 CH$_2$Cl$_2$/MeOH).

EXAMPLE 115

5-(5-Chloro-2-methyl-phenyl)-6-(4-chloro-phenyl)-3-fluoro-1-isopropyl-2-(2-methoxy-phenyl)-5,6-dihydro-1H-pyrrolo[3,4-b]pyrrol-4-one

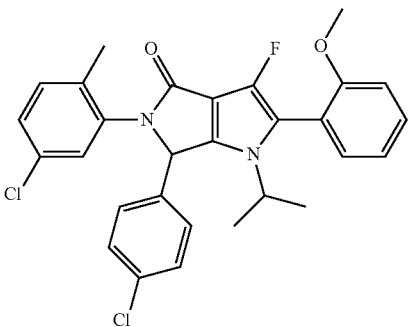

1-Fluoro-2,4,6-trimethyl-pyridinium triflate (0.902 mmol) was added to a solution of 5-(5-chloro-2-methyl-phenyl)-6-(4-chloro-phenyl)-1-isopropyl-2-(2-methoxy-phenyl)-5,6-dihydro-1H-pyrrolo[3,4-b]pyrrol-4-one (Example 9) (0.301 mmol) in 1,2-dichloroethane (4 mL) and then the mixture was heated to 80° C. in the dark. After 16 h, the reaction mixture was cooled to rt, poured into a 2% aqueous solution of sodium sulfite and extracted with EtOAc (2×). The combined organic layers were successively washed with 1M aqueous citric acid, 1M aqueous NaHCO$_3$ and brine, dried (Na$_2$SO$_4$), filtered and concentrated. The residue was purified using a RediSep® silica gel column to afford the title compound as a beige foam. ESI-MS: $t_R$=1.40 min, [M]$^+$523/525 (LC-MS 1); TLC: $R_f$=0.25 (1:2 EtOAc/heptanes).

EXAMPLE 116

5-(5-Chloro-2-methyl-phenyl)-6-(4-chloro-phenyl)-1-isopropyl-2-(2-methoxy-phenyl)-6-methyl-5,6-dihydro-1H-pyrrolo[3,4-b]pyrrol-4-one

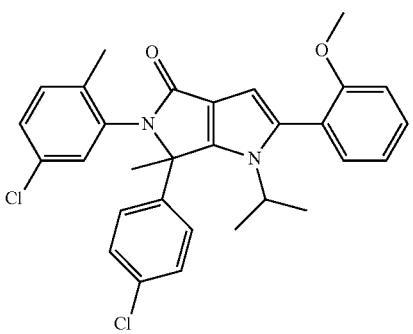

KHMDS (1M/THF) (0.237) was added to a solution of 5-(5-chloro-2-methyl-phenyl)-6-(4-chloro-phenyl)-1-isopropyl-2-(2-methoxy-phenyl)-5,6-dihydro-1H-pyrrolo[3,4-b]pyrrol-4-one (Example 9) (0.198 mmol) in THF (2 mL) at −78° C. and the mixture was stirred at −78° C. for 15 min.

Methyl iodide (0.594 mmol) was added and the mixture was allowed to warm to rt. After 2.5 h, the reaction mixture was diluted with EtOAc and washed with a 5% aqueous citric acid solution. The organic layer was washed with brine, dried (Na$_2$SO$_4$), filtered and concentrated. The residue was purified using a RediSep® silica gel column to afford the title compound as a white solid. t$_R$: 1.49 min (HPLC 3); ESI-MS: t$_R$=1.43 min, [M]$^+$ 519/521/523 (LC-MS 1); TLC: R$_f$=0.41 (1:1 EtOAc/heptanes).

EXAMPLE 117

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one

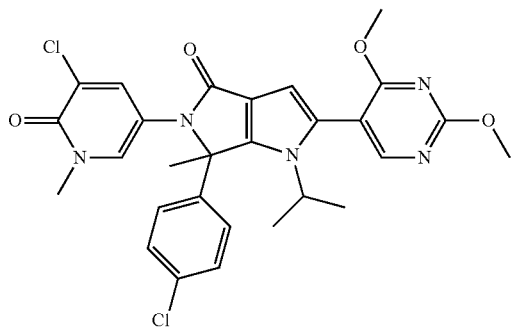 [SMILES: COc1ncc(-c2cc3c(n2C(C)C)C(C)(c2ccc(Cl)cc2)N(c2cc(Cl)c(=O)n(C)c2)C3=O)c(OC)n1]

The title compound was prepared in analogy to the procedure described for Example 116 but 5-(5-chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one (Example 48) was used instead of 5-(5-chloro-2-methyl-phenyl)-6-(4-chloro-phenyl)-1-isopropyl-2-(2-methoxy-phenyl)-5,6-dihydro-1H-pyrrolo[3,4-b]pyrrol-4-one. The title compound was obtained as a light yellow solid. t$_R$: 1.10 min (HPLC 3); ESI-MS: t$_R$=1.03 min, [M+H]$^+$ 568/570/572 (LC-MS 1); TLC: R$_f$=0.07 (EtOAc); $^1$H-NMR (d$_6$-DMSO, 600 MHz): 8.32 (s, 1H), 7.45 (m, 2H), 7.37 (m, 1H), 7.23 (m, 2H), 7.04 (m, 1H), 6.32 (s, 1H), 3.96 (m, 1H), 3.95 (s, 3H), 3.89 (s, 3H), 3.41 (s, 3H), 1.97 (s, 3H), 0.91 (m, 3H), 0.86 (m, 3H).

EXAMPLE 118

{3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid

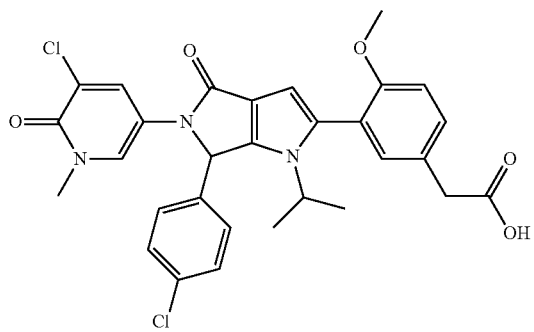 [SMILES: COc1ccc(CC(=O)O)cc1-c1cc2c(n1C(C)C)C(c1ccc(Cl)cc1)N(c1cc(Cl)c(=O)n(C)c1)C2=O]

A mixture of {3-[5-(5-chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid ethyl ester (Step 118.1) (0.338 mmol) and LiOH (0.675 mmol) in MeOH (1.6 mL) and H$_2$O (0.4 mL) was stirred at rt. After 4 h, the reaction mixture was acidified to pH 4 with 10% aqueous citric acid and extracted with EtOAc (2×). The combined organic phases were dried (Na$_2$SO$_4$), filtered and concentrated. The residue was purified using a RediSep® silica gel column to afford the title compound as a white solid. t$_R$: 6.18 min (HPLC 2); ESI-MS: t$_R$=0.98 min, [M]$^+$ 580/582/584 (LC-MS 1); TLC: R$_f$=0.24 (9:1 CH$_2$Cl$_2$/MeOH).

Step 118.1: {3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid ethyl ester

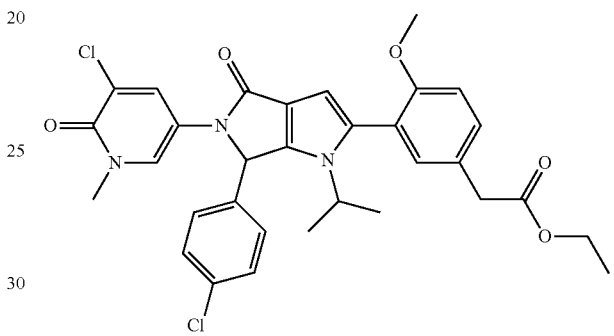

The title compound was prepared in analogy to the procedure described for Example 17 but 2-bromo-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one (Intermediate E) and [4-methoxy-3-(4,4,5,5-tetramethyl-[1,3,2]dioxaborolan-2-yl)-phenyl]-acetic acid ethyl ester (Intermediate AQ) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound (partially hydrolyzed to the acid) was obtained as a yellow foam. t$_R$: 6.78 min (HPLC 2); ESI-MS: t$_R$=1.12 min, [M+H]$^+$ 594/596 (LC-MS 1).

EXAMPLE 119

5-(5-Chloro-1-methyl-6-oxo-1,6-dihydro-pyridin-3-yl)-6-(4-chloro-phenyl)-1-isopropyl-2-(5-methanesulfonyl-2-methoxy-phenyl)-5,6-dihydro-1H-pyrrolo[3,4-b]pyrrol-4-one

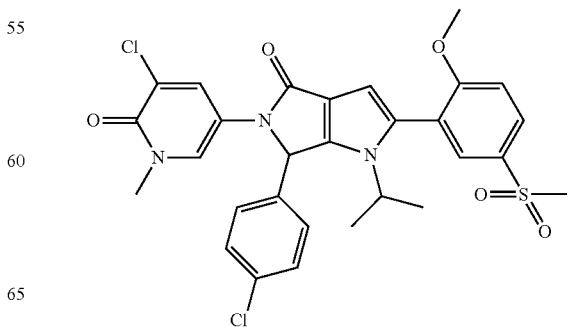

The title compound was prepared in analogy to the procedure described for Example 114 but 2-bromo-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one (Intermediate E) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a white solid. $t_R$: 1.07 min (HPLC 3); ESI-MS: $t_R$=0.97 min, [M+H]⁺ 600/602 (LC-MS 1); TLC: $R_f$=0.07 (EtOAc); ¹H-NMR (d₆-DMSO, 600 MHz): 7.98 (m, 1H), 7.90 (m, 1H), 7.88 (m, 1H), 7.75 (m, 1H), 7.43 (m, 2H), 7.35 (m, 1H), 7.32 (m, 2H), 6.35 (s, 1H), 6.34 (m, 1H), 3.89 (m, 1H), 3.85 (s, 3H), 3.44 (s, 3H), 3.20 (s, 3H), 1.34 (m, 3H), 0.43 (m, 3H).

EXAMPLE 120

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carbonitrile

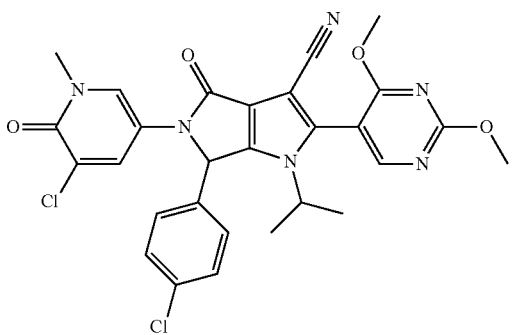 [SMILES: COc1ncc(-c2c(C#N)c3c(n2C(C)C)C(c2ccc(Cl)cc2)N(c2cc(Cl)c(=O)n(C)c2)C3=O)c(OC)n1]

The title compound was prepared in analogy to the procedure described for Example 59 but 5-(5-chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one (Example 48) was used instead of 5-(5-chloro-2-methyl-phenyl)-6-(4-chloro-phenyl)-1-isopropyl-2-(2-methoxy-phenyl)-5,6-dihydro-1H-pyrrolo[3,4-b]pyrrol-4-one. The title compound was obtained as a beige solid. $t_R$: 4.33 min (HPLC 1); ESI-MS: $t_R$=1.03 min, [M+H]⁺ 579/581 (LC-MS 1); TLC: $R_f$=0.16 (EtOAc); ¹H-NMR (d₆-DMSO, 600 MHz, 100° C.): (rotamers) 8.47 (s, 1H), 7.75-7.79 (m, 2H), 7.45 (m, 2H), 7.36 (m, 2H), 6.36 (s, 1H), 4.11 (m, 1H), 4.05 (s, 3H), 4.00 (s, 3H), 3.47 (s, 3H), 1.35 (m, 3H), 0.63 (m, 3H).

EXAMPLE 121

(S)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one

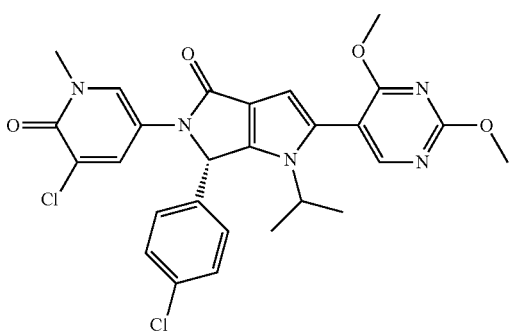 [SMILES: COc1ncc(-c2cc3c(n2C(C)C)[C@H](c2ccc(Cl)cc2)N(c2cc(Cl)c(=O)n(C)c2)C3=O)c(OC)n1]

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one (Example 48) was purified by chiral chromatography (Chiral-HPLC 1) to afford the title compound as a white solid. $t_R$: 7.73 min (Column: Chiralpak AD-H, 4.6×250 mm. Flow 1 mL/min. heptane/EtOH 50:50); $t_R$: 6.34 min (HPLC 2); ESI-MS: $t_R$=1.03 min, [M+H]⁺ 554/556 (LC-MS 1); ¹H-NMR (d₆-DMSO, 600 MHz): 8.29 (s, 1H), 7.91 (m, 1H), 7.87 (m, 1H), 7.44 (m, 2H), 7.32 (m, 2H), 6.35 (s, 1H), 6.34 (s, 1H), 3.94 (s, 3H), 3.93 (m, 1H), 3.90 (s, 3H), 3.44 (s, 3H), 1.34 (m, 3H), 0.45 (m, 3H).

EXAMPLE 122

(R)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one

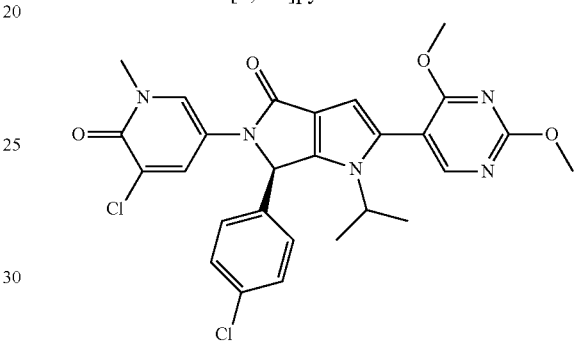

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one (Example 48) was purified by chiral chromatography (Chiral-HPLC 1) to afford the title compound as a white solid. $t_R$: 17.38 min (Column: Chiralpak AD-H, 4.6×250 mm. Flow 1 mL/min. heptane/EtOH 50:50); $t_R$: 6.34 min (HPLC 2); ESI-MS: $t_R$=1.03 min, [M+H]⁺ 554/556/558 (LC-MS 1).

EXAMPLE 123

5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one

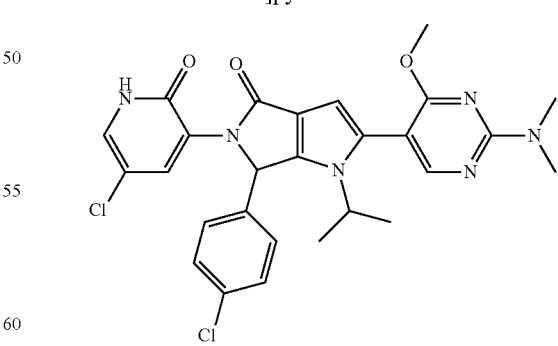

The title compound was prepared in analogy to the procedure described for Example 25 but 2-bromo-5-(5-chloro-2-oxo-1,2-dihydro-pyridin-3-yl)-6-(4-chloro-phenyl)-1-isopropyl-5,6-dihydro-1H-pyrrolo[3,4-b]pyrrol-4-one (Intermediate M) and 4-methoxy-N,N-dimethyl-5-(4,4,5,5-tetramethyl-1,3,2-dioxaborolan-2-yl)pyrimidin-2-amine (Intermediate W) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively to afford the title compound as a white solid. ESI-MS: $t_R$=1.14 min, [M+H]$^+$ 553/555 (LC-MS 1); $^1$H-NMR (d$_6$-DMSO, 400 MHz): 12.15 (br s, 1H), 8.02 (s, 1H), 7.44 (s, 1H), 7.35-7.42 (m, 3H), 7.22 (m, 2H), 6.66 (s, 1H), 6.23 (s, 1H), 3.93 (m, 1H), 3.84 (s, 3H), 3.14 (s, 6H), 1.28 (m, 3H), 0.45 (m, 3H).

EXAMPLE 124

5-(5-Chloro-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one

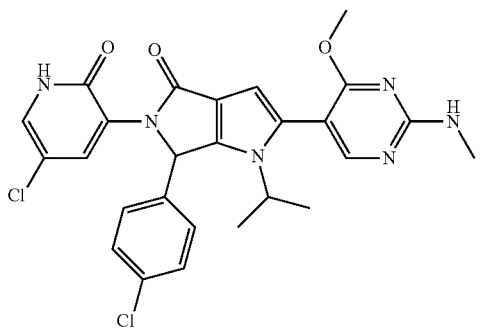

The title compound was prepared in analogy to the procedure described for Example 123 but [4-methoxy-5-(4,4,5,5-tetramethyl-[1,3,2]dioxaborolan-2-yl)-pyrimidin-2-yl]-methyl-amine (Intermediate V) was used instead of 4-methoxy-N,N-dimethyl-5-(4,4,5,5-tetramethyl-1,3,2-dioxaborolan-2-yl)pyrimidin-2-amine to afford the title compound as a white solid. ESI-MS: $t_R$=0.98 min, [M+H]$^+$539/541 (LC-MS 1).

EXAMPLE 125

4-[2-(2-Amino-4-methoxy-pyrimidin-5-yl)-5-(5-chloro-2-oxo-1,2-dihydro-pyridin-3-yl)-1-isopropyl-4-oxo-1,4,5,6-tetrahydro-pyrrolo[3,4-b]pyrrol-6-yl]-benzonitrile

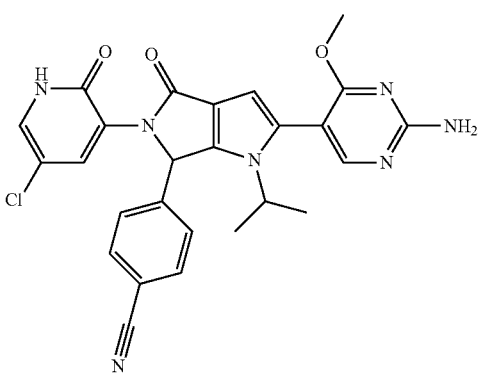 [SMILES: COc1nc(N)ncc1-c1cc2c(n1C(C)C)C(c1ccc(C#N)cc1)N(c1cc(Cl)c[nH]c1=O)C2=O]

A solution of 4-{2-(2-amino-4-methoxy-pyrimidin-5-yl)-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-benzonitrile (Step 125.1) (0.137 mmol) in TFA (1 mL) was stirred at 100° C. for 30 min and then the reaction mixture was concentrated. The residue was purified by flash chromatography to afford the title compound as a white solid. ESI-MS: $t_R$=0.75 min, [M+]$^+$516/518 (LC-MS 1).

Step 125.1: 4-{2-(2-Amino-4-methoxy-pyrimidin-5-yl)-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-benzonitrile

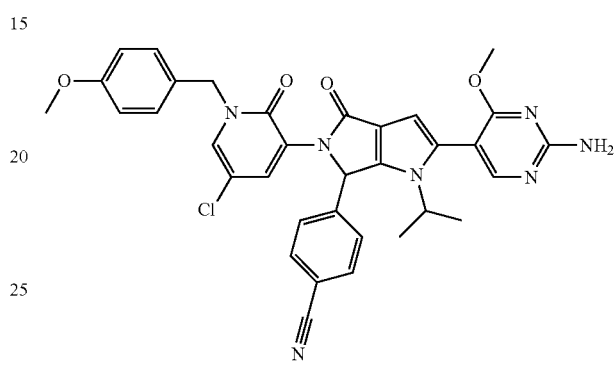

The title compound was prepared in analogy to the procedure described for Example 25 but 4-{2-bromo-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-benzonitrile (Intermediate AH) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one to afford the title compound as a white solid. ESI-MS: $t_R$=1.00 min, [M+H]$^+$ 636/638 (LC-MS 1).

EXAMPLE 126

4-[5-(5-Chloro-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

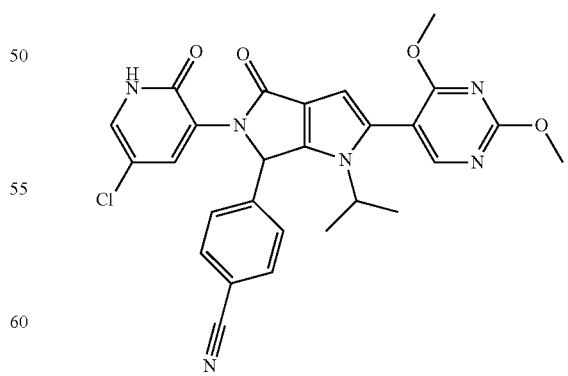

The title compound was prepared in analogy to the procedure described for Example 125 but in the step corresponding to Step I25.1, 2,4-dimethoxypyrimidine-5-boronic acid was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=0.93 min, [M+H]$^+$ 531/533 (LC-MS 1).

EXAMPLE 127

4-[5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

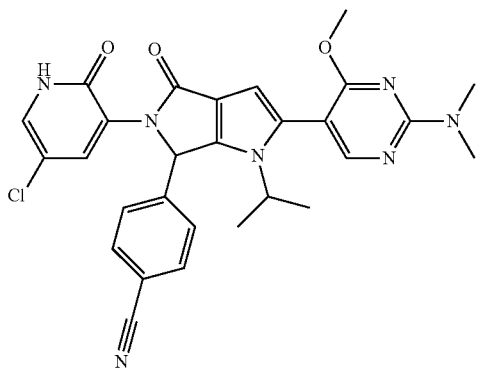 [SMILES: COc1nc(N(C)C)ncc1-c1cc2c(n1C(C)C)C(c1ccc(C#N)cc1)N(c1cc(Cl)c[nH]c1=O)C2=O]

The title compound was prepared in analogy to the procedure described for Example 125 but in the step corresponding to Step 125.1, 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=0.99 min, [M+H]$^+$ 544/546 (LC-MS 1); $^1$H-NMR (d$_6$-DMSO, 400 MHz): 12.18 (br s, 1H), 8.03 (s, 1H), 7.81 (m, 2H), 7.33-7.51 (m, 4H), 6.73 (s, 1H), 6.25 (s, 1H), 3.94 (m, 1H), 3.83 (s, 3H), 3.14 (s, 6H), 1.27 (m, 3H), 0.42 (m, 3H).

EXAMPLE 128

4-[5-(5-Chloro-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile

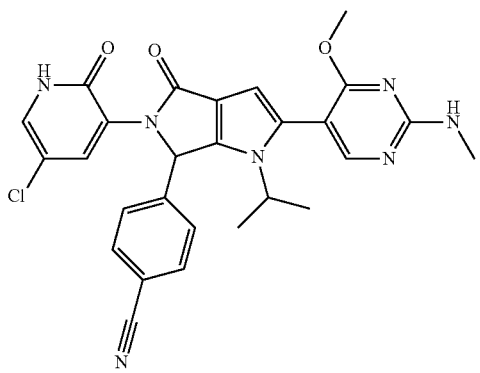 [SMILES: CNc1ncc(-c2cc3c(n2C(C)C)C(c2ccc(C#N)cc2)N(c2cc(Cl)c[nH]c2=O)C3=O)c(OC)n1]

The title compound was prepared in analogy to the procedure described for Example 125 but in the step corresponding to Step 125.1, [4-methoxy-5-(4,4,5,5-tetramethyl-[1,3,2]di-oxaborolan-2-yl)-pyrimidin-2-yl]-methyl-amine (Intermediate V) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=0.83 min, [M+H]$^+$ 530/532 (LC-MS 1).

EXAMPLE 129

4-[2-(2-Amino-4-methoxy-pyrimidin-5-yl)-5-(5-chloro-1-methyl-2-oxo-1,2-dihydro-pyridin-3-yl)-1-isopropyl-4-oxo-1,4,5,6-tetrahydro-pyrrolo[3,4-b]pyrrol-6-yl]-benzonitrile

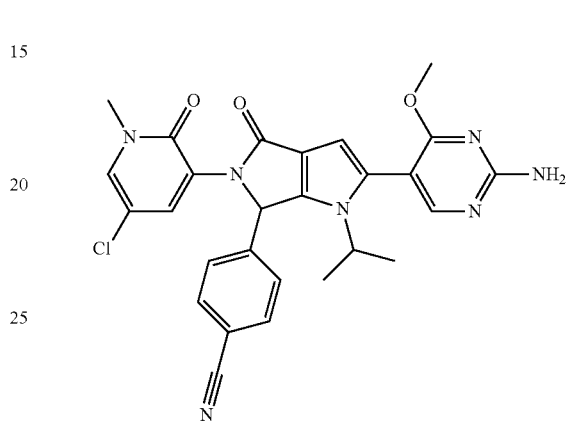

The title compound was prepared in analogy to the procedure described for Example 25 but 4-[2-bromo-5-(5-chloro-1-methyl-2-oxo-1,2-dihydro-pyridin-3-yl)-1-isopropyl-4-oxo-1,4,5,6-tetrahydro-pyrrolo[3,4-b]pyrrol-6-yl]-benzonitrile (Intermediate AG) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one to afford the title compound as a white solid. ESI-MS: $t_R$=0.80 min, [M+H]$^+$ 530/532 (LC-MS 1).

EXAMPLE 130

4-[5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile

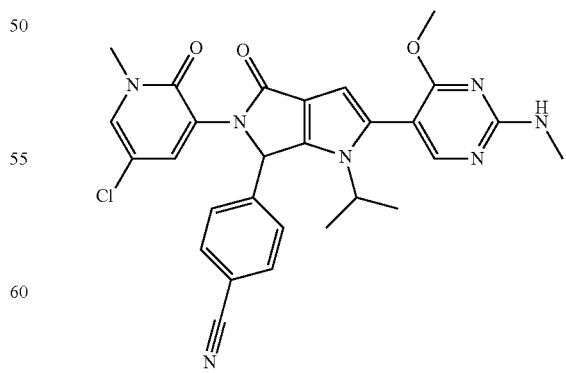

The title compound was prepared in analogy to the procedure described for Example 129 but [4-methoxy-5-(4,4,5,5-tetramethyl-[1,3,2]dioxaborolan-2-yl)-pyrimidin-2-yl]methyl-amine (Intermediate V) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=0.89 min, [M+H]$^+$ 544/546 (LC-MS 1); $^1$H-NMR (d$_6$-DMSO, 400 MHz): 7.96 (m, 1H), 7.87 (m, 1H), 7.80 (m, 2H), 7.38-7.46 (m, 3H), 7.30 (m, 1H), 6.70 (s, 1H), 6.25 (s, 1H), 3.95 (m, 1H), 3.80 (m, 3H), 3.41 (s, 3H), 2.81 (m, 3H), 1.27 (m, 3H), 0.42 (m, 3H).

EXAMPLE 131

4-[5-(5-Chloro-1-methyl-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

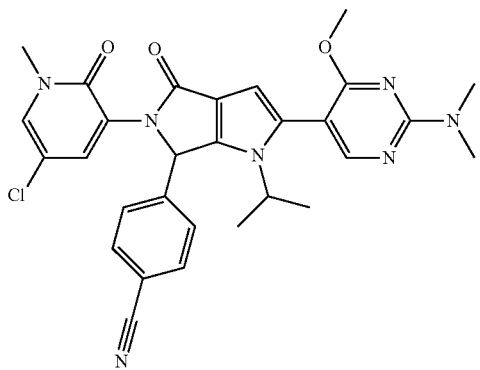 [SMILES: COc1nc(N(C)C)ncc1-c1cc2c(n1C(C)C)C(c1ccc(C#N)cc1)N(c1cc(Cl)cn(C)c1=O)C2=O]

The title compound was prepared in analogy to the procedure described for Example 129 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=1.06 min, [M+H]$^+$558/560 (LC-MS 1).

EXAMPLE 132

4-[5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

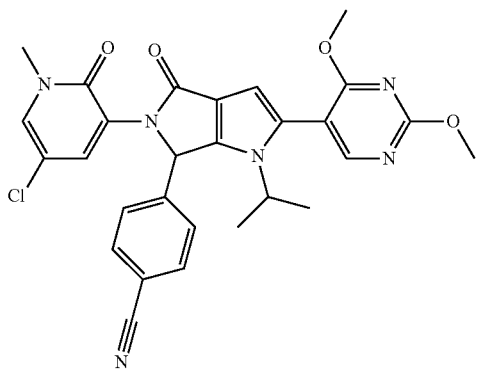 [SMILES: COc1ncc(-c2cc3c(n2C(C)C)C(c2ccc(C#N)cc2)N(c2cc(Cl)cn(C)c2=O)C3=O)c(OC)n1]

The title compound was prepared in analogy to the procedure described for Example 129 but 2,4-dimethoxypyrimidine-5-boronic acid was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=0.97 min, [M+H]$^+$ 545/547 (LC-MS 1); TLC: R$_f$=0.63 (9:1 CH$_2$Cl$_2$/MeOH).

EXAMPLE 133

4-[5-(5-Chloro-1-methyl-6-oxo-1,6-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile

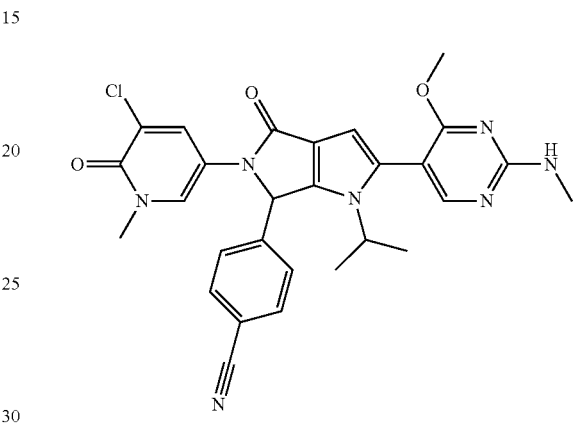

The title compound was prepared in analogy to the procedure described for Example 25 but 4-[2-bromo-5-(5-chloro-1-methyl-6-oxo-1,6-dihydro-pyridin-3-yl)-1-isopropyl-4-oxo-1,4,5,6-tetrahydro-pyrrolo[3,4-b]pyrrol-6-yl]-benzonitrile (Intermediate AE) and [4-methoxy-5-(4,4,5,5-tetramethyl-[1,3,2]dioxaborolan-2-yl)-pyrimidin-2-yl]-methyl-amine (Intermediate V) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively to afford the title compound as a white solid. ESI-MS: $t_R$=0.83 min, [M+H]$^+$ 544/546 (LC-MS 1); TLC: R$_f$=0.38 (9:1 CH$_2$Cl$_2$/MeOH).

EXAMPLE 134

4-[2-(2-Amino-4-methoxy-pyrimidin-5-yl)-5-(5-chloro-6-oxo-1,6-dihydro-pyridin-3-yl)-1-isopropyl-4-oxo-1,4,5,6-tetrahydro-pyrrolo[3,4-b]pyrrol-6-yl]-benzonitrile

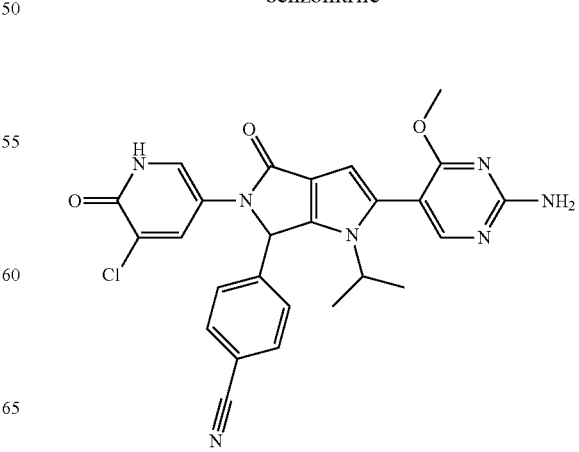

The title compound was prepared in analogy to the procedure described for Example 125 but in the step corresponding to Step 125.1, 4-{2-bromo-5-[5-chloro-1-(4-methoxy-benzyl)-6-oxo-1,6-dihydro-pyridin-3-yl]-1-isopropyl-4-oxo-1,4,5,6-tetrahydro-pyrrolo[3,4-b]pyrrol-6-yl}-benzonitrile (Intermediate AF) was used instead of 4-{2-bromo-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-benzonitrile to afford the title compound as a white solid. ESI-MS: $t_R$=0.70 min, [M+H]$^+$ 516/518 (LC-MS 1).

EXAMPLE 135

4-[5-(5-Chloro-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

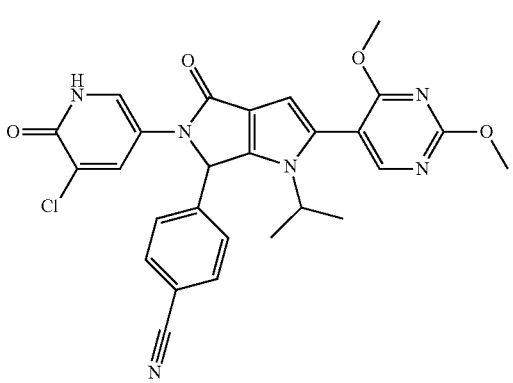 [SMILES: COc1ncc(-c2cc3c(n2C(C)C)C(c2ccc(C#N)cc2)N(c2c[nH]c(=O)c(Cl)c2)C3=O)c(OC)n1]

The title compound was prepared in analogy to the procedure described for Example 134 but in the step corresponding to Step 125.1, 2,4-dimethoxypyrimidine-5-boronic acid was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=0.86 min, [M+H]$^+$ 531/533 (LC-MS 1).

EXAMPLE 136

4-[5-(5-Chloro-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

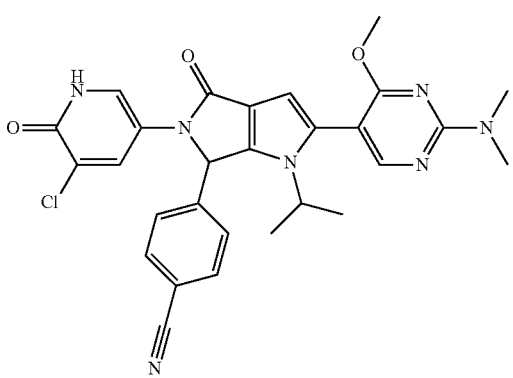 [SMILES: COc1nc(N(C)C)ncc1-c1cc2c(n1C(C)C)C(c1ccc(C#N)cc1)N(c1c[nH]c(=O)c(Cl)c1)C2=O]

The title compound was prepared in analogy to the procedure described for Example 134 but in the step corresponding to Step 125.1, 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=0.96 min, [M+H]$^+$ 544/546 (LC-MS 1).

EXAMPLE 137

4-[5-(5-Chloro-6-oxo-1,6-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile

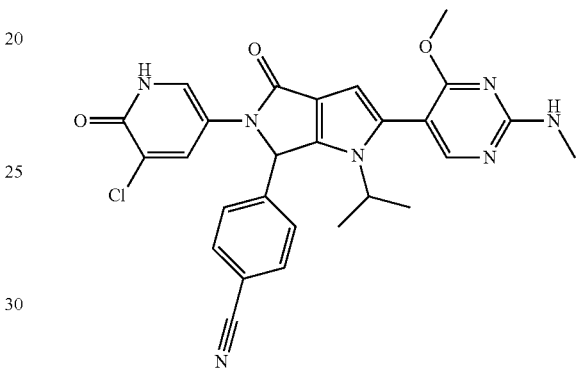

The title compound was prepared in analogy to the procedure described for Example 134 but in the step corresponding to Step 125.1, [4-methoxy-5-(4,4,5,5-tetramethyl-[1,3,2]dioxaborolan-2-yl)-pyrimidin-2-yl]-methyl-amine (Intermediate V) was used instead of 4-methoxy-5-(4,4,5,5-tetramethyl-[1,3,2]dioxaborolan-2-yl)-pyrimidin-2-ylamine to afford the title compound as a white solid. ESI-MS: $t_R$=0.79 min, [M+H]$^+$ 530/532 (LC-MS 1).

EXAMPLE 138

2-(2-Amino-4-methoxy-pyrimidin-5-yl)-5-(5-chloro-6-oxo-1,6-dihydro-pyridin-3-yl)-6-(4-chloro-phenyl)-1-isopropyl-5,6-dihydro-1H-pyrrolo[3,4-b]pyrrol-4-one

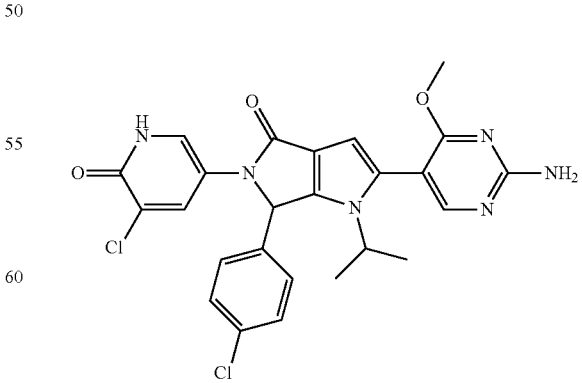

The title compound was prepared in analogy to the procedure described for Example 125 but in the step corresponding to Step 125.1, 2-bromo-5-[5-chloro-1-(4-methoxy-benzyl)-6-oxo-1,6-dihydro-pyridin-3-yl]-6-(4-chloro-phenyl)-1-isopropyl-5,6-dihydro-1H-pyrrolo[3,4-b]pyrrol-4-one (Intermediate O) was used instead of 4-{2-bromo-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-benzonitrile to afford the title compound as a gray-brown solid. $t_R$: 4.92 min (HPLC 2); ESI-MS: $t_R$=0.80 min, [M+H]$^+$ 516/518 (LC-MS 1); TLC: $R_f$=0.34 (9:1 CH$_2$Cl$_2$/MeOH).

EXAMPLE 139

5-(5-Chloro-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one

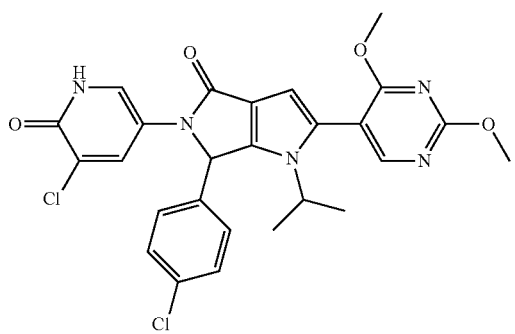 [SMILES: COc1ncc(-c2cc3c(n2C(C)C)C(c2ccc(Cl)cc2)N(c2c[nH]c(=O)c(Cl)c2)C3=O)c(OC)n1]

The title compound was prepared in analogy to the procedure described for Example 138 but in the step corresponding to Step 125.1, 2,4-dimethoxypyrimidine-5-boronic acid was used instead of 4-methoxy-5-(4,4,5,5-tetramethyl-[1,3,2]dioxaborolan-2-yl)-pyrimidin-2-ylamine to afford the title compound as a white solid. $t_R$: 6.05 min (HPLC 2); ESI-MS: $t_R$=0.96 min, [M+H]$^+$ 540/542 (LC-MS 1); TLC: $R_f$=0.09 (EtOAc).

EXAMPLE 140

5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-1-5,6-dihydro-1H-pyrrolo[3,4-b]pyrrol-4-one

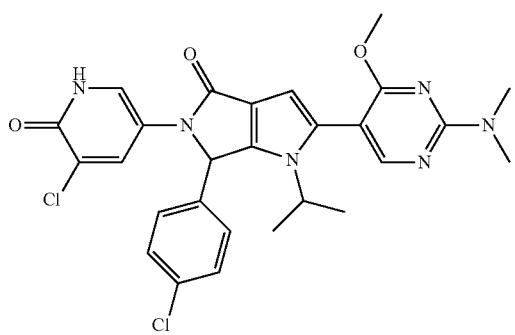 [SMILES: COc1nc(N(C)C)ncc1-c1cc2c(n1C(C)C)C(c1ccc(Cl)cc1)N(c1c[nH]c(=O)c(Cl)c1)C2=O]

The title compound was prepared in analogy to the procedure described for Example 138 but in the step corresponding to Step 125.1, 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. $t_R$: 5.24 min (HPLC 2); ESI-MS: $t_R$=1.07 min, [M+H]$^+$ 553/555 (LC-MS 1); TLC: $R_f$=0.07 (EtOAc); $^1$H-NMR (d$_6$-DMSO, 600 MHz): 12.20 (br s, 1H), 8.02 (s, 1H), 7.88 (m, 1H), 7.37-7.51 (m, 3H), 7.31 (m, 2H), 6.35 (s, 1H), 6.22 (s, 1H), 3.92 (m, 1H), 3.84 (s, 3H), 3.14 (s, 6H), 1.32 (m, 3H), 0.44 (m, 3H).

EXAMPLE 141

2-(2-Amino-4-methoxy-pyrimidin-5-yl)-6-(4-chloro-phenyl)-1-isopropyl-5-(trans-4-methoxy-cyclohexyl)-5,6-dihydro-1H-pyrrolo[3,4-b]pyrrol-4-one

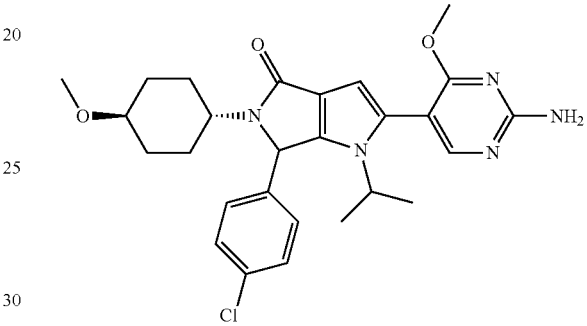

The title compound was prepared in analogy to the procedure described for Example 17 but (S)-2-bromo-6-(4-chloro-phenyl)-1-isopropyl-5-(trans-4-methoxy-cyclohexyl)-5,6-dihydro-1H-pyrrolo[3,4-b]pyrrol-4-one (Intermediate AD) and 4-methoxy-5-(4,4,5,5-tetramethyl-[1,3,2]dioxaborolan-2-yl)-pyrimidin-2-ylamine (Intermediate U) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a light beige solid. $t_R$: 4.08 min (HPLC 1); ESI-MS: $t_R$=0.99 min, [M+H]$^+$ 510/512 (LC-MS 1); TLC: $R_f$=0.10 (EtOAc).

EXAMPLE 142

6-(4-Chloro-phenyl)-2-(2-dimethylamino-4-methoxy-pyrimidin-5-yl)-1-isopropyl-5-(trans-4-methoxy-cyclohexyl)-5,6-dihydro-1H-pyrrolo[3,4-b]pyrrol-4-one

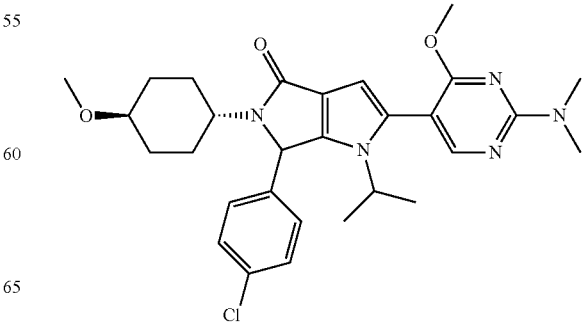

The title compound was prepared in analogy to the procedure described for Example 141 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine to afford the title compound as a white solid. $t_R$: 1.06 min (HPLC 3); ESI-MS: $t_R$=1.26 min, [M+H]$^+$ 538/540 (LC-MS 1); TLC: $R_f$=0.35 (EtOAc).

EXAMPLE 143

6-(4-Chloro-phenyl)-2-(2,4-dimethoxy-pyrimidin-5-yl)-1-isopropyl-5-(trans-4-methoxy-cyclohexyl)-5,6-dihydro-1H-pyrrolo[3,4-b]pyrrol-4-one

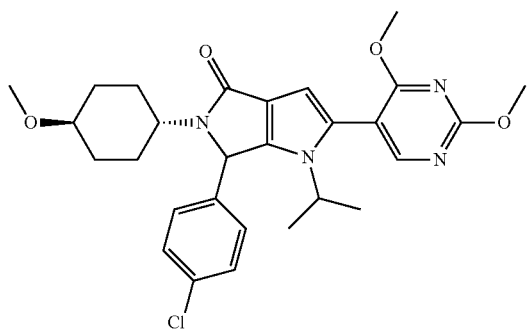

The title compound was prepared in analogy to the procedure described for Example 141 but 2,4-dimethoxypyrimidine-5-boronic acid was used instead of 4-methoxy-5-(4,4,5,5-tetramethyl-[1,3,2]dioxaborolan-2-yl)-pyrimidin-2-ylamine to afford the title compound as a white solid. $t_R$: 4.72 min (HPLC 1); ESI-MS: $t_R$=1.16 min, [M+H]$^+$ 525/527 (LC-MS 1); TLC: $R_f$=0.33 (EtOAc).

EXAMPLE 144

5-(5-Chloro-1-methyl-6-oxo-1,6-dihydro-pyridin-3-yl)-6-(4-chloro-2-methyl-phenyl)-1-isopropyl-2-(2-methoxy-phenyl)-5,6-dihydro-1H-pyrrolo[3,4-b]pyrrol-4-one

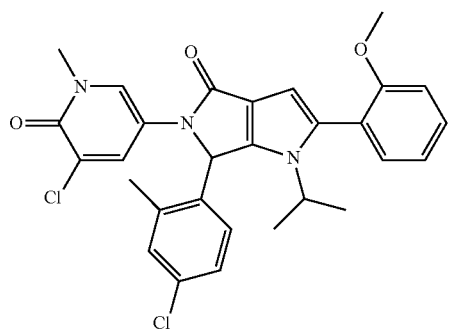 [SMILES: COc1ccccc1-c1cc2c(n1C(C)C)C(c1ccc(Cl)cc1C)N(c1cc(Cl)c(=O)n(C)c1)C2=O]

The title compound was prepared in analogy to the procedure described for Example 17 but 2-bromo-5-(5-chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one (Intermediate N) and 2-methoxyphenylboronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a light yellow solid. $t_R$: 7.25 min (HPLC 2); ESI-MS: $t_R$=1.21 min, [M+H]$^+$ 536/538 (LC-MS 1); TLC: $R_f$=0.20 (EtOAc).

EXAMPLE 145

3-[5-(5-Chloro-1-methyl-6-oxo-1,6-dihydro-pyridin-3-yl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide

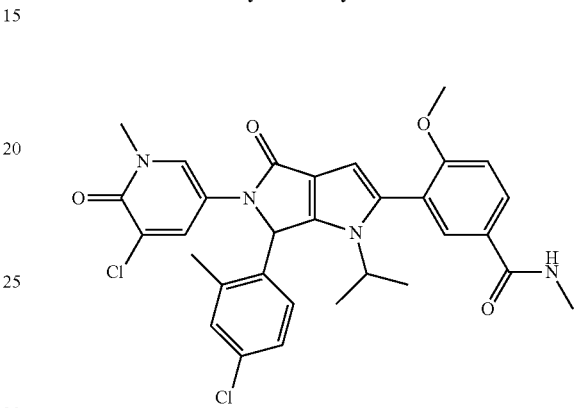

The title compound was prepared in analogy to the procedure described for Example 144 but 2-methoxy-5-[(methylamino)carbonyl]phenylboronic acid (Intermediate R) was used instead of 2-methoxyphenylboronic acid. The title compound was obtained as a white solid. $t_R$: 6.21 min (HPLC 2); ESI-MS: $t_R$=0.98 min, [M+H]$^+$ 593/595 (LC-MS 1); TLC: $R_f$=0.15 (95:5 CH$_2$Cl$_2$/MeOH).

EXAMPLE 146

5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one

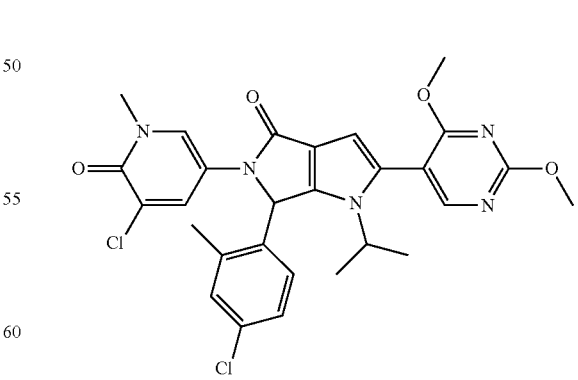

The title compound was prepared in analogy to the procedure described for Example 144 but 2,4-dimethoxypyrimidine-5-boronic acid was used instead of 2-methoxyphenylboronic acid. The title compound was obtained as a pale yellow solid. $t_R$: 6.54 min (HPLC 2); ESI-MS: $t_R$=1.08 min, [M+H]$^+$ 568/570 (LC-MS 1); TLC: $R_f$=0.11 (EtOAc).

EXAMPLE 147

5-(5-Chloro-1-methyl-6-oxo-1,6-dihydro-pyridin-3-yl)-6-(4-chloro-2-methyl-phenyl)-2-(2-dimethylamino-4-methoxy-pyrimidin-5-yl)-1-isopropyl-5,6-dihydro-1H-pyrrolo[3,4-b]pyrrol-4-one

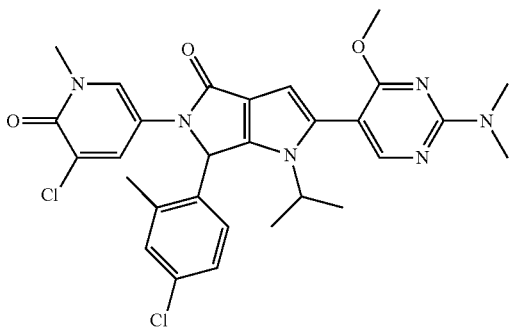 [SMILES: COc1nc(N(C)C)ncc1-c1cc2c(n1C(C)C)C(c1ccc(Cl)cc1C)N(c1cc(Cl)c(=O)n(C)c1)C2=O]

The title compound was prepared in analogy to the procedure described for Example 144 but 4-methoxy-N,N-dimethyl-5-(4,4,5,5-tetramethyl-1,3,2-dioxaborolan-2-yl)pyrimidin-2-amine (Intermediate W) was used instead of 2-methoxyphenylboronic acid. The title compound was obtained as a white solid. $t_R$: 5.61 min (HPLC 2); ESI-MS: $t_R$=1.17 min, [M+H]$^+$ 581/583/585 (LC-MS 1); TLC: $R_f$=0.11 (EtOAc).

EXAMPLE 148

2-(2-Amino-4-methoxy-pyrimidin-5-yl)-5-(5-chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one

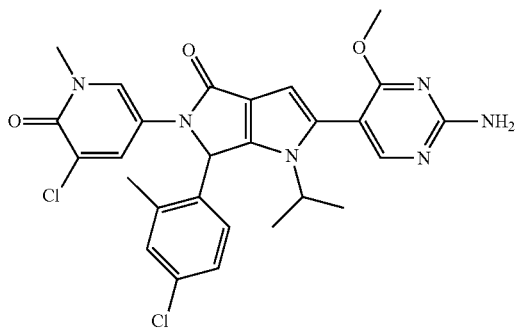 [SMILES: COc1nc(N)ncc1-c1cc2c(n1C(C)C)C(c1ccc(Cl)cc1C)N(c1cc(Cl)c(=O)n(C)c1)C2=O]

The title compound was prepared in analogy to the procedure described for Example 144 but 4-methoxy-5-(4,4,5,5-tetramethyl-[1,3,2]dioxaborolan-2-yl)-pyrimidin-2-ylamine (Intermediate U) was used instead of 2-methoxyphenylboronic acid. The title compound was obtained as a white solid.

$t_R$: 5.29 min (HPLC 2); ESI-MS: $t_R$=0.89 min, [M+H]$^+$ 553/555 (LC-MS 1); TLC: $R_f$=0.15 (95:5 $CH_2Cl_2$/MeOH).

EXAMPLE 149

5-(5-Chloro-2-methyl-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-b]pyrrol-4-one

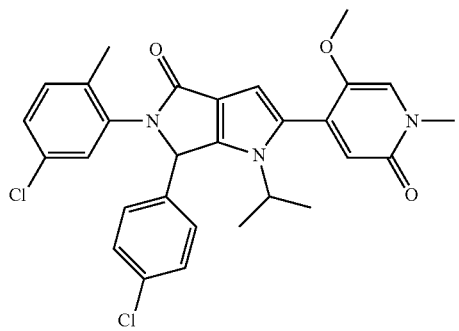 [SMILES: COc1cn(C)c(=O)cc1-c1cc2c(n1C(C)C)C(c1ccc(Cl)cc1)N(c1cc(Cl)ccc1C)C2=O]

The title compound was prepared in analogy to the procedure described for Example 17 but 5-methoxy-1-methyl-4-(4,4,5,5-tetramethyl-[1,3,2]dioxaborolan-2-yl)-1H-pyridin-2-one (Intermediate AR) was used instead of 5-cyano-2-methoxyphenylboronic acid. The title compound was obtained as a gray solid. $t_R$: 1.22 min (HPLC 3); ESI-MS: $t_R$=1.11 min, [M+H]$^+$ 536/538/540 (LC-MS 1); TLC: $R_f$=0.38 (9:1 $CH_2Cl_2$/MeOH).

EXAMPLE 150

5-(5-Chloro-1-methyl-6-oxo-1,6-dihydro-pyridin-3-yl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-b]pyrrol-4-one

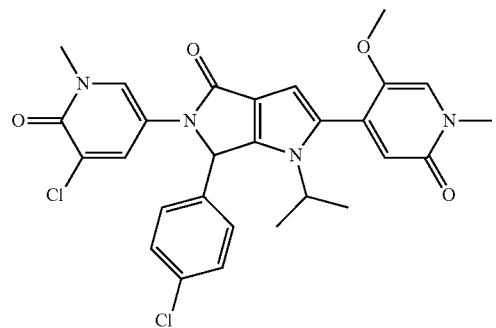 [SMILES: COc1cn(C)c(=O)cc1-c1cc2c(n1C(C)C)C(c1ccc(Cl)cc1)N(c1cc(Cl)c(=O)n(C)c1)C2=O]

The title compound was prepared in analogy to the procedure described for Example 46 but 5-methoxy-1-methyl-4-(4,4,5,5-tetramethyl-[1,3,2]dioxaborolan-2-yl)-1H-pyridin-2-one (Intermediate AR) was used instead of 2-methoxyphenylboronic acid. The title compound was obtained as a gray solid. $t_R$: 0.95 min (HPLC 3); ESI-MS: $t_R$=0.83 min, [M+H]⁺ 553/555 (LC-MS 1); TLC: $R_f$=0.16 (9:1 CH₂Cl₂/MeOH).

EXAMPLE 151

5-(5-Chloro-1-methyl-6-oxo-1,6-dihydro-pyridin-3-yl)-6-(4-chloro-2-methyl-phenyl)-1-isopropyl-2-(4-methoxy-2-methylamino-pyrimidin-5-yl)-5,6-dihydro-1H-pyrrolo[3,4-b]pyrrol-4-one

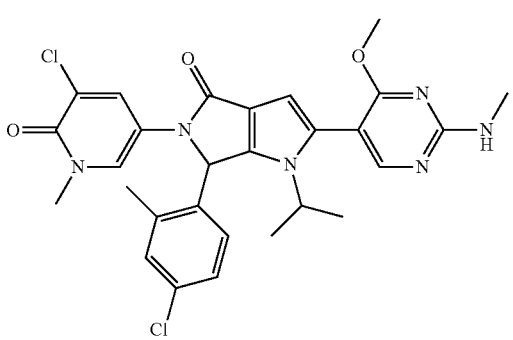 [SMILES: CNc1ncc(-c2cc3c(n2C(C)C)C(c2ccc(Cl)cc2C)N(c2cc(Cl)c(=O)n(C)c2)C3=O)c(OC)n1]

The title compound was prepared in analogy to the procedure described for Example 144 but [4-methoxy-5-(4,4,5,5-tetramethyl-[1,3,2]dioxaborolan-2-yl)-pyrimidin-2-yl]-methyl-amine (Intermediate V) was used instead of 2-methoxyphenylboronic acid. The title compound was obtained as a light yellow solid. $t_R$: 5.49 min (HPLC 2); ESI-MS: $t_R$=1.00 min, [M+H]⁺ 567/569/571 (LC-MS 1); TLC: $R_f$=0.25 (95:5 CH₂Cl₂/MeOH).

EXAMPLE 152

5-(5-Chloro-6-oxo-1,6-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one

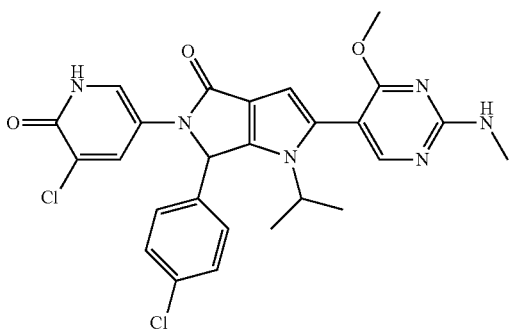 [SMILES: CNc1ncc(-c2cc3c(n2C(C)C)C(c2ccc(Cl)cc2)N(c2c[nH]c(=O)c(Cl)c2)C3=O)c(OC)n1]

The title compound was prepared in analogy to the procedure described for Example 138 but in the step corresponding to Step 125.1, [4-methoxy-5-(4,4,5,5-tetramethyl-[1,3,2]dioxaborolan-2-yl)-pyrimidin-2-yl]-methyl-amine (Intermediate V) was used instead of 4-methoxy-5-(4,4,5,5-tetramethyl-[1,3,2]dioxaborolan-2-yl)-pyrimidin-2-ylamine to afford the title compound as a light gray solid. $t_R$: 5.14 min (HPLC 2); ESI-MS: $t_R$=0.90 min, [M+H]⁺ 539/541/543 (LC-MS 1); TLC: $R_f$=0.13 (95:5 CH₂Cl₂/MeOH).

EXAMPLE 153

4-[5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

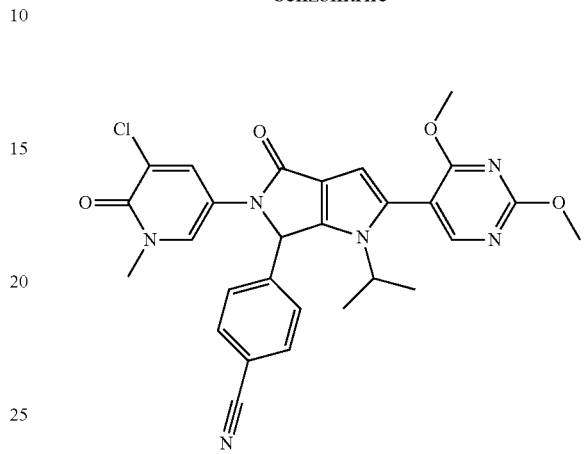

The title compound was prepared in analogy to the procedure described for Example 25 but 4-[2-bromo-5-(5-chloro-1-methyl-6-oxo-1,6-dihydro-pyridin-3-yl)-1-isopropyl-4-oxo-1,4,5,6-tetrahydro-pyrrolo[3,4-b]pyrrol-6-yl]-benzonitrile (Intermediate AS) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a beige solid. $t_R$: 2.69 min (HPLC 5); ESI-MS: $t_R$=0.90 min, [M+H]⁺ 545/547 (LC-MS 1).

EXAMPLE 154

4-[(S)-2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile

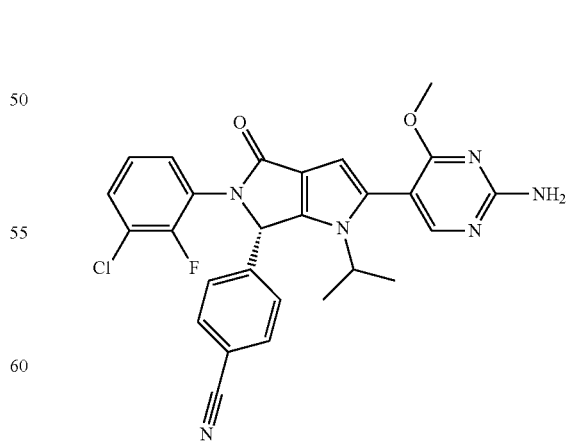

4-[2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile (Example 41) was purified by chiral chromatography (Chiral-HPLC 1) to afford the title compound. $t_R$: 33.44 min (Column: Chiralpak IC, 4.6× 250 mm. Flow 1 mL/min. heptane/(98:2 EtOH/CH$_3$CN) 75:25); $t_R$: 4.52 min (HPLC 4); ESI-MS: $t_R$=0.97 min, [M+H]$^+$ 517/519 (LC-MS 1).

EXAMPLE 155

4-[(R)-2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile

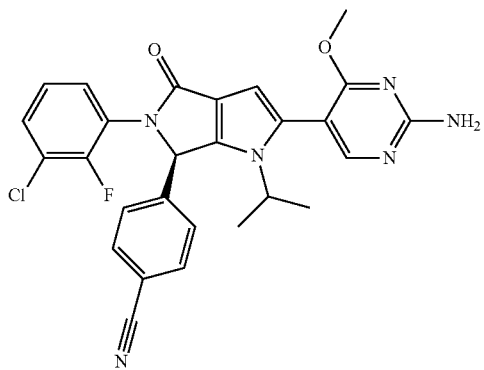 [SMILES: COc1nc(N)ncc1-c1cc2c(n1C(C)C)[C@@H](c1ccc(C#N)cc1)N(c1cccc(Cl)c1F)C2=O]

4-[2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile (Example 41) was purified by chiral chromatography (Chiral-HPLC 1) to afford the title compound. $t_R$: 39.70 min (Column: Chiralpak IC, 4.6× 250 mm. Flow 1 mL/min. heptane/(98:2 EtOH/CH$_3$CN) 75:25); $t_R$: 4.52 min (HPLC 4); ESI-MS: $t_R$=0.97 min, [M+H]$^+$ 517/519 (LC-MS 1).

EXAMPLE 156

5-(5-Chloro-2-fluoro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one

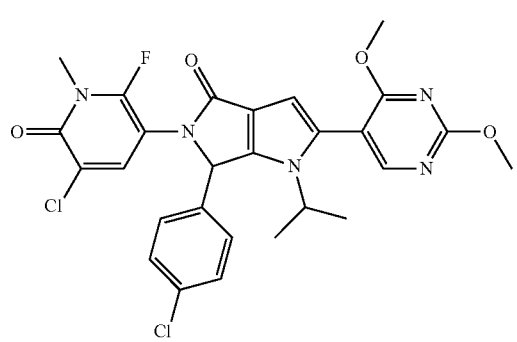 [SMILES: COc1ncc(-c2cc3c(n2C(C)C)C(c2ccc(Cl)cc2)N(c2cc(Cl)c(=O)n(C)c2F)C3=O)c(OC)n1]

The title compound was prepared in analogy to the procedure described for Example 25 but 2-bromo-5-(5-chloro-2-fluoro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one (Intermediate AT) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a light pink foam. ESI-MS: $t_R$=1.08 min, [M+H]$^+$ 572/574/576 (LC-MS 1); TLC: R$_f$=0.14 (4:1 EtOAc/heptanes).

EXAMPLE 157

4-[2-(2,4-Dimethoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile

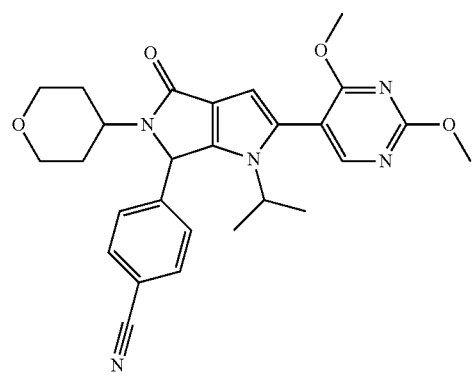 [SMILES: COc1ncc(-c2cc3c(n2C(C)C)C(c2ccc(C#N)cc2)N(C2CCOCC2)C3=O)c(OC)n1]

The title compound was prepared in analogy to the procedure described for Example 17 but 4-[2-bromo-1-isopropyl-4-oxo-5-(tetrahydro-pyran-4-yl)-1,4,5,6-tetrahydro-pyrrolo[3,4-b]pyrrol-6-yl]-benzonitrile (Intermediate AU) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$: 0.98 min (HPLC 3); ESI-MS: $t_R$=0.92 min, [M+H]$^+$ 488 (LC-MS 1); TLC: R$_f$=0.20 (EtOAc).

EXAMPLE 158

4-[2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile

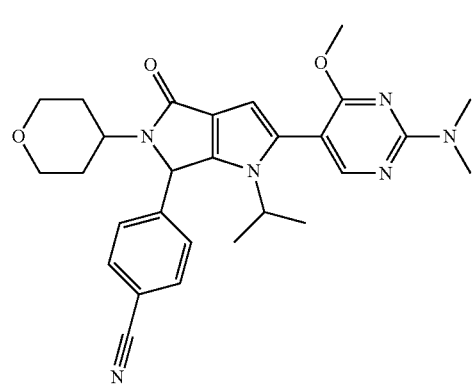 [SMILES: COc1nc(N(C)C)ncc1-c1cc2c(n1C(C)C)C(c1ccc(C#N)cc1)N(C1CCOCC1)C2=O]

The title compound was prepared in analogy to the procedure described for Example 157 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. $t_R$: 0.86 min (HPLC 3); ESI-MS: $t_R$=1.00 min, [M+H]$^+$ 501 (LC-MS 1); TLC: $R_f$=0.13 (EtOAc).

EXAMPLE 159

6-(4-Chloro-phenyl)-2-(2-dimethylamino-4-methoxy-pyrimidin-5-yl)-5-(1,3-dimethyl-2-oxo-hexahydro-pyrimidin-5-yl)-1-isopropyl-5,6-dihydro-1H-pyrrolo[3,4-b]pyrrol-4-one

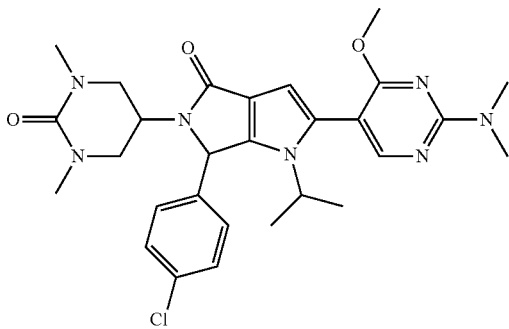 [SMILES: COc1nc(N(C)C)ncc1-c1cc2c(n1C(C)C)C(c1ccc(Cl)cc1)N(C1CN(C)C(=O)N(C)C1)C2=O]

The title compound was prepared in analogy to the procedure described for Example 110 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. $t_R$: 2.41 min (HPLC 5); ESI-MS: $t_R$=1.07 min, [M+H]$^+$ 552/554 (LC-MS 1); $^1$H-NMR (d$_6$-DMSO, 400 MHz): 7.99 (s, 1H), 7.50 (m, 2H), 7.35 (m, 2H), 6.13 (s, 1H), 5.82 (s, 1H), 4.07 (m, 1H), 3.88 (m, 1H), 3.83 (s, 3H), 3.80 (m, 1H), 3.23 (m, 1H), 3.15 (s, 6H), 3.10 (m, 1H), 2.92 (m, 1H), 2.69 (s, 3H), 2.60 (s, 3H), 1.27 (m, 3H), 0.39 (m, 3H).

EXAMPLE 160

(S)-5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one

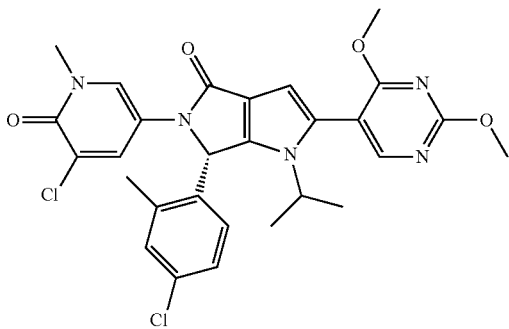 [SMILES: COc1ncc(-c2cc3c(n2C(C)C)[C@H](c2ccc(Cl)cc2C)N(c2cc(Cl)c(=O)n(C)c2)C3=O)c(OC)n1]

5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one (Example 146) was purified by chiral chromatography (Chiral-HPLC 3) to afford the title compound as a white solid. $t_R$: 1.64 min (Column: Chiralpak AS-H, 4.6×250 mm. Flow 3 mL/min. scCO$_2$/EtOH 30-50%); $t_R$: 6.51 min (HPLC 2); ESI-MS: $t_R$=1.06 min, [M+H]$^+$ 568/570 (LC-MS 1); $^1$H-NMR (d$_6$-DMSO, 600 MHz): (rotamers) 8.31 (m, 1H), 7.75/7.98 (s, 1H), 7.75/7.90 (s, 1H), 7.25/7.35 (d, 1H), 7.23/7.31 (s, 1H), 6.82/7.69 (d, 1H), 6.42/6.49 (s, 1H), 6.34/6.36 (s, 1H), 3.95 (s, 3H), 3.94 (m, 1H), 3.90 (s, 3H), 3.43/3.45 (s, 3H), 1.79/2.42 (s, 3H), 1.26 (m, 3H), 0.48/0.52 (m, 3H).

EXAMPLE 161

(R)-5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one

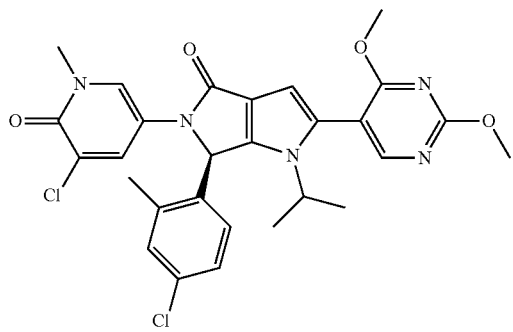

5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one (Example 146) was purified by chiral chromatography (Chiral-HPLC 3) to afford the title compound as a white solid. $t_R$: 4.57 min (Column: Chiralpak AS-H, 4.6×250 mm. Flow 3 mL/min. scCO$_2$/EtOH 30-50%); $t_R$: 6.51 min (HPLC 2); ESI-MS: $t_R$=1.06 min, [M+H]$^+$ 568/570 (LC-MS 1).

EXAMPLE 162

(S)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one

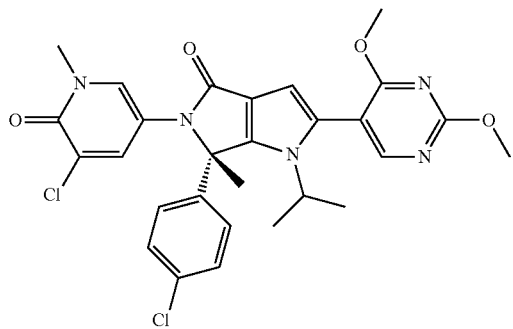 [SMILES: COc1ncc(-c2cc3c(n2C(C)C)[C@](C)(c2ccc(Cl)cc2)N(c2cc(Cl)c(=O)n(C)c2)C3=O)c(OC)n1]

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one (Example 117) was purified by chiral chromatography (Chiral-HPLC 4) to afford the title compound as a white solid. $t_R$: 6.00 min (Column: Lux Cel2, 4.6×250 mm. Flow 3 mL/min. scCO$_2$/MeOH 50:50); $t_R$: 1.10 min (HPLC 3); ESI-MS: $t_R$=1.03 min, [M+H]$^+$ 568/570 (LC-MS 1); $^1$H-NMR (d$_6$-DMSO, 400 MHz): 8.30 (s, 1H), 7.44 (m, 2H), 7.35 (m, 1H), 7.22 (m, 2H), 7.03 (m, 1H), 6.30 (s, 1H), 3.95 (m, 1H), 3.93 (s, 3H), 3.88 (s, 3H), 3.39 (s, 3H), 1.96 (s, 3H), 0.89 (m, 3H), 0.85 (m, 3H).

EXAMPLE 163

(R)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one

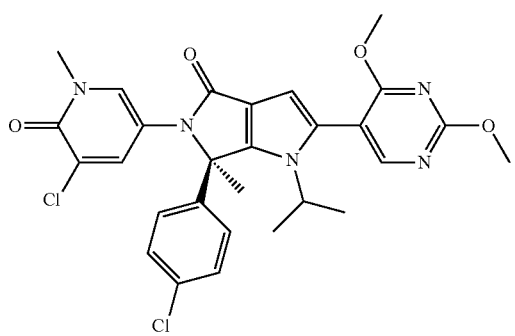 [SMILES: COc1ncc(-c2cc3c(n2C(C)C)[C@@](C)(c2ccc(Cl)cc2)N(c2cc(Cl)c(=O)n(C)c2)C3=O)c(OC)n1]

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one (Example 117) was purified by chiral chromatography (Chiral-HPLC 4) to afford the title compound as a white solid. $t_R$: 8.28 min (Column: Lux Cel2, 4.6×250 mm. Flow 3 mL/min. scCO$_2$/MeOH 50:50); $t_R$: 1.10 min (HPLC 3); ESI-MS: $t_R$=1.03 min, [M+H]$^+$ 568/570 (LC-MS 1).

EXAMPLE 164

5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-4-oxo-1,4,5,6-tetrahydro-pyrrolo[3,4-b]pyrrole-3-carbonitrile

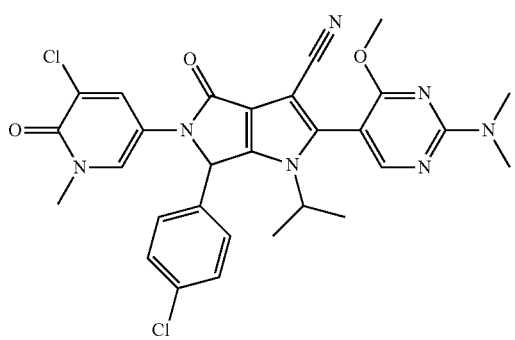 [SMILES: COc1nc(N(C)C)ncc1-c1c(C#N)c2c(n1C(C)C)C(c1ccc(Cl)cc1)N(c1cc(Cl)c(=O)n(C)c1)C2=O]

The title compound was prepared in analogy to the procedure described for Example 59 but 5-(5-chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one (Example 52) was used instead of 5-(5-chloro-2-methyl-phenyl)-6-(4-chloro-phenyl)-1-isopropyl-2-(2-methoxy-phenyl)-5,6-dihydro-1H-pyrrolo[3,4-b]pyrrol-4-one. The title compound was obtained as a white solid. $t_R$: 4.09 min (HPLC 1); ESI-MS: $t_R$=1.14 min, [M+H]$^+$ 592/594/596 (LC-MS 1); TLC: R$_f$=0.26 (EtOAc); $^1$H-NMR (d$_6$-DMSO, 600 MHz): (rotamers) 8.18/8.20 (s, 1H), 7.89 (m, 2H), 7.45 (m, 2H), 7.32-7.41 (m, 2H), 6.42/6.44 (s, 1H), 4.05 (m, 1H), 3.85/3.91 (s, 3H), 3.43 (s, 3H), 3.18 (s, 6H), 1.30/1.37 (m, 3H), 0.43/0.55 (m, 3H).

EXAMPLE 165

4-[(S)-5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile

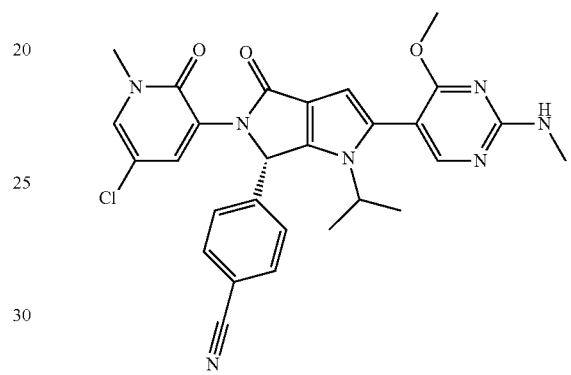

4-[5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile (Example 130) was purified by chiral chromatography (Chiral-HPLC 5) to afford the title compound as an off-white solid. $t_R$: 13.26 min (Column: Chiralcel Oz i, 4.6×250 mm. Flow 1.4 mL/min. heptane/EtOH 50:50); ESI-MS: $t_R$=0.88 min, [M+H]$^+$ 544/546 (LC-MS 1); $^1$H-NMR (d$_6$-DMSO, 400 MHz): 7.90-8.04 (m, 1H), 7.86 (m, 1H), 7.79 (m, 2H), 7.43 (s, 1H), 7.41 (m, 2H), 7.25-7.36 (m, 1H), 6.70 (s, 1H), 6.24 (s, 1H), 3.94 (m, 1H), 3.73-3.88 (m, 3H), 3.41 (s, 3H), 2.81 (m, 3H), 1.27 (m, 3H), 0.42 (m, 3H).

EXAMPLE 166

4-[(R)-5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile

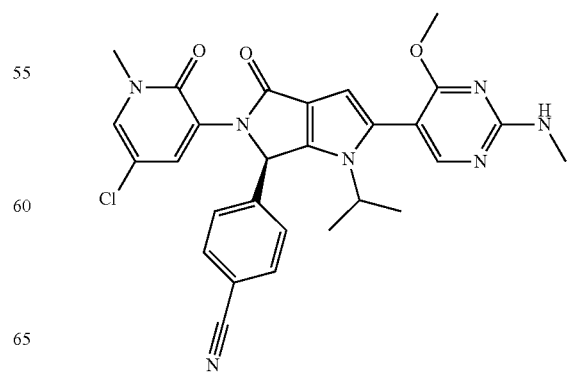

4-[5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile (Example 130) was purified by chiral chromatography (Chiral-HPLC 5) to afford the title compound as an off-white solid. $t_R$: 28.74 min (Column: Chiralcel Oz i, 4.6×250 mm. Flow 1.4 mL/min. heptane/EtOH 50:50); ESI-MS: $t_R$=0.88 min, [M+H]$^+$ 544/546 (LC-MS 1).

EXAMPLE 167

4-[(S)-5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

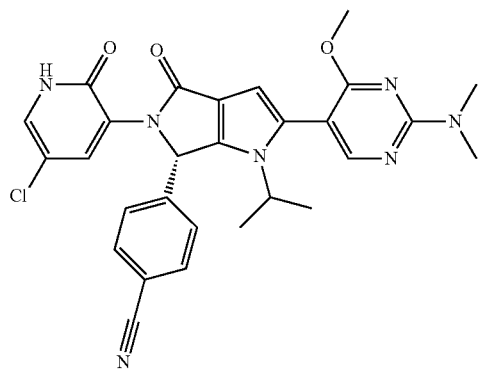 [SMILES: COc1nc(N(C)C)ncc1-c1cc2c(n1C(C)C)[C@H](c1ccc(C#N)cc1)N(c1cc(Cl)c[nH]c1=O)C2=O]

4-[5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile (Example 127) was purified by chiral chromatography (Chiral-HPLC 6) to afford the title compound as a white solid. $t_R$: 11.01 min (Column: Chiralpak AD-H, 4.6×250 mm. Flow 0.5 mL/min. EtOH); ESI-MS: $t_R$=0.98 min, [M+H]$^+$ 544/546 (LC-MS 1); $^1$H-NMR (d$_6$-DMSO, 400 MHz): 12.16 (br s, 1H), 8.02 (s, 1H), 7.80 (m, 2H), 7.44 (m, 2H), 7.42 (m, 2H), 6.73 (s, 1H), 6.25 (s, 1H), 3.94 (m, 1H), 3.83 (s, 3H), 3.13 (s, 6H), 1.26 (m, 3H), 0.42 (m, 3H).

EXAMPLE 168

4-[(R)-5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

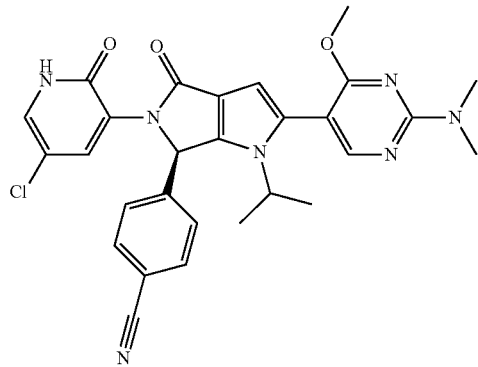 [SMILES: COc1nc(N(C)C)ncc1-c1cc2c(n1C(C)C)[C@@H](c1ccc(C#N)cc1)N(c1cc(Cl)c[nH]c1=O)C2=O]

4-[5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile (Example 127) was purified by chiral chromatography (Chiral-HPLC 6) to afford the title compound as a white solid. $t_R$: 17.94 min (Column: Chiralpak AD-H, 4.6×250 mm. Flow 0.5 mL/min. EtOH); ESI-MS: $t_R$=0.98 min, [M+H]$^+$ 544/546 (LC-MS 1).

EXAMPLE 169

4-[(S)-5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

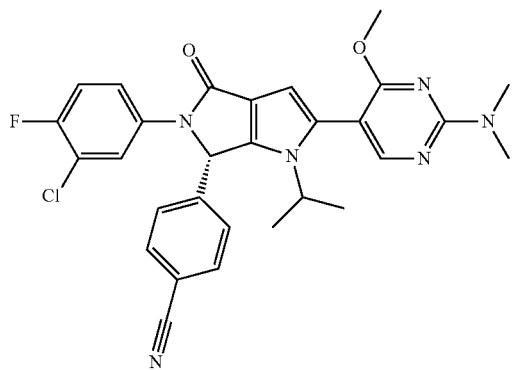

4-[5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile (Example 93) was purified by chiral chromatography (Chiral-HPLC 7) to afford the title compound. $t_R$: 3.31 min (Column: Chiralcel IC, 4.6×250 mm. Flow 3 mL/min. scCO$_2$/EtOH 50:50); ESI-MS: $t_R$=1.23 min, [M+H]$^+$ 545/547 (LC-MS 1).

EXAMPLE 170

4-[(R)-5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

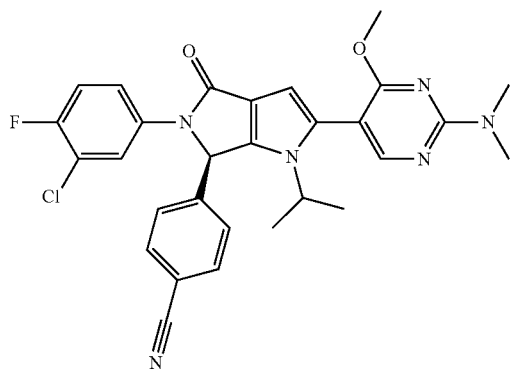

4-[5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile (Example 93) was purified by chiral chromatography (Chiral-HPLC 7) to afford the title compound. $t_R$: 4.23 min (Column: Chiralcel IC, 4.6×250 mm. Flow 3 mL/min. scCO$_2$/EtOH 50:50); ESI-MS: t$_R$=1.23 min, [M+H]$^+$ 545/547 (LC-MS 1).

EXAMPLE 171

4-[(S)-2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile

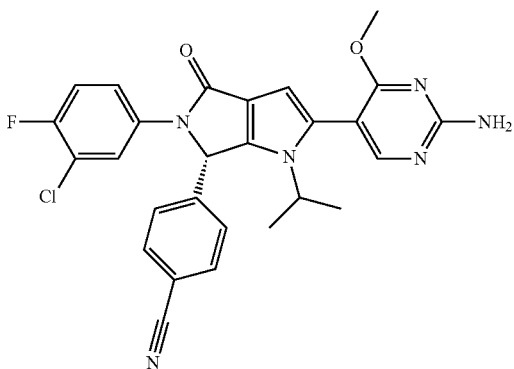 [SMILES: COc1nc(N)ncc1-c1cc2c(n1C(C)C)[C@H](c1ccc(C#N)cc1)N(c1ccc(F)c(Cl)c1)C2=O]

4-[2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile (Example 39) was purified by chiral chromatography (Chiral-HPLC 1) to afford the title compound. t$_R$: 8.75 min (Column: Chiralpak IC 5 μm, 4.6×250 mm. Flow 1 mL/min. heptane/CH$_2$Cl$_2$/isopropanol 50:30:20); ESI-MS: t$_R$=1.01 min, [M+H]$^+$ 517/519 (LC-MS 1); $^1$H-NMR (d$_6$-DMSO, 600 MHz): 7.92 (s, 1H), 7.86 (m, 1H), 7.81 (m, 2H), 7.51-7.62 (m, 3H), 7.32 (m, 1H), 6.90 (s, 2H), 6.73 (s, 1H), 6.27 (s, 1H), 3.95 (m, 1H), 3.79 (s, 3H), 1.36 (m, 3H), 0.40 (m, 3H).

EXAMPLE 172

4-[(R)-2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile

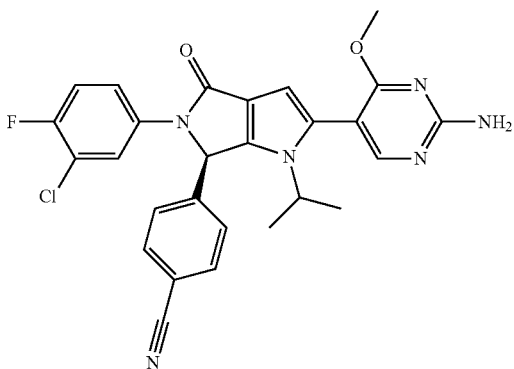 [SMILES: COc1nc(N)ncc1-c1cc2c(n1C(C)C)[C@@H](c1ccc(C#N)cc1)N(c1ccc(F)c(Cl)c1)C2=O]

4-[2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile (Example 39) was purified by chiral chromatography (Chiral-HPLC 1) to afford the title compound. t$_R$: 12.31 min (Column: Chiralpak IC 5 μm, 4.6×250 mm. Flow 1 mL/min. heptane/CH$_2$Cl$_2$/isopropanol 50:30:20); ESI-MS: t$_R$=1.00 min, [M+H]$^+$ 517/519 (LC-MS 1).

EXAMPLE 173

4-[2-(2,4-Dimethoxy-pyrimidin-5-yl)-5-(trans-4-hydroxy-cyclohexyl)-1-isopropyl-4-oxo-1,4,5,6-tetrahydro-pyrrolo[3,4-b]pyrrol-6-yl]-benzonitrile

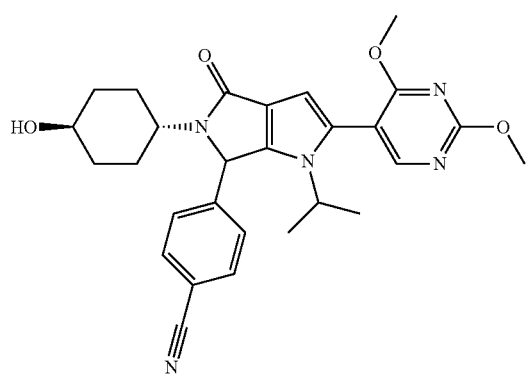

The title compound was prepared in analogy to the procedure described for Example 17 but 4-[2-bromo-5-(trans-4-hydroxy-cyclohexyl)-1-isopropyl-4-oxo-1,4,5,6-tetrahydro-pyrrolo[3,4-b]pyrrol-6-yl]-benzonitrile (Intermediate AV) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. t$_R$: 5.54 min (HPLC 2); ESI-MS: t$_R$=0.86 min, [M+H]$^+$ 502 (LC-MS 1); TLC: R$_f$=0.11 (EtOAc).

EXAMPLE 174

4-[2-(2-Dimethylamino-4-methoxy-pyrimidin-5-yl)-5-(trans-4-hydroxy-cyclohexyl)-1-isopropyl-4-oxo-1,4,5,6-tetrahydro-pyrrolo[3,4-b]pyrrol-6-yl]-benzonitrile

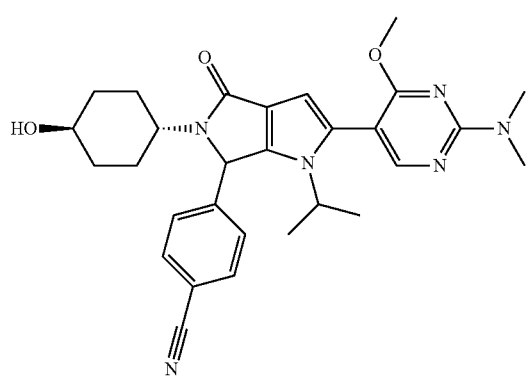 [SMILES: COc1nc(N(C)C)ncc1-c1cc2c(n1C(C)C)C(c1ccc(C#N)cc1)N([C@H]1CC[C@H](O)CC1)C2=O]

The title compound was prepared in analogy to the procedure described for Example 173 but 4-methoxy-N,N-dimethyl-5-(4,4,5,5-tetramethyl-1,3,2-dioxaborolan-2-yl)(pyrimidin-2-amine (Intermediate W) was used instead of 2,4-dimethoxypyrimidine-5-boronic acid. The title compound was obtained as a white solid. $t_R$: 4.85 min (HPLC 2); ESI-MS: $t_R$=0.94 min, [M+H]⁺ 515 (LC-MS 1); TLC: $R_f$=0.11 (EtOAc).

EXAMPLE 175

2-(2-Amino-4-methoxy-pyrimidin-5-yl)-6-(4-chloro-phenyl)-5-(2,5-dimethyl-2H-pyrazol-3-yl)-1-isopropyl-5,6-dihydro-1H-pyrrolo[3,4-b]pyrrol-4-one

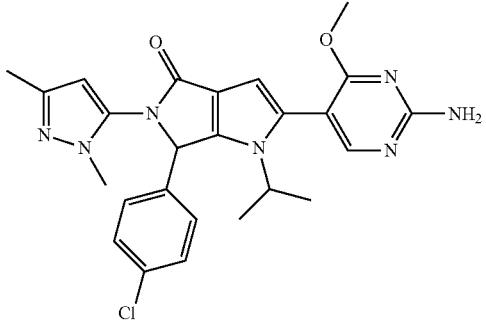 [SMILES: COc1nc(N)ncc1-c1cc2c(n1C(C)C)C(c1ccc(Cl)cc1)N(c1cc(C)nn1C)C2=O]

The title compound was prepared in analogy to the procedure described for Example 25 but 2-bromo-6-(4-chloro-phenyl)-5-(2,5-dimethyl-2H-pyrazol-3-yl)-1-isopropyl-5,6-dihydro-1H-pyrrolo[3,4-b]pyrrol-4-one (Intermediate AW) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. The title compound was obtained as a white solid. ESI-MS: $t_R$=0.91 min, [M+H]⁺ 492/494 (LC-MS 1).

EXAMPLE 176

6-(4-Chloro-phenyl)-2-(2,4-dimethoxy-pyrimidin-5-yl)-5-(2,5-dimethyl-2H-pyrazol-3-yl)-1-isopropyl-5,6-dihydro-1H-pyrrolo[3,4-b]pyrrol-4-one

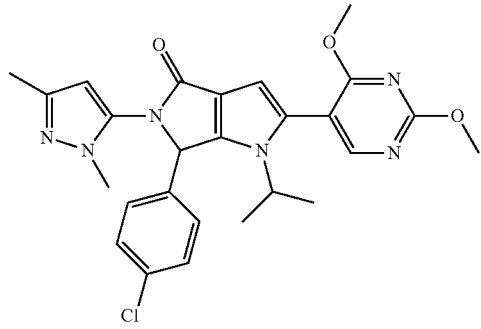

The title compound was prepared in analogy to the procedure described for Example 175 but 2,4-dimethoxypyrimidine-5-boronic acid was used instead of 4-methoxy-5-(4,4,5,5-tetramethyl-[1,3,2]dioxaborolan-2-yl)-pyrimidin-2-ylamine. The title compound was obtained as a white solid. ESI-MS: $t_R$=1.07 min, [M+H]⁺ 507/509 (LC-MS 1).

EXAMPLE 177

6-(4-Chloro-phenyl)-2-(2-dimethylamino-4-methoxy-pyrimidin-5-yl)-5-(2,5-dimethyl-2H-pyrazol-3-yl)-1-isopropyl-5,6-dihydro-1H-pyrrolo[3,4-b]pyrrol-4-one

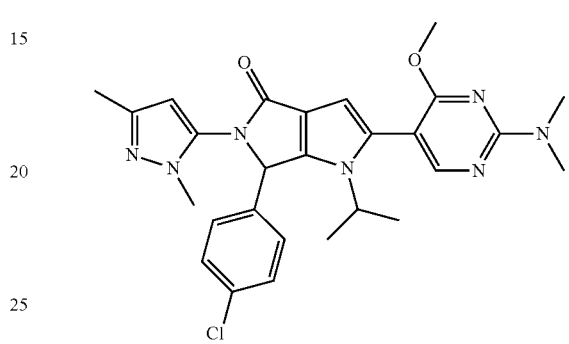

The title compound was prepared in analogy to the procedure described for Example 175 but 4-methoxy-N,N-dimethyl-5-(4,4,5,5-tetramethyl-1,3,2-dioxaborolan-2-yl)pyrimidin-2-amine (Intermediate W) was used instead of 4-methoxy-5-(4,4,5,5-tetramethyl-[1,3,2]dioxaborolan-2-yl)-pyrimidin-2-ylamine. The title compound was obtained as a white solid. ESI-MS: $t_R$=1.17 min, [M+H]⁺ 520/522 (LC-MS 1).

EXAMPLE 178

6-(4-Chloro-phenyl)-5-(2,5-dimethyl-2H-pyrazol-3-yl)-1-isopropyl-2-(5-methoxy-1-methyl-2-oxo-1,2-dihydro-pyridin-4-yl)-5,6-dihydro-1H-pyrrolo[3,4-b]pyrrol-4-one

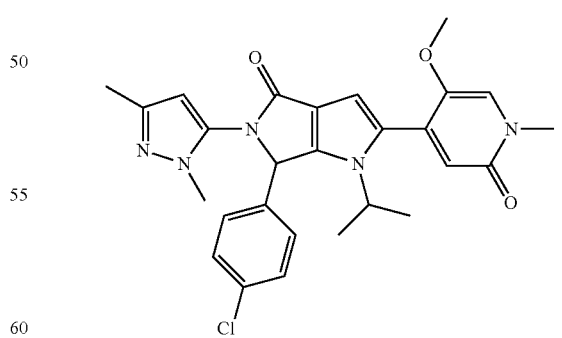

The title compound was prepared in analogy to the procedure described for Example 175 but 5-methoxy-1-methyl-4-(4,4,5,5-tetramethyl-[1,3,2]dioxaborolan-2-yl)-1H-pyridin-2-one (Intermediate AR) was used instead of 4-methoxy-5-(4,4,5,5-tetramethyl-[1,3,2]dioxaborolan-2-yl)-pyrimidin-2- ylamine. The title compound was obtained as a white solid. ESI-MS: $t_R$=0.89 min, [M+H]$^+$ 506/508 (LC-MS 1).

EXAMPLE 179

4-[2-(2,4-Dimethoxy-pyrimidin-5-yl)-5-(2,5-dimethyl-2H-pyrazol-3-yl)-1-isopropyl-4-oxo-1,4,5,6-tetrahydro-pyrrolo[3,4-b]pyrrol-6-yl]-benzonitrile

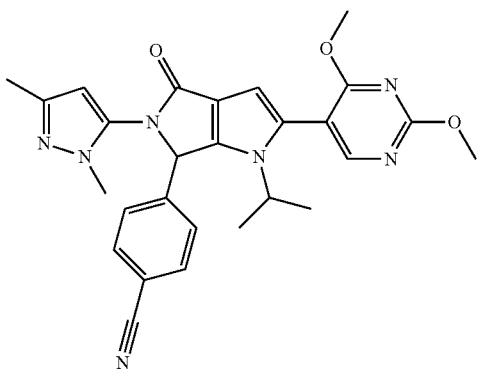

The title compound was prepared in analogy to the procedure described for Example 25 but 4-[2-bromo-5-(2,5-dimethyl-2H-pyrazol-3-yl)-1-isopropyl-4-oxo-1,4,5,6-tetrahydro-pyrrolo[3,4-b]pyrrol-6-yl]-benzonitrile (Intermediate AX) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a white solid. ESI-MS: $t_R$=0.94 min, [M+H]$^+$ 498 (LC-MS 1).

EXAMPLE 180

4-[2-(2-Dimethylamino-4-methoxy-pyrimidin-5-yl)-5-(2,5-dimethyl-2H-pyrazol-3-yl)-1-isopropyl-4-oxo-1,4,5,6-tetrahydro-pyrrolo[3,4-b]pyrrol-6-yl]-benzonitrile

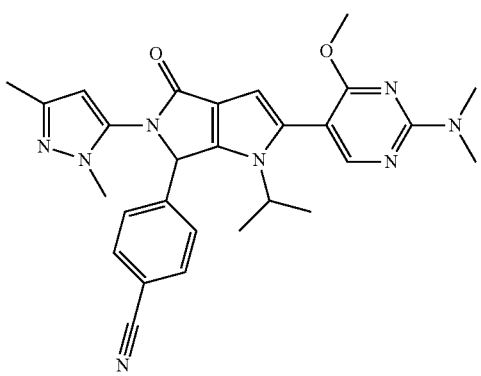

The title compound was prepared in analogy to the procedure described for Example 179 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. ESI-MS: $t_R$=1.04 min, [M+H]$^+$ 511 (LC-MS 1).

EXAMPLE 181

6-(4-Chloro-phenyl)-2-(2,4-dimethoxy-pyrimidin-5-yl)-5-(1,3-dimethyl-1H-pyrazol-4-yl)-1-isopropyl-5,6-dihydro-1H-pyrrolo[3,4-b]pyrrol-4-one

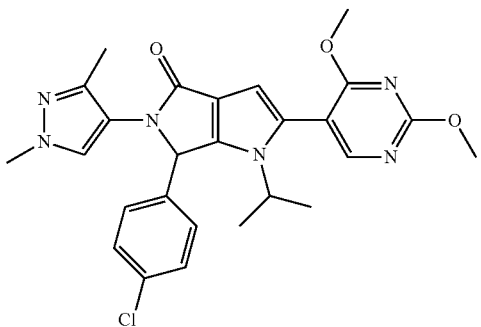

The title compound was prepared in analogy to the procedure described for Example 17 but 2-bromo-6-(4-chloro-phenyl)-5-(1,3-dimethyl-1H-pyrazol-4-yl)-1-isopropyl-5,6-dihydro-1H-pyrrolo[3,4-b]pyrrol-4-one (Intermediate AY) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$: 1.06 min (HPLC 3); ESI-MS: $t_R$=1.01 min, [M+H]$^+$ 507/509 (LC-MS 1); TLC: $R_f$=0.22 (9:1 CH$_2$Cl$_2$/MeOH).

EXAMPLE 182

6-(4-Chloro-phenyl)-2-(2-dimethylamino-4-methoxy-pyrimidin-5-yl)-5-(1,3-dimethyl-1H-pyrazol-4-yl)-1-isopropyl-5,6-dihydro-1H-pyrrolo[3,4-b]pyrrol-4-one

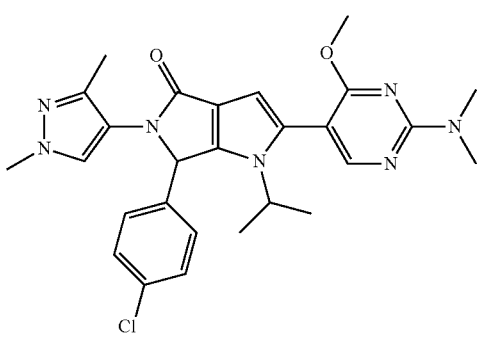

The title compound was prepared in analogy to the procedure described for Example 181 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. $t_R$: 0.92 min (HPLC 3); ESI-MS: $t_R$=1.10 min, [M+H]$^+$ 520/522 (LC-MS 1); TLC: $R_f$=0.04 (EtOAc).

EXAMPLE 183

6-(4-Chloro-phenyl)-5-(1,3-dimethyl-1H-pyrazol-4-yl)-1-isopropyl-2-(5-methanesulfonyl-2-methoxy-phenyl)-5,6-dihydro-1H-pyrrolo[3,4-b]pyrrol-4-one

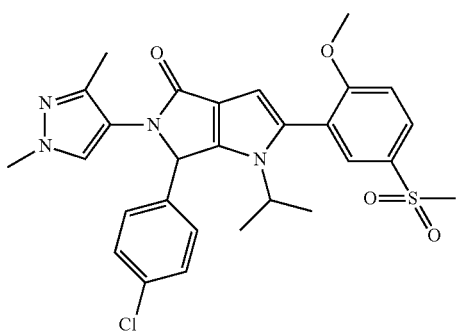

The title compound was prepared in analogy to the procedure described for Example 181 but 2-(5-methanesulfonyl-2-methoxy-phenyl)-4,4,5,5-tetramethyl-[1,3,2]dioxaborolane (Intermediate AP) was used instead of 2,4-dimethoxypyrimidine-5-boronic acid. The title compound was obtained as a white solid. $t_R$: 1.04 min (HPLC 3); ESI-MS: $t_R$=0.96 min, [M+H]$^+$ 553/555 (LC-MS 1); TLC: $R_f$=0.17 (9:1 CH$_2$Cl$_2$/MeOH).

EXAMPLE 184

6-(4-Chloro-phenyl)-5-(1,3-dimethyl-1H-pyrazol-4-yl)-1-isopropyl-2-(5-methoxy-1-methyl-2-oxo-1,2-dihydro-pyridin-4-yl)-5,6-dihydro-1H-pyrrolo[3,4-b]pyrrol-4-one

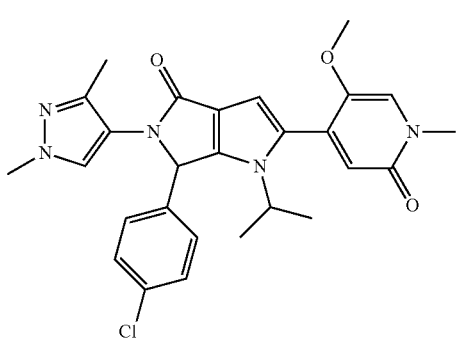

The title compound was prepared in analogy to the procedure described for Example 181 but 5-methoxy-1-methyl-4-(4,4,5,5-tetramethyl-[1,3,2]dioxaborolan-2-yl)-1H-pyridin-2-one (Intermediate AR) was used instead of 2,4-dimethoxypyrimidine-5-boronic acid. The title compound was obtained as a beige solid. $t_R$: 0.93 min (HPLC 3); ESI-MS: $t_R$=0.82 min, [M+H]$^+$ 506/508 (LC-MS 1); TLC: $R_f$=0.37 (9:1 CH$_2$Cl$_2$/MeOH).

EXAMPLE 185

4-[5-(5-Chloro-1-methyl-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

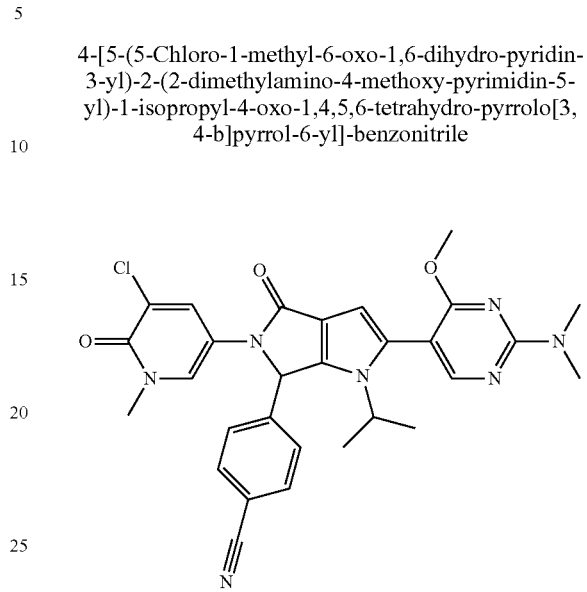

The title compound was prepared in analogy to the procedure described for Example 153 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a beige solid. $t_R$: 2.30 min (HPLC 5); ESI-MS: $t_R$=1.00 min, [M+H]$^+$ 558/560 (LC-MS 1).

EXAMPLE 186

4-[(S)-5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

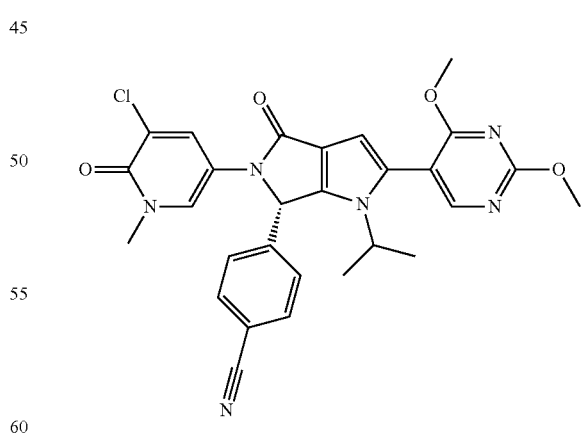

4-[5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile (Example 153) was purified by chiral chromatography (Chiral-HPLC 3) to afford the title compound as a beige solid. $t_R$: 1.84 min (Column: Chiralpak AS-H, 4.6×250 mm. Flow 3 mL/min. scCO$_2$/EtOH 60:40); t$_R$: 2.70 min (HPLC 5); ESI-MS: t$_R$=0.90 min, [M+H]$^+$ 545/547 (LC-MS 1).

EXAMPLE 187

4-[(R)-5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

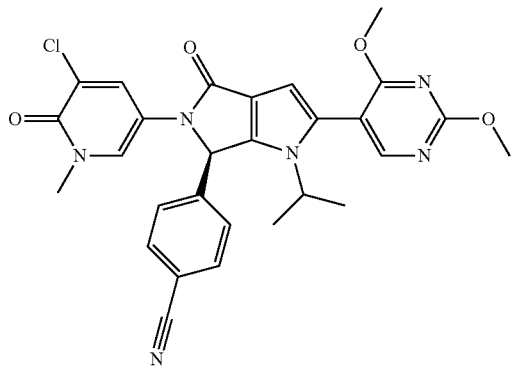 [SMILES: COc1ncc(-c2cc3c(n2C(C)C)[C@@H](c2ccc(C#N)cc2)N(c2cc(Cl)c(=O)n(C)c2)C3=O)c(OC)n1]

4-[5-(5-Chloro-1-methyl-6-oxo-1,6-dihydro-pyridin-3-yl)-2-(2,4-dimethoxy-pyrimidin-5-yl]-1-isopropyl-4-oxo-1,4,5,6-tetrahydro-pyrrolo[3,4-b]pyrrol-6-yl]-benzonitrile (Example 153) was purified by chiral chromatography (Chiral-HPLC 3) to afford the title compound as a beige solid. t$_R$: 4.13 min (Column: Chiralpak AS-H, 4.6×250 mm. Flow 3 mL/min. scCO$_2$/EtOH 60:40); t$_R$: 2.69 min (HPLC 5); ESI-MS: t$_R$=0.90 min, [M+H]$^+$ 545/547 (LC-MS 1).

EXAMPLE 188

(S)-5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one

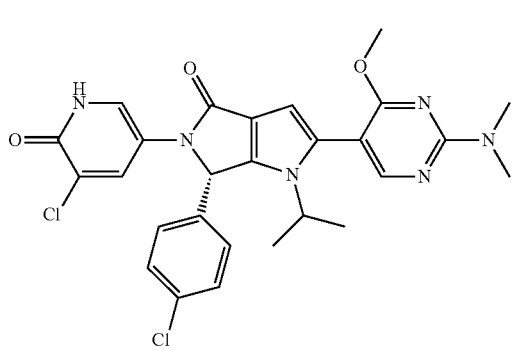 [SMILES: COc1nc(N(C)C)ncc1-c1cc2c(n1C(C)C)[C@H](c1ccc(Cl)cc1)N(c1c[nH]c(=O)c(Cl)c1)C2=O]

5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one (Example 140) was purified by chiral chromatography (Chiral-HPLC 3) to afford the title compound as a light brown solid. t$_R$: 6.04 min (Column: Chiralpak AS-H, 4.6×250 mm.

Flow 3 mL/min. scCO$_2$/EtOH 80:20); t$_R$: 5.25 min (HPLC 2); ESI-MS: t$_R$=1.06 min, [M+H]$^+$ 553/555 (LC-MS 1).

EXAMPLE 189

(R)-5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one

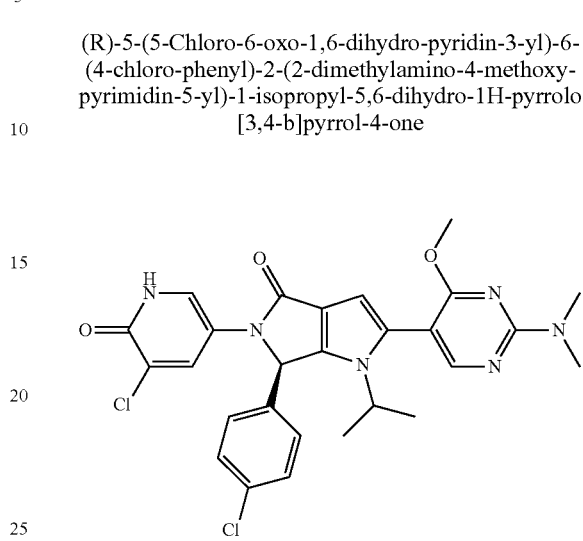

5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one (Example 140) was purified by chiral chromatography (Chiral-HPLC 3) to afford the title compound as a light brown solid. t$_R$: 8.06 min (Column: Chiralpak AS-H, 4.6×250 mm. Flow 3 mL/min. scCO$_2$/EtOH 80:20); t$_R$: 5.26 min (HPLC 2); ESI-MS: t$_R$=1.07 min, [M+H]$^+$ 553/555 (LC-MS 1).

EXAMPLE 190

4-[(S)-2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile

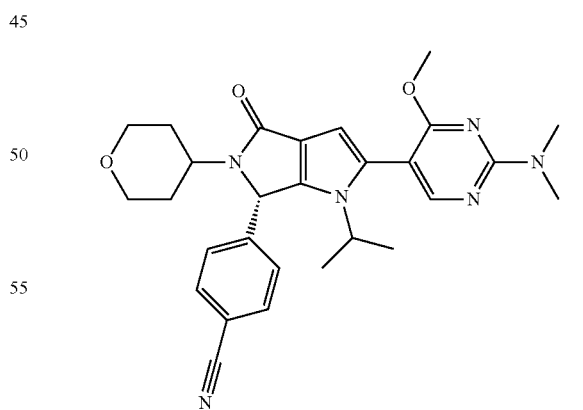

4-[2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile (Example 158) was purified by chiral chromatography (Chiral-HPLC 7 with 65:35:0.35 scCO$_2$/MeOH/2-propylamine) to afford the title compound as a white solid. t$_R$: 4.04 min (Column: Chiralpak AD-H, 4.6×250 mm. Flow 3 mL/min. scCO$_2$/EtOH/2-propylamine 80:20:0.2); t$_R$: 0.84 min (HPLC 3); ESI-MS: t$_R$=1.01 min, [M+H]$^+$ 501 (LC-MS 1).

EXAMPLE 191

4-[(R)-2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile

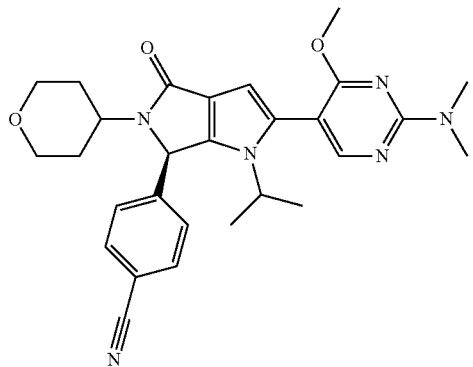 [SMILES: COc1nc(N(C)C)ncc1-c1cc2c(n1C(C)C)[C@@H](c1ccc(C#N)cc1)N(C1CCOCC1)C2=O]

4-[2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile (Example 158) was purified by chiral chromatography (Chiral-HPLC 7 with 65:35:0.35 scCO$_2$/MeOH/2-propylamine) to afford the title compound as a white solid. t$_R$: 5.63 min (Column: Chiralpak AD-H, 4.6×250 mm. Flow 3 mL/min. scCO$_2$/EtOH/2-propylamine 80:20:0.2); t$_R$: 0.84 min (HPLC 3); ESI-MS: t$_R$=1.01 min, [M+H]$^+$ 501 (LC-MS 1).

EXAMPLE 192

6-(4-Chloro-3-fluoro-phenyl)-5-(5-chloro-1-methyl-6-oxo-1,6-dihydro-pyridin-3-yl)-2-(2,4-dimethoxy-pyrimidin-5-yl)-1-isopropyl-5,6-dihydro-1H-pyrrolo[3,4-b]pyrrol-4-one

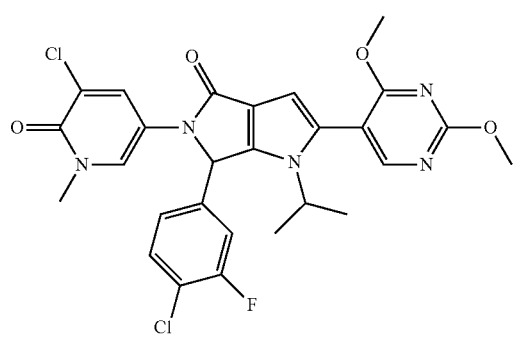 [SMILES: COc1ncc(-c2cc3c(n2C(C)C)C(c2ccc(Cl)c(F)c2)N(c2cc(Cl)c(=O)n(C)c2)C3=O)c(OC)n1]

The title compound was prepared in analogy to the procedure described for Example 17 but 2-bromo-6-(4-chloro-3-fluoro-phenyl)-5-(5-chloro-1-methyl-6-oxo-1,6-dihydro-pyridin-3-yl)-1-isopropyl-5,6-dihydro-1H-pyrrolo[3,4-b]pyrrol-4-one (Intermediate AZ) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. t$_R$: 1.10 min (HPLC 3); ESI-MS: t$_R$=1.03 min, [M+H]$^+$ 572/574/576 (LC-MS 1); TLC: R$_f$=0.08 (EtOAc).

EXAMPLE 193

6-(4-Chloro-3-fluoro-phenyl)-5-(5-chloro-1-methyl-6-oxo-1,6-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one

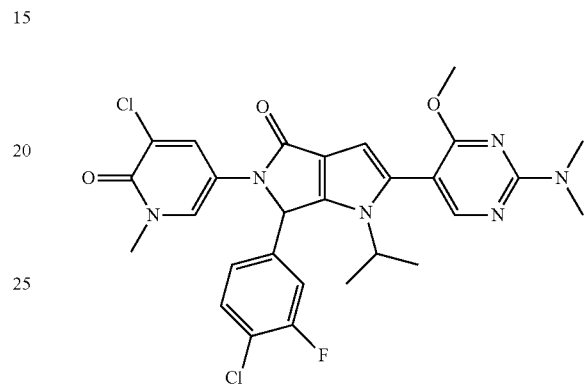

The title compound was prepared in analogy to the procedure described for Example 192 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. t$_R$: 0.95 min (HPLC 3); ESI-MS: t$_R$=1.14 min, [M+H]$^+$ 585/587/589 (LC-MS 1); TLC: R$_f$=0.53 (9:1 CH$_2$Cl$_2$/MeOH).

EXAMPLE 194

4-[5-(5-Chloro-1-methyl-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-2-fluoro-benzonitrile

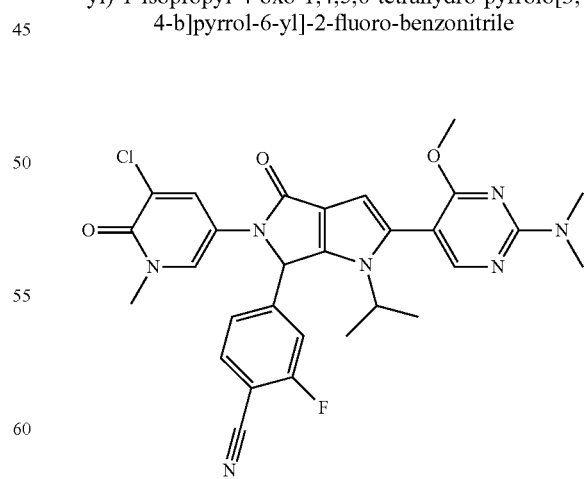

The title compound was prepared in analogy to the procedure described for Example 17 but 4-[2-bromo-5-(5-chloro-1-methyl-6-oxo-1,6-dihydro-pyridin-3-yl)-1-isopropyl-4-oxo-1,4,5,6-tetrahydro-pyrrolo[3,4-b]pyrrol-6-yl]-2-fluorobenzonitrile (Intermediate BC) and 4-methoxy-N,N-dimethyl-5-(4,4,5,5-tetramethyl-1,3,2-dioxaborolan-2-yl)pyrimidin-2-amine (Intermediate W) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$: 0.93 min (HPLC 3); ESI-MS: $t_R$=1.03 min, [M+H]⁺576/578 (LC-MS 1); TLC: $R_f$=0.07 (EtOAc).

EXAMPLE 195

4-[5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile

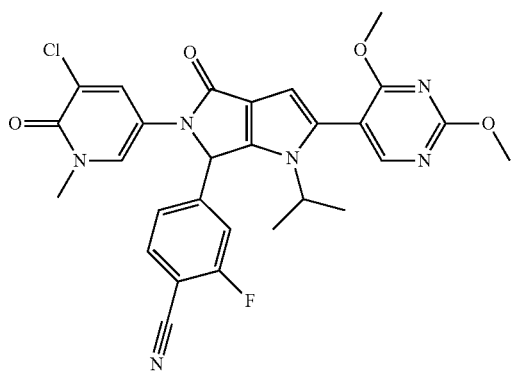 [SMILES: COc1ncc(-c2cc3c(n2C(C)C)C(c2ccc(C#N)c(F)c2)N(c2cc(Cl)c(=O)n(C)c2)C3=O)c(OC)n1]

The title compound was prepared in analogy to the procedure described for Step H1 but diethylaluminium chloride (1.8M in toluene) [96-10-6] was used instead of trimethylaluminium chloride, and 2-[(5-chloro-1-methyl-6-oxo-1,6-dihydro-pyridin-3-ylamino)-(4-cyano-3-fluoro-phenyl)-methyl]-5-(2,4-dimethoxy-pyrimidin-5-yl)-1-isopropyl-1H-pyrrole-3-carboxylic acid methyl ester (Step 195.1) was used instead of 2-[(3-chloro-4-fluoro-phenylamino)-(4-cyano-phenyl)-methyl]-1-isopropyl-1H-pyrrole-3-carboxylic acid ethyl ester. The title compound was obtained as a white solid. $t_R$: 1.07 min (HPLC 3); ESI-MS: $t_R$=0.93 min, [M+H]⁺ 563/565 (LC-MS 1); TLC: $R_f$=0.06 (EtOAc).

Step 195.1: 2-[(5-Chloro-1-methyl-6-oxo-1,6-dihydro-pyridin-3-ylamino)-(4-cyano-3-fluoro-phenyl)-methyl]-5-(2,4-dimethoxy-pyrimidin-5-yl)-1-isopropyl-1H-pyrrole-3-carboxylic acid methyl ester

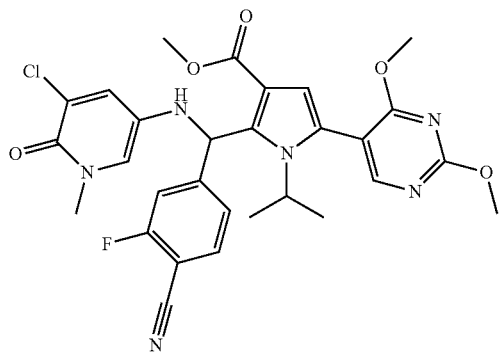 [SMILES: COC(=O)c1cc(-c2cnc(OC)nc2OC)n(C(C)C)c1C(Nc1cc(Cl)c(=O)n(C)c1)c1ccc(C#N)c(F)c1]

The title compound was prepared in analogy to the procedures described for Step H2 and Step H3 but 2-[(4-cyano-3-fluoro-phenyl)-hydroxy-methyl]-5-(2,4-dimethoxy-pyrimidin-5-yl)-1-isopropyl-1H-pyrrole-3-carboxylic acid methyl ester (Step 195.2) and 5-amino-3-chloro-1-methyl-1H-pyridin-2-one (Step E5) were used instead of 2-[(4-cyano-phenyl)-hydroxy-methyl]-1-isopropyl-1H-pyrrole-3-carboxylic acid ethyl ester and 3-chloro-4-fluoroaniline respectively. The title compound was obtained as a blue solid. $t_R$: 1.10 min (HPLC 3); ESI-MS: $t_R$=1.07 min, [M+H]⁺ 595/597 (LC-MS 1); TLC: $R_f$=0.29 (EtOAc).

Step 195.2: 2-[(4-Cyano-3-fluoro-phenyl)-hydroxy-methyl]-5-(2,4-dimethoxy-pyrimidin-5-yl)-1-isopropyl-1H-pyrrole-3-carboxylic acid methyl ester

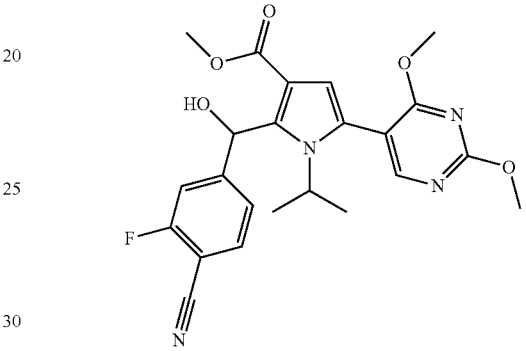

The title compound was prepared in analogy to the procedure described for Step D3 but 5-(2,4-dimethoxy-pyrimidin-5-yl)-1-isopropyl-1H-pyrrole-3-carboxylic acid methyl ester (Step 195.3) and 2-fluoro-4-formyl-benzonitrile [101048-76-4] were used instead of 5-bromo-1-isopropyl-1H-pyrrole-3-carboxylic acid methyl ester and 4-chlorobenzaldehyde respectively. The title compound was obtained as a yellow solid. $t_R$: 1.12 min (HPLC 3); ESI-MS: $t_R$=1.11 min, [M+H]⁺ 455 (LC-MS 1); TLC: $R_f$=0.30 (1:1 EtOAc/heptanes).

Step 195.3: 5-(2,4-Dimethoxy-pyrimidin-5-yl)-1-isopropyl-1H-pyrrole-3-carboxylic acid methyl ester

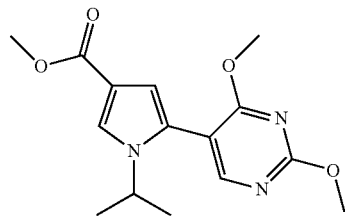

The title compound was prepared in analogy to the procedure described for Example 17 but 5-bromo-1-isopropyl-1H-pyrrole-3-carboxylic acid methyl ester (Step D4) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a yellow solid. $t_R$: 0.97

241 min (HPLC 3); ESI-MS: $t_R$=0.97 min, [M+H]$^+$ 306 (LC-MS 1); TLC: $R_f$=0.43 (1:1 EtOAc/heptanes).

EXAMPLE 196

6-(4-Chloro-3-fluoro-phenyl)-5-(5-chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-b]pyrrol-4-one

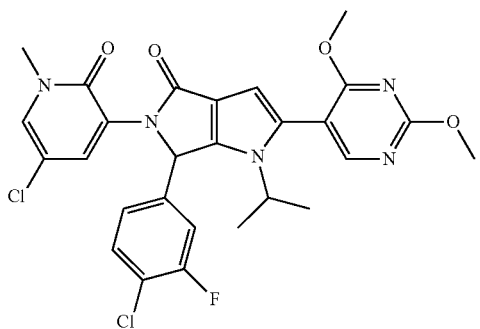 [SMILES: COc1ncc(-c2cc3c(n2C(C)C)C(c2ccc(Cl)c(F)c2)N(c2cc(Cl)cn(C)c2=O)C3=O)c(OC)n1]

The title compound was prepared in analogy to the procedure described for Example 25 but 2-bromo-6-(4-chloro-3-fluoro-phenyl)-5-(5-chloro-1-methyl-2-oxo-1,2-dihydro-pyridin-3-yl)-1-isopropyl-5,6-dihydro-1H-pyrrolo[3,4-b]pyrrol-4-one (Intermediate BA) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a white solid. $t_R$: 1.15 min (HPLC 3); ESI-MS: $t_R$=1.13 min, [M+H]$^+$ 572/574/576 (LC-MS 1); TLC: $R_f$=0.25 (EtOAc).

EXAMPLE 197

6-(4-Chloro-3-fluoro-phenyl)-5-(5-chloro-1-methyl-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one

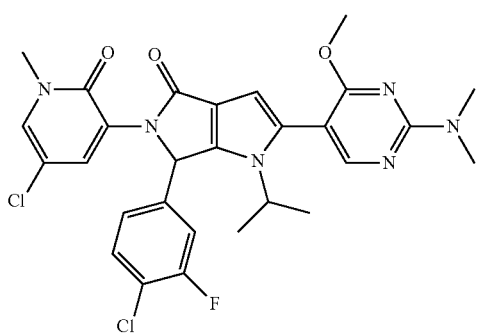 [SMILES: COc1nc(N(C)C)ncc1-c1cc2c(n1C(C)C)C(c1ccc(Cl)c(F)c1)N(c1cc(Cl)cn(C)c1=O)C2=O]

The title compound was prepared in analogy to the procedure described for Example 196 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. $t_R$: 1.01 min (HPLC 3); ESI-MS: $t_R$=1.23 min, [M+H]$^+$ 585/587/589 (LC-MS 1); TLC: $R_f$=0.27 (EtOAc).

EXAMPLE 198

4-[5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile

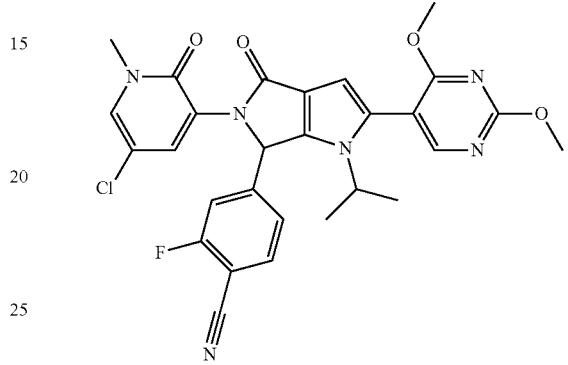

The title compound was prepared in analogy to the procedure described for Example 25 but 4-[2-bromo-5-(5-chloro-1-methyl-2-oxo-1,2-dihydro-pyridin-3-yl)-1-isopropyl-4-oxo-1,4,5,6-tetrahydro-pyrrolo[3,4-b]pyrrol-6-yl]-2-fluoro-benzonitrile (Intermediate BD) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively to afford the title compound as a white solid. $t_R$: 1.04 min (HPLC 3); ESI-MS: $t_R$=1.01 min, [M+H]$^+$ 563/565 (LC-MS 1); TLC: $R_f$=0.27 (EtOAc).

EXAMPLE 199

4-[5-(5-Chloro-1-methyl-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-2-fluoro-benzonitrile

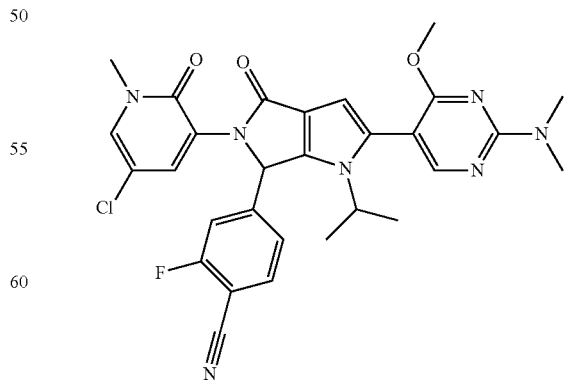

The title compound was prepared in analogy to the procedure described for Example 198 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. $t_R$: 0.92 min (HPLC 3); ESI-MS: $t_R$=1.09 min, [M+H]$^+$ 576/578 (LC-MS 1); TLC: $R_f$=0.21 (EtOAc).

EXAMPLE 200

4-[5-(5-Chloro-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile

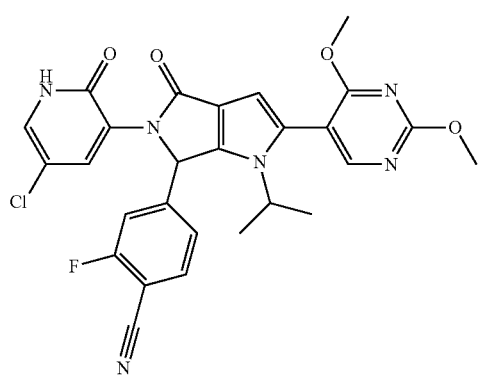 [SMILES: COc1ncc(-c2cc3c(n2C(C)C)C(c2ccc(C#N)c(F)c2)N(c2cc(Cl)c[nH]c2=O)C3=O)c(OC)n1]

The title compound was prepared in analogy to the procedure described for Example 125 but in the step corresponding to Step 125.1, 4-{2-bromo-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-2-fluoro-benzonitrile (Intermediate BE) and 2,4-dimethoxypyrimidine-5-boronic acid were used instead of 4-{2-bromo-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-benzonitrile and 4-methoxy-5-(4,4,5,5-tetramethyl-[1,3,2]dioxaborolan-2-yl)-pyrimidin-2-ylamine respectively. Moreover, in this step, Pd(PPh$_3$)$_4$ was used instead of PdCl$_2$(dppf).CH$_2$Cl$_2$ adduct. The title compound was obtained as a white solid. $t_R$: 5.84 min (H PLC 2); ESI-MS: $t_R$=0.94 min, [M+H]$^+$ 549/551 (LC-MS 1); TLC: $R_f$=0.19 (EtOAc).

EXAMPLE 201

4-[5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-2-fluoro-benzonitrile

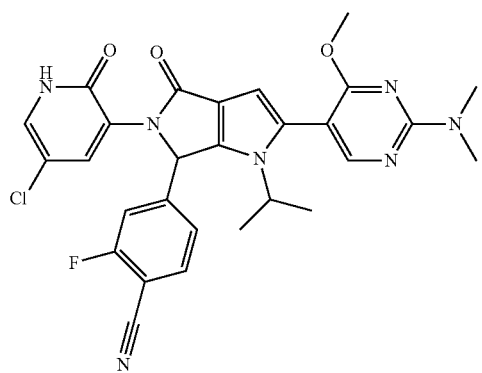 [SMILES: COc1nc(N(C)C)ncc1-c1cc2c(n1C(C)C)C(c1ccc(C#N)c(F)c1)N(c1cc(Cl)c[nH]c1=O)C2=O]

The title compound was prepared in analogy to the procedure described for Example 200 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. $t_R$: 5.19 min (HPLC 2); ESI-MS: $t_R$=1.02 min, [M+H]$^+$ 562/564 (LC-MS 1).

EXAMPLE 202

6-(4-Chloro-3-fluoro-phenyl)-5-(5-chloro-2-oxo-1,2-dihydro-pyridin-3-yl)-2-(2,4-dimethoxy-pyrimidin-5-yl)-1-isopropyl-5,6-dihydro-1H-pyrrolo[3,4-b]pyrrol-4-one

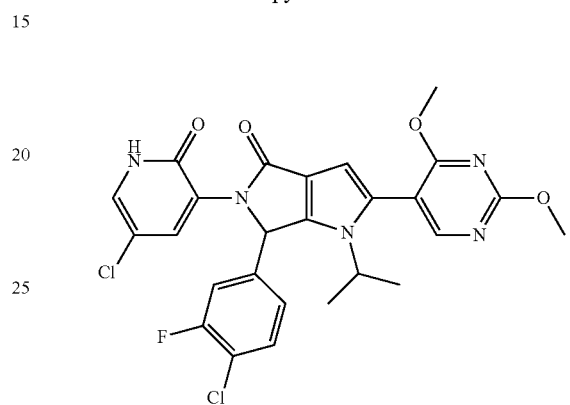

The title compound was prepared in analogy to the procedure described for Example 200 but 2-bromo-6-(4-chloro-3-fluoro-phenyl)-5-[5-chloro-1-(4-methoxy-benzyl)-2-oxo-1,2-dihydro-pyridin-3-yl]-1-isopropyl-5,6-dihydro-1H-pyrrolo[3,4-b]pyrrol-4-one (Intermediate BB) was used instead of 4-{2-bromo-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-2-fluoro-benzonitrile. The title compound was obtained as a white solid. $t_R$: 6.37 min (HPLC 2); ESI-MS: $t_R$=1.05 min, [M+H]$^+$ 558/560/562 (LC-MS 1).

EXAMPLE 203

6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one

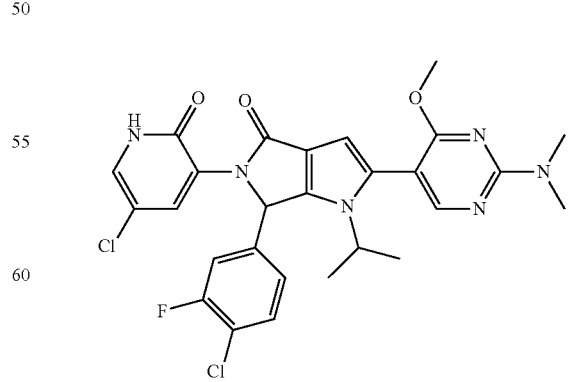

The title compound was prepared in analogy to the procedure described for Example 202 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. $t_R$: 5.60 min (HPLC 2); ESI-MS: $t_R$=1.14 min, [M+H]$^+$ 571/573/575 (LC-MS 1).

EXAMPLE 204

5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one

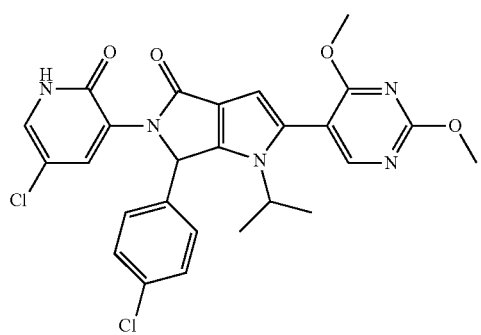 [SMILES: COc1ncc(-c2cc3c(n2C(C)C)C(c2ccc(Cl)cc2)N(c2cc(Cl)c[nH]c2=O)C3=O)c(OC)n1]

The title compound was prepared in analogy to the procedure described for Example 200 but 2-bromo-5-[5-chloro-1-(4-methoxy-benzyl)-2-oxo-1,2-dihydro-pyridin-3-yl]-6-(4-chloro-phenyl)-1-isopropyl-5,6-dihydro-1H-pyrrolo[3,4-b]pyrrol-4-one (Intermediate BN) was used instead of 4-{2-bromo-5-[5-chloro-1-(4-methoxy-benzyl)-2-oxo-1,2-dihydro-pyridin-3-yl]-1-isopropyl-4-oxo-1,4,5,6-tetrahydro-pyrrolo[3,4-b]pyrrol-6-yl}-2-fluoro-benzonitrile. The title compound was obtained as a white solid. $t_R$: 1.15 min (HPLC 3); ESI-MS: $t_R$=1.03 min, [M+H]$^+$ 540/542/544 (LC-MS 1); TLC: $R_f$=0.43 (EtOAc).

EXAMPLE 205

5-(5-Chloro-2-methoxy-pyridin-3-yl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-b]pyrrol-4-one

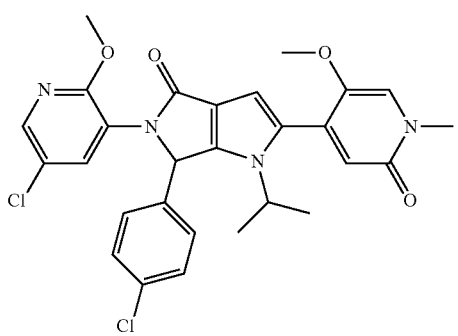 [SMILES: COc1cn(C)c(=O)cc1-c1cc2c(n1C(C)C)C(c1ccc(Cl)cc1)N(c1cc(Cl)cnc1OC)C2=O]

The title compound was prepared in analogy to the procedure described for Example 25 but 2-bromo-5-(5-chloro-2-methoxy-pyridin-3-yl)-6-(4-chloro-phenyl)-1-isopropyl-5,6-dihydro-1H-pyrrolo[3,4-b]pyrrol-4-one (Intermediate BF) and 5-methoxy-1-methyl-4-(4,4,5,5-tetramethyl-[1,3,2]dioxaborolan-2-yl)-1H-pyridin-2-one (Intermediate AR) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. ESI-MS: $t_R$=1.09 min, [M+H]$^+$ 553/555/557 (LC-MS 1).

EXAMPLE 206

2-(2-Amino-4-methoxy-pyrimidin-5-yl)-5-(5-chloro-2-methoxy-pyridin-3-yl)-6-(4-chloro-phenyl)-1-isopropyl-5,6-dihydro-1H-pyrrolo[3,4-b]pyrrol-4-one

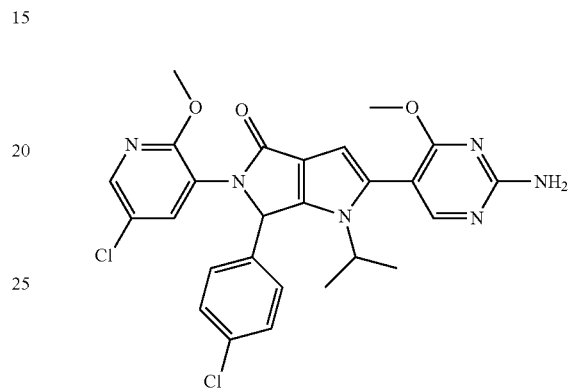

The title compound was prepared in analogy to the procedure described for Example 25 but 2-bromo-5-(5-chloro-2-methoxy-pyridin-3-yl)-6-(4-chloro-phenyl)-1-isopropyl-5,6-dihydro-1H-pyrrolo[3,4-b]pyrrol-4-one (Intermediate BF) was used instead of 2-bromo-5-(5-chloro-2-methyl-phenyl)-6-(4-chloro-phenyl)-1-isopropyl-5,6-dihydro-1H-pyrrolo[3,4-b]pyrrol-4-one. ESI-MS: $t_R$=1.11 min, [M+H]$^+$ 539/541/543 (LC-MS 1).

EXAMPLE 207

4-[5-[5-Chloro-2-methoxy-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile

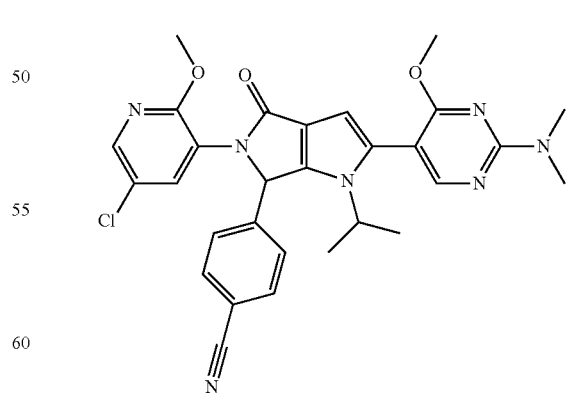

The title compound was prepared in analogy to the procedure described for Example 25 but 4-[2-bromo-5-(5-chloro-2-methoxy-pyridin-3-yl)-1-isopropyl-4-oxo-1,4,5,6-tetrahydro-pyrrolo[3,4-b]pyrrol-6-yl]-benzonitrile (Intermediate BG) and 4-methoxy-N,N-dimethyl-5-(4,4,5,5-tetramethyl-1,3,2-dioxaborolan-2-yl)pyrimidin-2-amine (Intermediate W) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. ESI-MS: $t_R$=1.20 min, [M+H]$^+$ 558/560 (LC-MS 1).

EXAMPLE 208

6-(4-Chloro-phenyl)-5-(4-fluoro-2,5-dimethyl-2H-pyrazol-3-yl)-1-isopropyl-2-(5-methoxy-1-methyl-2-oxo-1,2-dihydro-pyridin-4-yl)-5,6-dihydro-1H-pyrrolo[3,4-b]pyrrol-4-one

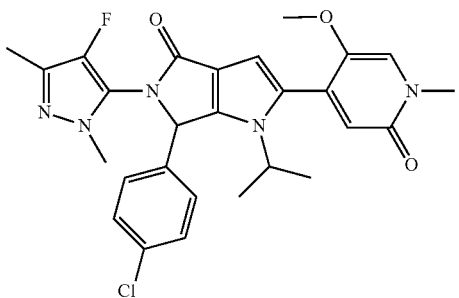

The title compound was prepared in analogy to the procedure described for Example 205 but 2-bromo-6-(4-chloro-phenyl)-5-(4-fluoro-2,5-dimethyl-2H-pyrazol-3-yl)-1-isopropyl-5,6-dihydro-1H-pyrrolo[3,4-b]pyrrol-4-one (Intermediate BH) was used instead of 2-bromo-5-(5-chloro-2-methoxy-pyridin-3-yl)-6-(4-chloro-phenyl)-1-isopropyl-5,6-dihydro-1H-pyrrolo[3,4-b]pyrrol-4-one. ESI-MS: $t_R$=0.95 min, [M+H]$^+$ 524/526 (LC-MS 1).

EXAMPLE 209

6-(4-Chloro-phenyl)-2-(2-dimethylamino-4-methoxy-pyrimidin-5-yl)-5-(4-fluoro-2,5-dimethyl-2H-pyrazol-3-yl)-1-isopropyl-5,6-dihydro-1H-pyrrolo[3,4-b]pyrrol-4-one

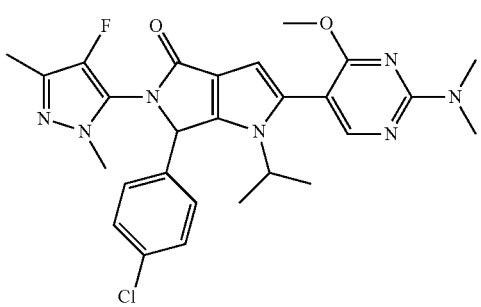

The title compound was prepared in analogy to the procedure described for Example 208 but 4-methoxy-N,N-dimethyl-5-(4,4,5,5-tetramethyl-1,3,2-dioxaborolan-2-yl)pyrimidin-2-amine (Intermediate W) was used instead of 5-methoxy-1-methyl-4-(4,4,5,5-tetramethyl-[1,3,2]dioxaborolan-2-yl)-1H-pyridin-2-one. ESI-MS: $t_R$=1.24 min, [M+H]$^+$ 538/540 (LC-MS 1).

EXAMPLE 210

2-(2-Amino-4-methoxy-pyrimidin-5-yl)-6-(4-chloro-phenyl)-5-(4-fluoro-2,5-dimethyl-2H-pyrazol-3-yl)-1-isopropyl-5,6-dihydro-1H-pyrrolo[3,4-b]pyrrol-4-one

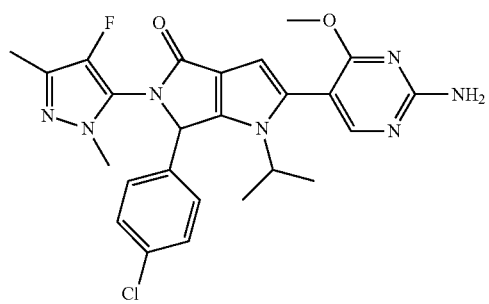 [SMILES: COc1nc(N)ncc1-c1cc2c(n1C(C)C)C(c1ccc(Cl)cc1)N(c1c(F)c(C)nn1C)C2=O]

The title compound was prepared in analogy to the procedure described for Example 208 but 4-methoxy-5-(4,4,5,5-tetramethyl-[1,3,2]dioxaborolan-2-yl)-pyrimidin-2-ylamine (Intermediate U) was used instead of 5-methoxy-1-methyl-4-(4,4,5,5-tetramethyl-[1,3,2]dioxaborolan-2-yl)-1H-pyridin-2-one. ESI-MS: $t_R$=0.97 min, [M+H]$^+$ 510/512 (LC-MS 1).

EXAMPLE 211

4-[2-(2,4-Dimethoxy-pyrimidin-5-yl)-5-(4-fluoro-2,5-dimethyl-2H-pyrazol-3-yl)-1-isopropyl-4-oxo-1,4,5,6-tetrahydro-pyrrolo[3,4-b]pyrrol-6-yl]-benzonitrile

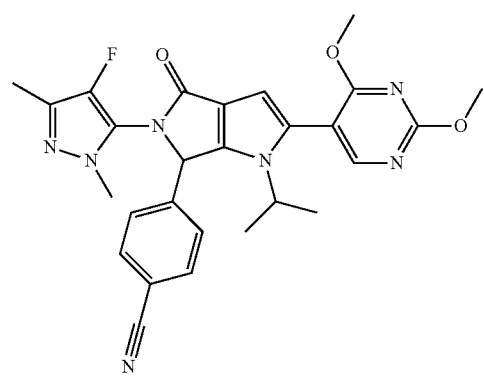

The title compound was prepared in analogy to the procedure described for Example 25 but 4-[2-bromo-5-(4-fluoro-2,5-dimethyl-2H-pyrazol-3-yl)-1-isopropyl-4-oxo-1,4,5,6-tetrahydro-pyrrolo[3,4-b]pyrrol-6-yl]-benzonitrile (Intermediate BJ) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. ESI-MS: $t_R$=1.00 min, [M+H]$^+$ 516 (LC-MS 1).

EXAMPLE 212

6-(4-Chloro-2-fluoro-phenyl)-2-(2-dimethylamino-4-methoxy-pyrimidin-5-yl)-5-(2,5-dimethyl-2H-pyrazol-3-yl)-1-isopropyl-5,6-dihydro-1H-pyrrolo[3,4-b]pyrrol-4-one

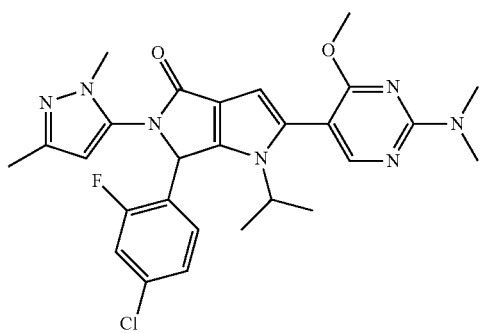

The title compound was prepared in analogy to the procedure described for Example 25 but 2-bromo-6-(4-chloro-2-fluoro-phenyl)-5-(2,5-dimethyl-2H-pyrazol-3-yl)-1-isopropyl-5,6-dihydro-1H-pyrrolo[3,4-b]pyrrol-4-one (Intermediate BI) and 4-methoxy-N,N-dimethyl-5-(4,4,5,5-tetramethyl-1,3,2-dioxaborolan-2-yl)pyrimidin-2-amine (Intermediate W) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. ESI-MS: $t_R$=1.19 min, [M+H]$^+$ 538/540 (LC-MS 1).

EXAMPLE 213

5-(5-Chloro-1-methyl-2-oxo-1,2-dihydro-pyridin-3-yl)-6-(5-chloro-pyridin-2-yl)-2-(2,4-dimethoxy-pyrimidin-5-yl)-1-isopropyl-5,6-dihydro-1H-pyrrolo[3,4-b]pyrrol-4-one

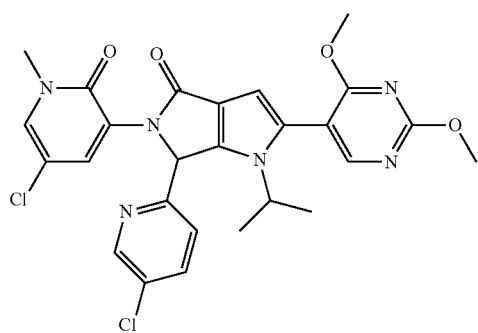

The title compound was prepared in analogy to the procedure described for Example 25 but 2-bromo-5-(5-chloro-1-methyl-2-oxo-1,2-dihydro-pyridin-3-yl)-6-(5-chloro-pyridin-2-yl)-1-isopropyl-5,6-dihydro-1H-pyrrolo[3,4-b]pyrrol-4-one (Intermediate BK) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a yellow solid. ESI-MS: $t_R$=0.99 min, [M+H]$^+$ 555/557/559 (LC-MS 1).

EXAMPLE 214

5-(3-Chloro-4-fluoro-phenyl)-6-(5-chloro-pyridin-2-yl)-2-(2,4-dimethoxy-pyrimidin-5-yl)-1-isopropyl-5,6-dihydro-1H-pyrrolo[3,4-b]pyrrol-4-one

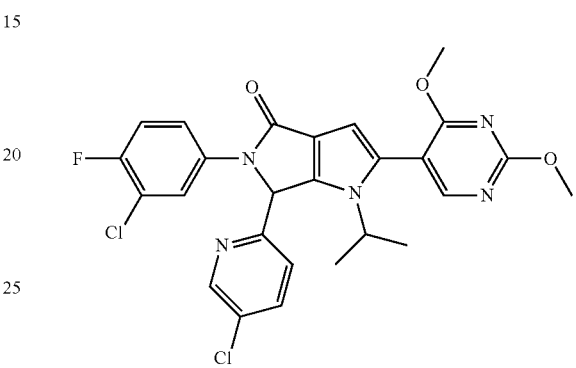

The title compound was prepared in analogy to the procedure described for Example 25 but 2-bromo-5-(3-chloro-4-fluoro-phenyl)-6-(5-chloro-pyridin-2-yl)-1-isopropyl-5,6-dihydro-1H-pyrrolo[3,4-b]pyrrol-4-one (Intermediate BL) and 2,4-dimethoxypyrimidine-5-boronic acid were used instead of 2-bromo-5-(5-chloro-1-methyl-2-oxo-1,2-dihydro-pyridin-3-yl)-6-(5-chloro-pyridin-2-yl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a white solid. ESI-MS: $t_R$=1.23 min, [M+H]$^+$ 542/544 (LC-MS 1).

EXAMPLE 215

4-[(S)-5-(5-Chloro-1-methyl-2-oxo-1,2-dihydro-pyridin-3-yl)-2-(2,4-dimethoxy-Pyrimidin-5-yl)-1-isopropyl-4-oxo-1,4,5,6-tetrahydro-pyrrolo[3,4-b]pyrrol-6-yl]-benzonitrile

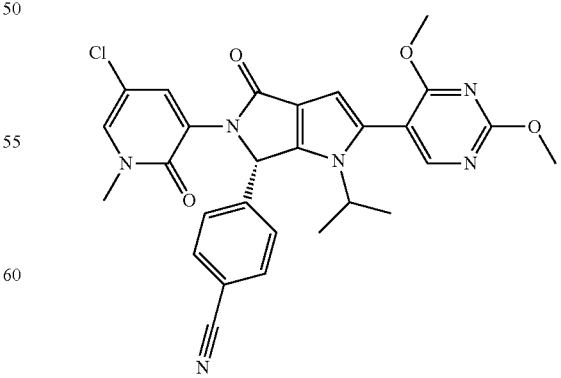

4-[5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile (Example 132) was purified by chiral chromatography (Chiral-HPLC 8) to afford the title compound as a white solid. $t_R$: 5.28 min (Column: Chiralpak IA, 4.6×250 mm. Flow 1 mL/min. EtOH; ESI-MS: $t_R$=0.97 min, [M+H]⁺ 545/547 (LC-MS 1).

EXAMPLE 216

4-[(R)-5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile

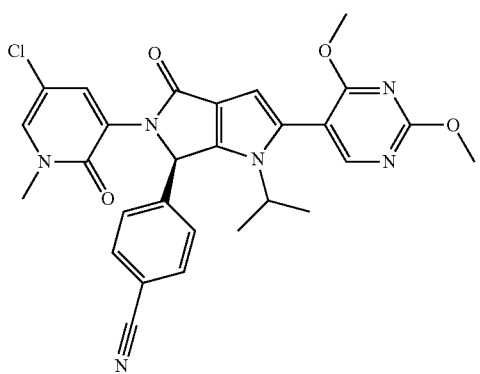 [SMILES: COc1ncc(-c2cc3c(n2C(C)C)[C@@H](c2ccc(C#N)cc2)N(c2cc(Cl)cn(C)c2=O)C3=O)c(OC)n1]

4-[5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile (Example 132) was purified by chiral chromatography (Chiral-HPLC 8) to afford the title compound as a white solid. $t_R$: 10.38 min (Column: Chiralpak IA, 4.6×250 mm. Flow 1 mL/min. EtOH; ESI-MS: $t_R$=0.97 min, [M+H]⁺545/547 (LC-MS 1).

EXAMPLE 217

5-(5-Chloro-1-methyl-6-oxo-1,6-dihydro-pyridin-3-yl)-6-(4-chloro-phenyl-2-(2,4-d₆-dimethoxy-pyrimidin-5-yl)-1-isopropyl-5,6-dihydro-1H-pyrrolo[3,4-b]pyrrol-4-one

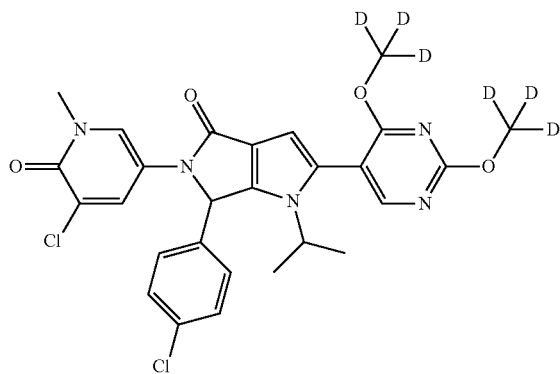 [SMILES: [2H]C([2H])([2H])Oc1ncc(-c2cc3c(n2C(C)C)C(c2ccc(Cl)cc2)N(c2cc(Cl)c(=O)n(C)c2)C3=O)c(OC([2H])([2H])[2H])n1]

The title compound was prepared in analogy to the procedure described for Example 25 but 2-bromo-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one (Intermediate E) and 2,4-d₆-dimethoxypyrimidineboronic acid (Intermediate BS) were used instead of 2-bromo-5-(5-chloro-1-methyl-2-oxo-1,2-dihydro-pyridin-3-yl)-6-(5-chloro-pyridin-2-yl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a white solid. $t_R$: 5.52 min (HPLC 7); ESI-MS: $t_R$=1.03 min, [M+H]⁺ 560/562/564 (LC-MS 1).

EXAMPLE 218

(S)-5-(5-Chloro-1-methyl-6-oxo-1,6-dihydro-pyridin-3-yl)-6-(4-chloro-phenyl)-2-(2,4-d₆-dimethoxy-pyrimidin-5-yl)-1-isopropyl-5,6-dihydro-1H-pyrrolo[3,4-b]pyrrol-4-one

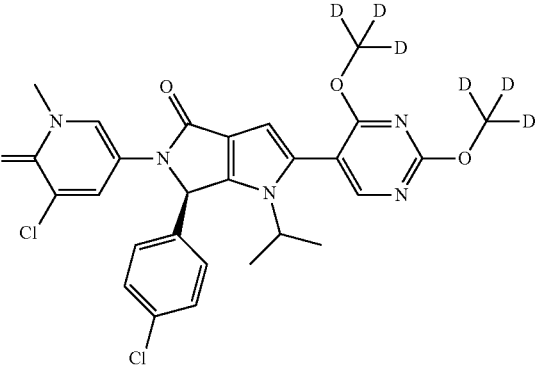

5-(5-Chloro-1-methyl-6-oxo-1,6-dihydro-pyridin-3-yl)-6-(4-chloro-phenyl)-2-(2,4-d₆-dimethoxy-pyrimidin-5-yl)-1-isopropyl-5,6-dihydro-1H-pyrrolo[3,4-b]pyrrol-4-one (Example 217) was purified by chiral chromatography (Chiral-HPLC 9) to afford the title compound as a white solid. $t_R$: 3.89 min (Column: Chiralpak AY, 4.6×250 mm. Flow 1.3 mL/min. 1:1 EtOH/MeOH; $t_R$: 5.53 min (HPLC 7); ESI-MS: $t_R$=1.02 min, [M+H]⁺ 560/562/564 (LC-MS 1).

EXAMPLE 219

(R)-5-(5-Chloro-1-methyl-6-oxo-1,6-dihydro-pyridin-3-yl)-6-(4-chloro-phenyl)-2-(2,4-d₆-dimethoxy-pyrimidin-5-yl)-1-isopropyl-5,6-dihydro-1H-pyrrolo[3,4-b]pyrrol-4-one 5-(5-Chloro-1-methyl-6-oxo-1,6-dihydro-pyridin-3-yl)-6-(4-chloro-phenyl)-2-(2,4-d₆-dimethoxy-pyrimidin-5-yl)-

1-isopropyl-5,6-dihydro-1H-pyrrolo[3,4-b]pyrrol-4-one (Example 217) was purified by chiral chromatography (Chiral-HPLC 9) to afford the title compound as a white solid. $t_R$: 7.13 min (Column: Chiralpak AY, 4.6×250 mm. Flow 1.3 mL/min. 1:1 EtOH/MeOH; $t_R$: 5.53 min (HPLC 7); ESI-MS: $t_R$=1.02 min, [M+H]$^+$ 560/562/564 (LC-MS 1).

EXAMPLE 220

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carboxylic acid ethyl ester

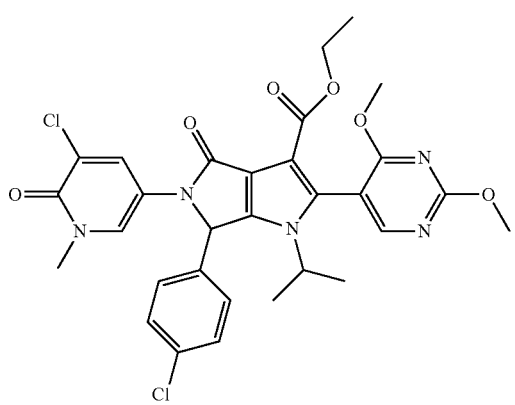 [SMILES: CCOC(=O)c1c2c(n(C(C)C)c1-c1cnc(OC)nc1OC)C(c1ccc(Cl)cc1)N(c1cc(Cl)c(=O)n(C)c1)C2=O]

The title compound was prepared in analogy to the procedure described for Example 17 but 2-bromo-5-(5-chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrole-3-carboxylic acid ethyl ester (Intermediate BM) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound was obtained as a white solid. $t_R$=1.10 min (HPLC 3); ESI-MS: $t_R$=1.05 min, [M+H]$^+$ 626/628 (LC-MS 1); TLC: $R_f$=0.05 (EtOAc).

EXAMPLE 221

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carboxylic acid

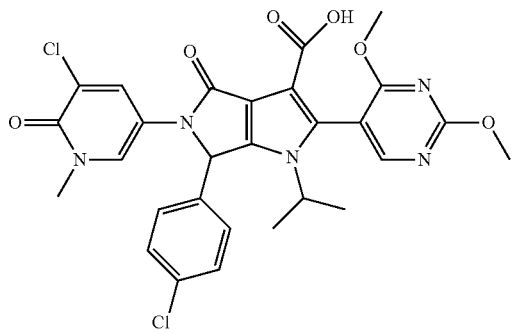 [SMILES: COc1ncc(-c2c(C(=O)O)c3c(n2C(C)C)C(c2ccc(Cl)cc2)N(c2cc(Cl)c(=O)n(C)c2)C3=O)c(OC)n1]

2N Aqueous NaOH (0.208 mmol) was added to a solution of 5-(5-chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carboxylic acid ethyl ester (Example 220) (0.104 mmol) in 1:1 THF/MeOH (2 mL) and the mixture was stirred at 80° C. for 1 h. After evaporation of MeOH, the pH was adjusted to 5 with addition of 10% w/w aqueous citric acid and extracted with EtOAc (3×). The combined organic phases were successively washed with H$_2$O and brine, dried (Na$_2$SO$_4$), filtered and concentrated. The residue was purified by SFC to afford the title compound as a white solid. $t_R$: 1.10 min (HPLC 3); ESI-MS: $t_R$=0.97 min, [M+H]$^+$ 598/600/602 (LC-MS 1); TLC: $R_f$=0.31 (9:1 CH$_2$Cl$_2$/MeOH).

EXAMPLE 222

4-[(R,S)-5-(3-Chloro-4-fluoro-phenyl)-2-(2,4-dimethoxy-pyrimidin-5-yl)-1-((R)-2-methoxy-1-methyl-ethyl)-4-oxo-1,4,5,6-tetrahydro-pyrrolo[3,4-b]pyrrol-6-yl]-benzonitrile

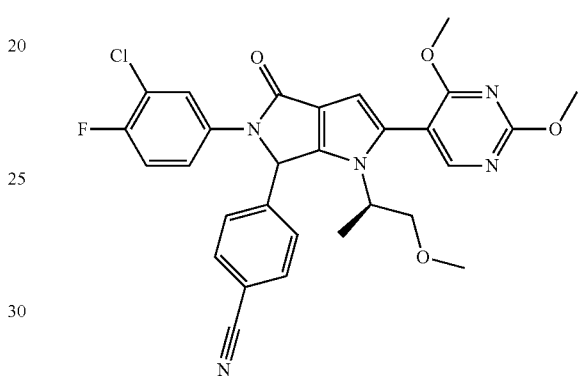

The title compound was prepared in analogy to the procedure described for Example 17 but (R,S)-4-[2-bromo-5-(3-chloro-4-fluoro-phenyl)-1-((R)-2-methoxy-1-methyl-ethyl)-4-oxo-1,4,5,6-tetrahydro-pyrrolo[3,4-b]pyrrol-6-yl]-benzonitrile (Intermediate BQ) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 5-cyano-2-methoxyphenylboronic acid respectively. The title compound (mixture of diastereomers) was obtained as a white solid. $t_R$=6.60/6.70 min (HPLC 2); ESI-MS: $t_R$=1.11/1.12 min, [M+H]$^+$ 562/564 (LC-MS 1).

EXAMPLE 223

4-[(R,S)-2-(2-Amino-4-methoxy-pyrimidin-5-yl)-5-(3-chloro-4-fluoro-phenyl)-1-(R)-2-methoxy-1-methyl-ethyl)-4-oxo-1,4,5,6-tetrahydro-pyrrolo[3,4-b]pyrrol-6-yl]-benzonitrile

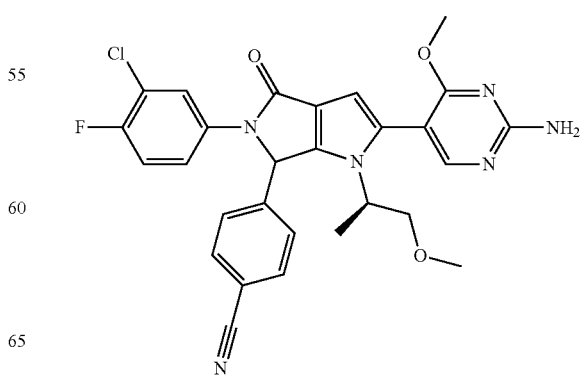

The title compound was prepared in analogy to the procedure described for Example 222 but 4-methoxy-5-(4,4,5,5-tetramethyl-[1,3,2]dioxaborolan-2-yl)-pyrimidin-2-ylamine (Intermediate U) was used instead of 2,4-dimethoxypyrimidine-5-boronic acid. The title compound (mixture of diastereomers) was obtained as an off-white solid. $t_R$=5.74 min (HPLC 2); ESI-MS: $t_R$=0.97/0.99 min, [M+H]$^+$ 547/549 (LC-MS 1).

EXAMPLE 224

(R,S)-2-(2-Amino-4-methoxy-pyrimidin-5-yl)-5-(3-chloro-4-fluoro-phenyl)-6-(4-chloro-phenyl)-1-(R)-2-methoxy-1-methyl-ethyl)-5,6-dihydro-1H-pyrrolo[3,4-b]pyrrol-4-one

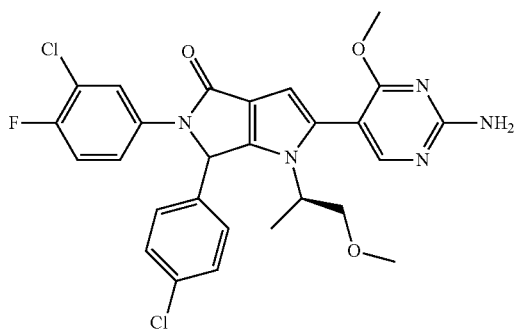 [SMILES: COC[C@@H](C)n1c(-c2cnc(N)nc2OC)cc2c1C(c1ccc(Cl)cc1)N(c1ccc(F)c(Cl)c1)C2=O]

The title compound was prepared in analogy to the procedure described for Example 223 but (R,S)-2-bromo-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one (Intermediate BO) was used instead of (R,S)-4-[2-bromo-5-(3-chloro-4-fluoro-phenyl)-1-((R)-2-methoxy-1-methyl-ethyl)-4-oxo-1,4,5,6-tetrahydro-pyrrolo[3,4-b]pyrrol-6-yl]-benzonitrile. The title compound (mixture of diastereomers) was obtained as a light yellow solid. $t_R$=6.15/6.26 min (HPLC 2); ESI-MS: $t_R$=1.11/1.13 min, [M+H]$^+$ 556/558/560 (LC-MS 1).

EXAMPLE 225

(R,S)-5-(5-Chloro-1-methyl-6-oxo-1,6-dihydro-pyridin-3-yl)-6-(4-chloro-phenyl)-2-[2,4-dimethoxy-pyrimidin-5-yl)-1-(R)-2-methoxy-1-methyl-ethyl)-5,6-dihydro-1H-pyrrolo[3,4-b]pyrrol-4-one

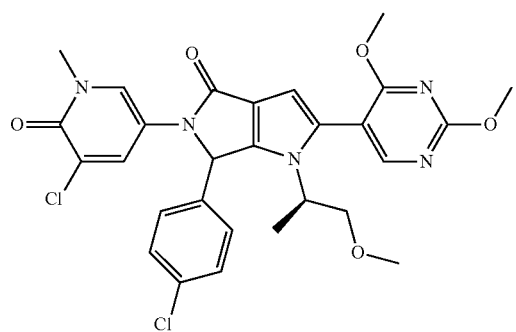 [SMILES: COC[C@@H](C)n1c(-c2cnc(OC)nc2OC)cc2c1C(c1ccc(Cl)cc1)N(c1cc(Cl)c(=O)n(C)c1)C2=O]

The title compound was prepared in analogy to the procedure described for Example 222 but (R,S)-2-bromo-5-(5-chloro-1-methyl-6-oxo-1,6-dihydro-pyridin-3-yl)-6-(4-chloro-phenyl)-1-((R)-2-methoxy-1-methyl-ethyl)-5,6-dihydro-1H-pyrrolo[3,4-b]pyrrol-4-one (Intermediate BP) was used instead of (R,S)-4-[2-bromo-5-(3-chloro-4-fluoro-phenyl)-1-((R)-2-methoxy-1-methyl-ethyl)-4-oxo-1,4,5,6-tetrahydro-pyrrolo[3,4-b]pyrrol-6-yl]benzonitrile. The title compound (mixture of diastereomers) was obtained as a white solid. $t_R$=6.07/6.22 min (HPLC 2); ESI-MS: $t_R$=1.02/1.04 min, [M+H]$^+$ 584/586/588 (LC-MS 1).

EXAMPLE 226

5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-4-oxo-1,4,5,6-tetrahydro-pyrrolo[3,4-b]pyrrole-3-carboxylic acid

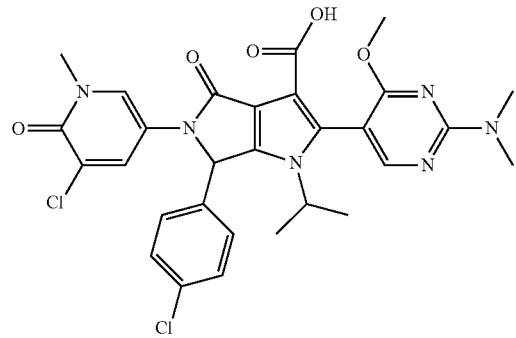 [SMILES: COc1nc(N(C)C)ncc1-c1c(C(=O)O)c2c(n1C(C)C)C(c1ccc(Cl)cc1)N(c1cc(Cl)c(=O)n(C)c1)C2=O]

The title compound was prepared in analogy to the procedures described for Example 220 and Example 221 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. The title compound was obtained as a white solid. $t_R$=5.34 min (HPLC 2); ESI-MS: $t_R$=1.08 min, [M+H]$^+$611/613 (LC-MS 1); TLC: $R_f$=0.38 (9:1 CH$_2$Cl$_2$/MeOH).

EXAMPLE 227

(S)-6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one

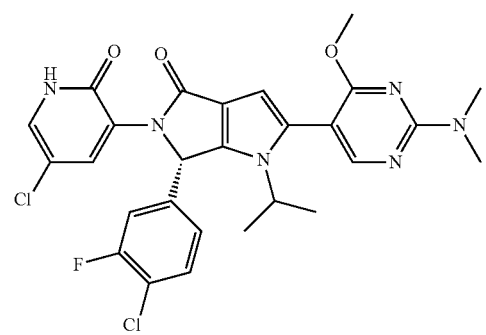

6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one (Example 203) was purified by chiral chromatography (Chiral-HPLC 4) to afford the title compound as a white solid. $t_R$: 3.68 min (Column: Lux Cel2, 4.6×250 mm. Flow 3 mL/min. scCO$_2$/MeOH 50:50); $t_R$: 5.55 min (HPLC 2); ESI-MS: $t_R$=1.16 min, [M+H]$^+$ 571/573 (LC-MS 1).

EXAMPLE 228

(R)-6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one

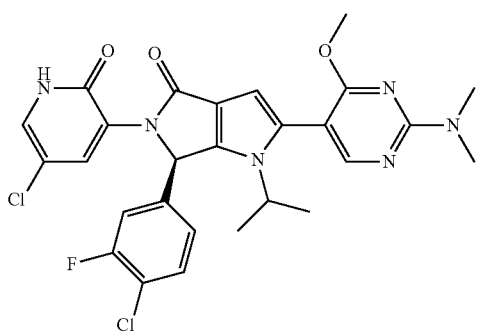 [SMILES: COc1nc(N(C)C)ncc1-c1cc2c(n1C(C)C)[C@@H](c1ccc(Cl)c(F)c1)N(c1cc(Cl)c[nH]c1=O)C2=O]

6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one (Example 203) was purified by chiral chromatography (Chiral-HPLC 4) to afford the title compound as a white solid. $t_R$: 6.39 min (Column: Lux Cel2, 4.6×250 mm. Flow 3 mL/min. scCO$_2$/MeOH 50:50); $t_R$: 5.59 min (HPLC 2); ESI-MS: $t_R$=1.16 min, [M+H]$^+$ 571/573 (LC-MS 1).

EXAMPLE 229

(S)-2-(2-Amino-4-methoxy-pyrimidin-5-yl)-5-(3-chloro-4-fluoro-phenyl)-6-(4-chloro-phenyl)-1-(R)-2-methoxy-1-methyl-ethyl)-5,6-dihydro-1H-pyrrolo[3,4-b]pyrrol-4-one

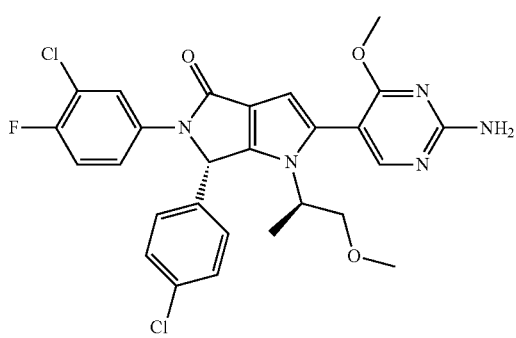 [SMILES: COC[C@@H](C)n1c(-c2cnc(N)nc2OC)cc2c1[C@H](c1ccc(Cl)cc1)N(c1ccc(F)c(Cl)c1)C2=O]

(R,S)-2-(2-Amino-4-methoxy-pyrimidin-5-yl)-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one (Example 224) was purified by chiral chromatography (Chiral-HPLC 3 with 70:30 scCO$_2$/(MeOH+1% isopropylamine)) to afford the title compound as a white solid. $t_R$: 2.16 min (Column: Chiralpak AS-H, 4.6× 250 mm. Flow 3 mL/min. scCO$_2$/(MeOH+1% isopropylamine) 70:30); $t_R$: 6.24 min (HPLC 2); ESI-MS: $t_R$=1.16 min, [M+H]$^+$ 556/558 (LC-MS 1).

EXAMPLE 230

(R)-2-(2-Amino-4-methoxy-pyrimidin-5-yl)-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one

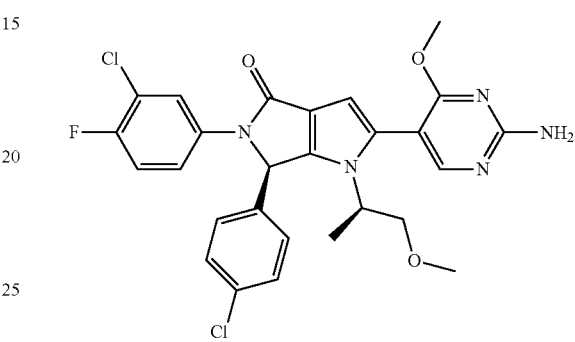

(R,S)-2-(2-Amino-4-methoxy-pyrimidin-5-yl)-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one (Example 224) was purified by chiral chromatography (Chiral-HPLC 3 with 70:30 scCO$_2$/(MeOH+1% isopropylamine)) to afford the title compound as a white solid. $t_R$: 4.01 min (Column: Chiralpak AS-H, 4.6× 250 mm. Flow 3 mL/min. scCO$_2$/(MeOH+1% isopropylamine) 70:30); $t_R$: 6.17 min (HPLC 2); ESI-MS: $t_R$=1.15 min, [M+H]$^+$ 556/558 (LC-MS 1).

EXAMPLE 231

4-(2-(2-(Dimethylamino)-4-methoxypyrimidin-5-yl)-5-(4-fluoro-1,3-dimethyl-1H-pyrazol-5-yl)-1-isopropyl-4-oxo-1,4,5,6-tetrahydropyrrolo[3,4-b]ppyrrol-6-yl)benzonitrile

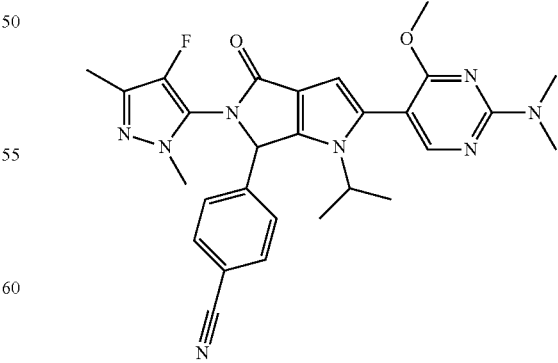

The title compound was prepared in analogy to the procedure described for Example 211 but 4-methoxy-N,N-dimethyl-5-(4,4,5,5-tetramethyl-1,3,2-dioxaborolan-2-yl)pyrimidin-2-amine (Intermediate W) was used instead of 2,4-dimethoxypyrimidine-5-boronic acid. ESI-MS: $t_R$=1.13 min, [M+H]$^+$ 529 (LC-MS 1).

EXAMPLE 232

(S)-4-(5-(5-Chloro-1-methyl-6-oxo-1,6-dihydropyridin-3-yl)-2-(2-(dimethylamino)-4-methoxypyrimidin-5-yl)-1-isopropyl-4-oxo-1,4,5,6-tetrahydropyrrolo[3,4-b]pyrrol-6-yl)benzonitrile

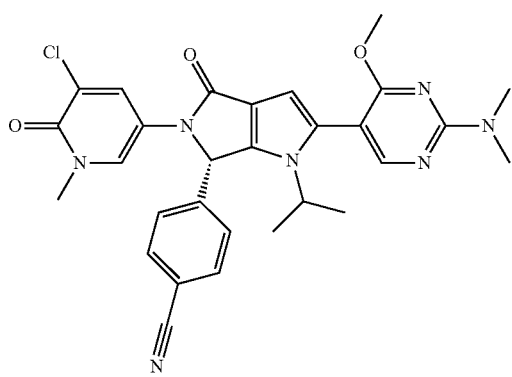 [SMILES: COc1nc(N(C)C)ncc1-c1cc2c(n1C(C)C)[C@H](c1ccc(C#N)cc1)N(c1cc(Cl)c(=O)n(C)c1)C2=O]

4-[5-(5-Chloro-1-methyl-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile (Example 185) was purified by chiral chromatography (Chiral-HPLC 10) to afford the title compound as a beige solid. $t_R$: 11.14 min (Column: Chiralpak IC, 4.6×250 mm. Flow 1 mL/min. 1:1 EtOH/MeOH; ESI-MS: $t_R$=1.00 min, [M+H]$^+$ 558/560 (LC-MS 1).

EXAMPLE 233

(R)-4-(5-(5-Chloro-1-methyl-6-oxo-1,6-dihydropyridin-3-yl)-2-(2-(dimethylamino)-4-methoxypyrimidin-5-yl)-1-isopropyl-4-oxo-1,4,5,6-tetrahydropyrrolo[3,4-b]pyrrol-6-yl)benzonitrile

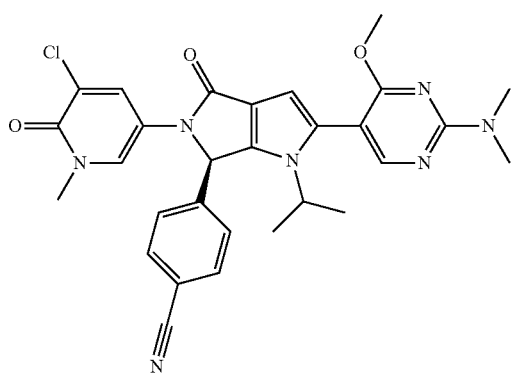 [SMILES: COc1nc(N(C)C)ncc1-c1cc2c(n1C(C)C)[C@@H](c1ccc(C#N)cc1)N(c1cc(Cl)c(=O)n(C)c1)C2=O]

4-[5-(5-Chloro-1-methyl-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile (Example 185) was purified by chiral chromatography (Chiral-HPLC 10) to afford the title compound as a white solid. $t_R$: 14.38 min (Column: Chiralpak IC, 4.6×250 mm. Flow 1 mL/min. 1:1 EtOH/MeOH; ESI-MS: $t_R$=1.02 min, [M+H]$^+$ 558/560 (LC-MS 1).

EXAMPLE 234

5-(3-Chloro-2-fluorophenyl)-6-(5-chloropyridin-2-yl)-2-(2-(dimethylamino)-4-methoxypyrimidin-5-yl)-1-isopropyl-5,6-dihydropyrrolo[3,4-b]pyrrol-4(1H)-one

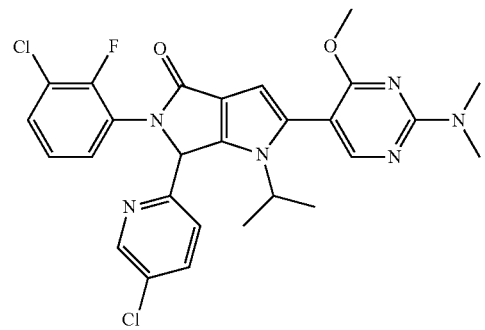 [SMILES: COc1nc(N(C)C)ncc1-c1cc2c(n1C(C)C)C(c1ccc(Cl)cn1)N(c1cccc(Cl)c1F)C2=O]

The title compound was prepared in analogy to the procedure described for Example 25 but 2-bromo-5-(3-chloro-2-fluorophenyl)-6-(5-chloropyridin-2-yl)-1-isopropyl-5,6-dihydropyrrolo[3,4-b]pyrrol-4(1H)-one (Intermediate BT) and 4-methoxy-N,N-dimethyl-5-(4,4,5,5-tetramethyl-1,3,2-dioxaborolan-2-yl)pyrimidin-2-amine (Intermediate W) were used instead of 2-bromo-5-(5-chloro-2-methyl-phenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a brown solid. ESI-MS: $t_R$=1.32 min, [M+H]$^+$ 555/557/559 (LC-MS 1).

EXAMPLE 235

5-(5-Chloro-2-methylphenyl)-6-(5-chloropyridin-2-yl)-2-(2,4-dimethoxypyrimidin-5-yl)-1-isopropyl-1-5,6-dihydropyrrolo[3,4-b]pyrrol-4(1H)-one

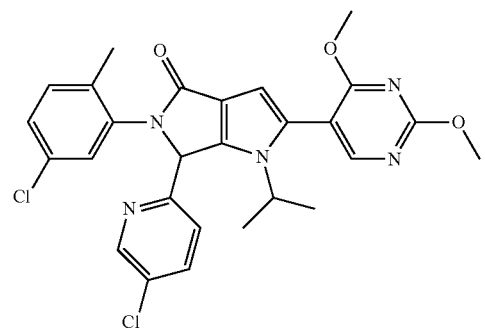 [SMILES: COc1ncc(-c2cc3c(n2C(C)C)C(c2ccc(Cl)cn2)N(c2cc(Cl)ccc2C)C3=O)c(OC)n1]

The title compound was prepared in analogy to the procedure described for Example 25 but 2-bromo-5-(5-chloro-2-methylphenyl)-6-(5-chloropyridin-2-yl)-1-isopropyl-5,6-dihydropyrrolo[3,4-b]pyrrol-4(1H)-one (Intermediate BU) and 2,4-dimethoxypyrimidine-5-boronic acid were used instead of 2-bromo-5-(5-chloro-2-methyl-phenyl)-6-(4-chloro-phenyl)-1-isopropyl-5,6-dihydro-1H-pyrrolo[3,4-b]pyrrol-4- one and 4-methoxy-5-(4,4,5,5-tetramethyl-[1,3,2]dioxaborolan-2-yl)-pyrimidin-2-ylamine respectively. The title compound was obtained as a white solid. ESI-MS: $t_R$=1.23 min, [M+H]$^+$ 538/540 (LC-MS 1).

EXAMPLE 236

4-(5-(5-Chloro-1-methyl-6-oxo-1,6-dihydropyridin-3-yl)-1-isopropyl-2-(4-methoxypyrimidin-5-yl)-4-oxo-1,4,5,6-tetrahydropyrrolo[3,4-b]pyrrol-6-yl)benzonitrile

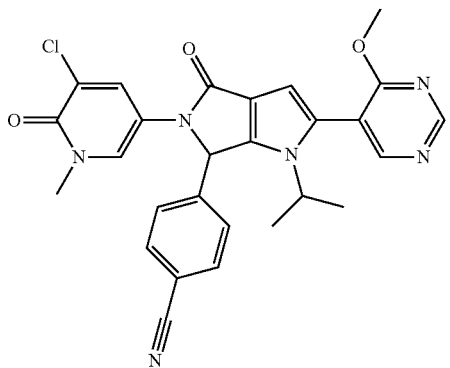 [SMILES: COc1ncncc1-c1cc2c(n1C(C)C)C(c1ccc(C#N)cc1)N(c1cc(Cl)c(=O)n(C)c1)C2=O]

The title compound was prepared in analogy to the procedure described for Example 153 but 4-methoxy-5-(4,4,5,5-tetramethyl-[1,3,2]dioxaborolan-2-yl)-pyrimidine (Intermediate T) was used instead of 2,4-dimethoxypyrimidine-5-boronic acid. The title compound was obtained as a beige solid. ESI-MS: $t_R$=0.84 min, [M+H]$^+$ 515/517 (LC-MS 1).

EXAMPLE 237

(S)-4-(5-(5-Chloro-1-methyl-6-oxo-1,6-dihydropyridin-3-yl)-2-(2,4-dimethoxypyrimidin-5-yl)-1-isopropyl-4-oxo-1,4,5,6-tetrahydropyrrolo[3,4-b]pyrrol-6-yl)-2-fluorobenzonitrile

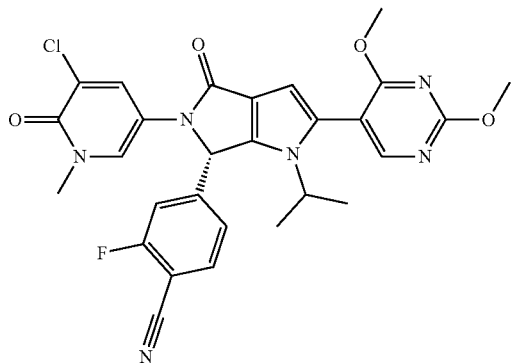 [SMILES: COc1ncc(-c2cc3c(n2C(C)C)[C@H](c2ccc(C#N)c(F)c2)N(c2cc(Cl)c(=O)n(C)c2)C3=O)c(OC)n1]

4-[5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile (Example 195) was purified by chiral chromatography (Chiral-HPLC 8 using 70:15:15 heptane/EtOH/MeOH, 12 mL/min) to afford the title compound as a white solid. $t_R$: 5.28 min (Column: Chiralpak IA, 4.6×250 mm. Flow 1 mL/min. 60:20:20 heptane/EtOH/MeOH; ESI-MS: $t_R$=0.95 min, [M+H]$^+$ 563/565 (LC-MS 1).

EXAMPLE 238

(R)-4-(5-(5-Chloro-1-methyl-6-oxo-1,6-dihydropyridin-3-yl)-2-(2,4-dimethoxypyrimidin-5-yl)-1-isopropyl-4-oxo-1,4,5,6-tetrahydropyrrolo[3,4-b]pyrrol-6-yl)-2-fluorobenzonitrile

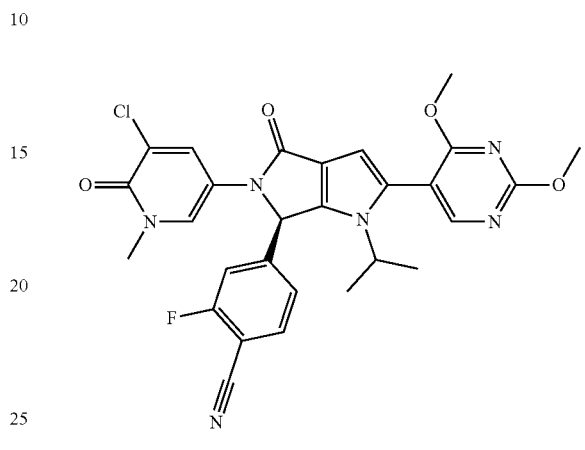

4-[5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile (Example 195) was purified by chiral chromatography (Chiral-HPLC 8 using 70:15:15 heptane/EtOH/MeOH, 12 mL/min) to afford the title compound as a white solid. $t_R$: 8.47 min (Column: Chiralpak IA, 4.6×250 mm. Flow 1 mL/min. 60:20:20 heptane/EtOH/MeOH; ESI-MS: $t_R$=0.95 min, [M+H]$^+$ 563/565 (LC-MS 1).

EXAMPLE 239

6-(4-Chlorophenyl-1)-2-(2,4-dimethoxypyrimidin-5-yl)-5-(1,5-dimethyl-2-oxo-1,2-dihydropyridin-3-yl)-1-isopropyl-5,6-dihydropyrrolo[3,4-b]pyrrol-4(1H)-one

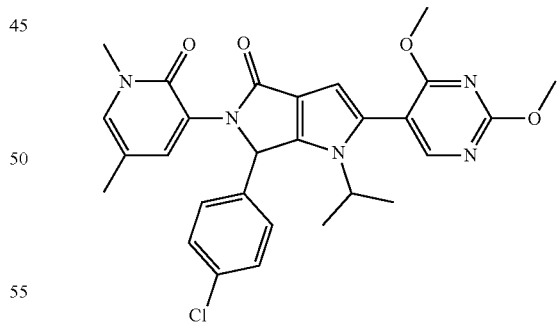

The title compound was prepared in analogy to the procedure described for Example 25 but 2-bromo-6-(4-chlorophenyl)-5-(1,5-dimethyl-2-oxo-1,2-dihydropyridin-3-yl)-1-isopropyl-5,6-dihydropyrrolo[3,4-b]pyrrol-4(1H)-one (Intermediate BV) and 2,4-dimethoxypyrimidine-5-boronic acid were used instead of 2-bromo-5-(5-chloro-2-methylphenyl)-6-(4-chloro-phenyl)-1-isopropyl-5,6-dihydro-1H-pyrrolo[3,4-b]pyrrol-4-one and 4-methoxy-5-(4,4,5,5-tetramethyl-[1,3,2]dioxaborolan-2-yl)-pyrimidin-2-ylamine respectively. The title compound was obtained as a white solid. ESI-MS: $t_R$=1.07 min, [M+H]$^+$ 534/536 (LC-MS 1).

EXAMPLE 240

6-(4-Chlorophenyl-1)-1-cyclopropyl-2-(2,4-dimethoxypyrimidin-5-yl)-5-(1,5-dimethyl-6-oxo-1,6-dihydropyridin-3-yl)-5,6-dihydropyrrolo[3,4-b]pyrrol-4(1H)-one

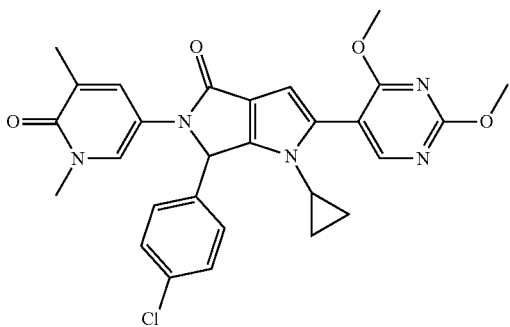 [SMILES: COc1ncc(-c2cc3c(n2C2CC2)C(c2ccc(Cl)cc2)N(c2cc(C)c(=O)n(C)c2)C3=O)c(OC)n1]

[1,1'-Bis(diphenylphosphino)ferrocene]dichloropalladium(II)dichloromethane complex (39 mg, 0.032 mmol) was added to a stirred solution of 2-bromo-6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one (Step 240.1) (150 mg, 0.317 mmol) and potassium phosphate tribasic (269 mg, 1.269 mmol) (3 in dioxane (3 mL) and water (1 mL) at 80° C. Then, (88 mg, 0.476 mmol) was added at 110° C. Reactants were stirred at 110° C. for 15 min. 2,4-Dimethoxypyrimidin-5-ylboronic acid (88 mg, 0.476 mmol) was added. The reaction mixture was stirred at 110° C. for 15 min, diluted in CH$_2$Cl$_2$/water, and extracted twice with CH$_2$Cl$_2$. The combined organic extracts were washed with brine, dried (Na$_2$SO$_4$), and concentrated. The crude product was loaded onto a Varian PL-Thiol MP SPE cartridge (to remove residual metals traces) and eluted with MeOH. After concentration, the residue was purified by silica gel column chromatography (CH$_2$Cl$_2$/MeOH/NH$_3$ 94:5:1) to afford a yellow solid. This solid was purified by SFC (Thar 100, column CN-Diol, 25 cm, Ø3 cm, 5 µm, 60 Å; flow 100 mL/min; gradient: 15% B for 1 min, 15-20% B over 6 min, 20-50% B over 1 min, 50% B for 1.5 min, 50%-15% B in 1 min, 15% for 0.5 min; A: scCO$_2$, B: MeOH) followed by trituration in diethyl ether to provide the title compound (54 mg, 34% yield) as a white solid. $t_R$: 1.00 min (LC-MS 6); ESI-MS: 532.2 [M+H]$^+$ (LC-MS 6); TLC (CH$_2$Cl$_2$/MeOH/NH$_3$ 94:5:1): R$_f$=0.28; $^1$H NMR (400 MHz, DMSO-d$_6$) δ ppm 0.08-0.26 (m, 1 H) 0.46-0.70 (m, 2 H) 0.95-1.08 (m, 1 H) 1.92 (s, 3 H) 2.74-2.90 (m, 1 H) 3.34 (s, 3 H) 3.92 (s, 3 H) 3.87 (s, 3 H) 6.24 (s, 1 H) 6.37 (s, 1 H) 7.22-7.34 (m, 2 H) 7.34-7.45 (m, 3 H) 7.62 (d, J=2.74 Hz, 1 H) 8.31 (s, 1 H).

Step 240.1: 2-Bromo-6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one

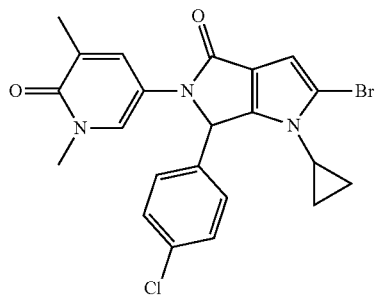 [SMILES: Cc1cc(N2C(=O)c3cc(Br)n(C4CC4)c3C2c2ccc(Cl)cc2)cn(C)c1=O]

NBS (0.497 g, 2.79 mmol) was added to a mixture of 6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one (Step 240.2) (1.1 g, 2.79 mmol) in CCl$_4$ (40 mL) at 0° C. The reaction mixture was stirred for 40 h at rt, concentrated, diluted with EtOAc/water, and extracted twice with EtOAc. The combined organic extracts were washed with brine, dried (Na$_2$SO$_4$), and concentrated. The crude product was purified by silica gel column chromatography (CH$_2$Cl$_2$/MeOH 95:5) to afford a white solid and mixed fractions. The mixed fractions were purified by SFC (column 2-EP 250×30 mm, 5 µm, 60 Å, Princeton; flow 100 mL/min; gradient: isocratic 5% B for 25 min; A: scCO$_2$, B: MeOH) to afford a white solid. Both solids were dissolved in CH$_2$Cl$_2$ and concentrated to afford the title compound (935 mg, 70.8% yield) as a white solid. $t_R$: 1.07 min (LC-MS 6); ESI-MS: 472.1/474.1 [M+H]$^+$ (LC-MS 6); TLC (CH$_2$Cl$_2$/MeOH 95:5): R$_f$=0.27.

Step 240.2: 6-(4-Chlorophenyl)-1-cyclopropyl-5-(1,5-dimethyl-6-oxo-1,6-dihydropyridin-3-yl)-5,6-dihydropyrrolo[3,4-b]pyrrol-4(1H)-one

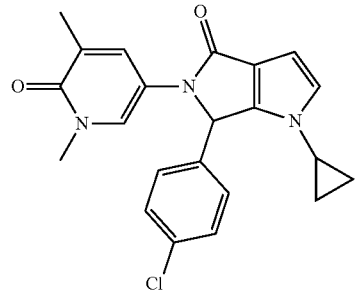 [SMILES: Cc1cc(N2C(=O)c3ccn(C4CC4)c3C2c2ccc(Cl)cc2)cn(C)c1=O]

1-Chloro-N,N-2-trimethyl-1-propenylamine (0.899 mL, 6.80 mmol) was added to a solution of 2-((4-chlorophenyl)((1,5-dimethyl-6-oxo-1,6-dihydropyridin-3-yl)amino)methyl)-1-cyclopropyl-1H-pyrrole-3-carboxylic acid (Step 240.3) (2 g, 4.86 mmol) in CH$_2$Cl$_2$ (40 mL) at 5° C. The reaction mixture was stirred at RT for 30 min, diluted in CH$_2$Cl$_2$ and a saturated aqueous solution of sodium bicarbonate, and extracted twice with CH$_2$Cl$_2$. The combined organic extracts were washed with water and brine, dried (Na$_2$SO$_4$), and concentrated. The crude product was purified by silica gel column chromatography (CH$_2$Cl$_2$/MeOH 95:5) to afford a red foam. This foam was refluxed in Et$_2$O for 3 hrs. The title compound (1.35 g, 70.6% yield) was collected by filtration and obtained as an off-white solid. $t_R$: 0.95 min (LC-MS 6); ESI-MS: 394.2 [M+H]$^+$ (LC-MS 6); TLC (CH$_2$Cl$_2$/MeOH 95:5): R$_f$=0.30.

Step 240.3: 2-((4-Chlorophenyl)((1,5-dimethyl-6-oxo-1,6-dihydropyridin-3-yl)amino)methyl)-1-cyclopropyl-1H-pyrrole-3-carboxylic acid

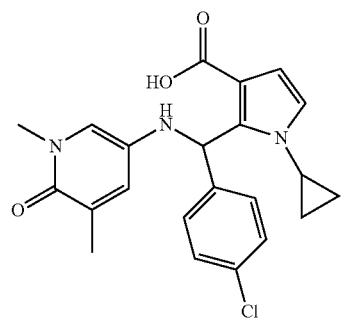 [SMILES: Cc1cc(NC(c2ccc(Cl)cc2)c2c(C(=O)O)ccn2C2CC2)cn(C)c1=O]

A mixture of methyl 2-((4-chlorophenyl)((1,5-dimethyl-6-oxo-1,6-dihydropyridin-3-yl)amino)methyl)-1-cyclopropyl-1H-pyrrole-3-carboxylate (Step 240.4) (2.2 g, 5.17 mmol) and 2M NaOH (20.7 mL, 41.3 mmol) in THF (20 mL) and MeOH (20 mL) was stirred at 70° C. for 2 hr and concentrated. The aqueous residue was acidified with 2N HCl to pH 5, and extracted twice with EtOAc. The combined organic extracts were washed with brine, dried (Na$_2$SO$_4$), and concentrated to afford the title compound (2 g, 89% yield) as a red foam. t$_R$: 0.94 min (LC-MS 6); ESI-MS: 412.2 [M+H]$^+$ (LC-MS 6).

Step 240.4: Methyl 2-((4-chlorophenyl)((1,5-dimethyl-6-oxo-1,6-dihydropyridin-3-yl)amino)methyl)-1-cyclopropyl-1H-pyrrole-3-carboxylate

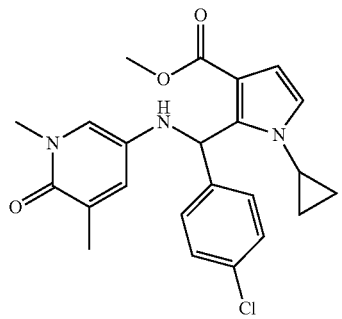 [SMILES: COC(=O)c1ccn(C2CC2)c1C(Nc1cc(C)c(=O)n(C)c1)c1ccc(Cl)cc1]

Methanesulfonic anhydride (3.42 g, 19.62 mmol) was added at −40° C. to a stirred solution of methyl 2-((4-chlorophenyl)(hydroxy)methyl)-1-cyclopropyl-1H-pyrrole-3-carboxylate (Step 240.5) (3 g, 9.81 mmol) and triethylamine (6.84 mL, 49.1 mmol) in CH$_2$Cl$_2$ (60 mL). After 15 min at −40° C., 5-amino-1,3-dimethylpyridin-2(1H)-one (Step 240.7) (1.762 g, 12.76 mmol) was added. The resulting mixture was allowed to warm from −40° C. to rt over 18 hr under stirring, diluted in CH$_2$Cl$_2$//water, and extracted twice with CH$_2$Cl$_2$. The combined organic extracts were dried and concentrated. The crude material was purified by silica gel column chromatography (CH$_2$Cl$_2$/MeOH 97.5:2.5) to afford the title compound (2.2 g, 51.6% yield) as a brown foam. t$_R$: 1.13 min (LC-MS 6); ESI-MS: 426.2 [M+H]$^+$ (LC-MS 6); TLC (CH$_2$Cl$_2$/MeOH 97.5:2.5): R$_f$=0.29.

Step 240.5: Methyl 2-((4-chlorophenyl)(hydroxy)methyl)-1-cyclopropyl-1H-pyrrole-3-carboxylate

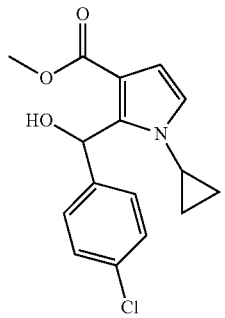 [SMILES: COC(=O)c1ccn(C2CC2)c1C(O)c1ccc(Cl)cc1]

LDA (1.8M, 18.97 mL, 34.2 mmol) was added dropwise to a solution of methyl 1-cyclopropyl-1H-pyrrole-3-carboxylate (Step 240.6) (4.03 g, 24.40 mmol) in THF (80 mL) at −78° C. and the mixture was stirred for 30 min. A solution of 4-chlorobenzaldehyde (3.77 g, 26.8 mmol) in THF (20 mL) was added at −78° C. The mixture was allowed to warm to −50° C. over 2 hrs, quenched with a saturated aqueous solution of ammonium chloride, and taken up in EtOAc/saturated ammonium chloride solution. The aqueous layer was separated and extracted twice with EtOAc. The combined organic extracts were washed with brine, dried (Na$_2$SO$_4$), and concentrated. The crude material was purified by silica gel column chromatography (hexane/EtOAc 4:1) to afford the title compound (6.1 g, 79% yield) as a yellow solid. TLC (hexane/EtOAc 4:1): R$_f$=0.21.

Step 240.6: Methyl 1-cyclopropyl-1H-pyrrole-3-carboxylate

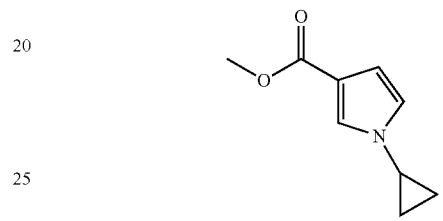

A mixture of methyl 1H-pyrrole-3-carboxylate (500 mg, 4.00 mmol), cyclopropylboronic acid (686 mg, 7.99 mmol), copper(II) acetate (726 mg, 4.00 mmol), 2,2'-bipyridyl (624 mg, 4.00 mmol), sodium carbonate (847 mg, 7.99 mmol) was stirred at 70° C. for 16 hr, concentrated, diluted in EtOAc/water, and extracted twice with EtOAc. The combined organic extracts were washed with brine, dried (Na$_2$SO$_4$), and concentrated. The crude material was purified by silica gel column chromatography (hexane/EtOAc 4:1) to afford the title compound (377 mg, 57% yield) as a yellow oil. TLC (hexane/EtOAc 4:1): R$_f$=0.26.

Step 240.7: 5-Amino-1,3-dimethylpyridin-2(1H)-one

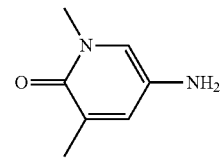

A mixture of 1,3-dimethyl-5-nitropyridin-2(1H)-one (8.315 g, 49.4 mmol) and Pd/C 10% (1 g) in MeOH (100 mL) and THF (100 mL) was stirred under an atmospheric pressure of H$_2$ at RT for 1.5 hr, filtered through celite, and concentrated. The residue was triturated in Et$_2$O to afford the title compound (6.12 g, 90% yield) as a beige solid. $^1$H NMR (400 MHz, DMSO-d$_6$) δ ppm 1.94 (s, 3 H) 3.31 (s, 3 H covered by water signal) 4.15 (br s, 2 H) 6.70 (s, 1 H) 6.95 (s, 1 H).

Step 240.8: 1,3-Dimethyl-5-nitropyridin-2(1H)-one

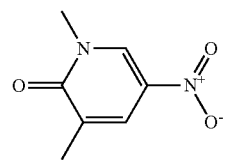

The title compound was prepared in analogy to the procedure described in Step E6 starting with 3-methyl-5-nitropyridin-2-ol. $t_R$: 0.59 min (LC-MS 6); ESI-MS: 169.1 [M+H]$^+$ (LC-MS 6).

EXAMPLE 241

6-(4-Chlorophenyl)-1-cyclopropyl-5-(1,5-dimethyl-6-oxo-1,6-dihydropyridin-3-yl)-2-(2-methoxypyrimidin-5-yl)-5,6-dihydropyrrolo[3,4-b]pyrrol-4(1H)-one

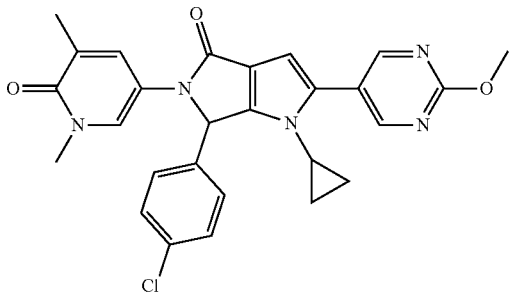 [SMILES: COc1ncc(-c2cc3c(n2C2CC2)C(c2ccc(Cl)cc2)N(c2cc(C)c(=O)n(C)c2)C3=O)cn1]

The title compound was prepared in analogy to the procedure described in Example 240 but using (2-methoxypyrimidin-5-yl)boronic acid [628692-15-9]. $t_R$: 0.94 min (LC-MS 6); ESI-MS: 502.2 [M+H]$^+$ (LC-MS 6); TLC (CH$_2$Cl$_2$/MeOH/NH$_3$ 94:5:1): R$_f$=0.32; $^1$H NMR (400 MHz, DMSO-d$_6$) δ ppm 0.15-0.40 (m, 1 H) 0.61-0.86 (m, 2 H) 1.12-1.27 (m, 1 H) 1.92 (s, 3 H) 3.11-3.21 (m, 1 H) 3.35 (s, 3 H) 3.94 (s, 3 H) 6.28 (s, 1 H) 6.63 (s, 1 H) 7.26-7.36 (m, 2 H) 7.36-7.48 (m, 3 H) 7.65 (d, J=2.34 Hz, 1 H) 8.82 (s, 2 H).

EXAMPLE 242

6-(4-Chlorophenyl)-1-cyclopropyl-5-(1,5-dimethyl-6-oxo-1,6-dihydropyridin-3-yl)-2-(1-methyl-2-oxo-1,2-dihydropyridin-4-yl)-5,6-dihydropyrrolo[3,4-b]pyrrol-4(1H)-one

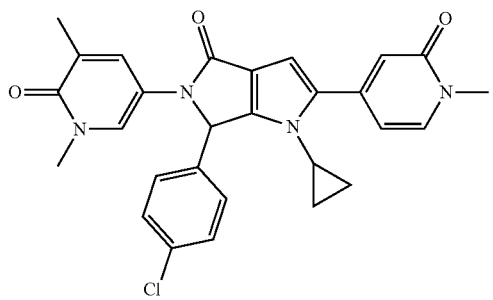 [SMILES: Cc1cc(N2C(=O)c3cc(-c4ccn(C)c(=O)c4)n(C4CC4)c3C2c2ccc(Cl)cc2)cn(C)c1=O]

The title compound was prepared in analogy to the procedure described in Example 240 but using 1-methyl-4-(4,4,5,5-tetramethyl-1,3,2-dioxaborolan-2-yl)pyridin-2(1H)-one (Step 242.1). $t_R$: 0.80 min (LC-MS 6); ESI-MS: 501.2 [M+H]$^+$ (LC-MS 6); TLC (CH$_2$Cl$_2$/MeOH/NH$_3$ 94:5:1): R$_f$=0.18; $^1$H NMR (400 MHz, DMSO-d$_6$) δ ppm 0.36-0.46 (m, 1 H) 0.68-0.89 (m, 2 H) 1.15-1.28 (m, 1 H) 1.91 (s, 3 H) 3.07-3.17 (m, 1 H) 3.34 (s, 3 H) 3.39 (s, 3 H) 6.25 (s, 1 H) 6.49 (dd, J=7.04, 1.96 Hz, 1 H) 6.58 (d, J=1.96 Hz, 1 H) 6.71 (s, 1 H) 7.21-7.34 (m, 2 H) 7.34-7.44 (m, 3 H) 7.56-7.70 (m, 2 H).

Step 242.1: 1-Methyl-4-(4,4,5,5-tetramethyl-1,3,2-dioxaborolan-2-yl)pyridin-2(1H)-one

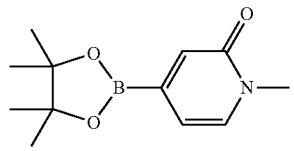

A mixture of 4-bromo-1-methylpyridin-2(1H)-one (1.11 g, 5.90 mmol), bis(pinacolato)diboron (1.799 g, 7.08 mmol), [1,1'-bis(diphenylphosphino)ferrocene]dichloropalladium (II) dichloromethane complex (579 mg, 0.708 mmol), and potassium acetate (1.738 g, 17.71 mmol) in dioxane (20 mL) was stirred at 110° C. for 2 hr, diluted with toluene, sonicated for 30 min at 40° C., filtered (rinsing the filter cake with hot toluene) and concentrated to afford a brown oil, which was used without further purification. $t_R$: 0.29 min (LC-MS 6); ESI-MS: 154.1 (boronic acid) [M+H]$^+$ (LC-MS 6).

EXAMPLE 243

5-(5-Chloro-1-methyl-6-oxo-1,6-dihydropyridin-3-yl)-6-(4-chlorophenyl)-1-cyclopropyl-2-(1-methyl-2-oxo-1,2-dihydropyridin-4-yl)-5,6-dihydropyrrolo[3,4-b]pyrrol-4(1H)-one

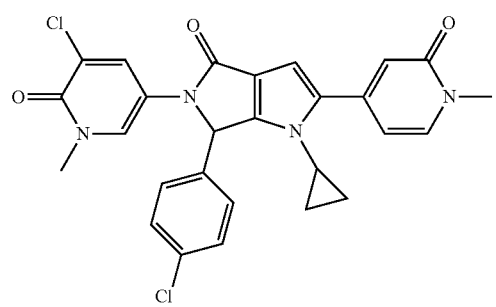 [SMILES: Cn1ccc(-c2cc3c(n2C2CC2)C(c2ccc(Cl)cc2)N(c2cc(Cl)c(=O)n(C)c2)C3=O)cc1=O]

The title compound was prepared in analogy to the procedure described in Example 240 but using 1-methyl-4-(4,4,5,5-tetramethyl-1,3,2-dioxaborolan-2-yl)pyridin-2(1H)-one (Step 242.1) and 2-bromo-5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one (Step 250.1). $t_R$: 0.83 min (LC-MS 6); ESI-MS: 521.2/523.2 [M+H]$^+$ (LC-MS 6); TLC (CH$_2$Cl$_2$/MeOH/NH$_3$ 94:5:1): R$_f$=0.18; $^1$H NMR (400 MHz, DMSO-d$_6$) δ ppm 0.35-0.450 (m, 1 H) 0.74-0.84 (m, 2 H) 1.12-1.25 (m, 1 H) 3.06-3.18 (m, 1 H) 3.41 (s, 3 H) 3.37 (s, 3 H) 6.30 (s, 1 H) 6.47 (dd, J=7.04, 1.95 Hz, 1 H) 6.52-6.61 (m, 1 H) 6.71 (s, 1 H) 7.30 (m, J=8.21 Hz, 2 H) 7.38 (m, J=8.60 Hz, 2 H) 7.62 (d, J=7.04 Hz, 1 H) 7.80-7.95 (m, 2 H).

269

Step 243.1: 2-Bromo-5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one

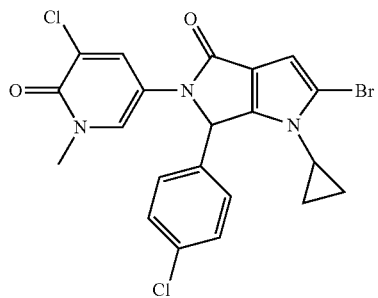 [SMILES: Cn1cc(N2C(=O)c3cc(Br)n(C4CC4)c3C2c2ccc(Cl)cc2)cc(Cl)c1=O]

The title compound was prepared in analogy to the procedure described in Step 240.1 but using 5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one (Step 243.2). The reaction mixture was concentrated and then diluted in EtOAc/water. Filtration afforded the title compound as a white solid. $t_R$: 1.11 min (LC-MS 6); ESI-MS: 492.0/494.0 [M+H]$^+$ (LC-MS 6).

Step 243.2: 5-(5-Chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one

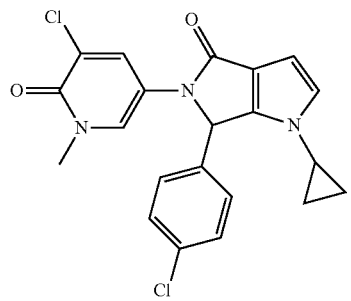 [SMILES: Cn1cc(N2C(=O)c3ccn(C4CC4)c3C2c2ccc(Cl)cc2)cc(Cl)c1=O]

The title compound was prepared in analogy to the procedure described in Step 240.2 but using 2-(((5-chloro-1-methyl-6-oxo-1,6-dihydropyridin-3-yl)amino)(4-chlorophenyl)methyl)-1-cyclopropyl-1H-pyrrole-3-carboxylic acid (Step 243.3) and stirring the reaction mixture for 2 hr. $t_R$: 0.99 min (LC-MS 6); ESI-MS: 414.1 [M+H]$^+$ (LC-MS 6); TLC (CH$_2$Cl$_2$/MeOH 95:5): R$_f$=0.32.

Step 243.3: 2-(((5-Chloro-1-methyl-6-oxo-1,6-dihydropyridin-3-ynamino)(4-chlorophenyl)methyl)-1-cyclopropyl-1H-pyrrole-3-carboxylic acid

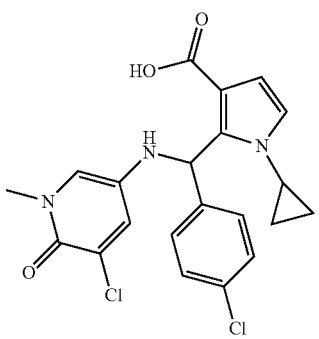 [SMILES: Cn1cc(NC(c2ccc(Cl)cc2)c2c(C(=O)O)ccn2C2CC2)cc(Cl)c1=O]

270

The title compound was prepared in analogy to the procedure described in Step 240.3 but using methyl 2-(((5-chloro-1-methyl-6-oxo-1,6-dihydropyridin-3-yl)amino)(4-chlorophenyl)methyl)-1-cyclopropyl-1H-pyrrole-3-carboxylate (Step 243.4). $t_R$: 0.98 min (LC-MS 6); ESI-MS: 432.1 [M+H]$^+$ (LC-MS 6).

Step 243.4: Methyl 2-(((5-chloro-1-methyl-6-oxo-1,6-dihydropyridin-3-yl)amino)(4-chlorophenyl)methyl)-1-cyclopropyl-1H-pyrrole-3-carboxylate

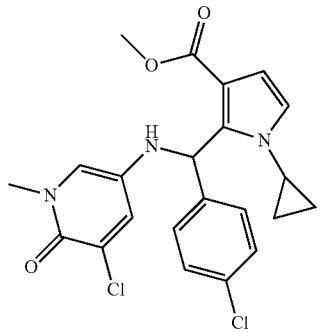 [SMILES: COC(=O)c1ccn(C2CC2)c1C(Nc1cc(Cl)c(=O)n(C)c1)c1ccc(Cl)cc1]

The title compound was prepared in analogy to the procedure described in Step 240.4 but using 5-amino-3-chloro-1-methyl-1H-pyridin-2-one (Step E5). $t_R$: 1.16 min (LC-MS 6); ESI-MS: 446.1 [M+H]$^+$ (LC-MS 6); TLC (CH$_2$Cl$_2$/MeOH 97.5:2.5): R$_f$=0.38.

EXAMPLE 244

5-(5-Chloro-1-methyl-6-oxo-1,6-dihydropyridin-3-yl)-6-(4-chlorophenyl)-1-cyclopropyl-2-(2,4-dimethoxypyrimidin-5-yl)-5,6-dihydropyrrolo[3,4-b]pyrrol-4(1H)-one

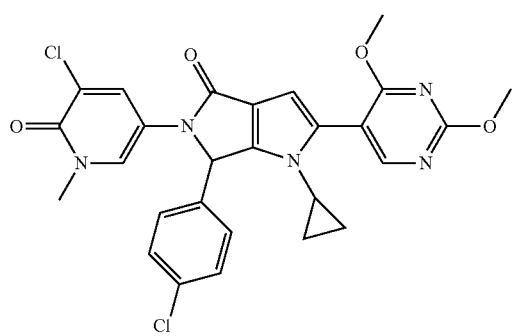 [SMILES: COc1ncc(-c2cc3c(n2C2CC2)C(c2ccc(Cl)cc2)N(c2cc(Cl)c(=O)n(C)c2)C3=O)c(OC)n1]

The title compound was prepared in analogy to the procedure described in Example 240 but using 2-bromo-5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one (Step 243.1). $t_R$: 1.03 min (LC-MS 6); ESI-MS: 552.2 [M+H]$^+$ (LC-MS 6); TLC (CH$_2$Cl$_2$/MeOH/NH$_3$ 94:5:1): R$_f$=0.44; $^1$H NMR (400 MHz, DMSO-d$_6$) δ ppm 0.09-0.25 (m, 1 H) 0.45-0.69 (m, 2 H) 0.91-1.06 (m, 1 H) 2.75-2.85 (m, 1 H) 3.41 (s, 3 H) 3.91 (s, 3 H) 3.86 (s, 3 H) 6.29 (s, 1 H) 6.38 (s, 1 H) 7.30 (m, J=8.60 Hz, 2 H) 7.40 (m, J=8.60 Hz, 2 H) 7.76-7.96 (m, 2 H) 8.30 (s, 1 H).

EXAMPLE 245

5-(5-Chloro-1-methyl-6-oxo-1,6-dihydropyridin-3-yl)-6-(4-chlorophenyl)-1-cyclopropyl-2-(2-methoxypyrimidin-5-yl)-5,6-dihydropyrrolo[3,4-b]pyrrol-4(1H)-one

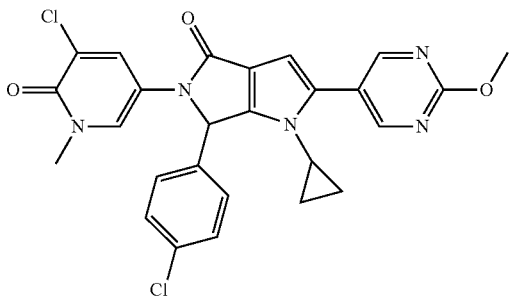 [SMILES: COc1ncc(-c2cc3c(n2C2CC2)C(c2ccc(Cl)cc2)N(c2cc(Cl)c(=O)n(C)c2)C3=O)cn1]

The title compound was prepared in analogy to the procedure described in Example 240 but using 2-bromo-5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one (Step 243.1) and (2-methoxypyrimidin-5-yl) boronic acid. $t_R$: 0.97 min (LC-MS 6); ESI-MS: 522.1 $[M+H]^+$ (LC-MS 6); TLC ($CH_2Cl_2$/MeOH/$NH_3$ 94:5:1): $R_f$=0.38; $^1$H NMR (400 MHz, DMSO-$d_6$) δ ppm 0.18-0.40 (m, 1 H) 0.60-0.85 (m, 2 H) 1.09-1.19 (m, 1 H) 3.10-3.20 (m, 1 H) 3.42 (s, 3 H) 3.92 (s, 3 H) 6.33 (s, 1 H) 6.62 (s, 1 H) 7.32 (m, J=8.60 Hz, 2 H) 7.40 (m, J=8.60 Hz, 2 H) 7.80-7.97 (m, 2 H) 8.81 (s, 2 H).

Biological Data:
Time Resolved Fluorescence Energy Transfer (TR-FRET) Assay

The inhibition of p53-MDM2 and p53-MDM4 interactions is measured by time resolved fluorescence energy transfer (TR-FRET). Fluorescence energy transfer (or Foerster resonance energy transfer) describes an energy transfer between donor and acceptor fluorescent molecules. For this assay, human MDM2 protein (amino acids 2-188) and human MDM4 protein (amino acids 2-185), tagged with a C-terminal biotin moiety, are used in combination with a Europium labeled streptavidin (Perkin Elmer, Inc., Waltham, Mass., USA) serving as the donor fluorophore. The p53 derived, Cy5 labeled peptide Cy5-TFSDLWKLL (p53 aa18-26) is the energy acceptor. Upon excitation of the donor molecule at 340 nm, binding interaction between MDM2 or MDM4 and the p53 peptide induces energy transfer and enhanced response at the acceptor emission wavelength at 665 nm. Disruption of the formation of the p53-MDM2 or p53-MDM4 complex due to an inhibitor molecule binding to the p53 binding site of MDM2 or MDM4 results in increased donor emission at 620 nm. The ratiometric FRET assay readout is calculated from the raw data of the two distinct fluorescence signals measured in time resolved mode (fluorescence 665 nm/fluorescence 620 nm×1000).

The test is performed in white 384-well plates (Greiner Bio-One, reference 781207) in a total volume of 60 µL by adding 1 µL of compounds tested at different concentrations diluted in 100% DMSO (1.7% final DMSO concentration) in reaction buffer (PBS, 125 mM NaCl, 0.001% Novexin (consists of carbohydrate polymers), designed to increase the solubility and stability of proteins; Expedeon Ltd., Cambridgeshire, United Kingdom), 0.01% Gelatin, 0.01% 0.2%, Pluronic F-127 (block copolymer from ethylenoxide and propyleneoxide), 1 mM DTT). After addition of 1.25 nM MDM2-biotinylated or 2.5 nM MDM4-biotinylated (internal preparations), and 0.625 nM Europium labeled streptavidin (Perkin Elmer), the solution is pre-incubated for 15 minutes at room temperature, then 10 nM Cy5-p53 peptide (internal preparation) is added before an incubation at room temperature for 15 minutes prior to reading the plate. For measurement of samples, a Victor II microplate reader (Perkin Elmer) is used with the following settings: Excitation 340 nm, Emission Donor 620 nm and Emission Acceptor 665 nm. $IC_{50}$ values are calculated by curve fitting using XLfit. If not specified, reagents are purchased from Sigma-Aldrich Chemie GmBH, Buchs, Switzerland.

This assay was used to evaluate compounds displaying inhibition of p53-MDM2 interaction and p53-MDM4 interaction at $IC_{50}$s of 0.005 to 50 µM (p53-MDM2 Assay 1 and p53-MDM4 Assay 1, respectively). For selected compounds displaying $IC_{50}$s between 0.05 and 5 nM on MDM2, a slightly modified assay is used with the following adaptations: 0.1 nM MDM2, 0.1 nM Europium labeled streptavidin and Tecan genios Pro is used as a microplate reader for the fluorescence measurements (p53-MDM2 Assay 2).

| | $IC_{50}$ (µM) | | $IC_{50}$ (nM) |
|---|---|---|---|
| Example | p53-MDM2 Assay 1 | p53-MDM4 Assay 1 | p53-MDM2 Assay 2 |
| 1 | 0.0095 | 27.8352 | n.d. |
| 2 | 0.0029 | 2.9019 | 0.757 |
| 3 | 0.0060 | 54.2383 | n.d. |
| 4 | n.d. | n.d. | 0.286 |
| 5 | n.d. | n.d. | 1.696 |
| 6 | n.d. | n.d. | 0.172 |
| 7 | 0.0006 | 0.5075 | 0.119 |
| 8 | n.d. | n.d. | 49.027 |
| 9 | 0.0006 | 4.0259 | 0.298 |
| 10 | 0.0009 | 0.4775 | 0.116 |
| 11 | n.d. | n.d. | 0.113 |
| 12 | n.d. | n.d. | 0.490 |
| 13 | n.d. | n.d. | 0.176 |
| 14 | n.d. | n.d. | 0.068 |
| 15 | n.d. | n.d. | 0.133 |
| 16 | n.d. | n.d. | 0.308 |
| 17 | n.d. | n.d. | 0.281 |
| 18 | n.d. | n.d. | 0.095 |
| 19 | n.d. | n.d. | 180.517 |
| 20 | n.d. | n.d. | 0.075 |
| 21 | n.d. | n.d. | 620.830 |
| 22 | n.d. | n.d. | 0.323 |
| 23 | n.d. | n.d. | 0.065 |
| 24 | n.d. | n.d. | 29.593 |
| 25 | n.d. | n.d. | 0.263 |
| 26 | n.d. | n.d. | 0.195 |
| 27 | n.d. | n.d. | 0.225 |
| 28 | n.d. | n.d. | 0.106 |
| 29 | n.d. | n.d. | 0.306 |
| 30 | n.d. | n.d. | 0.376 |
| 31 | n.d. | n.d. | 0.184 |
| 32 | 0.0005 | 0.2643 | 0.094 |
| 33 | n.d. | n.d. | 44.560 |
| 34 | n.d. | n.d. | 0.188 |
| 35 | n.d. | n.d. | 0.169 |
| 36 | n.d. | n.d. | 0.115 |
| 37 | 0.0011 | 0.3271 | 0.125 |
| 38 | n.d. | n.d. | 0.444 |
| 39 | n.d. | n.d. | 0.556 |
| 40 | n.d. | n.d. | 0.478 |
| 41 | n.d. | n.d. | 0.349 |
| 42 | n.d. | n.d. | 0.246 |
| 43 | n.d. | n.d. | 0.401 |
| 44 | n.d. | n.d. | 0.167 |
| 45 | n.d. | n.d. | 87.626 |
| 46 | n.d. | n.d. | 0.203 |
| 47 | n.d. | n.d. | 0.150 |

| Example | IC$_{50}$ (μM) p53-MDM2 Assay 1 | IC$_{50}$ (μM) p53-MDM4 Assay 1 | IC$_{50}$ (nM) p53-MDM2 Assay 2 |
|---|---|---|---|
| 48 | n.d. | n.d. | 0.188 |
| 49 | n.d. | n.d. | 0.137 |
| 50 | n.d. | n.d. | 0.234 |
| 51 | n.d. | n.d. | 0.461 |
| 52 | n.d. | n.d. | 0.137 |
| 53 | n.d. | n.d. | 0.323 |
| 54 | n.d. | n.d. | 0.267 |
| 55 | n.d. | n.d. | 0.287 |
| 56 | n.d. | n.d. | 0.351 |
| 57 | n.d. | n.d. | n.d. |
| 58 | n.d. | n.d. | 0.458 |
| 59 | n.d. | n.d. | 0.163 |
| 60 | n.d. | n.d. | 0.155 |
| 61 | n.d. | n.d. | 0.104 |
| 62 | n.d. | n.d. | 0.169 |
| 63 | n.d. | n.d. | 8.132 |
| 64 | n.d. | n.d. | 1.001 |
| 65 | 0.0123 | 8.7889 | 4.907 |
| 66 | n.d. | n.d. | 1.385 |
| 67 | n.d. | n.d. | 2.486 |
| 68 | 0.0126 | 7.8586 | 14.168 |
| 69 | n.d. | n.d. | 0.777 |
| 70 | n.d. | n.d. | 0.235 |
| 71 | n.d. | n.d. | 0.635 |
| 72 | n.d. | n.d. | 0.295 |
| 73 | n.d. | n.d. | 0.161 |
| 74 | n.d. | n.d. | 2.566 |
| 75 | n.d. | n.d. | 1.087 |
| 76 | n.d. | n.d. | 1.640 |
| 77 | n.d. | n.d. | 1.509 |
| 78 | 0.0085 | 14.0247 | 5.081 |
| 79 | n.d. | n.d. | 0.423 |
| 80 | n.d. | n.d. | 0.115 |
| 81 | n.d. | n.d. | 0.148 |
| 82 | n.d. | n.d. | 0.152 |
| 83 | n.d. | n.d. | 4.163 |
| 84 | n.d. | n.d. | 0.482 |
| 85 | n.d. | n.d. | 3.158 |
| 86 | n.d. | n.d. | 0.334 |
| 87 | n.d. | n.d. | 0.359 |
| 88 | n.d. | n.d. | 1.640 |
| 89 | n.d. | n.d. | 0.080 |
| 90 | n.d. | n.d. | 6.210 |
| 91 | n.d. | n.d. | 0.061 |
| 92 | n.d. | n.d. | 41.925 |
| 93 | n.d. | n.d. | 0.361 |
| 94 | n.d. | n.d. | 0.188 |
| 95 | n.d. | n.d. | 0.194 |
| 96 | n.d. | n.d. | 1.949 |
| 97 | n.d. | n.d. | 0.378 |
| 98 | n.d. | n.d. | 0.316 |
| 99 | n.d. | n.d. | 1.441 |
| 100 | n.d. | n.d. | 0.316 |
| 101 | 0.0270 | 2.9899 | 31.855 |
| 102 | 0.0127 | 2.3757 | 13.586 |
| 103 | 0.0207 | 4.7148 | 30.146 |
| 104 | n.d. | n.d. | 15.344 |
| 105 | 0.0102 | 6.2862 | 14.333 |
| 106 | n.d. | n.d. | 904.200 |
| 107 | 0.0030 | 3.6434 | 2.692 |
| 108 | 0.0033 | 9.0230 | 3.698 |
| 109 | n.d. | n.d. | 1.600 |
| 110 | n.d. | n.d. | 0.741 |
| 111 | n.d. | n.d. | 1.843 |
| 112 | n.d. | n.d. | 0.393 |
| 113 | n.d. | n.d. | 0.216 |
| 114 | n.d. | n.d. | 0.184 |
| 115 | n.d. | n.d. | 0.485 |
| 116 | n.d. | n.d. | 0.496 |
| 117 | n.d. | n.d. | 0.208 |
| 118 | n.d. | n.d. | 0.311 |
| 119 | n.d. | n.d. | 0.168 |
| 120 | n.d. | n.d. | 0.167 |
| 121 | 0.0006 | 1.0551 | 0.087 |
| 122 | n.d. | n.d. | 76.872 |
| 123 | n.d. | n.d. | 0.106 |
| 124 | n.d. | n.d. | 0.185 |
| 125 | n.d. | n.d. | 3.220 |
| 126 | n.d. | n.d. | 0.779 |
| 127 | n.d. | n.d. | 0.359 |
| 128 | n.d. | n.d. | 0.527 |
| 129 | n.d. | n.d. | 5.658 |
| 130 | n.d. | n.d. | 1.076 |
| 131 | n.d. | n.d. | 0.295 |
| 132 | n.d. | n.d. | 1.150 |
| 133 | n.d. | n.d. | 0.327 |
| 134 | n.d. | n.d. | 1.252 |
| 135 | n.d. | n.d. | 0.427 |
| 136 | n.d. | n.d. | 0.131 |
| 137 | n.d. | n.d. | 0.321 |
| 138 | n.d. | n.d. | 0.341 |
| 139 | n.d. | n.d. | 0.266 |
| 140 | n.d. | n.d. | 0.231 |
| 141 | n.d. | n.d. | 6.845 |
| 142 | n.d. | n.d. | 0.740 |
| 143 | n.d. | n.d. | 1.688 |
| 144 | n.d. | n.d. | 0.554 |
| 145 | n.d. | n.d. | 0.187 |
| 146 | n.d. | n.d. | 0.216 |
| 147 | n.d. | n.d. | 0.164 |
| 148 | n.d. | n.d. | 0.592 |
| 149 | n.d. | n.d. | 0.110 |
| 150 | n.d. | n.d. | 0.254 |
| 151 | n.d. | n.d. | 0.243 |
| 152 | n.d. | n.d. | 0.166 |
| 153 | n.d. | n.d. | 0.422 |
| 154 | n.d. | n.d. | 0.328 |
| 155 | n.d. | n.d. | 43.009 |
| 156 | n.d. | n.d. | 0.122 |
| 157 | n.d. | n.d. | 7.896 |
| 158 | n.d. | n.d. | 1.344 |
| 159 | n.d. | n.d. | 0.161 |
| 160 | n.d. | n.d. | 0.144 |
| 161 | n.d. | n.d. | 307.543 |
| 162 | n.d. | n.d. | 49.021 |
| 163 | n.d. | n.d. | 42.727 |
| 164 | n.d. | n.d. | 0.121 |
| 165 | n.d. | n.d. | 0.578 |
| 166 | n.d. | n.d. | 293.200 |
| 167 | 0.0008 | 0.7165 | 0.161 |
| 168 | n.d. | n.d. | 107.250 |
| 169 | n.d. | n.d. | 0.357 |
| 170 | n.d. | n.d. | 31.310 |
| 171 | n.d. | n.d. | 0.699 |
| 172 | n.d. | n.d. | 115.009 |
| 173 | n.d. | n.d. | 13.637 |
| 174 | n.d. | n.d. | 1.666 |
| 175 | n.d. | n.d. | 3.717 |
| 176 | n.d. | n.d. | 0.870 |
| 177 | n.d. | n.d. | 0.514 |
| 178 | n.d. | n.d. | 1.074 |
| 179 | n.d. | n.d. | 3.462 |
| 180 | n.d. | n.d. | 0.647 |
| 181 | n.d. | n.d. | 2.391 |
| 182 | n.d. | n.d. | 0.659 |
| 183 | n.d. | n.d. | 2.573 |
| 184 | n.d. | n.d. | 5.599 |
| 185 | n.d. | n.d. | 0.225 |
| 186 | n.d. | n.d. | 0.108 |
| 187 | n.d. | n.d. | 143.802 |
| 188 | n.d. | n.d. | 0.079 |
| 189 | n.d. | n.d. | 10.588 |
| 190 | n.d. | n.d. | 0.631 |
| 191 | n.d. | n.d. | 279.883 |
| 192 | n.d. | n.d. | 0.128 |
| 193 | n.d. | n.d. | 0.139 |
| 194 | n.d. | n.d. | 0.194 |
| 195 | n.d. | n.d. | 0.252 |
| 196 | n.d. | n.d. | 0.395 |
| 197 | n.d. | n.d. | 0.356 |

-continued

| Example | IC$_{50}$ (µM) p53-MDM2 Assay 1 | IC$_{50}$ (µM) p53-MDM4 Assay 1 | IC$_{50}$ (nM) p53-MDM2 Assay 2 |
|---|---|---|---|
| 198 | n.d. | n.d. | 0.691 |
| 199 | n.d. | n.d. | 0.257 |
| 200 | n.d. | n.d. | 0.370 |
| 201 | n.d. | n.d. | 0.250 |
| 202 | n.d. | n.d. | 0.201 |
| 203 | n.d. | n.d. | 0.119 |
| 204 | n.d. | n.d. | 0.195 |
| 205 | n.d. | n.d. | 0.198 |
| 206 | n.d. | n.d. | 0.509 |
| 207 | n.d. | n.d. | 0.185 |
| 208 | n.d. | n.d. | 0.861 |
| 209 | n.d. | n.d. | 0.158 |
| 210 | n.d. | n.d. | 3.901 |
| 211 | n.d. | n.d. | 1.675 |
| 212 | n.d. | n.d. | 0.769 |
| 213 | n.d. | n.d. | 14.236 |
| 214 | n.d. | n.d. | 1.887 |
| 215 | n.d. | n.d. | 0.527 |
| 216 | n.d. | n.d. | 883.000 |
| 217 | n.d. | n.d. | n.d. |
| 218 | n.d. | n.d. | 0.106 |
| 219 | n.d. | n.d. | 28.315 |
| 220 | n.d. | n.d. | 0.134 |
| 221 | n.d. | n.d. | 0.140 |
| 222 | n.d. | n.d. | 0.303 |
| 223 | n.d. | n.d. | 0.631 |
| 224 | n.d. | n.d. | 0.362 |
| 225 | n.d. | n.d. | 0.277 |
| 226 | n.d. | n.d. | 0.132 |
| 227 | n.d. | n.d. | 0.071 |
| 228 | n.d. | n.d. | 48.682 |
| 229 | n.d. | n.d. | 0.078 |
| 230 | n.d. | n.d. | 280.998 |
| 231 | n.d. | n.d. | 0.224 |
| 232 | n.d. | n.d. | 0.069 |
| 233 | n.d. | n.d. | 60.198 |
| 234 | n.d. | n.d. | 0.657 |
| 235 | n.d. | n.d. | 7.156 |
| 236 | n.d. | n.d. | 2.980 |
| 237 | n.d. | n.d. | 0.107 |
| 238 | n.d. | n.d. | 126.144 |
| 239 | n.d. | n.d. | 1.156 |
| 240 | 0.0333 | 77.6060 | n.d. |
| 241 | 3.9168 | >100 | n.d. |
| 242 | 2.0443 | >100 | n.d. |
| 243 | n.d. | n.d. | n.d. |
| 244 | n.d. | n.d. | n.d. |
| 245 | n.d. | n.d. | n.d. | n.d.: not determined

There are also assays that could be used to demonstrate the effect of the compounds of this invention in a cellular context.

Cellular proliferation assay in SJSA-1 and SAOS-2 cells based on YO-PRO®-1 iodide staining The effect of PPI (protein-protein interaction) inhibitors on cell growth of p53 wild-type or mutant cells is assessed in a proliferation assay based on YO-PRO®-1 iodide staining (J Immunol Methods. 1995; 185(2):249-58). The principal of this assay is the use of the DNA-intercalating dye YO-PRO®-1 iodide which upon binding to DNA emits a strong fluorescence signal. In addition, the dye is membrane-impermeant and thus, apoptotic cells can be distinguished from the viable cell population during the same assay. In the absence of cell permeabilization, the dye is only entering into cells that are beginning to undergo apoptosis. After treatment of the cells with a lysis buffer, the total cell number can be estimated.

To test PPI inhibitors on cell growth, SJSA-1 cells (p53 wild-type cells) and SAOS-2 cells (p53 null cells) are plated out into 96-well micro-titer plates and treated with decreasing concentrations of the compounds. After a 72 hour incubation period, 2.5 µM YO-PRO®-1 iodide is directly added to the cells and a first read-out is performed using a standard fluorescence plate reader (filter setting 485/530 nm) revealing the relative number of apoptotic cells. Subsequently, cells are permeabilized by directly adding lysis buffer containing the detergent NP40, EDTA and EGTA to obtain final concentrations of 0.01% and 5 mM, respectively. After complete permeabilization, the total cell number is quantified during a second read using the fluorescence plate reader with the same settings.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

The following examples are intended to illustrate the invention and are not to be construed as being limitations thereon. Temperatures are given in degrees centrigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

In Vivo Experiments

There are also experiments that can demonstrate the anti-tumor activity of compounds of the formula (I) in vivo.

For example, female Harlan (Indianapolis, Ind., USA) athymic nu/nu mice with s.c. transplanted human osteosarcoma SJSA-1 tumors can be used to determine the anti-tumor activity of p53/MDM2 interaction inhibitors. On day 0, with the animals under peroral Forene® (1-chloro-2,2,2-trifluoro-ethyldifluormethylether, Abbot, Wiesbaden, Germany) narcosis, 3×10$^6$ cells are injected under the skin on the animals' left flank. When tumors reach a volume of 100 mm$^3$, the mice are divided at random into groups of 6-8 animals and treatment commences. The treatment is carried out for a 2-3 weeks period with peroral, intravenous or intra-peritoneal administration twice daily (or less frequently) of a compound of the formula (I) in a suitable vehicle at defined doses. The tumors are measured twice a week with a slide gauge and the volume of the tumors is calculated. As an alternative to cell line SJSA-1, other cell lines may also be used in the same manner, for example, the HCT116 colon carcinoma cell line (ATCC No. CCL-247);

the LNCaP clone FGC prostate carcinoma cell line (ATCC No. CRL-1740);

the RKO colon carcinoma cell line (ATCC No. CRL-2577);

the HT1080 fibrosarcoma cell line (ATCC No. CCL-121);

the A375 malignant melanoma cell line (ATCC No. CRL-1619), the NCI-H460 large cell lung carcinoma cell line (ATCC No. HTB-177);
the JEG-3 choriocarcinoma (ATCC No. HTB-36)
the ZR-75-1 breast ductal carcinoma (ATCC No. CRL-1500)

We claim:
1. A compound of formula (I) or a salt thereof,

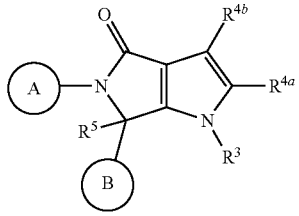

wherein:
A is selected from the group consisting of:

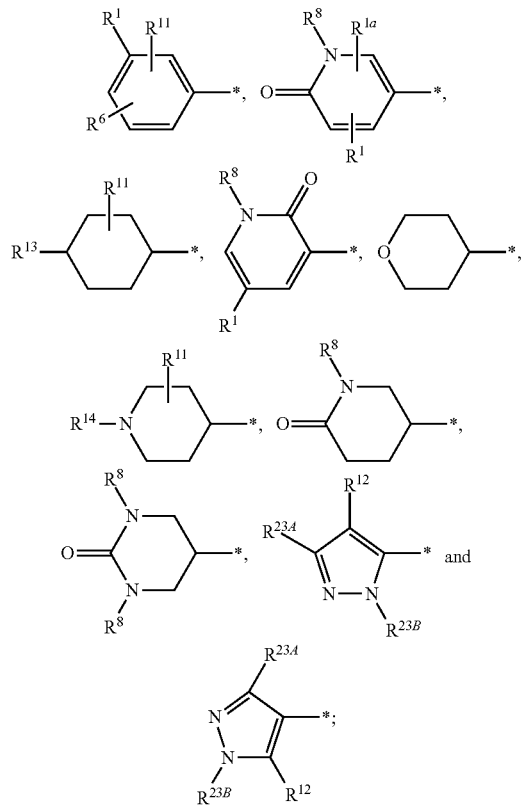

B is selected from the group consisting of:

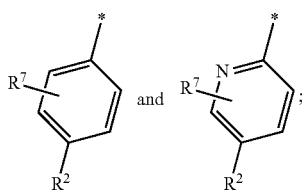

each $R^1$ is independently selected from the group consisting of halo and methyl;
$R^{1a}$ is selected from the group consisting of H, halo and $(C_1-C_4)$alkyl;

$R^2$ is selected from the group consisting of chloro, fluoro, trifluoromethyl, methyl and cyano;
$R^3$ is selected from the group consisting of ethyl, isopropyl, cyclopropyl, isobutyl, cyclobutyl and cyclopentyl, or $R^3$ is:

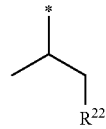

wherein $R^{22}$ is selected from the group consisting of OH, $OCH_3$, $NH_2$, NHMe, $NMe_2$, NHCOMe and NHCOH;
$R^5$ is selected from the group consisting of:
H,
$(C_1-C_4)$alkyl-, said $(C_1-C_4)$alkyl- being optionally substituted with 1 or 2 substituents independently selected from the group consisting of OH and =O,
$(C_1-C_4)$alkyl-O—C(O)—$(CH_2)_m$—, and
cyano;
$R^6$ is selected from the group consisting of:
H,
$(C_1-C_4)$alkyl,
$(C_1-C_4)$alkoxy,
halo,
cyano, and
$R^9(R^{10})N$—$(CH_2)_m$—;
$R^7$ is selected from the group consisting of: H, halo and $(C_1-C_4)$alkyl;
each $R^8$ is independently selected from the group consisting of H, $(C_1-C_4)$alkyl, —$CHF_2$, hydroxyethyl- and methoxyethyl-;
each $R^9$ is independently selected from the group consisting of H, methyl or ethyl;
each $R^{10}$ is independently selected from the group consisting of H, $(C_1-C_4)$alkoxy and $(C_1-C_4)$alkyl wherein said $(C_1-C_4)$alkoxy and $(C_1-C_4)$alkyl are each independently optionally substituted by 1 or 2 substituents independently selected from the group consisting of methoxy, ethoxy, hydroxy, halo and $S(O)_vR^y$;
or $R^9$ and $R^{10}$, together with the N atom to which they are attached, can join to form a saturated 5 or 6 membered heterocyclic ring further comprising ring carbon atoms and optionally one ring heteroatom independently selected from N, O and S;
$R^{11}$ is H, $(C_1-C_4)$alkyl, $(C_1-C_4)$alkoxy or halo;
$R^{12}$ is H or halo;
$R^{13}$ is selected from the group consisting of hydroxy, $(C_1-C_2)$alkoxy, $NH_2$, —C(O)OH, —NH(C(O)—$CH_3$) and —C(O)—$NH(CH_3)$;
$R^{14}$ is selected from the group consisting of H, —C(O)—$NR^9(R^{10})$, $(C_1-C_4)$alkyl, —C(O)$(C_1-C_4)$alkyl, —C(O)O$(C_1-C_4)$alkyl;
$R^{23A}$ is selected from the group consisting of H, halo and $(C_1-C_4)$alkyl;
$R^{23B}$ is selected from the group consisting of H and $(C_1-C_4)$alkyl;

$R^{4a}$ is selected from the group consisting of:

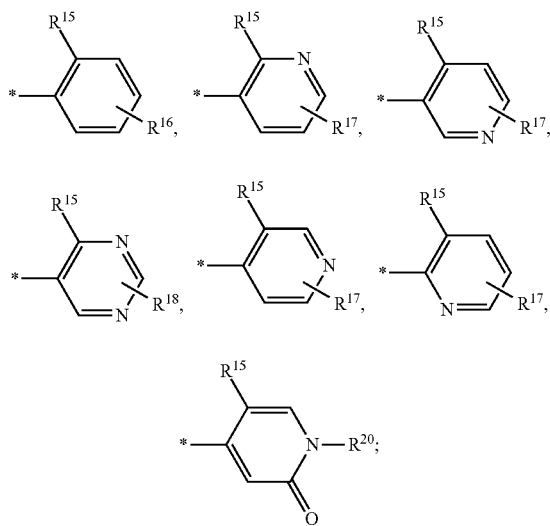

$R^{15}$ is independently selected from the group consisting of $OCH_3$, $OCD_3$, OH, $CH_2CH_3$, $OCF_3$ and H;

$R^{16}$ is selected from the group consisting of H, —C(O)$NR^9R^{10}$, halo, CN, —O—($C_1$-$C_4$)alkyl, —C(O)—morpholinyl-4-yl, tetrazolyl, —C(O)OH, —$CH_2$C(O)OH, —S(O)$_v$$NR^9R^{10}$, —$CH_2$C(O)$NR^9R^{10}$, S(O)$_v$$R^y$, $OCF_3$, hydroxy-azetidin-1-yl-carbonyl, —$CH_2NR^9R^{10}$, —$CH_2NR^9$—C(O)$R^{10}$, $CH_2$CN, methyl-imidazolyl-, —$CH_2$C(O)O—($C_1$-$C_4$)alkyl, —N($R^9$)—C(O)—($C_1$-$C_4$)alkyl, —$NR^9R^{10}$ and ($C_1$-$C_4$)alkyl, wherein said ($C_1$-$C_4$)alkyl is optionally substituted by 1 or 2 OH;

$R^{17}$ is selected from the group consisting of H, O($C_1$-$C_4$)alkyl, —$CH_2$C(O)O—($C_1$-$C_4$)alkyl, —$CH_2$C(O)OH, —$CH_2$C(O)$NR^9R^{10}$, —$CH_2$CN, —$NR^9R^{10}$, —C(O)$NR^9R^{10}$, —$CH_2NR^9R^{10}$ and —C(O)O—($C_1$-$C_4$)alkyl;

$R^{18}$ is selected from the group consisting of O($C_1$-$C_4$)alkyl, $OCD_3$, H, —$NR^9R^{10}$, $CH_2NR^9R^{10}$ and azetidin-1-yl, said azetidin-1-yl being optionally substituted with OH or both $CH_3$ and OH;

$R^{20}$ is selected from the group consisting of $CH_3$, H and —$CH_2CH_3$;

$R^{4b}$ is selected from the group consisting of H, CN, halo, ($C_1$-$C_4$)alkyl, —C(O)OH, $CH_2$C(O)OH and —C(O)O—($C_1$-$C_4$)alkyl;

$R^y$ is selected from the group consisting of H, ($C_1$-$C_4$)alkyl and $NR^9R^{10}$;

m is 0, 1 or 2; and v is 0, 1 or 2;

and wherein * indicates the point of attachment to the remainder of the molecule.

2. The compound of the formula (I) or salt thereof as defined in claim 1, wherein A is selected from the group consisting of:

3. The compound of the formula (I) or salt thereof as defined in claim 1, wherein A is selected from the group consisting of:

4. The compound of the formula (I) or salt thereof as defined in claim 1, wherein B is:

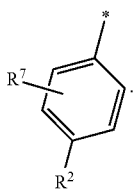

5. The compound of the formula (I) or salt thereof as defined in claim 1, wherein $R^3$ is isopropyl.

6. The compound of the formula (I) or salt thereof as defined in claim 1, wherein $R^{4a}$ is selected from the group consisting of:

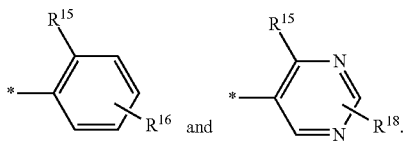

7. The compound of the formula (I) or salt thereof as defined in claim 1, wherein $R^{4a}$ is selected from the group consisting of:

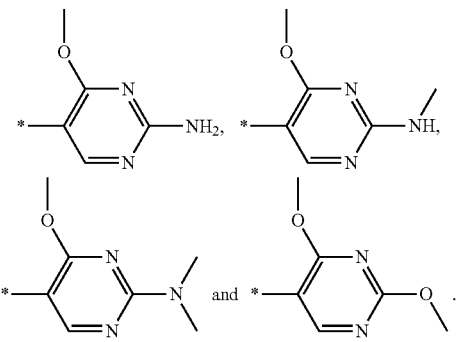

8. The compound of the formula (I) or salt thereof as defined in claim 1, wherein $R^5$ is selected from the group consisting of H and $(C_1\text{-}C_2)$alkyl.

9. The compound of the formula (I) or salt thereof as defined in claim 1, wherein $R^{4b}$ is H.

10. A compound or a salt thereof, selected from the group consisting of:

1: 5-(3-Chloro-2-fluoro-phenyl)-6-(4-chloro-2-methyl-phenyl)-1-isopropyl-2-(2-methoxy-phenyl)-5,6-dihydro-1H-pyrrolo[3,4-b]pyrrol-4-one 2: 3-[5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide 3: 5-(3-Chloro-2-fluoro-phenyl)-6-(4-chloro-2-methyl-phenyl)-2-(5-fluoro-2-methoxy-phenyl)-1-isopropyl-5,6-dihydro-1H-pyrrolo[3,4-b]pyrrol-4-one 4: 5-(3-Chloro-2-fluoro-phenyl)-6-(4-chloro-2-methyl-phenyl)-2-(5-hydroxymethyl-2-methoxy-phenyl)-1-isopropyl-5,6-dihydro-1H-pyrrolo[3,4-b]pyrrol-4-one 5: 5-(3-Chloro-2-fluoro-phenyl)-6-(4-chloro-2-methyl-phenyl)-1-isopropyl-2-(2-methoxy-pyridin-3-yl)-5,6-dihydro-1H-pyrrolo[3,4-b]pyrrol-4-one 6: 5-(3-Chloro-2-fluoro-phenyl)-6-(4-chloro-2-methyl-phenyl)-1-isopropyl-2-(4-methoxy-pyridin-3-yl)-5,6-dihydro-1H-pyrrolo[3,4-b]pyrrol-4-one 7: 3-[(S)-5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide 8: 3-[(R)-5-(3-Chloro-2-fluoro-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide 9: 5-(5-Chloro-2-methyl-phenyl)-6-(4-chloro-phenyl)-1-isopropyl-2-(2-methoxy-phenyl)-5,6-dihydro-1H-pyrrolo[3,4-b]pyrrol-4-one 10: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide 11: 5-(5-Chloro-2-methyl-phenyl)-6-(4-chloro-phenyl)-2-(5-hydroxymethyl-2-methoxy-phenyl)-1-isopropyl-5,6-dihydro-1H-pyrrolo[3,4-b]pyrrol-4-one 12: 5-(5-Chloro-2-methyl-phenyl)-6-(4-chloro-phenyl)-1-isopropyl-2-(2-methoxy-pyridin-3-yl)-5,6-dihydro-1H-pyrrolo[3,4-b]pyrrol-4-one 13: 5-(5-Chloro-2-methyl-phenyl)-6-(4-chloro-phenyl)-1-isopropyl-2-(4-methoxy-pyridin-3-yl)-5,6-dihydro-1H-pyrrolo[3,4-b]pyrrol-4-one 14: 5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one 15: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide 16: 5-(5-Chloro-2-methyl-phenyl)-6-(4-chloro-phenyl)-1-isopropyl-2-(4-methoxy-pyrimidin-5-yl)-5,6-dihydro-1H-pyrrolo[3,4-b]pyrrol-4-one 17: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzonitrile 18: 3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-b enz amide 19: 3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-b enz amide 20: 3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-b enzamide 21: 3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N,N-dimethyl-benzamide 22: 5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-b]pyrrol-4-one 23: (S)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one 24: (R)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one 25: 2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-b]pyrrol-4-one 26: 5-(5-Chloro-2-methyl-phenyl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one 27: 5-(5-Chloro-2-methyl-phenyl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 28: 5-(5-Chloro-2-methyl-phenyl)-6-(4-chloro-phenyl)-1-isopropyl-242-methoxy-5-(morpholine-4-carbonyl)-phenyl]-5,6-dihydro-1H-pyrrolo[3,4-b]pyrrol-4-one 29: 5-(5-Chloro-2-methyl-phenyl)-6-(4-chloro-phenyl)-2-(2-hydroxy-phenyl)-1-isopropyl-5,6-dihydro-1H-pyrrolo[3,4-b]pyrrol-4-one 30: 5-(5-Chloro-2-methyl-phenyl)-6-(4-chloro-2-methyl-phenyl)-1-isopropyl-2-(2-methoxy-phenyl)-5,6-dihydro-1H-pyrrolo[3,4-b]pyrrol-4-one 31: 3-[5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide 32: 3-[(S)-5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide 33: 3-[(R)-5-(5-Chloro-2-methyl-phenyl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide 34: 5-(5-Chloro-2-methyl-phenyl)-6-(4-chloro-phenyl)-1-isopropyl-2-[2-methoxy-5-(1H-tetrazol-5-yl)-phenyl]-5,6-dihydro-1H-pyrrolo[3,4-b]pyrrol-4-one 35: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid 36: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-N-(2-methanesulfonyl-ethyl)-4-methoxy-benzamide 37: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-N-(2-hydroxy-ethoxy)-4-methoxy-benzamide 38: 5-(5-Chloro-2-methyl-phenyl)-6-(4-chloro-phenyl)-2-(2,4-dimethoxy-phenyl)-1-isopropyl-5,6-dihydro-1H-pyrrolo[3,4-b]pyrrol-4-one 39: 4-[2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile 40: 4-[5-(3-Chloro-4-fluoro-phenyl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 41: 4-[2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile 42: 4-[5-(3-Chloro-2-fluoro-phenyl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 43: 4-[2-(2-Amino-4-methoxy-pyrimidin-5-yl)-5-(5-chloro-2-methyl-phenyl)-1-isopropyl-4-oxo-1,4,5,6-tetrahydro-pyrrolo[3,4-b]pyrrol-6-yl]-benzonitrile 44: 4-[5-(5-Chloro-2-methyl-phenyl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 45: 5-(5-Chloro-2-methyl-phenyl)-6-(4-chloro-phenyl)-2-(2,4-dimethoxy-pyrimidin-5-yl)-1-ethyl-5,6-dihydro-1H-pyrrolo[3,4-b]pyrrol-4-one 46: 5-(5-Chloro-1-methyl-6-oxo-1,6-dihydro-pyridin-3-yl)-6-(4-chloro-phenyl)-1-isopropyl-2-(2-methoxy-phenyl)-5,6-dihydro-1H-pyrrolo[3,4-b]pyrrol-4-one 47: 5-(5-Chloro-1-methyl-6-oxo-1,6-dihydro-pyridin-3-yl)-6-(4-chloro-phenyl)-1-isopropyl-2-[2-methoxy-5-(morpholine-4-carbonyl)-phenyl]-5,6-dihydro-1H-pyrrolo[3,4-B]pyrrol-4-one 48: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 49: 3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrol-2-yl]-4-methoxy-N-methyl-benzamide 50: 3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4S-b]pyrrol-2-yl]-4-methoxy-benzoic acid 51: 2-(2-Amino-4-methoxy-pyrimidin-5-yl)-5-(5-chloro-1-methyl-6-oxo-1,6-dihydro-pyridin-3-yl)-6-(4-chloro-phenyl)-1-isopropyl-5,6-dihydro-1H-pyrrolo[3,4-b]pyrrol-4-one 52: 5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 53: 3-[5-(3-Chloro-4-fluoro-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide 54: 5-(3-Chloro-4-fluoro-phenyl)-6-(4-chloro-phenyl)-2-(2,4-dimethoxy-pyrimidin-5-yl)-1-isopropyl-5,6-dihydro-1H-pyrrolo[3,4-b]pyrrol-4-one 55: 5-(3-Chloro-4-fluoro-phenyl)-6-(4-chloro-phenyl)-1-isopropyl-2-[2-methoxy-5-(morpholine-4-carbonyl)-phenyl]-5,6-dihydro-1H-pyrrolo[3,4-b]pyrrol-4-one 56: 3-[5-(3-Chloro-4-fluoro-phenyl)-6-(4-chloro-phenyl)-1-isopropyl-4-oxo-1,4,5,6-tetrahydro-pyrrolo[3,4-b]pyrrol-2-yl]-4-methoxy-benzoic acid 57: 2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-b]pyrrol-4-one 58: 5-(3-Chloro-4-fluoro-phenyl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 59: 5-(5-Chloro-2-methyl-phenyl)-6-(4-chloro-phenyl)-1-isopropyl-2-(2-methoxy-phenyl)-4-oxo-1,4,5,6-tetrahydro-pyrrolo[3,4-b]pyrrole-3-carbonitrile 60: {3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid 61: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzamide 62: 3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzenesulfonamide 63: 6-(4-Chloro-phenyl)-5-(trans-4-hydroxy-cyclohexyl)-1-isopropyl-2-(2-methoxy-phenyl)-5,6-dihydro-1H-pyrrolo[3,4-b]pyrrol-4-one 64: 3-[6-(4-Chloro-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-N-methyl-benzamide 65: 3-[6-(4-Chloro-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-benzoic acid 66: 6-(4-Chloro-phenyl)-2-(2,4-dimethoxy-pyrimidin-5-yl)-5-(trans-4-hydroxy-cyclohexyl)-1-isopropyl-5,6-dihydro-1H-pyrrolo[3,4-b]pyrrol-4-one 67: 3-[6-(4-Chloro-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-benzonitrile
68: 2-(2-Amino-4-methoxy-pyrimidin-5-yl)-6-(4-chloro-phenyl)-5-(trans-4-hydroxy-cyclohexyl)-1-isopropyl-5,6-dihydro-1H-pyrrolo[3,4-b]pyrrol-4-one
69: 6-(4-Chloro-phenyl)-2-(2-dimethylamino-4-methoxy-pyrimidin-5-yl)-5-(trans-4-hydroxy-cyclohexyl)-1-isopropyl-5,6-dihydro-1H-pyrrolo[3,4-b]pyrrol-4-one
70: 5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one
71: 2-(2-Amino-4-methoxy-pyrimidin-5-yl)-5-(5-Chloro-1-methyl-2-oxo-1,2-dihydro-pyridin-3-yl)-6-(4-chloro-phenyl)-1-isopropyl-5,6-dihydro-1H-pyrrolo[3,4-b]pyrrol-4-one
72: 5-(5-Chloro-1-methyl-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one
73: 5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one
74: 6-(4-Chloro-phenyl)-1-isopropyl-2-(2-methoxy-phenyl)-5-(tetrahydro-pyran-4-yl)-5,6-dihydro-1H-pyrrolo[3,4-b]pyrrol-4-one
75: 3-[6-(4-Chloro-phenyl)-1-isopropyl-4-oxo-5-(tetrahydro-pyran-4-yl)-1,4,5,6-tetrahydro-pyrrolo[3,4-b]pyrrol-2-yl]-4-methoxy-N-methyl-benzamide
76: 6-(4-Chloro-phenyl)-2-(2,4-dimethoxy-pyrimidin-5-yl)-1-isopropyl-5-(tetrahydro-pyran-4-yl)-5,6-dihydro-1H-pyrrolo[3,4-b]pyrrol-4-one
77: 3-[6-(4-Chloro-phenyl)-1-isopropyl-4-oxo-5-(tetrahydro-pyran-4-yl)-1,4,5,6-tetrahydro-pyrrolo[3,4-b]pyrrol-2-yl]-4-methoxy-benzonitrile
78: 2-(2-Amino-4-methoxy-pyrimidin-5-yl)-6-(4-chloro-phenyl)-1-isopropyl-5-(tetrahydro-pyran-4-yl)-5,6-dihydro-1H-pyrrolo[3,4-b]pyrrol-4-one
79: 6-(4-Chloro-phenyl)-2-(2-dimethylamino-4-methoxy-pyrimidin-5-yl)-1-isopropyl-5-(tetrahydro-pyran-4-yl)-5,6-dihydro-1H-pyrrolo[3,4-b]pyrrol-4-one
80: 2-{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetamide
81: 2-{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-N-methyl-acetamide
82: 2-{3-[5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-N,N-dimethyl-acetamide
83: {5-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-acetic acid ethyl ester
84: {4-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-acetic acid
85: 2-{5-[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-6-methoxy-pyridin-3-yl}-N-methyl-acetamide
86: 2-{4-4[5-(3-Chloro-2-fluoro-phenyl)-6-(4-cyano-phenyl)-1-isopropyl-4-oxo-1,4,5,6-tetrahydro-pyrrolo[3,4-b]pyrrol-2-yl]-5-methoxy-pyridin-2-yl}-N-methyl-acetamide
87: 4-[5-(3-Chloro-2-fluoro-phenyl)-2-(2-cyanomethyl-5-methoxy-pyridin-4-yl)-1-isopropyl-4-oxo-1,4,5,6-tetrahydro-pyrrolo[3,4-b]pyrrol-6-yl]-benzonitrile
88: 4-[5-(3-Chloro-2-fluoro-phenyl)-2-(5-cyanomethyl-2-methoxy-pyridin-3-yl)-1-isopropyl-4-oxo-1,4,5,6-tetrahydro-pyrrolo[3,4-b]pyrrol-6-yl]-benzonitrile
89: 3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid
90: 3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-benzoic acid
91: {3-[(S)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid
92: {3-[(R)-5-(5-Chloro-2-methyl-phenyl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid
93: 4-[5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile
94: 4-[5-(3-Chloro-2-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile
95: 4-[5-(5-Chloro-2-methyl-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile
96: 4-Chloro-2-[6-(4-chloro-phenyl)-1-isopropyl-2-(2-methoxy-phenyl)-4-oxo-4,6-dihydro-1H-pyrrolo[3,4-b]pyrrol-5-yl]-benzonitrile
97: 3-[5-(5-Chloro-2-cyano-phenyl)-6-(4-chloro-phenyl)-1-isopropyl-4-oxo-1,4,5,6-tetrahydro-pyrrolo[3,4-b]pyrrol-2-yl]-4-methoxy-N-methyl-benzamide
98: 4-Chloro-2-[6-(4-chloro-phenyl)-2-(2,4-dimethoxy-pyrimidin-5-yl)-1-isopropyl-4-oxo-4,6-dihydro-1H-pyrrolo[3,4-b]pyrrol-5-yl]-benzonitrile
99: 2-[2-(2-Amino-4-methoxy-pyrimidin-5-yl)-6-(4-chloro-phenyl)-1-isopropyl-4-oxo-4,6-dihydro-1H-pyrrolo[3,4-b]pyrrol-5-yl]-4-chloro-benzonitrile
100: 4-Chloro-2-[6-(4-chloro-phenyl)-2-(2-dimethylamino-4-methoxy-pyrimidin-5-yl)-1-isopropyl-4-oxo-4,6-dihydro-1H-pyrrolo[3,4-b]pyrrol-5-yl]-benzonitrile
101: 6-(4-Chloro-2-methyl-phenyl)-5-(trans-4-hydroxy-cyclohexyl)-1-isopropyl-2-(2-methoxy-phenyl)-5,6-dihydro-1H-pyrrolo[3,4-b]pyrrol-4-one
102: 3-[6-(4-Chloro-2-methyl-phenyl)-5-(trans-4-hydroxy-cyclohexyl)-1-isopropyl-4-oxo-1,4,5,6-tetrahydro-pyrrolo[3,4-b]pyrrol-2-yl]-4-methoxy-N-methyl-benzamide
103: 6-(4-Chloro-2-methyl-phenyl)-2-(2,4-dimethoxy-pyrimidin-5-yl)-5-(trans-4-hydroxy-cyclohexyl)-1-isopropyl-5,6-dihydro-1H-pyrrolo[3,4-b]pyrrol-4-one
104: 6-(4-Chloro-2-methyl-phenyl)-1-isopropyl-2-(2-methoxy-phenyl)-5-(tetrahydro-pyran-4-yl)-5,6-dihydro-1H-pyrrolo[3,4-b]pyrrol-4-one
105: 6-(4-Chloro-2-methyl-phenyl)-2-(2,4-dimethoxy-pyrimidin-5-yl)-1-isopropyl-5-(tetrahydro-pyran-4-yl)-5,6-dihydro-1H-pyrrolo[3,4-b]pyrrol-4-one 106: 6-(4-Chloro-phenyl)-2-(2,4-dimethoxy-pyrimidin-5-yl)-1-isopropyl-5-piperidin-4-yl-5,6-dihydro-1H-pyrrolo[3,4-b]pyrrol-4-one 107: 4-[6-(4-Chloro-phenyl)-2-(2,4-dimethoxy-pyrimidin-5-yl)-1-isopropyl-4-oxo-4,6-dihydro-1H-pyrrolo[3,4-b]pyrrol-5-yl]-piperidine-1-carboxylic acid methylamide 108: 2-(2-Amino-4-methoxy-pyrimidin-5-yl)-6-(4-chloro-phenyl)-1-isopropyl-5-(1-methyl-6-oxo-piperidin-3-yl)-5,6-dihydro-1H-pyrrolo[3,4-b]pyrrol-4-one 109: 6-(4-Chloro-phenyl)-2-(2,4-dimethoxy-pyrimidin-5-yl)-1-isopropyl-5-(1-methyl-6-oxo-piperidin-3-yl)-5,6-dihydro-1H-pyrrolo[3,4-b]pyrrol-4-one 110: 6-(4-Chloro-phenyl)-2-(2,4-dimethoxy-pyrimidin-5-yl)-5-(1,3-dimethyl-2-oxo-hexahydro-pyrimidin-5-yl)-1-isopropyl-5,6-dihydro-1H-pyrrolo[3,4-b]pyrrol-4-one 111: 6-(4-Chloro-phenyl)-2-(2,4-dimethoxy-pyrimidin-5-yl)-5-(1,4-dimethyl-6-oxo-1,6-dihydro-pyridin-3-yl)-1-isopropyl-5,6-dihydro-1H-pyrrolo[3,4-b]pyrrol-4-one 112: 6-(4-Chloro-phenyl)-2-(2-dimethylamino-4-methoxy-pyrimidin-5-yl)-5-(1,4-dimethyl-6-oxo-1,6-dihydro-pyridin-3-yl)-1-isopropyl-5,6-dihydro-1H-pyrrolo[3,4-b]pyrrol-4-one 113: 5-(5-Chloro-2-methyl-phenyl)-6-(4-chloro-phenyl)-1-isopropyl-2-(3-methoxy-pyridin-2-yl)-5,6-dihydro-1H-pyrrolo[3,4-b]pyrrol-4-one 114: 5-(5-Chloro-2-methyl-phenyl)-6-(4-chloro-phenyl)-1-isopropyl-2-(5-methanesulfonyl-2-methoxy-phenyl)-5,6-dihydro-1H-pyrrolo[3,4-b]pyrrol-4-one 115: 5-(5-Chloro-2-methyl-phenyl)-6-(4-chloro-phenyl)-3-fluoro-1-isopropyl-2-(2-methoxy-phenyl)-5,6-dihydro-1H-pyrrolo[3,4-b]pyrrol-4-one 116: 5-(5-Chloro-2-methyl-phenyl)-6-(4-chloro-phenyl)-1-isopropyl-2-(2-methoxy-phenyl)-6-methyl-5,6-dihydro-1H-pyrrolo[3,4-b]pyrrol-4-one 117: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one 118: {3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-b]pyrrol-2-yl]-4-methoxy-phenyl}-acetic acid 119: 5-(5-Chloro-1-methyl-6-oxo-1,6-dihydro-pyridin-3-yl)-6-(4-chloro-phenyl)-1-isopropyl-2-5-methanesulfonyl-2-methoxy-phenyl)-5,6-dihydro-1H-pyrrolo[3,4-b]pyrrol-4-one 120: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carbonitrile 121: (S)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 122: (R)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 123: 5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 124: 5-(5-Chloro-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one 125: 4-[2-(2-Amino-4-methoxy-pyrimidin-5-yl)-5-(5-chloro-2-oxo-1,2-dihydro-pyridin-3-yl)-1-isopropyl-4-oxo-1,4,5,6-tetrahydro-pyrrolo[3,4-b]pyrrol-6-yl]-benzonitrile 126: 4-[5-(5-Chloro-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 127: 4-[5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 128: 4-[5-(5-Chloro-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 129: 4-[2-(2-Amino-4-methoxy-pyrimidin-5-yl)-5-(5-chloro-1-methyl-2-oxo-1,2-dihydro-pyridin-3-yl)-1-isopropyl-4-oxo-1,4,5,6-tetrahydro-pyrrolo[3,4-b]pyrrol-6-yl]-benzonitrile 130: 4-[5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 131: 4-[5-(5-Chloro-1-methyl-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 132: 4-[5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 133: 4-[5-(5-Chloro-1-methyl-6-oxo-1,6-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 134: 4-[2-(2-Amino-4-methoxy-pyrimidin-5-yl)-5-(5-chloro-6-oxo-1,6-dihydro-pyridin-3-yl)-1-isopropyl-4-oxo-1,4,5,6-tetrahydro-pyrrolo[3,4-b]pyrrol-6-yl]-benzonitrile 135: 4-[5-(5-Chloro-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 136: 4-[5-(5-Chloro-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 137: 4-[5-(5-Chloro-6-oxo-1,6-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 138: 2-(2-Amino-4-methoxy-pyrimidin-5-yl)-5-(5-chloro-6-oxo-1,6-dihydro-pyridin-3-yl)-6-(4-chloro-phenyl)-1-isopropyl-5,6-dihydro-1H-pyrrolo[3,4-b]pyrrol-4-one 139: 5-(5-Chloro-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 140: 5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 141: 2-(2-Amino-4-methoxy-pyrimidin-5-yl)-6-(4-chloro-phenyl)-1-isopropyl-5-(trans-4-methoxy-cyclohexyl)-5,6-dihydro-1H-pyrrolo[3,4-b]pyrrol-4-one 142: 6-(4-Chloro-phenyl)-2-(2-dimethylamino-4-methoxy-pyrimidin-5-yl)-1-isopropyl-5-(trans-4-methoxy-cyclohexyl)-5,6-dihydro-1H-pyrrolo[3,4-b]pyrrol-4-one 143: 6-(4-Chloro-phenyl)-2-(2,4-dimethoxy-pyrimidin-5-yl)-1-isopropyl-5-(trans-4-methoxy-cyclohexyl)-5,6-dihydro-1H-pyrrolo[3,4-b]pyrrol-4-one 144: 5-(5-Chloro-1-methyl-6-oxo-1,6-dihydro-pyridin-3-yl)-6-(4-chloro-2-methyl-phenyl)-1-isopropyl-2-(2-methoxy-phenyl)-5,6-dihydro-1H-pyrrolo[3,4-b]pyrrol-4-one 145: 3-[5-(5-Chloro-1-methyl-6-oxo-1,6-dihydro-pyridin-3-yl)-6-(4-chloro-2-methyl-phenyl)-1-isopropyl-4-oxo-1,4,5,6-tetrahydro-pyrrolo[3,4-b]pyrrol-2-yl]-4-methoxy-N-methyl-benzamide 146: 5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one 147: 5-(5-Chloro-1-methyl-6-oxo-1,6-dihydro-pyridin-3-yl)-6-(4-chloro-2-methyl-phenyl)-2-(2-dimethylamino-4-methoxy-pyrimidin-5-yl)-1-isopropyl-5,6-dihydro-1H-pyrrolo[3,4-b]pyrrol-4-one 148: 2-(2-Amino-4-methoxy-pyrimidin-5-yl)-5-(5-Chloro-1-methyl-6-oxo-1,6-dihydro-pyridin-3-yl)-6-(4-chloro-2-methyl-phenyl)-1-isopropyl-5,6-dihydro-1H-pyrrolo[3,4-b]pyrrol-4-one 149: 5-(5-Chloro-2-methyl-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-b]pyrrol-4-one 150: 5-(5-Chloro-1-methyl-6-oxo-1,6-dihydro-pyridin-3-yl)-6-(4-chloro-phenyl)-1-isopropyl-245-methoxy-1-methyl-2-oxo-1,2-dihydro-pyridin-4-yl)-5,6-dihydro-1H-pyrrolo[3,4-b]pyrrol-4-one 151: 5-(5-Chloro-1-methyl-6-oxo-1,6-dihydro-pyridin-3-yl)-6-(4-chloro-2-methyl-phenyl)-1-isopropyl-2-(4-methoxy-2-methylamino-pyrimidin-5-yl)-5,6-dihydro-1H-pyrrolo[3,4-b]pyrrol-4-one 152: 5-(5-Chloro-6-oxo-1,6-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-b]pyrrol-4-one 153: 4-[5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 154: 4-[(S)-2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile 155: 4-[(R)-2-(2-Amino-4-methoxy-pyrimidin-5-yl)-5-(3-chloro-2-fluoro-phenyl)-1-isopropyl-4-oxo-1,4,5,6-tetrahydro-pyrrolo[3,4-b]pyrrol-6-yl]-benzonitrile 156: 5-(5-Chloro-2-fluoro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 157: 4-[2-(2,4-Dimethoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile 158: 442-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile 159: 6-(4-Chloro-phenyl)-2-(2-dimethylamino-4-methoxy-pyrimidin-5-yl)-5-(1,3-dimethyl-2-oxo-hexahydro-pyrimidin-5-yl)-1-isopropyl-5,6-dihydro-1H-pyrrolo[3,4-b]pyrrol-4-one 160: (S)-5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one 161: (R)-5-(5-Chloro-1-methyl-6-oxo-1,6-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-b]pyrrol-4-one 162: (S)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one 163: (R)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-b]pyrrol-4-one 164: 5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-4-oxo-1,4,5,6-tetrahydro-pyrrolo[3,4-b]pyrrole-3-carbonitrile 165: 4-[(S)-5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 166: 4-[(R)-5-(5-Chloro-1-methyl-2-oxo-1,2-dihydro-pyridin-3-yl)-1-isopropyl-2-(4-methoxy-2-methylamino-pyrimidin-5-yl)-4-oxo-1,4,5,6-tetrahydro-pyrrolo[3,4-b]pyrrol-6-yl]-benzonitrile 167: 4-[(S)-5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 168: 4-[(R)-5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 169: 4-[(S)-5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 170: 4-[(R)-5-(3-Chloro-4-fluoro-phenyl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 171: 4-[(S)-2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile 172: 4-[(R)-2-(2-Amino-4-methoxy-pyrimidin-5-yl)-5-(3-chloro-4-fluoro-phenyl)-1-isopropyl-4-oxo-1,4,5,6-tetrahydro-pyrrolo[3,4-b]pyrrol-6-yl]-benzonitrile 173: 442-(2,4-Dimethoxy-pyrimidin-5-yl)-5-(trans-4-hydroxy-cyclohexyl)-1-isopropyl-4-oxo-1,4,5,6-tetrahydro-pyrrolo[3,4-b]pyrrol-6-yl]-benzonitrile 174: 4-[2-(2-Dimethylamino-4-methoxy-pyrimidin-5-yl)-5-(trans-4-hydroxy-cyclohexyl)-1-isopropyl-4-oxo-1,4,5,6-tetrahydro-pyrrolo[3,4-b]pyrrol-6-yl]-benzonitrile 175: 2-(2-Amino-4-methoxy-pyrimidin-5-yl)-6-(4-chloro-phenyl)-5-(2,5-dimethyl-2H-pyrazol-3-yl)-1-isopropyl-5,6-dihydro-1H-pyrrolo[3,4-b]pyrrol-4-one 176: 6-(4-Chloro-phenyl)-2-(2,4-dimethoxy-pyrimidin-5-yl)-5-(2,5-dimethyl-2H-pyrazol-3-yl)-1-isopropyl-5,6-dihydro-1H-pyrrolo[3,4-b]pyrrol-4-one 177: 6-(4-Chloro-phenyl)-2-(2-dimethylamino-4-methoxy-pyrimidin-5-yl)-5-(2,5-dimethyl-2H-pyrazol-3-yl)-1-isopropyl-5,6-dihydro-1H-pyrrolo[3,4-b]pyrrol-4-one 178: 6-(4-Chloro-phenyl)-5-(2,5-dimethyl-2H-pyrazol-3-yl)-1-isopropyl-2-(5-methoxy-1-methyl-2-oxo-1,2-dihydro-pyridin-4-yl)-5,6-dihydro-1H-pyrrolo[3,4-b]pyrrol-4-one 179: 4-[2-(2,4-Dimethoxy-pyrimidin-5-yl)-5-(2,5-dimethyl-2H-pyrazol-3-yl)-1-isopropyl-4-oxo-1,4,5,6-tetrahydro-pyrrolo[3,4-b]pyrrol-6-yl]-benzonitrile 180: 4-[2-(2-Dimethylamino-4-metho xy-pyrimidin-5-yl)-5-(2,5-dimethyl-2H-pyrazol-3-yl)-1-isopropyl-4-oxo-1,4,5,6-tetrahydro-pyrrolo[3,4-b]pyrrol-6-yl]-benzonitrile 181: 6-(4-Chloro-phenyl)-2-(2,4-dimethoxy-pyrimidin-5-yl)-5-(1,3-dimethyl-1H-pyrazol-4-yl)-1-isopropyl-5,6-dihydro-1H-pyrrolo[3,4-b]pyrrol-4-one 182: 6-(4-Chloro-phenyl)-2-(2-dimethylamino-4-methoxy-pyrimidin-5-yl)-5-(1,3-dimethyl-1H-pyrazol-4-yl)-1-isopropyl-5,6-dihydro-1H-pyrrolo[3,4-b]pyrrol-4-one 183: 6-(4-Chloro-phenyl)-5-(1,3-dimethyl-1 H-pyrazol-4-yl)-1-isopropyl-2-(5-methanesulfonyl-2-methoxy-phenyl)-5,6-dihydro-1H-pyrrolo[3,4-b]pyrrol-4-one 184: 6-(4-Chloro-phenyl)-5-(1,3-dimethyl-1H-pyrazol-4-yl)-1-isopropyl-2-(5-methoxy-1-methyl-2-oxo-1,2-dihydro-pyridin-4-yl)-5,6-dihydro-1H-pyrrolo[3,4-b]pyrrol-4-one 185: 4-[5-(5-Chloro-1-methyl-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 186: 4-[(S)-5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 187: 4-[(R)-5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 188: (S)-5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 189: (R)-5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-b]pyrrol-4-one 190: 4-[(S)-2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile 191: 4-[(R)-2-(2-Dimethylamino-4-methoxy-pyrimidin-5-yl)-1-isopropyl-4-oxo-5-(tetrahydro-pyran-4-yl)-1,4,5,6-tetrahydro-pyrrolo[3,4-b]pyrrol-6-yl]-benzonitrile 192: 6-(4-Chloro-3-fluoro-phenyl)-5-(5-Chloro-1-methyl-6-oxo-1,6-dihydro-pyridin-3-yl)-2-(2,4-dimethoxy-pyrimidin-5-yl)-1-isopropyl-5,6-dihydro-1H-pyrrolo[3,4-b]pyrrol-4-one 193: 6-(4-Chloro-3-fluoro-phenyl)-5-(5-Chloro-1-methyl-6-oxo-1,6-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 194: 4-[5-(5-Chloro-1-methyl-6-oxo-1,6-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-2-fluoro-benzonitrile 195: 4-[5-(5-Chloro-1-methyl-6-oxo-1,6-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile 196: 6-(4-Chloro-3-fluoro-phenyl)-5-(5-Chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-b]pyrrol-4-one 197: 6-(4-Chloro-3-fluoro-phenyl)-5-(5-Chloro-1-methyl-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 198: 4-[5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile 199: 4-[5-(5-Chloro-1-methyl-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-2-fluoro-benzonitrile 200: 4-[5-(5-Chloro-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-2-fluoro-benzonitrile 201: 4-[5-(5-Chloro-2-oxo-1,2-dihydro-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-2-fluoro-benzonitrile 202: 6-(4-Chloro-3-fluoro-phenyl)-5-(5-chloro-2-oxo-1,2-dihydro-pyridin-3-yl)-2-(2,4-dimethoxy-pyrimidin-5-yl)-1-isopropyl-5,6-dihydro-1H-pyrrolo[3,4-b]pyrrol-4-one 203: 6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 204: 5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-b]pyrrol-4-one 205: 5-(5-Chloro-2-methoxy-pyridin-3-yl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-b]pyrrol-4-one 206: 2-(2-Amino-4-methoxy-pyrimidin-5-yl)-5-(5-chloro-2-methoxy-pyridin-3-yl)-6-(4-chloro-phenyl)-1-isopropyl-5,6-dihydro-1H-pyrrolo[3,4-b]pyrrol-4-one 207: 4-[5-(5-Chloro-2-methoxy-pyridin-3-yl)-2-(2-dimethylamino-4-methoxy-pyrimidin-5-yl)-1-isopropyl-4-oxo-1,4,5,6-tetrahydro-pyrrolo[3,4-b]pyrrol-6-yl]-benzonitrile 208: 6-(4-Chloro-phenyl)-5-(4-fluoro-2,5-dimethyl-2H-pyrazol-3-yl)-1-isopropyl-2-(5-methoxy-1-methyl-2-oxo-1,2-dihydro-pyridin-4-yl)-5,6-dihydro-1H-pyrrolo[3,4-b]pyrrol-4-one 209: 6-(4-Chloro-phenyl)-2-(2-dimethylamino-4-methoxy-pyrimidin-5-yl)-5-(4-fluoro-2,5-dimethyl-2H-pyrazol-3-yl)-1-isopropyl-5,6-dihydro-1H-pyrrolo[3,4-b]pyrrol-4-one 210: 2-(2-Amino-4-methoxy-pyrimidin-5-yl)-6-(4-chloro-phenyl)-5-(4-fluoro-2,5-dimethyl-2H-pyrazol-3-yl)-1-isopropyl-5,6-dihydro-1H-pyrrolo[3,4-b]pyrrol-4-one 211: 4-[2-(2,4-Dimethoxy-pyrimidin-5-yl)-5-(4-fluoro-2,5-dimethyl-2H-pyrazol-3-yl)-1-isopropyl-4-oxo-1,4,5,6-tetrahydro-pyrrolo[3,4-b]pyrrol-6-yl]-benzonitrile 212: 6-(4-Chloro-2-fluoro-phenyl)-2-(2-dimethylamino-4-methoxy-pyrimidin-5-yl)-5-(2,5-dimethyl-2H-pyrazol-3-yl)-1-isopropyl-5,6-dihydro-1H-pyrrolo[3,4-b]pyrrol-4-one 213: 5-(5-Chloro-1-methyl-2-oxo-1,2-dihydro-pyridin-3-yl)-6-(5-chloro-pyridin-2-yl)-2-(2,4-dimethoxy-pyrimidin-5-yl)-1-isopropyl-5,6-dihydro-1H-pyrrolo[3,4-b]pyrrol-4-one 214: 5-(3-Chloro-4-fluoro-phenyl)-6-(5-chloro-pyridin-2-yl)-2-(2,4-dimethoxy-pyrimidin-5-yl)-1-isopropyl-5,6-dihydro-1H-pyrrolo[3,4-b]pyrrol-4-one 215: 4-[(S)-5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 216: 4-[(R)-5-(5-Chloro-1-methyl-2-oxo-1,2-dihydro-pyridin-3-yl)-2-(2,4-dimethoxy-pyrimidin-5-yl)-1-isopropyl-4-oxo-1,4,5,6-tetrahydro-pyrrolo[3,4-b]pyrrol-6-yl]-benzonitrile 217: 5-(5-Chloro-1-methyl-6-oxo-1,6-dihydro-pyridin-3-yl)-6-(4-chloro-phenyl)-2-(2,4-$d_6$-dimethoxy-pyrimidin-5-yl)-1-isopropyl-5,6-dihydro-1H-pyrrolo[3,4-b]pyrrol-4-one 218: (S)-5-(5-Chloro-1-methyl-6-oxo-1,6-dihydro-pyridin-3-yl)-6-(4-chloro-phenyl)-2-(2,4-$d_6$-dimethoxy-pyrimidin-5-yl)-1-isopropyl-5,6-dihydro-1H-pyrrolo[3,4-b]pyrrol-4-one 219: (R)-5-(5-Chloro-1-methyl-6-oxo-1,6-dihydro-pyridin-3-yl)-6-(4-chloro-phenyl)-2-(2,4-$d_6$-dimethoxy-pyrimidin-5-yl)-1-isopropyl-5,6-dihydro-1H-pyrrolo[3,4-b]pyrrol-4-one 220: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carboxylic acid ethyl ester 221: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-4-oxo-1,4,5,6-tetrahydro-pyrrolo[3,4-b]pyrrole-3-carboxylic acid 222: 4-[(R,S)-5-(3-Chloro-4-fluoro-phenyl)-2-(2,4-dimethoxy-pyrimidin-5-yl)-1-((R)-2-methoxy-1-methyl-ethyl)-4-oxo-1,4,5,6-tetrahydro-pyrrolo[3,4-b]pyrrol-6-yl]-benzonitrile 223: 4-[(R,S)-2-(2-Amino-4-methoxy-pyrimidin-5-yl)-5-(3-chloro-4-fluoro-phenyl)-1-((R)-2-methoxy-1-methyl-ethyl)-4-oxo-1,4,5,6-tetrahydro-pyrrolo[3,4-b]pyrrol-6-yl]-benzonitrile 224: (R,S)-2-(2-Amino-4-methoxy-pyrimidin-5-yl)-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one 225: (R,S)-5-(5-Chloro-1-methyl-6-oxo-1,6-dihydro-pyridin-3-yl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-b]pyrrol-4-one 226: 5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-4-oxo-1,4,5,6-tetrahydro-pyrrolo[3,4-b]pyrrole-3-carboxylic acid 227: (S)-6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 228: (R)-6-(4-Chloro-3-fluoro-phenyl)-5-(5-chloro-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-b]pyrrol-4-one 229: (S)-2-(2-Amino-4-methoxy-pyrimidin-5-yl)-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one 230: (R)-2-(2-Amino-4-methoxy-pyrimidin-5-yl)-5-(3-chloro-4-fluoro-phenyl)-6-(4-chloro-phenyl)-1-((R)-2-methoxy-1-methyl-ethyl)-5,6-dihydro-1H-pyrrolo[3,4-b]pyrrol-4-one 231: 4-(2-(2-(Dimethylamino)-4-methoxypyrimidin-5-yl)-5-(4-fluoro-1,3-dimethyl-1H-pyrazol-5-yl)-1-isopropyl-4-oxo-1,4,5,6-tetrahydropyrrolo[3,4-b]pyrrol-6-yl)benzonitrile 232: (S)-4-(5-(5-Chloro-1-methyl-6-oxo-1,6-dihydropyridin-3-yl)-2-(2-(dimethylamino)-4-methoxypyrimidin-5-yl)-1-isopropyl-4-oxo-1,4,5,6-tetrahydropyrrolo[3,4-b]pyrrol-6-yl)benzonitrile 233: (R)-4-(5-(5-Chloro-1-methyl-6-oxo-1,6-dihydropyridin-3-yl)-2-(2-(dimethylamino)-4-methoxypyrimidin-5-yl)-1-isopropyl-4-oxo-1,4,5,6-tetrahydropyrrolo[3,4-b]pyrrol-6-yl)benzonitrile 234: 5-(3-Chloro-2-fluorophenyl)-6-(5-chloropyridin-2-yl)-2-(2-(dimethylamino)-4-methoxypyrimidin-5-yl)-1-isopropyl-5,6-dihydropyrrolo[3,4-b]pyrrol-4(1H)-one 235: 5-(5-Chloro-2-methylphenyl)-6-(5-chloropyridin-2-yl)-2-(2,4-dimethoxypyrimidin-5-yl)-1-isopropyl-5,6-dihydropyrrolo[3,4-b]pyrrol-4(1H)-one 236: 4-(5-(5-Chloro-1-methyl-6-oxo-1,6-dihydropyridin-3-yl)-1-isopropyl-2-(4-methoxypyrimidin-5-yl)-4-oxo-1,4,5,6-tetrahydropyrrolo[3,4-b]pyrrol-6-yl)benzonitrile 237: (S)-4-(5-(5-Chloro-1-methyl-6-oxo-1,6-dihydropyridin-3-yl)-2-(2,4-dimethoxypyrimidin-5-yl)-1-isopropyl-4-oxo-1,4,5,6-tetrahydropyrrolo[3,4-b]pyrrol-6-yl)-2-fluorobenzonitrile 238: (R)-4-(5-(5-Chloro-1-methyl-6-oxo-1,6-dihydropyridin-3-yl)-2-(2,4-dimethoxypyrimidin-5-yl)-1-isopropyl-4-oxo-1,4,5,6-tetrahydropyrrolo[3,4-b]pyrrol-6-yl)-2-fluorobenzonitrile 239: 6-(4-Chlorophenyl)-2-(2,4-dimethoxypyrimidin-5-yl)-5-(1,5-dimethyl-2-oxo-1,2-dihydropyridin-3-yl)-1-isopropyl-5,6-dihydropyrrolo[3,4-b]pyrrol-4(1H)-one 240: 6-(4-Chlorophenyl)-1-cyclopropyl-2-(2,4-dimethoxypyrimidin-5-yl)-5-(1,5-dimethyl-6-oxo-1,6-dihydropyridin-3-yl)-5,6-dihydropyrrolo[3,4-b]pyrrol-4(1H)-one 241: 6-(4-Chlorophenyl)-1-cyclopropyl-5-(1,5-dimethyl-6-oxo-1,6-dihydropyridin-3-yl)-2-(2-methoxypyrimidin-5-yl)-5,6-dihydropyrrolo[3,4-b]pyrrol-4(1H)-one 242: 6-(4-Chlorophenyl)-1-cyclopropyl-5-(1,5-dimethyl-6-oxo-1,6-dihydropyridin-3-yl)-2-(1-methyl-2-oxo-1,2-dihydropyridin-4-yl)-5,6-dihydropyrrolo[3,4-b]pyrrol-4(1H)-one 243: 5-(5-Chloro-1-methyl-6-oxo-1,6-dihydropyridin-3-yl)-6-(4-chlorophenyl)-1-cyclopropyl-2-(1-methyl-2-oxo-1,2-dihydropyridin-4-yl)-5,6-dihydropyrrolo[3,4b]pyrrol-4(1H)-one 244: 5-(5-Chloro-1-methyl-6-oxo-1,6-dihydropyridin-3-yl)-6-(4-chlorophenyl)-1-cyclopropyl-2-(2,4-dimethoxypyrimidin-5-yl)-5,6-dihydropyrrolo[3,4-b)]pyrrol-4(1H)-one; and 245: 5-(5-Chloro-1-methyl-6-oxo-1,6-dihydropyridin-3-yl)-6-(4-chlorophenyl)-1-cyclopropyl-2-(2-methoxypyrimidin-5-yl)-5,6-dihydropyrrolo[3,4-b)]pyrrol-4(1H)-one.

11. A pharmaceutical composition comprising a compound of formula (I) or salt thereof as defined in claim 1, and one or more pharmaceutically acceptable carriers.

12. A composition comprising a compound of the formula (I) or salt thereof as claimed in claim 1, in combination with one or more therapeutically active agents.

\* \* \* \* \*